(12) United States Patent
Lee et al.

(10) Patent No.: US 9,073,830 B2
(45) Date of Patent: Jul. 7, 2015

(54) COMPOUND FOR INHIBITING 11β-HYDROXY STEROID DEHYDROGENASE 1, AND A PHARMACEUTICAL COMPOSITION COMPRISING THE SAME

(75) Inventors: Inhee Lee, Gyeonggi-do (KR); Doohyeok Pyeon, Gyeonggi-do (KR); Myounghyeon Shin, Gyeonggi-do (KR); Jeongun Hwang, Gyeonggi-do (KR); Changmin Park, Gyeonggi-do (KR); Sehoan Kim, Gyeonggi-do (KR); Heeil Chae, Gyeonggi-do (KR); Soonyoung Moon, Gyeonggi-do (KR); Soyoun Kim, Gyeonggi-do (KR); Jaekeol Rhee, Gyeonggi-do (KR)

(73) Assignee: Hyundai Pharm Co., Ltd., Cheonan-si, Chungcheongnam-do (KR)

( * ) Notice: Subject to any disclaimer, the term of this patent is extended or adjusted under 35 U.S.C. 154(b) by 0 days.

(21) Appl. No.: 14/237,060

(22) PCT Filed: Aug. 6, 2012

(86) PCT No.: PCT/KR2012/006216
§ 371 (c)(1),
(2), (4) Date: Mar. 18, 2014

(87) PCT Pub. No.: WO2013/019091
PCT Pub. Date: Feb. 7, 2013

(65) Prior Publication Data
US 2014/0206875 A1    Jul. 24, 2014

(30) Foreign Application Priority Data

Aug. 4, 2011   (KR) .................... 10-2011-0077913

(51) Int. Cl.
| | | |
|---|---|---|
| *C07C 311/29* | (2006.01) | |
| *C07D 213/71* | (2006.01) | |
| *C07D 215/36* | (2006.01) | |
| *C07C 311/20* | (2006.01) | |
| *C07C 311/19* | (2006.01) | |
| *A61K 31/18* | (2006.01) | |
| *C07C 311/13* | (2006.01) | |
| *C07C 311/39* | (2006.01) | |

(52) U.S. Cl.
CPC ............ *C07C 311/19* (2013.01); *C07C 311/13* (2013.01); *C07C 311/20* (2013.01); *C07C 311/29* (2013.01); *C07C 311/39* (2013.01); *C07C 2101/02* (2013.01); *C07C 2101/04* (2013.01); *C07C 2101/08* (2013.01); *C07C 2101/14* (2013.01); *C07C 2103/74* (2013.01); *A61K 31/18* (2013.01); *C07D 213/71* (2013.01); *C07D 215/36* (2013.01)

(58) Field of Classification Search
CPC .. C07C 311/29; C07C 311/20; C07C 311/19; C07D 213/71; C07D 215/36; A61K 31/18

USPC ............... 564/91, 89; 546/291; 514/602
See application file for complete search history.

(56) References Cited

U.S. PATENT DOCUMENTS

| | | |
|---|---|---|
| 7,842,707 B2 | 11/2010 | Royalty et al. |
| 2006/0149070 A1 | 7/2006 | Rohde et al. |
| 2008/0064693 A1* | 3/2008 | Jaroskova et al. ......... 514/230.5 |

FOREIGN PATENT DOCUMENTS

| | | |
|---|---|---|
| KR | 10-2007-0094954 A | 9/2007 |
| KR | 10-2011-0129340 A | 12/2011 |
| KR | 10-2012-0111347 A | 10/2012 |
| KR | 10-1409847 B1 | 6/2014 |
| WO | 2007057768 A2 | 5/2007 |

OTHER PUBLICATIONS

Kwon; Bioorganic and Medicinal Chemistry Letters, 2011, 21, 435-439.*
Chemical Abstracts STN Registry Database Record for RN 1296583-03-3, dated May 18, 2011.*
Chemical Abstracts STM Registry Database Record for RN 1089496-59-2, dated Dec. 24, 2008.*
Chemical Abstracts STN Registry Database Record for RN 1089455-50-4, dated Dec. 24, 2008.*
Chemical Abstracts STN Registry Database Record for RN 1015631-65-8, dated Apr. 18, 2008.*
Chemical Abstracts STN Registry Database Record for RN 1010253-21-0, dated Mar. 26, 2008.*
Hollis, et al., "11β-Hydroxysteroid dehydrogenase type 1 inhibition in type 2 diabetes mellitus", Diabetes, Obesity and Metabolism, vol. 13, pp. 1-6, (2011).
Kim, et al., "Synthesis and Biological Evaluation of Cyclic Sulfamide Derivatives as 11β-Hydroxysteroid Dehydrogenase 1 Inhibitors", ACS Med. Chem. Lett., vol. 3, pp. 88-93, (2012).
Sundbom, et al., "Inhibition of 11βHSD1 with the S-phenylethylaminothiazolone BVT116429 increases adiponectin concentrations and improves glucose homeostasis in diabetic KKAγ mice", BMC Pharmacology, vol. 8, No. 3, pp. 1-10, (2008).
Véniant, et al., "Time of the day for 11β-HSD1 inhibition plays a role in improving glucose homeostasis in DIO mice", Diabetes, Obesity and Metabolism, vol. 11, pp. 109-117, (2009).
Véniant, et al., "Discovery of a Potent, Orally Active 11β-Hydroxysteroid Dehydrogenase Type 1 Inhibitor for Clinical Study: Identification of (S)-2-((1S,2S,4R)-Bicyclo[2.2.1]heptan-2-ylamino)-5-isopropyl-5-methylthiazol-4(5H)-one (AMG 221)", J. Med. Chem., vol. 53, pp. 4481-4487, (2010).

* cited by examiner

*Primary Examiner* — John Mabry
*Assistant Examiner* — Daniel Carcanague
(74) *Attorney, Agent, or Firm* — Vorys, Sater, Seymour and Pease LLP; Mihsun Koh

(57) ABSTRACT

Disclosed are a novel compound or a pharmaceutically acceptable salt thereof, and a pharmaceutical composition including the same for inhibiting human 11-β-hydroxy steroid dehydrogenase type 1 (11β-HSD1). The disclosed compound and the pharmaceutical composition including the same for inhibiting human 11-β-hydroxy steroid dehydrogenase type 1 (11β-HSD1) are excellent in activity and solubility, and is more efficient in formulation and transfer.

7 Claims, No Drawings

COMPOUND FOR INHIBITING 11β-HYDROXY STEROID DEHYDROGENASE 1, AND A PHARMACEUTICAL COMPOSITION COMPRISING THE SAME

TECHNICAL FIELD

The present invention relates to a novel compound or a pharmaceutically acceptable salt thereof, and a pharmaceutical composition including the same for inhibiting human 11-β-hydroxy steroid dehydrogenase type 1 (11β-HSD1).

BACKGROUND ART

11-β-hydroxy steroid dehydrogenase type 1 (11β-hydroxy steroid dehydrogenase 1) glucocorticoid (cortisol in human, corticosterone in rodent) is a counter-regulatory hormone, which resists against the action of insulin (Dallman M F, Strack A M, Akana S F et al., 1993; Front Neuroendocrinol 14, 303-347). This controls the expression of hepatic enzymes related to gluconeogenesis, and increases substrate supply by releasing amino acid (decrease of protein synthesis and increase of proteolysis) from muscle, and glycerol (increase of lipolysis) from adipose tissue. Glucocorticoid is also important in differentiation of preadipocytes into mature adipocytes capable of storing triglyceride (Bujalska I J et al., 1999; Endocrinology 140, 3188-3196). This may be critical in disease states where glucocorticoid induced by "stress" is related to central obesity which itself is a strong risk factor of type 2 diabetes mellitus, hypertension and cardiovascular disease (Bjorntorp P and Rosmond R, 2000; Int. J. Obesity 24, S80-S85).

Activity of glucocorticoid is controlled not only by secretion of cortisol but also at the tissue level by intracellular interconversion of inactive cortisone and active cortisol by 11-β hydroxy steroid dehydrogenase, 11βHSD1 (activating cortisone) and 11βHSD2 (inactivating cortisol) (Sandeep T C and Walker B R, 2001 Trends in Endocrinol & Metab. 12, 446-453). Isoform 11-β hydroxy steroid dehydrogenase type 1 (11βHSD1) is expressed in liver, adipose tissue, brain, lung and other glucocorticoid tissues, and is a potential target for treating a number of diseases (such as diabetes mellitus, obesity and age-related cognitive disorder) that can be improved by a reduction of action of glucocorticoid (Seckl et al. 2001; Endocrinology 142, 1371-1376).

The role of 11βHSD1, as an important regulatory system in local glucocorticoid efficacy, and thus production of hepatic glucose have proved (Jamieson et al. 2000; J. Endocrinol, 165, 685-692). The fact that an intracellular interconversion mechanism of inactive cortisone and active cortisol may be important in humans was initially shown by treatment with carbenoxolone (antiulcerative drug inhibiting both 11βHSD1 and 2) (Walker B R et al., 1995; J. Clin. Endocrinol. Metab. 80, 3155-3159). This leads to increased insulin sensitivity indicating that 11βHSD1 may control the effects of insulin by reducing tissue levels of active glucocorticoids (Walker B R et al, 1995; J. Clin. Endocrinol. Metab. 80, 3155-3159). Also, studies on compounds having a therapeutic effect on type 2 diabetes mellitus by inhibition of 11βHSD1 have been recently actively conducted (Ji Seon Part et al., biological pharmacology, Anti-diabetic and anti-adipogenic effects of a novel selective 11βhydroxysteroid dehydrogenase type 1 inhibitor, 2-(3-benzoyl)-4-hydroxy-1,1-dioxo-2H-1,2-benzothiazine-2-yl-1-phenylethanone (KR-66344), 2011; Sundbom M et al., Inhibition of 11beta HSD1 with the S-phenyl-ethylaminothiazolone BVT116429 increases adiponectin concentrations and improves glucose homeostasis in diabetic KKAy mice, BMC Pharmacology 2008; 8:3 (12 Feb. 2008); Clarence Hale et al., Chem Bio/Drug Des 2008; 71:36-44; Clarence Hale et al., Diabetes, Obesity and Metabolism 11: 2009, 109-117; G. Hollis R. Huber, 2010; Diabetes, Obesity and Metabolism 13: 1-6, 2011: Clarence Hale et al., J. Med. Chem. 2010, 53, 4481-4487)

Clinically, Cushing's syndrome is related to an excess of cortisol, which is associated with glucose tolerance, central obesity (caused by simulation of preadipocyte differentiation in this depot), dyslipidemia and hypertension. Cushing s syndrome clearly shows a number of similarities to metabolic syndrome. Although the metabolic syndrome is not generally related to excess circulating cortisol levels (Jessop D S et al., 2001; J. Clin. Endocrinol. Metab. 86, 4109-4114), abnormally high 11βHSD1 activity within tissues would be expected to have the same effect. In a case of an obese person, although he has a plasma cortisol level lower than or similar to a lean control, the 11βHSD1 activity in his subcutaneous fat was highly increased (Rask E, et al. 2001; J. Clin. Endocrinol. Metab. 1418-1421). Also, the central fat related to the metabolic syndrome shows a much higher 11βHSD1 activity than subcutaneous fat (Bujalska I J et al., 1997; Lancet 349, 1210-1213). Accordingly, it is thought that glucocorticoid, 11βHSD1 and metabolic syndrome have relations therebetween.

11βHSD1 knockout mice show attenuated glucocorticoid-induced activation of gluconeogenesis enzymes in response to plasma glucose levels lacking or reduced in response to stress or obesity (Kotelevtsev Y et al., 1997; Proc. Natl. Acad. Sci USA 94, 14924-14929). This indicates that inhibition of 11βHSD1 is useful in reduction of plasma glucose and hepatic glucose output in type 2 diabetes mellitus. Also, these mice express an anti-arteriosclerotic lipoprotein profile that shows a low triglyceride level, an increase of HDL cholesterol and an increase of apo-lipoprotein AI level (Morton N M et al., 2001; J. Biol. Chem. 276, 41293-41300). Such a phenotype is caused by an increase of hepatic expression of enzymes of fat catabolism and PPARα. Also, this indicates that 11βHSD1 inhibition is useful in treatment of dyslipidemia of the metabolic syndrome.

The most reliable demonstration of a relation between metabolic syndrome and 11βHSD1 was obtained from a recent study on transgenic mice over-expressing 11βHSD1 (Masuzaki H et al., 2001; Science 294, 2166-2170). When 11βHSD1 is expressed under the control of an adipocyte specific promoter, 11βHSD1 transgenic mice show high adipose levels of corticosterone, central obesity, insulin resistant diabetes mellitus, hyperlipidemia and bulimia nervosa. Most importantly, an increase levels of 11βHSD1 in the fat of these mice are similar to those observed in diabetes mellitus individuals. Fat 11βHSD1 activity and plasma corticosterone levels were normal, but hepatic portal vein levels of corticosterone were increased three times. This is thought to be a cause of themetabolic effects in liver.

It is clear that a mouse can completely imitate metabolic syndrome by over-expressing 11βHSD1 only in fat to a similar level as that of an obese human.

Tissue distribution of 11βHSD1 is widely spread, and overlaps with that of glucocorticoid receptor. Accordingly, inhibition of 11βHSD1 may potentially oppose the effects of glucocorticoid in a large number of physiological/pathological roles. It is widely disclosed that 11βHSD1 is present in human skeletal muscle and glucocorticoid opposes insulin's anabolic effects on protein turnover and glucose metabolism (Whorwood C B et al., 2001; J. Clin. Endocrinol. Metab. 86, 2296-2308). Accordingly, skeletal muscle may be an important target for 11βHSD1-based treatment.

Glucocorticoid can also reduce insulin secretion and worsen the effects of glucocorticoid induced insulin resistance. Pancreatic islets express 11βHSD1, and carbenoxolone can inhibit the effects of 11-dehydro corticosterone on insulin release (Davani B et al., 2000; J. Biol. Chem. 275, 34841-34844). Accordingly, in treatment of diabetes mellitus, 11βHSD1 inhibitor may not only act at the tissue level on insulin resistance but also increase insulin secretion itself.

Skeletal development and bone function are also regulated by glucocorticoid action. 11βHSD1 is present in human bone osteoclasts and osteoblasts, and treatment of healthy volunteers with carbenoxolone showed a decrease in bone resorption with no change in bone formation markers (Cooper M S, et al. 2000; Bone 27, 375-381). Inhibition of 11βHSD1 activity in bone could be used as a protection mechanism in treatment of osteoporosis.

Glucocorticoid may also be involved in ocular disease such as glaucoma. 11βHSD1 has been shown to affect intraocular pressure in humans and inhibition of 11βHSD1 may be expected to alleviate an increase of intraocular pressure associated with glaucoma (Rauz S et al., 2001; Investigative Opthalmology & Visual Science 42, 2037-2042).

It is known that stress and glucocorticoid affect a cognitive function (de Quervain et al., 1998; Nature 394, 787-790). 11βHSD1 controls the level of the glucocorticoid action in the brain and thus is helpful in neurotoxicity (Rajan, V. et al., 1996; Neuroscience 16, 65-70; Seckl et al., 2000; Neuroendocrinol, 18, 49-99). Based on the known efficacy of gluticorticoid in the brain, inhibition of 11βHSD1 in the brain may result in reduced anxiety (Tronche, F. et al., 1999; Nature Genetics, 23, 99-103). Inhibition of 11βHSD1 in a human brain may prevent reactivation of cortisone into cortisol, and protect against harmful glucocorticoid-mediated effects on neuronal survival and other aspects of neuronal function, including cognitive disorder, depression and increase of appetite.

There appears to be a certain relation between 11βHSD1 and metabolic syndrome both in humans and rodents. A drug that specifically inhibits 11βHSD1 in type 2 obese diabetic patients will lower blood sugar by inhibiting hepatic gluconeogenesis, reduce central obesity, improve the atherogenic lipoprotein phenotype, lower blood pressure, and reduce insulin resistance. Insulin effects in muscle will be enhanced, and insulin secretion from beta cells of Pancreatic islets may also be increased.

At present, there are two main recognized definitions of metabolic syndrome.

1) The adult treatment panel (ATP III 2001 JMA) definition of metabolic syndrome indicates that it is present if the patient has three or more of the following symptoms:
- waist measurements of 40 inches (102 cm) or more for men, and 35 inches (88 cm) or more for women
- serum triglyceride level of 150 mg/dl (1.69 mmol/1) or more
- HDL cholesterol levels of less than 40 mg/dl (1.04 mmol/1) for men, and less than 50 mg/dl (1.29 mmol/1) for women
- blood pressure of 135/80 mm Hg or more and/or
- blood sugar (serum glucose) of 110 mg/dl (6.1 mmol/1) or more.

2) The WHO advisory committee has recommended the following definition which does not imply causal relationships and is suggested as a working definition to be improved upon in due course:
The patient has at least one of the following symptoms:
glucose tolerance, impaired glucose tolerance (IGT) or diabetes mellitus and/or insulin resistance together with two or more of the following:
- raised arterial pressure
- raised plasma triglycerides
- central obesity
- microalbuminuria.

Accordingly, The present invention provides a novel compound and a pharmaceutical composition including the same for inhibiting human 11-β-hydroxy steroid dehydrogenase type 1, which are more excellent in activity and solubility, and is more efficient in formulation and transfer.

DISCLOSURE OF INVENTION

Technical Problem

Therefore, the present invention provides a novel compound or a pharmaceutically acceptable salt thereof, and a pharmaceutical composition including the same for inhibiting human 11-β-hydroxy steroid dehydrogenase type 1 (11β-HSD1).

Solution to Problem

In accordance with an aspect of the present invention, there is provided a compound of Formula I below, or an enantiomer, a diastereomer, a geometric isomer, a solvate or a pharmaceutically acceptable salt thereof.

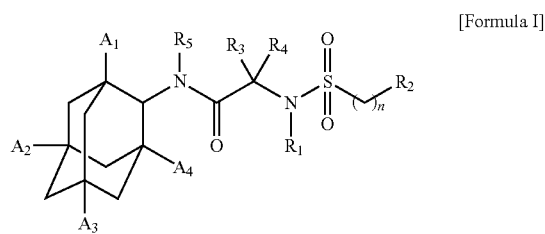

[Formula I]

In Formula I above, $A_{1-4}$ each is independently selected from the group consisting of H, —CHR'R", —OR', —COOR', and —CONR'R";

R' and R" each is independently H, a linear or branched optionally substituted $C_{1-5}$ alkyl group, or $C_{3-10}$ cycloalkyl group;

$R_1$ and $R_5$ each is independently H or a linear or branched optionally substituted $C_{1-5}$ alkyl group;

$R_2$ is selected from the group consisting of an optionally substituted $C_{5-10}$ aryl group, an optionally substituted $C_{5-10}$ heteroaryl group, an optionally substituted $C_{3-10}$ cycloalkyl group, an optionally substituted $C_{3-12}$ heterocycloalkyl group and a combination thereof;

$R_3$ and $R_4$ each is independently H or a linear or branched optionally substituted $C_{1-5}$ alkyl group, wherein $R_3$ and $R_4$ may be linked to each other to form an optionally substituted $C_{3-10}$ cycloalkyl group;

n represents an integer of 0 to 2, wherein if n is 1 or 2, a constituent carbon may be substituted with a linear or branched $C_{1-5}$ alkyl group;

wherein, a $C_{5-10}$ heteroaryl group and a $C_{3-12}$ heterocycloalkyl group each represents a group in which a carbon constituting the ring is substituted with at least one atom selected from the group consisting of N, O and S;

a substituted $C_{1-5}$ alkyl, a substituted $C_{5-10}$ aryl group, a substituted $C_{5-10}$ heteroaryl group, a substituted $C_{3-10}$ cycloalkyl group and a substituted C₃₋₁₂ heterocycloalkyl group each independently represents a group substituted with at least one substituent selected from the group consisting of —OR', —SR', —NO₂, —CN, sulfonyl, azide, halogen, C₁₋₅ alkyl, C₁₋₅ alkyl substituted with at least one —OH group or halogen atom, a C₃₋₁₀ cycloalkyl group, a C₅₋₁₀ aryl group, a C₅₋₁₀ heteroaryl group, —COR', —COOR', —CONR'R", and —NR'R";

wherein R' and R" are the same as previously defined.

In the compound, or the enantiomer, the diastereomer, the geometric isomer, the solvate or the pharmaceutically acceptable salt thereof, R₂ is selected from the group consisting of an optionally substituted C₅₋₁₀ aryl group, an optionally substituted C₅₋₁₀ heteroaryl group and a combination thereof, wherein the substituted C₅₋₁₀ aryl group or the substituted C₅₋₁₀ heteroaryl group each independently represents a group substituted with at least one substituent selected from the group consisting of —OR', —SR', —NO₂, —CN, sulfonyl, azide, halogen, C₁₋₅ alkyl, C₁₋₅ alkyl substituted with at least one —OH group or halogen atom, a C₃₋₁₀ cycloalkyl group, a C₅₋₁₀ aryl group, a C₅₋₁₀ heteroaryl group, —COR', —COOR', —CONR'R", and —NR'R".

In the compound, or the enantiomer, the diastereomer, the geometric isomer, the solvate or the pharmaceutically acceptable salt thereof, A₂ is selected from the group consisting of H, —CHR'R", —OR', —COOR', and —CONR'R".

Further, in the compound, or the enantiomer, the diastereomer, the geometric isomer, the solvate or the pharmaceutically acceptable salt thereof, the compound of Formula 1 is any one selected from the group consisting of compounds below.

1
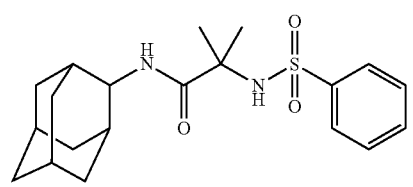

2
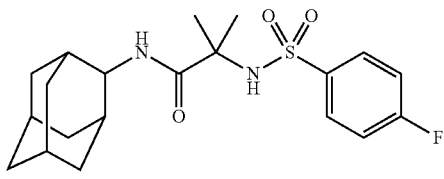

3
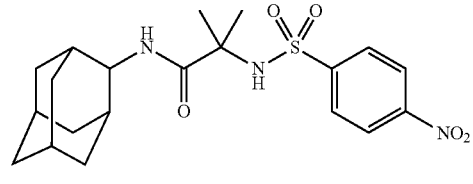

4
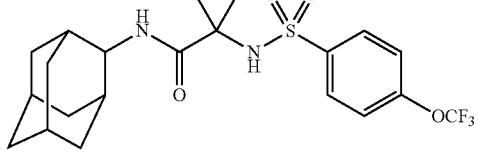

-continued

5
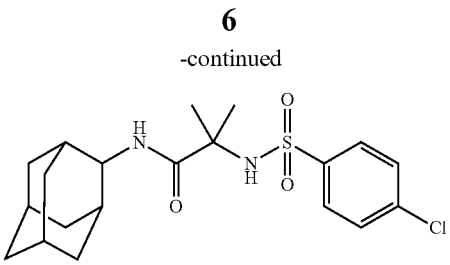

6
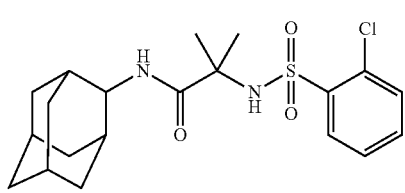

7
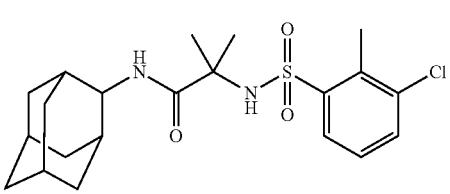

8
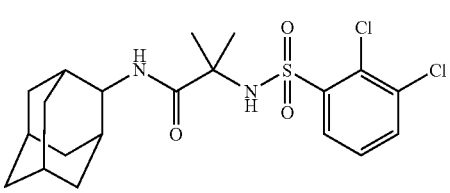

9
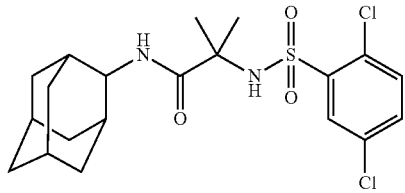

10
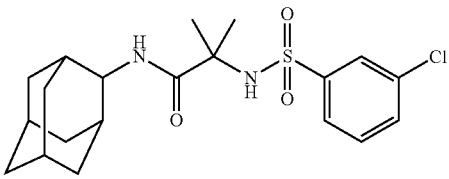

11
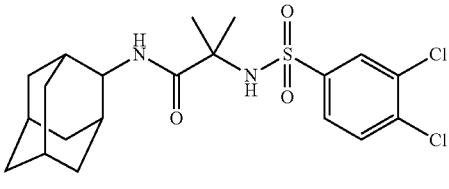

12
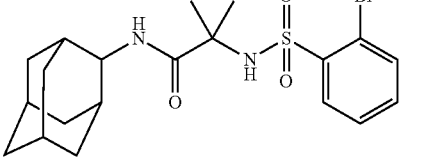

-continued
13
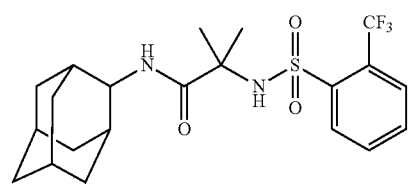
14
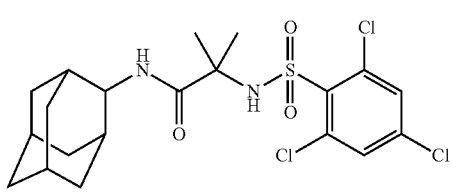
15
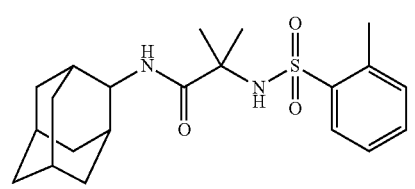
16
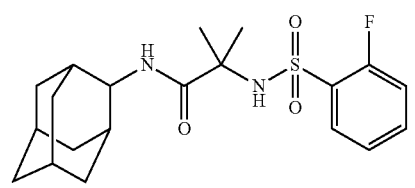
17
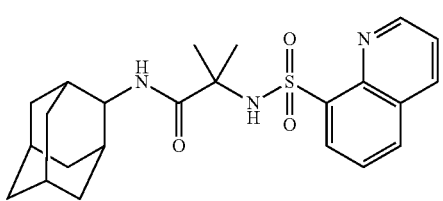
18
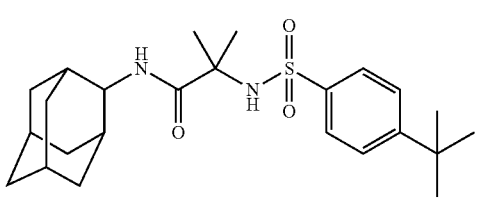
19
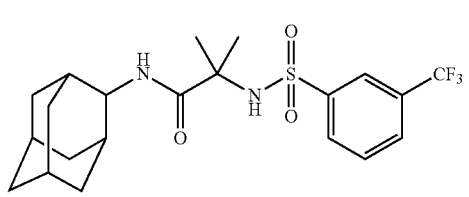
20
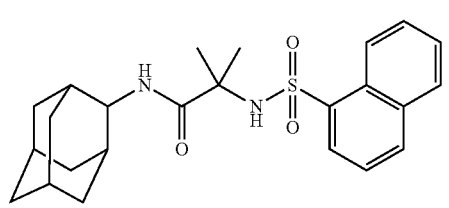
-continued
21
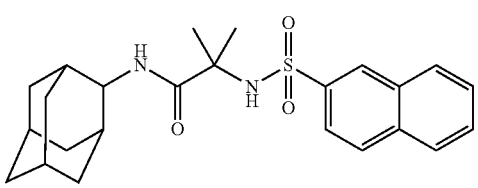
22
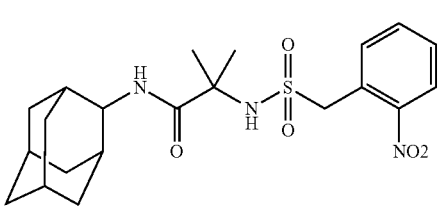
23
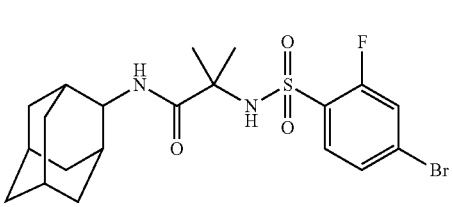
24
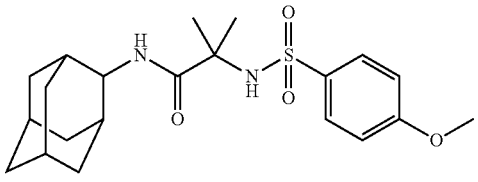
25
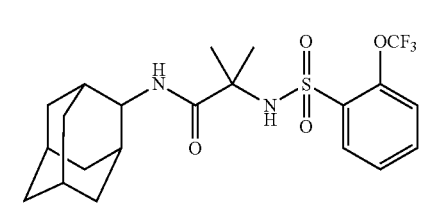
26
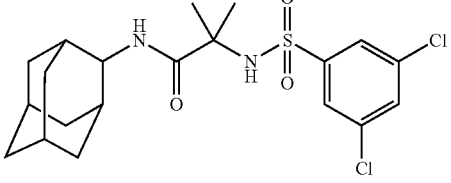
27
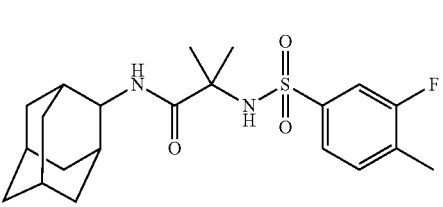
28
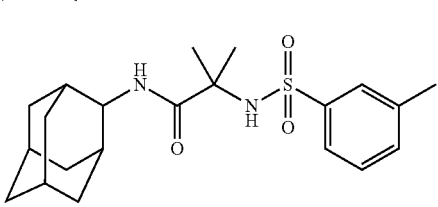

29 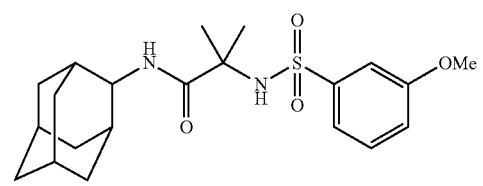
30 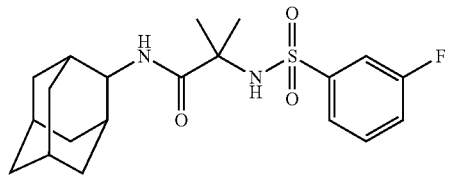
31 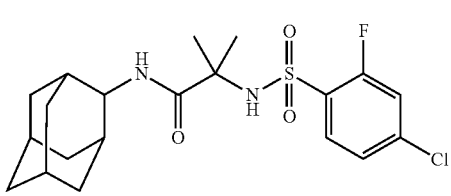
32 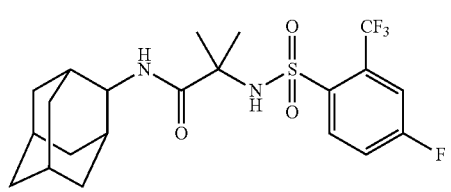
33 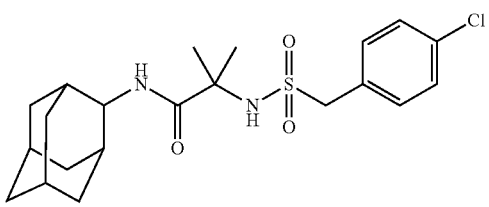
34 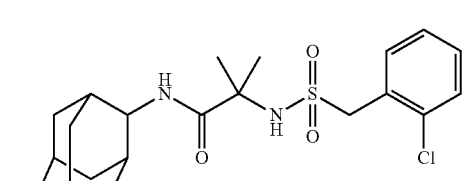
35 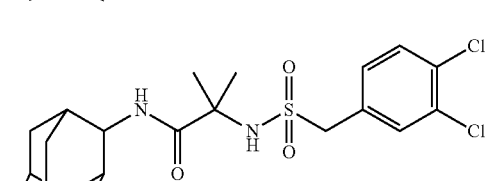
36 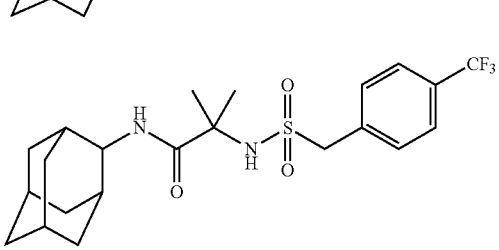
37 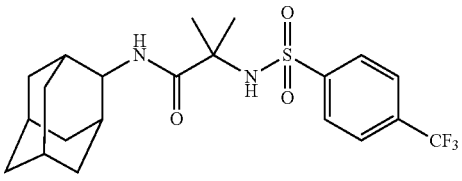
38 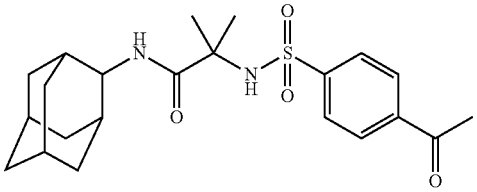
39 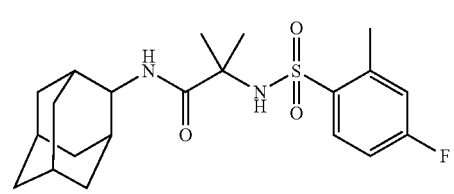
40 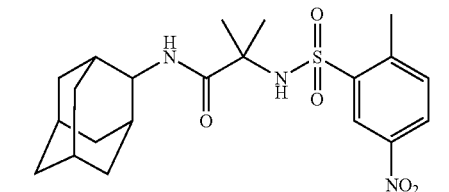
41 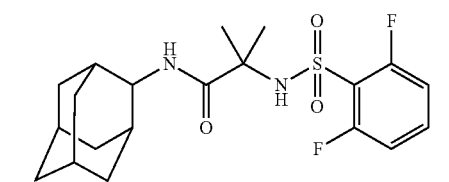
42 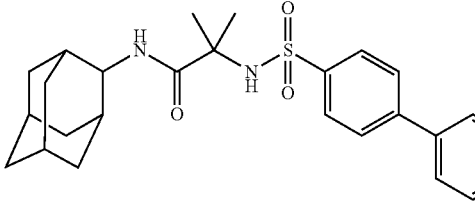
43 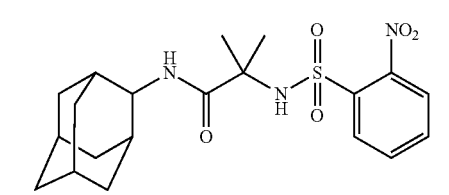
44 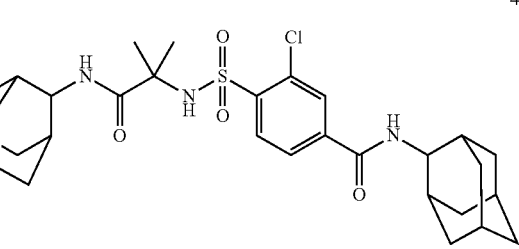

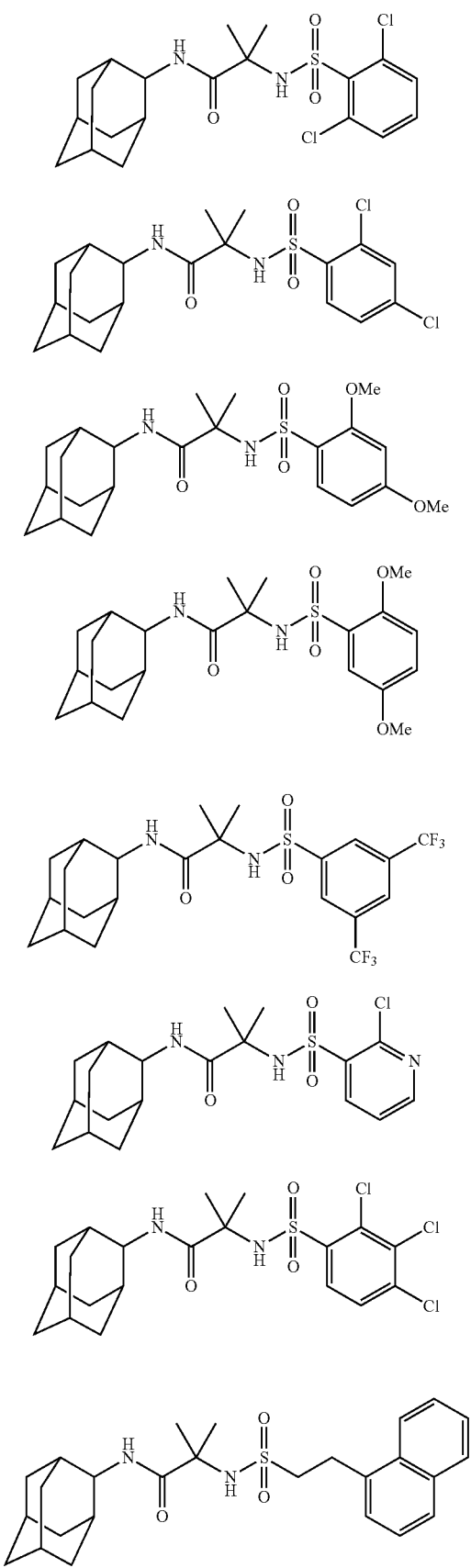
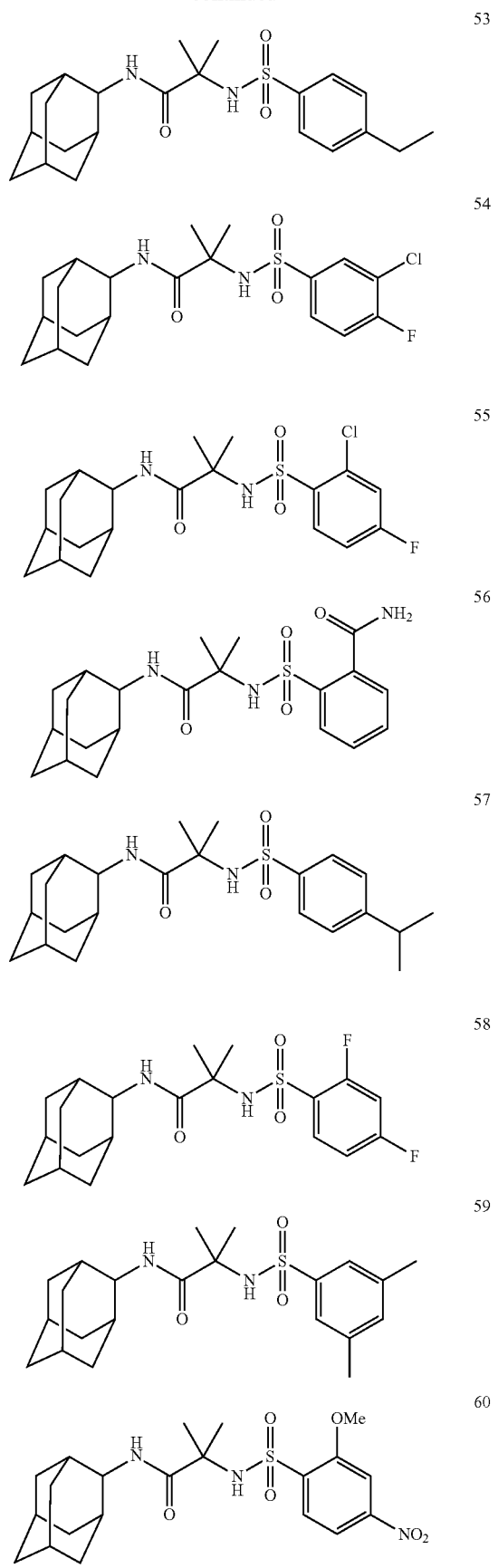

-continued
61 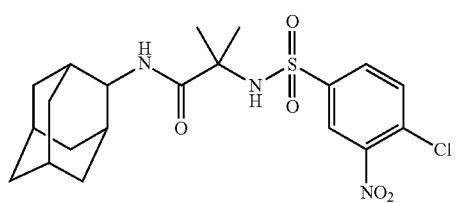
62 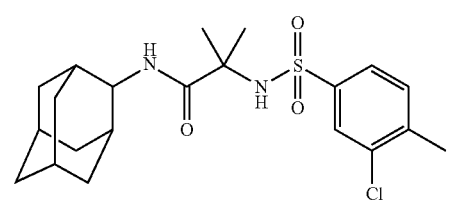
63 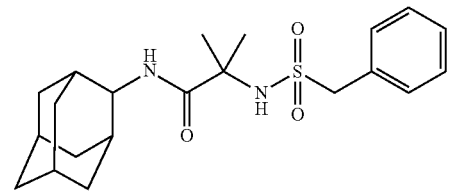
64 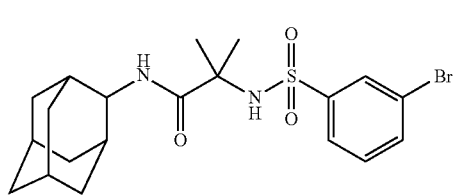
65 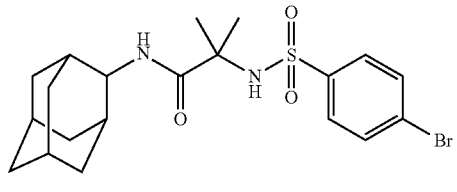
66 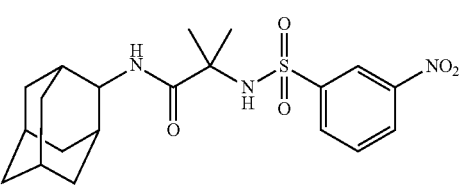
67 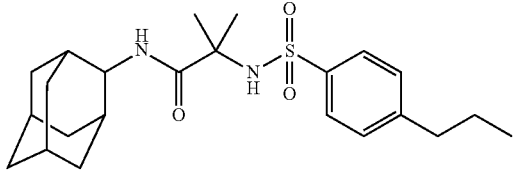
68 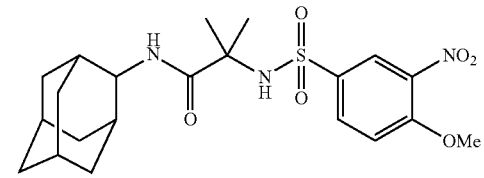
-continued
69 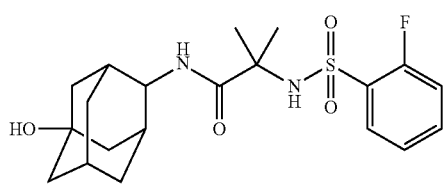
70 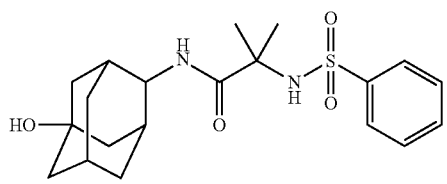
71 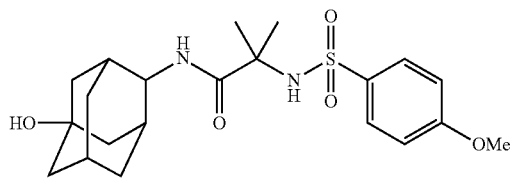
72 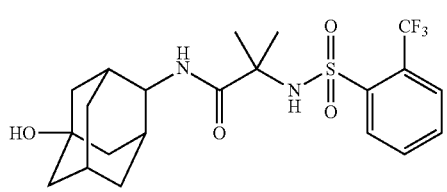
73 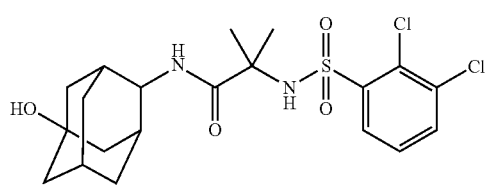
74 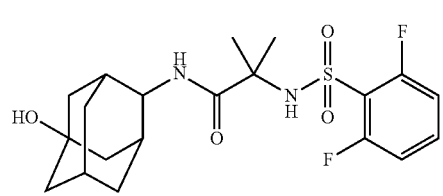
75 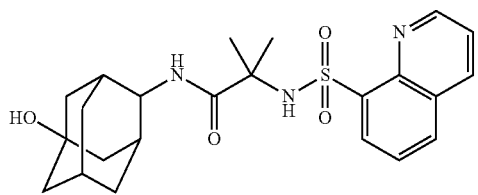
76 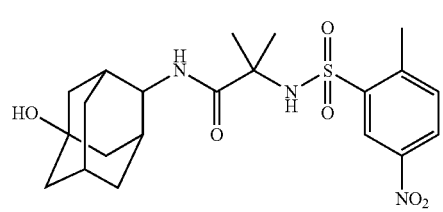

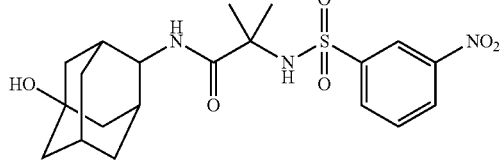 77
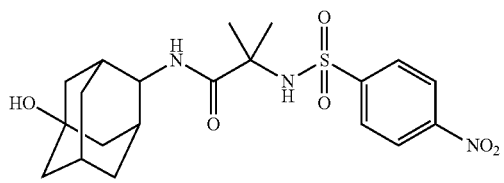 78
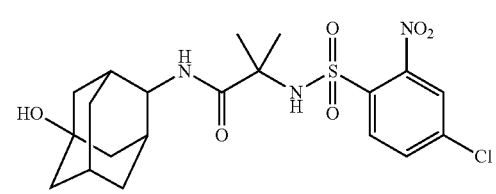 79
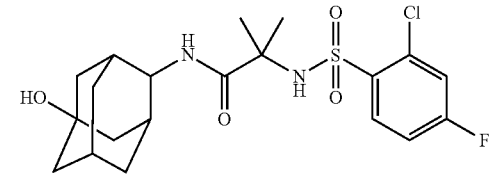 80
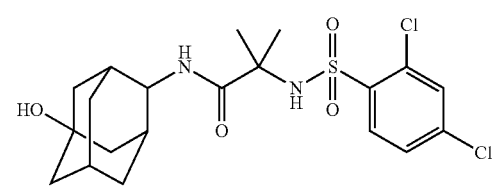 81
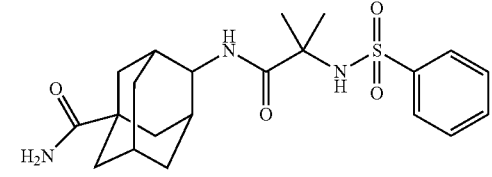 82
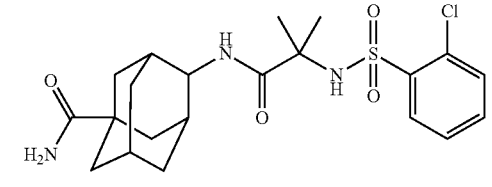 83
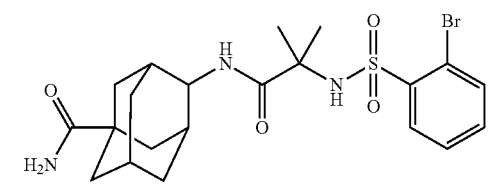 84
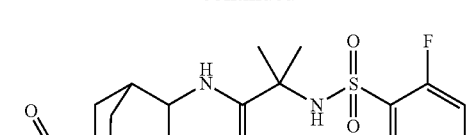 85
 86
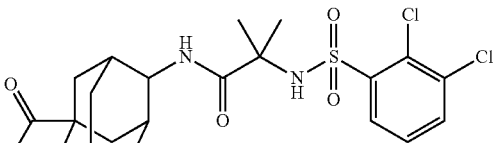 87
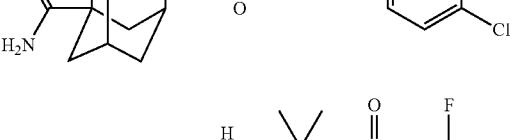 88
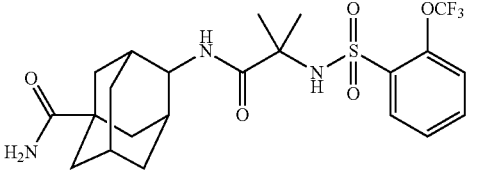 89
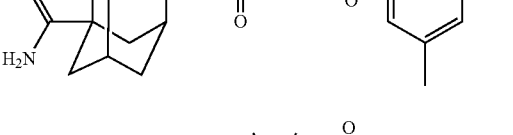 90
 91
92

93 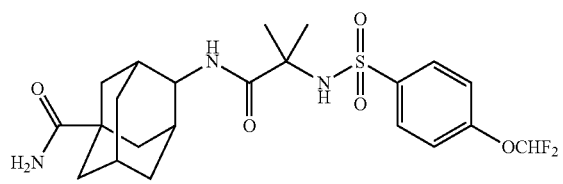
94 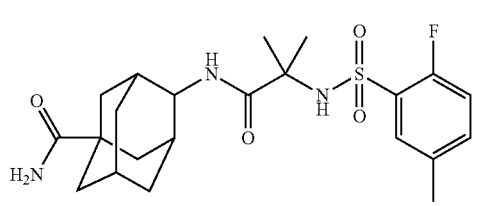
95 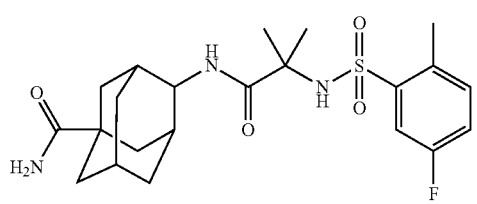
96 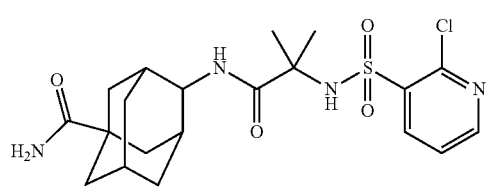
97 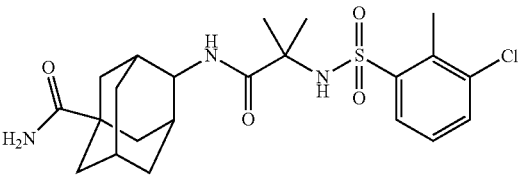
98 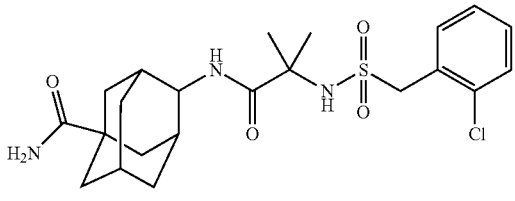
99 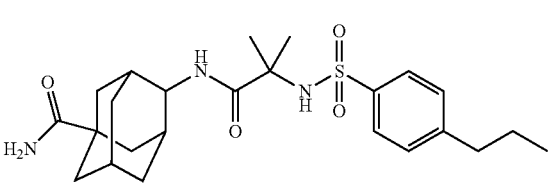
100 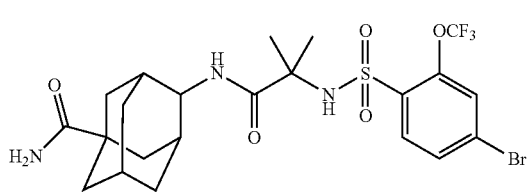
101 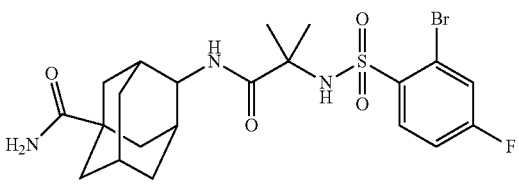
102 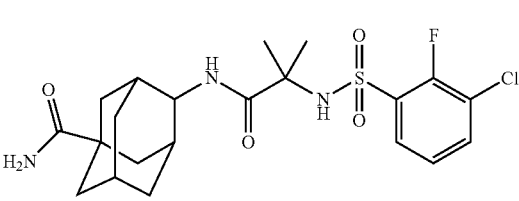
103 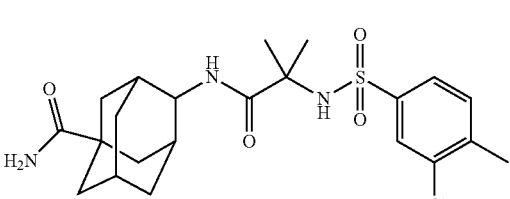
104 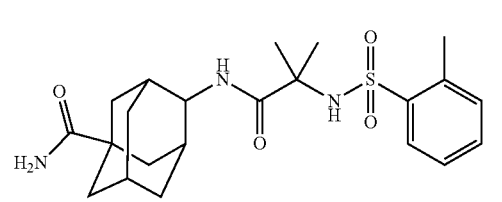
105 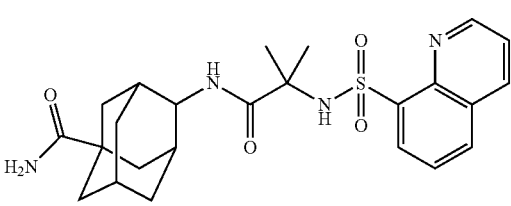
106 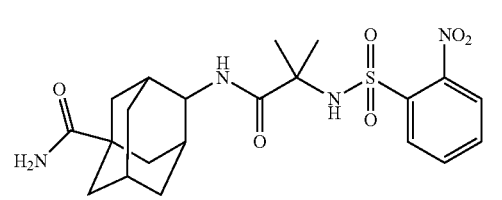
107 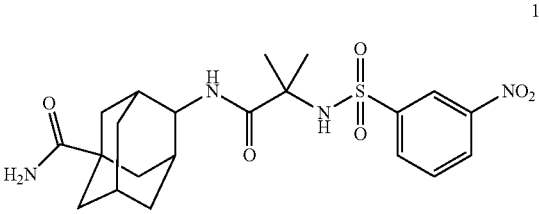
108 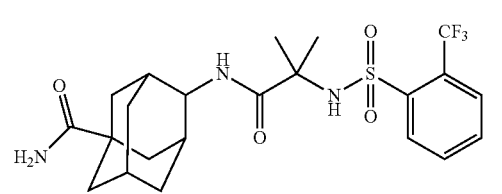

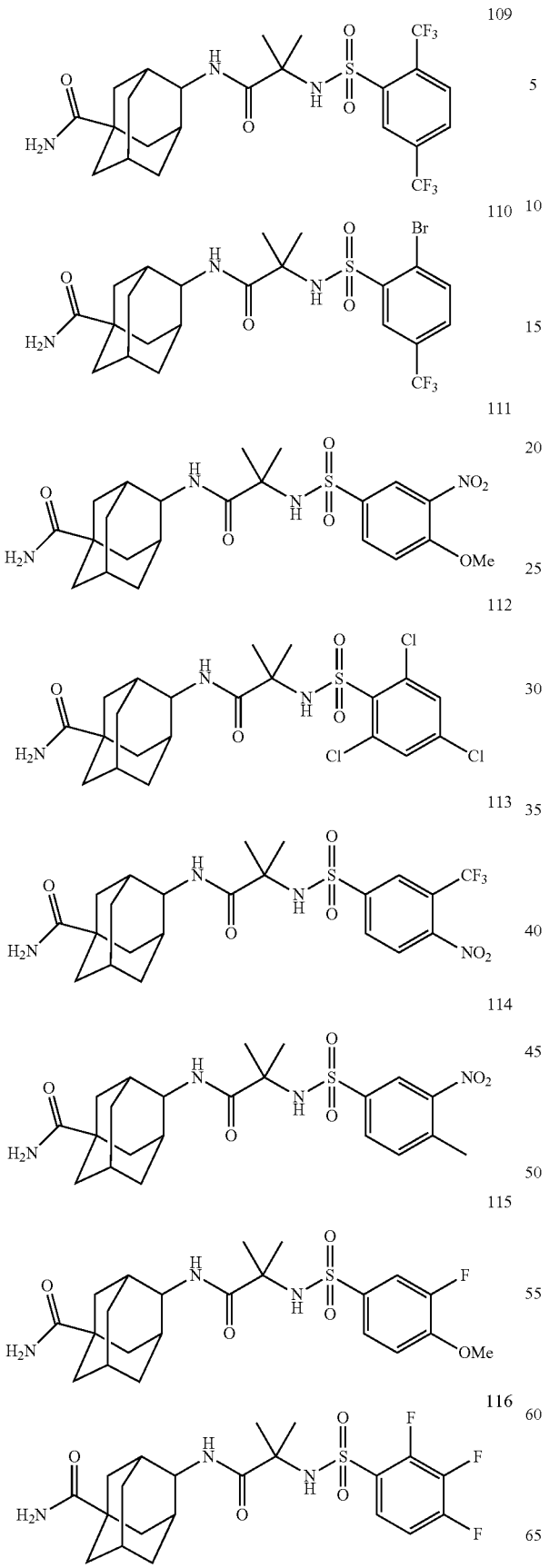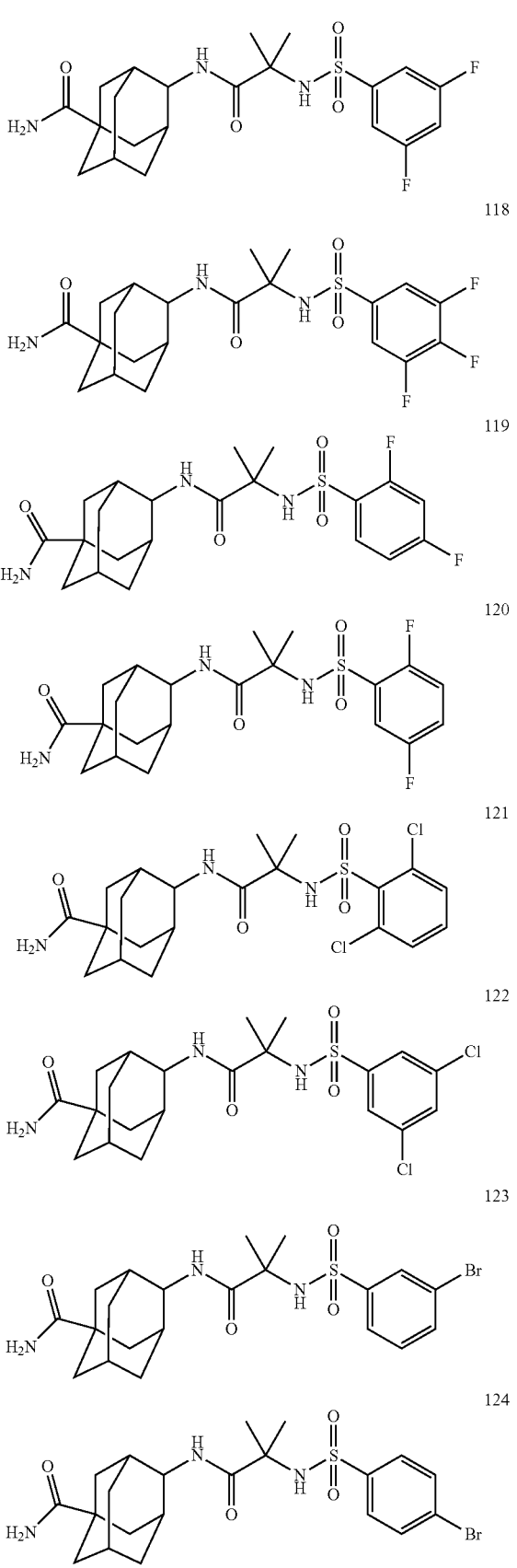

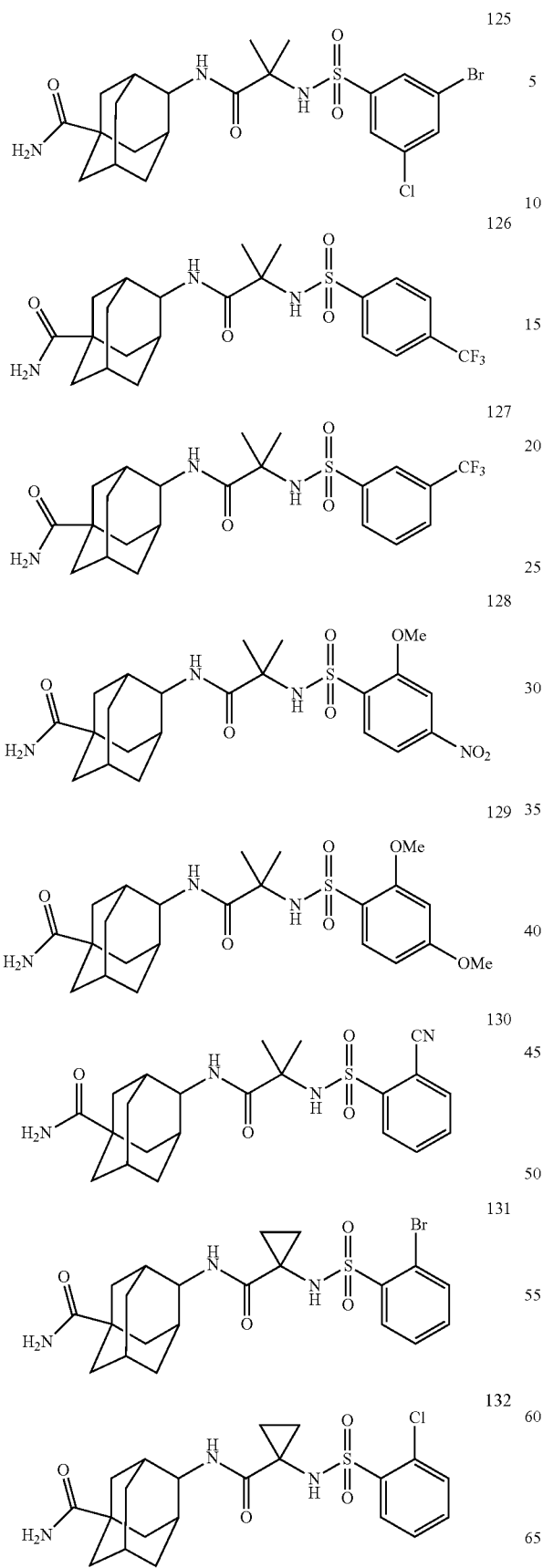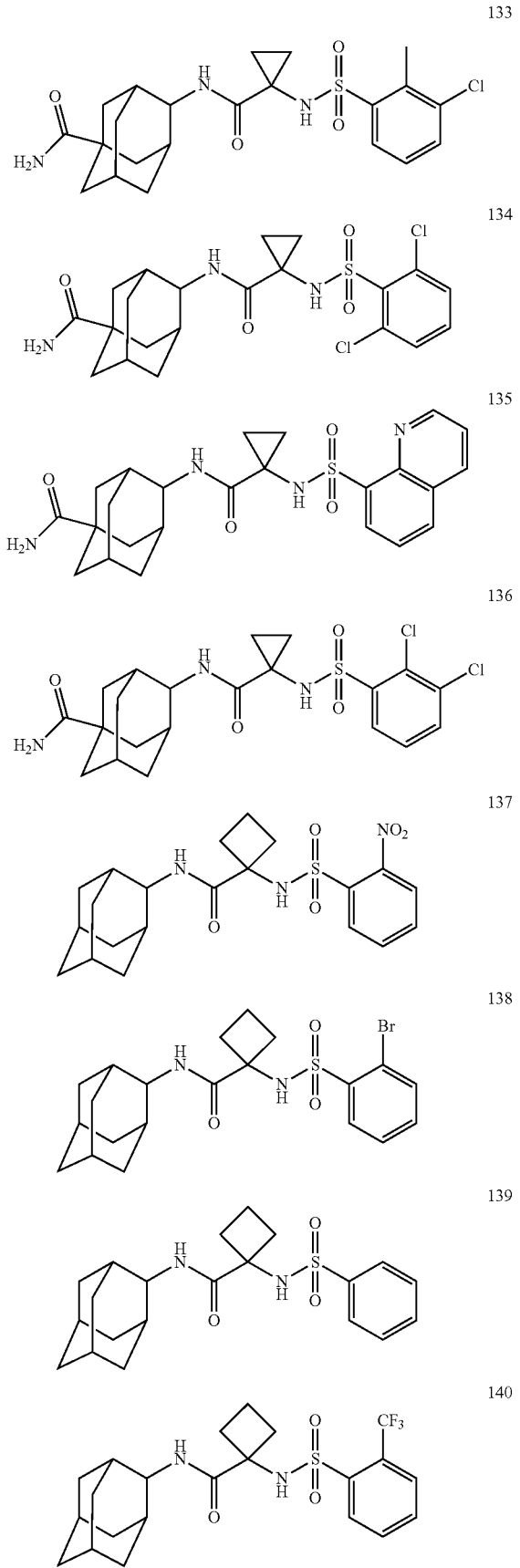

141 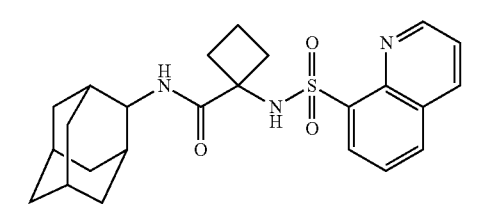
142 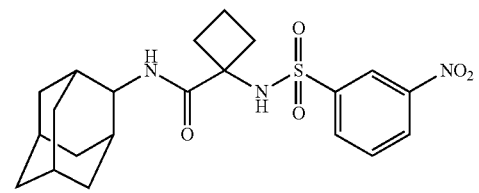
143 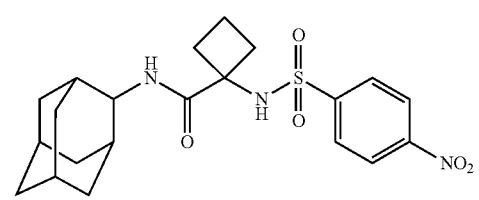
144 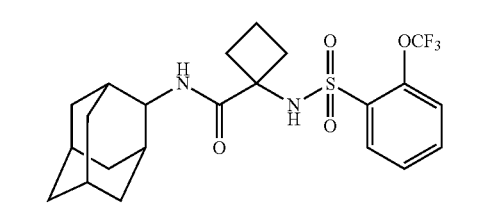
145 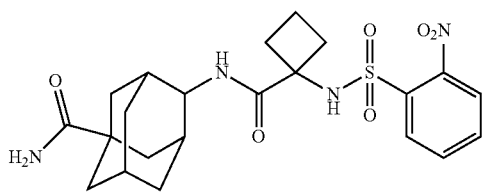
146 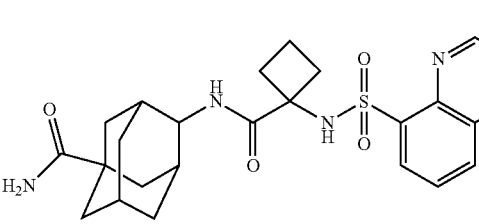
147 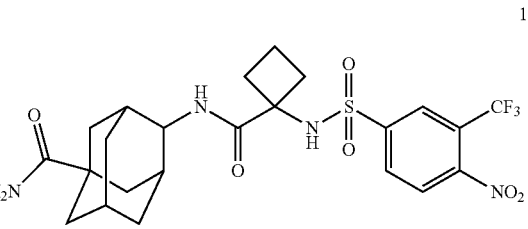
148 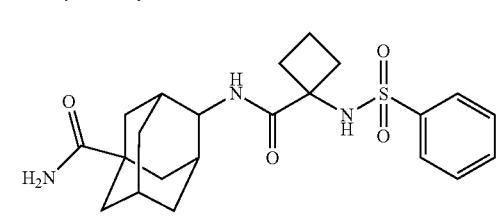
149 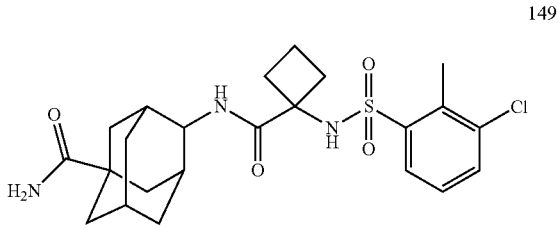
150 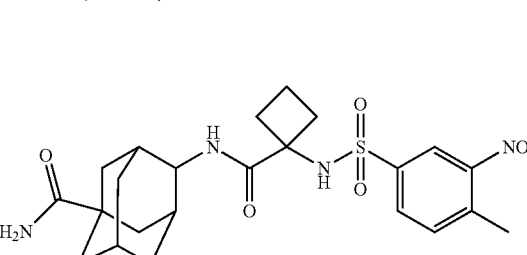
151 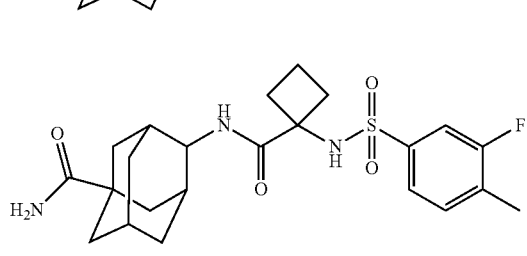
152 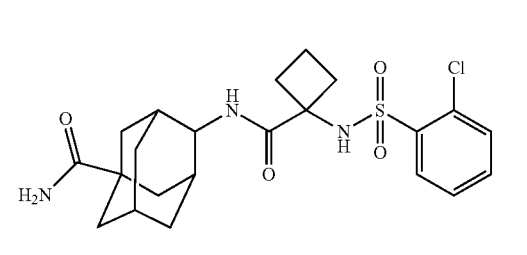
153 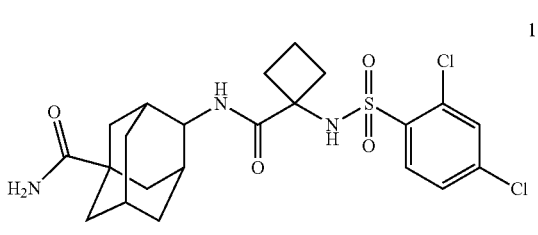
154 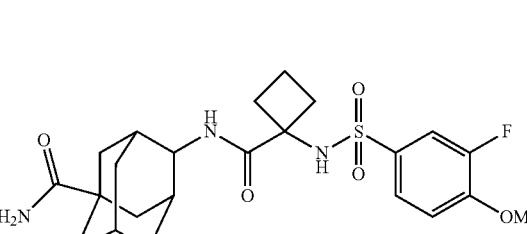
155 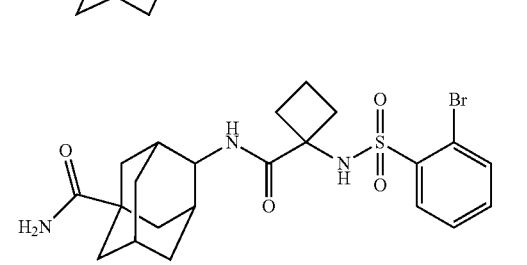

156 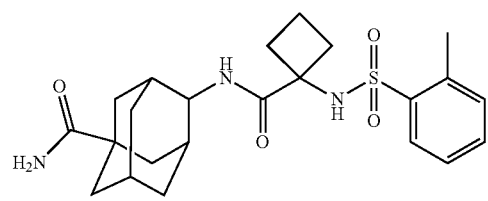
157 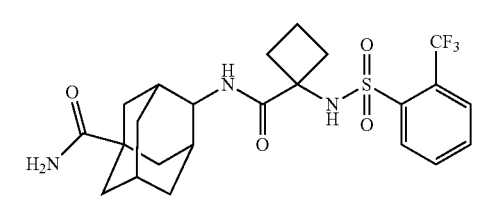
158 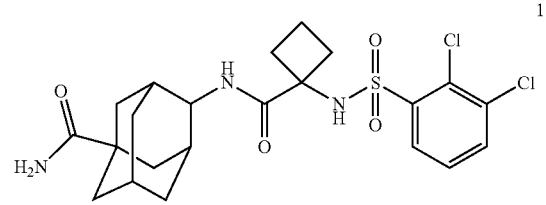
159 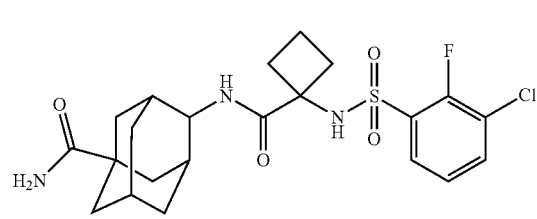
160 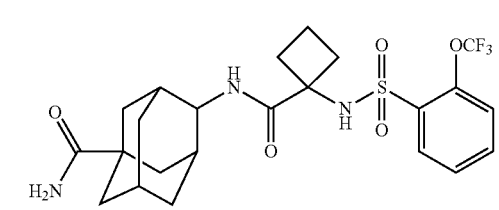
161 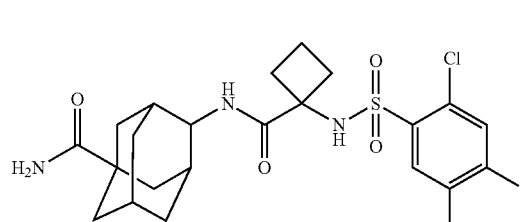
162 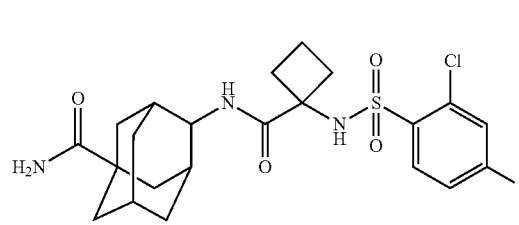
163 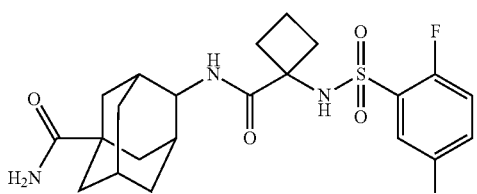
164 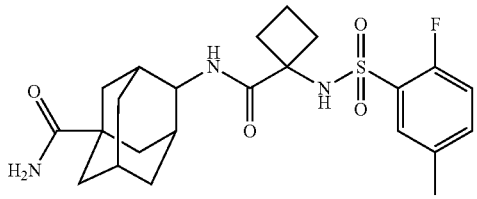
165 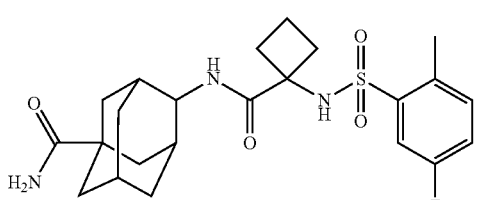
166 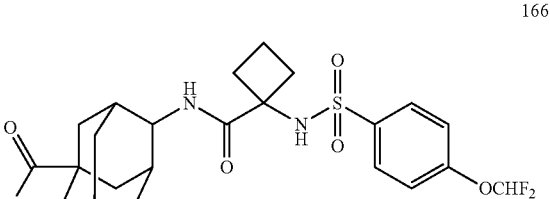
167 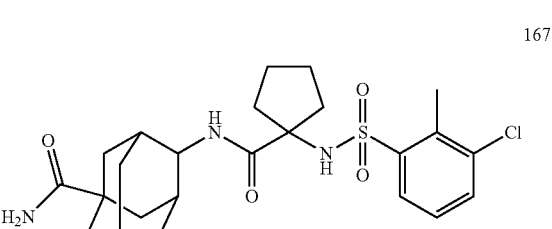
168 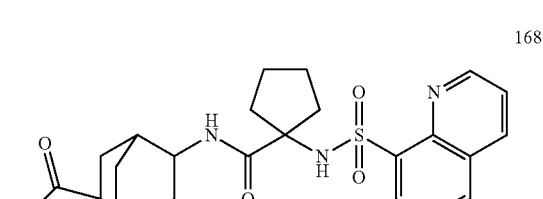
169 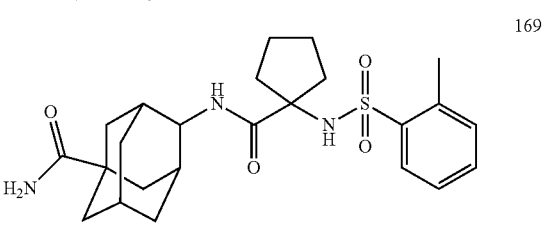

170 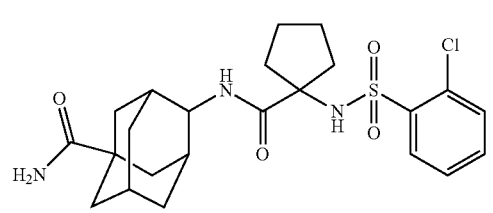
171 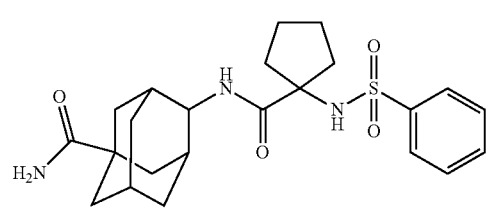
172 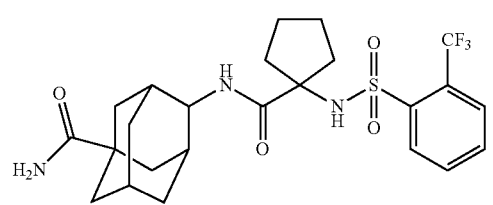
173 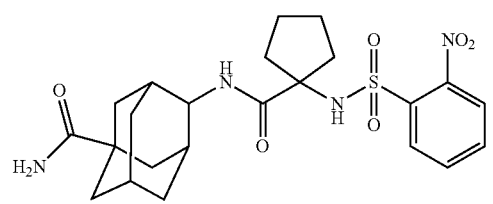
174 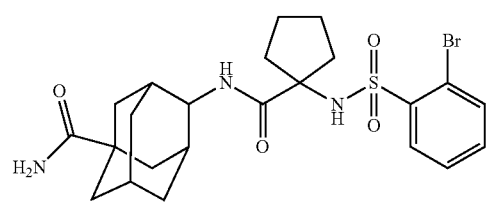
175 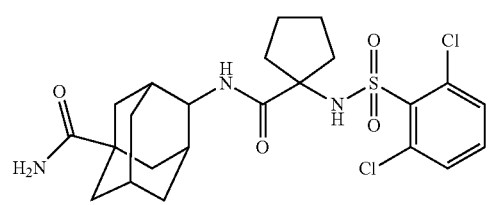
176 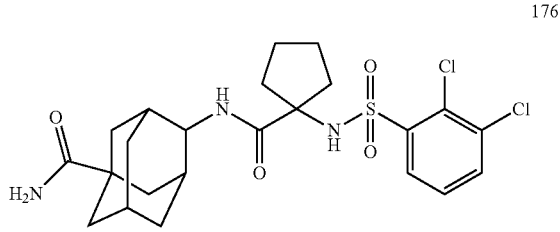 [SMILES: NC(=O)C12CC3CC(C1)C(NC(=O)C1(NS(=O)(=O)c4cccc(Cl)c4F)CCCC1)C(C3)C2]
177 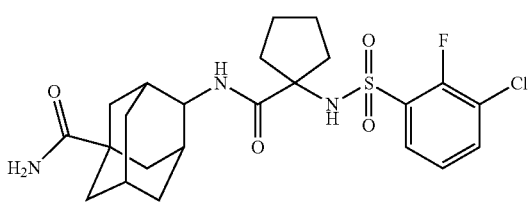
178 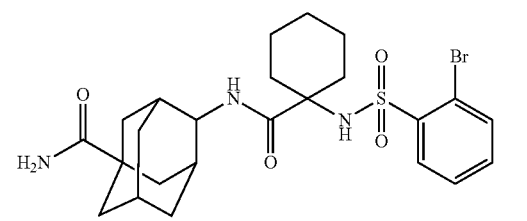
179 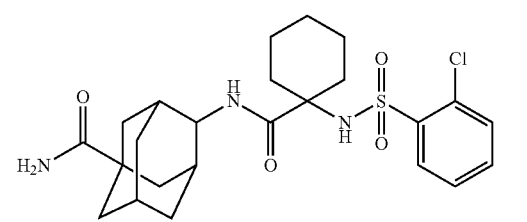
180 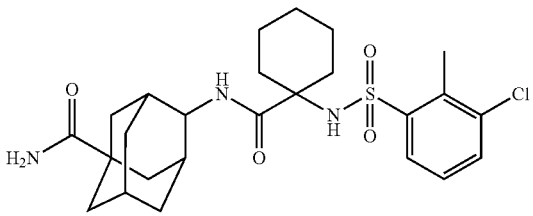
181 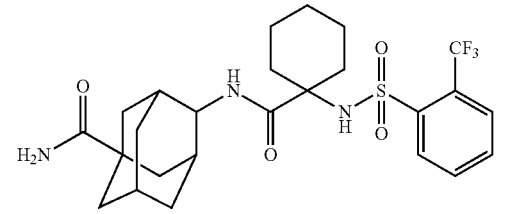
182 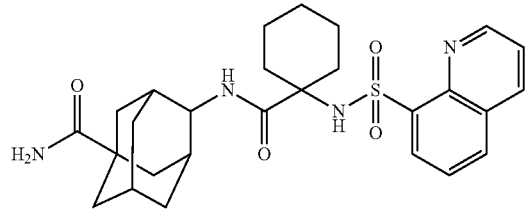
183 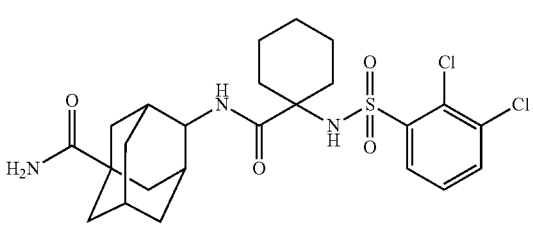

29
-continued
184
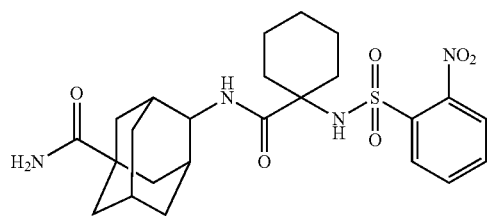
185
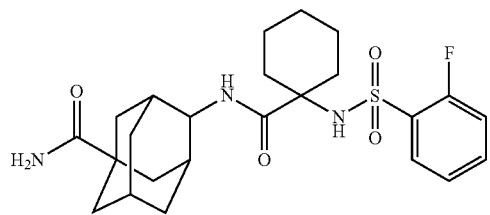
186
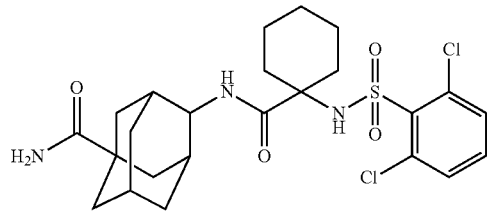
187
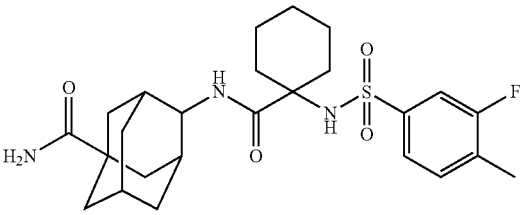
188
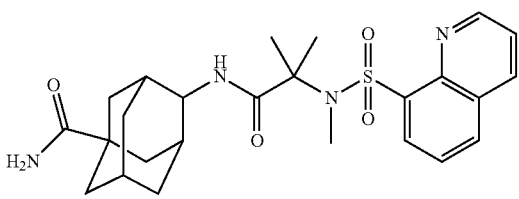
189
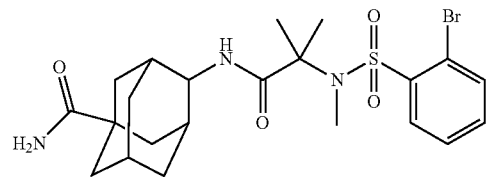
190
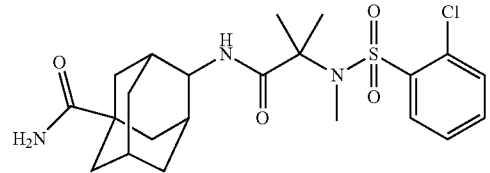
30
-continued
191
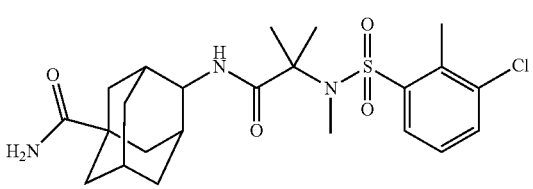
192
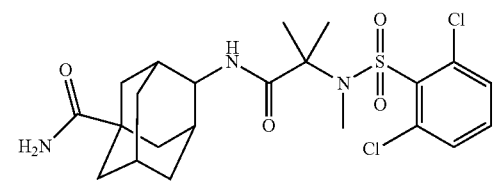
193
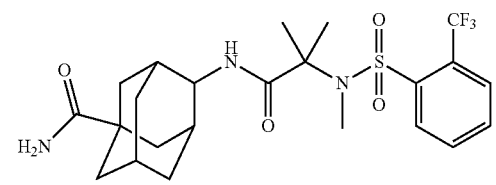
194
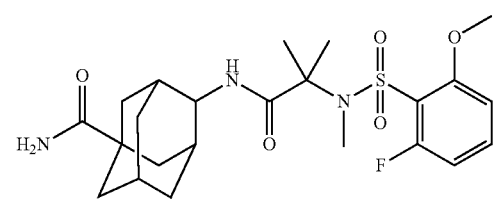
195
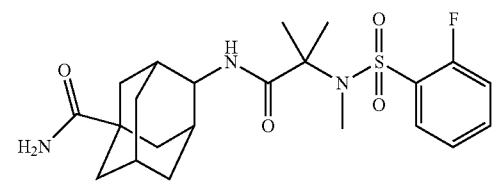
196
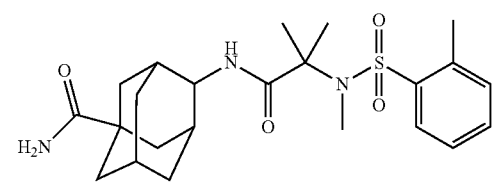
197
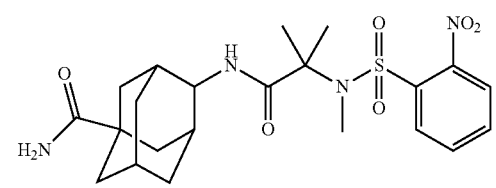
198
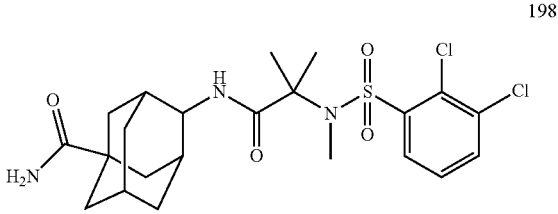

199 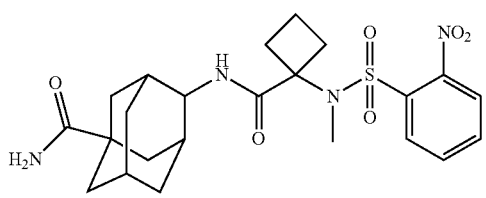
200 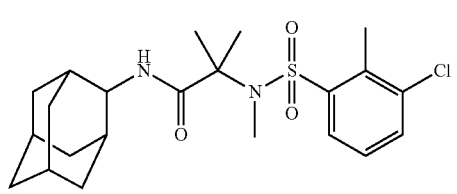
201 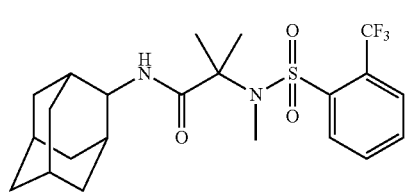
202 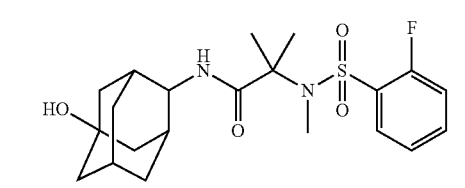
203 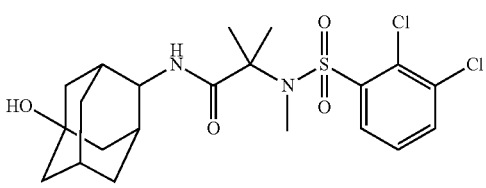
204 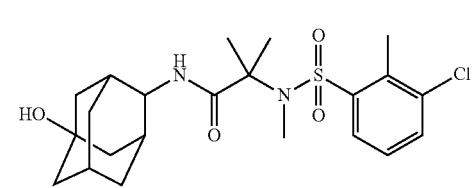
205 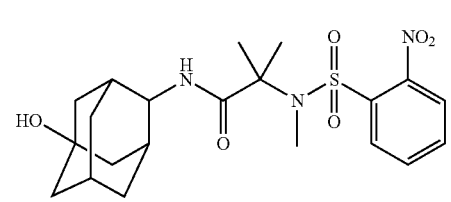
206 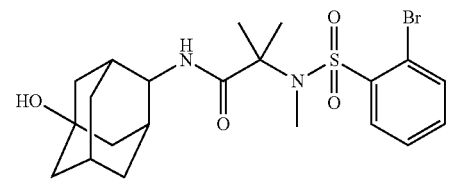
207 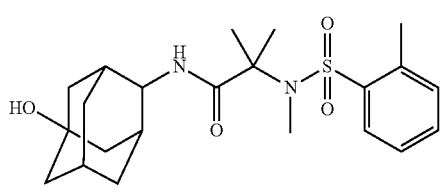
208 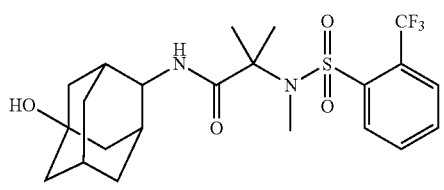
209 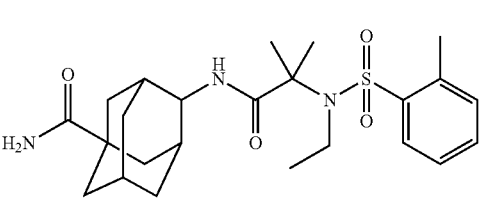
210 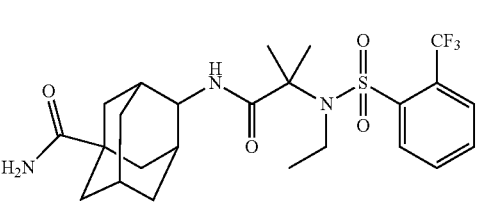
211 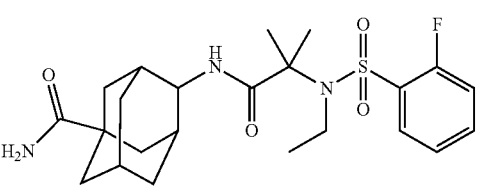
212 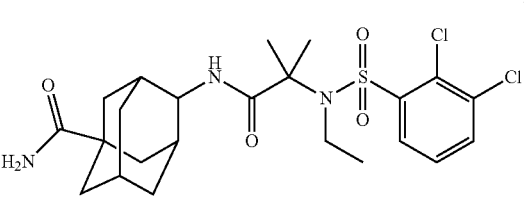
213 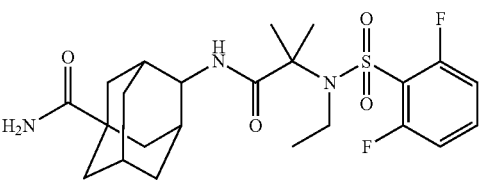
214 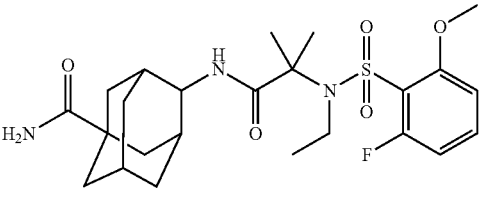

-continued
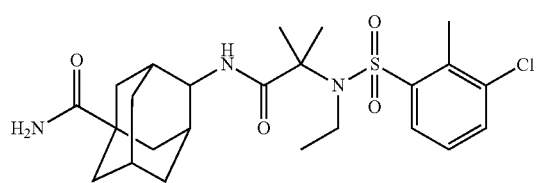 215
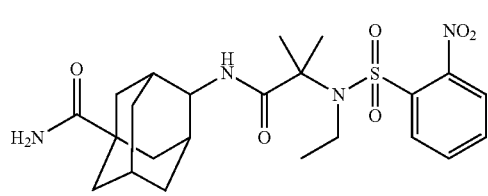 216
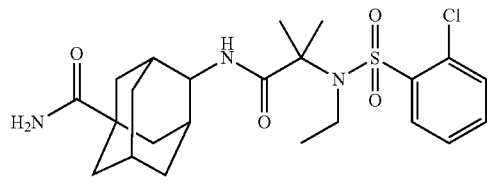 217
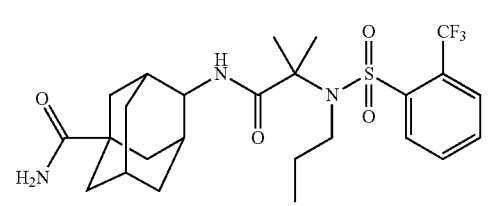 218
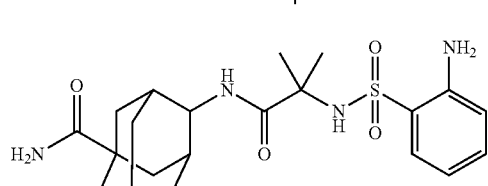 219
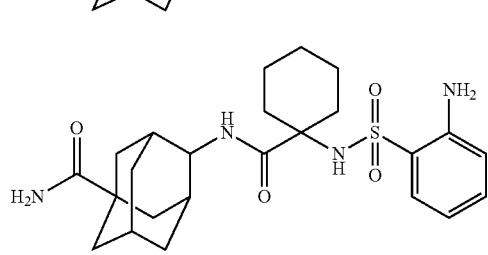 220
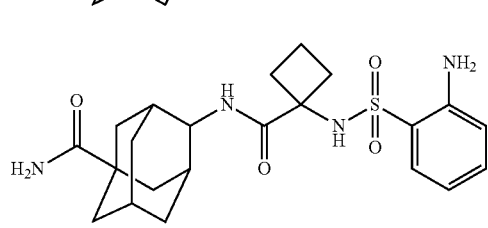 221
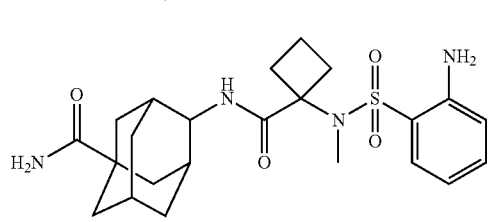 222
-continued
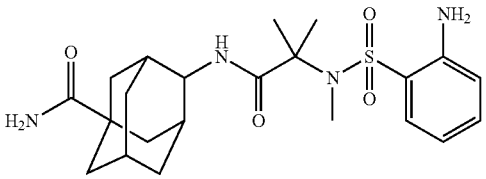 223
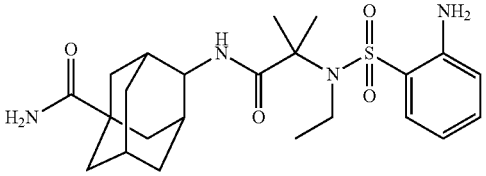 224
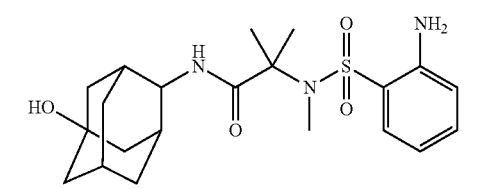 225
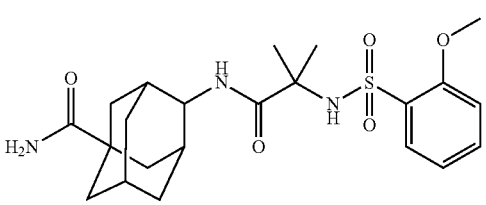 226
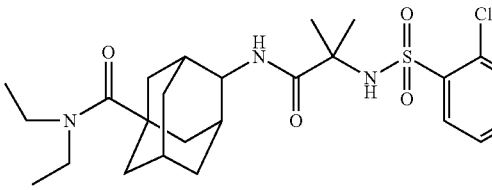 227
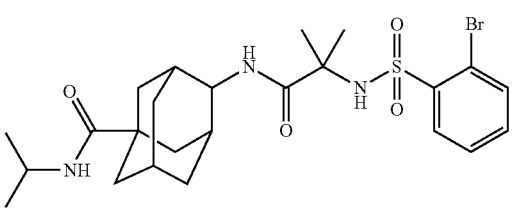 228
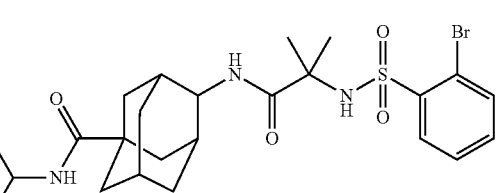 229
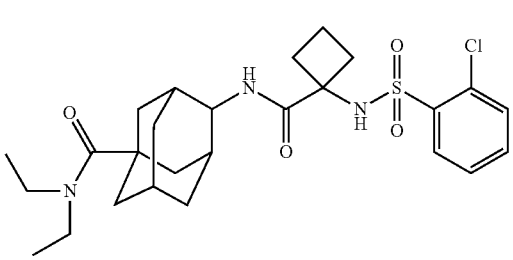 230

-continued

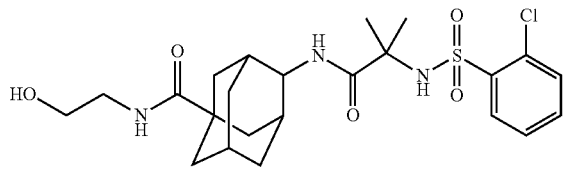
231

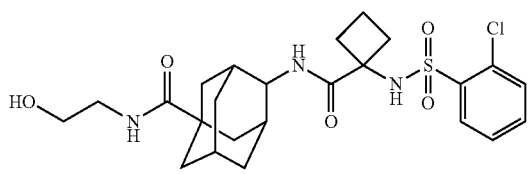
232

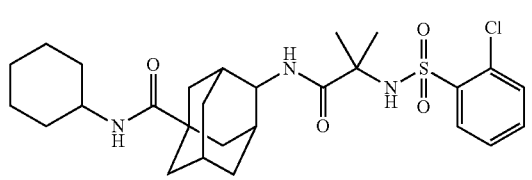
233

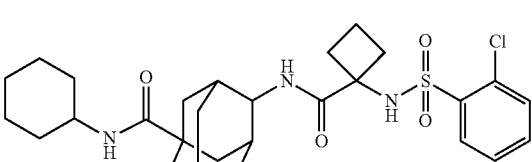
234

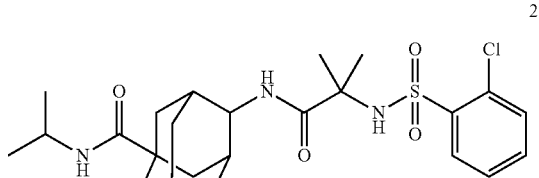
235

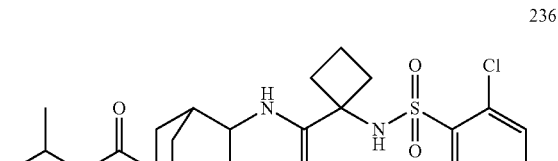
236

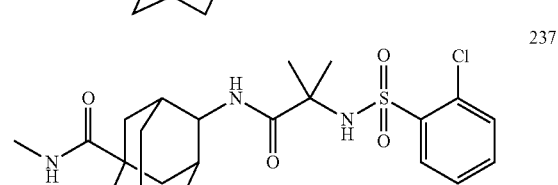
237

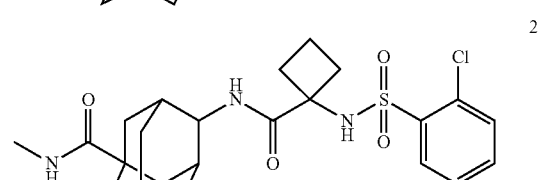
238

-continued

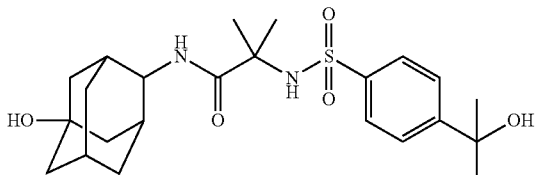
239

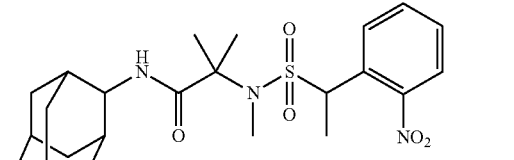
240

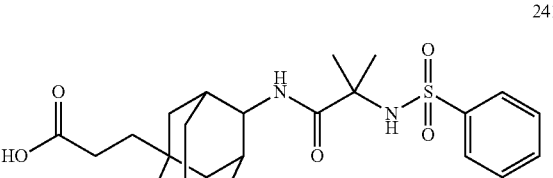
241

Further, in the compound, or the enantiomer, the diastereomer, the geometric isomer, the solvate or the pharmaceutically acceptable salt thereof, the compound of Formula 1 is any one selected from the group consisting of compound 75, compound 83, compound 84, compound 85, compound 87, compound 97, compound 101, compound 105, compound 106, compound 112, compound 121, compound 131, compound 133, compound 136, compound 135, compound 146, compound 167, compound 168, compound 170, compound 174, compound 175, compound 176, compound 177, compound 178, compound 179, compound 182, compound 186, compound 188, compound 190, compound 192, compound 191, compound 193, compound 194, compound 195, compound 197, compound 198, compound 205, compound 206, compound 207, compound 208, compound 214, compound 217, compound 222, compound 223, and compound 225.

In accordance with another aspect of the present invention, there is provided a pharmaceutical composition for inhibiting human 11-β-hydroxy steroid dehydrogenase type 1, which includes the inventive compound or a pharmaceutically acceptable salt thereof as an active ingredient.

In accordance with a further aspect of the present invention, there is provided a pharmaceutical composition for treating or preventing at least one disease selected from the group consisting of hypertension, heart failure, renal failure, liver failure, peripheral vascular disease, coronary artery disease, myocardial infarction, hyperlipidemia, diabetes mellitus, hyperglycemia, obesity, ischemic heart disease, myocardial infarction, diabetic nephropathy, diabetic heart failure, disorder of lipid metabolism, stroke, arteriosclerosis, inflammation, adult respiratory distress syndrome, nephropathy, Raynaud syndrome, obstructive pulmonary disease, interstitial pulmonary disease, asthma, and arthritis, which includes the inventive compound or a pharmaceutically acceptable salt thereof as an active ingredient.

In accordance with a still further aspect of the present invention, there is provided a pharmaceutical composition for treating or preventing at least one disease selected from the group consisting of diabetes mellitus, metabolic syndrome, obesity, polycystic ovary syndrome, eating disorder, craniopharyngioma, Prader-Willi syndrome, Frohlich's syndrome, hyperlipidemia, disorder of lipid metabolism, hypercholesterolemia, hypertriglyceridemia, low high-density lipoprotein (HDL) level, high low-density lipoprotein level (LDL), hyperglycemia, insulin resistance, hyperinsulinemia, Cushing's syndrome, hypertension, arteriosclerosis, restenosis, retinopathy, nephrosis, neurodegenerative disease, neurological disorder, muscle weakness, cognitive disorder, dementia, psoriasis, glaucoma, osteoporosis, viral infection, inflammatory disease, and immune disease, which includes the inventive compound or a pharmaceutically acceptable salt thereof as an active ingredient.

Advantageous Effects of Invention

The inventive novel compound or a pharmaceutically acceptable salt thereof, and a pharmaceutical composition including the same for inhibiting human 11-β-hydroxy steroid dehydrogenase type 1 (11β-HSD1) are more excellent in activity and solubility, and more efficient in formulation and transfer.

MODE FOR THE INVENTION

Hereinafter, the present invention will be described in detail with reference to following Examples. However, the following Examples are only for illustrative purposes and are not intended to limit the scope of the invention.

In the following Examples, all reagents were bought from sigma aldrich, Fluka, and TCI, and $^1$H NMR Spectra were recorded on a Bruker Biospin AVANCE II 400 using tetramethyl silane as internal standard.

Example 1

Preparation Example 1

Synthesis of N-(adamantane-2-yl)-2-methyl-2-(phenylsulfonamido)propanamide (compound 1)

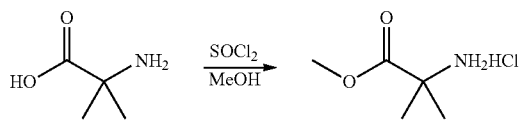

A 100-mL flask was charged with 2-amino-2-methylpropionic acid (3.0 g, 29.1 mmol) and methanol (45 ml). An ice bath was set, and thionyl chloride (4.25 ml, 58.2 mmol) was slowly added thereto. After the addition was completed, the ice bath was removed. At room temperature, the mixture was stirred for 3 hours. The resultant product was vacuum-distilled to remove a solvent, and then added with ethyl ether (30 ml), stirred at room temperature for 30 minutes, and filtered. The solid obtained through filtering was dried in a 60° C. oven to obtain methyl-2-amino-2-methylpropanoate hydrochloride (4.2 g, 94%).

$^1$H NMR (400 MHz, DMSO-$d_6$) δ 8.75 (s, 3H), 3.75 (s, 3H), 4.05 (m, 1H), 1.45 (s, 6H).

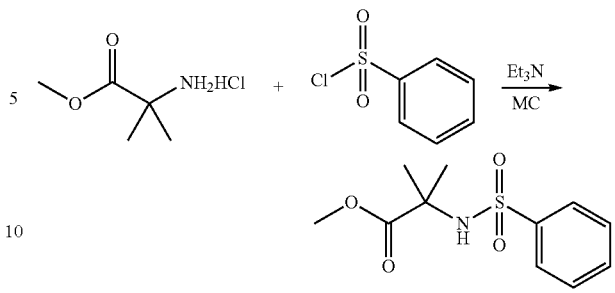

Into a 50-mL flask, methyl-2-amino-2-methylpropanoate hydrochloride (400 mg, 2.61 mmol) and methylenechloride (10 mL) were charged, and triethylamine (1.46 ml, 10.47 mmol) was charged, followed by stirring at room temperature for 30 minutes. The mixture was added with benzenesulfonylchloride (554 mg, 3.14 mmol), stirred overnight, and then added with H$_2$O (10 ml) to bring the reaction to an end. The organic layer was separated, and washed with saturated ammonium chloride solution (15 ml). Then, the washed organic layer was separated, dried with MgSO$_4$, and filtered. Then, through vacuum distillation, the solvent was removed. The resultant mixture was purified with column chromatography so as to obtain methyl-2-amino-2-(phenylsulfonylamido)propanoate (507 mg, 75%).

$^1$H NMR (400 MHz, CDCl$_3$) δ 7.89-7.92 (t, 2H), 7.52-7.57 (m, 3H), 5.35 (s, —NH—SO$_2$), 3.67-3.68 (d, 3H), 1.47-1.48 (d, 6H).

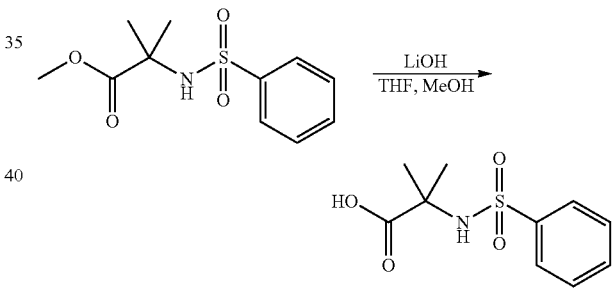

Into a 50-mL flask, methyl-2-amino-2-(phenylsulfonylamido)propanoate (500 mg, 1.94 mmol) was charged and dissolved through addition of THF (6 ml) and methanol (6 ml). LiOH.H$_2$O dissolved in H$_2$O (6 ml) was added thereto, followed by stirring for 12 hours at room temperature. After the stirring for 12 hours, the resultant solution was vacuum-evaporated, acidified with 2N—HCl to pH 1~2, and extracted with addition of EA (20 ml). The organic layer was dried with MgSO$_4$, and filtered. Then, through vacuum distillation, the solvent was removed so as to obtain methyl-2-amino-2-(phenylsulfonylamido)propionic acid compound (402 mg, 85%).

$^1$H NMR (400 MHz, CDCl$_3$) δ 7.91-7.94 (m, 2H), 7.50-7.61 (m, 3H), 5.52 (s, —NH—SO$_2$), 1.51 (s, 6H).

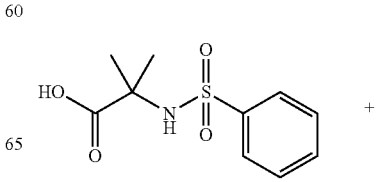

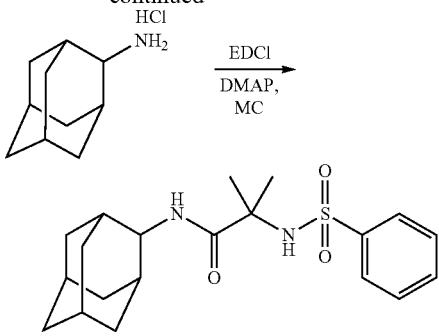

Into a 10-mL flask, methyl-2-amino-2-(phenylsulfonyla-mido)propionic acid (200 mg, 0.822 mmol), 2-adamantan-amine hydrochloride (185 mg, 0.986 mmol), and BOP (364 mg, 0.823 mmol) were charged, and $CH_2Cl_2$ (3 ml) was charged, followed by stirring for 30 minutes at room temperature. The resultant mixture was added with DIPEA (0.35 ml, 2.01 mmol), and stirred at room temperature for 12 hours. After the reaction was completed, the organic layer was separated using $CH_2Cl_2$ and $H_2O$, dried with $MgSO_4$, and filtered. Then, the resultant mixture was purified with column chromatography (EA/n-Hex=1:4) so as to obtain 4-(2-methyl-2-(phenylsulfonamido)propanamido)adamantane (284 mg, 92%).

$^1$H NMR (400 MHz, $CDCl_3$) δ 7.90-7.93 (m, 2), 7.51-7.62 (m, 3H), 6.82-6.83 (d, —NH—CO—), 5.39 (s, —NH—$SO_2$—), 3.97-3.99 (m, 1H), 1.66-1.92 (m, 14H), 1.44 (s, 6H)

Preparation Example 2

Synthesis of N-(adamantane-2-yl)-2-methyl-2-(4-fluorophenylsulfonamido)propanamide (compound 2)

An aimed compound was obtained in the same manner as described in Preparation Example 1 of Example 1 except that 2-(4-fluorophenylsulfonamido)-2-methylpropionic acid was used.

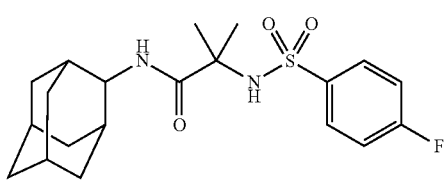 [SMILES: CC(C)(NS(=O)(=O)c1ccc(F)cc1)C(=O)NC1C2CC3CC(C2)CC1C3]

$^1$H NMR (400 MHz, $CDCl_3$) δ 7.90-7.95 (m, 2H), 7.18-7.23 (m, 2H), 6.65 (d, J=6.8 Hz, —NH—CO—), 5.40 (s, —NH—$SO_2$), 3.97 (d, J=8.0 Hz, 1H), 1.67-1.90 (m, 14H), 1.46 (s, 6H).

Preparation Example 3

Synthesis of N-(adamantane-2-yl)-2-methyl-2-(4-nitrophenylsulfonamido)propanamide (compound 3)

An aimed compound was obtained in the same manner as described in Preparation Example 1 of Example 1 except that 2-(4-nitrophenylsulfonamido)-2-methylpropionic acid was used.

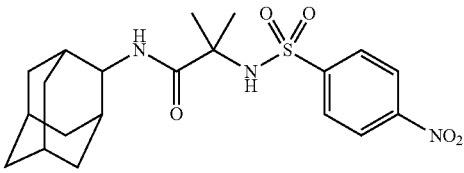 [SMILES: CC(C)(NS(=O)(=O)c1ccc([N+](=O)[O-])cc1)C(=O)NC1C2CC3CC(C2)CC1C3]

$^1$H NMR (400 MHz, $CDCl_3$) δ 8.37 (dt, J=2.4, 8.8 Hz, 2H), 8.10 (dt, J=2.4, 9.2 Hz, 2H), 6.36 (d, J=7.6 Hz, —NH—CO—), 5.85 (s, —NH—$SO_2$), 3.96 (d, J=7.6 Hz, 1H), 1.67-1.89 (m, 14H), 1.50 (s, 6H).

Preparation Example 4

Synthesis of N-(adamantane-2-yl)-2-methyl-2-(4-(trifluoromethoxy)phenylsulfonamido)propanamide (compound 4)

An aimed compound was obtained in the same manner as described in Preparation Example 1 of Example 1 except that 2-(4-(trifluoromethoxy)phenylsulfonamido)-2-methylpropionic acid was used.

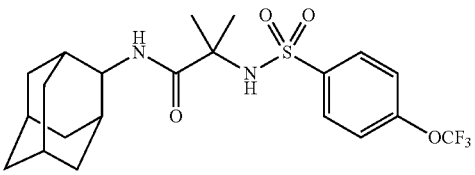 [SMILES: CC(C)(NS(=O)(=O)c1ccc(OC(F)(F)F)cc1)C(=O)NC1C2CC3CC(C2)CC1C3]

$^1$H NMR (400 MHz, $CDCl_3$) δ 7.96 (dt, J=2.8, 8.8 Hz, 2H), 7.35 (d, J=8.0 Hz, 2H), 6.58 (d, J=7.6 Hz, —NH—CO—), 5.55 (s, —NH—$SO_2$), 3.97 (d, J=7.6 Hz, 1H), 1.66-1.90 (m, 14H), 1.46 (s, 6H).

Preparation Example 5

Synthesis of N-(adamantane-2-yl)-2-methyl-2-(4-chlorophenylsulfonamido)propanamide (compound 5)

An aimed compound was obtained in the same manner as described in Preparation Example 1 of Example 1 except that 2-(4-chlorophenylsulfonamido)-2-methylpropionic acid was used.

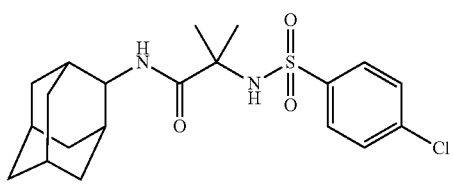 [SMILES: CC(C)(NS(=O)(=O)c1ccc(Cl)cc1)C(=O)NC1C2CC3CC(C2)CC1C3]

$^1$H NMR (400 MHz, $CDCl_3$) δ 7.84 (d, J=8.8 Hz, 2H), 7.50 (d, J=8.4 Hz, 2H), 6.6 (d, J=6.8 Hz, —NH—CO—), 5.48 (s, —NH—$SO_2$), 3.95 (d, J=7.6 Hz, 1H), 1.64-1.89 (m, 14H), 1.46 (s, 6H).

Preparation Example 6

Synthesis of N-(adamantane-2-yl)-2-methyl-2-(2-chlorophenylsulfonamido)propanamide (compound 6)

An aimed compound was obtained in the same manner as described in Preparation Example 1 of Example 1 except that 2-(2-chlorophenylsulfonamido)-2-methylpropionic acid was used.

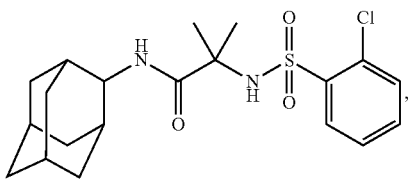 [SMILES: CC(C)(NS(=O)(=O)c1ccccc1Cl)C(=O)NC1C2CC3CC(C2)CC1C3]

$^1$H NMR (400 MHz, CDCl$_3$) δ 8.13-8.11 (m, 1H), 7.57-7.52 (m, 2H), 7.46-7.45 (m, 1H), 7.01 (s, —NH—CO—), 5.74 (s, —NH—SO$_2$), 4.02 (s, 1H), 1.64-1.96 (m, 14H), 1.40 (s, 6H).

Preparation Example 7

Synthesis of N-(adamantane-2-yl)-2-methyl-2-(3-chloro-2methylphenylsulfonamido)propanamide (compound 7)

An aimed compound was obtained in the same manner as described in Preparation Example 1 of Example 1 except that 2-(3-chloro-2methylphenylsulfonamido)-2-methylpropionic acid was used.

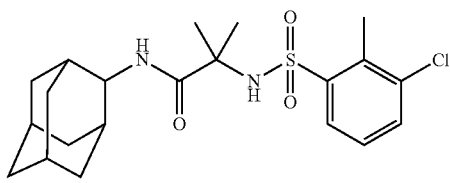

$^1$H NMR (400 MHz, CDCl$_3$) δ 7.98 (d, J=7.2 Hz, 1H), 7.60 (d, J=8.0 Hz, 1H), 7.26-7.3 (m, 2H), 6.63 (d, 6.4 Hz, —NH—CO—), 5.57 (s, —NH—SO$_2$), 3.99 (d, J=8.4 Hz, 1H), 2.76 (s, 3H), 1.63-1.93 (m, 14H), 1.43 (s, 6H).

Preparation Example 8

Synthesis of N-(adamantane-2-yl)-2-methyl-2-(2,3-dichlorophenylsulfonamido)propanamide (compound 8)

An aimed compound was obtained in the same manner as described in Preparation Example 1 of Example 1 except that 2-(2,3-dichlorophenylsulfonamido)-2-methylpropionic acid was used.

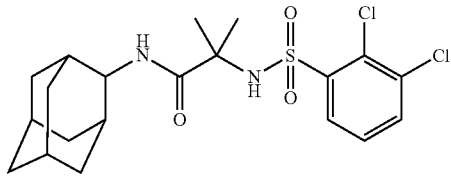 [SMILES: Cc1c(Cl)cccc1S(=O)(=O)NC(C)(C)C(=O)NC1C2CC3CC(C2)CC1C3]

$^1$H NMR (400 MHz, CDCl$_3$) δ 8.06 (dd, J=1.2 Hz, 8.2 Hz, 1H), 7.71 (dd, J=1.6 Hz, 8.0 Hz, 1H), 7.40 (t, J=8.0 Hz 1H), 6.87 (d, 6.8 Hz, —NH—CO—), 5.89 (s, —NH—SO$_2$), 4.02 (d, J=8.8 Hz, 1H), 1.64-1.96 (m, 14H), 1.42 (s, 6H).

Preparation Example 9

Synthesis of N-(adamantane-2-yl)-2-methyl-2-(2,5-dichlorophenylsulfonamido)propanamide (compound 9)

An aimed compound was obtained in the same manner as described in Preparation Example 1 of Example 1 except that 2-(2,5-dichlorophenylsulfonamido)-2-methylpropionic acid was used.

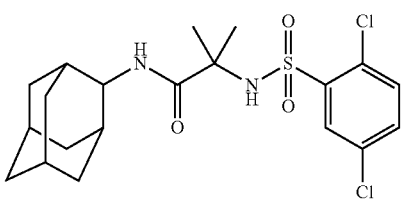 [SMILES: CC(C)(NS(=O)(=O)c1cc(Cl)ccc1Cl)C(=O)NC1C2CC3CC(C2)CC1C3]

$^1$H NMR (400 MHz, CDCl$_3$) δ 8.1 (d, J=3.2 Hz, 1H), 7.50 (d, J=3.2 Hz, 2H), 6.78 (s, —NH—CO—), 5.92 (s, —NH—SO$_2$), 4.00 (d, J=4 Hz, 1H), 1.65-1.95 (m, 14H), 1.44 (s, 6H).

Preparation Example 10

Synthesis of N-(adamantane-2-yl)-2-methyl-2-(3-chlorophenylsulfonamido)propanamide (compound 10)

An aimed compound was obtained in the same manner as described in Preparation Example 1 of Example 1 except that 2-(3-chlorophenylsulfonamido)-2-methylpropionic acid was used.

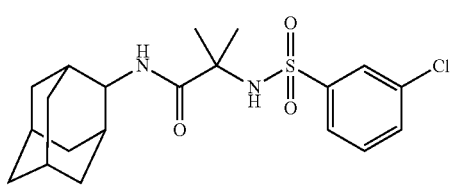 [SMILES: CC(C)(NS(=O)(=O)c1cccc(Cl)c1)C(=O)NC1C2CC3CC(C2)CC1C3]

$^1$H NMR (400 MHz, CDCl$_3$) δ 7.90 (t, J=3.6 Hz, 1H), 7.80 (dt, J=2.8 Hz, 8.0 Hz, 1H), 7.56 (dq, J=1.2 Hz, 2.0 Hz, 8.8 Hz, 1H), 7.48 (t, J=16.0 Hz, 1H), 6.63 (d, J=7.6 Hz, —NH—CO—), 5.55 (s, —NH—SW, 3.98 (d, J=8.0 Hz, 1H), 1.63-1.92 (m, 14H), 1.47 (s, 6H).

Preparation Example 11

Synthesis of N-(adamantane-2-yl)-2-methyl-2-(3,4-dichlorophenylsulfonamido)propanamide (compound 11)

An aimed compound was obtained in the same manner as described in Preparation Example 1 of Example 1 except that 2-(3,4-dichlorophenylsulfonamido)-2-methylpropionic acid was used.

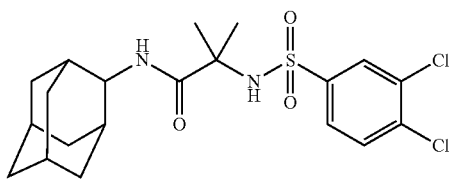 [SMILES: CC(C)(NS(=O)(=O)c1ccc(Cl)c(Cl)c1)C(=O)NC1C2CC3CC(C2)CC1C3]

$^1$H NMR (400 MHz, CDCl$_3$) δ 7.99 (d, J=2.0 Hz, 1H), 7.73 (dd, J=2.4 Hz, 8.4 Hz, 1H), 7.61 (d, J=8.4 Hz, 1H), 6.47 (d, J=7.2 Hz, —NH—CO—), 5.63 (s, —NH—SO$_2$), 3.95 (d, J=8.4 Hz, 1H), 1.65-1.89 (m, 14H), 1.49 (s, 6H).

Preparation Example 12

Synthesis of N-(adamantane-2-yl)-2-methyl-2-(2-bromophenylsulfonamido)propanamide (compound 12)

An aimed compound was obtained in the same manner as described in Preparation Example 1 of Example 1 except that 2-(2-bromophenylsulfonamido)-2-methylpropionic acid was used.

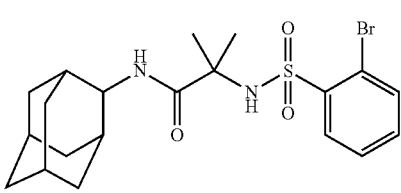

$^1$H NMR (400 MHz, CDCl$_3$) δ 8.17 (t, J=11.6 Hz, 1H), 7.78 (t, J=12.4 Hz, 1H), 7.43-7.51 (m, 2H), 7.29 (d, J=5.6 Hz, 1H), 7.03 (s, —NH—CO—), 5.89 (d, J=4.8 Hz, —NH—SO$_2$), 4.02 (s, 1H), 1.57-2.08 (m, 14H), 1.40 (s, 6H).

Preparation Example 13

Synthesis of N-(adamantane-2-yl)-2-methyl-2-(2-trifluoromethylphenylsulfonamido)propanamide (compound 13)

An aimed compound was obtained in the same manner as described in Preparation Example 1 of Example 1 except that 2-(2-trifluoromethylphenylsulfonamido)-2-methylpropionic acid was used.

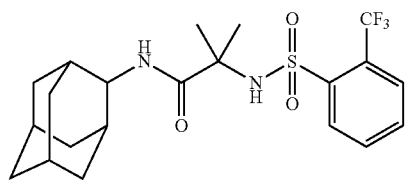 [SMILES: CC(C)(NS(=O)(=O)c1ccccc1C(F)(F)F)C(=O)NC1C2CC3CC(C2)CC1C3]

$^1$H NMR (400 MHz, CDCl$_3$) δ 8.30 (d, J=4.0 Hz, 1H), 7.91 (d, J=2.4 Hz, 1H), 7.74 (d, J=3.6 Hz, 2H), 6.84 (s, —NH—CO—), 5.52 (s, —NH—SO$_2$), 4.02 (s, 1H), 1.58-2.08 (m, 14H), 1.45 (s, 6H).

Preparation Example 14

Synthesis of N-(adamantane-2-yl)-2-methyl-2-(2,4,6-trichlorophenylsulfonamido)propanamide (compound 14)

An aimed compound was obtained in the same manner as described in Preparation Example 1 of Example 1 except that 2-(2,4,6-trichlorophenylsulfonamido)-2-methylpropionic acid was used.

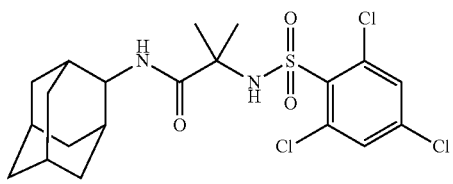 [SMILES: CC(C)(NS(=O)(=O)c1c(Cl)cc(Cl)cc1Cl)C(=O)NC1C2CC3CC(C2)CC1C3]

$^1$H NMR (400 MHz, CDCl$_3$) δ 7.52 (s, 2H), 6.65 (d, J=7.6 Hz —NH—CO—), 6.38 (s, —NH—SO$_2$), 4.00 (d, J=7.6 Hz, 1H), 2.76 (s, 3H), 1.68-1.95 (m, 14H), 1.50 (s, 6H).

Preparation Example 15

Synthesis of N-(adamantane-2-yl)-2-methyl-2-(2-methylphenylsulfonamido)propanamide (compound 15)

An aimed compound was obtained in the same manner as described in Preparation Example 1 of Example 1 except that 2-(2-methylphenylsulfonamido)-2-methylpropionic acid was used.

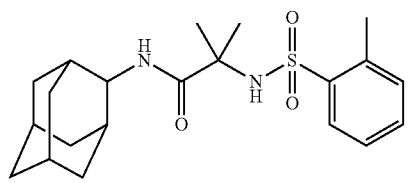 [SMILES: Cc1ccccc1S(=O)(=O)NC(C)(C)C(=O)NC1C2CC3CC(C2)CC1C3]

$^1$H NMR (400 MHz, CDCl$_3$) δ 8.02 (dd, J=1.2 Hz, 8.0 Hz, 1H), 7.48 (td, J=1.2 Hz, 14.0 Hz, 1H), 7.40 (m, 2H), 6.79 (d, 6.8 Hz, —NH—CO—), 5.39 (s, —NH—SO$_2$), 3.99 (d, J=8.0 Hz, 1H), 2.71 (s, 3H), 1.67-1.93 (m, 14H), 1.42 (s, 6H).

Preparation Example 16

Synthesis of N-(adamantane-2-yl)-2-methyl-2-(2-fluorophenylsulfonamido)propanamide (compound 16)

An aimed compound was obtained in the same manner as described in Preparation Example 1 of Example 1 except that 2-(2-fluorophenylsulfonamido)-2-methylpropionic acid was used.

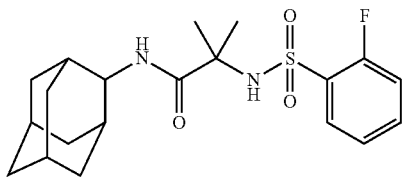 [SMILES: CC(C)(NS(=O)(=O)c1ccccc1F)C(=O)NC1C2CC3CC(C2)CC1C3]

$^1$H NMR (400 MHz, CDCl$_3$) δ 8.02 (td, J=1.6 Hz, J=16.0 Hz, 1H), 7.62 (m, 1H), 7.40 (m, 2H), 7.24-7.33 (m, 1H), 6.94 (s, —NH—CO—), 5.44 (s, —NH—SO$_2$), 4.00 (d, J=8.0 Hz, 1H), 1.68-1.95 (m, 14H), 1.42 (s, 6H).

Preparation Example 17

Synthesis of N-(adamantane-2-yl)-2-methyl-2-(quinoline-8-sulfonamido)propanamide (compound 17)

An aimed compound was obtained in the same manner as described in Preparation Example 1 of Example 1 except that 2-(quinoline-8-sulfonamido)-2-methylpropionic acid was used.

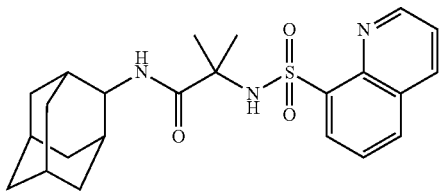 [SMILES: CC(C)(NS(=O)(=O)c1cccc2cccnc12)C(=O)NC1C2CC3CC(C2)CC1C3]

$^1$H NMR (400 MHz, CDCl$_3$) δ9.085 (dd, J=1.6 Hz, J=4.0 Hz, 1H), 8.43 (dd, J=1.6 Hz, 8.0 Hz, 1H), 8.35 (dd, J=1.6 Hz, 8.0 Hz, 1H), 8.10 (dd, J=1.2 Hz, 8.0 Hz, 1H), 7.79 (dd, J=7.6 Hz, 6.0 Hz, 1H), 7.63 (q, J=1.6 Hz, 12.4 Hz, 1H), 7.43 (d, J=8.0 Hz, —NH—CO—), 7.06 (s, —NH—SO$_2$), 4.05 (d, J=8.4 Hz, 1H), 1.62-1.93 (m, 14H), 1.3 (s, 6H).

Preparation Example 18

Synthesis of N-(adamantane-2-yl)-2-methyl-2-(4-(t-butyl)phenylsulfonamido)propanamide (compound 18)

An aimed compound was obtained in the same manner as described in Preparation Example 1 of Example 1 except that 2-(4-(t-butyl)phenylsulfonamido)-2-methylpropionic acid was used.

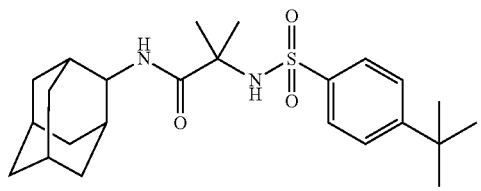 [SMILES: CC(C)(NS(=O)(=O)c1ccc(C(C)(C)C)cc1)C(=O)NC1C2CC3CC(C2)CC1C3]

$^1$H NMR (400 MHz, CDCl$_3$) δ 7.84 (dd, J=12.4 Hz, 20.0 Hz, 2H), 7.54 (dd, J=12.4 Hz, 16.0 Hz, 2H), 6.90 (s, —NH—CO—), 5.34 (s, —NH—SO$_2$), 3.98 (s, 1H), 1.62-1.90 (m, 14H), 1.47 (s, 6H), 1.36 (s, 9H)

Preparation Example 19

Synthesis of N-(adamantane-2-yl)-2-methyl-2-(3-trifluoromethylphenylsulfonamido)propanamide (compound 19)

An aimed compound was obtained in the same manner as described in Preparation Example 1 of Example 1 except that 2-(3-trifluoromethylphenylsulfonamido)-2-methylpropionic acid was used.

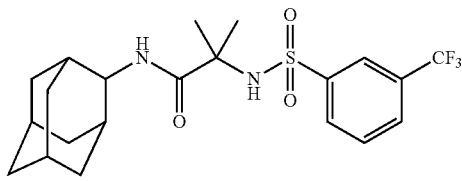 [SMILES: CC(C)(NS(=O)(=O)c1cccc(C(F)(F)F)c1)C(=O)NC1C2CC3CC(C2)CC1C3]

$^1$H NMR (400 MHz, CDCl$_3$) δ 8.18 (s, 1H), 8.11 (d, J=8.0 Hz, 1H), 7.85 (d, J=7.6 Hz, 1H), 7.69 (t, J=15.6 Hz, 1H), 6.58 (d, J=7.6 Hz, —NH—CO—), 5.75 (s, —NH—SO$_2$), 3.97 (d, J=8.0 Hz, 1H), 1.62-1.89 (m, 14H), 1.47 (s, 6H)

Preparation Example 20

Synthesis of N-(adamantane-2-yl)-2-methyl-2-(naphthalene-1-sulfonamido)propanamide (compound 20)

An aimed compound was obtained in the same manner as described in Preparation Example 1 of Example 1 except that 2-(napthalene-1-sulfonamido)-2-methylpropionic acid was used.

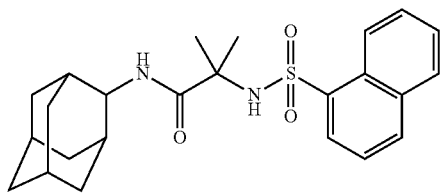 [SMILES: CC(C)(NS(=O)(=O)c1cccc2ccccc12)C(=O)NC1C2CC3CC(C2)CC1C3]

$^1$H NMR (400 MHz, CDCl$_3$) δ 8.59 (d, J=8.8 Hz, 1H), 8.43 (dd, J=1.2 Hz, 8.0 Hz, 1H), 8.10 (d, J=8.0 Hz, 1H), 7.99 (d, J=8.0 Hz, 1H), 7.71-7.75 (m, 1H), 7.63-7.67 (m, 1H), 7.57 (t, J=15.6 Hz, 1H), 6.88 (d, J=6.8 Hz, —NH—CO—), 5.47 (s, —NH—SO$_2$), 3.97 (d, J=7.6 Hz, 1H), 1.63-1.88 (m, 14H), 1.35 (s, 6H)

Preparation Example 21

Synthesis of N-(adamantane-2-yl)-2-methyl-2-(naphthalene-2-sulfonamido)propanamide (compound 21)

An aimed compound was obtained in the same manner as described in Preparation Example 1 of Example 1 except that 2-(naphthalene-2-sulfonamido)-2-methylpropionic acid was used.

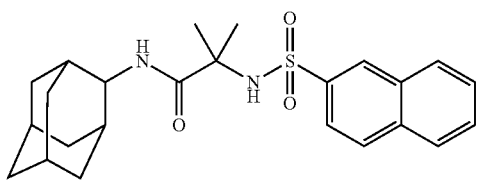 [SMILES: CC(C)(NS(=O)(=O)c1ccc2ccccc2c1)C(=O)NC1C2CC3CC(C2)CC1C3]

$^1$H NMR (400 MHz, CDCl$_3$) δ 8.47 (s, 1H), 7.93-8.01 (m, 3H), 7.88 (dd, J=2.0 Hz, 12.0 Hz, 1H), 7.66 (m, 2H), 6.79 (d, J=8.0 Hz, —NH—CO—), 5.47 (s, —NH—SO$_2$), 3.93 (d, J=8.0 Hz, 1H), 1.62-1.86 (m, 14H), 1.46 (s, 6H)

Preparation Example 22

Synthesis of N-(adamantane-2-yl)-2-methyl-2-((2-nitrophenyl)methylsulfonamido)propanamide (compound 22)

An aimed compound was obtained in the same manner as described in Preparation Example 1 of Example 1 except that 2-((2-nitrophenyl)methylsulfonamido)-2-methylpropionic acid was used.

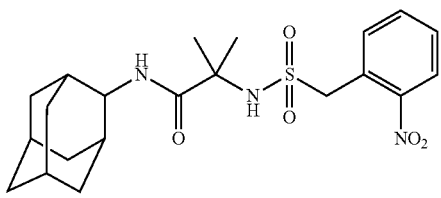 [SMILES: CC(C)(NS(=O)(=O)Cc1ccccc1[N+](=O)[O-])C(=O)NC1C2CC3CC(C2)CC1C3]

$^1$H NMR (400 MHz, CDCl$_3$) δ 8.03 (dd, J=0.8 Hz, 7.6 Hz, 1H), 7.64-7.69 (m, 2H), 7.55-7.61 (m, 1H), 6.53 (d, J=7.6 Hz, —NH—CO—), 5.05 (s, —NH—SO$_2$), 4.93 (s, 2H), 4.03 (d, J=7.6 Hz, 1H), 1.65-1.95 (m, 14H), 1.57 (s, 6H)

Preparation Example 23

Synthesis of N-(5-hydroxyadamantane-2-yl)-2-methyl-2-(2-fluorophenylsulfonamido)propanamide (compound 23)

An aimed compound was obtained in the same manner as described in Preparation Example 1 of Example 1 except that 2-(2-fluorophenylsulfonamido)-2-methylpropionic acid was used.

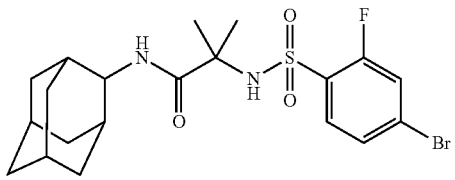 [SMILES: CC(C)(NS(=O)(=O)c1ccc(Br)cc1F)C(=O)NC1C2CC3CC(C2)CC1C3]

$^1$H NMR (400 MHz, CDCl$_3$) δ 7.75-7.79 (m, 1H), 7.43-7.47 (m, 2H), 6.76 (d, J=7.6 Hz, —NH—CO—), 5.58 (s, —NH—SO$_2$), 3.98 (d, J=7.2 Hz, 1H), 1.67-1.92 (m, 14H), 1.44 (s, 6H).

Preparation Example 24

Synthesis of N-(adamantane-2-yl)-2-methyl-2-(4-methoxyphenylsulfonamido)propanamide (compound 24)

An aimed compound was obtained in the same manner as described in Preparation Example 1 of Example 1 except that 2-(4-methoxyphenylsulfonamido)-2-methylpropionic acid was used.

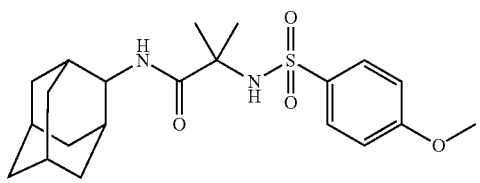 [SMILES: COc1ccc(S(=O)(=O)NC(C)(C)C(=O)NC2C3CC4CC(C3)CC2C4)cc1]

$^1$H NMR (400 MHz, CDCl$_3$) δ 7.83 (dt, J=3.2, 8.8 Hz, 2H), 6.99 (dt, J=3.2, 8.8 Hz, 2H), 6.86 (d, J=7.6 Hz, —NH—CO—), 5.18 (s, —NH—SO$_2$), 3.96-3.99 (m, 1H), 1.66-1.91 (m, 14H), 1.43 (s, 6H).

Preparation Example 25

Synthesis of N-(adamantane-2-yl)-2-methyl-2-(2-(trifluoromethoxy)phenylsulfonamido)propanamide (compound 25)

An aimed compound was obtained in the same manner as described in Preparation Example 1 of Example 1 except that 2-(2-(trifluoromethoxy)phenylsulfonamido)-2-methylpropionic acid was used.

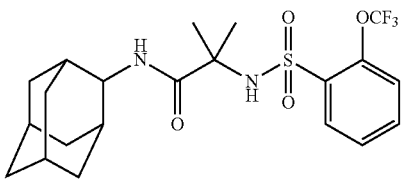 [SMILES: CC(C)(NS(=O)(=O)c1ccccc1OC(F)(F)F)C(=O)NC1C2CC3CC(C2)CC1C3]

$^1$H NMR (400 MHz, CDCl$_3$) δ 8.05 (dd, J=1.6, 8.0 Hz, 1H), 7.64-7.68 (m, 1H), 7.41-7.46 (m, 2H), 6.93 (d, J=7.2 Hz, —NH—CO—), 5.41 (s, —NH—SO$_2$), 4.01 (d, J=8.0 Hz, 1H), 1.68-1.96 (m, 14H), 1.40 (s, 6H).

Preparation Example 26

Synthesis of N-(adamantane-2-yl)-2-methyl-2-(3,5-dichlorophenylsulfonamido)propanamide (compound 26)

An aimed compound was obtained in the same manner as described in Preparation Example 1 of Example 1 except that 2-(3,5-dichlorophenylsulfonamido)-2-methylpropionic acid was used.

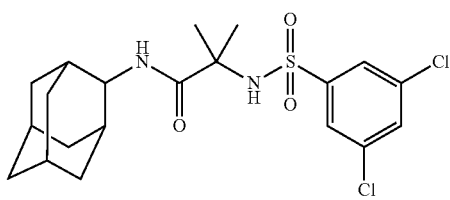 [SMILES: CC(C)(NS(=O)(=O)c1cc(Cl)cc(Cl)c1)C(=O)NC1C2CC3CC(C2)CC1C3]

$^1$H NMR (400 MHz, CDCl$_3$) δ 7.78 (d, J=2.0 Hz, 2H), 7.56 (t, J=2.0 Hz, 1H), 6.46 (d, J=7.6 Hz, —NH—CO—), 5.70 (s, —NH—SO$_2$), 3.99 (d, J=8.0 Hz, 1H), 1.67-1.92 (m, 14H), 1.51 (s, 6H).

Preparation Example 27

Synthesis of N-(adamantane-2-yl)-2-methyl-2-(4-methyl-3-fluorophenylsulfonamido)propanamide (compound 27)

An aimed compound was obtained in the same manner as described in Preparation Example 1 of Example 1 except that 2-(4-methyl-3-fluorophenyl sulfonamido)-2-methylpropionic acid was used.

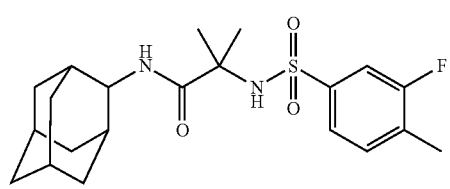 [SMILES: Cc1ccc(S(=O)(=O)NC(C)(C)C(=O)NC2C3CC4CC(C3)CC2C4)cc1F]

$^1$H NMR (400 MHz, CDCl$_3$) δ 7.53-7.60 (m, 2H), 7.35 (t, J=7.6 Hz, 2H), 6.70 (d, J=7.6 Hz, —NH—CO—), 5.38 (s, —NH—SO$_2$), 2.37 (d, J=1.6 Hz, 3H), 1.66-1.90 (m, 14H), 1.46 (s, 6H).

Preparation Example 28

Synthesis of N-(adamantane-2-yl)-2-methyl-2-(3-methylphenylsulfonamido)propanamide (compound 28)

An aimed compound was obtained in the same manner as described in Preparation Example 1 of Example 1 except that 2-(3-methylphenylsulfonamido)-2-methylpropionic acid was used.

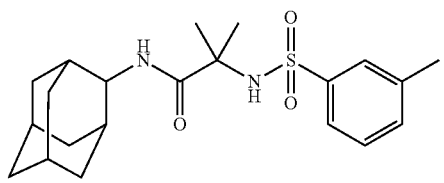 [SMILES: Cc1cccc(S(=O)(=O)NC(C)(C)C(=O)NC2C3CC4CC(C3)CC2C4)c1]

$^1$H NMR (400 MHz, CDCl$_3$) δ 7.70 (m, 2H), 7.39 (m, 2H), 6.87 (d, J=7.6 Hz, —NH—CO—), 5.33 (s, —NH—SO$_2$), 3.98 (d, J=8 Hz, 1H), 2.49 (s, 3H), 1.92-1.77 (m, 12H), 1.71 (m, 2H), 1.44 (s, 6H).

Preparation Example 29

Synthesis of N-(adamantane-2-yl)-2-methyl-2-(3-methoxyphenylsulfonamido)propanamide (compound 29)

An aimed compound was obtained in the same manner as described in Preparation Example 1 of Example 1 except that 2-(3-methoxyphenylsulfonamido)-2-methylpropionic acid was used.

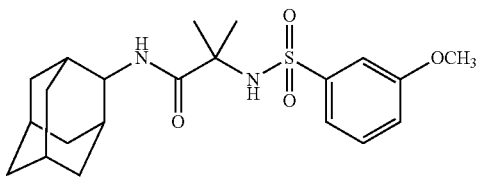 [SMILES: COc1cccc(S(=O)(=O)NC(C)(C)C(=O)NC2C3CC4CC(C3)CC2C4)c1]

$^1$H NMR (400 MHz, CDCl$_3$) δ 7.47 (m, 3H), 7.11 (m, 1H), 6.81 (d, J=7.2 Hz, —NH—CO—), 5.36 (s, —NH—SO$_2$), 3.98 (d, J=7.6 Hz, 1H), 3.88 (s, 3H), 1.92-1.77 (m, 12H), 1.67 (m, 2H), 1.45 (s, 6H).

Preparation Example 30

Synthesis of N-(adamantane-2-yl)-2-methyl-2-(3-fluorophenylsulfonamido)propanamide (compound 30)

An aimed compound was obtained in the same manner as described in Preparation Example 1 of Example 1 except that 2-(3-fluorophenylsulfonamido)-2-methylpropionic acid was used.

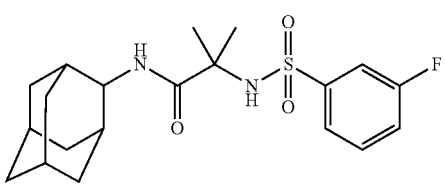 [SMILES: CC(C)(NS(=O)(=O)c1cccc(F)c1)C(=O)NC1C2CC3CC(C2)CC1C3]

$^1$H NMR (400 MHz, CDCl$_3$) δ 7.71 (m, 1H), 7.62 (dt, J=2.4, 8 Hz, 1H), 7.53 (m, 1H), 7.29 (m, 1H), 6.64 (d, J=7.6 Hz, —NH—CO—), 5.52 (s, —NH—SO$_2$), 3.98 (d, J=8 Hz, 1H), 1.92-1.77 (m, 12H), 1.66 (m, 2H), 1.47 (s, 6H).

Preparation Example 31

Synthesis of N-(adamantane-2-yl)-2-methyl-2-(4-chloro-2-fluorophenylsulfonamido)propanamide (compound 31)

An aimed compound was obtained in the same manner as described in Preparation Example 1 of Example 1 except that 2-(4-chloro-2-fluorophenylsulfonamido)-2-methylpropionic acid was used.

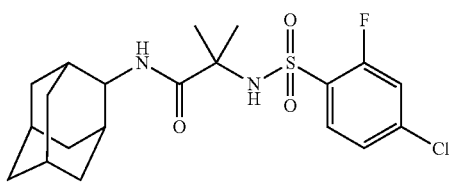 [SMILES: CC(C)(NS(=O)(=O)c1ccc(Cl)cc1F)C(=O)NC1C2CC3CC(C2)CC1C3]

$^1$H NMR (400 MHz, CDCl$_3$) δ 7.85 (t, J=8.8 Hz, 1H), 7.31 (m, 2H), 6.77 (d, J=7.6 Hz, —NH—CO—), 5.57 (s, —NH—SO$_2$), 3.98 (d, J=8 Hz, 1H), 1.97-1.77 (m, 12H), 1.68 (m, 2H), 1.44 (s, 6H).

Preparation Example 32

Synthesis of N-(adamantane-2-yl)-2-methyl-2-(4-fluoro-2-trifluoromethylphenylsulfonamido)propanamide (compound 32)

An aimed compound was obtained in the same manner as described in Preparation Example 1 of Example 1 except that 2-(4-fluoro-2-trifluoromethylphenylsulfonamido)-2-methylpropionic acid was used.

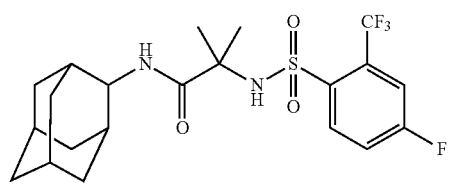 [SMILES: CC(C)(NS(=O)(=O)c1ccc(F)cc1C(F)(F)F)C(=O)NC1C2CC3CC(C2)CC1C3]

$^1$H NMR (400 MHz, CDCl$_3$) δ 8.32 (m, 1H), 7.59 (dd, J=2.4, 8.4 Hz, 1H), 7.39 (m, 1H), 6.71 (d, J=8.4 Hz, —NH—CO—), 4.01 (d, J=8.4 Hz, 1H), 1.95-1.78 (m, 12H), 1.68 (m, 2H), 1.46 (s, 6H).

Preparation Example 33

Synthesis of N-(adamantane-2-yl)-2-methyl-2-((4-chlorophenyl)methylsulfonamido)propanamide (compound 33)

An aimed compound was obtained in the same manner as described in Preparation Example 1 of Example 1 except that 2-((4-chlorophenyl)methylsulfonamido)-2-methylpropionic acid was used.

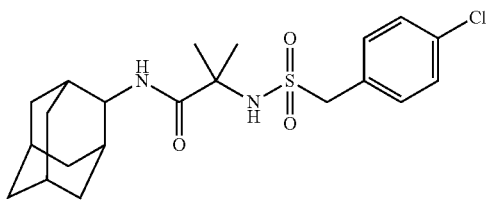 [SMILES: CC(C)(NS(=O)(=O)Cc1ccc(Cl)cc1)C(=O)NC1C2CC3CC(C2)CC1C3]

$^1$H NMR (400 MHz, CDCl$_3$) δ 7.41 (m, 4H), 6.61 (d, J=7.6 Hz, —NH—CO—), 4.69 (s, —NH—SO$_2$), 4.36 (s, 2H), 4.02 (d, J=7.6 Hz, 1H), 1.96-1.74 (m, 12H), 1.67 (m, 2H), 1.59 (s, 6H).

Preparation Example 34

Synthesis of N-(adamantane-2-yl)-2-methyl-2-((2-chlorophenyl)methylsulfonamido)propanamide (compound 34)

An aimed compound was obtained in the same manner as described in Preparation Example 1 of Example 1 except that 2-((2-chlorophenyl)methylsulfonamido)-2-methylpropionic acid was used.

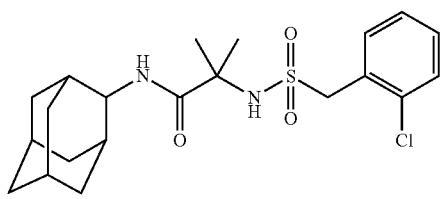

$^1$H NMR (400 MHz, CDCl$_3$) δ 7.61 (m, 1H), 7.46 (m, 1H), 7.34 (m, 2H), 7.69 (d, J=7.6 Hz, —NH—CO—), 4.87 (s, —NH—SO$_2$), 4.64 (s, 2H), 4.02 (d, J=7.6 Hz, 1H), 1.95-1.76 (m, 12H), 1.67 (m, 2H), 1.56 (s, 6H).

Preparation Example 35

Synthesis of N-(adamantane-2-yl)-2-methyl-2-((3,4-dichlorophenyl)methylsulfonamido)propanamide (compound 35)

An aimed compound was obtained in the same manner as described in Preparation Example 1 of Example 1 except that 2-((3,4-dichlorophenyl)methylsulfonamido)-2-methylpropionic acid was used.

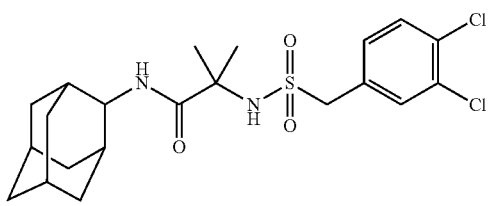 [SMILES: CC(C)(NS(=O)(=O)Cc1ccc(Cl)c(Cl)c1)C(=O)NC1C2CC3CC(C2)CC1C3]

$^1$H NMR (400 MHz, CDCl$_3$) δ7.62 (d, J=2 Hz, 1H), 7.48 (d, J=8 Hz, 1H), 7.35 (dd, J=2.4, 8.4 Hz, 1H), 6.52 (d, J=7.6 Hz, —NH—CO—), 4.67 (s, —NH—SO$_2$), 4.30 (s, 2H), 4.04 (d, J=8 Hz, 1H), 1.97-1.78 (m, 12H), 1.71 (m, 2H), 1.61 (s, 6H).

Preparation Example 36

Synthesis of N-(adamantane-2-yl)-2-methyl-2-((4-trifluoromethylphenyl)methylsulfonamido)propanamide (compound 36)

An aimed compound was obtained in the same manner as described in Preparation Example 1 of Example 1 except that 2-((4-trifluoromethylphenyl)methylsulfonamido)-2-methylpropionic acid was used.

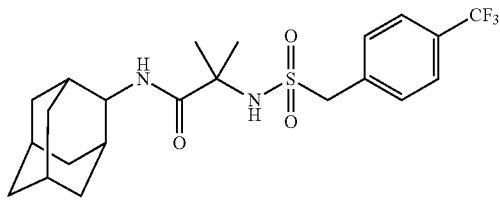 [SMILES: CC(C)(NS(=O)(=O)Cc1ccc(C(F)(F)F)cc1)C(=O)NC1C2CC3CC(C2)CC1C3]

$^1$H NMR (400 MHz, CDCl$_3$) δ 7.65 (m, 4H), 6.54 (d, J=8 Hz, —NH—CO—), 4.69 (s, —NH—SO$_2$), 4.41 (s, 2H), 4.04 (d, J=7.6 Hz, 1H), 1.97-1.77 (m, 12H), 1.71 (m, 2H), 1.61 (s, 6H).

Preparation Example 37

Synthesis of N-(adamantane-2-yl)-2-methyl-2-(4-trifluoromethylphenylsulfonamido)propanamide (compound 37)

An aimed compound was obtained in the same manner as described in Preparation Example 1 of Example 1 except that 2-(4-trifluoromethylphenylsulfonamido)-2-methylpropionic acid was used.

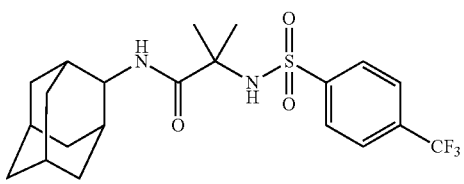 [SMILES: CC(C)(NS(=O)(=O)c1ccc(C(F)(F)F)cc1)C(=O)NC1C2CC3CC(C2)CC1C3]

$^1$H NMR (400 MHz, CDCl$_3$) δ 8.04 (d, J=8 Hz, 2H), 7.79 (d, J=8 Hz, 2H), 6.49 (d, J=7.2 Hz, —NH—CO—), 5.69 (s, —NH—SO$_2$), 3.94 (d, J=7.6 Hz, 1H), 1.88-1.64 (m, 14H), 1.48 (s, 6H).

Preparation Example 38

Synthesis of N-(adamantane-2-yl)-2-methyl-2-(4-acetylphenylsulfonamido)propanamide (compound 38)

An aimed compound was obtained in the same manner as described in Preparation Example 1 of Example 1 except that 2-(4-acetylphenylsulfonamido)-2-methylpropionic acid was used.

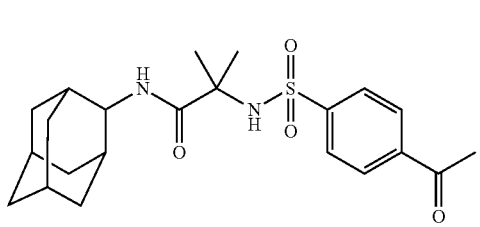 [SMILES: CC(=O)c1ccc(S(=O)(=O)NC(C)(C)C(=O)NC2C3CC4CC(C3)CC2C4)cc1]

$^1$H NMR (400 MHz, CDCl$_3$) δ 8.09 (dt, J=1.6, 8.4 Hz, 2H), 8.01 (dt, J=1.6, 8.4 Hz, 2H), 6.58 (d, J=8 Hz, —NH—CO—), 5.60 (s, —NH—SO$_2$), 3.96 (d, J=8 Hz, 1H), 2.68 (s, 3H), 1.89-1.77 (m, 12H), 1.67 (m, 2H), 1.46 (s, 6H).

Preparation Example 39

Synthesis of N-(adamantane-2-yl)-2-methyl-2-(4-fluoro-2-methylphenylsulfonamido)propanamide (compound 39)

An aimed compound was obtained in the same manner as described in Preparation Example 1 of Example 1 except that 2-(4-fluoro-2-methylphenylsulfonamido)-2-methylpropionic acid was used.

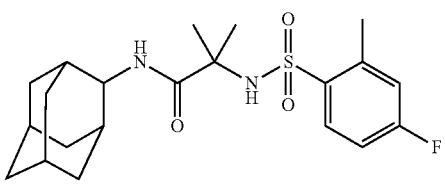 [SMILES: Cc1cc(F)ccc1S(=O)(=O)NC(C)(C)C(=O)NC1C2CC3CC(C2)CC1C3]

$^1$H NMR (400 MHz, CDCl$_3$) δ 8.02 (m, 1H), 7.01 (m, 2H), 6.65 (d, J=7.6 Hz, —NH—CO—), 5.51 (s, —NH—SO$_2$), 3.97 (d, J=8 Hz, 1H), 2.71 (s, 3H), 1.92-1.77 (m, 12H), 1.67 (m, 2H), 1.43 (s, 6H).

Preparation Example 40

Synthesis of N-(adamantane-2-yl)-2-methyl-2-(5-nitro-2-methylphenylsulfonamido)propanamide (compound 40)

An aimed compound was obtained in the same manner as described in Preparation Example 1 of Example 1 except that 2-(5-nitro-2-methylphenylsulfonamido)-2-methylpropionic acid was used.

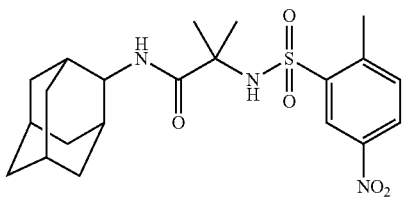 [SMILES: Cc1ccc([N+](=O)[O-])cc1S(=O)(=O)NC(C)(C)C(=O)NC1C2CC3CC(C2)CC1C3]

$^1$H NMR (400 MHz, CDCl$_3$) δ 8.86 (d, J=2.4 Hz, 1H), 8.31 (dd, J=2.4, 8 Hz, 1H), 7.53 (d, J=8.4 Hz, 1H), 6.32 (d, J=7.6 Hz, —NH—CO—), 5.96 (s, —NH—SO$_2$), 3.94 (d, J=7.6 Hz, 1H), 2.88 (s, 3H), 1.89-1.66 (m, 14H), 1.49 (s, 6H).

Preparation Example 41

Synthesis of N-(adamantane-2-yl)-2-methyl-2-(2,6-difluorophenylsulfonamido)propanamide (compound 41)

An aimed compound was obtained in the same manner as described in Preparation Example 1 of Example 1 except that 2-(2,6-difluorophenylsulfonamido)-2-methylpropionic acid was used.

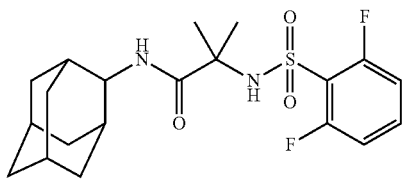 [SMILES: CC(C)(NS(=O)(=O)c1c(F)cccc1F)C(=O)NC1C2CC3CC(C2)CC1C3]

$^1$H NMR (400 MHz, CDCl$_3$) δ 7.54 (m, 1H), 7.07 (t, J=8.4 Hz, 2H), 6.79 (d, J=7.6 Hz, —NH—CO—), 5.82 (s, —NH—SO$_2$), 3.99 (d, J=8.4 Hz, 1H), 1.94-1.77 (m, 12H), 1.68 (m, 2H) 1.52 (s, 6H).

Preparation Example 42

Synthesis of N-(adamantane-2-yl)-2-methyl-2-([1,1-biphenyl]-4-ylsulfonamido)propanamide (compound 42)

An aimed compound was obtained in the same manner as described in Preparation Example 1 of Example 1 except that 2-([1,1-biphenyl]-4-ylsulfonamido)-2-methylpropionic acid was used.

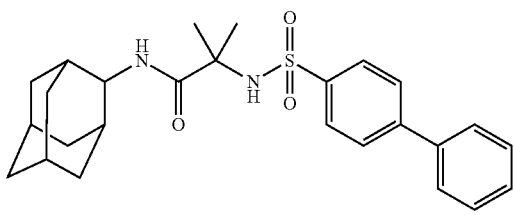 [SMILES: CC(C)(NS(=O)(=O)c1ccc(-c2ccccc2)cc1)C(=O)NC1C2CC3CC(C2)CC1C3]

$^1$H NMR (400 MHz, CDCl$_3$) δ 7.97 (dt, J=2, 8.4 Hz, 2H), 7.74 (dt, J=2, 8.4 Hz, 2H), 7.63 (m, 2H), 7.52 (m, 2H), 7.46 (m, 1H), 6.79 (d, J=7.6 Hz, —NH—CO—), 5.37 (s, —NH—SO$_2$), 3.97 (d, J=8 Hz, 1H), 1.91-1.76 (m, 12H), 1.67 (m, 2H), 1.48 (s, 6H).

Preparation Example 43

Synthesis of N-(adamantane-2-yl)-2-methyl-2-(2-nitrophenylsulfonamido)propanamide (compound 43)

An aimed compound was obtained in the same manner as described in Preparation Example 1 of Example 1 except that 2-(2-nitrophenylsulfonamido)-2-methylpropionic acid was used.

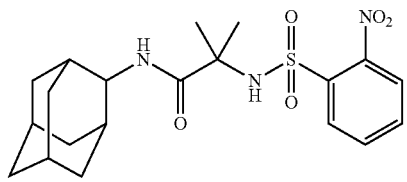 [SMILES: CC(C)(NS(=O)(=O)c1ccccc1[N+](=O)[O-])C(=O)NC1C2CC3CC(C2)CC1C3]

$^1$H NMR (400 MHz, CDCl$_3$) δ 8.18 (m, 1H), 7.95 (m, 1H), 7.78 (m, 2H), 6.89 (d, J=7.6 Hz, —NH—CO—), 6.10 (s, —NH—SO$_2$), 4.02 (d, J=8 Hz, 1H), 1.89-1.67 (m, 14H), 1.54 (s, 6H).

Preparation Example 44

Synthesis of N-(adamantane-2-yl)-4-(N-(adamantane-2-ylamido)-2-methyl-1-oxopropane-2-yl)sulfamoyl)-3-chlorobenzamide (compound 44)

An aimed compound was obtained in the same manner as described in Preparation Example 1 of Example 1 except that 2-(4-cyanide-2-chlorophenylsulfonamido)-2-methylpropionic acid was used.

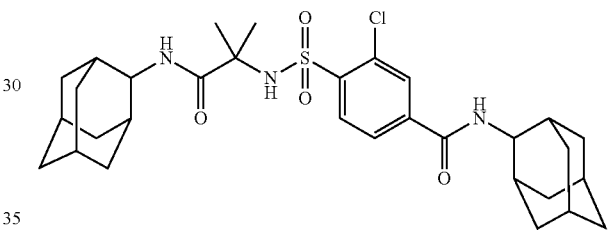

$^1$H NMR (400 MHz, CDCl$_3$) δ 8.17 (m, 1H), 7.96 (d, J=1.6 Hz, 1H), 7.75 (dd, J=1.6, 8 Hz, 1H), 6.84 (d, J=8.4 Hz, —NH—CO—), 6.42 (d, J=8 Hz, —NH—CO—), 5.91 (s, —NH—SO$_2$), 4.27 (d, J=8 Hz, 1H), 4.01 (d, J=8.4 Hz, 1H), 1.93-1.68 (m, 28H), 1.44 (s, 6H).

Preparation Example 45

Synthesis of N-(adamantane-2-yl)-2-methyl-2-(2,6-dichlorophenylsulfonamido)propanamide (compound 45)

An aimed compound was obtained in the same manner as described in Preparation Example 1 of Example 1 except that 2-(2,6-dichlorophenylsulfonamido)-2-methylpropionic acid was used.

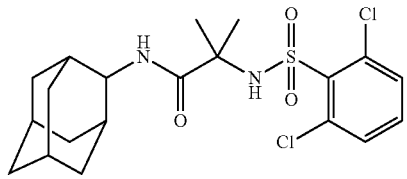 [SMILES: CC(C)(NS(=O)(=O)c1c(Cl)cccc1Cl)C(=O)NC1C2CC3CC(C2)CC1C3]

$^1$H NMR (400 MHz, CDCl$_3$) δ 7.52 (m, 2H), 7.37 (m, 1H), 6.82 (d, J=6.4 Hz, —NH—CO—), 6.32 (s, —NH—SO$_2$), 4.01 (d, J=8 Hz, 1H), 1.96-1.77 (m, 12H), 1.69 (m, 2H), 1.48 (s, 6H).

Preparation Example 46

Synthesis of N-(adamantane-2-yl)-2-methyl-2-(2,4-dichlorophenylsulfonamido)propanamide (compound 46)

An aimed compound was obtained in the same manner as described in Preparation Example 1 of Example 1 except that 2-(2,4-dichlorophenylsulfonamido)-2-methylpropionic acid was used.

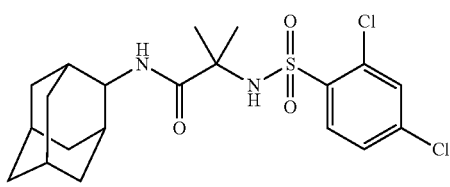

$^1$H NMR (400 MHz, CDCl$_3$) δ 8.04 (d, J=8.4 Hz, 1H), 7.57 (d, J=2 Hz, 1H), 7.42 (dd, J=2, 8.8 Hz, 1H), 6.84 (d, J=7.6 Hz, —NH—CO—), 5.85 (s, —NH—SO$_2$), 3.99 (d, J=8 Hz, 1H), 1.95-1.78 (m, 12H), 1.67 (m, 2H), 142 (s, 6H).

Preparation Example 47

Synthesis of N-(adamantane-2-yl)-2-methyl-2-(2,4-dimethoxyphenylsulfonamido)propanamide (compound 47)

An aimed compound was obtained in the same manner as described in Preparation Example 1 of Example 1 except that 2-(2,4-dimethoxyphenylsulfonamido)-2-methylpropionic acid was used.

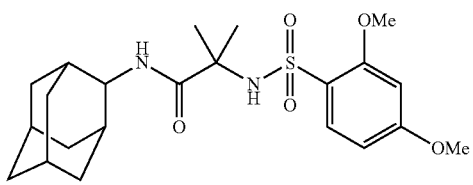 [SMILES: COc1ccc(S(=O)(=O)NC(C)(C)C(=O)NC2C3CC4CC(C3)CC2C4)c(OC)c1]

$^1$H NMR (400 MHz, CDCl$_3$) δ 7.82 (d, J=9.2 Hz, 1H), 7.22 (d, J=7.6 Hz, —NH—CO—), 6.58 (m, 2H), 5.38 (s, —NH—SO$_2$), 4.01 (d, J=8 Hz, 1H), 3.99 (s, 3H), 3.89 (s, 3H), 1.94-1.77 (m, 12H), 1.67 (m, 2H), 1.35 (s, 6H).

Preparation Example 48

Synthesis of N-(adamantane-2-yl)-2-methyl-2-(2,5-dimethoxyphenylsulfonamido)propanamide (compound 48)

An aimed compound was obtained in the same manner as described in Preparation Example 1 of Example 1 except that 2-(2,5-dimethoxyphenylsulfonamido)-2-methylpropionic acid was used.

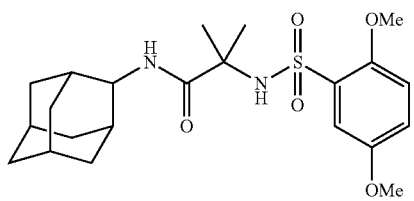 [SMILES: COc1ccc(OC)c(S(=O)(=O)NC(C)(C)C(=O)NC2C3CC4CC(C3)CC2C4)c1]

$^1$H NMR (400 MHz, CDCl$_3$) δ 7.43 (s, 1H), 7.09 (m, 2H), 6.99 (d, J=7.6 Hz, —NH—CO—), 5.58 (s, —NH—SO$_2$), 4.21 (d, J=8 Hz, 1H), 4.01 (s, 3H), 3.83 (s, 3H), 1.95-1.67 (m, 12H), 1.58 (m, 2H), 1.31 (s, 6H).

Preparation Example 49

Synthesis of N-(adamantane-2-yl)-2-methyl-2-(3,5-ditrifluoromethylphenylsulfonamido)propanamide (compound 49)

An aimed compound was obtained in the same manner as described in Preparation Example 1 of Example 1 except that 2-(3,5-ditrifluoromethylphenylsulfonamido)-2-methylpropionic acid was used.

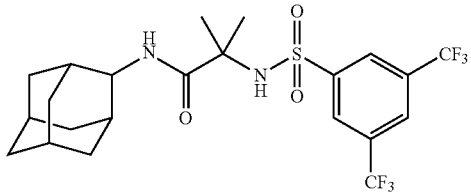 [SMILES: CC(C)(NS(=O)(=O)c1cc(C(F)(F)F)cc(C(F)(F)F)c1)C(=O)NC1C2CC3CC(C2)CC1C3]

$^1$H NMR (400 MHz, CDCl$_3$) δ 8.36 (s, 2H), 8.08 (s, 1H), 6.33 (d, J=7.2 Hz, —NH—CO—), 5.97 (s, —NH—SO$_2$), 3.96 (d, J=7.6 Hz, 1H), 1.89-1.71 (m, 14H), 1.52 (s, 6H).

Preparation Example 50

Synthesis of N-(adamantane-2-yl)-2-methyl-2-(2-chloropyridine-3-sulfonamido)propanamide (compound 50)

An aimed compound was obtained in the same manner as described in Preparation Example 1 of Example 1 except that 2-(2-chloropyridine-3-sulfonamido)-2-methylpropionic acid was used.

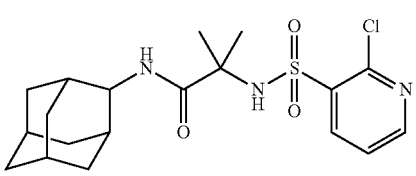 [SMILES: CC(C)(NS(=O)(=O)c1cccnc1Cl)C(=O)NC1C2CC3CC(C2)CC1C3]

$^1$H NMR (400 MHz, CDCl$_3$) δ 8.61 (dd, J=1.6, 4.8 Hz, 1H), 8.41 (dd, J=2, 8 Hz, 1H), 7.46 (m, 1H), 6.79 (d, J=6.8 Hz, —NH—CO—), 6.03 (s, —NH—SO$_2$), 4.01 (d, J=8 Hz, 1H), 1.96-1.84 (m, 12H), 1.66 (m, 2H), 1.43 (s, 6H).

Preparation Example 51

Synthesis of N-(adamantane-2-yl)-2-methyl-2-(2,3,4-trichlorophenylsulfonamido)propanamide (compound 51)

An aimed compound was obtained in the same manner as described in Preparation Example 1 of Example 1 except that 2-(2,3,4-trichlorophenylsulfonamido)-2-methylpropionic acid was used.

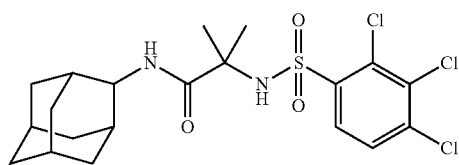 [SMILES: CC(C)(NS(=O)(=O)c1ccc(Cl)c(Cl)c1Cl)C(=O)NC1C2CC3CC(C2)CC1C3]

$^1$H NMR (400 MHz, CDCl$_3$) δ 7.99 (d, J=8.8 Hz, 1H), 7.57 (d, J=8.8 Hz, 1H), 7.31 (d, J=8.4 Hz, —NH—CO—), 5.99 (s, —NH—SO$_2$), 4.01 (d, J=8 Hz, 1H), 1.95-1.77 (m, 12H), 1.69 (m, 2H), 1.44 (s, 6H).

Preparation Example 52

Synthesis of N-(adamantane-2-yl)-2-methyl-2-(2-(naphthalene-1-yl)ethylsulfonamido)propanamide (compound 52)

An aimed compound was obtained in the same manner as described in Preparation Example 1 of Example 1 except that 2-(2-(naphthalene-1-yl)ethylsulfonamido)-2-methylpropionic acid was used.

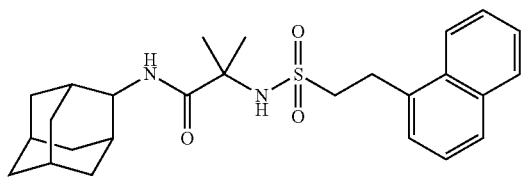 [SMILES: CC(C)(NS(=O)(=O)CCc1cccc2ccccc12)C(=O)NC1C2CC3CC(C2)CC1C3]

$^1$H NMR (400 MHz, CDCl$_3$) δ 8.04 (d, J=8.4 Hz, 1H), 7.92 (d, J=8.4 Hz, 1H), 7.82 (m, 1H), 7.58 (m, 2H), 7.45 (m, 2H), 6.74 (d, J=7.6 Hz, —NH—CO—), 4.62 (s, —NH—SO$_2$), 3.99 (d, J=8 Hz, 1H), 3.66 (q, J=6.4 Hz, 2H), 3.53 (q, J=4.6 Hz, 2H), 1.92-1.76 (m, 12H), 1.65 (m, 2H), 1.40 (s, 6H).

Preparation Example 53

Synthesis of N-(adamantane-2-yl)-2-methyl-2-(4-ethylphenylsulfonamido)propanamide (compound 53)

An aimed compound was obtained in the same manner as described in Preparation Example 1 of Example 1 except that 2-(4-ethylphenylsulfonamido)-2-methylpropionic acid was used.

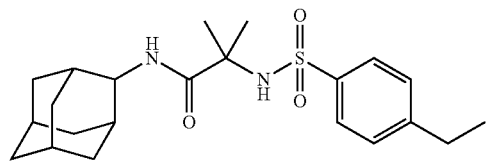 [SMILES: CCc1ccc(S(=O)(=O)NC(C)(C)C(=O)NC2C3CC4CC(C3)CC2C4)cc1]

$^1$H NMR (400 MHz, CDCl$_3$) δ 7.81 (d, J=8.4 Hz, 2H), 7.32 (d, J=8.4 Hz, 2H), 6.99 (d, J=8 Hz, —NH—CO—), 5.85 (s, —NH—SO$_2$), 3.95 (d, J=4.8 Hz, 1H), 2.72 (q, J=7.6 Hz, 2H), 1.94-1.75 (m, 12H), 1.63 (m, 2H), 1.41 (s, 6H), 1.26 (t, J=7.6 Hz, 3H).

Preparation Example 54

Synthesis of N-(adamantane-2-yl)-2-methyl-2-(4-fluoro-3-chlorophenylsulfonamido)propanamide (compound 54)

An aimed compound was obtained in the same manner as described in Preparation Example 1 of Example 1 except that 2-(4-fluoro-3-chlorophenylsulfonamido)-2-methylpropionic acid was used.

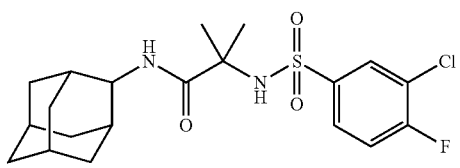 [SMILES: CC(C)(NS(=O)(=O)c1ccc(F)c(Cl)c1)C(=O)NC1C2CC3CC(C2)CC1C3]

$^1$H NMR (400 MHz, CDCl$_3$) δ 7.98 (dd, J=2, 6.4 Hz, 1H), 7.81 (m, 1H), 7.29 (t, J=8.8 Hz, 1H), 6.51 (d, J=7.6 Hz, —NH—CO—), 5.62 (s, —NH—SO$_2$), 3.96 (d, J=7.6 Hz, 1H), 1.89-1.75 (m, 12H), 1.67 (m, 2H), 1.49 (s, 6H).

Preparation Example 55

Synthesis of N-(adamantane-2-yl)-2-methyl-2-(4-fluoro-2-chlorophenylsulfonamido)propanamide (compound 55)

An aimed compound was obtained in the same manner as described in Preparation Example 1 of Example 1 except that 2-(4-fluoro-2-chlorophenylsulfonamido)-2-methylpropionic acid was used.

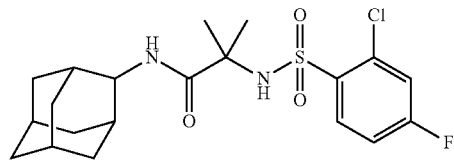 [SMILES: CC(C)(NS(=O)(=O)c1ccc(F)cc1Cl)C(=O)NC1C2CC3CC(C2)CC1C3]

$^1$H NMR (400 MHz, CDCl$_3$) δ 8.11 (d, J=8.4 Hz, 1H), 7.30 (m, 2H), 7.14 (d, J=7.2 Hz, —NH—CO—), 6.87 (s, —NH—SO$_2$), 5.81 (d, J=8 Hz, 1H), 1.94-1.61 (m, 12H), 1.48 (m, 2H), 1.35 (s, 6H).

Preparation Example 56

Synthesis of 2-(N-(1-adamantane-2-ylamino)-2-methyl-1-oxopropane-2-yl)sulfamoyl)benzamide (compound 56)

An aimed compound was obtained in the same manner as described in Preparation Example 1 of Example 1 except that 2-(2-cyanophenylsulfonamido)-2-methylpropionic acid was used.

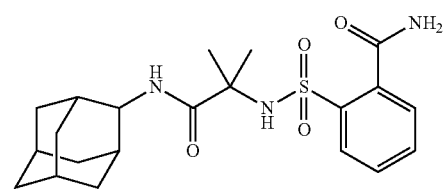 [SMILES: CC(C)(NS(=O)(=O)c1ccccc1C(N)=O)C(=O)NC1C2CC3CC(C2)CC1C3]

$^1$H NMR (400 MHz, CDCl$_3$) δ 8.11 (m, 1H), 7.72 (m, 1H), 7.61 (m, 2H), 7.53 (s, —NH—SO$_2$—), 6.49 (bs, NH$_2$—CO—), 6.38 (d, J=8 Hz, —NH—CO—), 4.04 (d, J=7.6 Hz, 1H), 1.94-1.72 (m, 12H), 1.72 (m, 2H).

Preparation Example 57

Synthesis of N-(adamantane-2-yl)-2-methyl-2-(4-isopropylphenylsulfonamido)propanamide (compound 57)

An aimed compound was obtained in the same manner as described in Preparation Example 1 of Example 1 except that 2-(4-isopropylphenylsulfonamido)-2-methylpropionic acid was used.

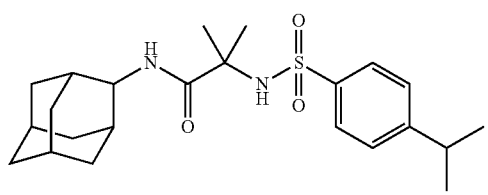 [SMILES: CC(C)c1ccc(S(=O)(=O)NC(C)(C)C(=O)NC2C3CC4CC(C3)CC2C4)cc1]

$^1$H NMR (400 MHz, CDCl$_3$) δ 7.81 (d, J=8.4 Hz, 2H), 7.36 (d, J=8.4 Hz, 1H), 6.87 (d, J=7.6 Hz, —NH—CO—), 5.25 (s, —NH—SO$_2$), 3.97 (d, J=8 Hz), 2.99 (m, 1H), 1.91-1.82 (m, 12H), 1.67 (m, 2H), 1.44 (s, 6H), 1.29 (d, J=6.8 Hz, 6H).

Preparation Example 58

Synthesis of N-(adamantane-2-yl)-2-methyl-2-(2,4-difluorophenylsulfonamido)propanamide (compound 58)

An aimed compound was obtained in the same manner as described in Preparation Example 1 of Example 1 except that 2-(2,4-difluorophenylsulfonamido)-2-methylpropionic acid was used.

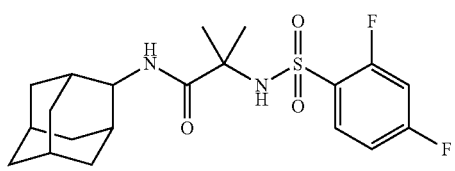 [SMILES: CC(C)(NS(=O)(=O)c1ccc(F)cc1F)C(=O)NC1C2CC3CC(C2)CC1C3]

$^1$H NMR (400 MHz, CDCl$_3$) δ 7.92 (m, 1H), 7.01 (m, 2H), 6.81 (d, J=6.8 Hz, —NH—CO—), 5.54 (s, —NH—SO$_2$), 3.98 (d, J=8 Hz, 1H), 1.94-1.78 (m, 12H), 1.44 (s, 6H).

Preparation Example 59

Synthesis of N-(adamantane-2-yl)-2-methyl-2-(3,5-dimethylphenylsulfonamido)propanamide (compound 59)

An aimed compound was obtained in the same manner as described in Preparation Example 1 of Example 1 except that 2-(3,5-dimethylphenylsulfonamido)-2-methylpropionic acid was used.

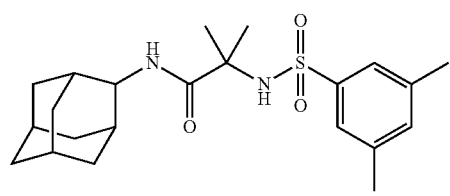 [SMILES: Cc1cc(C)cc(S(=O)(=O)NC(C)(C)C(=O)NC2C3CC4CC(C3)CC2C4)c1]

$^1$H NMR (400 MHz, CDCl$_3$) δ 7.51 (s, 2H), 7.21 (s, 1H), 6.92 (d, J=7.67 Hz, —NH—CO—), 5.30 (s, —NH—SO$_2$), 3.98 (d, J=7.6 Hz, 1H), 2.39 (s, 6H), 1.92-1.77 (m, 12H), 1.68 (m, 12H), 1.44 (m, 6H).

Preparation Example 60

Synthesis of N-(adamantane-2-yl)-2-methyl-2-(4-nitro-2-methoxyphenylsulfonamido)propanamide (compound 60)

An aimed compound was obtained in the same manner as described in Preparation Example 1 of Example 1 except that 2-(4-nitro-2-methoxyphenylsulfonamido)-2-methylpropionic acid was used.

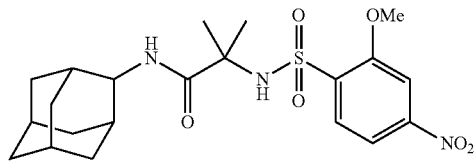 [SMILES: COc1cc([N+](=O)[O-])ccc1S(=O)(=O)NC(C)(C)C(=O)NC1C2CC3CC(C2)CC1C3]

$^1$H NMR (400 MHz, CDCl$_3$) δ 8.10 (d, J=8.4 Hz, 1H), 7.93 (m, 2H), 6.67 (d, J=7.2 Hz, —NH—CO—), 5.97 (s, —NH—SO$_2$), 4.17 (s, 3H), 3.95 (d, J=8 Hz, 1H), 1.91-1.77 (m, 12H), 1.68 (m, 2H), 1.42 (s, 6H).

Preparation Example 61

Synthesis of N-(adamantane-2-yl)-2-methyl-2-(4-chloro-3-nitrophenylsulfonamido)propanamide (compound 61)

An aimed compound was obtained in the same manner as described in Preparation Example 1 of Example 1 except that 2-(4-chloro-3-nitrophenylsulfonamido)-2-methylpropionic acid was used.

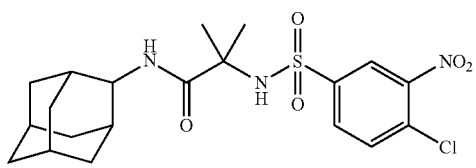 [SMILES: CC(C)(NS(=O)(=O)c1ccc(Cl)c([N+](=O)[O-])c1)C(=O)NC1C2CC3CC(C2)CC1C3]

$^1$H NMR (400 MHz, CDCl$_3$) δ 8.39 (d, J=2 Hz, 1H), 8.02 (dd, J=2.4, 8.4 Hz, 1H), 7.72 (d, J=8.8 Hz, 1H), 6.28 (d, J=6.4 Hz, —NH—CO—), 5.85 (s, —NH—SO$_2$), 3.95 (d, J=8 Hz, 1H), 1.89-1.86 (m, 8H), 1.81 (m, 2H), 1.70 (m, 4H), 1.53 (s, 6H).

Preparation Example 62

Synthesis of N-(adamantane-2-yl)-2-methyl-2-(4-methyl-3-chlorophenylsulfonamido)propanamide (compound 62)

An aimed compound was obtained in the same manner as described in Preparation Example 1 of Example 1 except that 2-(4-methyl-3-chlorophenylsulfonamido)-2-methylpropionic acid was used.

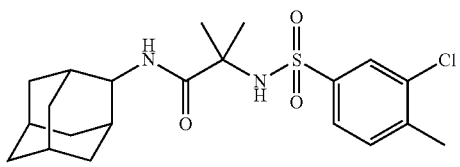 [SMILES: Cc1ccc(S(=O)(=O)NC(C)(C)C(=O)NC2C3CC4CC(C3)CC2C4)cc1Cl]

$^1$H NMR (400 MHz, CDCl$_3$) δ 7.88 (d, J=1.6 Hz, 1H), 7.68 (dd, J=2, 8 Hz, 1H), 7.38 (d, J=7.6 Hz, 1H), 6.67 (d, J=6.4 Hz, —NH—CO—), 5.39 (s, —NH—SO$_2$), 3.96 (d, J=7.6 Hz, 1H), 2.46 (s, 3H), 1.89-1.77 (m, 12H), 1.67 (m, 2H), 1.47 (s, 6H).

Preparation Example 63

Synthesis of N-(adamantane-2-yl)-2-methyl-2-(phenylmethylsulfonamido)propanamide (compound 63)

An aimed compound was obtained in the same manner as described in Preparation Example 1 of Example 1 except that 2-(phenylmethylsulfonamido)-2-methylpropionic acid was used.

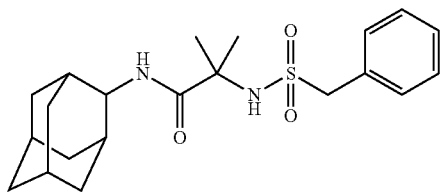 [SMILES: CC(C)(NS(=O)(=O)Cc1ccccc1)C(=O)NC1C2CC3CC(C2)CC1C3]

$^1$H NMR (400 MHz, CDCl$_3$) δ 7.46 (m, 2H), 7.42 (m, 3H), 6.74 (d, J=7.6 Hz, —NH—CO—), 4.62 (s, —NH—SO$_2$), 4.35 (s, 2H), 4.02 (d, J=8 Hz, 1H), 1.95-1.73 (m, 12H), 1.66 (m, 2H), 1.57 (s, 6H).

Preparation Example 64

Synthesis of N-(adamantane-2-yl)-2-methyl-2-(3-bromophenylsulfonamido)propanamide (compound 64)

An aimed compound was obtained in the same manner as described in Preparation Example 1 of Example 1 except that 2-(3-bromophenylsulfonamido)-2-methylpropionic acid was used.

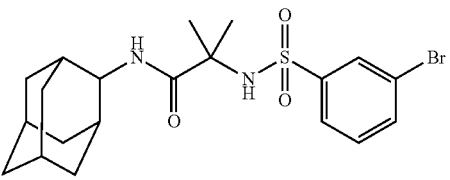 [SMILES: CC(C)(NS(=O)(=O)c1cccc(Br)c1)C(=O)NC1C2CC3CC(C2)CC1C3]

$^1$H NMR (400 MHz, CDCl$_3$) δ 8.05 (t, J=1.6 Hz, 1H), 7.84 (m, 1H), 7.72 (m, 1H), 7.41 (t, J=8 Hz, 1H), 6.62 (d, J=7.2 Hz, —NH—CO—), 5.56 (s, —NH—SO$_2$), 3.97 (d, J=8 Hz, 1H), 1.91-1.77 (m, 12H), 1.67 (m, 2H), 1.47 (s, 6H).

Preparation Example 65

Synthesis of N-(adamantane-2-yl)-2-methyl-2-(4-bromophenylsulfonamido)propanamide (compound 65)

An aimed compound was obtained in the same manner as described in Preparation Example 1 of Example 1 except that 2-(4-bromophenylsulfonamido)-2-methylpropionic acid was used.

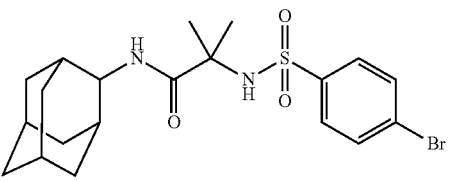 [SMILES: CC(C)(NS(=O)(=O)c1ccc(Br)cc1)C(=O)NC1C2CC3CC(C2)CC1C3]

$^1$H NMR (400 MHz, CDCl$_3$) δ 7.76 (dd, J=1.6, 8.4 Hz, 2H), 7.66 (dd, J=2.4, 11.2 Hz, 2H), 6.60 (d, J=6.8 Hz, —NH—CO—), 5.51 (s, —NH—SO$_2$), 3.94 (d, J=7.6 Hz, 1H), 1.89-1.76 (m, 12H), 1.67 (m, 2H), 1.46 (s, 6H).

Preparation Example 66

Synthesis of N-(adamantane-2-yl)-2-methyl-2-(3-nitrophenylsulfonamido)propanamide (compound 66)

An aimed compound was obtained in the same manner as described in Preparation Example 1 of Example 1 except that 2-(3-nitrophenylsulfonamido)-2-methylpropionic acid was used.

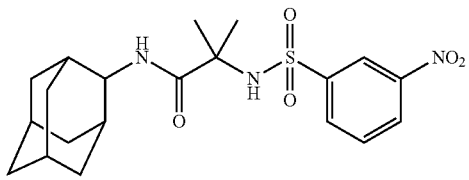 [SMILES: CC(C)(NS(=O)(=O)c1cccc([N+](=O)[O-])c1)C(=O)NC1C2CC3CC(C2)CC1C3]

$^1$H NMR (400 MHz, CDCl$_3$) δ 8.75 (t, J=2 Hz, 1H), 8.44 (m, 1H), 8.24 (m, 1H), 7.76 (t, J=8 Hz, 1H), 6.42 (d, J=7.6 Hz, —NH—CO—), 5.82 (s, —NH—SO$_2$), 3.95 (d, J=8 Hz, 1H), 1.95-1.86 (m, 8H), 1.81-1.73 (m, 4H), 1.66 (m, 2H), 1.51 (s, 6H).

Preparation Example 67

Synthesis of N-(adamantane-2-yl)-2-methyl-2-(4-propylphenylsulfonamido)propanamide (compound 67)

An aimed compound was obtained in the same manner as described in Preparation Example 1 of Example 1 except that 2-(4-propylphenylsulfonamido)-2-methylpropionic acid was used.

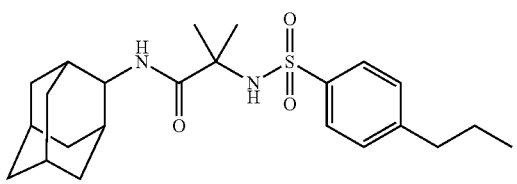 [SMILES: CCCc1ccc(S(=O)(=O)NC(C)(C)C(=O)NC2C3CC4CC(C3)CC2C4)cc1]

$^1$H NMR (400 MHz, CDCl$_3$) δ 7.81 (d, J=6.8 Hz, 2H), 7.32 (d, J=8.4 Hz, 2H), 6.88 (d, J=7.6 Hz, —NH—CO—), 5.26 (s, —NH—SO$_2$), 3.97 (d, J=7.6 Hz, 1H), 2.67 (t, J=7.6 Hz, 2H), 1.91-1.76 (m, 14H), 1.71-1.63 (m, 3H).

Preparation Example 68

Synthesis of N-(adamantane-2-yl)-2-methyl-2-(4-methoxy-3-nitrophenylsulfonamido)propanamide (compound 68)

An aimed compound was obtained in the same manner as described in Preparation Example 1 of Example 1 except that 2-(4-methoxy-3-nitrophenylsulfonamido)-2-methylpropionic acid was used.

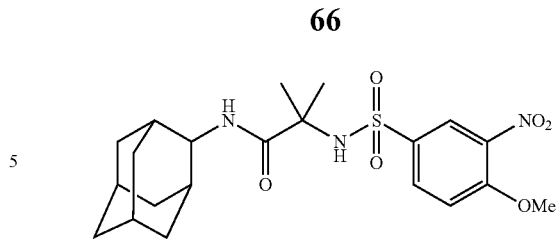

$^1$H NMR (400 MHz, CDCl$_3$) δ 8.38 (d, J=2.4 Hz, 1H), 8.07 (dd, J=2.4, 8.8 Hz, 1H), 7.22 (d, J=8.8 Hz, 1H), 6.50 (d, J=7.2 Hz, —NH—CO—), 5.61 (s, —NH—SO$_2$), 4.01 (s, 3H), 3.95 (d, J=7.6 Hz, 1H), 1.89-1.66 (m, 14H), 1.49 (s, 6H).

Preparation Example 69

Synthesis of N-(5-hydroxyadamantane-2-yl)-2-methyl-2-(2-fluorophenylsulfonamido)propanamide (compound 69)

An aimed compound was obtained in the same manner as described in Preparation Example 1 of Example 1 except that 2-(2-fluorophenylsulfonamido)-2-methylpropionic acid and 5-hydroxy-2-adamantanamine were used.

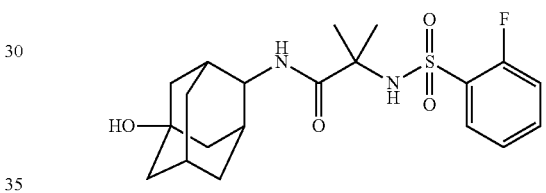

$^1$H NMR (400 MHz, CDCl$_3$) δ 7.91 (td, J=1.6 Hz, 16.0 Hz, 1H), 7.60-7.66 (m, 1H), 7.19-7.39 (m, 2H), 6.98 (d, J=7.6 Hz, —NH—CO—), 5.37 (s, —NH—SO$_2$), 3.97 (d, J=8.0 Hz, 1H), 1.50-1.92 (m, 13H), 1.43 (s, 6H)

Preparation Example 70

Synthesis of N-(5-hydroxyadamantane-2-yl)-2-methyl-2-(2-bromophenylsulfonamido)propanamide (compound 70)

An aimed compound was obtained in the same manner as described in Preparation Example 1 of Example 1 except that 2-(phenylsulfonamido)-2-methylpropionic acid and 5-hydroxy-2-adamantanamine were used.

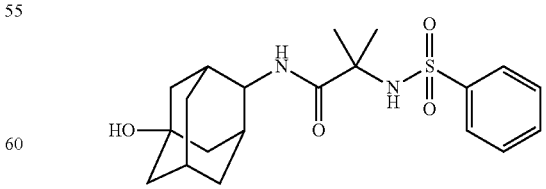

$^1$H NMR (400 MHz, CDCl$_3$) δ 7.80-7.92 (m, 2H), 7.59-7.63 (m, 1H), 7.52-7.56 (m, 2H), 6.90 (d, J=8.0 Hz, —NH—CO—), 5.32 (s, —NH—SO$_2$), 3.96 (d, J=8.0 Hz, 1H), 1.53-2.20 (m, 13H), 1.42 (s, 6H).

Preparation Example 71

Synthesis of N-(5-hydroxyadamantane-2-yl)-2-methyl-2-(4-methoxyphenylsulfonamido)propanamide (compound 71)

An aimed compound was obtained in the same manner as described in Preparation Example 1 of Example 1 except that 2-(4-methoxyphenylsulfonamido)-2-methylpropionic acid and 5-hydroxy-2-adamantanamine were used.

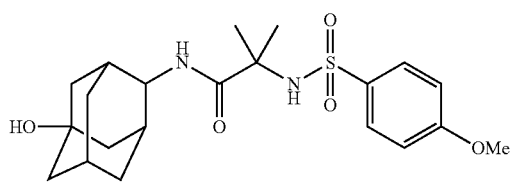 [SMILES: COc1ccc(S(=O)(=O)NC(C)(C)C(=O)NC2C3CC4CC2CC(O)(C4)C3)cc1]

$^1$H NMR (400 MHz, DMSO-d$_6$) δ 8.02 (s, —NH—SO$_2$), 7.73 (dd, J=2.0, 7.2 Hz, 2H), 7.10 (dd, J=2.0, 7.2 Hz, 2H), 7.05 (d, J=7.2 Hz, 1H), 4.44 (s, —OH), 3.84 (s, 3H), 3.52 (d, J=6.8 Hz, 1H), 1.35-2.02 (m, 13H), 1.22 (s, 6H)

Preparation Example 72

Synthesis of N-(5-hydroxyadamantane-2-yl)-2-methyl-2-(2-trifluoromethylphenylsulfonamido)propanamide (compound 72)

An aimed compound was obtained in the same manner as described in Preparation Example 1 of Example 1 except that 2-(2-trifluoromethylphenylsulfonamido)-2-methylpropionic acid and 5-hydroxy-2-adamantanamine were used.

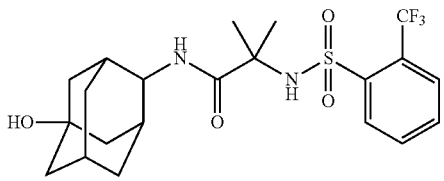

$^1$H NMR (400 MHz, DMSO-de) δ 8.34 (s, —NH—SO$_2$), 8.04-8.12 (m, 3H), 7.85 (t, J=8.0 Hz, 1H), 6.97 (d, J=6.8 Hz, —NH—CO—), 4.43 (s, —OH), 3.45 (d, J=6.8 Hz, 1H), 1.33-2.00 (m, 13H), 1.26 (s, 6H)

Preparation Example 73

Synthesis of N-(5-hydroxyadamantane-2-yl)-2-methyl-2-(2,3-dichlorophenylsulfonamido)propanamide (compound 73)

An aimed compound was obtained in the same manner as described in Preparation Example 1 of Example 1 except that 2-(2,3-dichlorophenylsulfonamido)-2-methylpropionic acid and 5-hydroxy-2-adamantanamine were used.

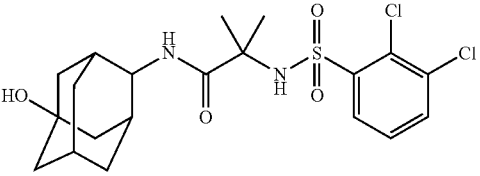

$^1$H NMR (400 MHz, DMSO-d$_6$) δ 8.51 (s, —NH—SO$_2$), 7.99 (dd, J=1.6, 8 Hz, 1H), 7.94 (dd, J=1.6, 8 Hz, 1H), 7.57 (t, J=8 Hz, 1H), 7.09 (d, J=7.2 Hz, —NH—CO—), 4.47 (s, —OH), 3.67 (d, J=7.2 Hz, 1H), 2.04-1.61 (m, 11H), 1.37 (m, 2H), 1.23 (s, 6H).

Preparation Example 74

Synthesis of N-(5-hydroxyadamantane-2-yl)-2-methyl-2-(2,6-difluorophenylsulfonamido)propanamide (compound 74)

An aimed compound was obtained in the same manner as described in Preparation Example 1 of Example 1 except that 2-(2,6-difluorophenylsulfonamido)-2-methylpropionic acid and 5-hydroxy-2-adamantanamine were used.

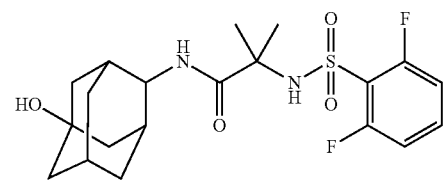 [SMILES: CC(C)(NS(=O)(=O)c1c(F)cccc1F)C(=O)NC1C2CC3CC1CC(O)(C3)C2]

$^1$H NMR (400 MHz, DMSO-d$_6$) δ 8.65 (s, —NH—SO$_2$, 1H), 7.71 (m, 1H), 7.27 (t, 2H), 7.04 (d, —NH—CO—, 1H), 4.46 (s, 1H), 3.60 (s, 1H), 1.36-2.02 (m, 13H), 1.23 (s, 6H).

Preparation Example 75

Synthesis of N-(5-hydroxyadamantane-2-yl)-2-methyl-2-(8-quinolinesulfonamido)propanamide (compound 75)

An aimed compound was obtained in the same manner as described in Preparation Example 1 of Example 1 except that 2-(8-quinolinesulfonamido)-2-methylpropionic acid and 5-hydroxy-2-adamantanamine were used.

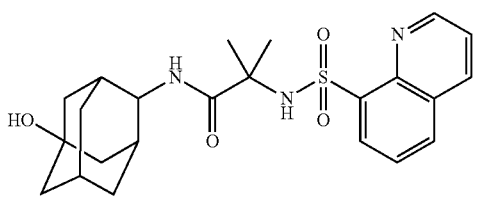 [SMILES: CC(C)(NS(=O)(=O)c1cccc2cccnc12)C(=O)NC1C2CC3CC1CC(O)(C3)C2]

$^1$H NMR (400 MHz, DMSO-d$_6$) δ 9.10 (s, —NH—SO$_2$, 1H), 8.56 (d, 1H), 8.29 (m, 1H), 7.91 (s, 1H), 7.74 (m, 2H), 7.24 (d, —NH—CO—, 1H), 4.45 (s, 1H), 3.62 (s, 1H), 1.23-2.00 (m, 13H), 1.18 (s, 6H).

Preparation Example 76

Synthesis of N-(5-hydroxyadamantane-2-yl)-2-methyl-2-(2-methyl-5-nitrophenylsulfonamido)propanamide (compound 76)

An aimed compound was obtained in the same manner as described in Preparation Example 1 of Example 1 except that 2-(2-methyl-5-nitrophenylsulfonamido)-2-methylpropionic acid and 5-hydroxy-2-adamantanamine were used.

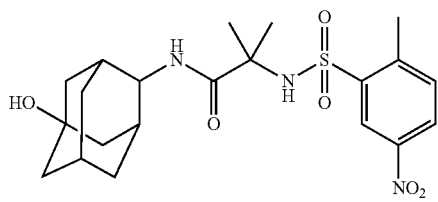 [SMILES: Cc1ccc([N+](=O)[O-])cc1S(=O)(=O)NC(C)(C)C(=O)NC1C2CC3CC1CC(O)(C3)C2]

$^1$H NMR (400 MHz, DMSO-d$_6$) δ 8.54 (s, —NH—SO$_2$, 1H), 8.54 (s, 1H), 8.36 (d, 1H), 7.71 (d, 1H), 7.02 (d, —NH—CO—, 1H), 4.46 (s, 1H), 3.61 (s, 1H), 2.50 (s, 3H), 1.35-2.02 (m, 13H), 1.24 (s, 6H).

Preparation Example 77

Synthesis of N-(5-hydroxyadamantane-2-yl)-2-methyl-2-(3-nitrophenylsulfonamido)propanamide (compound 77)

An aimed compound was obtained in the same manner as described in Preparation Example 1 of Example 1 except that 2-(3-nitrophenylsulfonamido)-2-methylpropionic acid and 5-hydroxy-2-adamantanamine were used.

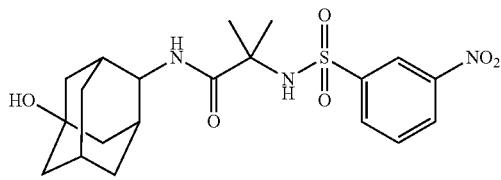 [SMILES: CC(C)(NS(=O)(=O)c1cccc([N+](=O)[O-])c1)C(=O)NC1C2CC3CC1CC(O)(C3)C2]

$^1$H NMR (400 MHz, DMSO-d$_6$) δ 8.53 (s, —NH—SO$_2$, 1H), 8.47 (d, 1H), 8.42 (s, 1H), 8.21 (d, 1H), 7.87 (t, 1H), 6.97 (d, —NH—CO—, 1H), 4.45 (s, 1H), 3.62 (s, 1H), 1.23-1.99 (m, 13H), 1.19 (s, 6H).

Preparation Example 78

Synthesis of N-(5-hydroxyadamantane-2-yl)-2-methyl-2-(4-nitrophenylsulfonamido)propanamide (compound 78)

An aimed compound was obtained in the same manner as described in Preparation Example 1 of Example 1 except that 2-(4-nitrophenylsulfonamido)-2-methylpropionic acid and 5-hydroxy-2-adamantanamine were used.

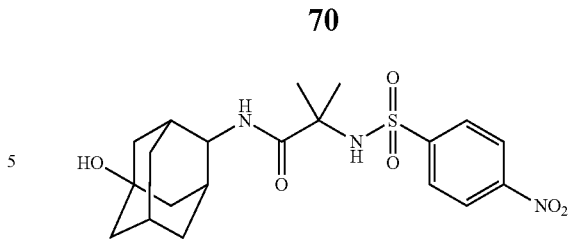

$^1$H NMR (400 MHz, DMSO-d$_6$) δ 8.46 (s, —NH—SO$_2$, 1H), 8.39 (d, 2H), 8.04 (d, 2H), 6.98 (d, —NH—CO—, 1H), 4.45 (s, 1H), 3.63 (s, 1H), 1.33-2.00 (m, 13H), 1.21 (s, 6H).

Preparation Example 79

Synthesis of N-(5-hydroxyadamantane-2-yl)-2-methyl-2-(4-chloro-2-nitrophenylsulfonamido)propanamide (compound 79)

An aimed compound was obtained in the same manner as described in Preparation Example 1 of Example 1 except that 2-(4-chloro-2-nitrophenylsulfonamido)-2-methylpropionic acid and 5-hydroxy-2-adamantanamine were used.

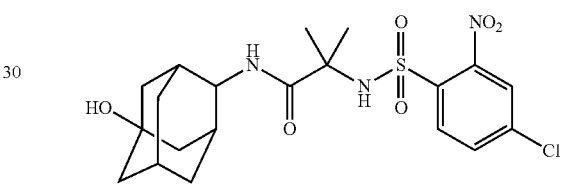

$^1$H NMR (400 MHz, DMSO-d$_6$) δ 8.47 (s, —NH—SO$_2$, 1H), 8.28 (d, 1H), 8.06 (d, 1H), 7.94 (dd, 1H), 7.04 (d, —NH—CO—, 1H), 4.45 (s, 1H), 3.64 (s, 1H), 1.33-2.01 (m, 13H), 1.25 (s, 6H).

Preparation Example 80

Synthesis of N-(5-hydroxyadamantane-2-yl)-2-methyl-2-(4-fluoro-2-chlorophenylsulfonamido)propanamide (compound 80)

An aimed compound was obtained in the same manner as described in Preparation Example 1 of Example 1 except that 2-(4-fluoro-2-chlorophenylsulfonamido)-2-methylpropionic acid and 5-hydroxy-2-adamantanamine were used.

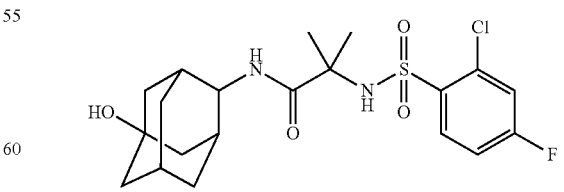

$^1$H NMR (400 MHz, DMSO-d$_6$) δ 8.41 (s, —NH—SO$_2$, 1H), 8.03 (m, 1H), 7.74 (d, 1H), 7.40 (m, 1H), 7.12 (d, —NH—CO—, 1H), 4.47 (s, 1H), 3.69 (s, 1H), 1.23-2.09 (m, 13H), 1.21 (s, 6H).

Preparation Example 81

Synthesis of N-(5-hydroxyadamantane-2-yl)-2-methyl-2-(2,4-dichlorophenylsulfonamido)propanamide (compound 81)

An aimed compound was obtained in the same manner as described in Preparation Example 1 of Example 1 except that 2-(2,4-dichlorophenylsulfonamido)-2-methylpropionic acid and 5-hydroxy-2-adamantanamine were used.

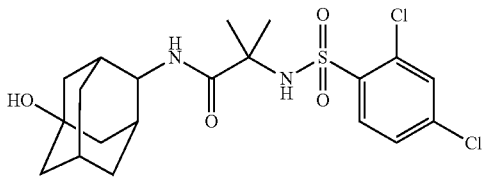

$^1$H NMR (400 MHz, DMSO-$d_6$) δ 8.45 (s, —NH—SO$_2$, 1H), 7.97 (d, 1H), 7.90 (d, 1H), 7.62 (dd, 1H), 7.10 (d, —NH—CO—, 1H), 4.47 (s, 1H), 3.67 (s, 1H), 1.21-2.09 (m, 13H), 1.17 (s, 6H).

Example 2

Preparation Example 1

Synthesis of (4-(2-methyl-2-(phenylsulfonamido)propanamido)adamantane-1-carboxyamide (compound 82)

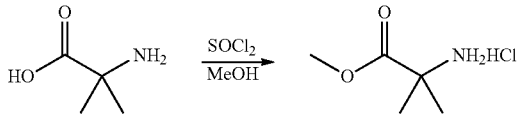

A 100-mL flask was charged with 2-amino-2-methylpropionic acid (3.0 g, 29.1 mmol) and methanol (45 ml). An ice bath was set, and thionyl chloride (4.25 ml, 58.2 mmol) was slowly added thereto. After the addition was completed, the ice bath was removed. At room temperature, the mixture was stirred for 3 hours. The resultant product was vacuum-distilled to remove a solvent, and then added with ethyl ether (30 ml), stirred at room temperature for 30 minutes, and filtered. The solid obtained through filtering was dried in a 60° C. oven to obtain methyl-2-amino-2-methylpropanoate hydrochloride (4.2 g, 94%).

$^1$H NMR (400 MHz, DMSO-$d_6$) δ 8.75 (s, 3H), 3.75 (s, 3H), 4.05 (m, 1H), 1.45 (s, 6H).

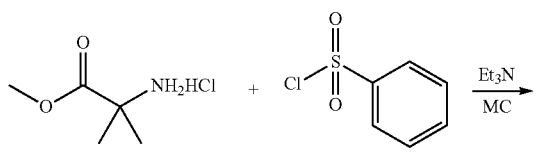

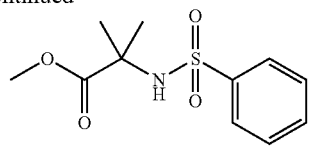

Into a 50-mL flask, methyl-2-amino-2-methylpropanoate hydrochloride (400 mg, 2.61 mmol) and methylenechloride (10 mL) were charged, and triethylamine (1.46 ml, 10.47 mmol) was charged, followed by stirring at room temperature for 30 minutes. The mixture was added with benzenesulfonylchloride (554 mg, 3.14 mmol), stirred overnight, and then added with H$_2$O (10 ml) to bring the reaction to an end. The organic layer was separated, and washed with saturated ammoniumchloride solution (15 ml). Then, the washed organic layer was separated, dried with MgSO$_4$, and filtered. Then, through vacuum distillation, the solvent was removed. The resultant mixture was purified with column chromatography so as to obtain methyl-2-amino-2-(phenylsulfonylamido)propanoate (507 mg, 75%).

$^1$H NMR (400 MHz, CDCl$_3$) δ 7.89-7.92 (t, 2H), 7.52-7.57 (m, 3H), 5.35 (s, —NH—SO$_2$), 3.67-3.68 (d, 3H), 1.47-1.48 (d, 6H).

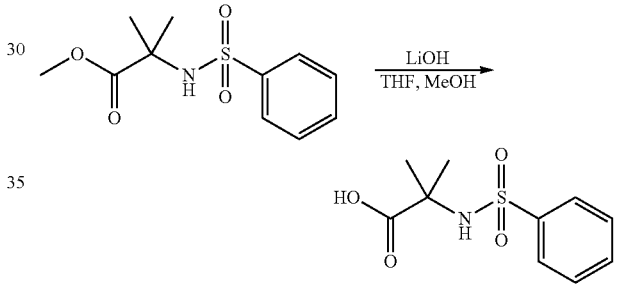

Into a 50-mL flask, methyl-2-amino-2-(phenylsulfonylamido)propanoate (500 mg, 1.94 mmol) was charged and dissolved through addition of THF (6 ml), and methanol (6 ml). LiOH.H$_2$O dissolved in H$_2$O (6 ml) was added thereto, followed by stirring for 12 hours at room temperature. After the stirring for 12 hours, the resultant solution was vacuum-evaporated, acidified with 2N—HCl to pH 1-2, and extracted with addition of EA (20 ml). The organic layer was dried with MgSO$_4$, and filtered. Then, through vacuum distillation, the solvent was removed so as to obtain methyl-2-amino-2-(phenylsulfonylamido)propanoic acid compound (402 mg, 85%).

$^1$H NMR (400 MHz, CDCl$_3$) δ 7.91-7.94 (m, 2H), 7.50-7.61 (m, 3H), 5.52 (s, —NH—SO$_2$), 1.51 (s, 6H).

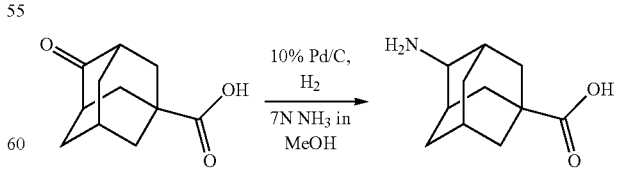

In a 250-mL flask, 4-oxo-adamantane-1-carboxylic acid (10 g, 51.5 mmol) was dissolved in 7N NH3 in MeOH (50 ml), and the resultant solution was added with 10% Pd/C (1 g, 10%), followed by stirring under hydrogen gas for 12 hours. After the reaction was completed, the resultant product was added with H₂O and filtered to obtain 4-amino-adamantane-1-carboxylic acid (8.17 g, 81%).

¹H NMR (400 MHz, CD3OD-d4) δ 3.36 (m, 1H), 2.03-1.53 (m, 13H).

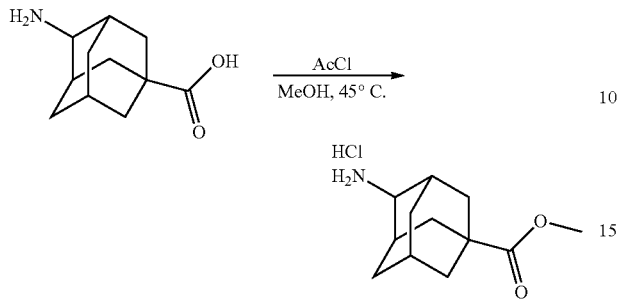

At 0° C., in a 250-mL flask, MeOH (85 ml) was added with AcCl (16.08 g, 204.85 mmol), and then at room temperature, 4-amino-adamantane-1-carboxylic acid (8.0 g, 40.97 mmol) was added thereto. At 45° C., the mixture was stirred for 12 hours. After the reaction was completed, the solid was filtered by acetonitrile to obtain 4-amino-adamantane-1-carboxylate hydrochloride (8.17 g, 81%).

¹H NMR (400 MHz, CDCl₃) δ 8.61 (m, 3H), 3.68 (s, 3H), 3.50 (s, 1H), 2.34-1.64 (m, 13H).

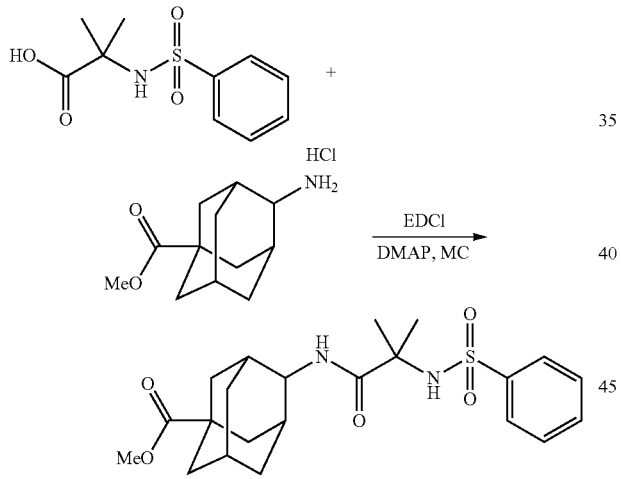

Into a 50-mL flask, methyl-2-amino-2-(phenylsulfonylamido)propanoic acid (100 mg, 0.39 mmol), 4-amino-adamantane-1-carboxylate hydrochloride (8.17 g, 81%), and EDCI (100 mg, 0.39 mmol) were charged, and CH₂Cl₂ (3 ml) was charged, followed by stirring for 30 minutes at room temperature. DMAP (82 mg, 0.39 mmol) was added thereto, followed by stirring at room temperature for 12 hours. After the reaction was completed, the organic layer was separated using CH₂Cl₂ and H₂O, dried with MgSO₄, and filtered. Then, the resultant mixture was purified with column chromatography (EA/n-Hex=1:4) so as to obtain 4-(2-methyl-2-(phenylsulfonamido)propanamido)adamantane-1-carboxylate (120 mg, 75%).

¹H NMR (400 MHz, CDCl₃) δ 7.89-7.96 (m, 2H), 7.51-7.63 (m, 3H), 7.53-7.40 (m, 3H), 6.95-6.97 (d, —NH—CO—), 6.73-6.75 (d, —NH—SO₂), 3.93-3.97 (m, 1H), 3.63-3.74 (m, 3H), 1.58-2.07 (m, 13H), 1.41-1.43 (m, 6H).

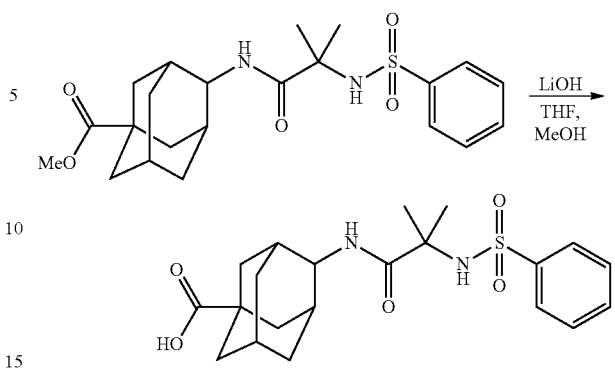

Into a 50-mL flask, 4-(2-methyl-2-(phenylsulfonamido)propanamido)adamantane-1-carboxylate (500 mg, 1.94 mmol) was charged, and dissolved through addition of THF (6 ml), and methanol (6 ml). LiOH.H₂O dissolved in H₂O (6 ml) was added thereto, followed by stirring for 12 hours at room temperature. After the stirring for 12 hours, the resultant solution was vacuum-evaporated, acidified with 2N—HCl to pH 1~2, and extracted with addition of EA (20 ml). The organic layer was dried with MgSO₄, and filtered. Then, through vacuum distillation, the solvent was removed so as to obtain 4-(2-methyl-2-(phenylsulfonamido)propanamido)adamantane-1-carboxylic acid compound (402 mg, 85%).

¹H NMR (400 MHz, CDCl₃) δ 7.89-7.92 (m, 2H), 7.51-7.62 (m, 3H), 7.53-7.40 (m, 3H), 6.84-6.86 (d, —NH—CO—), 5.82 (d, —NH—SO₂), 3.96-3.98 (m, 1H), 1.84-2.09 (m, 13H), 1.42 (s, 6H).

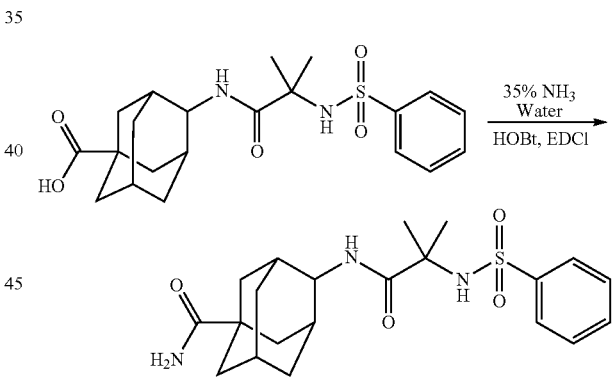

In a 50-mL flask, 4-(2-methyl-2-(phenylsulfonamido)propanamido)adamantane-1-carboxylic acid (3.49 g, 10.47 mmol) was dissolved in THF (20 ml) and MeOH (20 ml), and LiOH (2.45 g, 58.35 mmol) dissolved in H₂O (29 ml) was added thereto, followed by stirring at room temperature for 12 hours. The resultant solution was concentrated through vacuum distillation, acidified with 2N—HCl aqueous solution to pH 2, and extracted with CH₂Cl₂. The organic layer was dried with MgSO₄, and filtered. Then, through vacuum distillation, the solvent was removed so as to obtain 4-(2-methyl-2-(phenylsulfonamido)propanamido)adamantane-1-carboxyamide (3.25 g, 10.16 mmol, 97%) in the 50-mL flask.

¹H NMR (400 MHz, DMSO-d₆) δ 7.90-7.93 (m, 2H), 7.54-7.63 (m, 3H), 7.16 (s, —NH—CO—), 6.38-6.40 (d, —NH—SO₂), 6.01 (s, NH₂—CO—), 5.84 (s, NH₂—CO—), 3.99 (s, 1H), 1.59-2.15 (m, 13H), 1.41 (s, 6H).

Preparation Example 2

Synthesis of N-4-(2-(2-chlorophenylsulfonamido)-2-methylpropanamido)adamantane-1-carboxyamide (compound 83)

An aimed compound was obtained in the same manner as described in Preparation Example 1 of Example 2 except that 2-(2-chlorophenylsulfonamido)-2-methylpropionic acid was used.

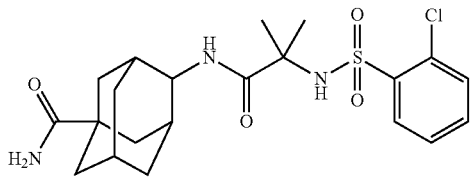

$^1$H NMR (400 MHz, DMSO-d$_6$) δ 8.37 (s, —NH—SO$_2$—), 8.00 (dd, J=1.2 Hz, 13.6 Hz, 1H), 7.60-7.73 (m, 2H), 7.50-7.56 (m, 1H), 7.22 (d, J=6.4 Hz, —NH—CO—), 7.02 (s, —NH$_2$—CO—, 1H), 6.75 (s, —NH$_2$—CO—, 1H), 3.75 (d, J=6.8 Hz, 1H), 1.48-1.99 (m, 13H), 1.22 (s, 6H).

Preparation Example 3

Synthesis of N-4-(2-(2-bromophenylsulfonamido)-2-methylpropanamido)adamantane-1-carboxyamide (compound 84)

An aimed compound was obtained in the same manner as described in Preparation Example 1 of Example 2 except that 2-(2-bromophenylsulfonamido)-2-methylpropionic acid was used.

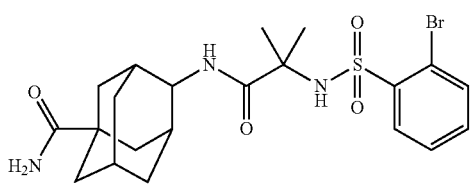 [SMILES: CC(C)(NS(=O)(=O)c1ccccc1Cl)C(=O)NC1C2CC3CC1CC(C(N)=O)(C3)C2]

$^1$H NMR (400 MHz, CDCl$_3$) δ 8.16 (dd, J=2.8 Hz, 7.6 Hz, 1H), 7.78 (dd, J=1.2 Hz, 7.6 Hz, 1H), 7.44-7.54 (m, 2H), 7.14 (d, J=7.6 Hz, —NH—CO—), 5.80 (s, —NH—SO$_2$), 5.61 (s, —NH$_2$—CO—, 1H), 5.26 (s, —NH$_2$—CO—, 1H), 4.02 (d, J=7.6 Hz, 1H), 1.60-2.20 (m, 13H), 1.44 (s, 6H)

Preparation Example 4

Synthesis of N-4-(2-(2-fluorophenylsulfonamido)-2-methylpropanamido)adamantane-1-carboxyamide (compound 85)

An aimed compound was obtained in the same manner as described in Preparation Example 1 of Example 2 except that 2-(2-fluorophenylsulfonamido)-2-methylpropionic acid was used.

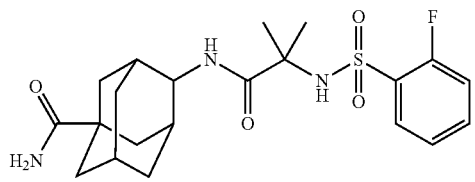 [SMILES: CC(C)(NS(=O)(=O)c1ccccc1F)C(=O)NC1C2CC3CC1CC(C(N)=O)(C3)C2]

$^1$H NMR (400 MHz, DMSO-d$_6$) δ 8.43 (s, —NH—SO$_2$—), 7.79 (m, 1H), 7.69-7.74 (m, 1H), 7.36-7.47 (m, 2H), 7.15 (s, —NH—CO—), 7.02 (s, —NH$_2$—CO—, 1H), 6.75 (s, —NH$_2$—CO—, 1H), 3.67 (d, J=7.2 Hz, 1H), 1.46-1.92 (m, 13H), 1.24 (s, 6H)

Preparation Example 5

Synthesis of N-4-(2-(4-methoxyphenylsulfonamido)-2-methylpropanamido)adamantane-1-carboxyamide (compound 86)

An aimed compound was obtained in the same manner as described in Preparation Example 1 of Example 2 except that 2-(4-methoxyphenylsulfonamido)-2-methylpropionic acid was used.

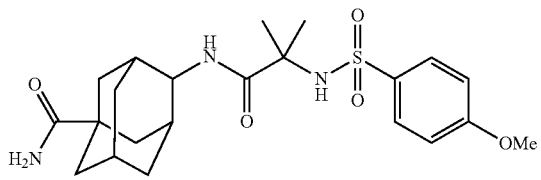 [SMILES: COc1ccc(S(=O)(=O)NC(C)(C)C(=O)NC2C3CC4CC2CC(C(N)=O)(C4)C3)cc1]

$^1$H NMR (400 MHz, CDCl$_3$) δ 7.82 (m, 2H), 7.19 (d, J=8.0 Hz —NH—CO—), 6.99-7.02 (m, 2H), 6.02 (s, —NH$_2$—CO—, 1H), 5.80 (s, —NH—SO$_2$), 5.61 (s, —NH$_2$—CO—, 1H), 3.97 (d, J=8.0 Hz, 1H), 3.90 (s, 3H), 1.76-2.20 (m, 13H), 1.42 (s, 6H).

Preparation Example 6

Synthesis of N-4-(2-(2,3-dichlorophenylsulfonamido)-2-methylpropanamido)adamantane-1-carboxyamide (compound 87)

An aimed compound was obtained in the same manner as described in Preparation Example 1 of Example 2 except that 2-(2,3-dichlorophenylsulfonamido)-2-methylpropionic acid was used.

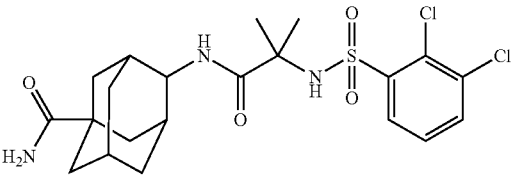 [SMILES: CC(C)(NS(=O)(=O)c1cccc(Cl)c1Cl)C(=O)NC1C2CC3CC1CC(C(N)=O)(C3)C2]

$^1$H NMR (400 MHz, CDCl$_3$) δ 8.04-8.08 (m, 1H), 7.72-7.76 (m, 1H), 7.36-7.43 (m, 1H), 7.01 (s, —NH—CO—), 5.83 (d, J=9.6 Hz —NH—SO$_2$), 5.61 (s, —NH$_2$—CO—, 1H), 5.29 (s, —NH$_2$—CO—, 1H), 4.03 (s, 1H), 3.90 (s, 3H), 1.59-2.13 (m, 13H), 1.41 (s, 6H)

Preparation Example 7

Synthesis of N-4-(2-(2,4-dichlorophenylsulfonamido)-2-methylpropanamido)adamantane-1-carboxyamide (compound 88)

An aimed compound was obtained in the same manner as described in Preparation Example 1 of Example 2 except that 2-(2,4-dichlorophenylsulfonamido)-2-methylpropionic acid was used.

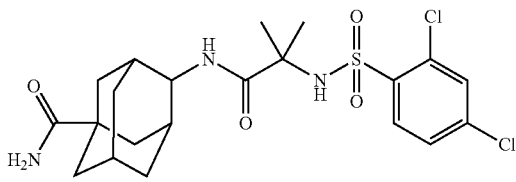

$^1$H NMR (400 MHz, DMSO-d$_6$) δ 8.43 (s, —NH—SO$_2$—), 7.99 (dd, J=5.2 Hz, 11.0 Hz, 1H), 7.91 (d, J=2.0 Hz, 1H), 7.63 (dd, J=2.0 Hz, 8.6 Hz, 1H), 7.20 (s, —NH—CO—), 7.03 (s, —NH$_2$—CO—, 1H), 6.76 (s, —NH$_2$—CO—, 1H), 3.74 (d, J=7.2 Hz, 1H), 1.47-1.93 (m, 13H), 1.22 (s, 6H)

Preparation Example 8

Synthesis of N-4-(2-(2,6-difluorophenylsulfonamido)-2-methylpropanamido)adamantane-1-carboxyamide (compound 89)

An aimed compound was obtained in the same manner as described in Preparation Example 1 of Example 2 except that 2-(2,6-difluorophenylsulfonamido)-2-methylpropionic acid was used.

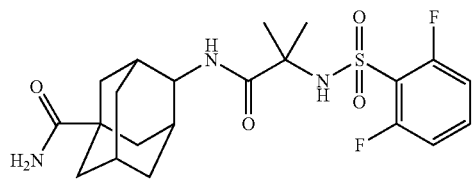 [SMILES: CC(C)(NS(=O)(=O)c1c(F)cccc1F)C(=O)NC1C2CC3CC1CC(C(N)=O)(C3)C2]

$^1$H NMR (400 MHz, DMSO-d$_6$) δ 8.67 (s, —NH—SO$_2$), 7.69-7.77 (m, 1H), 7.30 (t, J=18.0 Hz, 2H), 7.02 (s, —NH—CO—), 6.98 (s, —NH$_2$—CO—, 1H), 6.76 (s, —NH$_2$—CO—, 1H), 3.65 (d, J=6.8 Hz, 1H), 1.46-1.93 (m, 13H), 1.30 (s, 6H)

Preparation Example 9

Synthesis of N-4-(2-(2-trifluoromethoxyphenylsulfonamido)-2-methylpropanamido)adamantane-1-carboxyamide (compound 90)

An aimed compound was obtained in the same manner as described in Preparation Example 1 of Example 2 except that 2-(2-trifluoromethoxyphenylsulfonamido)-2-methylpropionic acid was used.

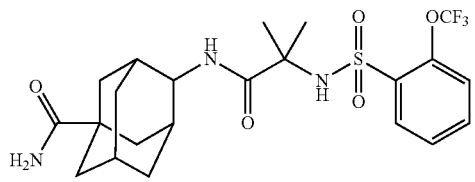

$^1$H NMR (400 MHz, CDCl$_3$) δ 8.04-8.08 (dd, J=1.6 Hz, 7.6 Hz, 1H), 7.66-7.70 (m, 1H), 7.41-7.47 (m, 2H), 7.05 (d, J=7.6 Hz, —NH—CO—), 5.60 (s, —NH$_2$—CO—, 1H), 5.30 (s, —NH—SO$_2$), 5.22 (s, —NH$_2$—CO—, 1H), 4.02 (d, J=6.8 Hz, 1H), 1.63-2.13 (m, 13H), 1.39 (s, 6H)

Preparation Example 10

Synthesis of N-4-(2-(3,5-dimethylphenylsulfonamido)-2-methylpropanamido)adamantane-1-carboxyamide (compound 91)

An aimed compound was obtained in the same manner as described in Preparation Example 1 of Example 2 except that 2-(3,5-dimethylphenylsulfonamido)-2-methylpropionic acid was used.

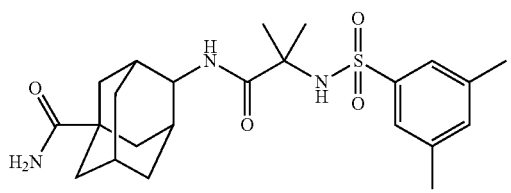 [SMILES: Cc1cc(C)cc(S(=O)(=O)NC(C)(C)C(=O)NC2C3CC4CC2CC(C(N)=O)(C4)C3)c1]

$^1$H NMR (400 MHz, DMSO-d$_6$) δ 8.08 (s, —NH—SO$_2$—), 7.42 (s, 2H), 7.26 (s, 1H), 7.12 (d, J=7.2 Hz, —NH—CO—), 7.02 (s, —NH$_2$—CO—, 1H), 6.76 (s, —NH$_2$—CO—, 1H), 3.59 (d, J=6.8 Hz, 1H), 2.35 (s, 6H), 1.45-1.91 (m, 13H), 1.24 (s, 6H)

Preparation Example 11

Synthesis of N-4-(2-(3-fluoro-4-methylphenylsulfonamido)-2-methylpropanamido)adamantane-1-carboxyamide (compound 92)

An aimed compound was obtained in the same manner as described in Preparation Example 1 of Example 2 except that 2-(3-fluoro-4-methylphenylsulfonamido)-2-methylpropionic acid was used.

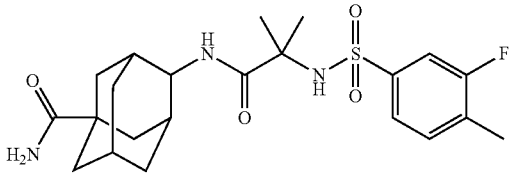 [SMILES: Cc1ccc(S(=O)(=O)NC(C)(C)C(=O)NC2C3CC4CC2CC(C(N)=O)(C4)C3)cc1F]

$^1$H NMR (400 MHz, DMSO-d$_6$) δ 8.22 (s, —NH—SO$_2$—), 7.49-7.56 (m, 3H), 7.11 (s, —NH—CO—), 7.02 (s, —NH$_2$—CO—, 1H), 6.76 (s, —NH$_2$—CO—, 1H), 3.56 (d, J=6.0 Hz, 1H), 2.31 (d, J=1.6 Hz, 3H), 1.44-1.91 (m, 13H), 1.25 (s, 6H)

Preparation Example 12

Synthesis of N-4-(2-(4-difluoromethoxyphenylsulfonamido)-2-methylpropanamido)adamantane-1-carboxyamide (compound 93)

An aimed compound was obtained in the same manner as described in Preparation Example 1 of Example 2 except that 2-(4-difluoromethoxyphenylsulfonamido)-2-methylpropionic acid was used.

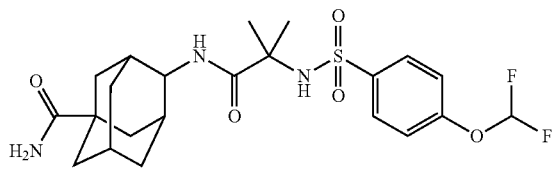 [SMILES: CC(C)(NS(=O)(=O)c1ccc(OC(F)F)cc1)C(=O)NC1C2CC3CC1CC(C(N)=O)(C3)C2]

$^1$H NMR (400 MHz, DMSO-$d_6$) δ 8.34 (s, —NH—SO$_2$—), 7.87 (dd, J=2.0 Hz, 6.8 Hz, 2H), 7.36 (d, J=8.8 Hz, 2H), 7.11 (d, J=7.2 Hz, —NH—CO—), 7.03 (s, —NH$_2$—CO—, 1H), 6.78 (s, —NH$_2$—CO—, 1H), 3.60 (d, J=6.4 Hz, 1H), 1.45-1.95 (m, 13H), 1.24 (s, 6H)

Preparation Example 13

Synthesis of N-4-(2-(2-fluoro-5-methylphenylsulfonamido)-2-methylpropanamido)adamantane-1-carboxyamide (compound 94)

An aimed compound was obtained in the same manner as described in Preparation Example 1 of Example 2 except that 2-(2-fluoro-5-methylphenylsulfonamido)-2-methylpropionic acid was used.

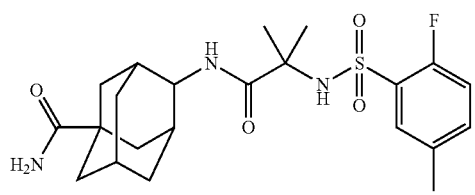 [SMILES: Cc1ccc(F)c(S(=O)(=O)NC(C)(C)C(=O)NC2C3CC4CC2CC(C(N)=O)(C4)C3)c1]

$^1$H NMR (400 MHz, DMSO-$d_6$) δ 8.38 (s, —NH—SO$_2$—), 7.59 (d, J=6.8 Hz, 1H), 7.49 (s, 1H), 7.32 (t, J=18.8 Hz, 1H), 7.16 (s, —NH—CO—), 7.03 (s, —NH$_2$—CO—, 1H), 6.76 (s, —NH$_2$—CO—, 1H), 3.67 (d, J=7.2 Hz, 1H), 2.35 (s, 3H), 1.46-1.92 (m, 13H), 1.24 (s, 6H)

Preparation Example 14

Synthesis of N-4-(2-(2-methyl-5-fluorophenylsulfonamido)-2-methylpropanamido)adamantane-1-carboxyamide (compound 95)

An aimed compound was obtained in the same manner as described in Preparation Example 1 of Example 2 except that 2-(2-methyl-5-fluorophenylsulfonamido)-2-methylpropionic acid was used.

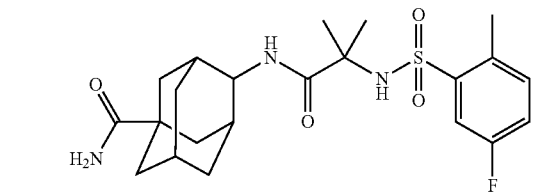

$^1$H NMR (400 MHz, DMSO-$d_6$) δ 8.36 (s, —NH—SO$_2$—), 7.61 (s, 1H), 7.45 (m, 2H), 7.17 (s, —NH—CO—), 7.03 (s, —NH$_2$—CO—, 1H), 6.76 (s, —NH$_2$—CO—, 1H), 3.73 (s, 1H), 2.58 (d, J=4.4 Hz, 3H), 1.47-1.93 (m, 13H), 1.22 (s, 6H)

Preparation Example 15

Synthesis of N-4-(2-(2-chloropyridine-3-sulfonamido)-2-methylpropanamido)adamantane-1-carboxyamide (compound 96)

An aimed compound was obtained in the same manner as described in Preparation Example 1 of Example 2 except that 2-(2-chloropyridine-3-sulfonamido)-2-methylpropionic acid was used.

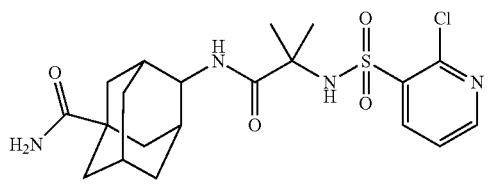 [SMILES: CC(C)(NS(=O)(=O)c1cccnc1Cl)C(=O)NC1C2CC3CC1CC(C(N)=O)(C3)C2]

$^1$H NMR (400 MHz, DMSO-$d_6$) δ 8.74 (s, —NH—SO$_2$), 8.61 (m, 1H), 8.41 (d, J=7.6 Hz, 1H), 7.65 (m, 1H), 7.31 (d, J=7.6 Hz, —NH—CO—), 7.09 (br, NH$_2$—CO—), 6.81 (br, NH$_2$—CO—), 3.73 (d, J=6.8 Hz, 1H), 1.93-1.76 (m, 11H), 1.51 (m, 2H), 1.23 (s, 6H).

Preparation Example 16

Synthesis of N-4-(2-(2-methyl-3-chlorophenylsulfonamido)-2-methylpropanamido)adamantane-1-carboxyamide (compound 97)

An aimed compound was obtained in the same manner as described in Preparation Example 1 of Example 2 except that 2-(2-methyl-3-chlorophenylsulfonamido)-2-methylpropionic acid was used.

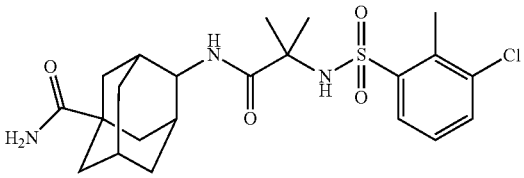 [SMILES: Cc1c(Cl)cccc1S(=O)(=O)NC(C)(C)C(=O)NC1C2CC3CC1CC(C(N)=O)(C3)C2]

$^1$H NMR (400 MHz, DMSO-$d_6$) δ 8.38 (s, —NH—SO$_2$), 7.87 (dd, J=0.8, 8 Hz, 1H), 7.73 (d, J=8 Hz, 1H), 7.41 (t, J=8 Hz, 1H), 7.14 (d, J=6.8 Hz, —NH—CO—), 7.02 (br, NH$_2$—CO—), 6.75 (br, NH$_2$—CO—), 3.72 (d, J=7.2 Hz, 1H), 2.66 (s, 3H), 1.92-1.77 (m, 11H), 1.45 (m, 2H), 1.22 (s, 6H).

Preparation Example 17

Synthesis of N-4-(2-((2-chlorophenyl)methylsulfonamido)-2-methylpropanamido)adamantane-1-carboxyamide (compound 98)

An aimed compound was obtained in the same manner as described in Preparation Example 1 of Example 2 except that 2-((2-chlorophenyl)methylsulfonamido)-2-methylpropionic acid was used.

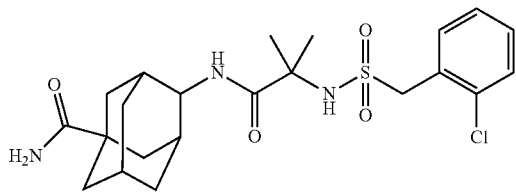 [SMILES: CC(C)(NS(=O)(=O)Cc1ccccc1Cl)C(=O)NC1C2CC3CC1CC(C(N)=O)(C3)C2]

$^1$H NMR (400 MHz, DMSO-d$_6$) δ 7.74 (s, —NH—SO$_2$), 7.53 (m, 2H), 7.39 (m, 2H), 7.06 (d, J=7.2 Hz, —NH—CO—), 6.89 (br, NH$_2$—CO—), 6.76 (br, NH$_2$—CO—), 4.51 (s, 2H), 3.74 (d, J=6.4 Hz, 1H), 1.88 (m, 5H), 1.65 (m, 8H), 1.43 (s, 6H).

Preparation Example 18

Synthesis of N-4-(2-(4-propylphenylsulfonamido)-2-methylpropanamido)adamantane-1-carboxyamide (compound 99)

An aimed compound was obtained in the same manner as described in Preparation Example 1 of Example 2 except that 2-(4-propylphenylsulfonamido)-2-methylpropionic acid was used.

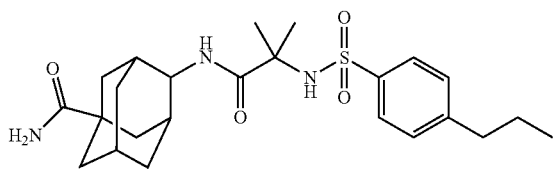 [SMILES: CCCc1ccc(S(=O)(=O)NC(C)(C)C(=O)NC2C3CC4CC2CC(C(N)=O)(C4)C3)cc1]

$^1$H NMR (400 MHz, DMSO-d$_6$) δ 8.15 (s, —NH—SO$_2$), 7.74 (d, J=8 Hz, 2H), 7.39 (d, J=8 Hz, 2H), 7.13 (d, J=6.8 Hz, —NH—CO—), 7.03 (br, NH$_2$—CO—), 6.77 (br, NH$_2$—CO—), 3.57 (d, J=6.8 Hz, 1H), 2.63 (t, J=7.2 Hz, 2H), 1.91-1.79 (m, 11H), 1.62 (sex, J=8.4 Hz, 2H), 1.47 (m, 2H), 1.22 (s, 6H), 0.89 (t, J=7.2 Hz, 3H).

Preparation Example 19

Synthesis of N-4-(2-(2-trifluoromethoxy-4-bromophenylsulfonamido)-2-methylpropanamido)adamantane-1-carboxyamide (compound 100)

An aimed compound was obtained in the same manner as described in Preparation Example 1 of Example 2 except that 2-(2-trifluoromethoxy-4-bromophenylsulfonamido)-2-methylpropionic acid was used.

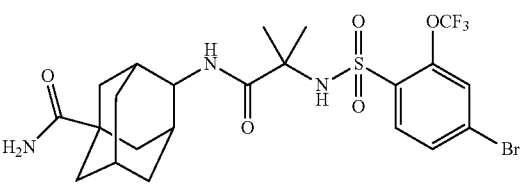 [SMILES: CC(C)(NS(=O)(=O)c1ccc(Br)cc1OC(F)(F)F)C(=O)NC1C2CC3CC1CC(C(N)=O)(C3)C2]

$^1$H NMR (400 MHz, DMSO-d$_6$) 8.42 (s, —NH—SO$_2$), 7.82 (m, 1H), 7.71 (m, 2H), 7.25 (d, J=6.8 Hz, —NH—CO—), 7.02 (br, NH$_2$—CO—), 6.76 (br, NH$_2$—CO—), 3.72 (d, J=7.2 Hz, 1H), 1.92-1.78 (m, 11H), 1.47 (m, 2H), 1.23 (s, 6H).

Preparation Example 20

Synthesis of N-4-(2-(2-bromo-4-fluorophenylsulfonamido)-2-methylpropanamido)adamantane-1-carboxyamide (compound 101)

An aimed compound was obtained in the same manner as described in Preparation Example 1 of Example 2 except that 2-(2-bromo-4-fluorophenylsulfonamido)-2-methylpropionic acid was used.

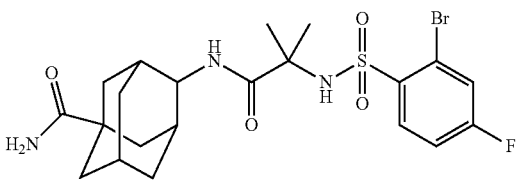 [SMILES: CC(C)(NS(=O)(=O)c1ccc(F)cc1Br)C(=O)NC1C2CC3CC1CC(C(N)=O)(C3)C2]

$^1$H NMR (400 MHz, DMSO-d$_6$) δ 8.42 (s, —NH—SO$_2$), 8.11 (m, 1H), 7.89 (m, 1H), 7.45 (t, J=7.2 Hz, 1H), 7.25 (d, J=7.2 Hz, —NH—CO—), 7.09 (br, NH$_2$—CO—), 6.76 (br, NH$_2$—CO—), 3.76 (d, J=7.2 Hz, 1H), 1.95-1.77 (m, 11H), 1.48 (m, 2H), 1.22 (s, 6H).

Preparation Example 21

Synthesis of N-4-(2-(2-fluoro-3-chlorophenylsulfonamido)-2-methylpropanamido)adamantane-1-carboxyamide (compound 102)

An aimed compound was obtained in the same manner as described in Preparation Example 1 of Example 2 except that 2-(2-fluoro-3-chlorophenylsulfonamido)-2-methylpropionic acid was used.

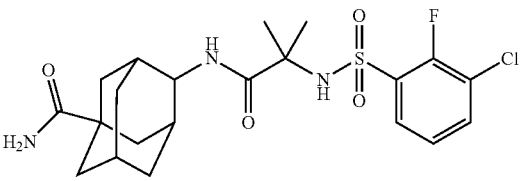 [SMILES: CC(C)(NS(=O)(=O)c1cccc(Cl)c1F)C(=O)NC1C2CC3CC1CC(C(N)=O)(C3)C2]

$^1$H NMR (400 MHz, DMSO-d$_6$) δ 8.59 (s, —NH—SO$_2$), 7.91 (t, J=6.4 Hz, 1H), 7.78 (m, 1H), 7.41 (t, J=8 Hz, 1H), 7.11 (d, J=6 Hz, —NH—CO—), 7.01 (br, NH$_2$—CO—), 6.74 (br, NH$_2$—CO—), 3.61 (d, J=6.8 Hz, 1H), 1.99-1.78 (m, 11H), 1.48 (m, 2H), 1.27 (s, 6H).

Preparation Example 22

Synthesis of N-4-(2-(3-chloro-4-methylphenylsulfonamido)-2-methylpropanamido)adamantane-1-carboxyamide (compound 103)

An aimed compound was obtained in the same manner as described in Preparation Example 1 of Example 2 except that 2-(3-chloro-4-methylphenylsulfonamido)-2-methylpropionic acid was used.

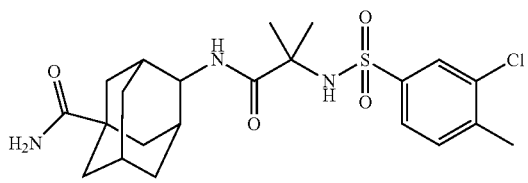 [SMILES: Cc1ccc(S(=O)(=O)NC(C)(C)C(=O)NC2C3CC4CC2CC(C(N)=O)(C4)C3)cc1Cl]

$^1$H NMR (400 MHz, DMSO-$d_6$) δ 8.20 (s, —NH—SO$_2$), 7.77 (d, J=2 Hz, 1H), 7.69 (m, 1H), 7.57 (m, 1H), 7.05 (d, J=7.2 Hz, —NH—CO—), 7.01 (br, NH$_2$—CO—), 6.75 (br, NH$_2$—CO—), 3.53 (d, J=6.8 Hz, 1H), 2.41 (s, 3H), 1.82-1.78 (m, 11H), 1.47 (m, 2H), 1.26 (s, 6H).

Preparation Example 23

Synthesis of N-4-(2-(2-methylphenylsulfonamido)-2-methylpropanamido)adamantane-1-carboxyamide (compound 104)

An aimed compound was obtained in the same manner as described in Preparation Example 1 of Example 2 except that 2-(2-methylphenylsulfonamido)-2-methylpropionic acid was used.

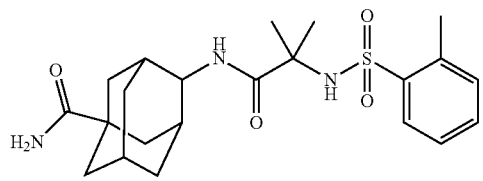 [SMILES: Cc1ccccc1S(=O)(=O)NC(C)(C)C(=O)NC1C2CC3CC1CC(C(N)=O)(C3)C2]

$^1$H NMR (400 MHz, DMSO-$d_6$) δ 8.21 (s, —NH—SO$_2$), 7.85 (d, J=7.6 Hz, 1H), 7.52 (m, 1H), 7.41 (m, 2H), 7.21 (d, J=7.2 Hz, —NH—CO—), 7.03 (br, NH$_2$—CO—), 6.76 (br, NH$_2$—CO—), 3.74 (d, J=7.2 Hz, 1H), 2.67 (s, 3H), 1.99-1.77 (m, 11H), 1.48 (m, 2H), 1.19 (s, 6H).

Preparation Example 24

Synthesis of N-4-(2-(quinoline-8-sulfonamido)-2-methylpropanamido)adamantane-1-carboxyamide (compound 105)

An aimed compound was obtained in the same manner as described in Preparation Example 1 of Example 2 except that 2-(quinoline-8-sulfonamido)-2-methylpropionic acid was used.

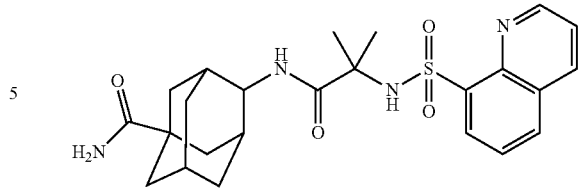

$^1$H NMR (400 MHz, DMSO-$d_6$) δ 9.10 (dd, J=1.6, 4 Hz, 1H), 8.58 (dd, J=1.6, 8.4 Hz, 1H), 8.31 (m, 2H), 7.93 (s, —NH—SO$_2$), 7.75 (m, 2H), 7.32 (d, J=7.2 Hz, —NH—CO—), 7.02 (br, NH$_2$—CO—), 6.76 (br, NH$_2$—CO—), 3.68 (d, J=6 Hz, 1H), 1.91-1.75 (m, 11H), 1.44 (m, 2H), 1.19 (s, 6H).

Preparation Example 25

Synthesis of N-4-(2-(2-nitrophenylsulfonamido)-2-methylpropanamido)adamantane-1-carboxyamide (compound 106)

An aimed compound was obtained in the same manner as described in Preparation Example 1 of Example 2 except that 2-(2-nitrophenylsulfonamido)-2-methylpropionic acid was used.

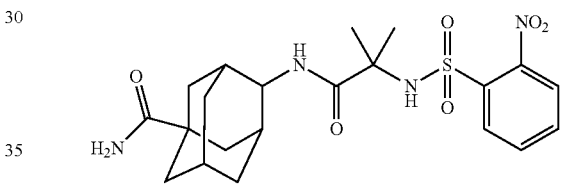

$^1$H NMR (400 MHz, DMSO-$d_6$) δ 8.39 (s, —NH—SO$_2$), 8.09 (m, 1H), 8.02 (m, 1H), 7.87 (m, 2H), 7.17 (d, J=7.2 Hz, —NH—CO—), 7.01 (br, NH$_2$—CO—), 6.69 (br, NH$_2$—CO—), 3.72 (d, J=6 Hz, 1H), 1.91-1.75 (m, 11H), 1.45 (m, 2H), 1.32 (s, 6H).

Preparation Example 26

Synthesis of N-4-(2-(3-nitrophenylsulfonamido)-2-methylpropanamido)adamantane-1-carboxyamide (compound 107)

An aimed compound was obtained in the same manner as described in Preparation Example 1 of Example 2 except that 2-(3-nitrophenylsulfonamido)-2-methylpropionic acid was used.

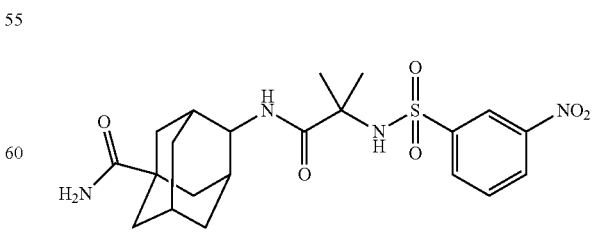

$^1$H NMR (400 MHz, DMSO-$d_6$) δ 8.54 (t, J=2 Hz, —NH—SO$_2$), 8.47 (m, 2H), 8.22 (m, 1H), 7.89 (t, J=8.4 Hz, 1H), 7.10 (d, J=6.8 Hz, —NH—CO—), 7.03 (br, NH$_2$—CO—), 6.77

(br, NH$_2$—CO—), 3.41 (d, J=6.4 Hz, 1H), 1.83-1.74 (m, 11H), 1.43 (m, 2H), 1.27 (s, 6H).

Preparation Example 27

Synthesis of N-4-(2-(2-trifluoromethylphenylsulfonamido)-2-methylpropanamido)adamantane-1-carboxyamide (compound 108)

An aimed compound was obtained in the same manner as described in Preparation Example 1 of Example 2 except that 2-(2-trifluoromethylphenylsulfonamido)-2-methylpropionic acid was used.

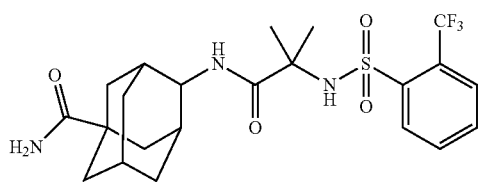 [SMILES: CC(C)(NS(=O)(=O)c1ccccc1C(F)(F)F)C(=O)NC1C2CC3CC1CC(C(N)=O)(C3)C2]

$^1$H NMR (400 MHz, DMSO-d$_6$) δ 8.36 (s, —NH—SO$_2$), 8.26 (d, J=7.6 Hz, 1H), 7.98 (d, J=7.6 Hz, 1H), 7.86 (m, 2H), 7.21 (d, J=7.6 Hz, —NH—CO—), 7.04 (br, NH$_2$—CO—), 6.77 (br, NH$_2$—CO—), 3.75 (d, J=7.2 Hz, 1H), 1.98-1.77 (m, 11H), 1.47 (m, 2H), 1.25 (s, 6H).

Preparation Example 28

Synthesis of N-4-(2-(2,5-bistrifluoromethylphenylsulfonamido)-2-methylpropanamido)adamantane-1-carboxyamide (compound 109)

An aimed compound was obtained in the same manner as described in Preparation Example 1 of Example 2 except that 2-(2,5-bistrifluoromethylphenylsulfonamido)-2-methylpropionic acid was used.

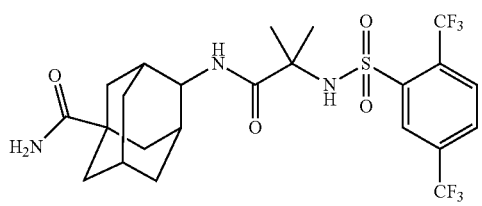

$^1$H NMR (400 MHz, DMSO-d$_6$) δ 8.59 (s, —NH—SO$_2$), 8.43 (m, 1H), 8.24 (m, 2H), 7.28 (d, J=7.6 Hz, —NH—CO—), 6.98 (br, NH$_2$—CO—), 6.69 (br, NH$_2$—CO—), 3.73 (d, J=7.6 Hz, 1H), 1.92-1.62 (m, 11H), 1.46 (m, 2H), 1.27 (s, 6H). (E/Z=4/1)

Preparation Example 29

Synthesis of N-4-(2-(2-bromo-5-trifluoromethylphenylsulfonamido)-2-methylpropanamido)adamantane-1-carboxyamide (compound 110)

An aimed compound was obtained in the same manner as described in Preparation Example 1 of Example 2 except that 2-(2-bromo-5-trifluoromethylphenylsulfonamido)-2-methylpropionic acid was used.

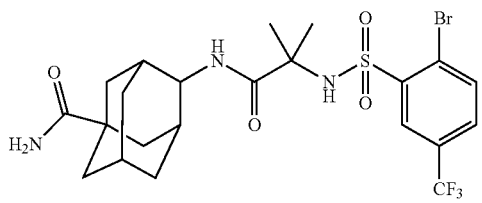

$^1$H NMR (400 MHz, DMSO-d$_6$) δ 8.56 (s, —NH—SO$_2$), 8.21 (m, 2H), 7.94 (m, 1H), 7.19 (d, J=7.6 Hz, —NH—CO—), 7.02 (br, NH$_2$—CO—), 6.76 (br, NH$_2$—CO—), 3.74 (d, J=7.6 Hz, 1H), 1.94-1.67 (m, 11H), 1.49 (m, 2H), 1.23 (s, 6H).

Preparation Example 30

Synthesis of N-4-(2-(3-nitro-4-methoxyphenylsulfonamido)-2-methylpropanamido)adamantane-1-carboxyamide (compound 111)

An aimed compound was obtained in the same manner as described in Preparation Example 1 of Example 2 except that 2-(3-nitro-4-methoxyphenylsulfonamido)-2-methylpropionic acid was used.

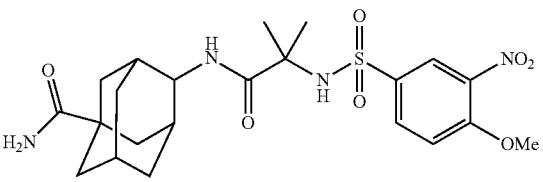 [SMILES: COc1ccc(S(=O)(=O)NC(C)(C)C(=O)NC2C3CC4CC2CC(C(N)=O)(C4)C3)cc1[N+](=O)[O-]]

$^1$H NMR (400 MHz, DMSO-d$_6$) δ 8.23 (s, —NH—SO$_2$), 8.28 (d, J=2 Hz, 1H), 8.05 (dd, J=2.4, 8.8 Hz, 1H), 7.55 (m, 1H), 7.09 (d, J=5.6 Hz, —NH—CO—), 7.03 (br, NH$_2$—CO—), 6.77 (br, NH$_2$—CO—), 4.02 (s, 3H), 3.55 (d, J=6.4 Hz, 1H), 1.84-1.74 (m, 11H), 1.43 (m, 2H), 1.27 (s, 6H).

Preparation Example 31

Synthesis of N-4-(2-(2,4,6-trichlorophenylsulfonamido)-2-methylpropanamido)adamantane-1-carboxy amide (compound 112)

An aimed compound was obtained in the same manner as described in Preparation Example 1 of Example 2 except that 2-(2,4,6-trichlorophenylsulfonamido)-2-methylpropionic acid was used.

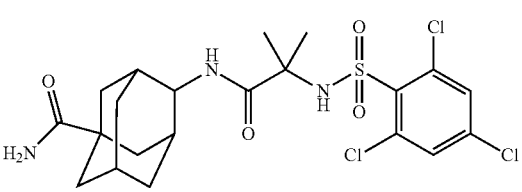 [SMILES: CC(C)(NS(=O)(=O)c1c(Cl)cc(Cl)cc1Cl)C(=O)NC1C2CC3CC1CC(C(N)=O)(C3)C2]

$^1$H NMR (400 MHz, DMSO-d$_6$) δ 8.62 (s, —NH—SO$_2$), 7.91 (s, 2H), 7.15 (d, J=6 Hz, —NH—CO—), 7.02 (br, NH$_2$—CO—), 6.75 (br, NH$_2$—CO—), 3.75 (d, J=6.8 Hz, 1H), 1.93-1.77 (m, 11H), 1.51 (m, 2H), 1.22 (s, 6H).

Preparation Example 32

Synthesis of N-4-(2-(3-trifluoromethyl-4-nitrophenylsulfonamido)-2-methylpropanamido)adamantane-1-carboxyamide (compound 113)

An aimed compound was obtained in the same manner as described in Preparation Example 1 of Example 2 except that 2-(3-trifluoromethyl-4-nitrophenylsulfonamido)-2-methylpropionic acid was used.

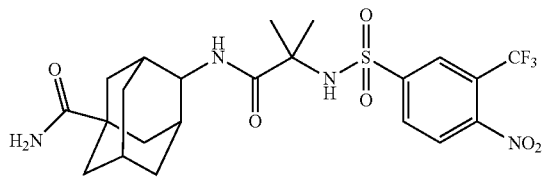 [SMILES: CC(C)(NS(=O)(=O)c1ccc([N+](=O)[O-])c(C(F)(F)F)c1)C(=O)NC1C2CC3CC1CC(C(N)=O)(C3)C2]

$^1$H NMR (400 MHz, DMSO-d$_6$) δ 8.53 (s, —NH—SO$_2$), 8.33 (m, 3H), 7.05 (d, J=7.6 Hz, —NH—CO—), 7.01 (br, NH$_2$—CO—), 6.75 (br, NH$_2$—CO—), 3.43 (d, J=7.6 Hz, 1H), 1.82-1.73 (m, 11H), 1.41 (m, 2H), 1.32 (s, 6H).

Preparation Example 33

Synthesis of N-4-(2-(3-nitro-4-methylphenylsulfonamido)-2-methylpropanamido)adamantane-1-carboxyamide (compound 114)

An aimed compound was obtained in the same manner as described in Preparation Example 1 of Example 2 except that 2-(3-nitro-4-methylphenylsulfonamido)-2-methylpropionic acid was used.

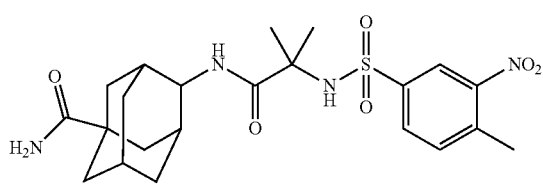 [SMILES: Cc1ccc(S(=O)(=O)NC(C)(C)C(=O)NC2C3CC4CC2CC(C(N)=O)(C4)C3)cc1[N+](=O)[O-]]

$^1$H NMR (400 MHz, DMSO-d$_6$) δ 8.36 (s, —NH—SO$_2$), 8.33 (d, J=2 Hz, 1H), 7.99 (dd, J=2, 8 Hz, 1H), 7.73 (d, J=8 Hz, 1H), 7.05 (d, J=7.2 Hz, —NH—CO—), 7.02 (br, NH$_2$—CO—), 6.76 (br, NH$_2$—CO—), 3.51 (d, J=6.8 Hz, 1H), 2.61 (s, 3H), 1.83-1.74 (m, 11H), 1.43 (m, 2H), 1.28 (s, 6H).

Preparation Example 34

Synthesis of N-4-(2-(3-fluoro-4-methoxyphenylsulfonamido)-2-methylpropanamido)adamantane-1-carboxyamide (compound 115)

An aimed compound was obtained in the same manner as described in Preparation Example 1 of Example 2 except that 2-(3-fluoro-4-methoxyphenylsulfonamido)-2-methylpropionic acid was used.

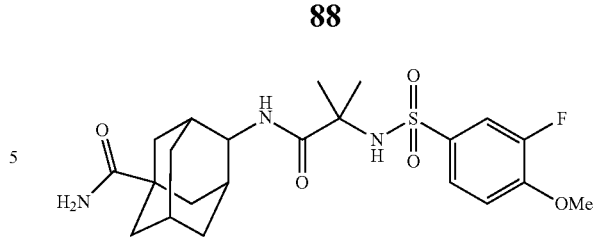

$^1$H NMR (400 MHz, DMSO-d$_6$) δ 8.13 (s, —NH—SO$_2$), 7.61 (dd, J=2, 7.6 Hz, 1H), 7.88 (dd, J=1.2, 7.6 Hz, 1H), 7.57 (m, 2H), 7.07 (d, J=7.6 Hz, —NH—CO—), 7.03 (br, NH$_2$—CO—), 6.77 (br, NH$_2$—CO—), 3.92 (s, 3H), 3.56 (d, J=6 Hz, 1H), 1.90-1.75 (m, 11H), 1.46 (m, 2H), 1.24 (s, 6H).

Preparation Example 35

Synthesis of N-4-(2-(2,3,4-trifluorophenylsulfonamido)-2-methylpropanamido)adamantane-1-carboxyamide (compound 116)

An aimed compound was obtained in the same manner as described in Preparation Example 1 of Example 2 except that 2-(2,3,4-trifluorophenylsulfonamido)-2-methylpropionic acid was used.

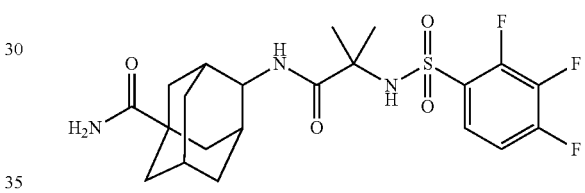

$^1$H NMR (400 MHz, DMSO-d$_6$) δ 8.63 (s, —NH—SO$_2$, 1H), 7.67 (s, 1H), 7.50 (s, 1H), 7.09 (s, —NH—CO—, 1H), 7.02 (s, NH$_2$—CO—, 1H), 6.76 (s, NH$_2$—CO—, 1H), 3.63 (s, 1H), 1.59-2.15 (m, 13H), 1.18 (s, 6H).

Preparation Example 36

Synthesis of N-4-(2-(3,5-difluorophenylsulfonamido)-2-methylpropanamido)adamantane-1-carboxyamide (compound 117)

An aimed compound was obtained in the same manner as described in Preparation Example 1 of Example 2 except that 2-(3,5-difluorophenylsulfonamido)-2-methylpropionic acid was used.


$^1$H NMR (400 MHz, DMSO-d$_6$) δ 8.37 (s, —NH—SO$_2$, 1H), 7.66 (t, 1H), 7.51 (d, 2H), 7.06 (d, —NH—CO—, 1H), 7.02 (s, NH$_2$—CO—, 1H), 6.76 (s, NH$_2$—CO—, 1H), 3.56 (s, 1H), 1.59-2.15 (m, 13H), 1.18 (s, 6H).

Preparation Example 37

Synthesis of N-4-(2-(3,4,5-trifluorophenylsulfonamido)-2-methylpropanamido)adamantane-1-carboxyamide (compound 118)

An aimed compound was obtained in the same manner as described in Preparation Example 1 of Example 2 except that 2-(3,4,5-trifluorophenylsulfonamido)-2-methylpropionic acid was used.

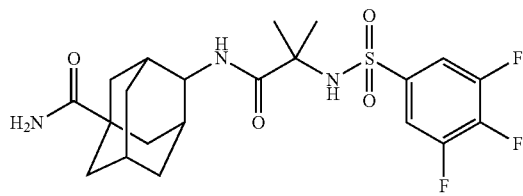 [SMILES: CC(C)(NS(=O)(=O)c1cc(F)c(F)c(F)c1)C(=O)NC1C2CC3CC1CC(C(N)=O)(C3)C2]

¹H NMR (400 MHz, DMSO-d₆) δ 8.36 (s, —NH—SO₂, 1H), 7.79 (t, 2H), 7.08 (d, —NH—CO—, 1H), 7.02 (s, NH₂—CO—, 1H), 6.76 (s, NH₂—CO—, 1H), 3.60 (s, 1H), 1.59-2.15 (m, 13H), 1.18 (s, 6H).

Preparation Example 38

Synthesis of N-(adamantane-2-yl)-2-methyl-2-(2,4-difluorophenylsulfonamido)propanamide (compound 119)

An aimed compound was obtained in the same manner as described in Preparation Example 1 of Example 2 except that 2-(2,4-difluorophenylsulfonamido)-2-methylpropionic acid was used.

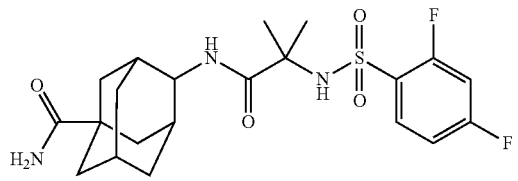 [SMILES: CC(C)(NS(=O)(=O)c1ccc(F)cc1F)C(=O)NC1C2CC3CC1CC(C(N)=O)(C3)C2]

¹H NMR (400 MHz, CDCl₃) δ 8.1 (d, J=3.2 Hz, 1H), 7.50 (d, J=3.2 Hz, 2H), 6.78 (s, —NH—CO—), 5.92 (s, —NH—SO₂), 4.00 (d, J=4 Hz, 1H), 1.65-1.95 (m, 14H), 1.44 (s, 6H).

Preparation Example 39

Synthesis of N-(adamantane-2-yl)-2-methyl-2-(2,5-difluorophenylsulfonamido)propanamide (compound 120)

An aimed compound was obtained in the same manner as described in Preparation Example 1 of Example 2 except that 2-(2,5-difluorophenylsulfonamido)-2-methylpropionic acid was used.

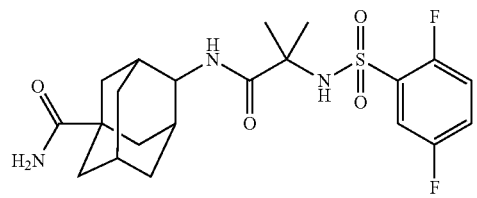

¹H NMR (400 MHz, DMSO-d₆) δ 8.54 (s, —NH—SO₂), 7.51-7.63 (m, 3H), 7.10 (d, J=7.2 Hz, —NH—CO—), 7.01 (s, —NH₂—CO), 6.74 (s, —NH₂—CO), 3.65 (d, J=7.2 Hz, 1H), 1.46-1.99 (m, 13H), 1.28 (s, 6H).

Preparation Example 40

Synthesis of N-(adamantane-2-yl)-2-methyl-2-(2,6-dichlorophenylsulfonamido)propanamide (compound 121)

An aimed compound was obtained in the same manner as described in Preparation Example 1 of Example 2 except that 2-(2,6-dichlorophenylsulfonamido)-2-methylpropionic acid was used.

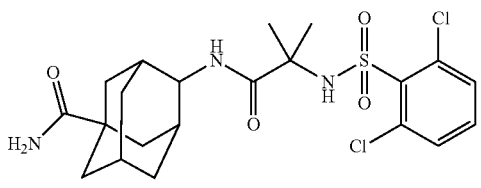 [SMILES: CC(C)(NS(=O)(=O)c1c(Cl)cccc1Cl)C(=O)NC1C2CC3CC1CC(C(N)=O)(C3)C2]

¹H NMR (400 MHz, DMSO-d₆) δ 8.56 (s, —NH—SO₂), 7.67 (m, 2H), 7.56 (m, 1H), 7.21 (br, —NH—CO—), 7.04 (br, NH₂—CO—), 6.77 (br, NH₂—CO—), 3.77 (d, J=6 Hz, 1H), 1.95-1.78 (m, 11H), 1.49 (m, 2H), 1.27 (s, 6H).

Preparation Example 41

Synthesis of N-(adamantane-2-yl)-2-methyl-2-(3,5-dichlorophenylsulfonamido)propanamide (compound 122)

An aimed compound was obtained in the same manner as described in Preparation Example 1 of Example 2 except that 2-(3,5-dichlorophenylsulfonamido)-2-methylpropionic acid was used.

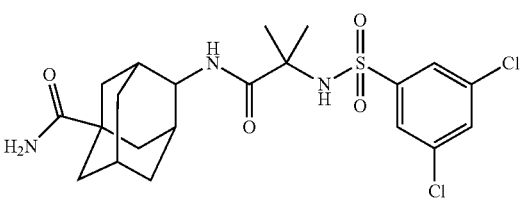 [SMILES: CC(C)(NS(=O)(=O)c1cc(Cl)cc(Cl)c1)C(=O)NC1C2CC3CC1CC(C(N)=O)(C3)C2]

¹H NMR (400 MHz, DMSO-d₆) δ 8.33 (s, —NH—SO₂), 7.97 (t, J=1.6 Hz, 1H), 7.76 (d, J=2 Hz, 2H), 7.02 (br, —NH—CO—), 7.01 (br, NH₂—CO—), 6.75 (br, NH₂—CO—), 3.49 (d, J=6.4 Hz, 1H), 1.89-1.74 (m, 11H), 1.43 (m, 2H), 1.31 (s, 6H).

Preparation Example 42

Synthesis of N-(adamantane-2-yl)-2-methyl-2-(3-bromophenylsulfonamido)propanamide (compound 123)

An aimed compound was obtained in the same manner as described in Preparation Example 1 of Example 2 except that 2-(3-bromophenylsulfonamido)-2-methylpropionic acid was used.

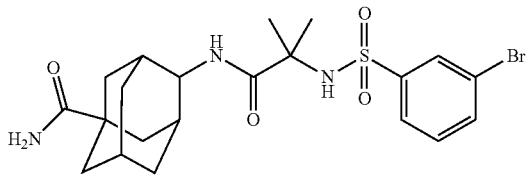 [SMILES: CC(C)(NS(=O)(=O)c1cccc(Br)c1)C(=O)NC1C2CC3CC1CC(C(N)=O)(C3)C2]

$^1$H NMR (400 MHz, DMSO-d$_6$) δ 8.27 (s, —NH—SO$_2$), 7.93 (t, J=1.6 Hz, 1H), 7.87 (m, 1H), 7.79 (m, 1H), 7.55 (t, J=7.6 Hz, 1H), 7.05 (d, J=6.8 Hz, 1H), 7.05 (d, J=6.8 Hz, —NH—CO—), 7.01 (br, NH$_2$—CO—), 6.75 (br, NH$_2$—CO—), 3.52 (d, J=6.4 Hz, 1H), 1.90-1.75 (m, 11H), 1.44 (m, 2H), 1.27 (s, 6H).

Preparation Example 43

Synthesis of N-(adamantane-2-yl)-2-methyl-2-(4-bromophenylsulfonamido)propanamide (compound 124)

An aimed compound was obtained in the same manner as described in Preparation Example 1 of Example 2 except that 2-(4-bromophenylsulfonamido)-2-methylpropionic acid was used.

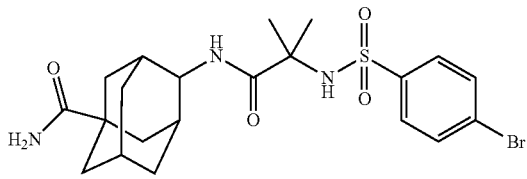

$^1$H NMR (400 MHz, DMSO-d$_6$) δ 8.25 (s, —NH—SO$_2$), 7.80 (m, 2H), 7.72 (m, 2H), 7.05 (d, J=7.2 Hz, —NH—CO—), 7.01 (br, NH$_2$—CO—), 6.75 (br, NH$_2$—CO—), 3.54 (d, J=6.8 Hz, 1H), 1.91-1.74 (m, 11H), 1.45 (m, 2H), 1.25 (s, 6H).

Preparation Example 44

Synthesis of N-(adamantane-2-yl)-2-methyl-2-(5-chloro-3-bromophenylsulfonamido)propanamide (compound 125)

An aimed compound was obtained in the same manner as described in Preparation Example 1 of Example 2 except that 2-(5-chloro-3-bromophenylsulfonamido)-2-methylpropionic acid was used.

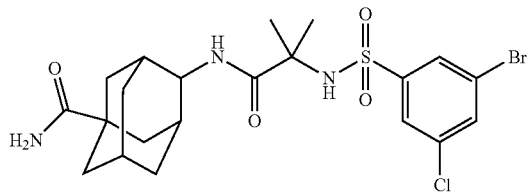

$^1$H NMR (400 MHz, DMSO-d$_6$) δ 8.46 (s, —NH—SO$_2$), 8.02 (m, 1H), 7.89 (m, 1H), 7.76 (m, 1H), 7.16 (d, J=6.4 Hz, —NH—CO—), 7.03 (br, NH$_2$—CO—), 6.76 (br, NH$_2$—CO—), 3.74 (d, J=6.8 Hz, 1H), 1.93-1.76 (m, 11H), 1.47 (m, 2H), 1.22 (s, 6H).

Preparation Example 45

Synthesis of N-(adamantane-2-yl)-2-methyl-2-(4-trifluoromethylphenylsulfonamido)propanamide (compound 126)

An aimed compound was obtained in the same manner as described in Preparation Example 1 of Example 2 except that 2-(4-trifluoromethylphenylsulfonamido)-2-methylpropionic acid was used.

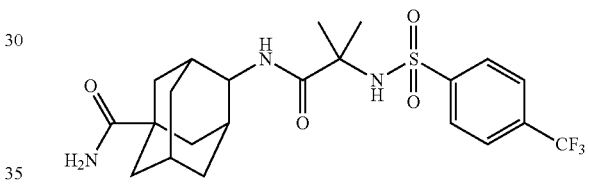

$^1$H NMR (400 MHz, DMSO-d$_6$) δ 8.04 (d, 2H), 7.81 (d, J=8.0 Hz, 2H), 6.68 (d, J 7.2 Hz, —NH—CO—), 5.57 (m, —NH$_2$—CO—, —NH—SO$_2$, 2H), 5.22 (s, —NH—SO$_2$), 3.98 (d, J=8.0 Hz, 1H), 1.64-2.12 (m, 13H), 1.47 (s, 6H).

Preparation Example 46

Synthesis of N-(adamantane-2-yl)-2-methyl-2-(3-trifluoromethylphenylsulfonamido)propanamide (compound 127)

An aimed compound was obtained in the same manner as described in Preparation Example 1 of Example 2 except that 2-(3-trifluoromethylphenylsulfonamido)-2-methylpropionic acid was used.

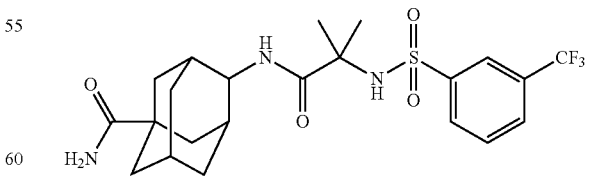

$^1$H NMR (400 MHz, DMSO-d$_6$) δ 8.18 (s, 1H), 8.11 (d, J=8.0 Hz, 1H), 7.87 (d, J=8.0 Hz, 1H), 7.71 (t, J=8.0 Hz, 1H), 6.72 (d, J=8.0 Hz, —NH—CO—), 5.59 (s, —NH$_2$—CO—, 1H), 5.54 (s, —NH—SO$_2$), 5.27 (s, —NH$_2$—CO—, 1H), 3.99 (d, J=8.0 Hz, 1H), 1.65-2.10 (m, 13H), 1.47 (s, 6H).

Preparation Example 47

Synthesis of N-(adamantane-2-yl)-2-methyl-2-(4-nitro-2-methoxyphenylsulfonamido)propanamide (compound 128)

An aimed compound was obtained in the same manner as described in Preparation Example 1 of Example 2 except that 2-(4-nitro-2-methoxyphenylsulfonamido)-2-methylpropionic acid was used.

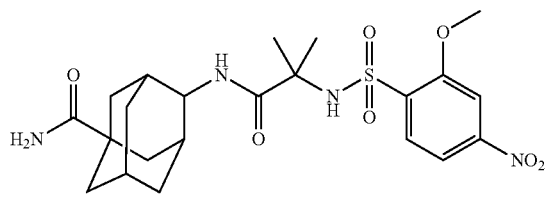 [SMILES: COc1cc([N+](=O)[O-])ccc1S(=O)(=O)NC(C)(C)C(=O)NC1C2CC3CC1CC(C(N)=O)(C3)C2]

$^1$H NMR (400 MHz, DMSO-d$_6$) δ 8.17 (s, —NH—SO$_2$, 1H), 7.98 (m, 2H), 7.91 (dd, 1H), 7.21 (d, —NH—CO—, 1H), 7.02 (s, NH$_2$—CO—, 1H), 6.76 (s, NH$_2$—CO—, 1H), 4.08 (s, 1H), 3.72 (s, 1H), 1.21-1.92 (m, 13H), 1.21 (s, 6H).

Preparation Example 48

Synthesis of N-(adamantane-2-yl)-2-methyl-2-(2,4-dimethoxyphenylsulfonamido)propanamide (compound 129)

An aimed compound was obtained in the same manner as described in Preparation Example 1 of Example 2 except that 2-(2,4-dimethoxyphenylsulfonamido)-2-methylpropionic acid was used.

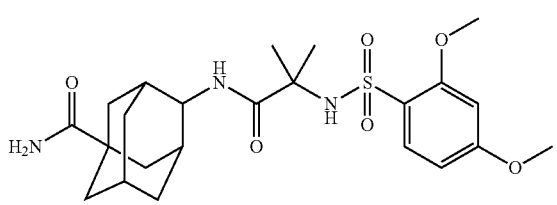 [SMILES: COc1ccc(S(=O)(=O)NC(C)(C)C(=O)NC2C3CC4CC2CC(C(N)=O)(C4)C3)c(OC)c1]

$^1$H NMR (400 MHz, DMSO-d$_6$) δ 7.68 (s, —NH—SO$_2$, 1H), 7.62 (d, 1H), 7.29 (d, —NH—CO—, 1H), 7.03 (s, NH$_2$—CO—, 1H), 6.76 (s, NH$_2$—CO—, 1H), 6.72 (d, 1H), 6.61 (dd, 1H), 3.91 (s, 3H), 3.84 (s, 3H), 3.71 (s, 1H), 1.23-1.99 (m, 13H), 1.17 (s, 6H).

Example 3

Preparation Example 1

Synthesis of 4-[2-(2-cyano-benzenesulfonylamino)-2-methyl-propionylamino]-adamantane-1-carboxylic acid amide (compound 130)

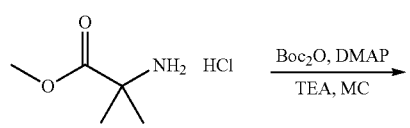

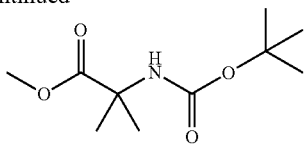

In a 100-mL flask, methyl-2-amino-2-methylpropanoate hydrochloride (1.0 g, 6.53 mmol) and methylenechloride (50 mL) were charged, and then completely dissolved through addition of pyridine (1.1 mL, 13.0 mmol), and dimethylaminopyridine (1.6 g, 13.0 mmol). The resultant solution was slowly added with di-tributoxy carbonyl (2.9 g, 13.0 mmol) at room temperature, and stirred for 12 hours to bring the reaction to an end. At 35° C., through concentration, the solvent was removed. The resultant product was added with purified water (30 mL), and neutralized with 2N hydrochloric acid aqueous solution. The product was extracted with methylenechloride (50 mL) in an aqueous solution twice, and moisture in the organic layer was removed by addition of magnesium sulfate. After filtering, through vacuum evaporation, the solvent was removed so as to obtain methyl-2-aminobutoxycarbonyl-2-methylpropanoate (327 mg, 23%).

$^1$H NMR (400 MHz, DMSO-d$_6$) δ 3.75 (s, 3H), 1.5 (s, 6H), 1.46 (s, C$_3$H$_9$—O—, 9H)

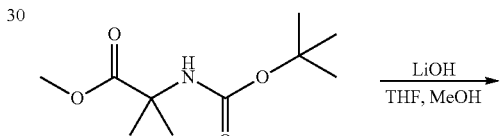

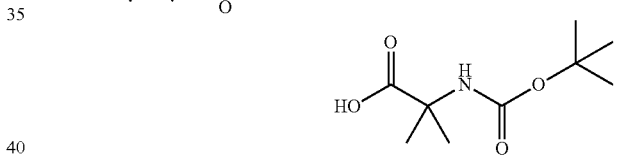

In a 50-mL flask, methyl-2-aminobutoxycarbonyl-2-methylpropanoate (327 mg, 1.50 mmol) was charged, and dissolved through addition of tetrahydrofuran (15 ml), and methanol (15 ml). Lithium hydroxide dissolved in purified water (15 ml) was added thereto, followed by stirring for 12 hours at room temperature. After stirring for 12 hours, the resultant solution was vacuum-evaporated, neutralized with 2N-hydrochloric acid aqueous solution, and extracted with ethyl acetate (20 mL). The organic layer was dried with magnesium sulfate, and filtered. Through vacuum distillation, the solvent was removed so as to obtain methyl-2-aminobutoxycarbonyl-2-methylpropanoic acid compound (335 mg, 99%).

$^1$H NMR (400 MHz, DMSO-d$_6$) δ 12.1 (s, HO—CO—, 1H), 7.05 (s, —NH—CO$_2$—, 1H), 1.40 (s, C$_3$H$_9$—O—, 9H), 1.25 (s, 6H).

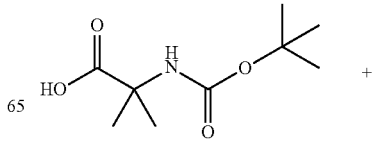

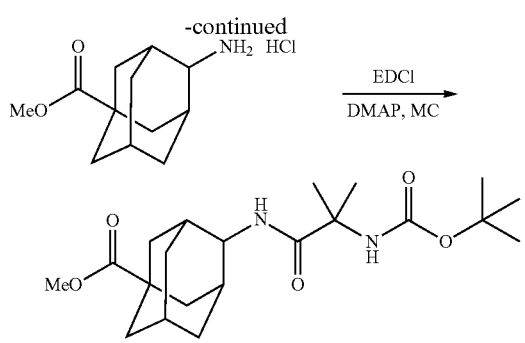

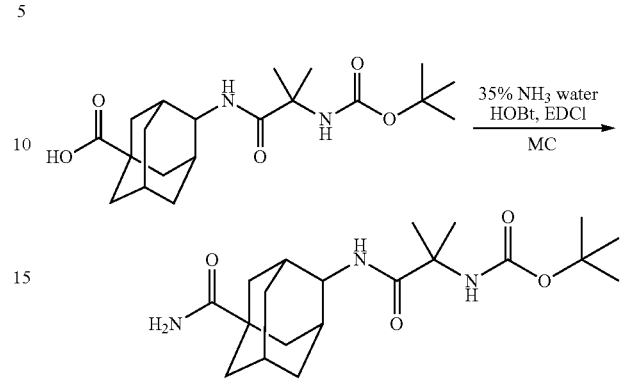

¹H NMR (400 MHz, DMSO-d₆) δ 12.1 (s, HO—CO₂—, 1H), 7.04 (s, —NH—CO₂—, 1H), 6.96 (s, —NH—CO—, 1H), 3.71 (d, 1H), 1.43-1.99 (m, 13H), 1.38 (s, C₃H₉—CO₂—, 9H), 1.71 (s, 6H)

In a 50-mL flask, methyl-2-aminobutoxycarbonyl-2-methylpropanoic acid (335 mg, 1.746 mmol), and methylenechloride (20 mL) were charged, and then 1-ethyl-3-(3-dimethylaminopropyl)carbodiimidehydrochloride (914 mg, 4.77 mmol) and dimethylaminopyridine (388 mg, 3.18 mmol) were sequentially charged, followed by stirring for 5 minutes at room temperature. The resultant solution was added with 2-adamantanamine hydrochloride (388 mg, 1.589 mmol), followed by stirring for 12 hours at room temperature. After the reaction was completed, purified water (20 mL) was added thereto, and the aqueous solution layer was washed with methylenechloride (30 mL) twice. The obtained organic layer was added with magnesium sulfate so as to remove remaining moisture. Through filtering and vacuum evaporation, the residue was obtained. The mixture was purified with column chromatography (EA/n-Hex=1:2) so as to obtain 4-(2-methyl-2-(butoxycarbonylamido)propanamido)adamantane-1-carboxylate (434 mg, 62%).

¹H NMR (400 MHz, DMSO-d₆) δ 5.31 (s, —NH—CO₂—, 1H), 4.91 (s, —NH—CO—, 1H), 3.99 (s, 1H), 3.74 (s, CH₃—CO₂—, 3H), 1.57-2.03 (m, 13H), 1.50 (s, 6H), 1.45 (s, C₃H₉—CO₂—, 9H)

In a 50-mL flask, 4-(2-methyl-2-(butoxycarbonylamido)propanamido)adamantane-1-carboxylic acid (170 mg, 0.449 mmol) and methylenechloride (20 mL) were charged, and sequentially, 1-ethyl-3-(3-dimethylaminopropyl)carbodiimidehydrochloride (171 mg, 0.893 mmol) and 1-hydroxybenzotriazol (120 mg, 3.18 mmol) were charged, followed by stirring for 5 minutes at room temperature. The resultant solution was added with 35% ammonia aqueous solution (2.5 mL), followed by stirring for 12 hours at room temperature. After the reaction was completed, purified water (10 mL) was added thereto, and the aqueous solution layer was washed with methylenechloride (30 mL) twice. The obtained organic layer was added with magnesium sulfate so as to remove remaining moisture. Through filtering and vacuum evaporation, the residue was obtained. The mixture was purified with column chromatography (MC/MeOH=15:1) so as to obtain 4-(2-methyl-2-(butoxycarbonylamido)propanamido)adamantane-1-carboxylic acid amide (151 mg, 89%).

¹H NMR (400 MHz, DMSO-d₆) δ 6.97-7.01 (m, —NH—CO₂—, —NH—CO—, NH₂—CO—, 3H), 6.74 (s, NH₂—CO—, 1H), 1.73-1.92 (m, 13H), 1.44 (s, C₃H₉—CO₂—, 9H), 1.09 (s, 6H).

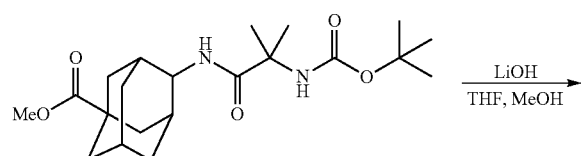

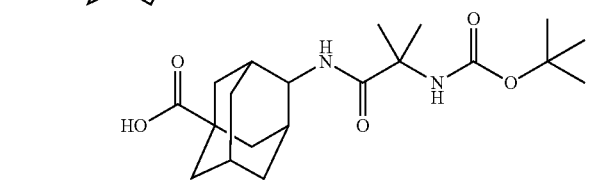

In a 50-mL flask, 4-(2-methyl-2-(butoxycarbonylamido)propanamido)adamantane-1-carboxylate (430 mg, 1.09 mmol) was charged, and dissolved through addition of tetrahydrofuran (15 ml), and methanol (15 ml). Lithium hydroxide dissolved in purified water (15 ml) was added thereto, followed by stirring for 12 hours at room temperature. After stirring for 12 hours, the resultant solution was vacuum-evaporated, neutralized with 2N hydrochloric acid aqueous solution, and extracted with ethyl acetate (30 ml). The organic layer was dried with magnesium sulfate, and filtered. Through vacuum distillation, the solvent was removed so as to obtain 4-(2-methyl-2-(butoxycarbonylamido)propanamido)adamantane-1-carboxylic acid compound (172 mg, 41%).

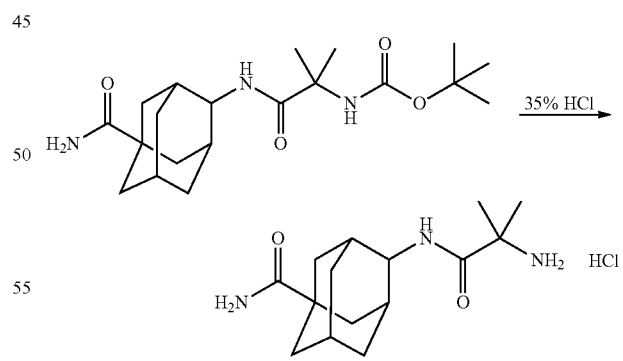

In a 25-mL flask, 4-(2-methyl-2-(butoxycarbonylamido)propanamido)adamantane-1-carboxylic acid amide (150 mg, 0.395 mmol) and 35% hydrochloric acid aqueous solution were charged, followed by stirring at room temperature for 4 hours. After the reaction was completed, at 50° C., through vacuum evaporation, N-(5-acetyl-adamantane-2-enyl)-2-amino-2-methyl-propionamide (140 mg) was obtained as a residue.

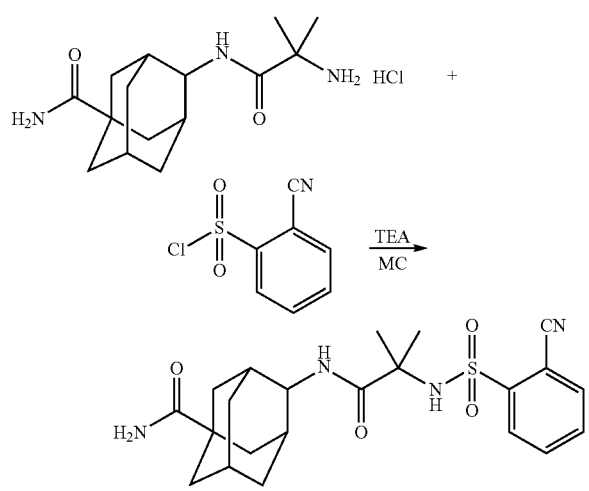

After concentration, in the 25-mL flask, N-(5-acetyl-adamantane-2-enyl)-2-amino-2-methyl-propionamide (140 mg) and methylenechloride (20 mL) were charged, and triethylamine (0.27 mL, 1.97 mmol) was charged, followed by stirring at room temperature for 30 minutes. 2-cyano-benzenesulfonylchloride (96 mg, 0.474 mmol) was added thereto, followed by stirring for 12 hours at room temperature. Then, purified water (10 ml) was added thereto to bring the reaction to an end. The organic layer was separated, and washed with saturated ammonium chloride solution (15 ml). Then, the washed organic layer was separated, and added with magnesium sulfate so as to remove remaining moisture. Then, through filtering and vacuum distillation, the solvent was removed so as to obtain the residue. The mixture was purified with column chromatography (MC/MeOH=15:1) so as to obtain 4-[2-(2-cyano-benzenesulfonylamino)-2-methyl-propionylamino]-adamantane-1-carboxylic acid amide (70 mg, 40%).

$^1$H NMR (400 MHz, DMSO-$d_6$) δ 8.59 (s, —NH—SO$_2$, 1H), 8.13 (dd, 1H), 8.05 (dd, 1H), 7.93 (td, 1H), 7.81 (td, 1H), 7.25 (d, —NH—CO—, 1H), 7.03 (s, NH$_2$—CO—, 1H), 6.75 (s, NH$_2$—CO—, 1H), 3.20 (s, 1H), 1.59-2.15 (m, 13H), 1.22 (s, 6H).

Example 4

Preparation Example 1

Synthesis of N-4-(1-(2-bromophenylsulfonamido) cyclopropanecarboxyamido)adamantane-1-carboxyamide (compound 131)

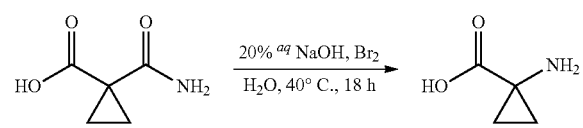

1-carbamoylcyclopropanecarboxylic acid (3.97 g, 30.76 mmol) was added with 20% NaOH (6.15 g, 153.82 mmol) aqueous solution at 0° C., followed by stirring for 10 minutes. The mixture was slowly added with bromine (1.7 ml, 33.84 mmol), and heated up to 40° C., followed by stirring for 18 h. The resultant mixture was adjusted with CONC. HCl to pH 5.4 at 0° C., and concentrated. The concentrated precipitate was washed with acetic acid while filtered (×2). The solution obtained after the filtering was concentrated. The resultant precipitate was added with ethanol, crystallized at 0° C., and filtered. Through vacuum distillation, the solvent was removed to obtain 1-aminocyclopropanecarboxylic acid (1.46 g, 30.76 mmol, 47%).

$^1$H NMR (400 MHz, D$_2$O) δ 1.05 (dd, J=1.2, 5.6 Hz, 2H), 1.59 (dd, J=1.2, 5.2 Hz, 2H).

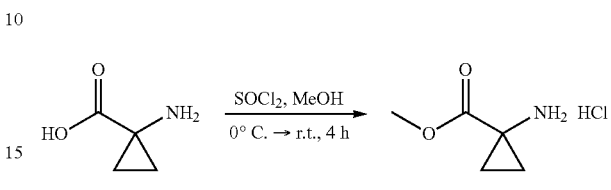

1-aminocyclopropanecarboxylic acid (1.46 g, 14.45 mmol) and methanol (50 ml) were charged. An ice bath was set and thionyl chloride (2.6 ml, 36.12 mmol) was slowly added thereto. Then, the ice bath was removed, and the mixture was stirred at room temperature for 4 hours. The resultant product was vacuum-distilled to remove a solvent, and dried in a 60° C. oven so as to obtain methyl-1-aminocyclopropanecarboxylate hydrochloride (2.08 g, 13.72 mmol, 98%).

$^1$H NMR (400 MHz, DMSO-$d_6$) δ 8.99 (br, 3H), 3.72 (s, 3H), 1.46 (m, 1H), 1.41 (m, 2H), 1.38 (m, 1H).

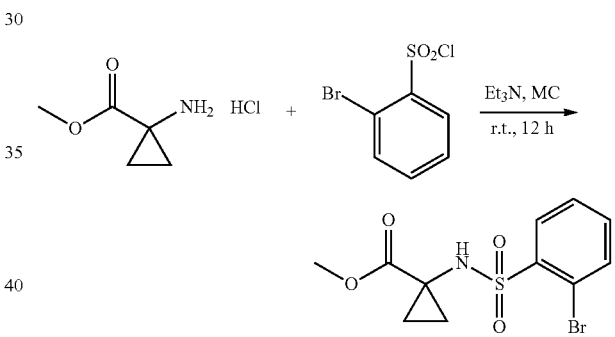

methyl-1-aminocyclopropanecarboxylate hydrochloride (300 mg, 1.979 mmol) was dissolved in CH$_2$Cl$_2$ (7 ml), added with 2-bromobenzene-1-sulfonyl chloride (550 mg, 2.17 mmol) and triethylamine (1.1 ml, 7.92 mmol), and stirred at room temperature for 12 hours. The resultant solution was added with H$_2$O, extracted with CH$_2$Cl$_2$ (×2), dried with MgSO$_4$, and filtered. Through vacuum distillation, the solvent was removed. The resultant mixture was purified with column chromatography so as to obtain methyl-1-(2-bromophenylsulfonamido)cyclopropanecarboxylate (560 mg, 1.68 mmol, 85%).

$^1$H NMR (400 MHz, CDCl$_3$) δ 8.09 (dd, J=2, 7.6 Hz, 1H), 7.78 (dd, J=1.2, 7.6 Hz, 1H), 7.45 (m, 2H), 5.99 (s, —NH—SO$_2$), 1.49 (m, 2H), 1.44 (m. 2H).

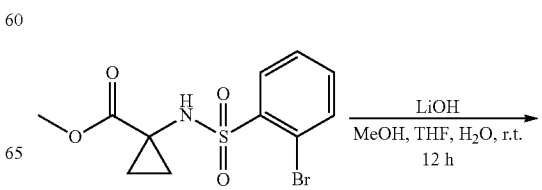

-continued

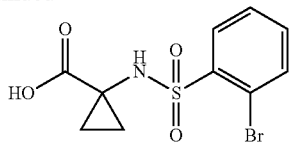

methyl-1-(2-bromophenylsulfonamido)cyclopropanecarboxylate (500 mg, 1.49 mmol) was charged, and dissolved through addition of THF (3 ml), and methanol (3 ml). LiOH.H₂O dissolved in H₂O (3 ml) was added thereto, followed by stirring for 12 hours at room temperature. After stirring for 12 hours, the resultant solution was vacuum-evaporated, acidified with 2N—HCl to pH 2-3, and extracted with EA (×2). The organic layer was dried with MgSO₄, and filtered. Through vacuum distillation, the solvent was removed so as to obtain 1-(2-bromophenylsulfonamido)cyclopropanecarboxylic acid (469 mg, 1.46 mmol, 98%).

¹H NMR (400 MHz, DMSO-d₆) δ 12.51 (bs, —COOH), 8.82 (s, —NH—SO₂), 7.94 (dd, J=2, 8 Hz, 1H), 7.81 (dd, J=1.2, 7.6 Hz, 1H), 7.53 (m, 2H), 1.23 (q, J=4.8, 2H), 0.94 (q, J=4.4 Hz, 2H).

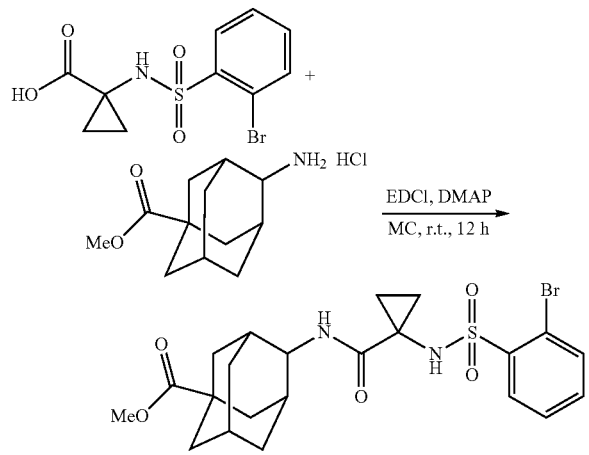

1-(2-bromophenylsulfonamido)cyclopropanecarboxylic acid (208 mg, 0.65 mmol), 4-amino-adamantane-1-carboxylate hydrochloride (176 mg, 0.71 mmol), and EDCI (375 mg, 1.95 mmol) were charged, and CH₂Cl₂ (4 ml) was added thereto, followed by stirring for 30 minutes at room temperature. DMAP (160 mg, 1.30 mmol) was added thereto, followed by stirring at room temperature for 12 hours. After the reaction was completed, the organic layer was separated using CH₂Cl₂ and H₂O, dried with MgSO₄, and filtered. Then, through vacuum distillation, the solvent was removed, and the resultant product was purified with column chromatography to obtain N-methyl-4-(1-(2-bromophenylsulfonamido)cyclopropanecarboxyamido)adamantane-1-carboxylate (299 mg, 0.58 mmol, 90%).

(1s,3R,5S,7s)-4-(1-(2-bromophenylsulfonamido)cyclopropanecarboxyamido) adamantane-1-carboxylic acid

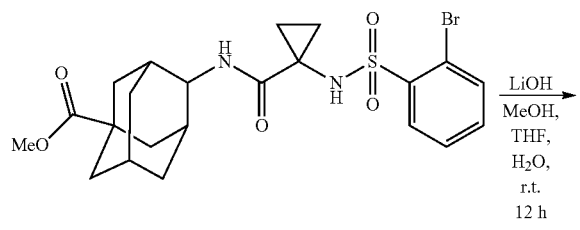

N-methyl-4-(1-(2-bromophenylsulfonamido)cyclopropanecarboxyamido)adamantane-1-carboxylate (241 mg, 0.47 mmol) was charged, and dissolved through addition of THF (4 ml), and methanol (4 ml). LiOH.H₂O dissolved in H₂O (4 ml) was added thereto, followed by stirring for 12 hours at room temperature. After stirring for 12 hours, the resultant solution was vacuum-evaporated, acidified with 2N—HCl to pH 2-3 and extracted with EA (×2). The organic layer was dried with MgSO₄, and filtered. Through vacuum distillation, the solvent was removed so as to obtain N-methyl-4-(1-(2-bromophenylsulfonamido)cyclopropanecarboxyamido)adamantane-1-carboxylic acid (229 mg, 0.46 mmol, 98%).

¹H NMR (400 MHz, DMSO-d₆) δ 12.15 (bs, —COOH), 9.15 (s, —NH—SO₂), 8.01 (dd, J=2.4, 7.6 Hz, 1H), 7.87 (dd, J=1.6, 7.6 Hz, 1H), 7.59 (m, 2H), 7.29 (d, J=7.6 Hz, —NH—CO—), 3.75 (d, J=7.2 Hz, 1H), 1.99-1.82 (m, 11H), 1.53 (m, 2H), 1.11 (q, J=4 Hz, 2H), 0.67 (q, J=4.4 Hz, 2H).

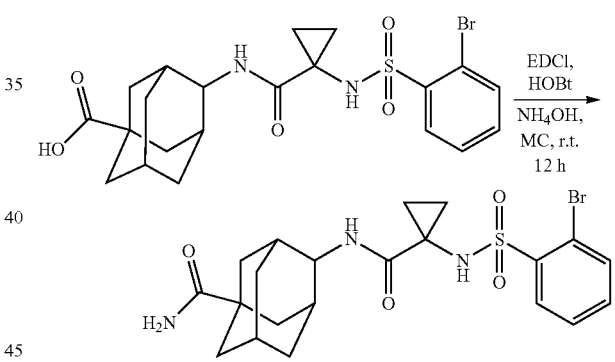

N-methyl-4-(1-(2-bromophenylsulfonamido)cyclopropanecarboxyamido)adamantane-1-carboxylic acid (222 mg, 0.45 mmol) was dissolved in CH₂Cl₂ (8 ml), and added with EDCI (171 mg, 0.89 mmol) and HOBT (121 mg, 0.89 mmol), followed by stirring for 30 minutes. 30% NH₄OH aqueous solution (4 ml) was added thereto, followed by stirring at room temperature for 12 hours. The resultant solution was added with H₂O, extracted with CH₂Cl₂ (×3), dried with MgSO₄, and filtered. Through vacuum distillation, the solvent was removed. The resultant mixture was purified with column chromatography so as to obtain N-methyl-4-(1-(2-bromophenylsulfonamido)cyclopropanecarboxyamido)adamantane-1-carboxyamide (177 mg, 0.36 mmol, 80%).

¹H NMR (400 MHz, DMSO-d₆) δ 9.15 (s, —NH—SO₂), 8.01 (dd, J=2, 7.6 Hz, 1H), 7.88 (dd, J=1.2, 7.2 Hz, 1H), 7.58 (m, 2H), 7.29 (d, J=7.6 Hz, —NH—CO—), 7.03 (br, NH₂—CO—), 6.77 (br, NH₂—CO—), 3.76 (d, J=7.2 Hz, 1H), 1.95-1.78 (m, 11H), 1.49 (m, 2H), 1.12 (q, J=4.4 Hz, 2H), 0.67 (q, J=4 Hz, 2H).

Preparation Example 2

Synthesis of N-4-(1-(2-chlorophenylsulfonamido)cyclopropanecarboxyamido)adamantane-1-carboxyamide (compound 132)

An aimed compound was obtained in the same manner as described in Preparation Example 1 of Example 4 except that 1-(2-chlorophenylsulfonamido)cyclopropanecarboxylic acid was used.

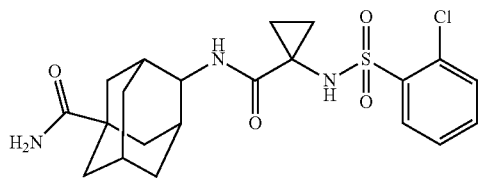

$^1$H NMR (400 MHz, DMSO-$d_6$) δ 9.27 (s, —NH—SO$_2$), 7.97 (d, J=7.2 Hz, 1H), 7.65 (m, 2H), 7.57 (m, 1H), 7.31 (d, J=7.2 Hz, —NH—CO—), 7.03 (br, NH$_2$—CO—), 6.76 (br, NH$_2$—CO—), 3.75 (d, J=6.8 Hz, 1H), 1.98-1.67 (m, 12H), 1.52 (m, 2H), 1.12 (q, J=4.4 Hz, 2H), 0.71 (q, J=4 Hz, 2H).

Preparation Example 3

Synthesis of N-4-(1-(2-methyl-3-chlorophenylsulfonamido)cyclopropanecarboxyamido)adamantane-1-carboxyamide (compound 133)

An aimed compound was obtained in the same manner as described in Preparation Example 1 of Example 4 except that 1-(2-methyl-3-chlorophenylsulfonamido)cyclopropanecarboxylic acid was used.

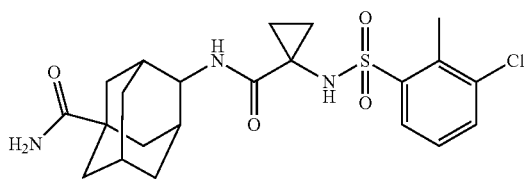

$^1$H NMR (400 MHz, DMSO-$d_6$) δ 9.14 (s, —NH—SO$_2$), 7.82 (dd, J=1.2, 8 Hz, 1H), 7.78 (m, 1H), 7.44 (t, J=8 Hz, 1H), 7.20 (d, J=7.6 Hz, —NH—CO—), 7.03 (br, NH$_2$—CO—), 6.76 (br, NH$_2$—CO—), 3.72 (d, J=7.6 Hz, 1H), 2.77 (s, 3H), 1.94-1.76 (m, 11H), 1.48 (m, 2H), 1.13 (q, J=4.4 Hz, 2H), 0.76 (q, J=4.4 Hz, 2H).

Preparation Example 4

Synthesis of N-4-(1-(2,6-dichlorophenylsulfonamido)cyclopropanecarboxyamido)adamantane-1-carboxyamide (compound 134)

An aimed compound was obtained in the same manner as described in Preparation Example 1 of Example 4 except that 1-(2,6-dichlorophenylsulfonamido)cyclopropanecarboxylic acid was used.

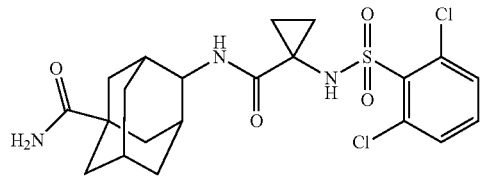 [SMILES: NC(=O)C12CC3CC(C1)C(NC(=O)C1(NS(=O)(=O)c4c(Cl)cccc4Cl)CC1)C(C3)C2]

$^1$H NMR (400 MHz, DMSO-$d_6$) δ 9.37 (s, —NH—SO$_2$), 7.68 (m, 2H), 7.58 (m, 1H), 7.20 (d, J=7.2 Hz, —NH—CO—), 7.03 (br, NH$_2$—CO—), 6.77 (br, NH$_2$—CO—), 3.75 (d, J=7.6 Hz, 1H), 1.95-1.77 (m, 11H), 1.51 (m, 2H), 1.19 (q, J=4.8 Hz, 2H), 0.73 (q, J=4.4 Hz, 2H).

Preparation Example 5

Synthesis of N-4-(1-(quinoline-8-sulfonamido)cyclopropanecarboxyamido)adamantane-1-carboxyamide (compound 135)

An aimed compound was obtained in the same manner as described in Preparation Example 1 of Example 4 except that 1-(quinoline-8-sulfonamido)cyclopropanecarboxylic acid was used.

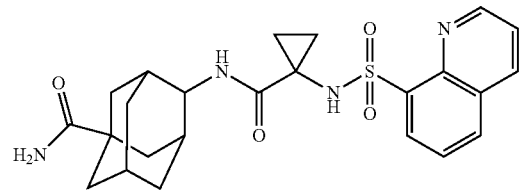

$^1$H NMR (400 MHz, DMSO-$d_6$) δ 9.07 (dd, J=2, 4.4 Hz, 1H), 8.65 (s, —NH—SO$_2$), 8.56 (dd, J=1.6, 8.4 Hz, 1H), 8.32 (m, 2H), 7.53 (m, 2H), 7.35 (d, J=8 Hz, —NH—CO—), 7.02 (br, NH$_2$—CO—), 6.76 (br, NH$_2$—CO—), 3.67 (d, J=7.6 Hz, 1H), 1.88-1.75 (m, 11H), 1.43 (m, 2H), 1.07 (q, J=4.4 Hz, 2H), 0.63 (q, J=4 Hz, 2H).

Preparation Example 6

Synthesis of N-4-(1-(2,3-dichlorophenylsulfonamido)cyclopropanecarboxyamido)adamantane-1-carboxyamide (compound 136)

An aimed compound was obtained in the same manner as described in Preparation Example 1 of Example 4 except that 2-(2,3-dichlorophenylsulfonamido)cyclopropanecarboxylic acid was used.

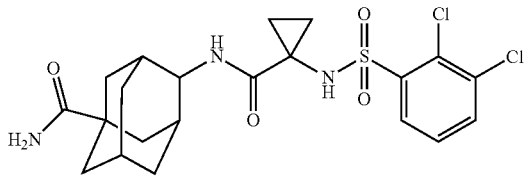

$^1$H NMR (400 MHz, DMSO-$d_6$) δ 7.95 (m, 2H), 7.62 (s, —NH—SO$_2$), 7.56 (t, J=8 Hz, 1H), 7.29 (d, J=8 Hz, —NH—CO—), 7.02 (br, NH$_2$—CO—), 6.76 (br, NH$_2$—CO—), 3.71

(d, J=7.6 Hz, 1H), 1.93-1.77 (m, 11H), 1.48 (m, 2H), 1.12 (q, J=4.4 Hz, 2H), 0.76 (q, J=4.4 Hz, 2H).

Example 5

Preparation Example 1

Synthesis of N-(adamantane-2-yl)-1-(2-nitrophenyl-sulfonamido)cyclobutanecarboxyamide (compound 137)

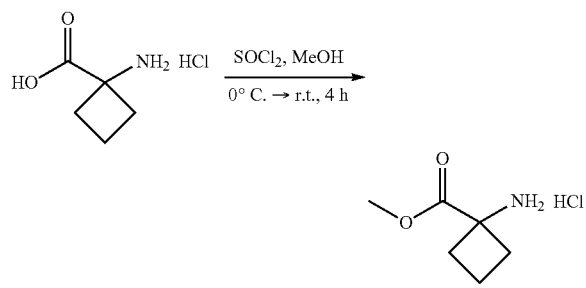

1-aminocyclobutanecarboxylic acid hydrochloride (5.2 g, 34.5 mmol) and methanol (120 ml) were charged. An ice bath was set, and thionyl chloride (3.7 ml, 51.7 mmol) was slowly added thereto. Then, the ice bath was removed, and the mixture was stirred at room temperature for 3 hours. The resultant product was vacuum-distilled to remove a solvent, and dried in a 60° C. oven so as to obtain methyl-1-aminocyclobutanecarboxylate hydrochloride (5.62 g, 37.1 mmol, 98%).

$^1$H NMR (400 MHz, DMSO-d$_6$) δ 8.94 (br, 3H), 3.79 (s, 3H), 2.47 (m, 4H), 2.07 (m, 2H).

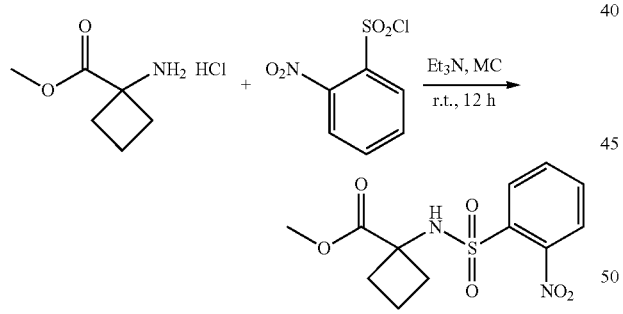

methyl-1-aminocyclobutanecarboxylate hydrochloride (300 mg, 1.81 mmol) was dissolved in CH$_2$Cl$_2$ (7 ml), and added with 2-nitrobenzene-1-sulfonyl chloride (441 mg, 1.99 mmol) and triethylamine (1 ml, 7.24 mmol), followed by stirring at room temperature for 12 hours. The resultant solution was added with H$_2$O, extracted with CH$_2$Cl$_2$ (×2), dried with MgSO$_4$, and filtered. Through vacuum distillation, the solvent was removed. The resultant mixture was purified with column chromatography so as to obtain methyl-1-(2-nitrophenylsulfonamido)cyclobutanecarboxylate (512 mg, 1.63 mmol, 90%).

$^1$H NMR (400 MHz, DMSO-d$_6$) δ 18.03 (m, 1H), 7.95 (m, 1H), 7.75 (m, 2H), 6.14 (s, —NH—SO$_2$), 3.48 (s, 3H), 2.61 (m, 2H), 2.51 (m, 2H), 2.03 (m, 2H).

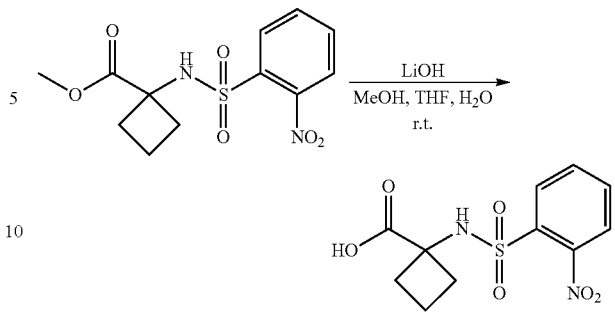

methyl-1-(2-nitrophenylsulfonamido)cyclobutanecarboxylate (500 mg, 1.59 mmol) was charged, and dissolved through addition of THF (5 ml), and methanol (5 ml). LiOH.H$_2$O dissolved in H$_2$O (5 ml) was added thereto, followed by stirring for 12 hours at room temperature. After stirring for 12 hours, the resultant solution was vacuum-evaporated, acidified with 2N—HCl to pH 2-3, and extracted with EA (×2). The organic layer was dried with MgSO$_4$, and filtered. Through vacuum distillation, the solvent was removed so as to obtain 1-(2-nitrophenylsulfonamido)cyclobutanecarboxylic acid (468 mg, 1.56 mmol, 98%).

$^1$H NMR (400 MHz, DMSO-d$_6$) δ 12.71 (bs, —COOH), 8.71 (s, —NH—SO$_2$), 8.03 (m, 1H), 7.97 (m, 1H), 7.86 (m, 2H), 2.38 (m, 2H), 2.19 (m, 2H), 1.79 (m, 2H).

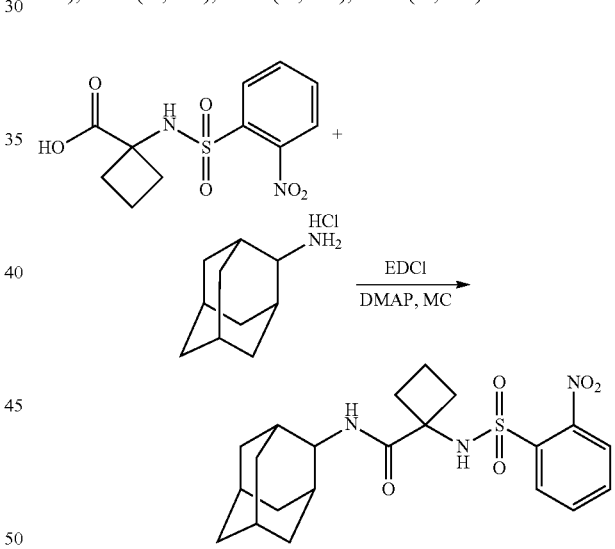

In a 10-mL flask, 1-(2-nitrophenylsulfonamido)cyclobutanecarboxylic acid (200 mg, 0.666 mmol), 2-adamantan-amine hydrochloride (150 mg, 0.799 mmol), and BOP (295 mg, 0.667 mmol) were charged, and CH$_2$Cl$_2$ (3 ml) was charged, followed by stirring for 30 minutes at room temperature. DIPEA (0.28 ml, 1.60 mmol) was added thereto, followed by stirring at room temperature for 12 hours. After the reaction was completed, the organic layer was separated using CH$_2$Cl$_2$ and H$_2$O, dried with MgSO$_4$, and filtered. The resultant mixture was purified with column chromatography (EA/n-Hex=1:2) to obtain N-(adamantane-2-yl)-1-(2-nitrophenylsulfonamido)cyclobutanecarboxyamide (282 mg, 97%).

$^1$H NMR (400 MHz, CDCl$_3$) δ 8.15-8.21 (m, 1H), 7.96-8.01 (m, 1H), 7.76-7.80 (m, 2H), 6.80 (d, J=7.6 Hz, —NH—

CO—), 6.16 (s, —NH—SO$_2$), 4.02 (d, J=8.4 Hz, 1H), 2.61-2.68 (m, 2H), 2.10-2.20 (m, 2H), 1.95-2.03 (m, 2H), 1.6-1.95 (m, 14H).

Preparation Example 2

Synthesis of N-(adamantane-2-yl)-1-(2-bromophenylsulfonamido)cyclobutanecarboxyamide (compound 138)

An aimed compound was obtained in the same manner as described in Preparation Example 1 of Example 5 except that 1-(2-bromophenylsulfonamido)cyclobutanecarboxylic acid was used.

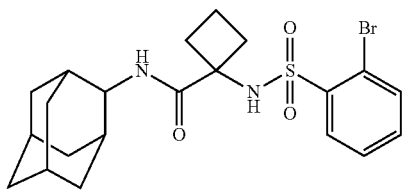 [SMILES: O=C(NC1C2CC3CC(C2)CC1C3)C1(NS(=O)(=O)c2ccccc2Br)CCC1]

$^1$H NMR (400 MHz, CDCl$_3$) δ 8.13-8.15 (m, 1H), 7.80-7.82 (m, 1H), 7.45-7.54 (m, 2H), 6.98 (d, J=7.2 Hz, —NH—CO—), 5.81 (s, —NH—SO$_2$), 5.62 (s, —NH$_2$—CO—, 1H), 4.01 (d, J=8.0 Hz, 1H), 2.53-2.59 (m, 2H), 2.01-2.08 (m, 4H), 1.59-1.95 (m, 14H)

Preparation Example 3

Synthesis of N-(adamantane-2-yl)-4-(phenylsulfonamido)cyclobutanecarboxyamide (compound 139)

An aimed compound was obtained in the same manner as described in Preparation Example 1 of Example 5 except that 1-(phenylsulfonamido)cyclobutanecarboxylic acid was used.

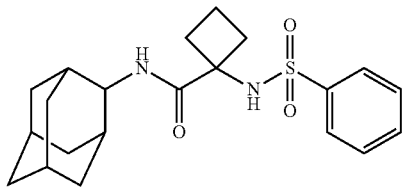 [SMILES: O=C(NC1C2CC3CC(C2)CC1C3)C1(NS(=O)(=O)c2ccccc2)CCC1]

$^1$H NMR (400 MHz, CDCl$_3$) δ 7.91-7.94 (m, 2H), 7.60-7.64 (m, 1H), 7.53-7.57 (m, 2H), 6.83 (d, J=8.0 Hz, —NH—CO—), 5.34 (s, —NH—SO$_2$), 3.98 (d, J=8.0 Hz, 1H), 2.49-2.55 (m, 2H), 2.17-2.24 (m, 2H), 1.60-1.94 (m, 16H)

Preparation Example 4

Synthesis of N-(adamantane-2-yl)-1-(2-trifluoromethylphenylsulfonamido)cyclobutanecarboxyamide (compound 140)

An aimed compound was obtained in the same manner as described in Preparation Example 1 of Example 5 except that 1-(2-trifluoromethylphenylsulfonamido)cyclobutanecarboxylic acid was used.

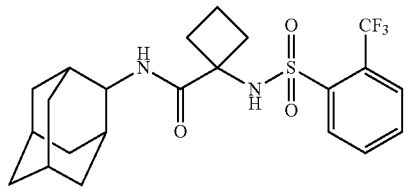 [SMILES: O=C(NC1C2CC3CC(C2)CC1C3)C1(NS(=O)(=O)c2ccccc2C(F)(F)F)CCC1]

$^1$H NMR (400 MHz, CDCl$_3$) δ 8.24-8.26 (m, 1H), 7.92-7.96 (m, 1H), 7.72-7.78 (m, 2H), 6.82 (d, J=8.0 Hz, —NH—CO—), 5.40 (s, —NH—SO$_2$), 4.01 (d, J=8.0 Hz, 1H), 2.53-2.60 (m, 2H), 1.99-2.12 (m, 4H), 1.6-1.94 (m, 14H).

Preparation Example 5

Synthesis of N-(adamantane-2-yl)-1-(quinoline-8-sulfonamido)cyclobutanecarboxyamide (compound 141)

An aimed compound was obtained in the same manner as described in Preparation Example 1 of Example 5 except that 1-(quinoline-8-sulfonamido)cyclobutanecarboxylic acid was used.

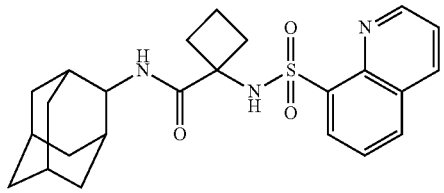 [SMILES: O=C(NC1C2CC3CC(C2)CC1C3)C1(NS(=O)(=O)c2cccc3cccnc23)CCC1]

$^1$H NMR (400 MHz, CDCl$_3$) δ 9.12 (dd, J=1.6, 4.4 Hz, 1H), 8.41 (dd, J=1.2, 7.6 Hz, 1H), 8.37 (dd, J=1.2, 7.6 Hz, 1H), 8.12 (dd, J=1.2, 7.6 Hz, 1H), 7.64-7.72 (m, 2H), 7.34 (s, —NH—SO$_2$), 7.24 (d, J=8.0 Hz, —NH—CO—), 4.04 (d, J=7.6 Hz, 1H), 2.54-2.61 (m, 2H), 1.67-1.99 (m, 16H), 1.31-1.32 (m, 2H).

Preparation Example 6

Synthesis of N-(adamantane-2-yl)-1-(3-nitrophenylsulfonamido)cyclobutanecarboxyamide (compound 142)

An aimed compound was obtained in the same manner as described in Preparation Example 1 of Example 5 except that 1-(3-nitrophenylsulfonamido)cyclobutanecarboxylic acid was used.

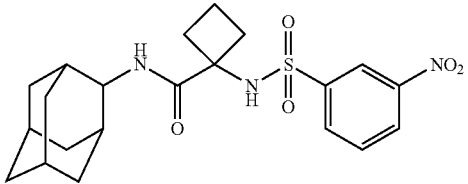 [SMILES: O=C(NC1C2CC3CC(C2)CC1C3)C1(NS(=O)(=O)c2cccc([N+](=O)[O-])c2)CCC1]

$^1$H NMR (400 MHz, CDCl$_3$) δ 8.75 (t, J=1.6 Hz, 1H), 8.45-8.48 (m, 8.22-8.25 (m, 1H), 7.77 (t, J=8.0 Hz, 1H), 6.65

(d, J=7.6 Hz, —NH—CO—), 5.67 (s, —NH—SO₂), 3.93 (d, J=8.0 Hz, 1H), 2.48-2.55 (m, 2H), 2.30-2.38 (m, 2H), 1.66-1.95 (m, 16H).

Preparation Example 7

Synthesis of N-(adamantane-2-yl)-1-(4-nitrophenyl-sulfonamido)cyclobutanecarboxyamide (compound 143)

An aimed compound was obtained in the same manner as described in Preparation Example 1 of Example 5 except that 1-(4-nitrophenylsulfonamido)cyclobutanecarboxylic acid was used.

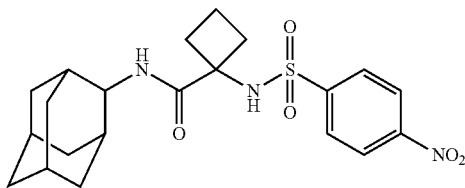 [SMILES: O=C(NC1C2CC3CC(C2)CC1C3)C1(NS(=O)(=O)c2ccc([N+](=O)[O-])cc2)CCC1]

¹H NMR (400 MHz, CDCl₃) δ 8.8 (dt, J=2.4, 8.8 Hz, 2H), 8.10 (dt, J=2.4, 9.2 Hz, 2H), 6.61 (d, J=7.6 Hz, —NH—CO—), 5.60 (s, —NH—SO₂), 3.93 (d, J=8.0 Hz, 1H), 2.46-2.53 (m, 2H), 2.31-2.38 (m, 2H), 1.66-1.95 (m, 16H)

Preparation Example 8

Synthesis of N-(adamantane-2-yl)-1-(2-trifluoromethoxyphenylsulfonamido)cyclobutanecarboxyamide (compound 144)

An aimed compound was obtained in the same manner as described in Preparation Example 1 of Example 5 except that 1-(2-trifluoromethoxyphenylsulfonamido)cyclobutanecarboxylic acid was used.

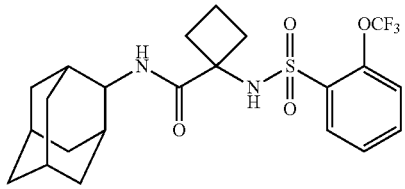 [SMILES: O=C(NC1C2CC3CC(C2)CC1C3)C1(NS(=O)(=O)c2ccccc2OC(F)(F)F)CCC1]

¹H NMR (400 MHz, CDCl₃) δ 8.08 (dd, J=2, 8 Hz, 1H), 7.68 (m, 1H), 7.46 (m, 2H), 6.89 (d, J=8 Hz, —NH—CO—), 5.36 (s, —NH—SO₂), 3.99 (d, J=8.4 Hz, 1H), 2.57 (m, 2H), 2.04 (m, 2H), 1.96-1.86 (m, 12H), 1.74-1.67 (m, 4H).

Example 6

Preparation Example 1

Synthesis of N-4-(1-(2-nitrophenylsulfonamido)cyclobutanecarboxyamido)adamantane-1-carboxyamide (compound 145)

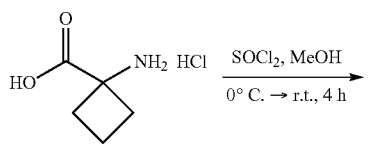

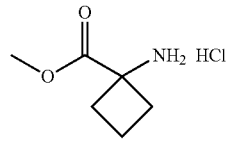

1-aminocyclobutanecarboxylic acid hydrochloride (5.2 g, 34.5 mmol) and methanol (120 ml) were charged. An ice bath was set and thionyl chloride (3.7 ml, 51.7 mmol) was slowly added thereto. Then, the ice bath was removed, and the mixture was stirred at room temperature for 3 hours. The resultant product was vacuum-distilled to remove a solvent, and dried in a 60° C. oven so as to obtain methyl-1-aminocyclobutanecarboxylate hydrochloride (5.62 g, 37.1 mmol, 98%).

¹H NMR (400 MHz, DMSO-d₆) δ 8.94 (br, 3H), 3.79 (s, 3H), 2.47 (m, 4H), 2.07 (m, 2H).

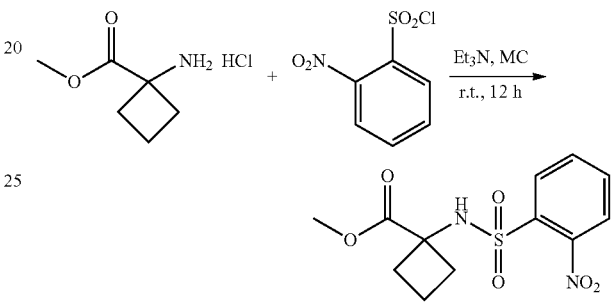

methyl-1-aminocyclobutanecarboxylate hydrochloride (300 mg, 1.81 mmol) was dissolved in CH₂Cl₂ (7 ml), added with 2-nitrobenzene-1-sulfonyl chloride (441 mg, 1.99 mmol) and triethylamine (1 ml, 7.24 mmol) and stirred at room temperature for 12 hours. The resultant solution was added with H₂O, extracted with CH₂Cl₂ (×2), dried with MgSO₄, and filtered. Through vacuum distillation, the solvent was removed. The resultant mixture was purified with column chromatography so as to obtain methyl-1-(2-nitrophenylsulfonamido)cyclobutanecarboxylate (512 mg, 1.63 mmol, 90%).

¹H NMR (400 MHz, CDCl₃) δ 8.03 (m, 1H), 7.95 (m, 1H), 7.75 (m, 2H), 6.14 (s, —NH—SO₂), 3.48 (s, 3H), 2.61 (m, 2H), 2.51 (m, 2H), 2.03 (m, 2H).

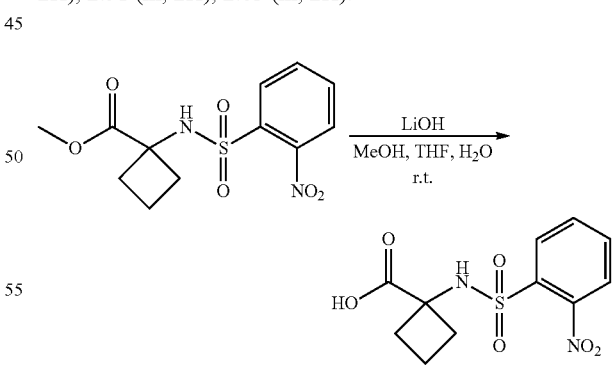

methyl-1-(2-nitrophenylsulfonamido)cyclobutanecarboxylate (500 mg, 1.59 mmol) was charged and dissolved through addition of THF (5 ml), and methanol (5 ml). LiOH.H₂O dissolved in H₂O (5 ml) was added thereto, followed by stirring for 12 hours at room temperature. After the stirring for 12 hours, the resultant solution was vacuum-evaporated, acidified with 2N—HCl to pH 2-3, and extracted with EA (×2). The organic layer was dried with MgSO₄, and filtered. Then, through vacuum distillation, the solvent was removed so as to obtain methyl-1-(2-nitrophenylsulfonamido)cyclobutanecarboxylic acid (468 mg, 1.56 mmol, 98%).

$^1$H NMR (400 MHz, DMSO-d$_6$) δ 12.71 (bs, —COOH), 8.71 (s, —NH—SO$_2$), 8.03 (m, 1H), 7.97 (m, 1H), 7.86 (m, 2H), 2.38 (m, 2H), 2.19 (m, 2H), 1.79 (m, 2H).

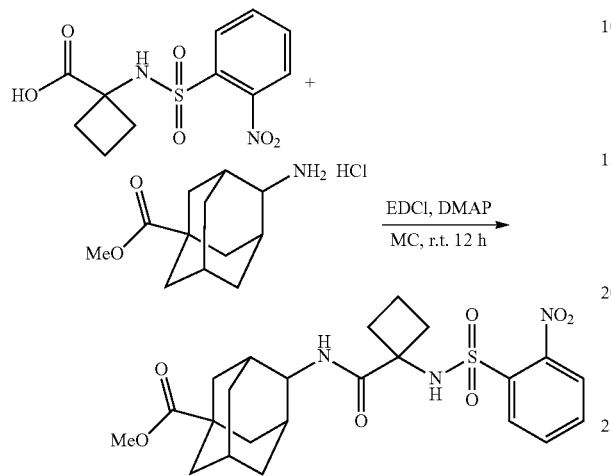

methyl-1-(2-nitrophenylsulfonamido)cyclobutanecarboxylic acid (452 mg, 1.51 mmol), 4-amino-adamantane-1-carboxylate hydrochloride (406 mg, 1.65 mmol), and EDCI (868 mg, 4.53 mmol) were charged, and CH$_2$Cl$_2$ (6 ml) was added thereto, followed by stirring for 30 minutes at room temperature. DMAP (369 mg, 3.02 mmol) was added thereto, followed by stirring at room temperature for 12 hours. After the reaction was completed, the organic layer was separated using CH$_2$Cl$_2$ and H$_2$O, dried with MgSO$_4$, and filtered. Then, through vacuum distillation, the solvent was removed, and the resultant product was purified with column chromatography to obtain N-methyl-4-(1-(2-nitrophenylsulfonamido)cyclobutanecarboxyamido)adamantane-1-carboxylate (680 mg, 1.38 mmol, 92%).

$^1$H NMR (400 MHz, CDCl$_3$) δ 8.16 (m, 1H), 7.97 (m, 1H), 7.79 (m, 2H), 6.79 (d, J=7.6 Hz, —NH—CO—), 6.15 (s, —NH—SO$_2$), 4.02 (d, J=8.4 Hz, 1H), 3.68 (s, 3H), 2.63 (m, 2H), 2.15-1.83 (m, 15H), 1.62 (m, 2H).

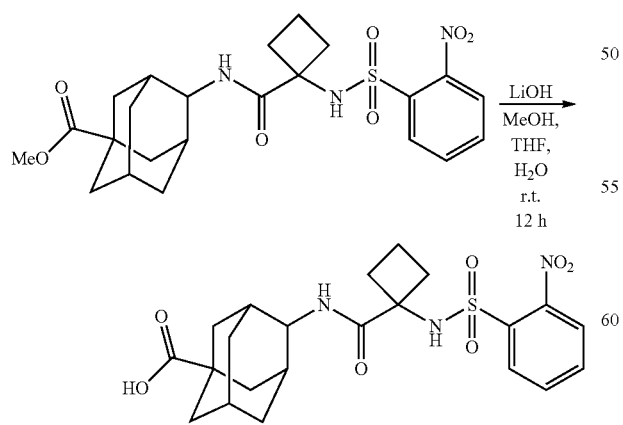

N-methyl-4-(1-(2-nitrophenylsulfonamido)cyclobutanecarboxyamido)adamantane-1-carboxylate (650 mg, 1.32 mmol) was charged and dissolved through addition of THF (6 ml), and methanol (6 ml). LiOH.H$_2$O dissolved in H$_2$O (6 ml) was added thereto, followed by stirring for 12 hours at room temperature. After the stirring for 12 hours, the resultant solution was vacuum-evaporated, acidified with 2N—HCl to pH 2-3, and extracted with EA (×2). The organic layer was dried with MgSO$_4$, and filtered. Then, through vacuum distillation, the solvent was removed so as to obtain N-methyl-4-(1-(2-nitrophenylsulfonamido)cyclobutanecarboxyamido)adamantane-1-carboxylic acid (618 mg, 1.29 mmol, 98%).

$^1$H NMR (400 MHz, CDCl$_3$) δ 8.15 (m, 1H), 7.98 (m, 1H), 7.79 (m, 2H), 6.82 (d, J=7.6 Hz, —NH—CO—), 6.18 (s, —NH—SO$_2$), 4.03 (d, J=8 Hz, 1H), 2.64 (m, 2H), 2.15-1.82 (m, 15H), 1.66 (m, 2H).

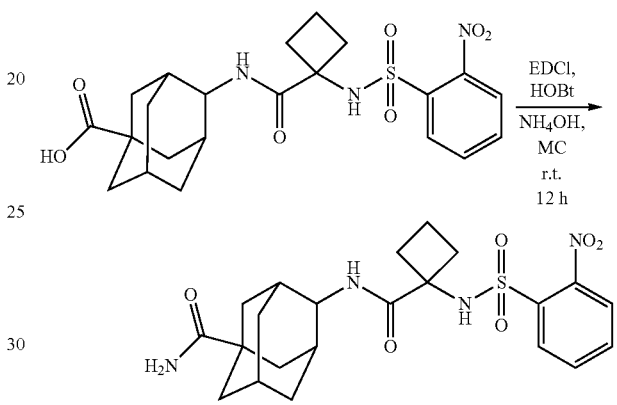

N-methyl-4-(1-(2-nitrophenylsulfonamido)cyclobutanecarboxyamido)adamantane-1-carboxylic acid (600 mg, 1.25 mmol) was dissolved in CH$_2$Cl$_2$ (14 ml), and added with EDCI (479 mg, 2.5 mmol) and HOBT (337 mg, 2.5 mmol), followed by stirring for 30 minutes. 30% NH$_4$OH aqueous solution (7 ml) was added thereto, followed by stirring for 12 hours at room temperature. The resultant solution was added with H$_2$O, extracted with CH$_2$Cl$_2$ (×3), dried with MgSO$_4$, and filtered. Through vacuum distillation, the solvent was removed. The resultant mixture was purified with column chromatography so as to obtain N-methyl-4-(1-(2-nitrophenylsulfonamido)cyclobutanecarboxyamido)adamantane-1-carboxyamide (508 mg, 1.06 mmol, 85%).

$^1$H NMR (400 MHz, DMSO-d$_6$) δ 8.59 (s, —NH—SO$_2$), 7.98 (m, 2H), 7.88 (m, 2H), 7.06 (d, J=6.4 Hz, —NH—CO—), 6.99 (br, NH$_2$—CO—), 6.73 (br, NH$_2$—CO—), 3.55 (d, J=6 Hz, 1H), 2.42 (m, 2H), 2.11 (m, 2H), 1.91-1.68 (m, 13H), 1.38 (m, 2H).

Preparation Example 2

Synthesis of N-4-(1-(quinoline-8-sulfonamido)cyclobutanecarboxyamido)adamantane-1-carboxyamide (compound 146)

An aimed compound was obtained in the same manner as described in Preparation Example 1 of Example 6 except that 1-(quinoline-8-sulfonamido)cyclobutanecarboxylic acid was used.

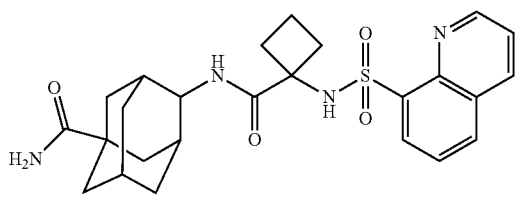 [SMILES: NC(=O)C12CC3CC(C1)C(NC(=O)C1(NS(=O)(=O)c4cccc5cccnc45)CCC1)C(C3)C2]

¹H NMR (400 MHz, DMSO-d₆) δ 9.13 (dd, J=2, 4.4 Hz, 1H), 8.58 (dd, J=1.6, 8.4 Hz, 1H), 8.29 (dd, J=1.2, 8 Hz, 1H), 8.24 (dd, J=1.2, 7.2 Hz, 1H), 8.17 (s, —NH—SO₂), 7.75 (m, 2H), 7.05 (d, J=7.2 Hz, —NH—CO—), 6.99 (br, NH₂—CO—), 6.74 (br, NH₂—CO—), 3.41 (d, J=8 Hz, 1H), 2.31 (m, 2H), 2.01 (m, 2H), 1.83-1.58 (m, 11H), 1.48 (m, 2H), 1.32 (m, 2H).

Preparation Example 3

Synthesis of N-4-(1-(3-trifluoromethyl-4-nitrophenylsulfonamido)cyclobutanecarboxyamido)adamantane-1-carboxyamide (compound 147)

An aimed compound was obtained in the same manner as described in Preparation Example 1 of Example 6 except that 1-(3-trifluoromethyl-4-nitrophenylsulfonamido)cyclobutanecarboxylic acid was used.

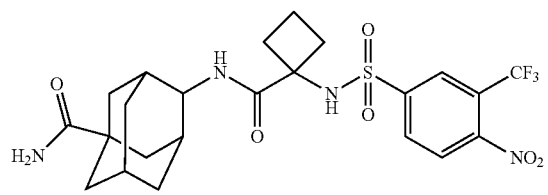 [SMILES: NC(=O)C12CC3CC(C1)C(NC(=O)C1(NS(=O)(=O)c4ccc([N+](=O)[O-])c(C(F)(F)F)c4)CCC1)C(C3)C2]

¹H NMR (400 MHz, DMSO-d₆) δ 8.75 (s, —NH—SO₂), 8.39 (d, J=8.4 Hz, 1H), 8.24 (dd, J=1.6, 8.4 Hz, 1H), 8.16 (m, 1H), 6.99 (br, NH₂—CO—), 6.86 (d, J=7.2 Hz, —NH—CO—), 6.75 (br, NH₂—CO—), 3.33 (d, J=5.2 Hz, 1H), 2.42 (m, 2H), 2.23 (m, 2H), 1.83-1.54 (m, 13H), 1.34 (m, 2H).

Preparation Example 4

Synthesis of N-4-(1-(phenylsulfonamido)cyclobutanecarboxyamido)adamantane-1-carboxyamide (compound 148)

An aimed compound was obtained in the same manner as described in Preparation Example 1 of Example 6 except that 1-(phenylsulfonamido)cyclobutanecarboxylic acid was used.

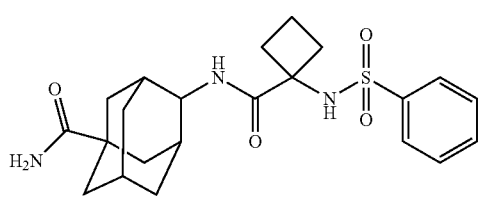 [SMILES: NC(=O)C12CC3CC(C1)C(NC(=O)C1(NS(=O)(=O)c4ccccc4)CCC1)C(C3)C2]

¹H NMR (400 MHz, DMSO-d₆) δ 8.42 (s, —NH—SO₂), 7.78 (m, 2H), 7.61 (m, 3H), 6.99 (br, NH₂—CO—), 6.89 (d, J=7.2 Hz, —NH—CO—), 6.74 (br, NH₂—CO—), 3.43 (d, J=7.6 Hz, 1H), 2.33 (m, 2H), 2.08 (m, 2H), 1.76-1.63 (m, 13H), 1.41 (m, 2H).

Preparation Example 5

Synthesis of N-4-(1-(2-methyl-3-chlorophenylsulfonamido)cyclobutanecarboxyamido)adamantane-1-carboxyamide (compound 149)

An aimed compound was obtained in the same manner as described in Preparation Example 1 of Example 6 except that 1-(2-methyl-3-chlorophenylsulfonamido)cyclobutanecarboxylic acid was used.

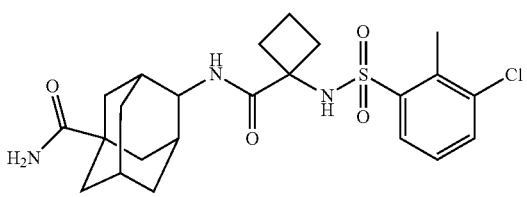

¹H NMR (400 MHz, DMSO-d₆) δ 8.58 (s, —NH—SO₂), 7.81 (dd, J=0.8, 8 Hz, 1H), 7.73 (d, J=8.4 Hz, 1H), 7.41 (t, J=8.4 Hz, 1H), 7.02 (br, NH₂—CO—), 6.97 (d, J=7.6 Hz, —NH—CO—), 6.76 (br, NH₂—CO—), 3.53 (d, J=6.8 Hz, 1H), 2.71 (s, 3H), 2.37 (m, 2H), 2.08 (m, 2H), 1.91-1.62 (m, 13H), 1.43 (m, 2H).

Preparation Example 6

Synthesis of N-4-(1-(3-nitro-4-methylphenylsulfonamido)cyclobutanecarboxyamido)adamantane-1-carboxyamide (compound 150)

An aimed compound was obtained in the same manner as described in Preparation Example 1 of Example 6 except that 1-(3-nitro-4-methylphenylsulfonamido)cyclobutanecarboxylic acid was used.

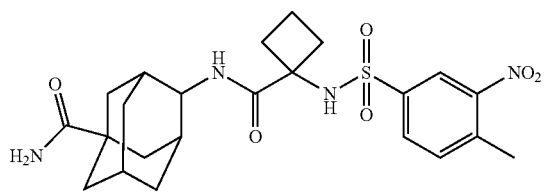 [SMILES: Cc1ccc(S(=O)(=O)NC2(C(=O)NC3C4CC5CC3CC(C(N)=O)(C5)C4)CCC2)cc1[N+](=O)[O-]]

¹H NMR (400 MHz, DMSO-d₆) δ 8.56 (s, —NH—SO₂), 8.26 (d, J=2 Hz, 1H), 7.92 (dd, J=2, 8 Hz, 1H), 7.73 (d, J=8.4 Hz, 1H), 7.00 (br, NH₂—CO—), 6.88 (d, J=7.2 Hz, —NH—CO—), 6.75 (br, NH₂—CO—), 3.32 (d, J=6.8 Hz, 1H), 2.61 (s, 3H), 2.39 (m, 2H), 2.17 (m, 2H), 1.84-1.59 (m, 13H), 1.34 (m, 2H).

Preparation Example 7

Synthesis of N-4-(1-(3-fluoro-4-methylphenylsulfonamido)cyclobutanecarboxyamido)adamantane-1-carboxyamide (compound 151)

An aimed compound was obtained in the same manner as described in Preparation Example 1 of Example 6 except that 1-(3-fluoro-4-methylnylsulfonamido)cyclobutanecarboxylic acid was used.

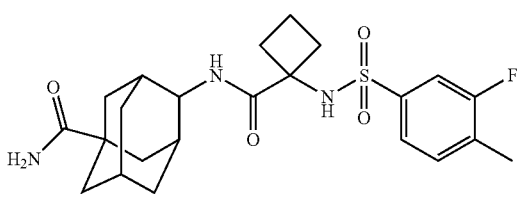 [SMILES: Cc1ccc(S(=O)(=O)NC2(C(=O)NC3C4CC5CC3CC(C(N)=O)(C5)C4)CCC2)cc1F]

¹H NMR (400 MHz, DMSO-d₆) δ 8.43 (s, —NH—SO₂), 7.49 (m, 3H), 7.01 (br, NH₂—CO—), 6.88 (d, J=7.2 Hz, —NH—CO—), 6.75 (br, NH₂—CO—), 3.44 (d, J=6.8 Hz, 1H), 2.33 (m, 5H), 2.14 (m, 2H), 1.86-1.62 (m, 13H), 1.38 (m, 2H).

Preparation Example 8

Synthesis of N-4-(1-(2-chlorophenylsulfonamido) cyclobutanecarboxyamido)adamantane-1-carboxyamide (compound 152)

An aimed compound was obtained in the same manner as described in Preparation Example 1 of Example 6 except that 1-(2-chlorophenylsulfonamido)cyclobutanecarboxylic acid was used.

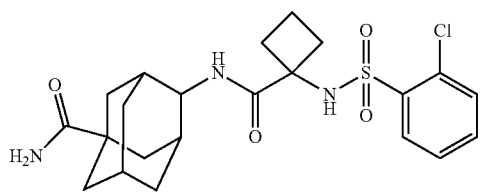

¹H NMR (400 MHz, DMSO-d₆) δ 8.67 (s, —NH—SO₂), 7.95 (dd, J=1.2, 7.6 Hz, 1H), 7.68 (m, 2H), 7.54 (m, 1H), 7.05 (d, J=7.6 Hz, —NH—CO—), 7.02 (br, NH₂—CO—), 6.76 (br, NH₂—CO—), 3.64 (d, J=6 Hz, 1H), 2.34 (m, 2H), 2.01 (m, 2H), 1.98-1.75 (m, 11H), 1.61 (m, 2H), 1.44 (m, 2H).

Preparation Example 9

Synthesis of N-4-(1-(2,4-dichlorophenylsulfonamido)cyclobutanecarboxyamido)adamantane-1-carboxyamide (compound 153)

An aimed compound was obtained in the same manner as described in Example 6 Preparation Example 1 except that 1-(2,4-dichlorophenylsulfonamido)cyclobutanecarboxylic acid was used.

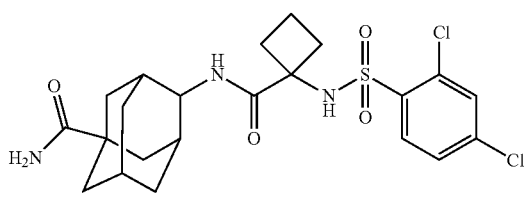 [SMILES: NC(=O)C12CC3CC(C1)C(NC(=O)C1(NS(=O)(=O)c4ccc(Cl)cc4Cl)CCC1)C(C3)C2]

¹H NMR (400 MHz, DMSO-d₆) δ 8.73 (s, —NH—SO₂), 7.92 (m, 2H), 7.64 (dd, J=2.8, 8.4 Hz, 1H), 7.03 (d, J=7.6 Hz, —NH—CO—), 7.01 (br, NH₂—CO—), 6.77 (br, NH₂—CO—), 3.61 (d, J=6.8 Hz, 1H), 2.38 (m, 2H), 2.01 (m, 2H), 1.92-1.76 (m, 11H), 1.62 (m, 2H).

Preparation Example 10

Synthesis of N-4-(1-(3-fluoro-4-methoxyphenylsulfonamido)cyclobutanecarboxyamido)adamantane-1-carboxyamide (compound 154)

An aimed compound was obtained in the same manner as described in Preparation Example 1 of Example 6 except that 1-(3-fluoro-4-methoxyphenylsulfonamido)cyclobutanecarboxylic acid was used.

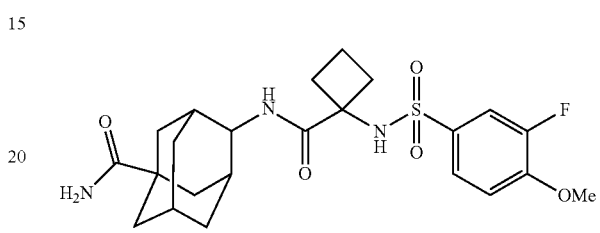

¹H NMR (400 MHz, DMSO-d₆) δ 8.33 (s, —NH—SO₂), 7.53 (m, 2H), 7.35 (t, J=8.4 Hz, 1H), 7.02 (br, NH₂—CO—), 6.89 (d, J=7.2 Hz, —NH—CO—), 6.76 (br, NH₂—CO—), 3.92 (s, 3H), 3.46 (d, J=6 Hz, 1H), 2.33 (m, 2H), 2.08 (m, 2H), 1.86-1.64 (m, 13H), 1.39 (m, 2H).

Preparation Example 11

Synthesis of N-4-(1-(2-bromophenylsulfonamido) cyclobutanecarboxyamido)adamantane-1-carboxyamide (compound 155)

An aimed compound was obtained in the same manner as described in Preparation Example 1 of Example 6 except that 1-(2-bromophenylsulfonamido)cyclobutanecarboxylic acid was used.

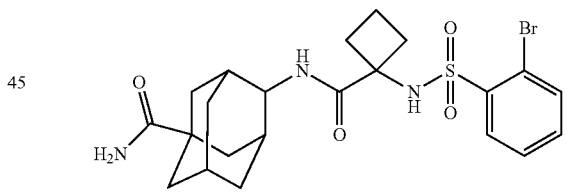

¹H NMR (400 MHz, DMSO-d₆) δ 8.64 (s, —NH—SO₂), 7.98 (dd, J=2, 7.6 Hz, 1H), 7.88 (dd, J=1.2, 7.6 Hz, 1H), 7.57 (m, 2H), 7.07 (d, J=7.6 Hz, —NH—CO—), 7.03 (br, NH₂—CO—), 6.77 (br, NH₂—CO—), 3.67 (d, J=7.2 Hz, 1H), 2.33 (m, 2H), 1.94-1.84 (m, 11H), 1.75 (m, 2H), 1.61 (m, 2H), 1.45 (m, 2H).

Preparation Example 12

Synthesis of N-4-(1-(2-methylphenylsulfonamido) cyclobutanecarboxyamido)adamantane-1-carboxyamide (compound 156)

An aimed compound was obtained in the same manner as described in Preparation Example 1 of Example 6 except that 1-(2-methylphenylsulfonamido)cyclobutanecarboxylic acid was used.

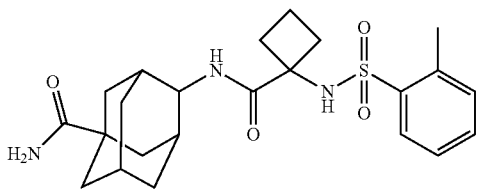

¹H NMR (400 MHz, DMSO-d₆) δ 8.45 (s, —NH—SO₂), 7.79 (d, J=7.6 Hz, 1H), 7.53 (m, 1H), 7.41 (m, 2H), 7.02 (d, J=7.2 Hz, —NH—CO—), 7.01 (br, NH₂—CO—), 6.76 (br, NH₂—CO—), 3.61 (d, J=7.2 Hz, 1H), 2.64 (s, 3H), 2.33 (m, 2H), 1.98 (m, 2H), 1.98-1.74 (m, 11H), 1.62 (m, 2H), 1.43 (m, 2H).

Preparation Example 13

Synthesis of N-4-(1-(2-trifluoromethylphenylsulfonamido)cyclobutanecarboxyamido)adamantane-1-carboxyamide (compound 157)

An aimed compound was obtained in the same manner as described in Preparation Example 1 of Example 6 except that 1-(2-trifluoromethylphenylsulfonamido)cyclobutanecarboxylic acid was used.

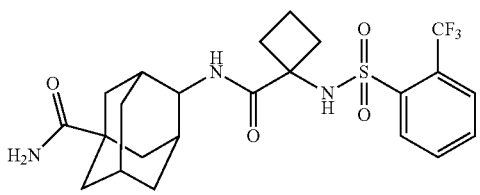

¹H NMR (400 MHz, DMSO-d₆) δ 8.53 (s, —NH—SO₂), 8.14 (d, J=7.6 Hz, 1H), 7.97 (m, 1H), 7.88 (m, 2H), 7.03 (br, NH₂—CO—), 7.02 (br, —NH—CO—), 6.76 (br, NH₂—CO—), 3.61 (d, J=7.2 Hz, 1H), 2.37 (m, 2H), 2.04 (m, 2H), 1.88-1.65 (m, 13H), 1.42 (m, 2H).

Preparation Example 14

Synthesis of N-4-(1-(2,3-dichlorophenylsulfonamido)cyclobutanecarboxyamido)adamantane-1-carboxyamide (compound 158)

An aimed compound was obtained in the same manner as described in Preparation Example 1 of Example 6 except that 1-(2,3-dichlorophenylsulfonamido)cyclobutanecarboxylic acid was used.

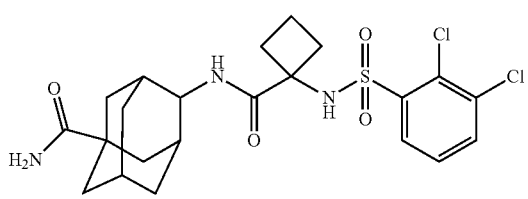

¹H NMR (400 MHz, DMSO-d₆) δ 8.83 (s, —NH—SO₂), 7.94 (m, 2H), 7.56 (t, J=8 Hz, 1H), 7.02 (br, —NH—CO—), 6.96 (br, NH₂—CO—), 6.76 (br, NH₂—CO—), 3.54 (d, J=6.8 Hz, 1H), 2.38 (m, 2H), 2.15 (m, 2H), 1.84-1.78 (m, 11H), 1.62 (m, 2H), 1.35 (m, 2H).

Preparation Example 15

Synthesis of N-4-(1-(2-fluoro-3-chlorophenylsulfonamido)cyclobutanecarboxyamido)adamantane-1-carboxyamide (compound 159)

An aimed compound was obtained in the same manner as described in Preparation Example 1 of Example 6 except that 1-(2-fluoro-3-chlorophenylsulfonamido)cyclobutanecarboxylic acid was used.

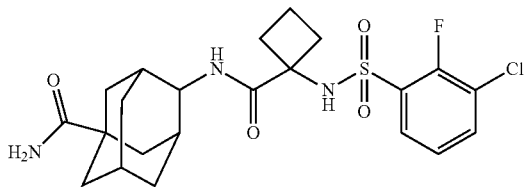 [SMILES: NC(=O)C12CC3CC(C1)C(NC(=O)C1(NS(=O)(=O)c4cccc(Cl)c4F)CCC1)C(C3)C2]

¹H NMR (400 MHz, DMSO-d₆) δ 8.78 (s, —NH—SO₂), 7.91 (m, 1H), 7.69 (m, 1H), 7.41 (t, J=8 Hz, 1H), 7.01 (br, NH₂—CO—), 6.98 (d, J=7.2 Hz, —NH—CO—), 6.76 (br, NH₂—CO—), 3.38 (d, J=6.8 Hz, 1H), 2.38 (m, 2H), 2.37 (m, 2H), 1.79-1.61 (m, 13H), 1.41 (m, 2H).

Preparation Example 16

Synthesis of N-4-(1-(2-trifluoromethoxyphenylsulfonamido)cyclobutanecarboxyamido)adamantane-1-carboxyamide (compound 160)

An aimed compound was obtained in the same manner as described in Preparation Example 1 of Example 6 except that 1-(2-trifluoromethoxyphenylsulfonamido)cyclobutanecarboxylic acid was used.

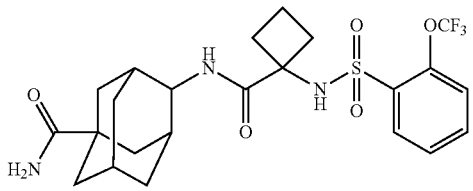

¹H NMR (400 MHz, CDCl₃) δ 8.02 (dd, J=1.6 Hz, 8.0 Hz, 1H), 7.66-7.72 (m, 1H), 7.40-7.51 (m, 2H), 6.93 (d, J=8.0 Hz, —NH—CO—), 5.60 (s, —NH₂—CO—, 1H), 5.38 (s, —NH—SO₂), 5.24 (s, —NH₂—CO—, 1H), 4.01 (d, J=8.8 Hz, 1H), 2.57-2.61 (m, 2H), 1.63-2.20 (m, 17H).

Preparation Example 17

Synthesis of N-4-(1-(2,4,5-trichlorophenylsulfonamido)cyclobutanecarboxyamido)adamantane-1-carboxyamide (compound 161)

An aimed compound was obtained in the same manner as described in Preparation Example 1 of Example 6 except that 1-(2,4,5-trichlorophenylsulfonamido)cyclobutanecarboxylic acid was used.

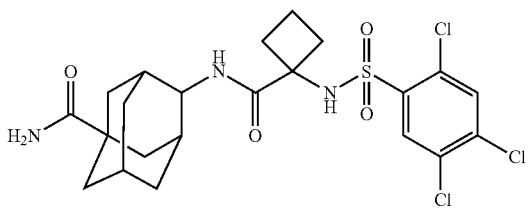 [SMILES: NC(=O)C12CC3CC(C1)C(NC(=O)C1(NS(=O)(=O)c4cc(Cl)c(Cl)cc4Cl)CCC1)C(C3)C2]

¹H NMR (400 MHz, DMSO-d₆) δ 8.81 (s, —NH—SO₂, 1H), 8.17 (s, 1H), 8.01 (s, 1H), 7.02 (s, —NH—CO—, NH₂—CO—, 2H), 6.77 (s, NH₂—CO—, 1H), 3.57 (s, 1H), 1.59-2.15 (m, 13H), 1.45-2.46 (m, 6H).

Preparation Example 18

Synthesis of N-4-(1-(2-chloro-4-bromophenylsulfonamido)cyclobutanecarboxyamido)adamantane-1-carboxyamide (compound 162)

An aimed compound was obtained in the same manner as described in Preparation Example 1 of Example 6 except that 1-(2-chloro-4-bromophenylsulfonamido)cyclobutanecarboxylic acid was used.

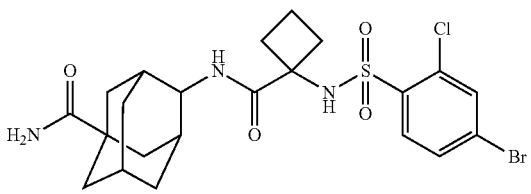 [SMILES: NC(=O)C12CC3CC(C1)C(NC(=O)C1(NS(=O)(=O)c4ccc(Br)cc4Cl)CCC1)C(C3)C2]

¹H NMR (400 MHz, DMSO-d₆) δ 8.71 (s, —NH—SO₂, 1H), 8.03 (s, 1H), 7.84 (d, 1H), 7.76 (d, 1H), 7.02 (s, NH₂—CO—, 1H), 6.99 (d, —NH—CO—, 1H), 6.76 (s, NH₂—CO—, 1H), 3.61 (s, 1H), 1.59-2.15 (m, 13H), 1.45-2.46 (m, 6H).

Preparation Example 19

Synthesis of N-4-(1-(2,5-difluorophenylsulfonamido)cyclobutanecarboxyamido)adamantane-1-carboxyamide (compound 163)

An aimed compound was obtained in the same manner as described in Preparation Example 1 of Example 6 except that 1-(2,5-difluorophenylsulfonamido)cyclobutanecarboxylic acid was used.

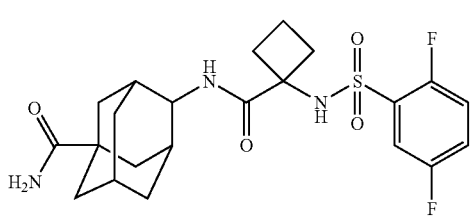 [SMILES: NC(=O)C12CC3CC(C1)C(NC(=O)C1(NS(=O)(=O)c4cc(F)ccc4F)CCC1)C(C3)C2]

¹H NMR (400 MHz, CDCl₃) δ 7.58-7.62 (m, 1H), 7.25-7.42 (m, 2H), 6.85 (d, J=7.6 Hz, —NH—CO—), 5.67 (s, —NH—SO₂), 5.62 (s, —NH₂—CO—, 1H), 5.31 (s, —NH₂—CO—, 1H), 3.98 (d, J=7.6 Hz, 1H), 2.56-2.62 (m, 2H), 1.60-2.20 (m, 17H).

Preparation Example 20

Synthesis of N-4-(1-(2-fluoro-5-methylphenylsulfonamido)cyclobutanecarboxyamido)adamantane-1-carboxyamide (compound 164)

An aimed compound was obtained in the same manner as described in Preparation Example 1 of Example 6 except that 1-(2-fluoro-5-methylphenylsulfonamido)cyclobutanecarboxylic acid was used.

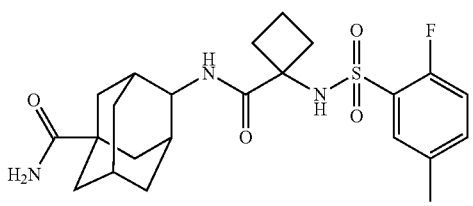

¹H NMR (400 MHz, DMSO-d₆) δ 8.63 (s, —NH—SO₂—), 7.49-7.54 (m, 2H), 7.33 (dd, J=8.4 Hz, 10.0 Hz, 1H), 7.02 (s, —NH₂—CO—, 1H), 6.97 (d, J=8.4 Hz, —NH—CO—), 6.76 (s, —NH₂—CO—, 1H), 3.55 (d, J=6.4 Hz, 1H), 2.34 (m, 7H), 2.04-2.11 (m, 2H), 1.42-1.89 (m, 13H).

Preparation Example 21

Synthesis of N-4-(1-(2-methyl-5-fluorophenylsulfonamido)cyclobutanecarboxyamido)adamantane-1-carboxyamide (compound 165)

An aimed compound was obtained in the same manner as described in Preparation Example 1 of Example 6 except that 1-(2-methyl-5-fluorophenylsulfonamido)cyclobutanecarboxylic acid was used.

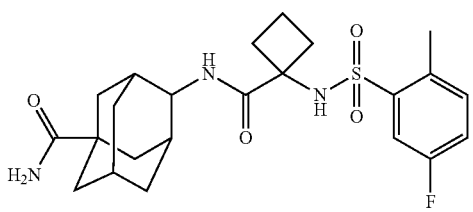

¹H NMR (400 MHz, DMSO-d₆) δ 8.60 (s, —NH—SO₂—), 7.54 (dd, J=2.8 Hz, 8.8 Hz, 1H), 7.31-7.48 (m, 2H), 7.02 (m, 2H), 6.76 (s, —NH₂—CO—, 1H), 3.57 (d, J=6.4 Hz, 1H), 2.59 (s, 3H), 2.31-2.38 (m, 4H), 2.01-2.08 (m, 2H), 1.45-1.89 (m, 13H)

Preparation Example 22

Synthesis of N-4-(1-(4-(difluoromethoxy)phenylsulfonamido)cyclobutanecarboxyamido)adamantane-1-carboxyamide (compound 166)

An aimed compound was obtained in the same manner as described in Preparation Example 1 of Example 6 except that 1-(4-(difluoromethoxy)phenylsulfonamido)cyclobutanecarboxylic acid was used.

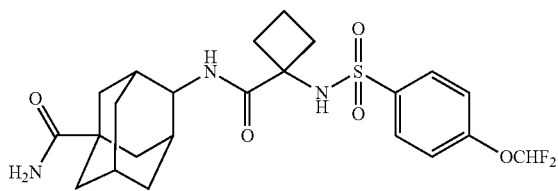

$^1$H NMR (400 MHz, DMSO-d$_6$) δ 8.42 (s, —NH—SO$_2$), 7.76-7.83 (m, 2H), 7.37 (s, 1H), 7.34 (d, J=2.8 Hz, 2H), 6.99 (s, NH$_2$—CO—), 6.89 (d, J=7.2 Hz, —NH—CO—), 6.73 (s, NH$_2$—CO—), 3.51 (d, J=7.2 Hz, 1H), 2.31-2.38 (m, 2H), 2.05-2.15 (m, 2H), 1.39-1.87 (m, 15H).

Example 7

Preparation Example 1

Synthesis of N-4-(1-(3-chloro-2-methylphenylsulfonamido)cyclopentanecarboxyamido)adamantane-1-carboxyamide (compound 167)

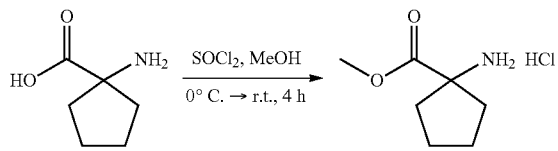

1-aminocyclopentanecarboxylic acid (3.5 g, 26.9 mmol) and methanol (100 ml) were charged. An ice bath was set and thionyl chloride (3.9 ml, 53.9 mmol) was slowly added thereto. Then, the ice bath was removed, and the mixture was stirred at room temperature for 3 hours. The resultant product was vacuum-distilled to remove a solvent, and dried in a 60° C. oven so as to obtain methyl-1-aminocyclopentanecarboxylate hydrochloride (4.74 g, 26.4 mmol, 98%).

$^1$H NMR (400 MHz, DMSO-d$_6$) δ 8.76 (br, 3H), 3.75 (s, 3H), 2.12 (m, 2H), 1.88 (m, 4H), 1.72 (m, 2H).

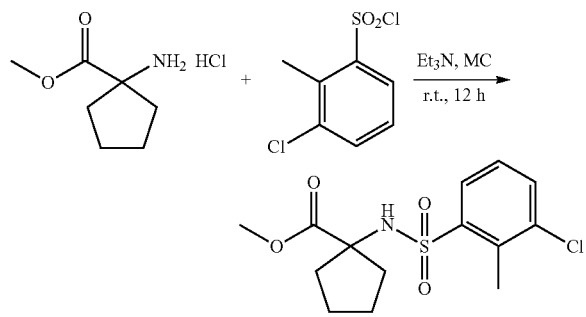

methyl-1-aminocyclopentanecarboxylate hydrochloride (300 mg, 1.67 mmol) was dissolved in CH$_2$Cl$_2$ (7 ml), added with 3-chloro-2-methylbenzene-1-sulfonyl chloride (413 mg, 1.83 mmol) and triethylamine (0.9 ml, 6.68 mmol), and stirred at room temperature for 12 hours. The resultant solution was added with H$_2$O, extracted with CH$_2$Cl$_2$ (×2), dried with MgSO$_4$, and filtered. Through vacuum distillation, the solvent was removed. The resultant mixture was purified with column chromatography so as to obtain methyl-1-(3-chloro-2-methylphenylsulfonamido)cyclopentanecarboxylate (554 mg, 1.67 mmol, 90%).

$^1$H NMR (400 MHz, CDCl$_3$) δ 7.95 (dd, J=1.2, 8 Hz, 1H), 7.59 (dd, J=0.8, 8 Hz, 1H), 7.27 (t, J=8 Hz, 1H), 5.14 (s, —NH—SO$_2$), 3.69 (s, 3H), 2.73 (s, 3H), 2.09 (m, 2H), 1.88 (m, 2H), 1.68 (m, 2H), 1.59 (m, 2H).

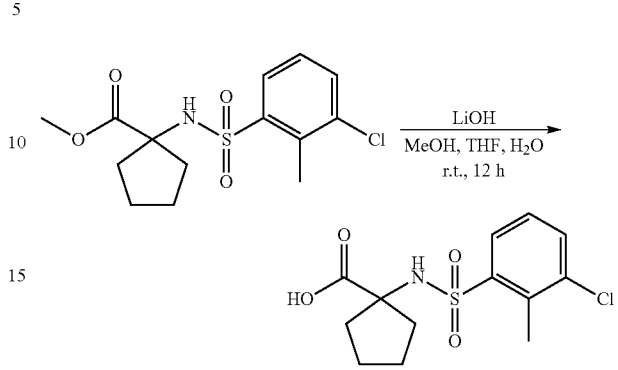

methyl-1-(3-chloro-2-methylphenylsulfonamido)cyclopentanecarboxylate (550 mg, 1.65 mmol) was charged and dissolved through addition of THF (5 ml), and methanol (5 ml). LiOH.H$_2$O dissolved in H$_2$O (5 ml) was added thereto, followed by stirring for 12 hours at room temperature. After the stirring for 12 hours, the resultant solution was vacuum-evaporated, adjusted with 2N—HCl to pH 5-6, and extracted with EA (×2). The organic layer was dried with MgSO$_4$, and filtered. Then, through vacuum distillation, the solvent was removed so as to obtain 1-(3-chloro-2-methylphenylsulfonamido)cyclopentanecarboxylic acid (516 mg, 1.62 mmol, 98%).

$^1$H NMR (400 MHz, DMSO-d$_6$) δ 12.59 (bs, —COOH), 8.32 (s, —NH—SO$_2$), 7.84 (dd, J=0.8, 8 Hz, 1H), 7.69 (dd, J=1.2, 8 Hz, 1H), 7.39 (t, J=8 Hz, 1H), 2.62 (s, 3H), 1.85 (m, 4H), 1.51 (m, 2H), 1.23 (m. 2H).

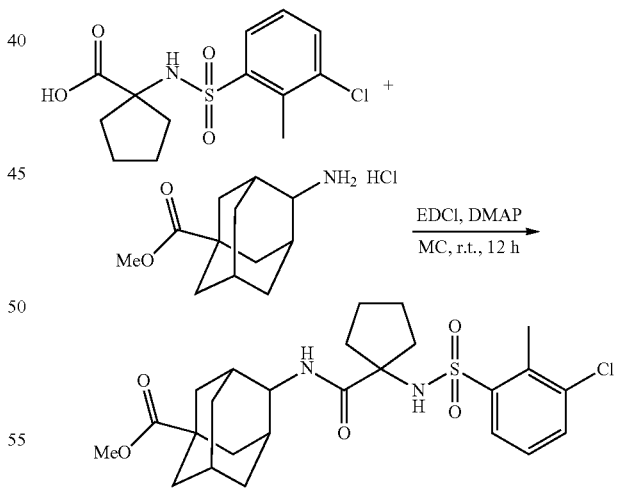

1-(3-chloro-2-methylphenylsulfonamido)cyclopentanecarboxylic acid (253 mg, 0.79 mmol), 4-amino-adamantane-1-carboxylate hydrochloride (215 mg, 2.87 mmol), and EDCI (457 mg, 2.38 mmol) were charged, and added with CH$_2$Cl$_2$ (4 ml), followed by stirring for 30 minutes at room temperature. DMAP (194 mg, 1.59 mmol) was added thereto, followed by stirring for 12 hours at room temperature. After the reaction was completed, the organic layer was separated using CH$_2$Cl$_2$ and H$_2$O, dried with MgSO$_4$, and filtered.

Then, through vacuum distillation, the solvent was removed, and the resultant product was purified with column chromatography to obtain N-methyl-4-(1-(3-chloro-2-methylphenylsulfonamido)cyclopentanecarboxyamido)adamantane-1-carboxylate (364 mg, 0.72 mmol, 90%).

$^1$H NMR (400 MHz, CDCl$_3$) δ 7.98 (dd, J=1.2, 8 Hz, 1H), 7.62 (dd, J=0.8, 8 Hz, 1H), 7.31 (t, J=8 Hz, 1H), 7.11 (d, J=8 Hz, —NH—CO—), 5.01 (s, —NH—SO$_2$), 3.99 (d, J=8 Hz, 1H), 3.69 (s, 3H), 2.69 (s, 3H), 2.19 (m, 2H), 2.06-1.86 (m, 13H), 1.67 (m, 4H), 1.26 (m, 2H).

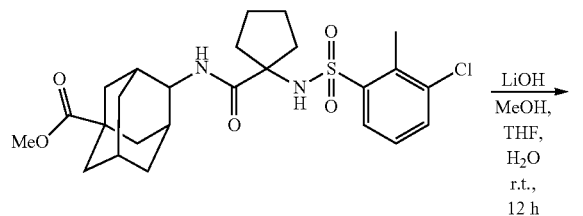

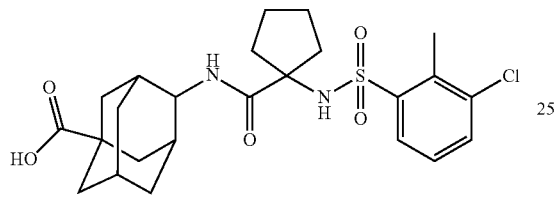

N-methyl-4-(1-(3-chloro-2-methylphenylsulfonamido)cyclopentanecarboxyamido)adamantane-1-carboxylate (360 mg, 0.71 mmol) was charged, and dissolved through addition of THF (4 ml), and methanol (4 ml). LiOH.H$_2$O dissolved in H$_2$O (4 ml) was added thereto, followed by stirring for 12 hours at room temperature. After stirring for 12 hours, the resultant solution was vacuum-evaporated, acidified with 2N—HCl to pH 2-3, and extracted with EA (×2). The organic layer was dried with MgSO$_4$, and filtered. Through vacuum distillation, the solvent was removed so as to obtain N-methyl-4-(1-(3-chloro-2-methylphenylsulfonamido)cyclopentanecarboxyamido)adamantane-1-carboxylic acid (343 mg, 0.69 mmol, 98%).

$^1$H NMR (400 MHz, DMSO-d$_6$) δ 12.26 (bs, —COOH), 8.39 (s, —NH—SO$_2$), 7.88 (dd, J=0.8, 8 Hz, 1H), 7.75 (dd, J=0.8, 8 Hz, 1H), 7.42 (t, J=8 Hz, 1H), 7.17 (d, J=7.2 Hz, —NH—CO—), 3.70 (d, J=6.8 Hz, 1H), 2.54 (s, 3H), 1.95-1.76 (m, 13H), 1.53 (m, 4H), 1.29 (m, 2H), 1.17 (m, 2H).

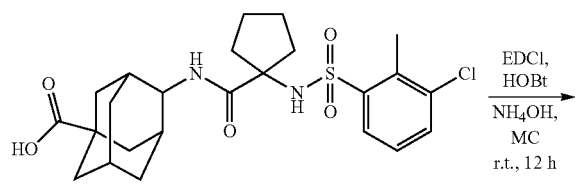

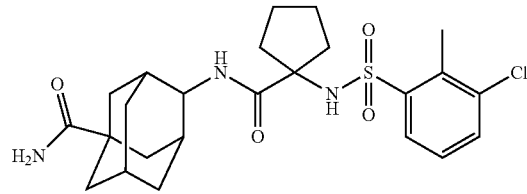

N-methyl-4-(1-(3-chloro-2-methylphenylsulfonamido)cyclopentanecarboxyamido)adamantane-1-carboxylic acid (337 mg, 0.68 mmol) was dissolved in CH$_2$Cl$_2$ (10 ml), and added with EDCI (261 mg, 1.36 mmol) and HOBT (184 mg, 1.36 mmol), followed by stirring for 30 minutes. 30% NH$_4$OH aqueous solution (5 ml) was added thereto, followed by stirring for 12 hours at room temperature. The resultant solution was added with H$_2$O, extracted with CH$_2$Cl$_2$ (×3), dried with MgSO$_4$, and filtered. Through vacuum distillation, the solvent was removed. The resultant mixture was purified with column chromatography so as to obtain N-methyl-4-(1-(3-chloro-2-methylphenylsulfonamido)cyclopentanecarboxyamido)adamantane-1-carboxyamide (286 mg, 0.58 mmol, 85%).

$^1$H NMR (400 MHz, DMSO-d$_6$) δ 8.39 (s, —NH—SO$_2$), 7.86 (dd, J=0.8, 8 Hz, 1H), 7.74 (d, J=8 Hz, 1H), 7.42 (t, J=8 Hz, 1H), 7.17 (d, J=7.2 Hz, —NH—CO—), 7.04 (br, NH$_2$—CO—), 6.78 (br, NH$_2$—CO—), 3.71 (d, J=7.2 Hz, 1H), 2.71 (s, 3H), 1.94-1.66 (m, 15H), 1.47 (m, 4H), 1.12 (m, 2H).

Preparation Example 2

Synthesis of N-4-(1-(quinoline-8-sulfonamido)cyclopentanecarboxyamido)adamantane-1-carboxyamide (compound 168)

An aimed compound was obtained in the same manner as described in Preparation Example 1 of Example 7 except that 1-(quinoline-8-sulfonamido)cyclopentanecarboxylic acid was used.

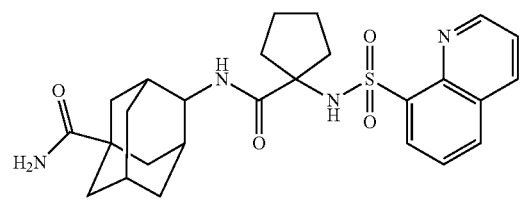

$^1$H NMR (400 MHz, DMSO-d$_6$) δ 9.11 (dd, J=1.2, 4 Hz, 1H), 8.58 (dd, J=2, 8.4 Hz, 1H), 8.31 (m, 2H), 7.84 (s, —NH—SO$_2$), 7.75 (m, 2H), 7.42 (d, J=7.6 Hz, —NH—CO—), 7.05 (br, NH$_2$—CO—), 6.78 (br, NH$_2$—CO—), 3.76 (d, J=7.2 Hz, 1H), 2.02-1.78 (m, 15H), 1.51 (m, 2H), 1.22 (m, 2H).

Preparation Example 3

Synthesis of N-4-(1-(2-methylphenylsulfonamido)cyclopentanecarboxyamido)adamantane-1-carboxyamide (compound 169)

An aimed compound was obtained in the same manner as described in Preparation Example 1 of Example 7 except that 1-(2-methylphenylsulfonamido)cyclopentanecarboxylic acid was used.

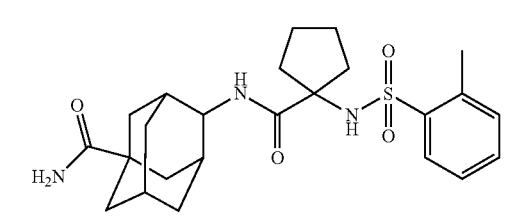 [SMILES: Cc1ccccc1S(=O)(=O)NC1(C(=O)NC2C3CC4CC2CC(C(N)=O)(C4)C3)CCCC1]

$^1$H NMR (400 MHz, DMSO-d$_6$) δ 8.19 (s, —NH—SO$_2$), 7.83 (d, J=8 Hz, 1H), 7.52 (m, 1H), 7.39 (m, 2H), 7.23 (d, J=7.2 Hz, —NH—CO—), 7.05 (br, NH$_2$—CO—), 6.78 (br, NH$_2$—CO—), 3.75 (d, J=7.6 Hz, 1H), 2.62 (s, 3H), 1.89-1.79 (m, 15H), 1.43 (m, 4H), 0.98 (m, 2H).

Preparation Example 4

Synthesis of N-4-(1-(2-chlorophenylsulfonamido)cyclopentanecarboxyamido)adamantane-1-carboxyamide (compound 170)

An aimed compound was obtained in the same manner as described in Preparation Example 1 of Example 7 except that 1-(2-chlorophenylsulfonamido)cyclopentanecarboxylic acid was used.

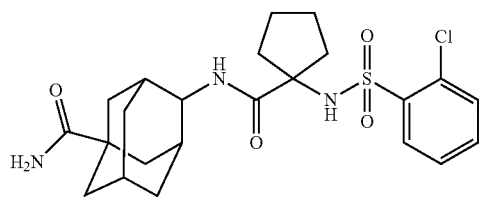

$^1$H NMR (400 MHz, DMSO-d$_6$) δ 8.09 (s, —NH—SO$_2$), 7.99 (d, J=6.8 Hz, 1H), 7.67 (m, 2H), 7.55 (m, 1H), 7.24 (d, J=7.6 Hz, —NH—CO—), 7.05 (br, NH$_2$—CO—), 6.78 (br, NH$_2$—CO—), 3.78 (d, J=7.2 Hz, 1H), 1.99-1.68 (m, 15H), 1.48 (m, 4H), 1.02 (m, 2H).

Preparation Example 5

Synthesis of N-4-(1-(phenylsulfonamido)cyclopentanecarboxyamido)adamantane-1-carboxyamide (compound 171)

An aimed compound was obtained in the same manner as described in Preparation Example 1 of Example 7 except that 1-(phenylsulfonamido)cyclopentanecarboxylic acid was used.

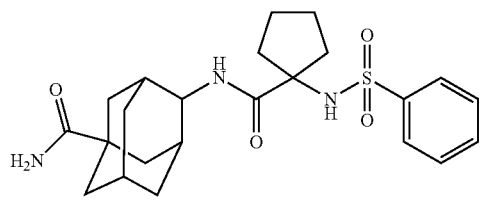 [SMILES: NC(=O)C12CC3CC(C1)C(NC(=O)C1(NS(=O)(=O)c4ccccc4)CCCC1)C(C3)C2]

$^1$H NMR (400 MHz, DMSO-d$_6$) δ 7.82 (m, 2H), 7.65 (s, —NH—SO$_2$), 7.62 (m, 3H), 7.14 (d, J=7.2 Hz, —NH—CO—), 7.02 (br, NH$_2$—CO—), 6.76 (br, NH$_2$—CO—), 3.56 (d, J=6.4 Hz, 1H), 1.89-1.75 (m, 15H), 1.45 (m, 4H), 1.21 (m, 2H).

Preparation Example 6

Synthesis of N-4-(1-(2-trifluoromethylphenylsulfonamido)cyclopentanecarboxyamido)adamantane-1-carboxyamide (compound 172)

An aimed compound was obtained in the same manner as described in Preparation Example 1 of Example 7 except that 1-(2-trifluoromethylphenylsulfonamido)cyclopentanecarboxylic acid was used.

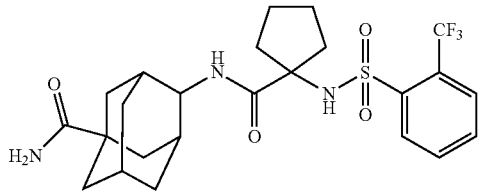

$^1$H NMR (400 MHz, DMSO-d$_6$) δ 8.26 (s, —NH—SO$_2$), 8.19 (d, J=7.6 Hz, 1H), 7.98 (d, J=7.2 Hz, 1H), 7.87 (m, 2H), 7.19 (d, J=6.8 Hz, —NH—CO—), 7.03 (br, NH$_2$—CO—), 6.76 (br, NH$_2$—CO—), 3.75 (d, J=7.2 Hz, 1H), 1.96-1.77 (m, 15H), 1.46 (m, 4H), 1.21 (m, 2H).

Preparation Example 7

Synthesis of N-4-(1-(2-nitrophenylsulfonamido)cyclopentanecarboxyamido)adamantane-1-carboxyamide (compound 173)

An aimed compound was obtained in the same manner as described in Preparation Example 1 of Example 7 except that 1-(2-nitrophenylsulfonamido)cyclopentanecarboxylic acid was used.

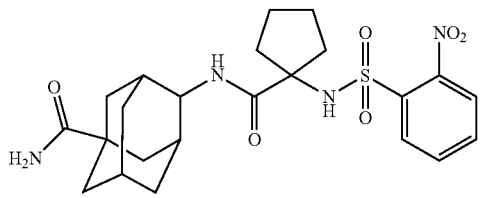

$^1$H NMR (400 MHz, DMSO-d$_6$) δ 8.35 (s, —NH—SO$_2$), 8.07 (m, 1H), 8.01 (m, 1H), 7.87 (m, 2H), 7.17 (d, J=7.6 Hz, —NH—CO—), 7.02 (br, NH$_2$—CO—), 6.75 (br, NH$_2$—CO—), 3.71 (d, J=6.8 Hz, 1H), 1.99-1.76 (m, 15H), 1.48 (m, 4H), 1.27 (m, 2H).

Preparation Example 8

Synthesis of N-4-(1-(2-bromophenylsulfonamido)cyclopentanecarboxyamido)adamantane-1-carboxyamide (compound 174)

An aimed compound was obtained in the same manner as described in Preparation Example 1 of Example 7 except that 1-(2-bromophenylsulfonamido)cyclopentanecarboxylic acid was used.

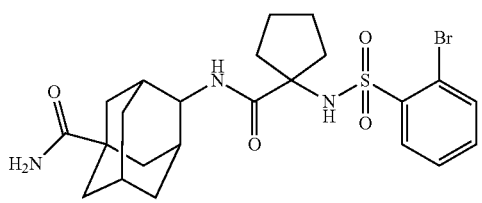

$^1$H NMR (400 MHz, DMSO-d$_6$) δ 8.31 (s, —NH—SO$_2$), 8.03 (dd, J=2, 7.6 Hz, 1H), 7.88 (dd, J=1.2, 7.6 Hz, 1H), 7.56 (m, 2H), 7.26 (d, J=7.6 Hz, —NH—CO—), 7.03 (br, NH$_2$—

CO—), 6.76 (br, NH$_2$—CO—), 3.79 (d, J=7.2 Hz, 1H), 2.01-1.78 (m, 15H), 1.48 (m, 4H), 1.12 (m, 2H).

Preparation Example 9

Synthesis of N-4-(1-(2,6-dichlorophenylsulfonamido)cyclopentanecarboxyamido)adamantane-1-carboxyamide (compound 175)

An aimed compound was obtained in the same manner as described in Preparation Example 1 of Example 7 except that 1-(2,6-dichlorophenylsulfonamido)cyclopentanecarboxylic acid was used.

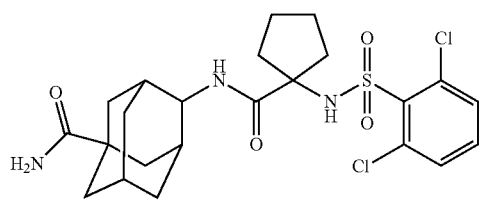 [SMILES: NC(=O)C12CC3CC(C1)C(NC(=O)C1(NS(=O)(=O)c4c(Cl)cccc4Cl)CCCC1)C(C3)C2]

$^1$H NMR (400 MHz, DMSO-d$_6$) δ 8.57 (s, —NH—SO$_2$), 7.68 (m, 2H), 7.57 (m, 1H), 7.18 (d, J=7.6 Hz, —NH—CO—), 7.04 (br, NH$_2$—CO—), 6.76 (br, NH$_2$—CO—), 3.79 (d, J=7.2 Hz, 1H), 1.98-1.78 (m, 15H), 1.49 (m, 4H), 1.08 (m, 2H).

Preparation Example 10

Synthesis of N-4-(1-(2,3-dichlorophenylsulfonamido)cyclopentanecarboxyamido)adamantane-1-carboxyamide (compound 176)

An aimed compound was obtained in the same manner as described in Preparation Example 1 of Example 7 except that 1-(2,3-dichlorophenylsulfonamido)cyclopentanecarboxylic acid was used.

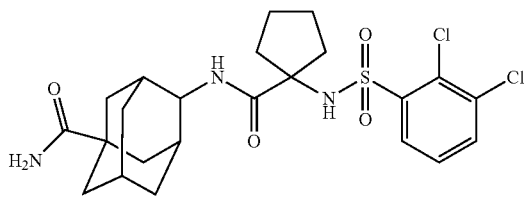

$^1$H NMR (400 MHz, DMSO-d$_6$) δ 8.48 (s, —NH—SO$_2$), 7.98 (m, 2H), 7.57 (t, J=8 Hz, 1H), 7.18 (d, J=7.6 Hz, —NH—CO—), 7.03 (br, NH$_2$—CO—), 6.76 (br, NH$_2$—CO—), 3.74 (d, J=7.2 Hz, 1H), 1.96-1.77 (m, 15H), 1.49 (m, 4H), 1.12 (m, 2H).

Preparation Example 11

Synthesis of N-4-(1-(2-fluoro-3-chlorophenylsulfonamido)cyclopentanecarboxyamido)adamantane-1-carboxyamide (compound 177)

An aimed compound was obtained in the same manner as described in Preparation Example 1 of Example 7 except that 1-(2-fluoro-3-chlorophenylsulfonamido)cyclopentanecarboxylic acid was used.

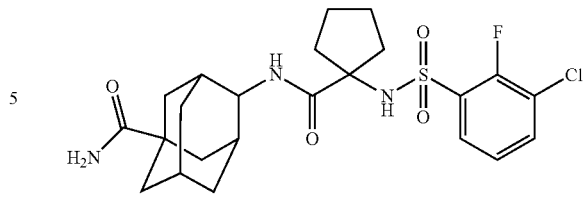

$^1$H NMR (400 MHz, DMSO-d$_6$) δ 8.62 (s, —NH—SO$_2$), 7.92 (m, 1H), 7.76 (m, 1H), 7.42 (t, J=7.6 Hz, 1H), 7.13 (d, J=7.2 Hz, —NH—CO—), 7.03 (br, NH$_2$—CO—), 6.77 (br, NH$_2$—CO—), 3.57 (d, J=6.8 Hz, 1H), 1.91-1.76 (m, 15H), 1.46 (m, 4H), 1.23 (m, 2H).

Example 8

Preparation Example 1

Synthesis of N-4-(1-(2-bromophenylsulfonamido)cyclohexanecarboxyamido)adamantane-1-carboxyamide (compound 178)

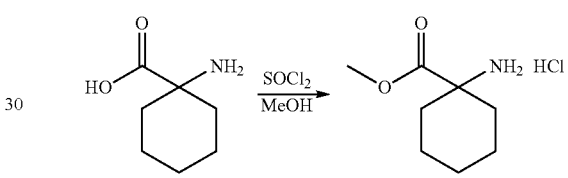

A 100-mL flask was charged with 1-amino-cyclohexanecarboxylic acid (3.0 g, 20.9 mmol) and methanol (50 mL). The mixture was cooled to 0-5° C. by ice bath and thionyl chloride (7.6 mL, 104 mmol) was slowly added thereto. After the addition was completed, the ice bath was removed. At room temperature, the mixture was stirred for 2 days. The resultant product was vacuum-distilled to remove a solvent, and then added with ethyl ether (50 ml), stirred at room temperature for 30 minutes, and filtered. The solid obtained through filtering was dried in a 60° C. oven to obtain 1-amino-cyclohexanecarboxylic acid methylester hydrochloride (3.2 g, 79%).

$^1$H NMR (400 MHz, DMSO-d$_6$) δ 8.73 (s, 3H), 3.75 (s, CH$_3$—CO$_2$—, 3H), 1.40-1.97 (m, 10H).

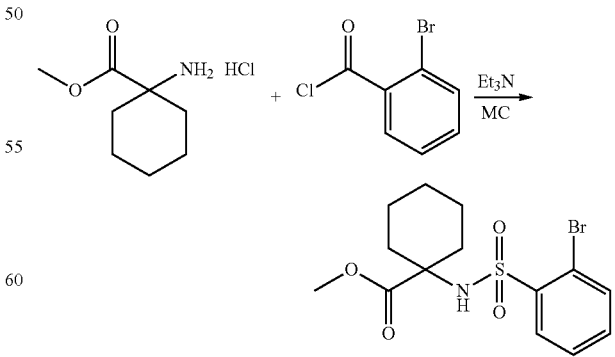

In a 50-mL flask, 1-amino-cyclohexanecarboxylic acid methylester hydrochloride (350 mg, 1.80 mmol) and methylenechloride (20 mL) were charged, and then triethylamine (0.836 mL, 5.99 mmol) was charged, followed by stirring for 30 minutes at room temperature. 2-bromo-benzenesulfonyl-chloride (383 mg, 1.49 mmol) was added thereto, followed by stirring for 12 hours at room temperature. Then, purified water (10 ml) was added thereto to bring the reaction to an end. The organic layer was separated, and washed with saturated ammonium chloride solution (20 ml). Then, the washed organic layer was separated, and added with magnesium sulfate so as to remove remaining moisture. Then, through filtering and vacuum distillation, the solvent was removed so as to obtain the residue. The mixture was purified with column chromatography (EA/n-Hex=1:5) so as to obtain 1-(2-bromo-benzenesulfonylamino)-cyclohexanecarboxylic acid methylester (285 mg, 51%).

$^1$H NMR (400 MHz, CDCl$_3$) δ 8.08 (dd, 1H), 7.74 (dd, 1H), 7.39-7.49 (m, 2H), 3.59 (s, CH$_3$—CO$_2$—, 3H), 1.25-2.19 (m, 10H).

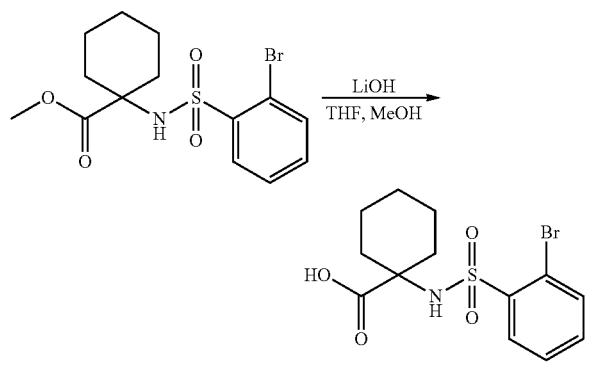

In a 50-mL flask, 1-(2-bromo-benzenesulfonylamino)-cyclohexanecarboxylic acid methyl ester (280 mg, 0.744 mmol) was charged, and dissolved through addition of tetrahydrofuran (5 mL), and methanol (5 mL). Lithium hydroxide dissolved in purified water (5 mL) was added thereto, followed by stirring for 12 hours at 40-45° C. After the reaction was completed, the resultant solution was vacuum-evaporated, acidified with 2N hydrochloric acid aqueous solution to pH 1-2, and extracted with addition of ethyl acetate (20 ml). The organic layer was added with magnesium sulfate so as to remove remaining moisture. Through filtering and vacuum distillation, the solvent was removed so as to obtain 1-(2-bromo-benzenesulfonamino)-cyclohexane carboxylic acid (256 mg, 94%).

$^1$H NMR (400 MHz, DMSO-d$_6$) δ 12.4 (s, HO—CO—, 1H), 8.37 (s, —NH—SO$_2$, 1H), 7.98 (dd, 1H), 7.82 (dd, 1H), 7.48-7.56 (m, 2H), 0.89-1.91 (m, 10H).

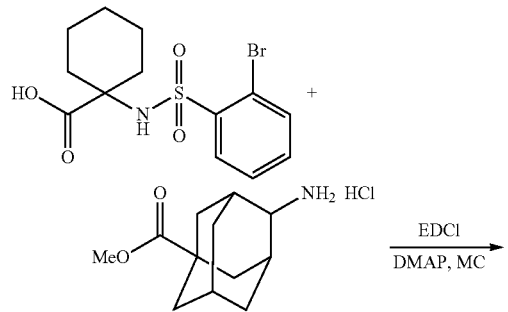

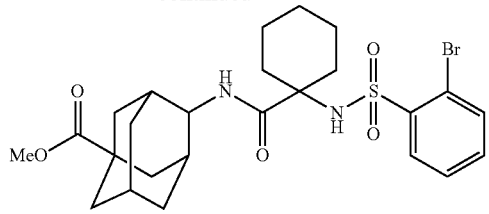

In a 50-mL flask, 1-(2-bromo-benzenesulfonamino)-cyclohexane carboxylic acid (163 mg, 0.450 mmol) and methylenechloride (20 mL) were charged, and 1-ethyl-3-(3-dimethylaminopropyl)carbodiimidehydrochloride (235 mg, 1.22 mmol) and dimethylaminopyridine (100 mg, 0.818 mmol) were sequentially added thereto, followed by stirring for 5 minutes at room temperature. 2-adamantanamine hydrochloride (100 mg, 0.409 mmol) was added thereto, followed by stirring for 12 hours at room temperature. After the reaction was completed, purified water (20 mL) was added thereto, and the aqueous solution layer was washed with methylenechloride (30 mL) twice. The obtained organic layer was added with magnesiumsulfate so as to remove remaining moisture. Through filtering and vacuum evaporation, the residue was obtained. The mixture was purified with column chromatography (EA/n-Hex=1:2) so as to obtain 4-{[1-(2-bromo-benzenesulfonylamino)-cyclohexanecarbonyl]-amino}-adamantane-1-carboxylic acid methylester (141 mg, 62%).

$^1$H NMR (400 MHz, CDCl$_3$) δ 8.12 (dd, 1H), 7.76 (dd, 1H), 7.43-7.50 (m, 2H), 6.94 (d, —NH—SO$_2$—, 1H), 5.59 (s, —NH—CO—, 1H), 4.01 (m, 1H), 3.68 (s, CH$_3$—CO$_2$—, 1H), 0.98-2.09 (m, 23H).

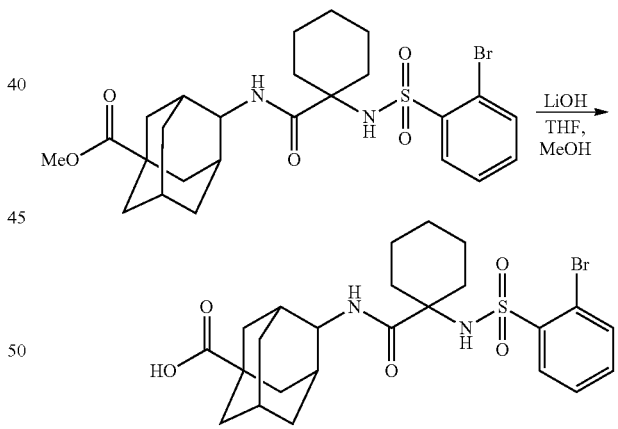

In a 25-mL flask, 4-{[1-(2-bromo-benzenesulfonylamino)-cyclohexanecarbonyl]-amino}-adamantane-1-carboxylic acid methylester (140 mg, 0.253 mmol) was charged, and dissolved through addition of tetrahydrofuran (5 mL), and methanol (5 mL). Lithium hydroxide dissolved in purified water (5 mL) was added thereto, followed by stirring for 12 hours at room temperature. After the reaction was completed, the resultant solution was vacuum-evaporated, acidified with 2N hydrochloric acid aqueous solution to pH 1-2, and extracted with addition of ethyl acetate (20 ml). The organic layer was added with magnesium sulfate so as to remove remaining moisture. Through filtering and vacuum distillation, the solvent was removed so as to obtain 4-{[1-(2- bromo-benzenesulfonylamino)-cyclohexanecarbonyl]-amino}-adamantane-1-carboxylic acid (106 mg, 79%).

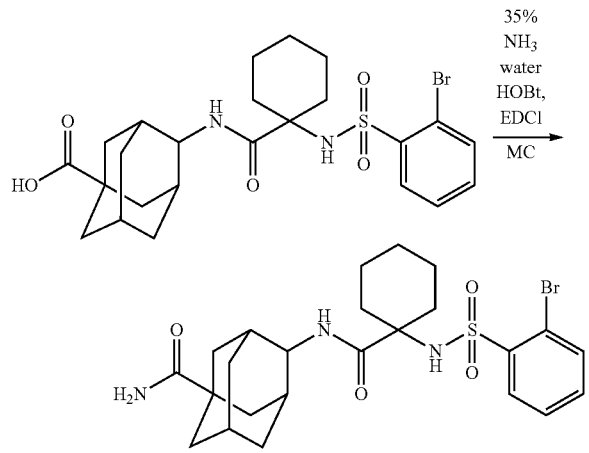

In a 25-mL flask, 4-{[1-(2-bromo-benzenesulfonylamino)-cyclohexanecarbonyl]-amino}-adamantane-1-carboxylic acid (106 mg, 0.196 mmol) and methylenechloride (20 mL) were charged, and then sequentially 1-ethyl-3-(3-dimethylaminopropyl)carbodiimidehydrochloride (76 mg, 0.392 mmol) and 1-hydroxybenzotriazol (54 mg, 0.392 mmol) were added thereto, followed by stirring for 5 minutes at room temperature. The resultant solution was added with 35% ammonia aqueous solution (1.1 mL), followed by stirring for 12 hours at room temperature. After the reaction was completed, purified water (10 mL) was added thereto, and the aqueous solution layer was washed with methylenechloride (30 mL) twice. The obtained organic layer was added with magnesium sulfate so as to remove remaining moisture. Through filtering and vacuum evaporation, the residue was obtained. The mixture was purified with column chromatography (MC/MeOH=20:1) so as to obtain 4-{[1-(2-bromo-benzenesulfonylamino)-cyclohexanecarbonyl]-amino}-adamantane-1-carboxylic acid amide (62 mg, 59%).

$^1$H NMR (400 MHz, DMSO-$d_6$) δ 8.07 (s, —NH—SO$_2$, 1H), 7.99 (d, 1H), 7.89 (d, 1H), 7.58 (m, 2H), 7.14 (d, —NH—CO—, 1H), 7.03 (s, NH$_2$—CO—, 1H), 6.75 (s, NH$_2$—CO—, 1H), 3.80 (s, 1H), 1.59-2.15 (m, 13H), 0.87-1.61 (m, 10H).

Preparation Example 2

Synthesis of N-4-(1-(2-chlorophenylsulfonamido)cyclohexanecarboxyamido)adamantane-1-carboxyamide (compound 179)

An aimed compound was obtained in the same manner as described in Preparation Example 1 of Example 8 except that 1-(2-chlorophenylsulfonamido)cyclohexanecarboxylic acid was used.

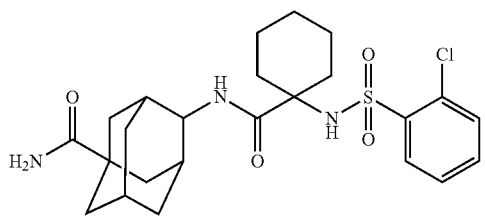

$^1$H NMR (400 MHz, DMSO-$d_6$) δ 8.15 (s, —NH—SO$_2$, 1H), 7.95 (d, 1H), 7.64-7.70 (m, 2H), 7.54 (d, 1H), 7.09 (d, —NH—CO—, 1H), 7.04 (s, NH$_2$—CO—, 1H), 6.77 (s, NH$_2$—CO—, 1H), 3.78 (s, 1H), 1.59-2.15 (m, 13H), 0.87-1.61 (m, 10H).

Preparation Example 3

Synthesis of N-4-(1-(3-chloro-2-methylphenylsulfonamido)cyclohexanecarboxyamido)adamantane-1-carboxyamide (compound 180)

An aimed compound was obtained in the same manner as described in Preparation Example 1 of Example 8 except that 1-(3-chloro-2-methylphenylsulfonamido)cyclohexanecarboxylic acid was used.

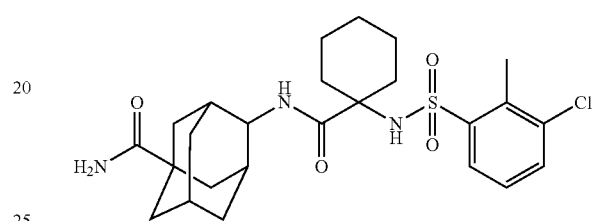

$^1$H NMR (400 MHz, DMSO-$d_6$) δ 8.15 (s, —NH—SO$_2$, 1H), 7.83 (d, 1H), 7.72 (d, 1H), 7.42 (t, 1H), 7.03 (s, NH$_2$—CO—, 1H), 6.96 (d, —NH—CO—, 1H), 6.77 (s, NH$_2$—CO—, 1H), 3.69 (s, 1H), 1.59-2.15 (m, 13H), 0.87-1.61 (m, 10H).

Preparation Example 4

Synthesis of N-4-(1-(2-trifluoromethylphenylsulfonamido)cyclohexanecarboxyamido)adamantane-1-carboxyamide (compound 181)

An aimed compound was obtained in the same manner as described in Preparation Example 1 of Example 8 except that 1-(2-trifluoromethylphenylsulfonamido)cyclohexanecarboxylic acid was used.

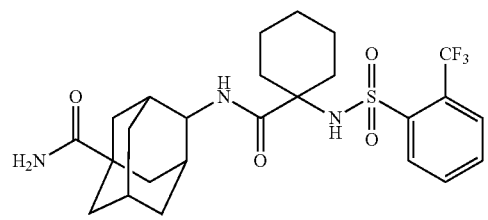

$^1$H NMR (400 MHz, DMSO-$d_6$) δ 8.30 (s, —NH—SO$_2$, 1H), 8.16 (d, 1H), 7.66-7.76 (m, 3H), 7.31 (d, —NH—CO—, 1H), 7.09 (s, NH$_2$—CO—, 1H), 6.77 (s, NH$_2$—CO—, 1H), 3.76 (s, 1H), 1.59-2.15 (m, 13H), 0.87-1.61 (m, 10H).

Preparation Example 5

Synthesis of N-4-(1-(quinoline-8-sulfonamido)cyclohexanecarboxyamido)adamantane-1-carboxyamide (compound 182)

An aimed compound was obtained in the same manner as described in Preparation Example 1 of Example 8 except that 1-(quinoline-8-sulfonamido)cyclohexanecarboxylic acid was used.

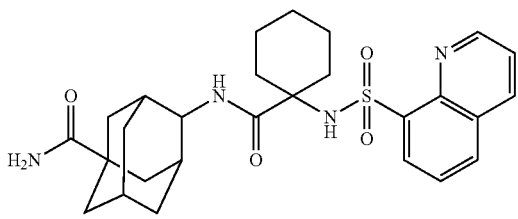

¹H NMR (400 MHz, DMSO-d₆) δ 9.14 (s, —NH—SO₂, 1H), 8.59 (d, 1H), 8.30 (dd, 2H), 7.76 (d, 2H), 7.65 (s, 1H), 7.31 (d, —NH—CO—, 1H), 7.04 (s, NH₂—CO—, 1H), 6.77 (s, NH₂—CO—, 1H), 3.70 (s, 1H), 1.59-2.15 (m, 13H), 0.87-1.61 (m, 10H).

Preparation Example 6

Synthesis of N-4-(1-(2,3-dichlorophenylsulfonamido)cyclohexanecarboxyamido)adamantane-1-carboxyamide (compound 183)

An aimed compound was obtained in the same manner as described in Preparation Example 1 of Example 8 except that 1-(2,3-dichlorophenylsulfonamido)cyclohexanecarboxylic acid was used.

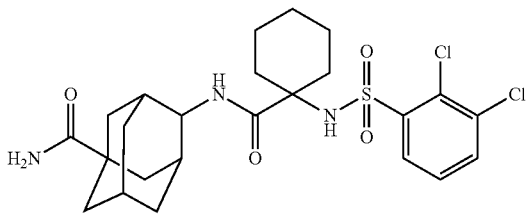

¹H NMR (400 MHz, DMSO-d₆) δ 8.29 (s, —NH—SO₂, 1H), 7.95 (s, 1H), 7.93 (s, 1H), 7.57 (t, 1H), 7.05 (s, —NH—CO—, 1H), 7.03 (s, NH₂—CO—, 1H), 6.75 (s, NH₂—CO—, 1H), 3.74 (s, 1H), 1.59-2.15 (m, 13H), 0.87-1.61 (m, 10H).

Preparation Example 7

Synthesis of N-4-(1-(2-nitrophenylsulfonamido)cyclohexanecarboxyamido)adamantane-1-carboxyamide (compound 184)

An aimed compound was obtained in the same manner as described in Preparation Example 1 of Example 8 except that 1-(2-nitrophenylsulfonamido)cyclohexanecarboxylic acid was used.

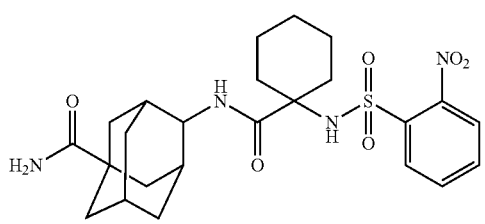

¹H NMR (400 MHz, DMSO-d₆) δ 8.03 (s, —NH—SO₂, 1H), 8.01 (s, 1H), 8.00 (s, 1H), 7.82-7.90 (m, 2H), 7.09 (d, —NH—CO—, 1H), 7.02 (s, NH₂—CO—, 1H), 6.75 (s, NH₂—CO—, 1H), 3.73 (s, 1H), 1.59-2.15 (m, 13H), 0.87-1.61 (m, 10H).

Preparation Example 8

Synthesis of N-4-(1-(2-fluorophenylsulfonamido)cyclohexanecarboxyamido)adamantane-1-carboxyamide (compound 185)

An aimed compound was obtained in the same manner as described in Preparation Example 1 of Example 8 except that 1-(2-fluorophenylsulfonamido)cyclohexanecarboxylic acid was used.

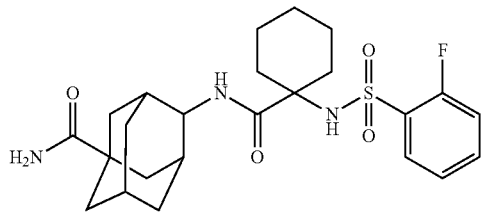

¹H NMR (400 MHz, DMSO-d₆) δ 8.20 (s, —NH—SO₂, 1H), 7.68-7.76 (m, 2H), 7.42 (t, 1H), 7.34 (t, 1H), 7.01-7.02 (s, —NH—CO—, NH₂—CO—, 2H), 6.75 (s, NH₂—CO—, 1H), 3.61 (s, 1H), 1.59-2.15 (m, 13H), 0.87-1.61 (m, 10H).

Preparation Example 9

Synthesis of N-4-(1-(2,6-dichlorophenylsulfonamido)cyclohexanecarboxyamido)adamantane-1-carboxyamide (compound 186)

An aimed compound was obtained in the same manner as described in Preparation Example 1 of Example 8 except that 1-(2,6-dichlorophenylsulfonamido)cyclohexanecarboxylic acid was used.

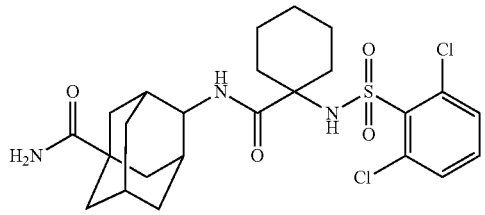

¹H NMR (400 MHz, DMSO-d₆) δ 8.33 (s, —NH—SO₂, 1H), 7.66 (d, 2H), 7.54 (d, 1H), 7.05 (s, —NH—CO—, 1H), 7.03 (s, NH₂—CO—, 1H), 6.76 (s, NH₂—CO—, 1H), 3.80 (s, 1H), 1.59-2.15 (m, 13H), 0.87-1.61 (m, 10H).

Preparation Example 10

Synthesis of N-4-(1-(3-fluoro-4-methylphenylsulfonamido)cyclohexanecarboxyamido)adamantane-1-carboxyamide (compound 187)

An aimed compound was obtained in the same manner as described in Preparation Example 1 of Example 8 except that 1-(3-fluoro-4-methylphenylsulfonamido)cyclohexanecarboxylic acid was used.

133

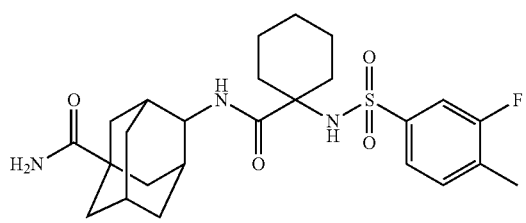 [SMILES: Cc1ccc(S(=O)(=O)NC2(C(=O)NC3C4CC5CC3CC(C(N)=O)(C5)C4)CCCCC2)cc1F]

$^1$H NMR (400 MHz, DMSO-d$_6$) δ 7.87 (s, —NH—SO$_2$, 1H), 7.48 (s, 2H), 7.42 (d, 1H), 7.01 (s, NH$_2$—CO—, 1H), 6.85 (d, —NH—CO—, 1H), 6.76 (s, NH$_2$—CO—, 1H), 3.29 (s, 1H), 2.30 (s, —CH3, 3H) 1.59-2.15 (m, 13H), 0.87-1.61 (m, 10H).

Example 9

Preparation Example 1

Synthesis of N-4-(2-methyl-2-(N-methylquinoline-8-sulfonamido)propanamido)adamantane-1-carboxyamide (compound 188)

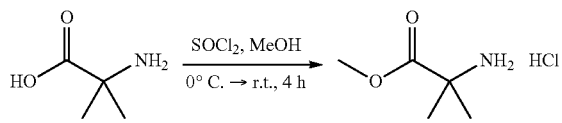

2-amino-2-methylpropionic acid (10 g, 96.9 mmol) and methanol (330 ml) were charged. An ice bath was set and thionyl chloride (17.68 ml, 242.25 mmol) was slowly added thereto. Then, the ice bath was removed, and the mixture was stirred at room temperature for 3 hours. The resultant product was vacuum-distilled to remove a solvent, and dried in a 60° C. oven so as to obtain methyl-2-amino-2-methylpropanoate hydrochloride (14.59 g, 94.9 mmol, 98%).

$^1$H NMR (400 MHz, DMSO-d$_6$) 8.75 (br, 3H), 3.75 (s, 3H), 1.45 (s, 6H).

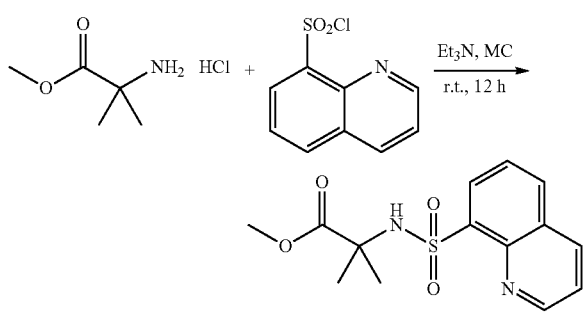

methyl-2-amino-2-methylpropanoate hydrochloride (5 g, 32.6 mmol) was dissolved in CH$_2$Cl$_2$ (110 ml), added with quinoline-8-sulfonyl chloride (8.18 g, 35.9 mmol) and triethylamine (18 ml, 130.6 mmol), and stirred at room temperature for 12 hours. The resultant solution was added with H$_2$O, extracted with CH$_2$Cl$_2$ (×2), dried with MgSO$_4$, and filtered. Through vacuum distillation, the solvent was removed. The resultant mixture was purified with column chromatography so as to obtain methyl-2-methyl-2-(quinoline-8-sulfonamido)propanoate (8.74 g, 32.8 mmol, 95%).

134

$^1$H NMR (400 MHz, CDCl$_3$) δ 9.09 (dd, J=1.6, 4.4 Hz, 1H), 8.39 (dd, J=1.2, 7.2 Hz, 1H), 8.31 (dd, J=2, 8.4 Hz, 1H), 8.05 (dd, J=1.2, 8 Hz, 1H), 7.68 (t, J=4.4 Hz, 1H), 7.59 (m, 1H), 7.36 (s, —NH—SO$_2$), 3.46 (s, 3H), 1.48 (s, 6H).

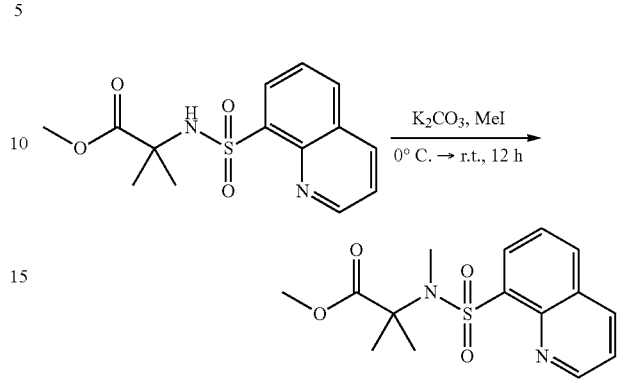

methyl-2-methyl-2-(quinoline-8-sulfonamido)propanoate (699 mg, 2.26 mmol) was dissolved in DMF (10 ml), added with MeI (0.49 ml, 7.93 mmol) at 0° C., and stirred at room temperature for 12 hours. The resultant solution was added with H$_2$O and extracted with EA (×2). The organic solution was washed with H$_2$O, dried with MgSO$_4$, and filtered. Through vacuum distillation, the solvent was removed. The resultant mixture was purified with column chromatography so as to obtain methyl-2-methyl-2-(N-methylquinoline-8-sulfonamido)propanoate (694 mg, 2.15 mmol, 95%).

$^1$H NMR (400 MHz, CDCl$_3$) δ 9.09 (dd, J=1.6 Hz, 1H), 8.41 (dd, J=1.2, 7.2 Hz, 1H), 8.24 (dd, J=2, 8.4 Hz, 1H), 8.02 (dd, J=1.2, 8 Hz, 1H), 7.68 (t, J=4 Hz, 1H), 7.54 (m, 1H), 3.58 (s, 3H), 3.43 (s, 3H), 1.52 (s, 6H).

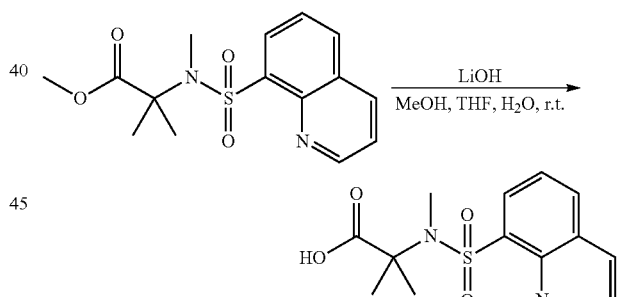

methyl-2-methyl-2-(N-methylquinoline-8-sulfonamido) propanoate (650 mg, 2.01 mmol) was charged, and dissolved through addition of THF (5 ml) and methanol (5 ml). LiOH.H$_2$O dissolved in H$_2$O (5 ml) was added thereto, followed by stirring for 12 hours at room temperature. After stirring for 12 hours, the resultant solution was vacuum-evaporated, adjusted with 2N—HCl to pH 5-6, and extracted with EA (×2). The organic layer was dried with MgSO$_4$, and filtered. Through vacuum distillation, the solvent was removed so as to obtain 2-methyl-2-(N-methylquinoline-8-sulfonamido)propionic acid (610 mg, 1.97 mmol, 98%).

$^1$H NMR (400 MHz, DMSO-d$_6$) δ 13.06 (bs, —COOH), 9.07 (dd, J=2, 4.4 Hz, 1H), 8.58 (dd, J=2, 8.4 Hz, 1H), 8.37 (dd, J=1.2, 7.6 Hz, 1H), 8.31 (dd, J=1.2, 8 Hz, 1H), 7.74 (m, 2H), 3.09 (s, 3H), 1.39 (s, 3H).

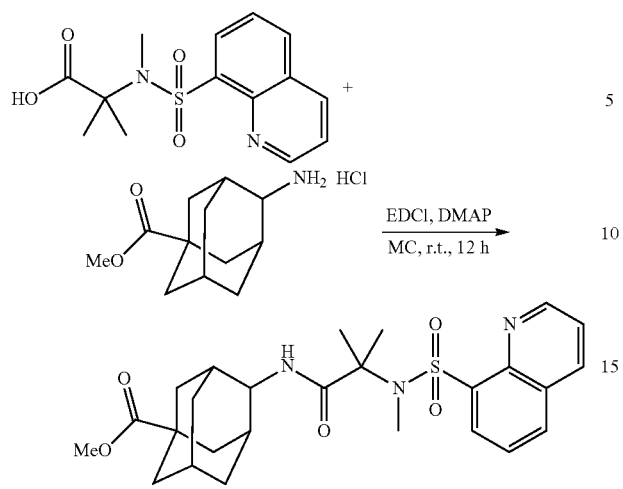

2-methyl-2-(N-methylquinoline-8-sulfonamido)propionic acid (461 mg, 1.49 mmol), 4-amino-adamantane-1-carboxylate hydrochloride (405 mg, 1.46 mmol), and EDCI (861 mg, 4.49 mmol) were charged, and $CH_2Cl_2$ (7 ml) was added thereto, followed by stirring for 30 minutes at room temperature. DMAP (365 mg, 2.99 mmol) was added thereto, followed by stirring at room temperature for 12 hours. After the reaction was completed, the organic layer was separated using $CH_2Cl_2$ and $H_2O$, dried with $MgSO_4$, and filtered. Then, through vacuum distillation, the solvent was removed, and the resultant product was purified with column chromatography to obtain N-4-(2-methyl-2-(N-methylquinoline-8-sulfonamido)propanamido)adamantane-1-carboxylate (673 mg, 1.34 mmol, 90%).

$^1$H NMR (400 MHz, $CDCl_3$) δ 9.11 (dd, J=1.6, 4 Hz, 1H), 8.55 (dd, J=1.6, 7.6 Hz, 1H), 8.29 (dd, J=2, 8.4 Hz, 1H), 8.09 (dd, J=1.6, 8.4 Hz, 1H), 7.68 (t, J=7.2 Hz, 1H), 7.58 (m, 1H), 7.16 (d, J=8 Hz, —NH—CO—), 3.97 (d, J=7.6 Hz, 1H), 3.68 (s, 3H), 3.34 (s, 3H), 1.99-1.89 (m, 9H), 1.58 (m, 2H), 1.51 (m, 2H), 1.39 (s, 6H).

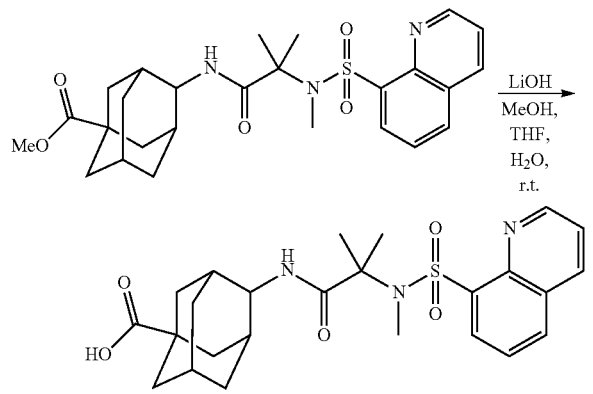

N-4-(2-methyl-2-(N-methylquinoline-8-sulfonamido)propanamido)adamantane-1-carboxylate (640 mg, 1.28 mmol) was charged, and dissolved through addition of THF (6 ml), and methanol (6 ml). $LiOH \cdot H_2O$ dissolved in $H_2O$ (6 ml) was added thereto, followed by stirring for 12 hours at room temperature. After stirring for 12 hours, the resultant solution was vacuum-evaporated, adjusted with 2N—HCl to pH 5~6, and extracted with EA (×2). The organic layer was dried with $MgSO_4$, and filtered. Through vacuum distillation, the solvent was removed so as to obtain N-4-(2-methyl-2-(N-methylquinoline-8-sulfonamido)propanamido)adamantane-1-carboxylic acid (610 mg, 1.25 mmol, 98%).

$^1$H NMR (400 MHz, DMSO-$d_6$) δ 12.13 (bs, —COOH), 8.21 (dd, J=2, 6.8 Hz, 1H), 7.92 (dd, J=2, 7.2 Hz, 1H), 7.61 (m, 2H), 6.94 (d, J=7.2 Hz, —NH—CO—), 3.76 (d, J=6.8 Hz, 1H), 2.97 (s, 3H), 1.91-1.71 (m, 11H), 1.46 (m, 2H), 1.38 (s, 6H).

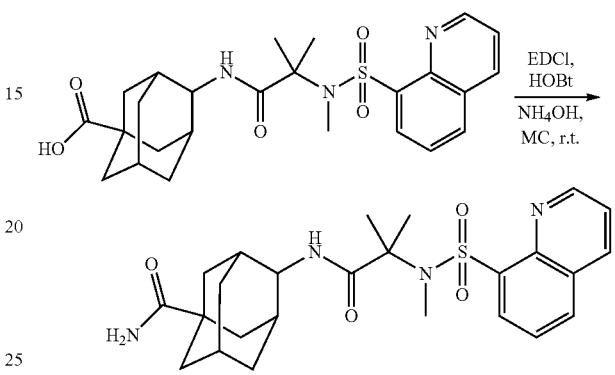

N-4-(2-methyl-2-(N-methylquinoline-8-sulfonamido)propanamido)adamantane-1-carboxylic acid (273 mg, 0.56 mmol) was dissolved in $CH_2Cl_2$ (8 ml), and added with EDCI (216 mg, 1.13 mmol) and HOBT (152 mg, 1.13 mmol), followed by stirring for 30 minutes. 30% $NH_4OH$ aqueous solution (4 ml) was added thereto, followed by stirring at room temperature for 12 hours. The resultant solution was added with $H_2O$, extracted with $CH_2Cl_2$ (×3), dried with $MgSO_4$, and filtered. Through vacuum distillation, the solvent was removed. The resultant mixture was purified with column chromatography so as to obtain N-4-(2-methyl-2-(N-methylquinoline-8-sulfonamido)propanamido)adamantane-1-carboxyamide (232 mg, 0.48 mmol, 85%).

$^1$H NMR (400 MHz, DMSO-$d_6$) δ 9.13 (dd, J=2, 4.4 Hz, 1H), 8.59 (dd, J=2, 8.4 Hz, 1H), 8.46 (dd, J=1.2, 7.2 Hz, 1H), 8.35 (dd, J=1.2, 8 Hz, 1H), 7.71 (m, 2H), 6.69 (s, $NH_2$—CO—), 6.75 (s, $NH_2$—CO—), 6.64 (d, J=7.6 Hz, —NH—CO—), 3.69 (d, J=7.6 Hz, 1H), 3.14 (s, 3H), 1.79-1.68 (m, 9H), 1.33 (s, 6H), 1.27 (m, 2H), 1.17 (m, 2H).

Preparation Example 2

Synthesis of N-4-(2-(2-bromo-N-methylphenylsulfonamido)-2-methylpropanamido)adamantane-1-carboxyamide (compound 189)

An aimed compound was obtained in the same manner as described in Preparation Example 1 of Example 9 except that 2-(2-bromo-N-methylphenylsulfonamido)-2-methylpropionic acid was used.

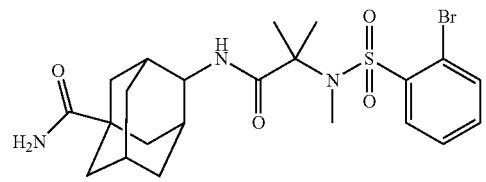 [SMILES: CN(C(C)(C)C(=O)NC1C2CC3CC1CC(C(N)=O)(C3)C2)S(=O)(=O)c1ccccc1Br]

$^1$H NMR (400 MHz, DMSO-d$_6$) δ 8.21 (dd, J=2.4, 8.4 Hz, 1H), 7.92 (dd, J=2, 7.2 Hz, 1H), 7.61 (m, 2H), 7.02 (s, NH$_2$—CO—), 6.94 (d, J=7.2 Hz, —NH—CO—), 6.76 (s, NH$_2$—CO—), 3.76 (d, J=6.8 Hz, 1H), 2.97 (s, 3H), 1.88-1.69 (m, 11H), 1.43 (m, 2H), 1.38 (s, 6H).

Preparation Example 3

Synthesis of N-4-(2-(2-chloro-N-methylphenylsulfonamido)-2-methylpropanamido)adamantane-1-carboxyamide (compound 190)

An aimed compound was obtained in the same manner as described in Preparation Example 1 of Example 9 except that 2-(2-chloro-N-methylphenylsulfonamido)-2-methylpropionic acid was used.

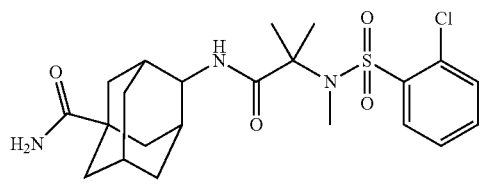

$^1$H NMR (400 MHz, DMSO-d$_6$) δ 8.17 (dd, J=1.6, 8 Hz, 1H), 7.74 (m, 2H), 7.58 (m, 1H), 7.02 (s, NH$_2$—CO—), 6.89 (d, J=7.2 Hz, —NH—CO—), 6.76 (s, NH$_2$—CO—), 3.76 (d, J=7.2 Hz, 1H), 2.96 (s, 3H), 1.87-1.68 (m, 11H), 1.44 (m, 2H), 1.38 (s, 6H).

Preparation Example 4

Synthesis of N-4-(2-(2-methyl-3-chloro-N-methylphenylsulfonamido)-2-methylpropanamido)adamantane-1-carboxyamide (compound 191)

An aimed compound was obtained in the same manner as described in Preparation Example 1 of Example 9 except that 2-(2-methyl-3-chloro-N-methylphenylsulfonamido)-2-methylpropionic acid was used.

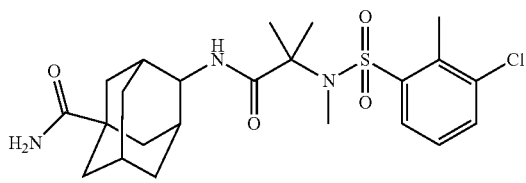 [SMILES: Cc1c(Cl)cccc1S(=O)(=O)N(C)C(C)(C)C(=O)NC1C2CC3CC1CC(C(N)=O)(C3)C2]

$^1$H NMR (400 MHz, DMSO-d$_6$) δ 8.07 (d, J=7.2 Hz, 1H), 7.76 (d, J=7.6 Hz, 1H), 7.43 (t, J=8 Hz, 1H), 6.99 (br, NH$_2$—CO—), 6.89 (d, J=7.2 Hz, —NH—CO—), 6.74 (br, NH$_2$—CO—), 3.73 (d, J=6.8 Hz, 1H), 2.90 (s, 3H), 2.59 (s, 3H), 1.84-1.69 (m, 11H), 1.45 (s, 6H), 1.37 (m, 2H).

Preparation Example 5

Synthesis of N-4-(2-(2,6-dichloro-N-methylphenylsulfonamido)-2-methylpropanamido)adamantane-1-carboxyamide (compound 192)

An aimed compound was obtained in the same manner as described in Preparation Example 1 of Example 9 except that 2-(2,6-dichloro-N-methylphenylsulfonamido)-2-methylpropionic acid was used.

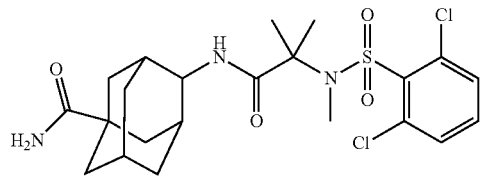 [SMILES: CN(C(C)(C)C(=O)NC1C2CC3CC1CC(C(N)=O)(C3)C2)S(=O)(=O)c1c(Cl)cccc1Cl]

$^1$H NMR (400 MHz, DMSO-d$_6$) δ 7.76 (m, 2H), 7.65 (m, 1H), 7.03 (br, NH$_2$—CO—), 6.89 (d, J=7.2 Hz, —NH—CO—), 6.76 (br, NH$_2$—CO—), 3.79 (d, J=7.2 Hz, 1H), 2.97 (s, 3H), 1.83-1.68 (m, 11H), 1.51 (m, 2H), 1.38 (s, 6H).

Preparation Example 6

Synthesis of N-4-(2-(2-trifluoromethyl-N-methylphenylsulfonamido)-2-methylpropanamido)adamantane-1-carboxyamide (compound 193)

An aimed compound was obtained in the same manner as described in Preparation Example 1 of Example 9 except that 2-(2-trifluoromethyl-N-methylphenylsulfonamido)-2-methylpropionic acid was used.

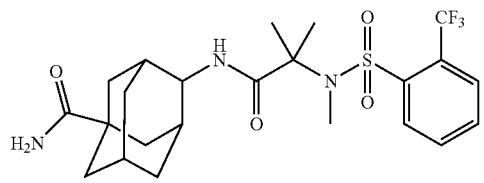 [SMILES: CN(C(C)(C)C(=O)NC1C2CC3CC1CC(C(N)=O)(C3)C2)S(=O)(=O)c1ccccc1C(F)(F)F]

$^1$H NMR (400 MHz, DMSO-d$_6$) δ 8.43 (d, J=7.6 Hz, 1H), 7.99 (dd, J=1.6, 7.6 Hz, 1H), 7.88 (m, 2H), 6.99 (br, NH$_2$—CO—), 6.83 (d, J=7.2 Hz, —NH—CO—), 6.73 (br, NH$_2$—CO—), 3.72 (d, J=6.8 Hz, 1H), 2.91 (s, 3H), 1.83-1.71 (m, 11H), 1.51 (s, 6H), 1.34 (m, 2H).

Preparation Example 7

Synthesis of N-4-(2-(2-methoxy-6-fluoro-N-methylphenylsulfonamido)-2-methylpropanamido)adamantane-1-carboxyamide (compound 194)

An aimed compound was obtained in the same manner as described in Preparation Example 1 of Example 9 except that 2-(2-methoxy-6-fluoro-N-methylphenylsulfonamido)-2-methylpropionic acid was used.

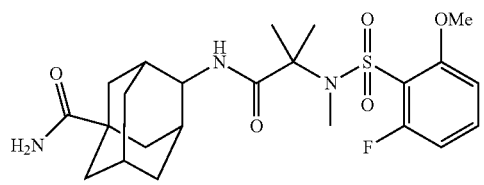 [SMILES: COc1cccc(F)c1S(=O)(=O)N(C)C(C)(C)C(=O)NC1C2CC3CC1CC(C(N)=O)(C3)C2]

$^1$H NMR (400 MHz, DMSO-d$_6$) δ 7.66 (m, 1H), 7.14 (m, 1H), 6.96 (m, 3H), 6.75 (br, NH$_2$—CO—), 3.97 (s, 3H), 3.78 (d, J=7.6 Hz, 1H), 2.91 (s, 3H), 1.92-1.66 (m, 11H), 1.49 (m, 2H), 1.37 (s, 6H).

Preparation Example 8

Synthesis of N-4-(2-(2-fluoro-N-methylphenylsulfonamido)-2-methylpropanamido)adamantane-1-carboxyamide (compound 195)

An aimed compound was obtained in the same manner as described in Preparation Example 1 of Example 9 except that 2-(2-fluoro-N-methylphenylsulfonamido)-2-methylpropionic acid was used.

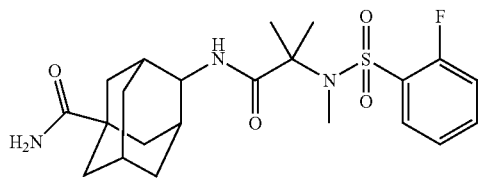

$^1$H NMR (400 MHz, DMSO-d$_6$) δ 7.94 (dt, J=1.6, 8 Hz, 1H), 7.77 (m, 1H), 7.51 (m, 1H), 7.44 (m, 1H), 7.01 (br, NH$_2$—CO—), 6.79 (d, J=7.6 Hz, —NH—CO—), 6.75 (br, NH$_2$—CO—), 3.77 (d, J=7.2 Hz, 1H), 2.92 (s, 3H), 1.89-1.75 (m, 11H), 1.45 (m, 2H), 138 (s, 6H).

Preparation Example 9

Synthesis of N-4-(2-(2-fluoro-N-methylphenylsulfonamido)-2-methylpropanamido)adamantane-1-carboxyamide (compound 196)

An aimed compound was obtained in the same manner as described in Preparation Example 1 of Example 9 except that 2-(2-fluoro-N-methylphenylsulfonamido)-2-methylpropionic acid was used.

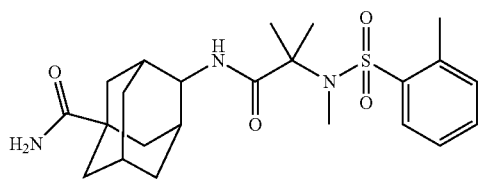 [SMILES: Cc1ccccc1S(=O)(=O)N(C)C(C)(C)C(=O)NC1C2CC3CC1CC(C(N)=O)(C3)C2]

$^1$H NMR (400 MHz, DMSO-d$_6$) δ 8.03 (d, J=8 Hz, 1H), 7.56 (dt, J=1.2, 7.6 Hz, 1H), 7.43 (m, 2H), 7.02 (d, J=6.8 Hz, —NH—CO—), 6.98 (br, NH$_2$—CO—), 6.74 (br, NH$_2$—CO—), 3.75 (d, J=7.2 Hz, 1H), 2.88 (s, 3H), 2.59 (s, 3H), 1.84-1.72 (m, 11H), 1.41 (s, 6H).

Preparation Example 10

Synthesis of N-4-(2-(2-nitro-N-methylphenylsulfonamido)-2-methylpropanamido)adamantane-1-carboxyamide (compound 197)

An aimed compound was obtained in the same manner as described in Preparation Example 1 of Example 9 except that 2-(2-nitro-N-methylphenylsulfonamido)-2-methylpropionic acid was used.

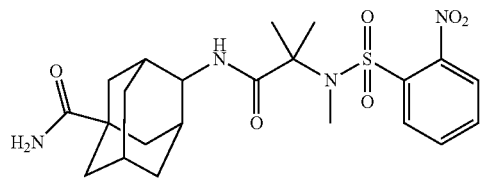

$^1$H NMR (400 MHz, DMSO-d$_6$) δ 8.31 (m, 1H), 7.79 (m, 1H), 7.87 (m, 2H), 6.99 (br, NH$_2$—CO—), 6.86 (d, J=6.8 Hz, —NH—CO—), 6.74 (br, NH$_2$—CO—), 3.76 (d, J=6.8 Hz, 1H), 2.84 (s, 3H), 1.89-1.73 (m, 11H), 1.48 (s, 6H), 1.39 (m, 2H).

Preparation Example 11

Synthesis of N-4-(2-(2,6-dichloro-N-methylphenylsulfonamido)-2-methylpropanamido)adamantane-1-carboxyamide (compound 198)

An aimed compound was obtained in the same manner as described in Preparation Example 1 of Example 9 except that 2-(2,6-dichloro-N-methylphenylsulfonamido)-2-methylpropionic acid was used.

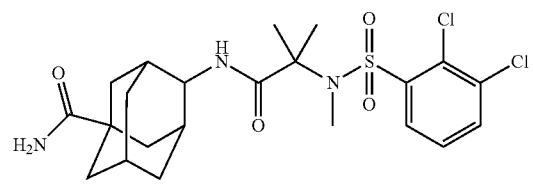 [SMILES: CN(C(C)(C)C(=O)NC1C2CC3CC1CC(C(N)=O)(C3)C2)S(=O)(=O)c1cccc(Cl)c1Cl]

$^1$H NMR (400 MHz, DMSO-d$_6$) δ 8.17 (dd, J=1.2, 8 Hz, 1H), 7.99 (dd, J=1.2, 8 Hz, 1H), 7.59 (t, J=12 Hz, 1H), 6.99 (br, NH$_2$—CO—), 6.79 (d, J=7.6 Hz, —NH—CO—), 6.74 (br, NH$_2$—CO—), 3.76 (d, J=7.2 Hz, 1H), 2.97 (s, 3H), 1.87-1.68 (m, 11H), 1.46 (m, 2H), 1.41 (s, 6H).

Preparation Example 12

Synthesis of N-4-(1-(N-methyl-2-nitrophenylsulfonamido)cyclobutanecarboxyamido)adamantane-1-carboxyamide (compound 199)

An aimed compound was obtained in the same manner as described in Preparation Example 1 of Example 9 except that 1-(N-methyl-2-nitrophenylsulfonamido)cyclobutanecarboxylic acid was used.

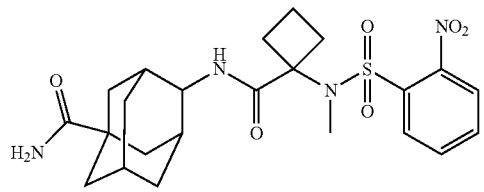 [SMILES: CN(C1(C(=O)NC2C3CC4CC2CC(C(N)=O)(C4)C3)CCC1)S(=O)(=O)c1ccccc1[N+](=O)[O-]]

$^1$H NMR (400 MHz, DMSO-d$_6$) δ 8.09 (m, 2H), 7.94 (m, 2H), 7.10 (d, J=7.2 Hz, —NH—CO—), 7.04 (s, NH$_2$—CO—), 6.77 (s, NH$_2$—CO—), 3.83 (d, J=8 Hz, 1H), 2.98 (s, 3H), 2.43 (m, 2H), 2.23 (m, 2H), 1.92-1.73 (m, 11H), 1.59 (m, 2H), 1.49 (m, 2H).

Preparation Example 13

Synthesis of N-(adamantane-2-yl)-2-(3-chloro-2-methyl-N-methylphenylsulfonamido)-2-methylpropanamide (compound 200)

An aimed compound was obtained in the same manner as described in Preparation Example 1 of Example 9 except that 1-(N-methyl-2-fluorophenylsulfonamido)-2-methylpropionic acid and 2-adamantanamine hydrochloride were used.

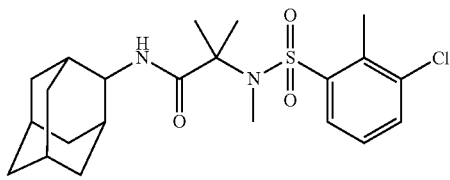 [SMILES: Cc1c(Cl)cccc1S(=O)(=O)N(C)C(C)(C)C(=O)NC1C2CC3CC(C2)CC1C3]

¹H NMR (400 MHz, CDCl₃) δ 8.01 (dd, J=1.2, 8 Hz, 1H), 7.61 (dd, J=0.8, 8 Hz, 1H), 7.39 (d, J=7.2 Hz, —NH—CO—), 7.31 (t, J=8H, 1H), 4.04 (d, J=8 Hz, 1H), 3.04 (s, 3H), 2.67 (s, 3H), 1.93-1.67 (m, 14H), 1.46 (s, 6H).

Preparation Example 14

Synthesis of N-(adamantane-2-yl)-2-(2-trifluoromethyl-N-methylphenylsulfonamido)-2-methylpropan amide (compound 201)

An aimed compound was obtained in the same manner as described in Preparation Example 1 of Example 9 except that 1-(N-methyl-2-trifluoromethylphenylsulfonamido)-2-methylpropionic acid and 2-adamantanamine hydrochloride were used.

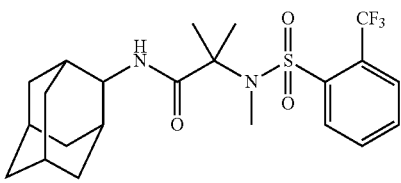 [SMILES: CN(C(C)(C)C(=O)NC1C2CC3CC(C2)CC1C3)S(=O)(=O)c1ccccc1C(F)(F)F]

¹H NMR (400 MHz, CDCl₃) δ 8.34 (m, 1H), 7.9 (m, 1H), 7.74 (m, 2H), 7.21 (d, J=7.6 Hz, —NH—CO—), 4.03 (d, J=8 Hz, 1H), 3.04 (s, 3H), 1.94-1.67 (m, 14H), 1.54 (s, 6H).

Preparation Example 15

Synthesis of N-(5-hydroxyadamantane-2-yl)-2-(2-fluoro-N-methylphenylsulfonamido)-2-methylpropanamide (compound 202)

An aimed compound was obtained in the same manner as described in Preparation Example 1 of Example 9 except that 1-(N-methyl-2-fluorophenylsulfonamido)-2-methylpropionic acid and 5-hydroxyadamantanamine were used.

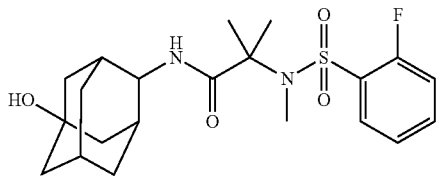

¹H NMR (400 MHz, DMSO-d₆) δ 7.93 (dt, J=1.6, 7.6 Hz, 1H), 7.76 (m, 1H), 7.51 (m, 1H), 7.42 (m, 1H), 6.74 (d, J=7.2 Hz, —NH—CO—), 4.46 (s, —OH), 3.71 (d, J=7.6 Hz, 1H), 2.58 (s, 3H), 1.98 (m, 3H), 1.69-1.61 (m, 8H), 1.33 (s, 6H), 1.24 (m, 2H).

Preparation Example 16

Synthesis of N-(5-hydroxyadamantane-2-yl)-2-(2,3-dichloro-N-methylphenylsulfonamido)-2-methylpropanamide (compound 203)

An aimed compound was obtained in the same manner as described in Preparation Example 1 of Example 9 except that 1-(N-methyl-2,3-dichlorophenylsulfonamido)-2-methylpropionic acid and 5-hydroxyadamantanamine were used.

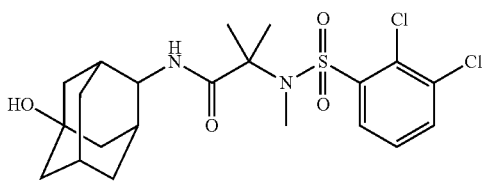

¹H NMR (400 MHz, DMSO-d₆) δ 8.16 (dd, J=1.2, 8 Hz, 1H), 7.98 (dd, J=1.2, 8 Hz, 1H), 7.59 (t, J=8 Hz, 1H), 6.73 (d, J=7.2 Hz, —NH—CO—), 4.47 (s, —OH), 3.69 (d, J=6.8 Hz, 1H), 2.92 (s, 3H), 1.99 (m, 3H), 1.67-1.59 (m, 8H), 1.39 (s, 6H), 1.32 (m, 2H).

Preparation Example 17

Synthesis of N-(5-hydroxyadamantane-2-yl)-2-(2-methyl-3-chloro-N-methylphenylsulfonamido)-2-methylpropanamide (compound 204)

An aimed compound was obtained in the same manner as described in Preparation Example 1 of Example 9 except that 1-(N-methyl-2-methyl-3-chlorophenylsulfonamido)-2-methylpropionic acid and 5-hydroxyadamantanamine were used.

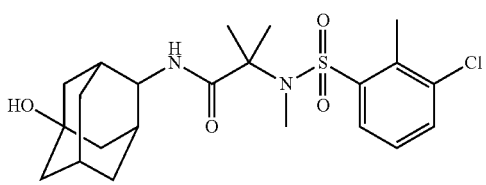

¹H NMR (400 MHz, DMSO-d₆) δ 8.06 (d, J=8 Hz, 1H), 7.76 (d, J=8 Hz, 1H), 7.43 (t, J=8 Hz, 1H), 6.84 (d, J=6.8 Hz, —NH—CO—), 4.43 (s, —OH), 3.67 (d, J=6 Hz, 1H), 2.89 (s, 3H), 2.56 (s, 3H), 1.89 (m, 3H), 1.63-1.49 (m, 8H), 1.44 (s, 6H), 1.27 (m, 2H).

Preparation Example 18

Synthesis of N-(5-hydroxyadamantane-2-yl)-2-(2-nitro-N-methylphenylsulfonamido)-2-methylpropanamide (compound 205)

An aimed compound was obtained in the same manner as described in Preparation Example 1 of Example 9 except that 1-(N-methyl-2-nitrophenylsulfonamido)-2-methylpropionic acid and 5-hydroxyadamantanamine were used.

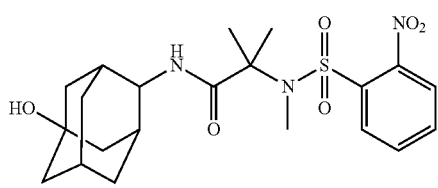

$^1$H NMR (400 MHz, DMSO-$d_6$) δ 8.28 (d, 1H), 8.01 (d, 1H), 7.86 (m, 2H), 6.78 (d, —NH—CO—, 1H), 4.42 (s, 1H), 3.70 (s, 1H), 2.91 (s, —N—SO$_2$, 3H), 2.55 (s, 3H), 1.58-1.93 (m, 13H), 1.39 (s, 6H).

Preparation Example 19

Synthesis of N-(5-hydroxyadamantane-2-yl)-2-(2-bromo-N-methylphenylsulfonamido)-2-methylpropanamide (compound 206)

An aimed compound was obtained in the same manner as described in Preparation Example 1 of Example 9 except that 1-(N-methyl-2-bromophenylsulfonamido)-2-methylpropionic acid and 5-hydroxyadamantanamine were used.

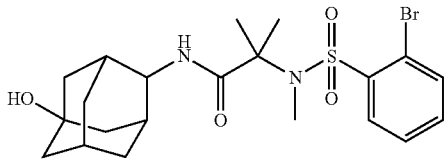 [SMILES: CN(C(C)(C)C(=O)NC1C2CC3CC1CC(O)(C3)C2)S(=O)(=O)c1ccccc1Br]

$^1$H NMR (400 MHz, DMSO-$d_6$) δ 8.19 (d, 1H), 7.90 (d, 1H), 7.56 (m, 2H), 6.87 (d, —NH—CO—, 1H), 4.46 (s, 1H), 3.71 (s, 1H), 2.95 (s, —N—SO$_2$, 3H), 1.60-1.93 (m, 13H), 1.33 (s, 6H).

Preparation Example 20

Synthesis of N-(5-hydroxyadamantane-2-yl)-2-(2-methyl-N-methylphenylsulfonamido)-2-methylpropanamide (compound 207)

An aimed compound was obtained in the same manner as described in Preparation Example 1 of Example 9 except that 1-(N-methyl-2-methylphenylsulfonamido)-2-methylpropionic acid and 5-hydroxyadamantanamine were used.

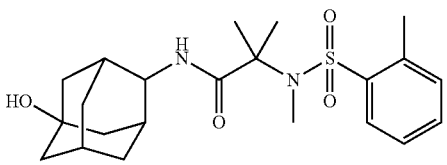 [SMILES: Cc1ccccc1S(=O)(=O)N(C)C(C)(C)C(=O)NC1C2CC3CC1CC(O)(C3)C2]

$^1$H NMR (400 MHz, DMSO-$d_6$) δ 8.00 (d, 1H), 7.53 (t, 1H), 7.38 (m, 2H), 6.92 (d, —NH—CO—, 1H), 4.43 (s, 1H), 3.69 (s, 1H), 2.86 (s, —N—SO$_2$, 3H), 2.55 (s, 3H), 1.58-1.93 (m, 13H), 1.39 (s, 6H).

Preparation Example 21

Synthesis of N-(5-hydroxyadamantane-2-yl)-2-(2-trifluoromethyl-N-methylphenylsulfonamido)-2-methylpropanamide (compound 208)

An aimed compound was obtained in the same manner as described in Preparation Example 1 of Example 9 except that 1-(N-methyl-2-trifluoromethylphenylsulfonamido)-2-methylpropionic acid and 5-hydroxyadamantanamine were used.

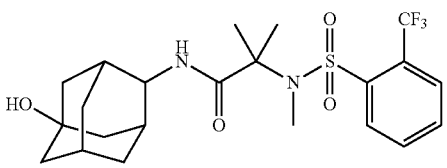

$^1$H NMR (400 MHz, DMSO-$d_6$) δ 8.41 (d, 1H), 7.99 (d, 1H), 7.86 (m, 2H), 6.76 (d, —NH—CO—, 1H), 4.41 (s, 1H), 3.67 (s, 1H), 2.90 (s, —N—SO$_2$, 3H), 1.57-1.88 (m, 13H), 1.49 (s, 6H).

Example 10

Preparation Example 1

Synthesis of N-4-(2-(2-methyl-N-ethylphenylsulfonamido)-2-methylpropanamido)adamantane-1-carboxyamide (compound 209)

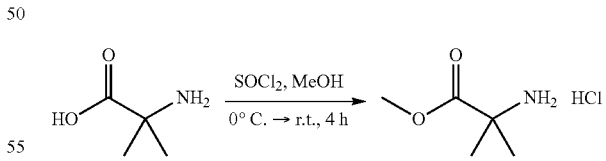

2-amino-2-methylpropionic acid (10 g, 96.9 mmol) and methanol (330 ml) were charged. An ice bath was set and thionyl chloride (17.68 ml, 242.25 mmol) was slowly added thereto. Then, the ice bath was removed, and the mixture was stirred at room temperature for 3 hours. The resultant product was vacuum-distilled to remove a solvent, and dried in a 60° C. oven so as to obtain methyl-2-amino-2-methylpropanoate hydrochloride (14.59 g, 94.9 mmol, 98%).

$^1$H NMR (400 MHz, DMSO-$d_6$) δ 8.75 (br, 3H), 3.75 (s, 3H), 1.45 (s, 6H).

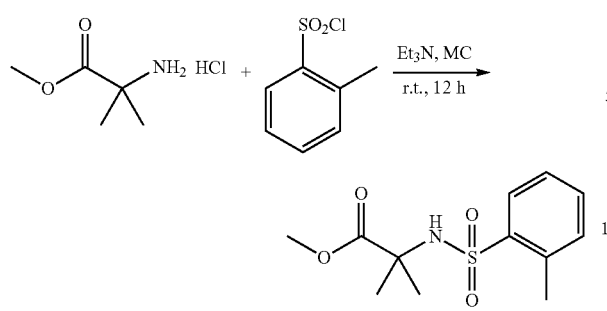

methyl-2-amino-2-methylpropanoate hydrochloride (2 g, 13.1 mmol) was dissolved in CH₂Cl₂ (50 ml), and added with 2-methylbenzene-1-sulfonylchloride (2.74 g, 14.4 mmol) and triethylamine (14 ml, 52.4 mmol), followed by stirring for 12 hours at room temperature. The resultant solution was added with H₂O, extracted with CH₂Cl₂ (×2), dried with MgSO₄, and filtered. Through vacuum distillation, the solvent was removed. The resultant mixture was purified with column chromatography so as to obtain methyl-2-(methylphenylsulfonamido)propanoate (3.2 g, 11.7 mmol, 90%).

$^1$H NMR (400 MHz, CDCl₃) δ 7.99 (m, 1H), 7.46 (dt, J=1.2, 7.2 Hz, 1H), 7.32 (m, 2H), 5.41 (s, —NH—SO₂), 3.76 (s, 3H), 2.69 (s, 3H), 1.47 (s, 6H).

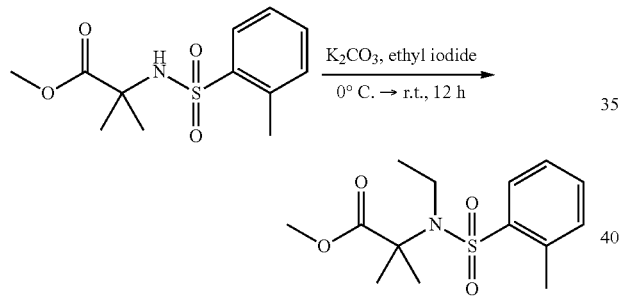

methyl-2-(methylphenylsulfonamido)propanoate (500 mg, 1.84 mmol) was dissolved in DMF (10 ml), added with ethyl iodide (0.52 ml, 6.45 mmol) at 0° C., and stirred at room temperature for 12 hours. The resultant solution was added with H₂O and extracted with EA (×2). The organic solution was washed with H₂O, dried with MgSO₄, and filtered. Through vacuum distillation, the solvent was removed. The resultant mixture was purified with column chromatography so as to obtain methyl-2-(N-ethyl-2-methylphenylsulfonamido)-2-methylpropanoate (524 mg, 1.75 mmol, 95%).

$^1$H NMR (400 MHz, CDCl₃) δ 7.9 (m, 1H), 7.43 (dt, J=1.6, 7.6 Hz, 1H), 7.3 (m, 2H), 3.69 (s, 3H), 3.42 (q, J=6.8 Hz, 2H), 2.69 (s, 3H), 1.67 (s, 6H), 1.28 (t, J=7.2 Hz, 3H).

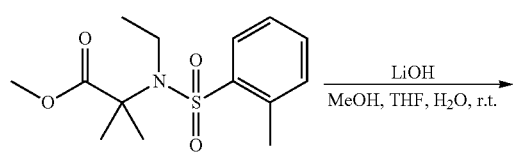

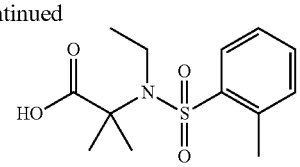

methyl-2-(N-ethyl-2-methylphenylsulfonamido)-2-methylpropanoate (524 mg, 1.75 mmol) was charged, and dissolved through addition of THF (5 ml), and methanol (5 ml). LiOH.H₂O dissolved in H₂O (5 ml) was added thereto, followed by stirring for 12 hours at room temperature. After stirring for 12 hours, the resultant solution was vacuum-evaporated, acidified with 2N—HCl to pH 2-3, and extracted with EA (×2). The organic layer was dried with MgSO₄, and filtered. Through vacuum distillation, the solvent was removed so as to obtain 2-(N-ethyl-2-methylphenylsulfonamido)-2-methylpropionic acid (490 mg, 1.72 mmol, 98%).

$^1$H NMR (400 MHz, DMSO-d₆) δ 12.64 (bs, —COOH), 7.87 (m, 1H), 7.51 (dt, J=1.2, 7.6 Hz, 1H), 7.39 (m, 2H), 3.38 (q, J=6.8 Hz, 2H), 2.58 (s, 3H), 1.49 (s, 6H), 1.16 (t, J=7.2 Hz, 3H).

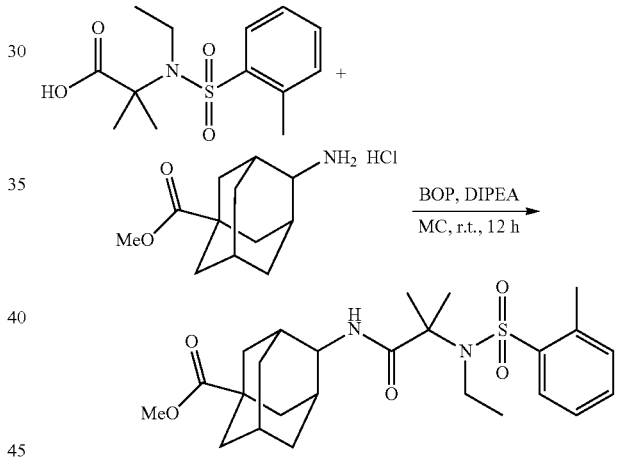

2-(N-ethyl-2-methylphenylsulfonamido)-2-methylpropionic acid (302 mg, 1.11 mmol), 4-amino-adamantane-1-carboxylate hydrochloride (301 mg, 1.23 mmol), and BOP (492 mg, 1.11 mmol) were charged, and CH₂Cl₂ (6 ml) was added thereto, followed by stirring for 30 minutes at room temperature. DIPEA (0.82 ml, 3.34 mmol) was added thereto, followed by stirring at room temperature for 12 hours. After the reaction was completed, the organic layer was separated using CH₂Cl₂ and H₂O, dried with MgSO₄, and filtered. Then, through vacuum distillation, the solvent was removed, and the resultant product was purified with column chromatography to obtain N-methyl-4-(2-(N-ethyl-2-methylphenylsulfonamido)-2-methylpropanamido)adamantane-1-carboxylate (403 mg, 0.85 mmol, 80%).

$^1$H NMR (400 MHz, CDCl₃) δ 7.89 (m, 2H), 7.48 (m, 1H), 7.35 (m, 2H), 4.04 (d, J=7.2 Hz, —NH—CO—), 3.69 (s, 3H), 3.61 (q, J=7.2 Hz, 2H), 2.69 (s, 3H), 2.07-1.89 (m, 11H), 1.62 (m, 2H), 1.50 (s, 6H), 1.34 (t, J=7.2 Hz, 3H).

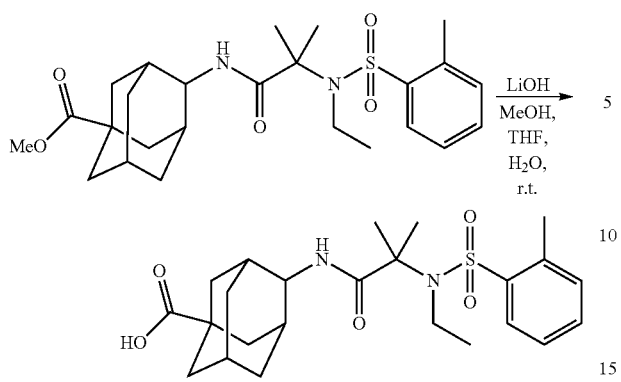

N-methyl-4-(2-(N-ethyl-2-methylphenylsulfonamido)-2-methylpropanamido)adamantane-1-carboxylate (400 mg, 0.84 mmol) was charged, and dissolved through addition of THF (5 ml), and methanol (5 ml). LiOH.H$_2$O dissolved in H$_2$O (4 ml) was added thereto, followed by stirring for 12 hours at room temperature. After stirring for 12 hours, the resultant solution was vacuum-evaporated, acidified with 2N—HCl to pH 2~3, and extracted with EA (×2). The organic layer was dried with MgSO$_4$, and filtered. Through vacuum distillation, the solvent was removed so as to obtain N-methyl-4-(2-(N-ethyl-2-methylphenylsulfonamido)-2-methylpropanamido)adamantane-1-carboxylic acid (380 mg, 0.82 mmol, 98%).

$^1$H NMR (400 MHz, DMSO-d$_6$) δ 12.12 (bs, —COOH), 7.89 (m, 1H), 7.54 (m, 1H), 7.42 (m, 2H), 7.21 (d, J=7.6 Hz, —NH—CO—), 3.78 (d, J=6.8 Hz, 1H), 3.48 (q, J=6.8 Hz, 2H), 2.58 (s, 3H), 1.91-1.79 (m, 11H), 1.52 (m, 2H), 1.48 (s, 6H), 1.23 (t, J=7.2 Hz, 3H).

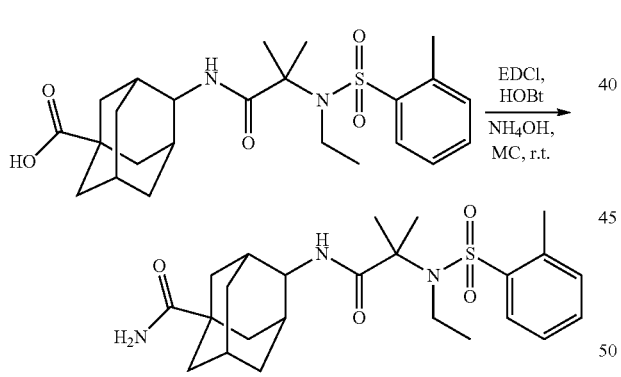

N-methyl-4-(2-(N-ethyl-2-methylphenylsulfonamido)-2-methylpropanamido)adamantane-1-carboxylic acid (380 mg, 0.82 mmol) was dissolved in CH$_2$Cl$_2$ (10 ml), and added with EDCI (314 mg, 1.64 mmol) and HOBT (222 mg, 1.64 mmol), followed by stirring for 30 minutes. 30% NH$_4$OH aqueous solution (5 ml) was added thereto, followed by stirring at room temperature for 12 hours. The resultant solution was added with H$_2$O, extracted with CH$_2$Cl$_2$ (×3), dried with MgSO$_4$, and filtered. Through vacuum distillation, the solvent was removed. The resultant mixture was purified with column chromatography so as to obtain N-methyl-4-(2-(N-ethyl-2-methylphenylsulfonamido)-2-methylpropanamido) adamantane-1-carboxamide (296 mg, 0.64 mmol, 78%).

$^1$H NMR (400 MHz, DMSO-d$_6$) δ 7.88 (m, 1H), 7.54 (m, 1H), 7.43 (m, 2H), 0.21 (d, J=8 Hz, —NH—CO—), 7.01 (br, NH$_2$—CO—), 6.74 (br, NH$_2$—CO—), 3.79 (d, J=7.6 Hz, 1H), 3.49 (q, J=7.2 Hz, 2H), 2.58 (s, 3H), 1.88-1.76 (m, 11H), 1.51 (m, 2H), 1.47 (s, 6H), 1.23 (t, J=6.8 Hz, 3H).

Preparation Example 2

Synthesis of N-4-(2-(2-trifluoromethyl-N-ethylphenylsulfonamido)-2-methylpropanamido)adamantane-1-carboxyamide (compound 210)

An aimed compound was obtained in the same manner as described in Preparation Example 1 of Example 10 except that 1-(N-ethyl-2-trifluoromethylphenylsulfonamido)-2-methylpropionic acid was used.

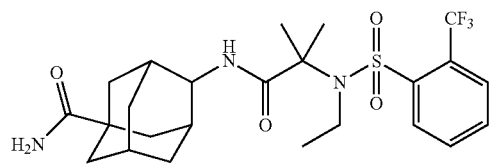 [SMILES: CCN(C(C)(C)C(=O)NC1C2CC3CC1CC(C(N)=O)(C3)C2)S(=O)(=O)c1ccccc1C(F)(F)F]

$^1$H NMR (400 MHz, DMSO-d$_6$) δ 8.25 (d, J=8 Hz, 1H), 8.01 (m, 1H), 7.91 (m, 2H), 7.00 (br, NH$_2$—CO—), 6.98 (d, J=8.4 Hz, —NH—CO—), 6.74 (br, NH$_2$—CO—), 3.78 (d, J=6.4 Hz, 1H), 3.48 (q, J=6.8 Hz, 2H), 1.89-1.75 (m, 11H), 1.54 (s, 6H), 1.45 (m, 2H), 1.28 (t, J=6.8 Hz, 3H).

Preparation Example 3

Synthesis of N-4-(2-(2-fluoro-N-ethylphenylsulfonamido)-2-methylpropanamido)adamantane-1-carboxyamide (compound 211)

An aimed compound was obtained in the same manner as described in Preparation Example 1 of Example 10 except that 1-(N-ethyl-2-fluorophenylsulfonamido)-2-methylpropionic acid was used.

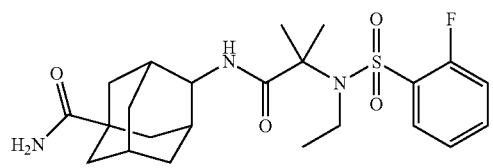 [SMILES: CCN(C(C)(C)C(=O)NC1C2CC3CC1CC(C(N)=O)(C3)C2)S(=O)(=O)c1ccccc1F]

$^1$H NMR (400 MHz, DMSO-d$_6$) δ 7.92 (dt, J=1.6, 8 Hz, 1H), 7.75 (m, 1H), 7.49 (m, 1H), 7.42 (m, 1H), 7.01 (br, NH$_2$—CO—), 6.98 (d, J=6.8 Hz, —NH—CO—), 6.75 (br, NH$_2$—CO—), 3.78 (d, J=6.8 Hz, 1H), 3.49 (q, J=6.8 Hz, 2H), 1.92-1.76 (m, 11H), 1.51 (m, 2H), 1.44 (s, 6H), 1.22 (t, J=6.8 Hz, 3H).

Preparation Example 4

Synthesis of N-4-(2-(2,6-dichloro-N-ethylphenylsulfonamido)-2-methylpropanamido)adamantane-1-carboxyamide (compound 212)

An aimed compound was obtained in the same manner as described in Preparation Example 1 of Example 10 except that 1-(N-ethyl-2,6-dichlorophenylsulfonamido)-2-methylpropionic acid was used.

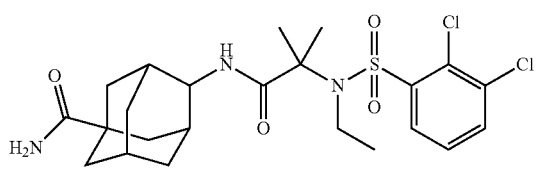 [SMILES: CCN(C(C)(C)C(=O)NC1C2CC3CC1CC(C(N)=O)(C3)C2)S(=O)(=O)c1cccc(Cl)c1Cl]

¹H NMR (400 MHz, DMSO-d₆) δ 8.11 (dd, J=1.2, 8 Hz, 1H), 7.96 (dd, J=1.2, 8 Hz, 1H), 7.59 (t, J=8 Hz, 1H), 7.08 (d, J=7.2 Hz, —NH—CO—), 7.02 (br, NH₂—CO—), 6.76 (br, NH₂—CO—), 3.77 (d, J=6.8 Hz, 1H), 3.59 (q, J=6.8 Hz, 2H), 1.88-1.76 (m, 11H), 1.51 (m, 2H), 1.48 (s, 6H), 1.25 (t, J=6.8 Hz, 3H).

Preparation Example 5

Synthesis of N-4-(2-(2,6-difluoro-N-ethylphenylsulfonamido)-2-methylpropanamido)adamantane-1-carboxyamide (compound 213)

An aimed compound was obtained in the same manner as described in Preparation Example 1 of Example 10 except that 1-(N-ethyl-2,6-difluorophenylsulfonamido)-2-methylpropionic acid was used.

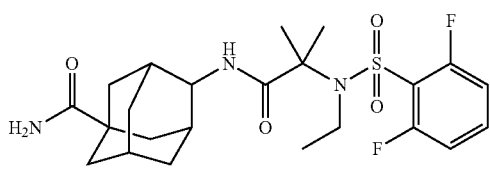 [SMILES: CCN(C(C)(C)C(=O)NC1C2CC3CC1CC(C(N)=O)(C3)C2)S(=O)(=O)c1c(F)cccc1F]

¹H NMR (400 MHz, DMSO-d₆) δ 7.74 (m, 1H), 7.31 (t, 2H), 7.01 (m, —NH—CO—, 1H), 7.02 (s, NH₂—CO—, 1H), 6.76 (s, NH₂—CO—, 1H), 3.76 (s, 1H), 3.51 (m, —N—SO₂, 2H), 1.46-1.93 (m, 13H), 1.48 (s, 6H), 1.15 (t, 3H).

Preparation Example 6

Synthesis of N-4-(2-methoxy-6-fluoro-N-ethylphenylsulfonamido)-2-methylpropanamido)adamantane-1-carboxyamide (compound 214)

An aimed compound was obtained in the same manner as described in Preparation Example 1 of Example 10 except that 1-(N-ethyl-2-methoxy-6-fluorophenylsulfonamido)-2-methylpropionic acid was used.

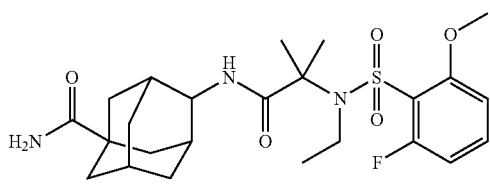 [SMILES: CCN(C(C)(C)C(=O)NC1C2CC3CC1CC(C(N)=O)(C3)C2)S(=O)(=O)c1c(F)cccc1OC]

¹H NMR (400 MHz, DMSO-d₆) δ 7.61 (m, 1H), 7.41 (d, 1H), 7.10 (d, —NH—CO—, 1H), 7.03 (s, NH₂—CO—, 1H), 6.95 (m, 1H), 6.76 (s, NH₂—CO—, 1H), 3.95 (s, 1H), 3.80 (s, 1H), 3.55 (m, —N—SO₂, 2H), 1.50-1.94 (m, 13H), 1.39 (s, 6H), 1.15 (t, 3H).

Preparation Example 7

Synthesis of N-4-(2-methyl-3-chloro-N-ethylphenylsulfonamido)-2-methylpropanamido)adamantane-1-carboxyamide (compound 215)

An aimed compound was obtained in the same manner as described in Preparation Example 1 of Example 10 except that 1-(N-ethyl-2-methyl-3-chlorophenylsulfonamido)-2-methylpropionic acid was used.

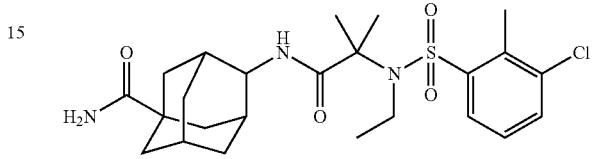

¹H NMR (400 MHz, DMSO-d₆) δ 7.91 (d, 1H), 7.72 (d, 1H), 7.41 (t, 1H), 7.05 (d, —NH—CO—, 1H), 7.01 (s, NH₂—CO—, 1H), 6.75 (s, NH₂—CO—, 1H), 3.76 (s, 1H), 3.49 (m, —N—SO₂, 2H), 2.61 (s, 3H), 1.44-1.90 (m, 13H), 1.45 (s, 6H), 1.23 (t, 3H).

Preparation Example 8

Synthesis of N-4-(2-nitro-N-ethylphenylsulfonamido)-2-methylpropanamido)adamantane-1-carboxyamide (compound 216)

An aimed compound was obtained in the same manner as described in Preparation Example 1 of Example 10 except that 1-(N-ethyl-2-nitrophenylsulfonamido)-2-methylpropionic acid was used.

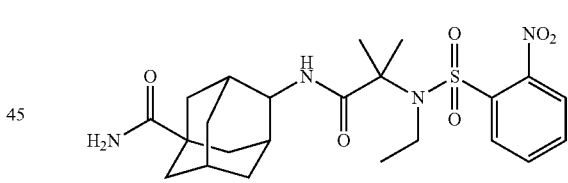

¹H NMR (400 MHz, DMSO-d₆) δ 8.21 (m, 1H), 7.97 (m, 1H), 7.87 (m, 2H), 7.00 (s, NH₂—CO—, 1H), 6.86 (d, —NH—CO—, 1H), 6.74 (s, NH₂—CO—, 1H), 3.77 (s, 1H), 3.42 (d, —N—SO₂, 2H), 1.44-1.90 (m, 13H), 1.51 (s, 6H), 1.19 (s, 3H).

Preparation Example 9

Synthesis of N-4-(2-chloro-N-ethylphenylsulfonamido)-2-methylpropanamido)adamantane-1-carboxyamide (compound 217)

An aimed compound was obtained in the same manner as described in Preparation Example 1 of Example 10 except that 1-(N-ethyl-2-chlorophenylsulfonamido)-2-methylpropionic acid was used.

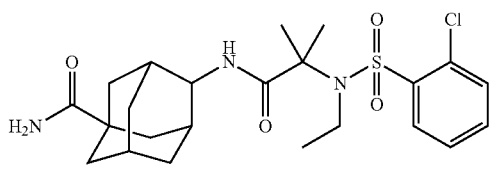 [SMILES: CCN(C(C)(C)C(=O)NC1C2CC3CC1CC(C(N)=O)(C3)C2)S(=O)(=O)c1ccccc1Cl]

¹H NMR (400 MHz, DMSO-d₆) δ 8.10 (d, 1H), 1.65 (m, 2H), 7.55 (m, 1H), 7.20 (d, —NH—CO—, 1H), 7.01 (s, NH₂—CO—, 1H), 6.75 (s, NH₂—CO—, 1H), 3.80 (s, 1H), 3.59 (s, —N—SO₂, 2H), 1.51-1.94 (m, 13H), 1.43 (s, 6H), 1.21 (s, 3H).

Example 11

Preparation Example 1

Synthesis of N-4-(2-(2-trifluoromethyl-N-propylphenylsulfonamido)-2-methylpropanamido)adamantane-1-carboxyamide (compound 218)

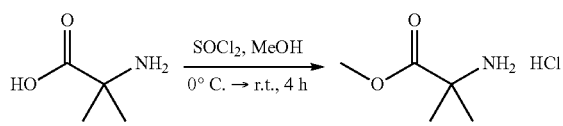

2-amino-2-methylpropionic acid (10 g, 96.9 mmol) and methanol (330 ml) were charged. An ice bath was set and thionyl chloride (17.68 ml, 242.25 mmol) was slowly added thereto. Then, the ice bath was removed, and the mixture was stirred at room temperature for 3 hours. The resultant product was vacuum-distilled to remove a solvent, and dried in a 60° C. oven so as to obtain methyl-2-amino-2-methylpropanoate hydrochloride (14.59 g, 94.9 mmol, 98%).

¹H NMR (400 MHz, DMSO-d₆) δ 8.75 (br, 3H), 3.75 (s, 3H), 1.45 (s, 6H).

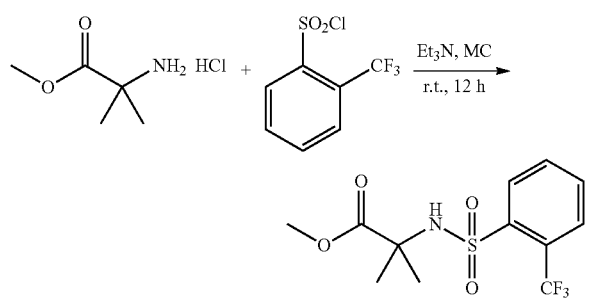

Methyl-2-amino-2-methylpropanoate hydrochloride (1 g, 6.53 mmol) was dissolved in CH₂Cl₂ (20 ml), and added with 2-(trifluoromethyl)benzene-1-sulfonylchloride (1.76 g, 7.18 mmol) and triethylamine (3.6 ml, 26.1 mmol), followed by stirring at room temperature for 12 hours. The resultant solution was added with H₂O, extracted with CH₂Cl₂ (×2), dried with MgSO₄, and filtered. Through vacuum distillation, the solvent was removed. The resultant mixture was purified with column chromatography so as to obtain methyl-2-methyl-2-(2-(trifluoromethyl)phenylsulfonamido)propanoate (1.98 g, 6.08 mmol, 93%).

¹H NMR (400 MHz, CDCl₃) δ 8.25 (m, 1H), 7.88 (m, 1H), 7.71 (m, 2H), 5.59 (s, —NH—SO₂), 3.67 (s, 3H), 1.49 (s, 6H).

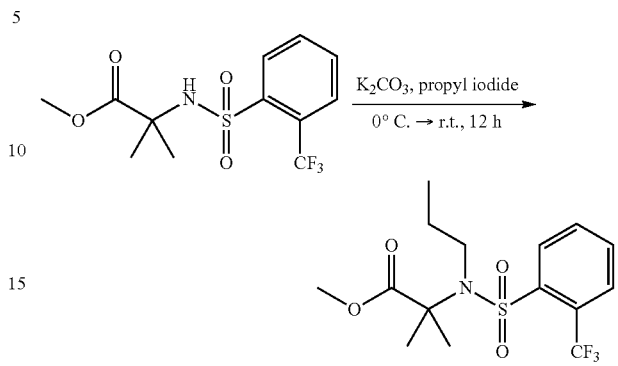

Methyl-2-methyl-2-(2-(trifluoromethyl)phenylsulfonamido)propanoate (310 mg, 0.95 mmol) was dissolved in DMF (8 ml), and added with propyl iodide (0.32 ml, 3.34 mmol) at 0° C., followed by stirring at room temperature for 12 hours. The resultant solution was added with H₂O and extracted with EA (×2). The organic solution was washed with H₂O, dried with MgSO₄, and filtered. Through vacuum distillation, the solvent was removed. The resultant mixture was purified with column chromatography so as to obtain methyl-2-methyl-2-(N-propyl-2-(trifluoromethyl)phenylsulfonamido)propanoate (340 mg, 0.93 mmol, 97%).

¹H NMR (400 MHz, CDCl₃) δ 8.24 (m, 1H), 7.88 (m, 1H), 7.69 (m, 2H), 3.68 (s, 3H), 3.27 (m, 2H), 1.82 (m, 2H), 1.69 (s, 6H), 0.86 (t, J=7.2 Hz, 3H).

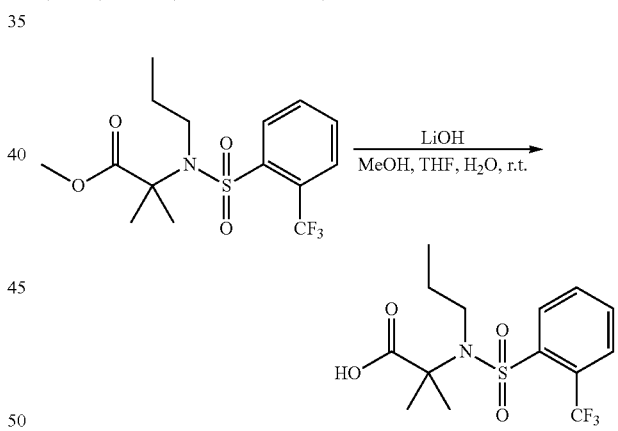

Methyl-2-methyl-2-(N-propyl-2-(trifluoromethyl)phenylsulfonamido)propanoate (340 mg, 0.93 mmol) was charged, and dissolved through addition of THF (4 ml), and methanol (4 ml). LiOH.H₂O dissolved in H₂O (4 ml) was added thereto, followed by stirring for 12 hours at room temperature. After stirring for 12 hours, the resultant solution was vacuum-evaporated, acidified with 2N—HCl to pH 2-3, and extracted with EA (×2). The organic layer was dried with MgSO₄, and filtered. Through vacuum distillation, the solvent was removed so as to obtain 2-methyl-2-(N-propyl-2-(trifluoromethyl)phenylsulfonamido)propionic acid (320 mg, 0.91 mmol, 98%).

¹H NMR (400 MHz, DMSO-d₆) δ 12.74 (bs, —COOH), 8.21 (m, 1H), 7.96 (m, 1H), 7.84 (m, 2H), 3.27 (t, J=8 Hz, 2H), 1.72 (m, 2H), 1.55 (s, 6H), 0.78 (t, J=7.8 Hz, 3H).

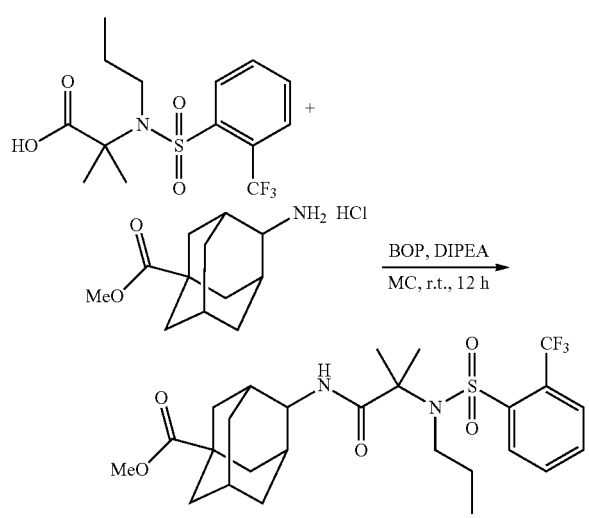

2-methyl-2-(N-propyl-2-(trifluoromethyl)phenylsulfonamido)propionic acid (320 mg, 0.91 mmol), 4-amino-adamantane-1-carboxylate hydrochloride (246 mg, 1.00 mmol), and BOP (402 mg, 0.91 mmol) were charged, and $CH_2Cl_2$ (7 ml) was added thereto, followed by stirring for 30 minutes at room temperature. DIPEA (0.45 ml, 2.73 mmol) was added thereto, followed by stirring at room temperature for 12 hours. After the reaction was completed, the organic layer was separated using $CH_2Cl_2$ and $H_2O$, dried with $MgSO_4$, and filtered. Then, through vacuum distillation, the solvent was removed, and the resultant product was purified with column chromatography to obtain N-4-(2-(2-trifluoromethyl-N-propylphenylsulfonamido)-2-methylpropanamido)adamantane-1-carboxylate (444 mg, 0.82 mmol, 90%).

$^1$H NMR (400 MHz, $CDCl_3$) δ 8.11 (m, 1H), 7.91 (m, 1H), 7.73 (m, 2H), 7.59 (d, J=8.8 Hz, —NH—CO—), 4.02 (d, J=7.2 Hz, 1H), 3.68 (s, 3H), 3.45 (m, 2H), 2.08-1.92 (m, 11H), 1.76 (m, 2H), 1.62 (m, 2H), 1.55 (s, 6H), 0.89 (t, J=7.6 Hz, 3H).

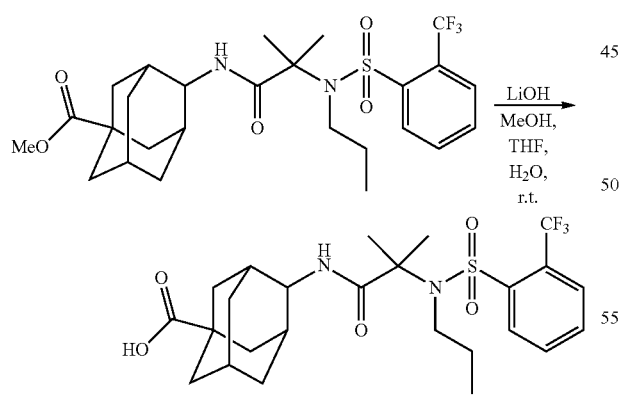

N-4-(2-(2-trifluoromethyl-N-propylphenylsulfonamido)-2-methylpropanamido)adamantane-1-carboxylate (444 mg, 0.82 mmol) was charged, and dissolved through addition of THF (5 ml), and methanol (5 ml). $LiOH \cdot H_2O$ dissolved in $H_2O$ (4 ml) was added thereto, followed by stirring for 12 hours at room temperature. After stirring for 12 hours, the resultant solution was vacuum-evaporated, acidified with 2N—HCl to pH 2-3, and extracted with EA (×2). The organic layer was dried with $MgSO_4$, and filtered. Through vacuum distillation, the solvent was removed so as to obtain N-4-(2-(2-trifluoromethyl-N-propylphenylsulfonamido)-2-methylpropanamido)adamantane-1-carboxylic acid (424 mg, 0.79 mmol, 98%).

$^1$H NMR (400 MHz, DMSO-$d_6$) δ12.08 (bs, —COOH), 8.24 (m, 1H), 8.01 (m, 1H), 7.88 (m, 2H), 6.99 (d, J=7.2 Hz, —NH—CO—), 3.77 (d, J=7.6 Hz, 1H), 3.35 (m, 2H), 1.91-1.72 (m, 11H), 1.68 (m, 2H), 1.54 (s, 6H), 1.52 (m, 2H), 0.80 (t, J=3.6 Hz, 3H).

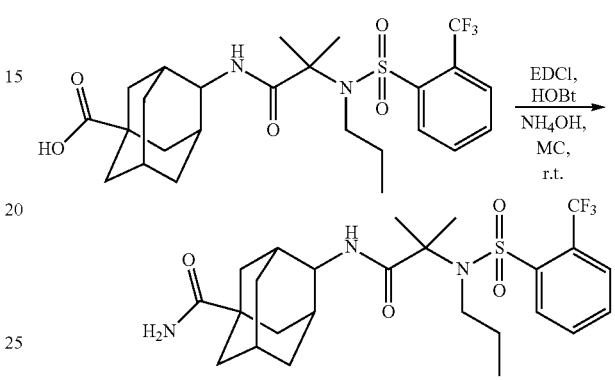

N-4-(2-(2-trifluoromethyl-N-propylphenylsulfonamido)-2-methylpropanamido)adamantane-1-carboxylic acid (424 mg, 0.79 mmol) was dissolved in $CH_2Cl_2$ (10 ml), and added with EDCI (303 mg, 1.58 mmol) and HOBT (213 mg, 1.58 mmol), followed by stirring for 30 minutes. 30% $NH_4OH$ aqueous solution (5 ml) was added thereto, followed by stirring at room temperature for 12 hours. The resultant solution was added with $H_2O$, extracted with $CH_2Cl_2$ (×3), dried with $MgSO_4$, and filtered. Through vacuum distillation, the solvent was removed. The resultant mixture was purified with column chromatography so as to obtain N-4-(2-(2-trifluoromethyl-N-propylphenylsulfonamido)-2-methylpropanamido)adamantane-1-carboxyamide (317 mg, 0.59 mmol, 75%).

$^1$H NMR (400 MHz, DMSO-$d_6$) δ 8.24 (m, 1H), 7.99 (m, 1H), 7.89 (m, 2H), 7.02 (d, J=6.8 Hz, —NH—CO—), 6.99 (br, $NH_2$—CO—), 6.74 (br, $NH_2$—CO—), 3.78 (d, J=6.8 Hz, 1H), 3.37 (m, 2H), 1.89-1.70 (m, 11H), 1.68 (m, 2H), 1.53 (s, 6H), 1.46 (m, 2H), 0.81 (t, J=7.2 Hz, 3H)

Example 12

Preparation Example 1

Synthesis of N-4-(2-(2-aminophenylsulfonamido)-2-methylpropanamido)adamantane-1-carboxyamide (compound 219)

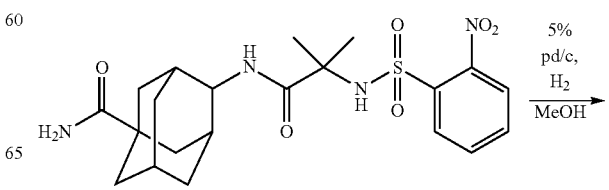

-continued

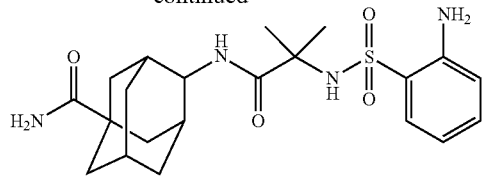

In a 25-mL flask, 4-[2-(2-nitro-benzenesulfonylamino)-2-methyl-propionylamino]-adamantane-1-carboxylic acid amide (30 mg, 0.0645 mmol) and methanol (5 mL) were charged and dissolved, and 5% Pd/c (10 mg) was added thereto. The reaction vessel was degassed under reduced pressure, and filled with hydrogen. At room temperature, through stirring for 3 hours, the reaction was completed. Then, through celite filtering, Pd was removed. At 35° C., through vacuum evaporation, 4-[2-(2-amino-benzenesulfonylamino)-2-methyl-propionylamino]-adamantane-1-carboxylic acid amide (21 mg, 75.0%) was obtained.

$^1$H NMR (400 MHz, DMSO-d$_6$) δ 8.10 (s, —NH—SO$_2$, 1H), 7.48 (dd, 1H), 7.27 (td, 1H), 7.20 (d, —NH—CO—, 1H), 7.03 (s, NH$_2$—CO—, 1H), 6.82 (d, 1H), 6.76 (s, NH$_2$—CO—, 1H), 6.60 (t, 1H), 5.93 (s, —NH$_2$, 2H), 3.74 (s, 1H), 1.59-2.15 (m, 13H), 1.22 (s, 6H).

Preparation Example 2

Synthesis of N-4-(1-(2-aminophenylsulfonamido)cyclohexanecarboxyamido)adamantane-1-carboxyamide (compound 220)

An aimed compound was obtained in the same manner as described in Preparation Example 1 of Example 12 except that N-4-(1-(2-nitrophenylsulfonamido)cyclohexanecarboxyamido)adamantane-1-carboxyamide was used.

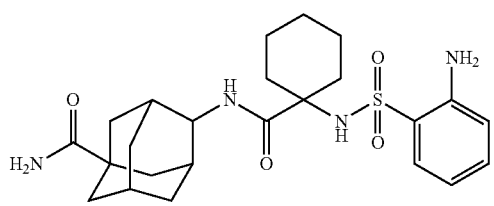 [SMILES: NC(=O)C12CC3CC(C1)C(NC(=O)C1(NS(=O)(=O)c4ccccc4N)CCCCC1)C(C3)C2]

$^1$H NMR (400 MHz, DMSO-d$_6$) δ 7.93 (s, —NH—SO$_2$, 1H), 7.43 (d, 1H), 7.21 (s, 1H), 7.20 (s, —NH—CO—, 1H), 6.75 (s, NH$_2$—CO—, 2H), 6.56 (m, 1H), 5.93 (s, —NH$_2$, 2H), 3.62 (s, 1H), 1.59-2.15 (m, 13H), 0.87-1.61 (m, 10H).

Preparation Example 3

Synthesis of N-4-(1-(2-aminophenylsulfonamido)cyclobutanecarboxyamido)adamantane-1-carboxyamide (compound 221)

An aimed compound was obtained in the same manner as described in Preparation Example 1 of Example 12 except that N-4-(1-(2-nitrophenylsulfonamido)cyclobutanecarboxyamido)adamantane-1-carboxyamide was used.

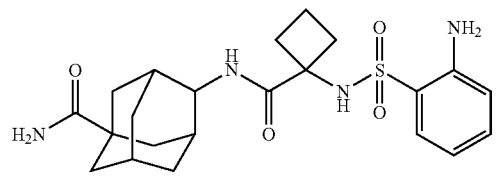

$^1$H NMR (400 MHz, DMSO-d$_6$) δ 8.39 (s, —NH—SO$_2$, 1H), 7.54 (dd, 1H), 7.22 (td, 1H), 7.02-7.06 (m, NH$_2$—CO—, 1H, 1H), 6.79 (d, —NH—CO—, 1H), 6.71 (s, NH$_2$—CO—, 1H), 6.57 (t, 1H), 5.93 (s, —NH2, 2H), 3.64 (s, 1H), 1.59-2.15 (m, 13H), 1.45-2.46 (m, 6H).

Preparation Example 4

Synthesis of N-4-(1-(N-methyl-2-aminophenylsulfonamido)cyclobutanecarboxyamido)adamantane-1-carboxyamide (compound 222)

An aimed compound was obtained in the same manner as described in Preparation Example 1 of Example 12 except that N-4-(1-(N-methyl-2-nitrophenylsulfonamido)cyclobutanecarboxyamido)adamantane-1-carboxyamide was used.

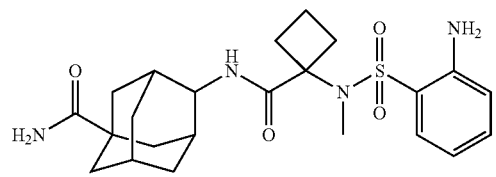 [SMILES: CN(C1(C(=O)NC2C3CC4CC2CC(C(N)=O)(C4)C3)CCC1)S(=O)(=O)c1ccccc1N]

$^1$H NMR (400 MHz, DMSO-d$_6$) δ 7.52 (dd, 1H), 7.33 (td, 1H), 7.23 (d, 1H), 6.90 (s, NH$_2$—CO—, 1H), 6.78 (d, —NH—CO—, 1H), 6.71 (s, NH$_2$—CO—, 1H), 6.67 (t, 1H), 5.77 (s, —NH$_2$, 2H), 3.17 (s, 1H), 2.79 (s, 3H), 1.59-2.15 (m, 13H), 1.45-2.46 (m, 6H).

Preparation Example 5

Synthesis of N-4-(2-(2-amino-N-methylphenylsulfonamido)-2-methylpropanamido)adamantane-1-carboxyamide (compound 223)

An aimed compound was obtained in the same manner as described in Preparation Example 1 of Example 12 except that N-4-(2-(2-nitro-N-methylphenylsulfonamido)-2-methylpropanamido)adamantane-1-carboxyamide was used.

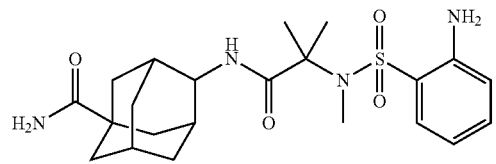 [SMILES: CN(C(C)(C)C(=O)NC1C2CC3CC1CC(C(N)=O)(C3)C2)S(=O)(=O)c1ccccc1N]

$^1$H NMR (400 MHz, DMSO-d$_6$) δ 7.57 (d, 1H), 7.29 (t, 1H), 7.01 (s, NH$_2$—CO—, 1H), 6.91 (d, —NH—CO—, 1H), 6.84 (d, 1H), 6.51 (s, NH$_2$—CO—, 1H), 6.63 (t, 1H), 6.20 (s, 2H), 3.77 (s, 1H), 3.16 (s, 1H), 2.66 (s, —N—SO$_2$, 3H), 1.74-1.93 (m, 13H), 1.38 (s, 6H).

Preparation Example 6

Synthesis of N-4-(2-(2-amino-N-ethylphenylsulfonamido)-2-methylpropanamido)adamantane-1-carboxyamide (compound 224)

An aimed compound was obtained in the same manner as described in Preparation Example 1 of Example 12 except that N-4-(2-(2-nitro-N-ethylphenylsulfonamido)-2-methylpropanamido)adamantane-1-carboxyamide was used.

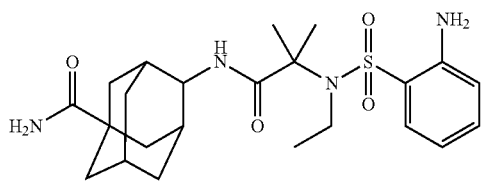

$^1$H NMR (400 MHz, DMSO-$d_6$) δ 7.53 (d, 1H), 7.27 (t, 1H), 7.02 (s, NH$_2$—CO—, 1H), 6.80 (d, —NH—CO—, 1H), 6.75 (d, 1H), 6.61 (s, NH$_2$—CO—, 1H), 6.32 (s, 2H), 3.79 (s, 1H), 3.20 (d, —N—SO$_2$, 2H), 1.44-1.96 (m, 13H), 1.45 (s, 6H), 1.03 (t, 3H).

Preparation Example 7

Synthesis of N-4-(2-(2-aminophenylsulfonamido)-2-methylpropanamido)adamantane-1-hydroxyamide (compound 225)

An aimed compound was obtained in the same manner as described in Preparation Example 1 of Example 12 except that 4-[2-(2-nitro-benzenesulfonylamino)-2-methyl-propionylamino]-adamantane-1-hydroxyamide was used.

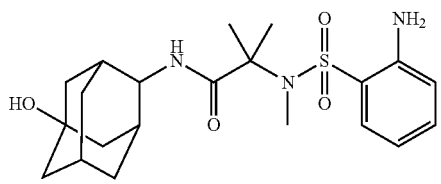

$^1$H NMR (400 MHz, DMSO-$d_6$) δ 7.54 (d, 1H), 7.29 (t, 1H), 6.83 (m, 1H), 6.83 (d, —NH—CO—, 1H), 6.62 (t, 1H), 6.19 (s, 2H), 4.74 (s, 1H), 3.73 (s, 1H), 2.65 (s, —N—SO$_2$, 3H), 1.58-1.93 (m, 13H), 1.32 (s, 6H).

Example 13

Preparation Example 1

Synthesis of 4-[2-(2-methoxy-benzenesulfonylamino)-2-methyl-propionylamino]-adamantane-1-carboxylic acid amide (compound 226)

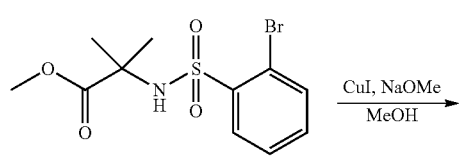 CuI, NaOMe / MeOH →

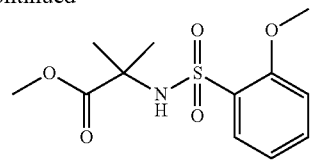

In a 100-mL flask, methyl-2-amino-(2-bromo-benzenesulfonylamino)propanoate (1.9 g, 5.65 mmol) and methanol (50 mL) were charged and dissolved, and monovalent copperiodide (1.1 g, 5.65 mmol) and 25% sodium methoxide methanol solution (2.4 mL, 11.3 mmol) were added thereto. The temperature was raised up to a reflux temperature and stirring was performed for 6 hours until the reaction was completed. The temperature was cooled to room temperature, and purified water (20 mL) was added thereto. At 45° C., vacuum evaporation was performed. The concentrated residue was neutralized with addition of 2N-hydrochloric acid aqueous solution. Through celite filtering, copper participated in the reaction was removed. The aqueous layer was washed with ethyl acetate (50 mL) twice, and treated with magnesium sulfate to remove remaining moisture. Then, after filtering and concentration, the residue was purified with column chromatography (EA/n-Hex=1:3) to obtain methyl-2-amino-(2-methoxy-benzenesulfonylamino)propanoate (195 mg, 16.3%).

$^1$H NMR (400 MHz, CDCl$_3$) δ 7.89 (dd, 1H), 7.55 (td, 1H), 7.03-7.08 (m, 2H), 6.03 (s, —NH—SO$_2$), 4.03 (s, CH$_3$—CO$_2$—, 3H), 3.62 (s, CH3-O—, 3H), 1.58 (s, 6H).

An aimed compound was obtained in the same manner as described in Preparation Example 1 of Example 2 except that methyl-2-amino-(2-methoxy-benzenesulfonylamino)propanoate was used.

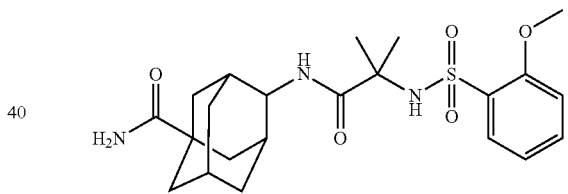

$^1$H NMR (400 MHz, DMSO-$d_6$) δ 7.79 (s, —NH—SO$_2$, 1H), 7.73 (d, 1H), 7.63 (t, 1H), 7.23-7.29 (m, 2H), 7.10 (t, —NH—CO—, 1H), 7.02 (s, NH$_2$—CO—, 1H), 6.75 (s, NH$_2$—CO—, 1H), 3.93 (s, —O—CH3, 3H), 3.74 (s, 1H), 1.59-2.15 (m, 13H), 1.22 (s, 6H).

Example 14

Preparation Example 1

Synthesis of 4-[2-(2-chloro-benzenesulfonylamino)-2-methyl-propionylamino]-adamantane-1-carboxylic acid diethylamide (compound 227)

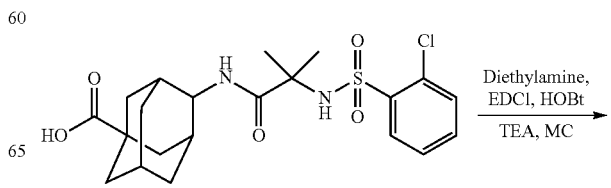 Diethylamine, EDCl, HOBt / TEA, MC →

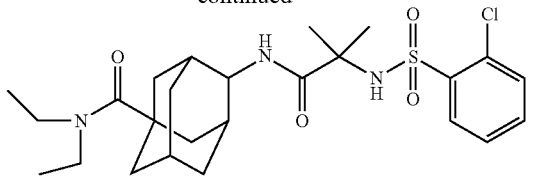

In a 25-mL flask, 4-[2-(2-chloro-benzenesulfonylamino)-2-methyl-propionylamino]-adamantane-1-carboxylic acid (100 mg, 0.22 mmol), 1-ethyl-3-(3-dimethylaminopropyl)carbodiimide hydrochloride (85 mg, 0.44 mmol), 1-hydroxybenzotriazol (60 mg, 0.44 mmol), and methylenechloride (10 mL) were charged, and stirred for 15 minutes at room temperature. Then, diethylamine (48 mg, 0.66 mmol) was added thereto, followed by stirring for 12 hours at room temperature. Purified water (5 mL) was added thereto, followed by stirring for 5 minutes. Then, the organic layer was separated, and added with magnesium sulfate (50 mg) so as to remove remaining moisture. The filtrate was concentrated and obtained as a residue. The mixture was purified with column chromatography (MC/MeOH=20:1) to obtain 4-[2-(2-chloro-benzenesulfonylamino)-2-methyl-propionylamino]-adamantane-1-carboxylic acid diethylamide (46 mg, 41.0%).

$^1$H NMR (400 MHz, DMSO-$d_6$) δ 8.37 (s, —NH—SO$_2$, 1H), 7.99 (dd, 1H), 7.63-7.70 (m, 2H), 7.52 (m, 1H), 7.21 (d, —NH—CO—, 1H), 3.76 (s, 1H), 2.00 (m, 4H), 1.59-2.00 (m, 13H), 1.21 (s, 6H), 0.98 (t, 6H).

Preparation Example 2

Synthesis of 4-[2-(2-bromo-benzenesulfonylamino)-2-methyl-propionylamino]-adamantane-1-carboxylic acid isopropylamide (compound 228)

An aimed compound was obtained in the same manner as described in Preparation Example 1 of Example 14 except that 4-(2-methyl-(2-bromophenylsulfonamido)propanamido)adamantane-1-carboxylic acid and isopropylamine were used.

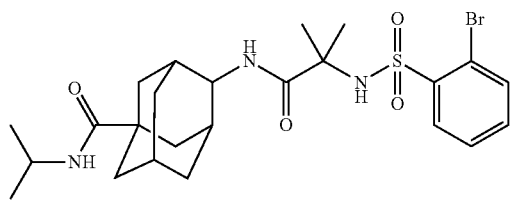 [SMILES: CC(C)NC(=O)C12CC3CC(C1)C(NC(=O)C(C)(C)NS(=O)(=O)c1ccccc1Br)C(C3)C2]

$^1$H NMR (400 MHz, CDCl$_3$) δ 8.16 (dd, J=2.0, 7.8 Hz, 1H), 7.78 (dd, J=1.2, 7.6 Hz, 1H), 7.44-7.54 (m, 2H), 7.12 (d, J=7.6 Hz —NH—CO—), 5.76 (s, —NH—SO$_2$), 5.36 (d, J=7.2 Hz —NH—CO—), 4.0 (d, J=7.6 Hz, 1H), 1.64-2.12 (m, 13H), 1.39 (s, 6H), 1.16 (d, J=6.4 Hz, 6H).

Preparation Example 3

Synthesis of 4-[2-(2-bromo-benzenesulfonylamino)-2-methyl-propionylamino]-adamantane-1-carboxylic acid cyclopropylamide (compound 229)

An aimed compound was obtained in the same manner as described in Preparation Example 1 of Example 14 except that 4-(2-methyl-(2-bromophenylsulfonamido)propanamido)adamantane-1-carboxylic acid and cyclopropylamine were used.

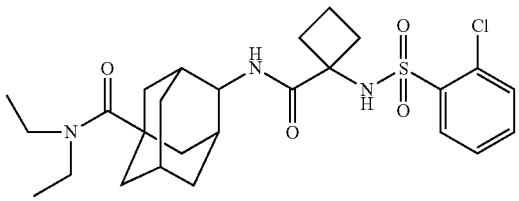 [SMILES: CCN(CC)C(=O)C12CC3CC(C1)C(NC(=O)C1(NS(=O)(=O)c4ccccc4Cl)CCC1)C(C3)C2]

$^1$H NMR (400 MHz, CDCl$_3$) δ 8.16 (dd, J=1.6, 7.6 Hz, 1H), 7.78 (dd, J=1.2, 8.0 Hz, 1H), 7.44-7.54 (m, 2H), 7.12 (d, J=8.0 Hz —NH—CO—), 5.75 (s, —NH—SO$_2$), 5.67 (s, —NH—CO—), 3.99 (d, J=7.6 Hz, 1H), 2.70-2.75 (m, 1H), 1.63-2.20 (m, 13H), 1.57 (s, 6H), 0.77-0.82 (m, 2H), 0.46-0.50 (m, 2H).

Preparation Example 4

Synthesis of 4-({1-[(2-chloro-benzenesulfonyl)-methyl-amino]-cyclobutanecarbonyl}-amino)-adamantane-1-carboxylic acid diethylamide (compound 230)

An aimed compound was obtained in the same manner as described in Preparation Example 1 of Example 14 except that 4-(2-methyl-(2-chlorophenylsulfonamido)cyclobutanamido)adamantane-1-carboxylic acid and 1-ethyl-3-(3-dimethylaminopropyl)carbodiimide hydrochloride were used.

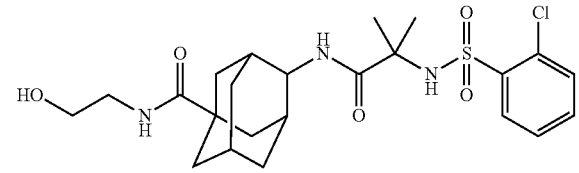 [SMILES: CC(C)(NS(=O)(=O)c1ccccc1Cl)C(=O)NC1C2CC3CC1CC(C(=O)NCCO)(C3)C2]

$^1$H NMR (400 MHz, DMSO-$d_6$) δ 8.65 (s, —NH—SO$_2$, 1H), 7.96 (d, 1H), 7.64-7.71 (m, 2H), 7.52 (t, 1H), 7.01 (d, —NH—CO—, 1H), 3.66 (s, 1H), 1.59-2.50 (m, 13H), 1.84-1.98 (m, 4H), 1.45-2.46 (m, 6H), 1.05 (s, 6H)

Preparation Example 5

Synthesis of 4-[2-(2-chloro-benzenesulfonylamino)-2-methyl-propionylamino]-adamantane-1-carboxylic acid ethanolamide (compound 231)

An aimed compound was obtained in the same manner as described in Preparation Example 1 of Example 14 except that 4-(2-methyl-(2-chlorophenylsulfonamido)propanamido)adamantane-1-carboxylic acid and 2-aminoethanol were used.

$^1$H NMR (400 MHz, DMSO-$d_6$) δ 8.36 (s, —NH—SO$_2$, 1H), 7.99 (dd, 1H), 7.63-7.77 (m, 2H), 7.47-7.52 (m, 1H), 7.38 (t, NH—CO—, 1H), 7.21 (d, —NH—CO—, 1H), 4.69 (t, 1H), 3.76 (s, 1H), 3.10 (m, 2H), 1.51-2.00 (m, 13H), 1.48 (d, 2H), 1.16 (s, 6H).

Preparation Example 6

Synthesis of 4-({1-[(2-chloro-benzenesulfonyl)-methyl-amino]-cyclobutanecarbonyl}-amino)-adamantane-1-carboxylic acid ethanolamide (compound 232)

An aimed compound was obtained in the same manner as described in Preparation Example 1 Example 14 except that 4-(2-methyl-(2-chlorophenylsulfonamido)cyclobutanamido)adamantane-1-carboxylic acid and 2-aminoethanol were used.

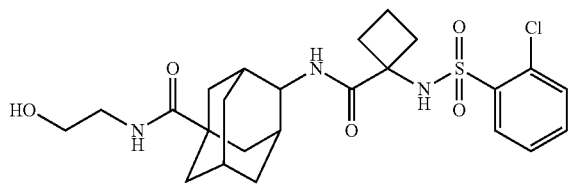 [SMILES: O=C(NCCO)C12CC3CC(C1)C(NC(=O)C1(NS(=O)(=O)c4ccccc4Cl)CCC1)C(C3)C2]

$^1$H NMR (400 MHz, DMSO-d$_6$) δ 8.66 (s, —NH—SO$_2$, 1H), 7.95 (d, 1H), 7.63-7.71 (m, 2H), 7.52 (m, 1H), 7.36 (t, NH—CO—, 1H), 7.02 (d, —NH—CO—, 1H), 4.62 (t, 1H), 3.66 (s, 1H), 3.08 (m, 2H), 1.59-2.50 (m, 13H), 1.75 (s, 2H), 1.45-2.46 (m, 6H)

Preparation Example 7

Synthesis of 4-[2-(2-chloro-benzenesulfonylamino)-2-methyl-propionylamino]-adamantane-1-carboxylic acid cyclohexylamide (compound 233)

An aimed compound was obtained in the same manner as described in Preparation Example 1 of Example 14 except that 4-(2-methyl-(2-chlorophenylsulfonamido)propanamido)adamantane-1-carboxylic acid and cyclohexanamine were used.

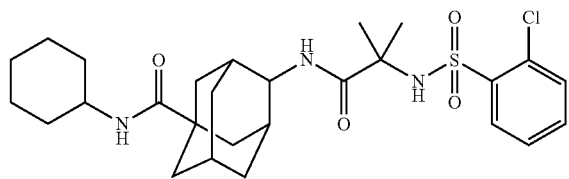 [SMILES: CC(C)(NS(=O)(=O)c1ccccc1Cl)C(=O)NC1C2CC3CC1CC(C(=O)NC1CCCCC1)(C3)C2]

$^1$H NMR (400 MHz, DMSO-d$_6$) δ 8.37 (s, —NH—SO$_2$, 1H), 7.99 (dd, 1H), 7.63-7.70 (m, 2H), 7.52 (m, 1H), 7.39 (d, NH—CO—, 1H), 7.20 (d, —NH—CO—, 1H), 3.76 (s, 1H), 2.62 (m, 1H), 1.59-1.93 (m, 13H), 1.47 (d, 2H), 1.22 (s, 1H), 1.20 (s, 6H), 0.56 (m, 2H), 0.39 (m, 2H).

Preparation Example 8

Synthesis of 4-({1-[(2-chloro-benzenesulfonyl)-methyl-amino]-cyclobutanecarbonyl}-amino)-adamantane-1-carboxylic acid cyclohexylamide (compound 234)

An aimed compound was obtained in the same manner as described in Preparation Example 1 of Example 14 except that 4-(2-methyl-(2-chlorophenylsulfonamido)cyclobutanamido)adamantane-1-carboxylic acid and cyclohexanamine were used.

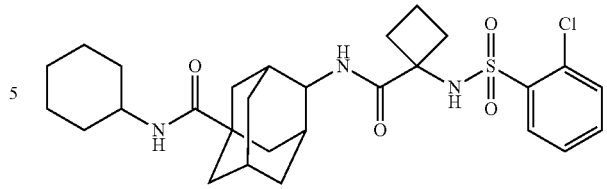

$^1$H NMR (400 MHz, DMSO-d$_6$) δ 8.63 (s, —NH—SO$_2$, 1H), 7.95 (d, 1H), 7.65-7.71 (m, 2H), 7.52 (m, 1H), 7.38 (d, NH—CO—, 1H), 7.01 (d, —NH—CO—, 1H), 3.64 (s, 1H), 2.59 (m, 1H), 2.31 (m, 2H), 1.98 (m, 2H), 1.59-2.50 (m, 13H), 1.45-2.46 (m, 6H), 0.58 (m, 2H), 0.40 (m, 2H)

Preparation Example 9

Synthesis of 4-[2-(2-chloro-benzenesulfonylamino)-2-methyl-propionylamino]-adamantane-1-carboxylic acid isopropylamide (compound 235)

An aimed compound was obtained in the same manner as described in Preparation Example 1 of Example 14 except that 4-(2-methyl-(2-chlorophenylsulfonamido)propanamido)adamantane-1-carboxylic acid and isopropylamine were used.

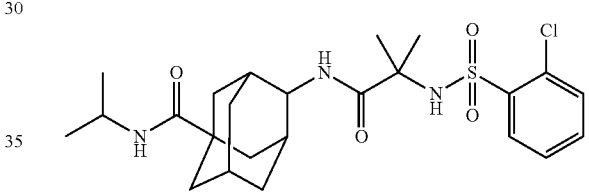

$^1$H NMR (400 MHz, DMSO-d$_6$) δ 8.38 (s, —NH—SO$_2$, 1H), 7.99 (dd, 1H), 7.63-7.70 (m, 2H), 7.52 (m, 1H), 7.21 (d, NH—CO—, 1H), 7.12 (d, —NH—CO—, 1H), 3.89 (m, 1H), 3.77 (s, 1H), 1.59-1.93 (m, 13H), 1.21 (s, 6H), 1.01 (d, 6H)

Preparation Example 10

Synthesis of 4-({1-[(2-chloro-benzenesulfonyl)-methyl-amino]-cyclobutanecarbonyl}-amino)-adamantane-1-carboxylic acid -isopropylamide (compound 236)

An aimed compound was obtained in the same manner as described in Preparation Example 1 of Example 14 except that 4-(2-methyl-(2-chlorophenylsulfonamido)cyclobutanamido)adamantane-1-carboxylic acid and isopropylamine were used.

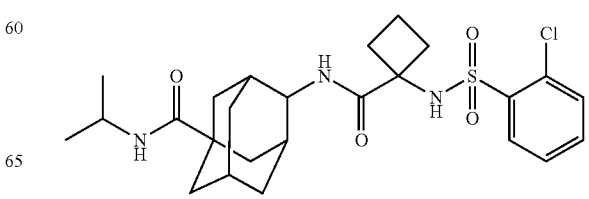

¹H NMR (400 MHz, DMSO-d₆) δ 8.82 (s, —NH—SO₂, 1H), 7.95 (d, 1H), 7.66-7.75 (m, 2H), 7.52 (td, 1H), 7.11 (d, NH—CO—, 1H), 7.01 (d, —NH—CO—, 1H), 3.80 (m, 1H), 3.66 (s, 1H), 2.30 (m, 1H), 1.59-2.50 (m, 13H), 1.45-2.46 (m, 6H), 1.04 (d, 6H)

Preparation Example 11

Synthesis of 4-[2-(2-chloro-benzenesulfonylamino)-2-methyl-propionylamino]-adamantane-1-carboxylic acid methylamide (compound 237)

An aimed compound was obtained in the same manner as described in Preparation Example 1 of Example 14 except that 4-(2-methyl-(2-chlorophenylsulfonamido)propanamido)adamantane-1-carboxylic acid and methylamine were used.

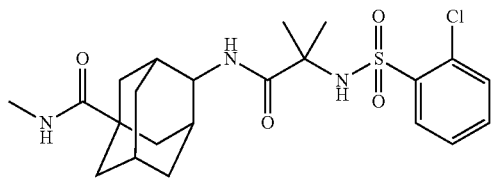 [SMILES: CNC(=O)C12CC3CC(C1)C(NC(=O)C(C)(C)NS(=O)(=O)c1ccccc1Cl)C(C3)C2]

¹H NMR (400 MHz, DMSO-d₆) δ 8.37 (s, —NH—SO₂, 1H), 7.99 (dd, 1H), 7.63-7.70 (m, 2H), 7.52 (m, 1H), 7.41 (m, NH—CO—, 1H), 7.21 (d, —NH—CO—, 1H), 3.75 (s, 1H), 2.50 (d, 3H), 1.59-1.93 (m, 13H), 1.21 (s, 6H)

Preparation Example 12

Synthesis of 4-({1-[(2-chloro-benzenesulfonyl)-methyl-amino]-cyclobutanecarbonyl}-amino)-adamantane-1-carboxylic acid methylamide (compound 238)

An aimed compound was obtained in the same manner as described in Preparation Example 1 of Example 14 except that 4-(2-methyl-(2-chlorophenylsulfonamido)cyclobutanamido)adamantane-1-carboxylic acid and methylamine were used.

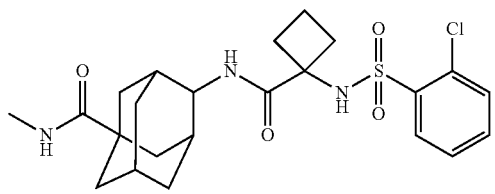 [SMILES: CNC(=O)C12CC3CC(C1)C(NC(=O)C1(NS(=O)(=O)c4ccccc4Cl)CCC1)C(C3)C2]

¹H NMR (400 MHz, DMSO-d₆) δ 8.65 (s, —NH—SO₂, 1H), 7.93 (dd, 1H), 7.64-7.71 (m, 2H), 7.52 (td, 1H), 7.40 (m, NH—CO—, 1H), 7.01 (d, —NH—CO—, 1H), 3.62 (s, 1H), 2.56 (d, 3H), 1.59-2.50 (m, 13H), 1.45-2.46 (m, 6H)

Example 15

Preparation Example 1

Synthesis of N-(5-hydroxyadamantane-2-yl)-2-(4-(2-hydroxypropane-2-yl)phenylsulfonamido)-2-methyl-propanamide (compound 239)

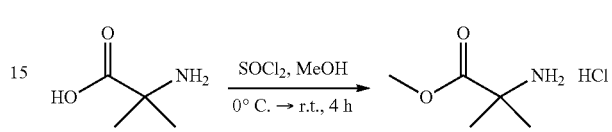

2-amino-2-methylpropionic acid (10 g, 96.9 mmol) and methanol (330 ml) were charged. An ice bath was set and thionyl chloride (17.68 ml, 242.25 mmol) was slowly added thereto. Then, the ice bath was removed, and the mixture was stirred at room temperature for 3 hours. The resultant product was vacuum-distilled to remove a solvent, and dried in a 60° C. oven so as to obtain methyl-2-amino-2-methylpropanoate hydrochloride (14.59 g, 94.9 mmol, 98%).

¹H NMR (400 MHz, DMSO-d₆) δ 8.75 (br, 3H), 3.75 (s, 3H), 1.45 (s, 6H).

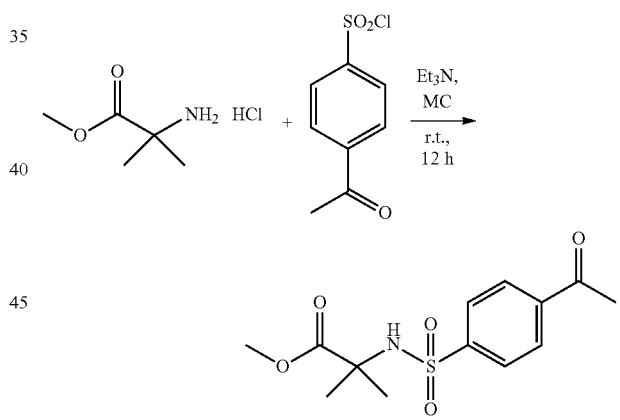

methyl-2-amino-2-methylpropanoate hydrochloride (2 g, 13.07 mmol) was dissolved in CH₂Cl₂ (50 ml), and added with 4-acetylbenzene-1-sulfonyl chloride (2.86 g, 13.07 mmol) and triethylamine (7.2 ml, 52.27 mmol), followed by stirring at room temperature for 12 hours. The resultant solution was added with H₂O, extracted with CH₂Cl₂ (×2), dried with MgSO₄, and filtered. Through vacuum distillation, the solvent was removed. The resultant mixture was purified with column chromatography so as to obtain methyl-2-(4-acetylphenylsulfonamido)-2-methylpropanoate (2.55 g, 8.52 mmol, 56%).

¹H NMR (400 MHz, CDCl₃) δ 8.07 (m, 2H), 7.99 (m, 2H), 5.49 (s, —NH—SO₂), 3.71 (s, 3H), 2.67 (s, 3H), 1.48 (s, 6H).

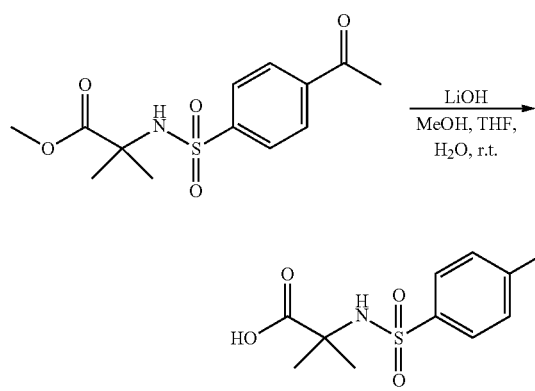

methyl-2-(4-acetylphenylsulfonamido)-2-methylpropanoate (2.55 g, 8.52 mmol) was charged, and dissolved through addition of THF (20 ml), and methanol (20 ml). LiOH.H$_2$O dissolved in H$_2$O (10 ml) was added thereto, followed by stirring for 12 hours at room temperature. After stirring for 12 hours, the resultant solution was vacuum-evaporated, acidified with 2N—HCl to pH 2-3, and extracted with EA (×2). The organic layer was dried with MgSO$_4$, and filtered. Through vacuum distillation, the solvent was removed so as to obtain 2-(4-acetylphenylsulfonamido)-2-methylpropionic acid (2.38 g, 8.35 mmol, 98%).

$^1$H NMR (400 MHz, DMSO-d$_6$) δ 12.63 (bs, —COOH), 8.29 (s, —NH—SO$_2$), 8.12 (m, 2H), 7.91 (m, 2H), 2.64 (s, 3H), 1.27 (s, 6H).

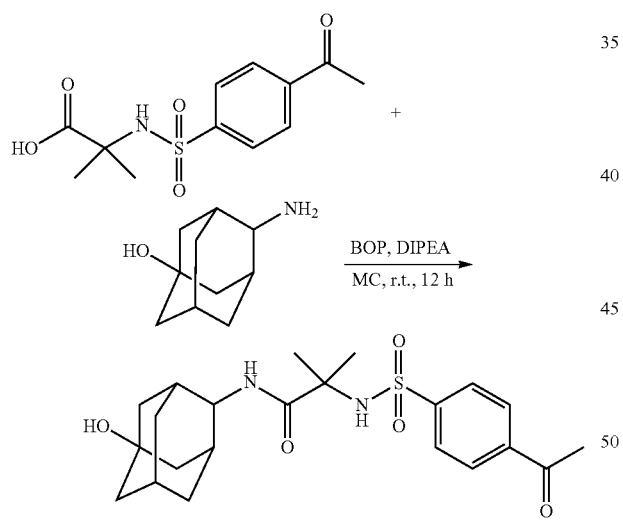

2-(4-acetylphenylsulfonamido)-2-methylpropionic acid (109 mg, 0.38 mmol), 5-hydroxy-2-adamantanamine (127 mg, 0.76 mmol), and BOP (168 mg, 0.38 mmol) were charged, and CH$_2$Cl$_2$ (5 ml) was added thereto, followed by stirring for 30 minutes at room temperature. DIPEA (0.18 ml, 1.14 mmol) was added thereto, followed by stirring at room temperature for 12 hours. After the reaction was completed, the organic layer was separated using CH$_2$Cl$_2$ and H$_2$O, dried with MgSO$_4$, and filtered. Then, through vacuum distillation, the solvent was removed, and the resultant product was purified with column chromatography to obtain 2-(4-acetylphenylsulfonamido)-N-(5-hydroxyadamantane-2-yl)-2-methylpropanamide (110 mg, 0.25 mmol, 69%).

$^1$H NMR (400 MHz, DMSO-d$_6$) δ 8.34 (s, —NH—SO$_2$), 8.12 (m, 2H), 7.93 (m, 2H), 7.01 (d, J=7.2 Hz, —NH—CO—), 4.45 (s, —OH), 3.47 (d, J=6.8 Hz, 1H), 2.64 (s, 3H), 2.01-1.57 (m, 11H), 1.35 (m, 2H), 1.24 (s, 6H).

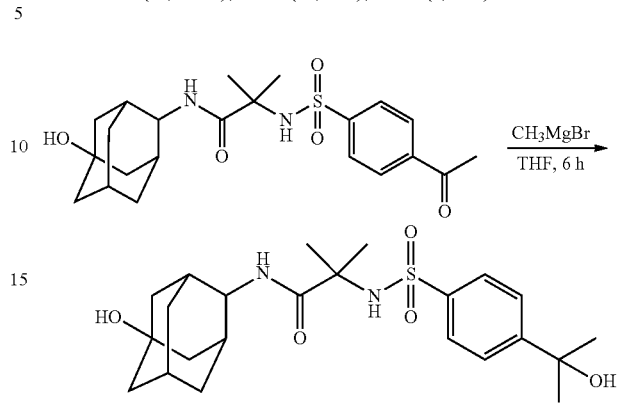

2-(4-acetylphenylsulfonamido)-N-(5-hydroxyadamantane-2-yl)-2-methylpropanamide (94 mg, 022 mmol) was dissolved in THF (4 ml). An ice bath was set, and 1.4M CH3MgBr (THF:toluene=1:3) was added thereto, followed by stirring for 6 hours. After the reaction was completed, ammonium chloride solution was added thereto. The organic layer was separated by CH$_2$Cl$_2$, dried with MgSO$_4$, and filtered. Through vacuum distillation, the solvent was removed. The resultant product was purified with column chromatography to obtain N-(5-hydroxyadamantane-2-yl)-2-(4-(2-hydropropane-2-yl)phenylsulfonamido)-2-methyl propanamide (51 mg, 0.11 mmol, 51%).

$^1$H NMR (400 MHz, DMSO-d$_6$) δ 8.13 (s, —NH—SO$_2$), 7.77 (m, 2H), 7.64 (m, 2H), 7.03 (d, J=7.2 Hz, —NH—CO—), 5.24 (s, —OH), 4.46 (s, —OH), 3.52 (d, J=7.2 Hz, 1H), 2.01-1.57 (m, 11H), 1.44 (s, 6H), 1.34 (m, 2H), 1.24 (s, 6H).

Example 16

Preparation Example 1

Synthesis of N-(adamantane-2-yl)-2-methyl-2-(N-methyl-1-(2-nitrophenyl)ethylsulfonamido)propanamide (compound 240)

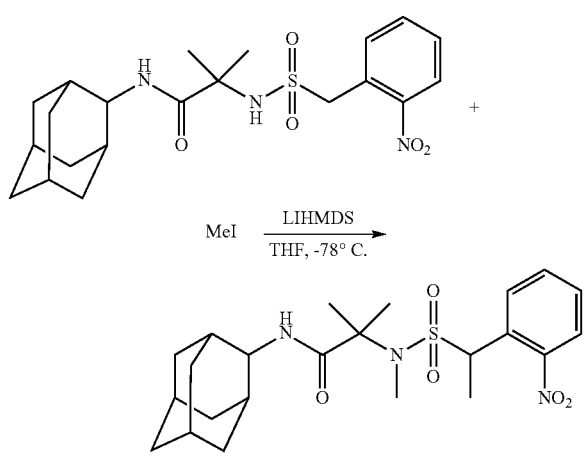

N-(adamantane-2-yl)-2-methyl-2-(N-methyl-1-(2-nitrophenyl)methylsulfonamido)propanamide (100 mg, 0.23 mmol) was dissolved in THF (2 ml), and cooled to −70° C. by using Dry ice and acetone. 1M LiHMDS (0.46 ml, 0.46 mmol) in THF was added thereto, followed by stirring for 1 hour at −70° C. Then, the temperature was raised up to −40° C., and MeI (0.143 ml, 2.3 mmol) was added thereto, followed by stirring at room temperature for 4 hours. After the stirring for 4 hours, ammonium chloride solution (4 ml) was added thereto to quench the reaction. The organic layer was washed with ammonium chloride solution (4 ml) twice, and separated. The separated organic layer was dried with $MgSO_4$, and filtered. Through vacuum distillation, the solvent was removed, and through column chromatography, N-(adamantane-2-yl)-2-methyl-2-(N-methyl-1-(2-nitrophenyl)ethylsulfonamido)propanamide (21 mg, 0.11 mmol, 19%) was obtained.

$^1$H NMR (400 MHz, $CDCl_3$) δ 7.87-7.93 (m, 2H), 7.67 (t, J=7.6, 1H), 7.51-7.53 (m, 1H), 6.71 (d, J=7.2 Hz —NH—CO—), 5.39-5.44 (q, 1H), 5.67 (s, —NH—CO—), 4.02 (d, J=7.6 Hz, 1H), 2.70 (s, 3H), 1.98-1.72 (m, 14H), 1.62 (s, 6H), 1.45 (s, 3H).

Example 17

Preparation Example 1

Synthesis of 4-(2-methyl-2-benzenesulfonylamino-propionylamino)-adamantane-1-propanoic acid (compound 241)

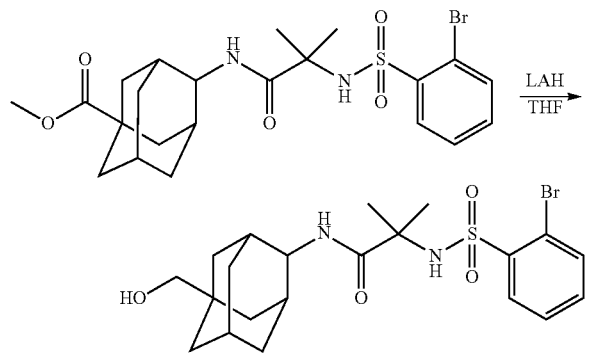

In a 50-mL flask, 4-{[1-(2-bromo-benzenesulfonylamino)-2-methyl-propionylamino]}-adamantane-1-carboxylic acid methylester (300 mg, 0.584 mmol) was charged and dissolved through addition of tetrahydrofuran (20 mL). The resultant solution was cooled to −30~−25° C., and lithiumaluminiumhydroxide (35 mg, 0.876 mmol) was added thereto. The temperature was raised up to 0~5° C., and the resultant mixture was stirred for 1 hour. After the reaction was completed, the purified water (10 ml) was added thereto at a low temperature. Through vacuum evaporation, the solvent was removed. The concentrated residue was extracted with addition of purified water (10 ml), and dichloromethane (20 ml). The organic layer was added with magnesium sulfate so as to remove remaining moisture. Then, through filtering and vacuum distillation, the solvent was removed, and the resultant product was purified with column chromatography (EA/n-Hex=1:1) to obtain 4-{[1-(2-bromo-benzenesulfonylamino)-2-methyl-propionylamino]}-adamantane-1-methyl hydroxide (168 mg, 59%).

$^1$H NMR (400 MHz, $CDCl_3$) δ 8.14 (d, 1H), 7.76 (d, 1H), 7.43 (m, 2H), 7.04 (d, —NH—CO—, 1H), 5.84 (d s, —NH—$SO_2$, 1H), 3.95 (s, 1H), 3.26 (s, 2H), 1.59-2.06 (m, 13H), 1.39 (s, 6H).

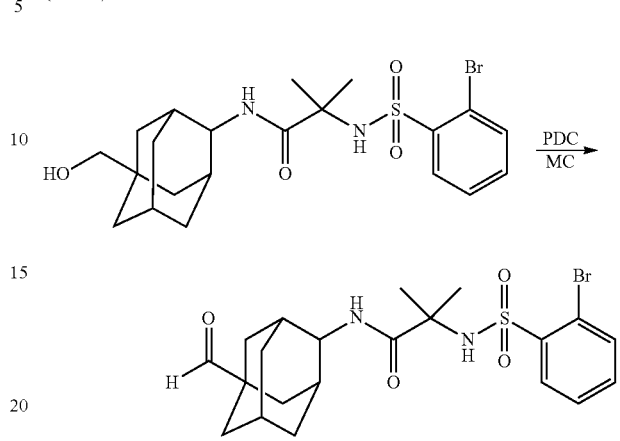

In a 25-mL flask, 4-{[1-(2-bromo-benzenesulfonylamino)-2-methyl-propionylamino]}-adamantane-1-methyl hydroxide (150 mg, 0.309 mmol) was charged and dissolved through addition of dichloromethane (10 mL). The resultant solution was cooled to 0~5° C., and pyridiniumdichromate (234 mg, 0618 mmol) was added thereto. The temperature was raised up to 0~5° C., and the resultant mixture was stirred for 3 hours under nitrogen gas reflux condition. After the reaction was completed, cooled diethyl ether (20 ml) was added thereto, followed by stirring for 5 minutes. Then, through filtering using silica gel-filled column, remaining metals were removed. The filtrate was vacuum-evaporated to remove solvent. The resultant concentrate was purified with column chromatography (EA/n-Hex=1:1) to obtain 4-{[1-(2-bromo-benzenesulfonylamino)-2-methyl-propionylamino]}-adamantane-1-aldehyde (47 mg, 32%).

$^1$H NMR (400 MHz, $CDCl_3$) δ 9.38 (s, —COH), 8.15 (dd, J=2.0, 7.6 Hz, 1H), 7.78 (d, J=7.6 Hz, 1H), 7.52-7.46 (m, 2H), 7.23 (d, J=7.2 Hz, —CONH), 5.79 (s, 1H), 4.00 (m, 1H), 2.15-1.63 (m, 13H), 1.38 (s, 6H).

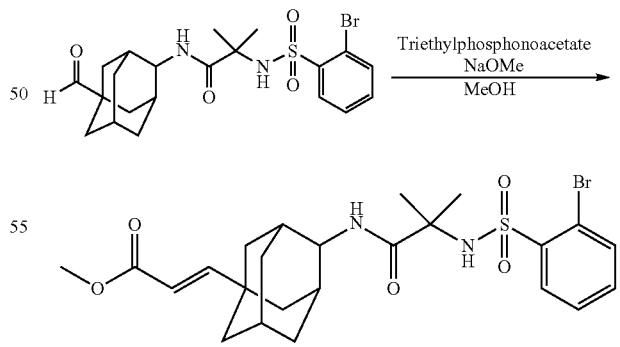

In a 25-mL flask, sodium methoxide (32 mg, 0.5792 mmol) and methanol (10 ml) were charged, and were cooled to 0-5° C. The cooled resultant solution was added with triethylphosphonoacetate (130 mg, 0.579 mmol), and stirred for 30 minutes at a low temperature. 4-{[1-(2-bromo-benzenesulfonylamino)-2-methyl-propionylamino]}-adamantane-1-aldehyde (140 mg, 0.289 mmol) dissolved in methanol (2 ml) was added dropwise thereto. The resultant solution was stirred for 2 hours under nitrogen gas reflux condition. After the reaction was completed, purified water (10 ml) was added thereto at a low temperature. Through vacuum evaporation, the solvent was removed. The concentrated residue was extracted with addition of purified water (10 ml), and dichloromethane (20 ml). The organic layer was added with magnesium sulfate so as to remove remaining moisture. Then, through filtering and vacuum distillation, the solvent was removed, and the resultant product was purified with column chromatography (EA/n-Hex=1:1) to obtain 4-{[1-(2-bromo-benzenesulfonylamino)-2-methyl-propionylamino]}-adamantane-1-trabsbutene carboxylic methylester (57 mg, 36%).

$^1$H NMR (400 MHz, CDCl$_3$) δ 8.15 (dd, J=1.6, 7.6 Hz, 1H), 7.77 (dd, J=1.6, 11.6 Hz, 1H), 7.50 (td, J=1.2, 7.6 Hz, 1H), 7.45 (td, J=2.0, 7.6 Hz, 1H), 7.12 (d, J=7.6 Hz, —CONH), 6.84 (d, J=16.0 Hz, 1H), 5.84 (s, 1H), 5.72 (d, J=16.0 Hz, 1H), 3.96 (m, 1H), 2.09-1.59 (m, 13H), 1.38 (s, 6H).

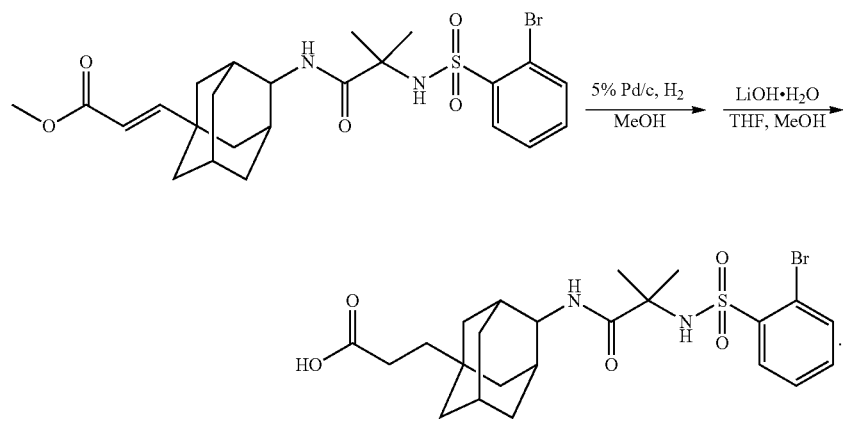

In a 25-mL flask, 4-{[1-(2-bromo-benzenesulfonylamino)-2-methyl-propionylamino]}-adamantane-1-trabsbutene carboxylic methylester (57 mg, 0.106 mmol) and methanol (5 ml) were charged, and 5% Pd/c (57 mg, 100% w/w) was added thereto. The reaction vessel was degassed under reduced pressure, and filled with hydrogen gas by hydrogen balloon. After stirring at room temperature for 3 hours, metals were removed through filtering using celite-filled filter. The filtrate was removed through vacuum evaporation, and in the residue, methanol (5 ml), and tetrahydrofuran (5 ml) were added and dissolved. Lithium hydroxide (44 mg, 1.06 mmol) dissolved in purified water (5 ml) was added thereto, followed by stirring at 20~25° C. for 3 hours. Through vacuum evaporation, the solvent was removed. The resultant product was added with purified water (10 ml), and acidified with 1N-hydrochloric acid. The aqueous solution layer with produced crystals was extracted with addition of dichloromethane (20 ml). The organic layer was added with magnesium sulfate so as to remove remaining moisture. Through filtering and vacuum distillation, the solvent was removed, and through column chromatography (MC/MeOH=10:1), 4-(2-methyl-2-benzenesulfonylamino-propionylamino)-adamantane-1-propanoic acid (21 mg, 38%) was obtained.

$^1$H NMR (400 MHz, CDCl$_3$) δ 7.92-7.90 (m, 2H), 7.62-7.51 (m, 3H), 6.90 (d, J=8.0 Hz, —CONH), 5.51 (s, 1H), 3.90 (m, 1H), 2.33 (t, J=8.0 Hz, 2H), 2.06-1.50 (m, 15H), 1.42 (s, 6H)

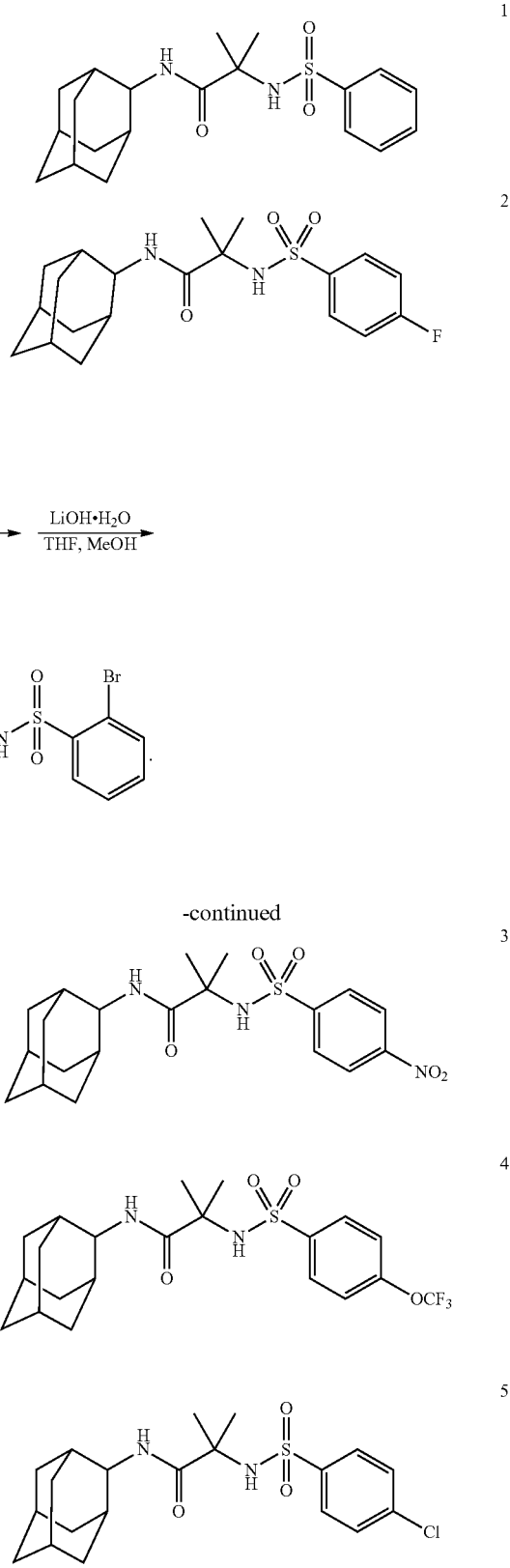

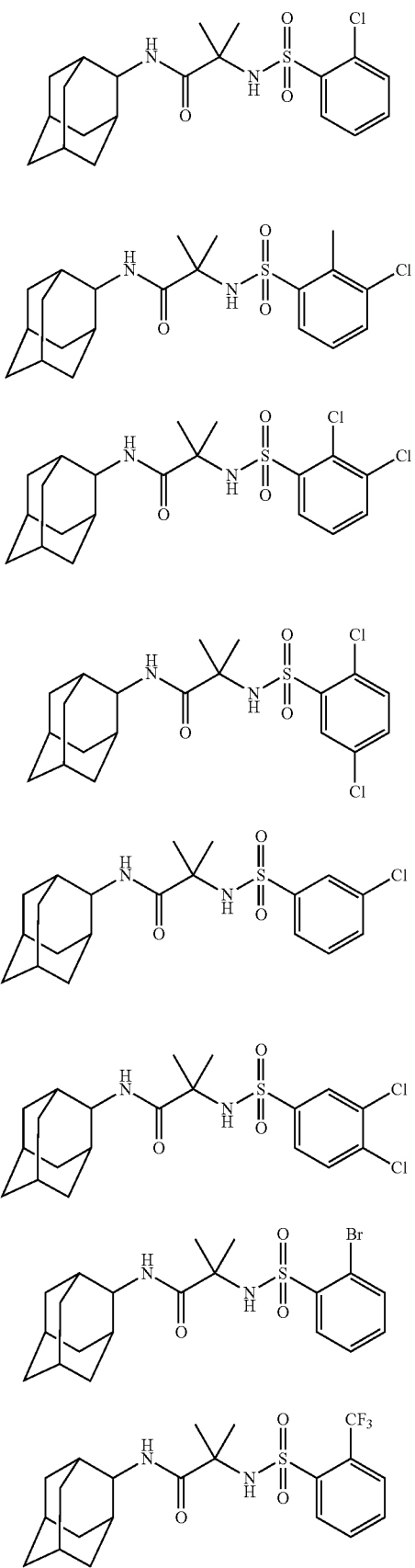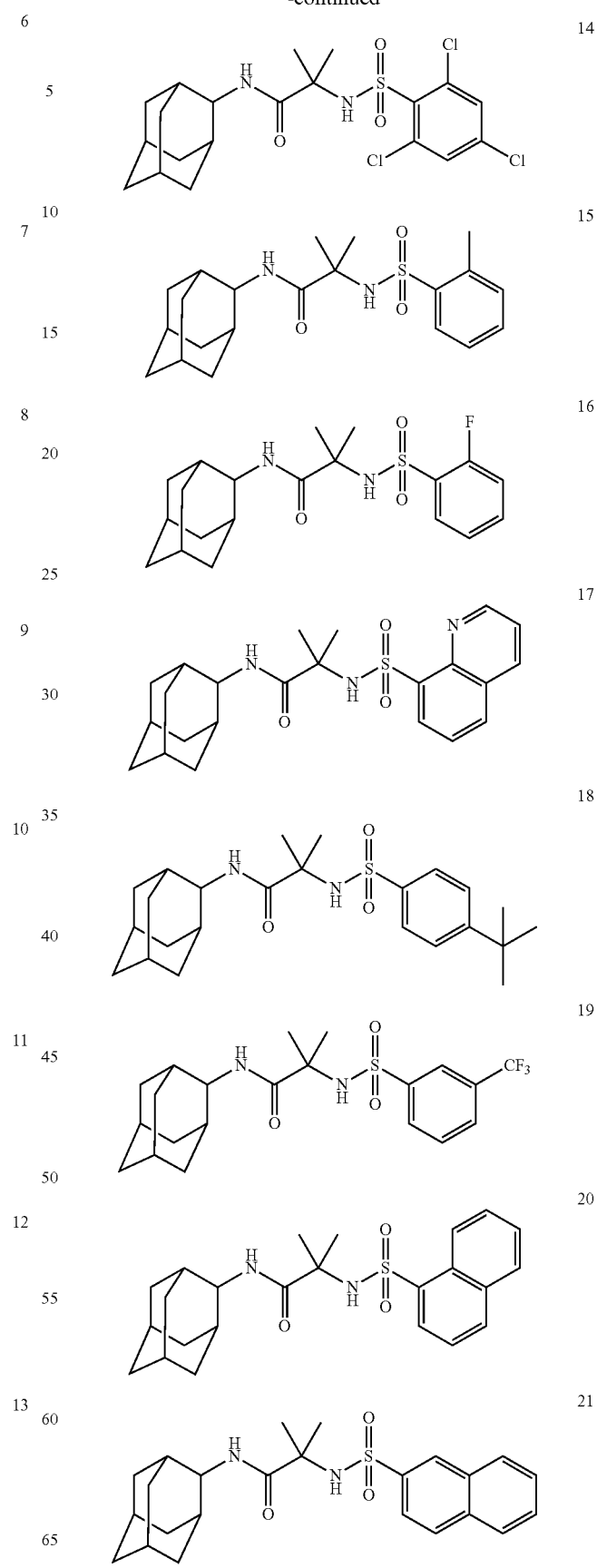

-continued
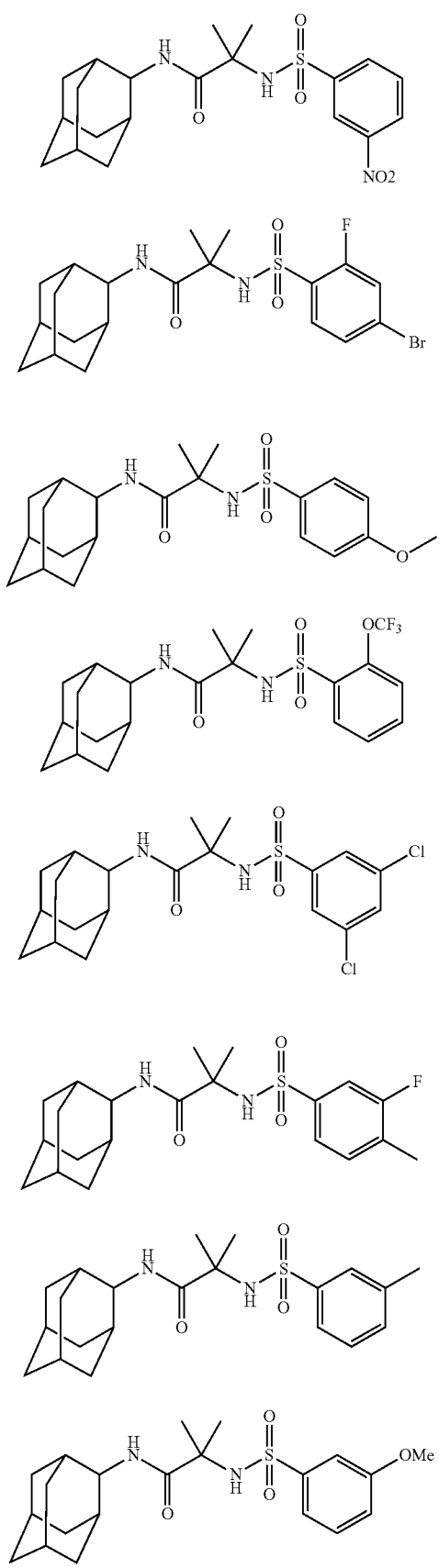
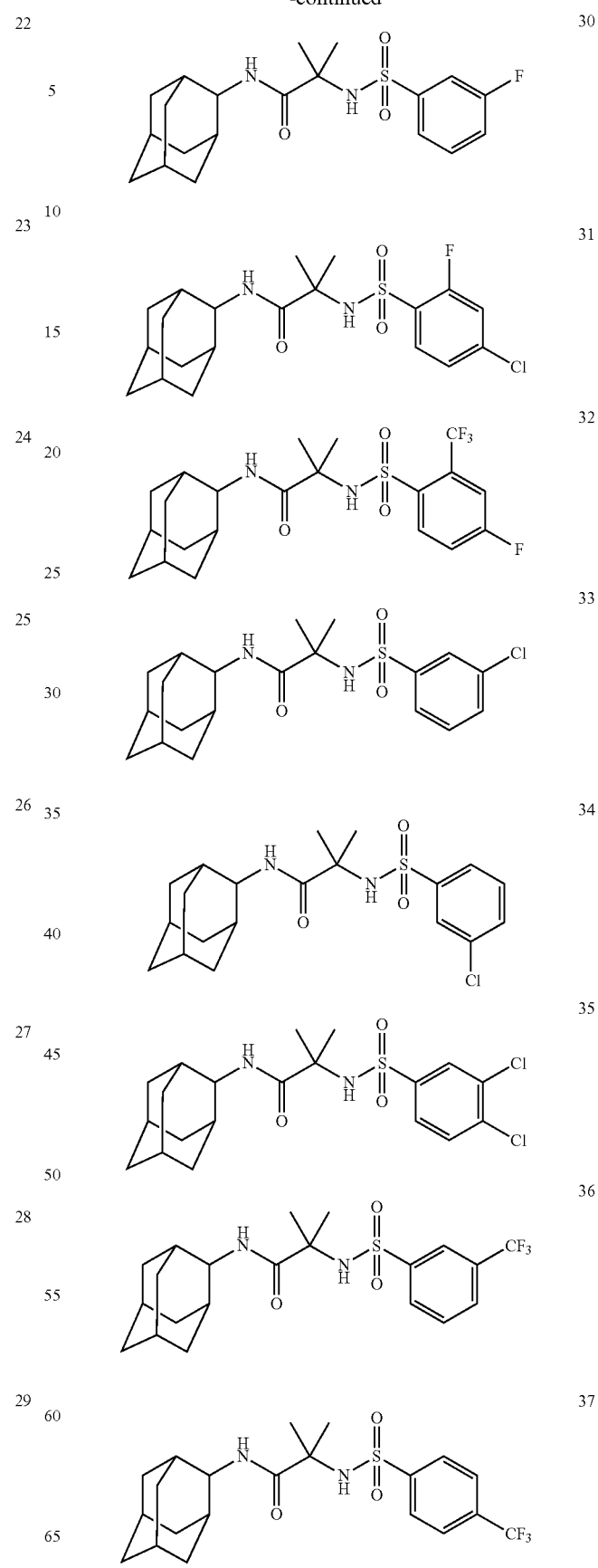

-continued

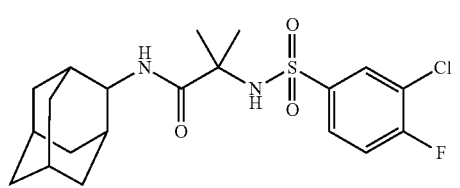
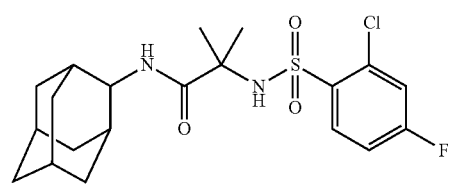
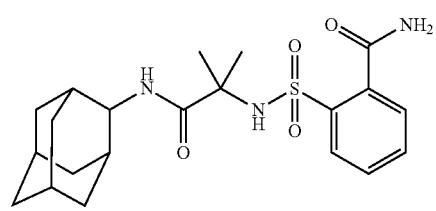
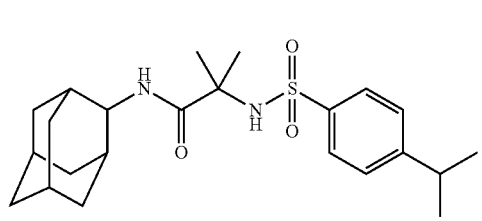
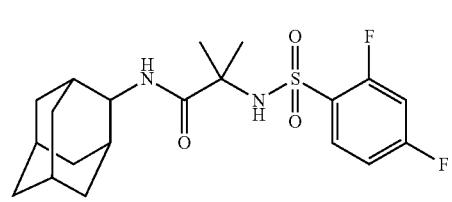
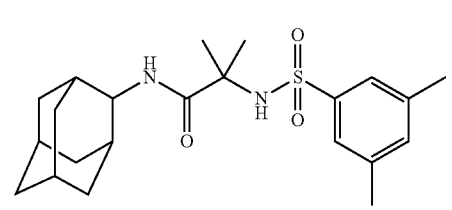
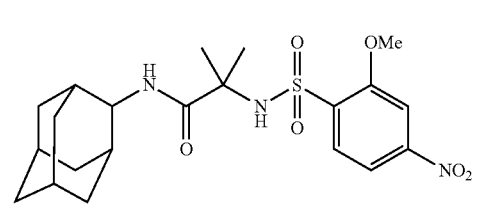
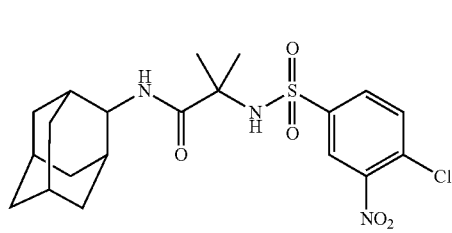
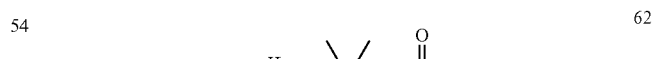
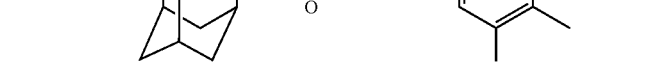
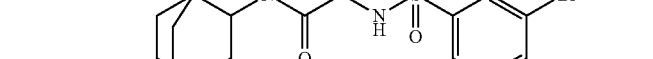

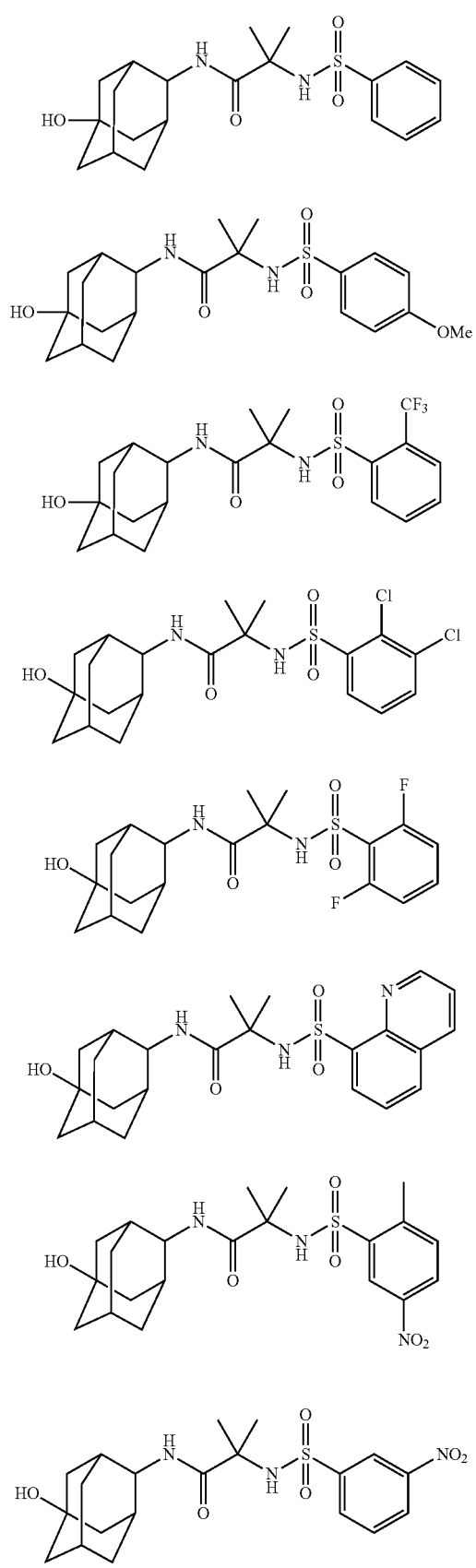
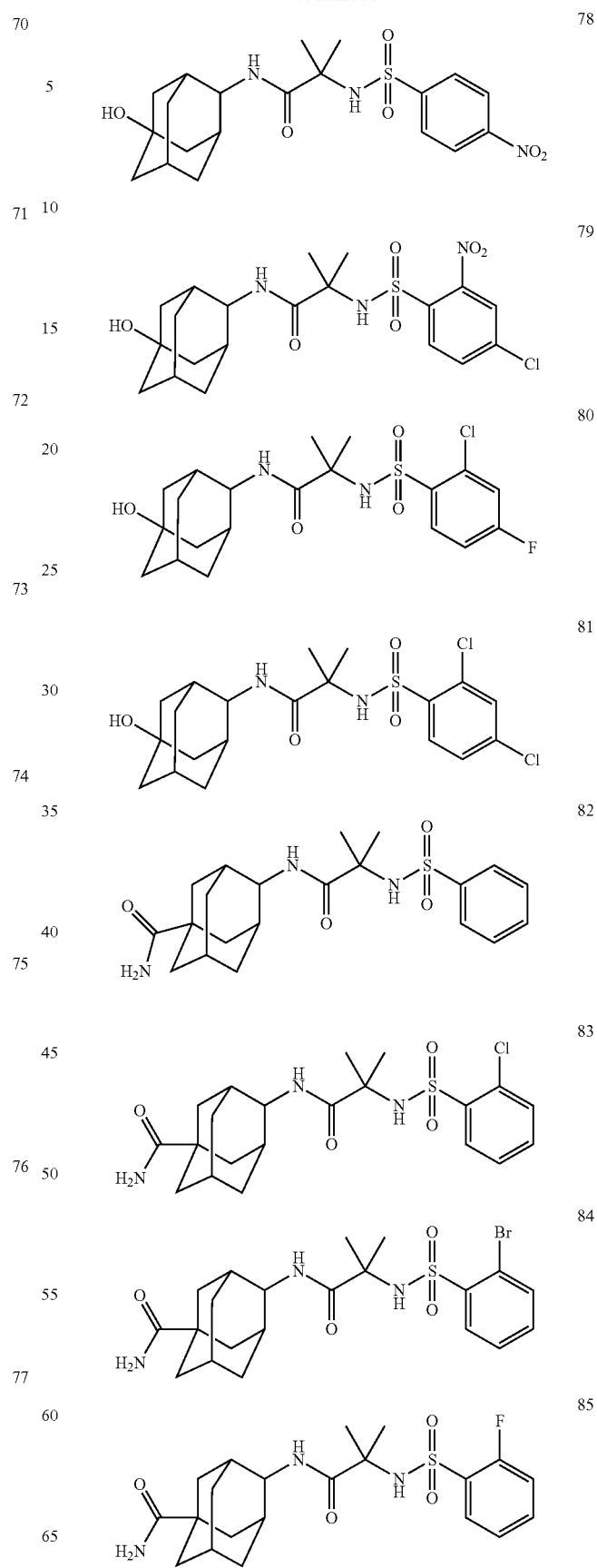

-continued
86
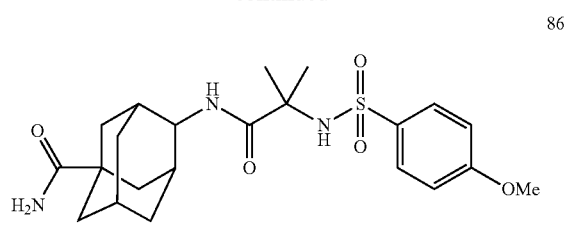
87
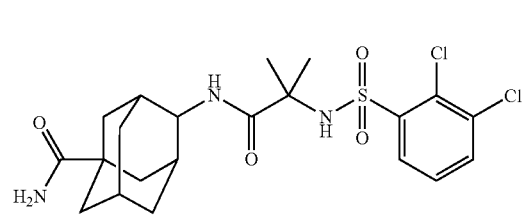
88
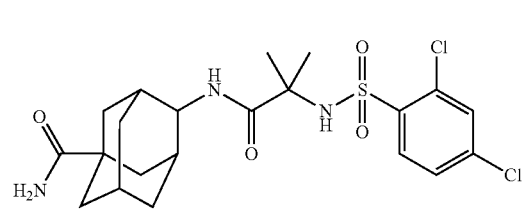
89
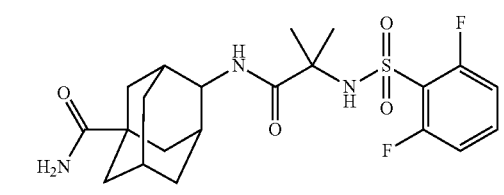
90
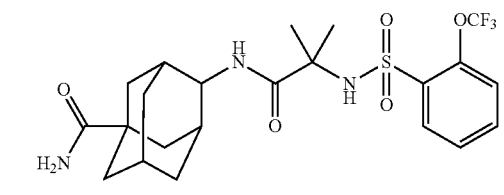
91
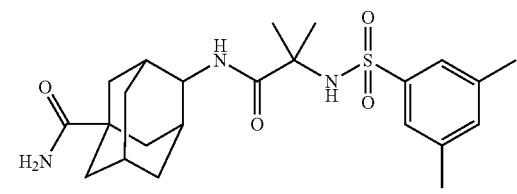
92
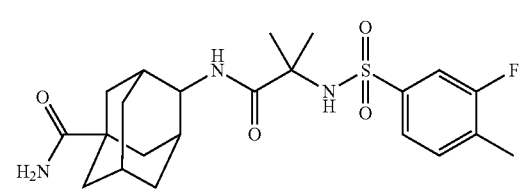
93
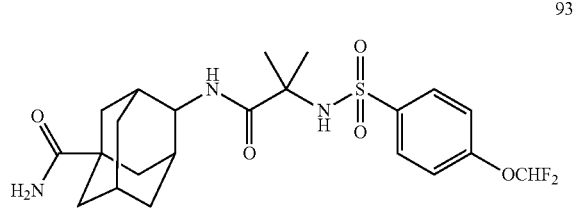
-continued
94
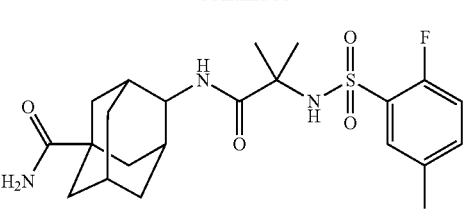
95
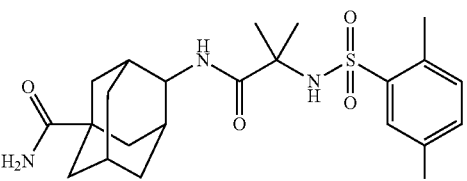
96
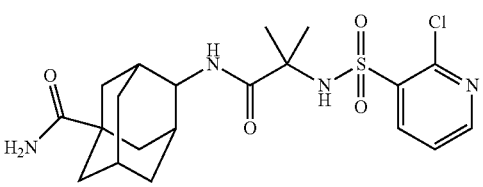
97
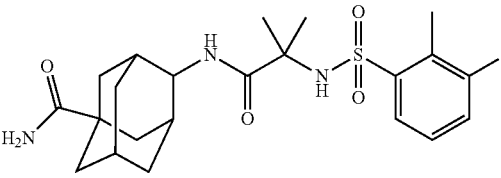
98
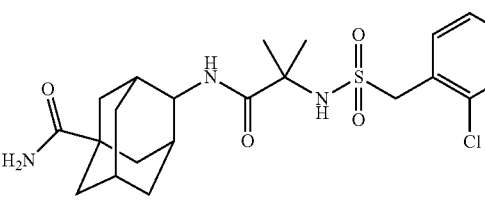
99
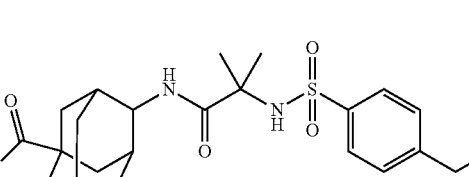
100
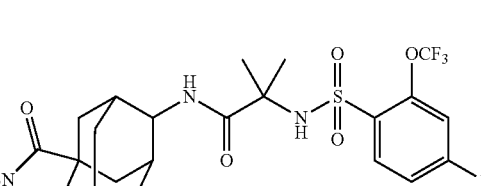
101
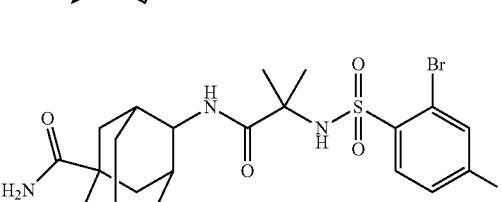

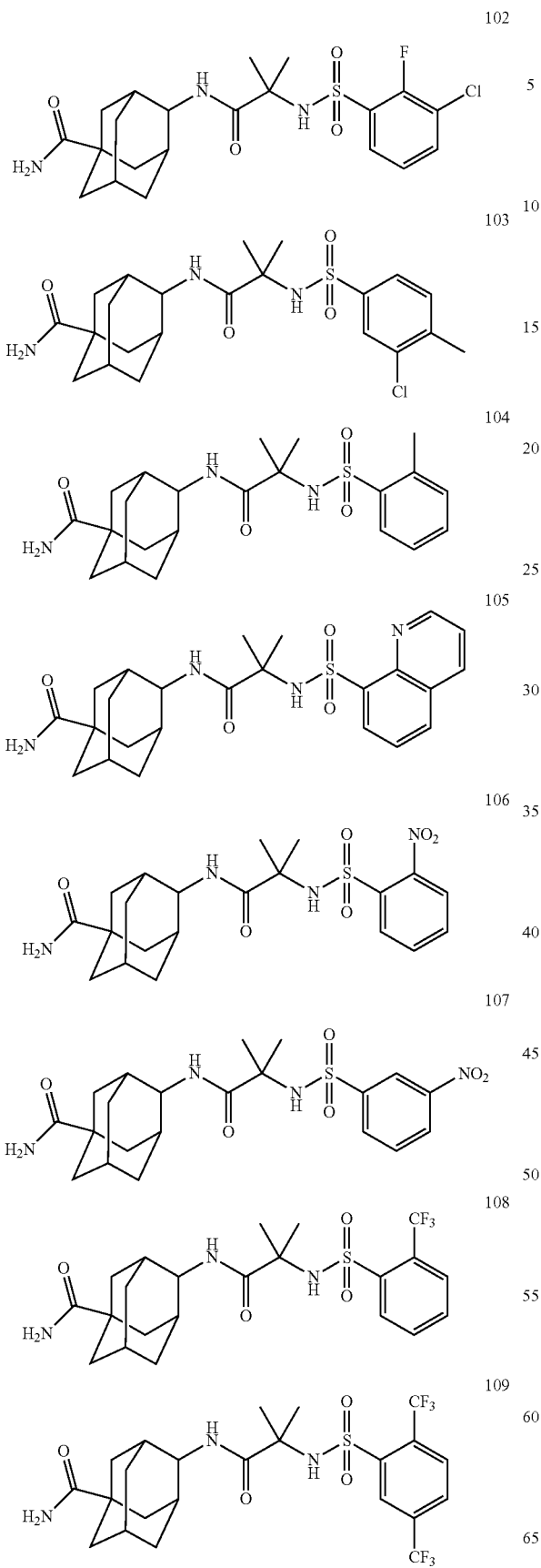
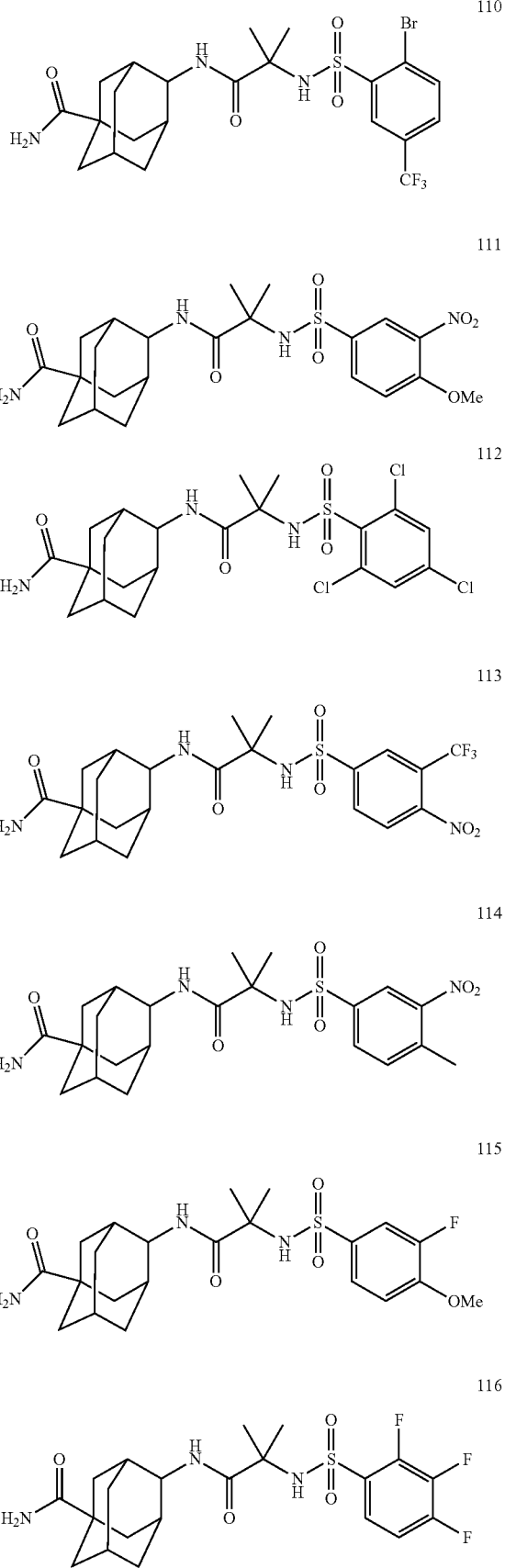

117 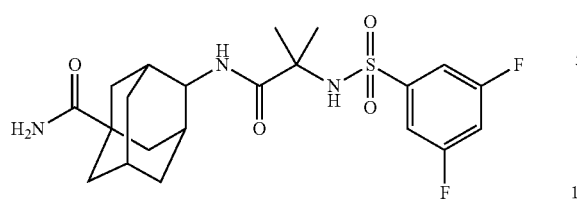
118 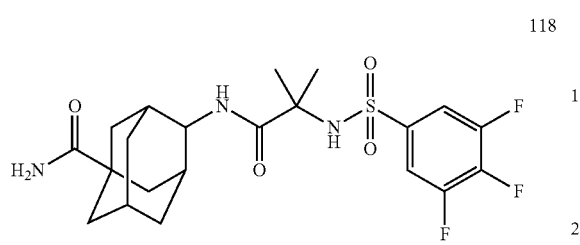
119 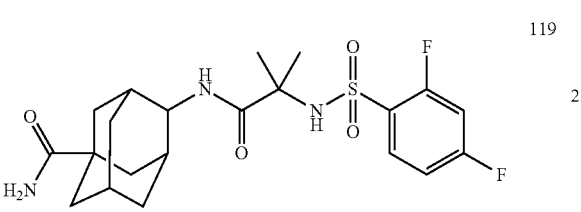
120 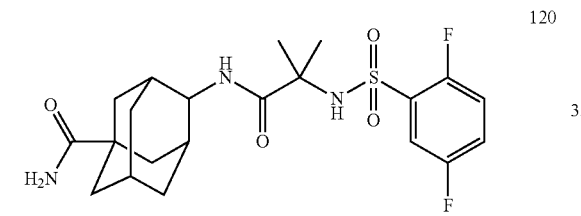
121 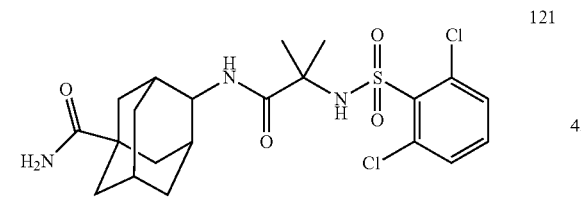
122 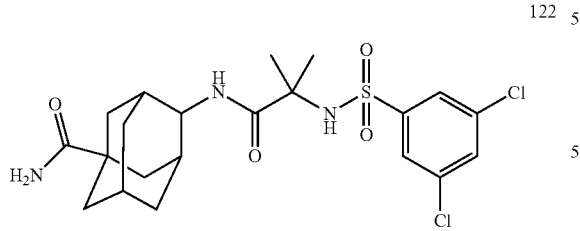
123 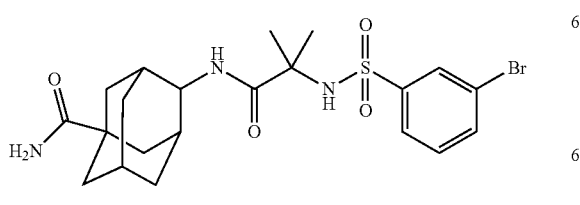
124 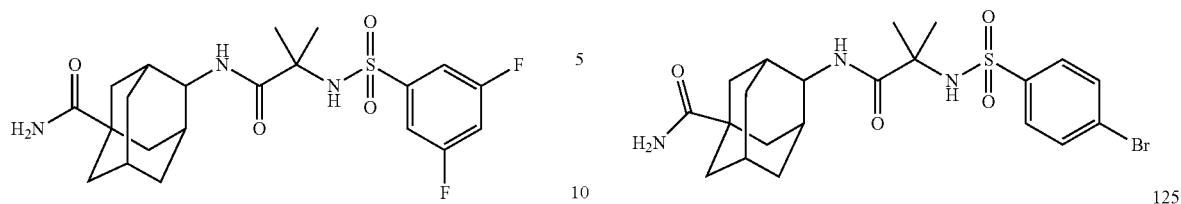
125 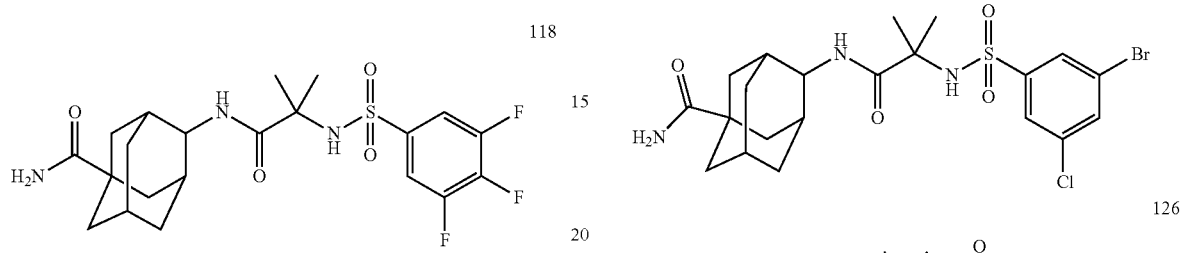
126 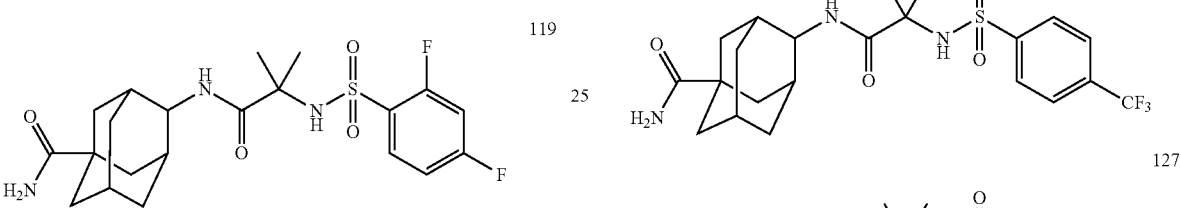
127 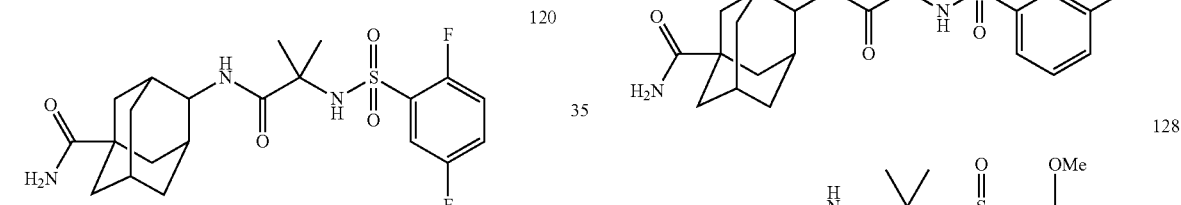
128 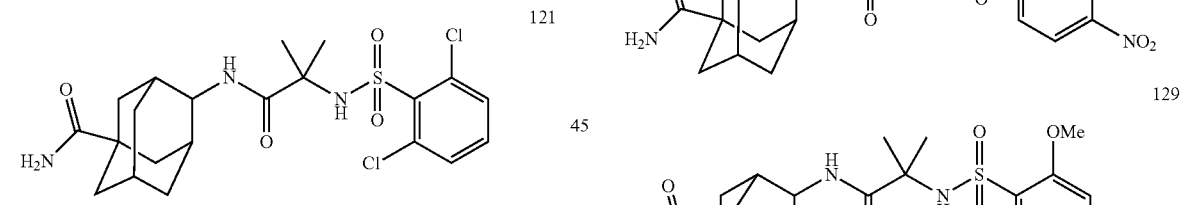
129 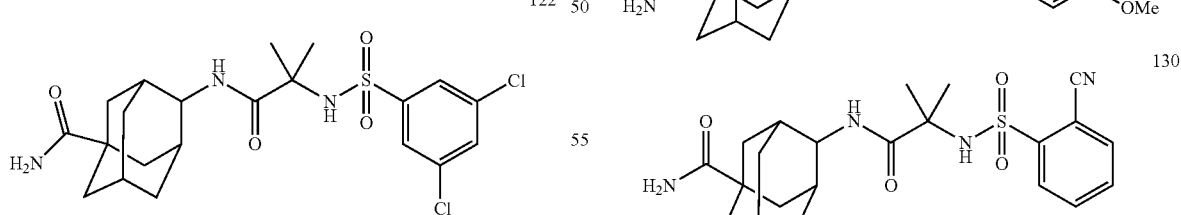
130 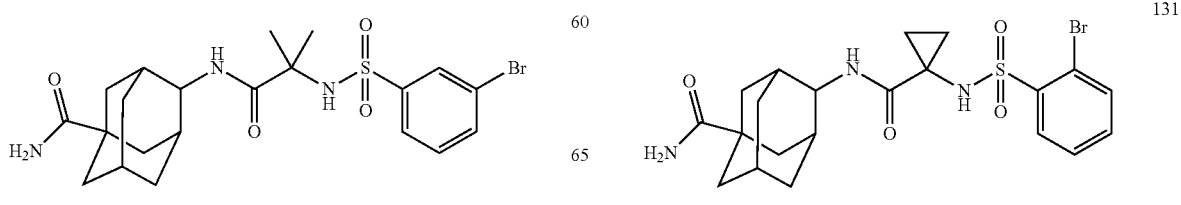
131 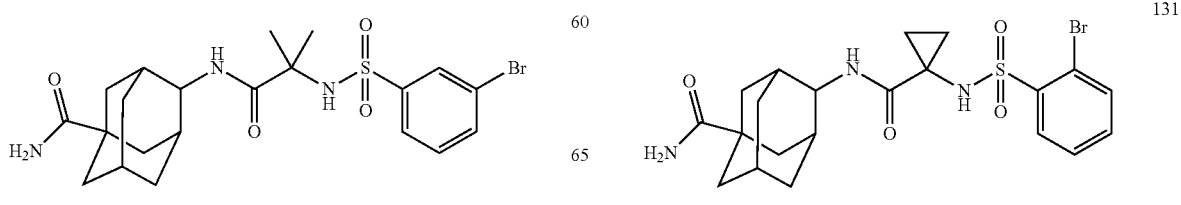

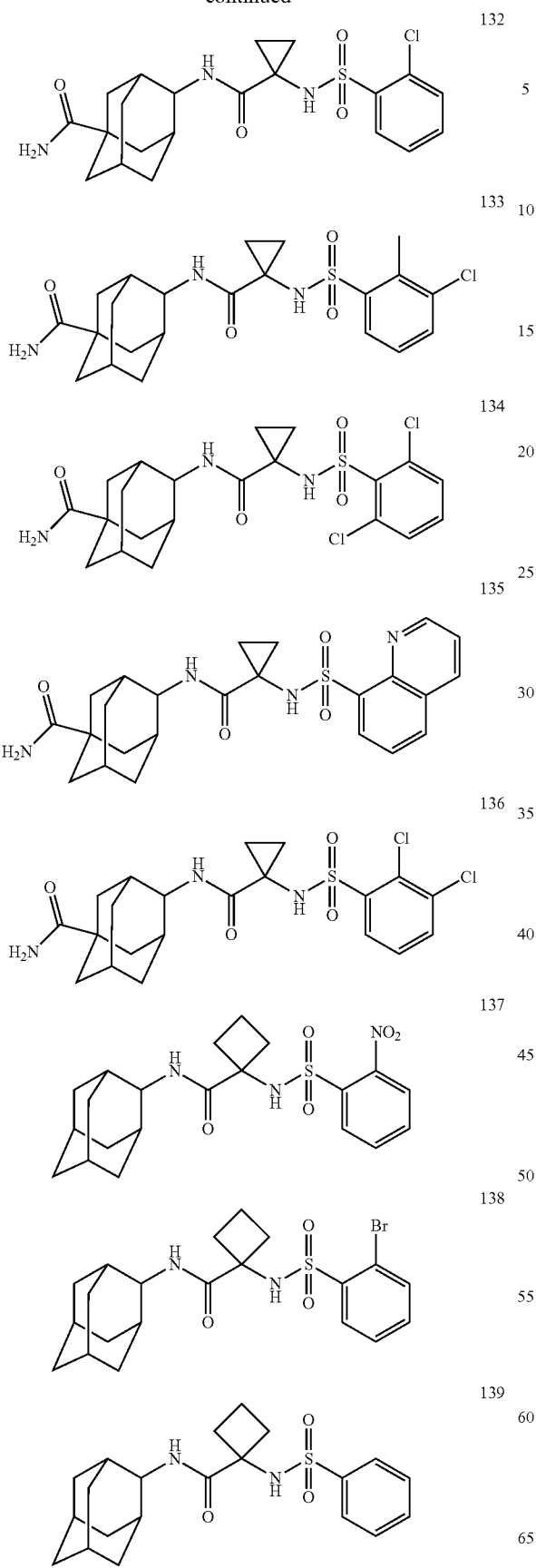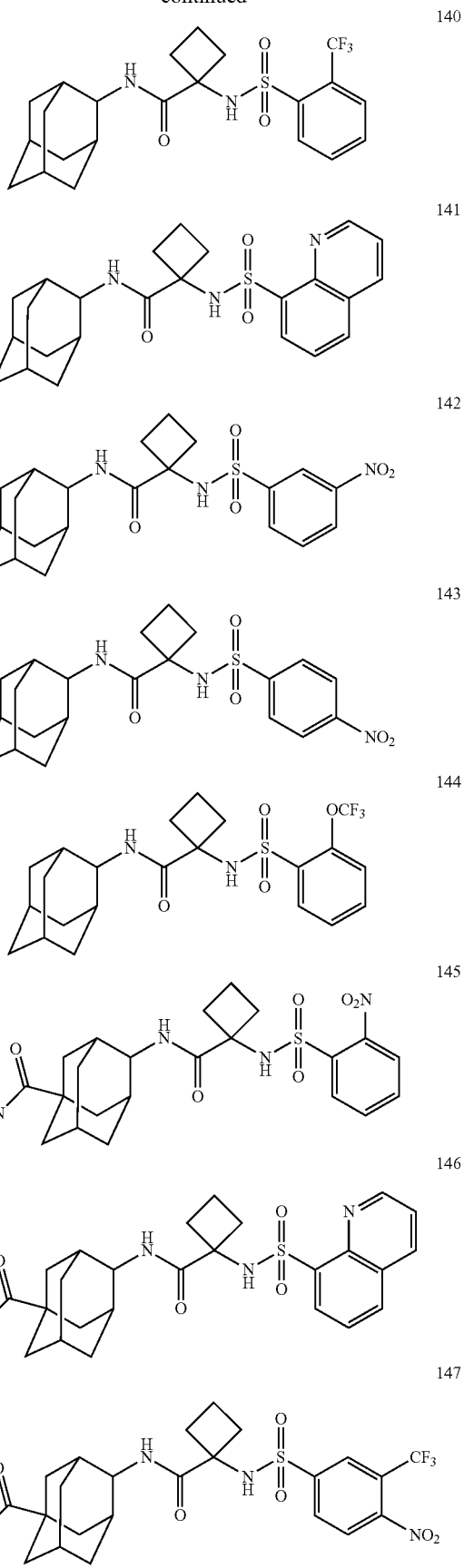

148
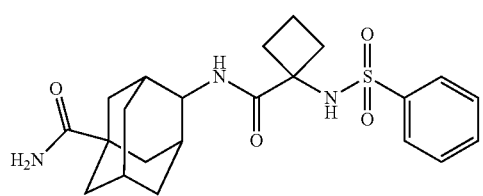
149
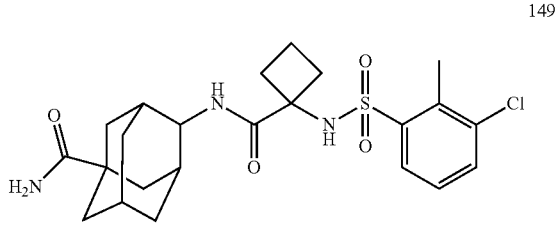
150
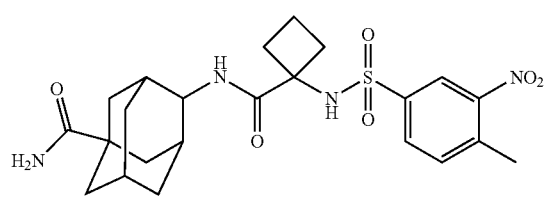
151
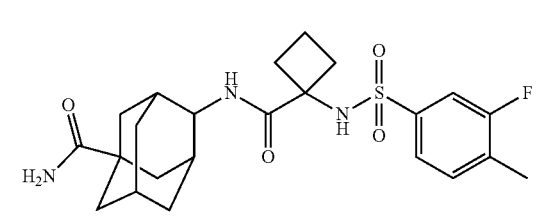
152
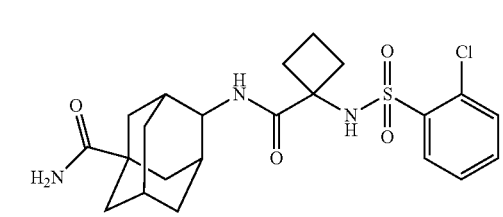
153
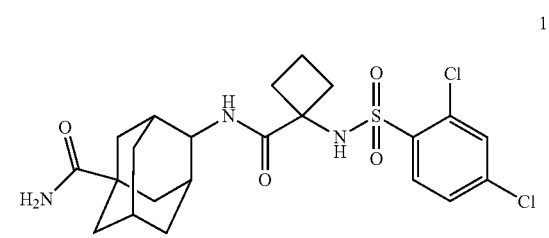
154
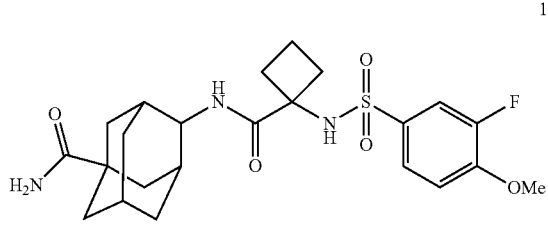
155
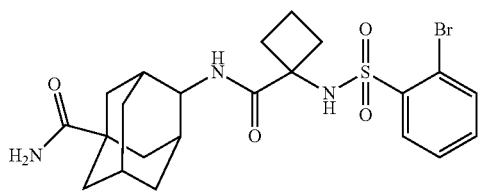
156
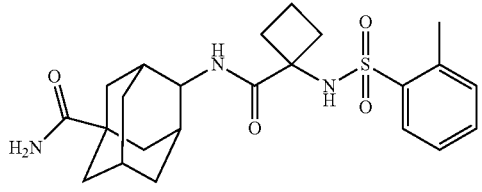
157
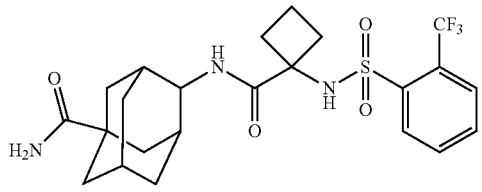
158
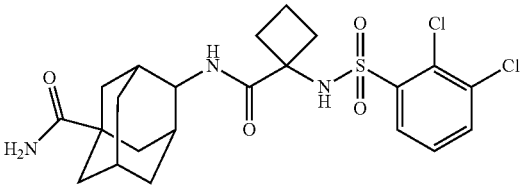
159
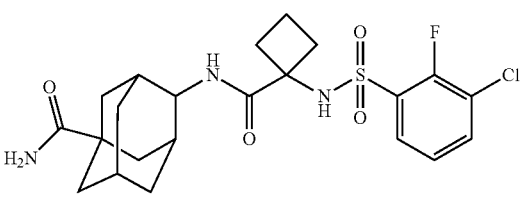
160
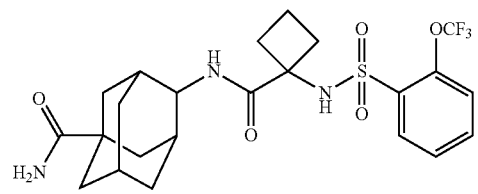
161
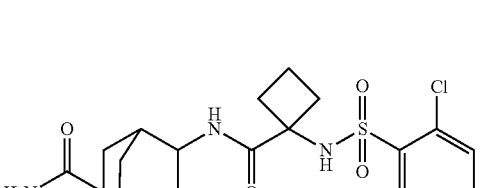

162 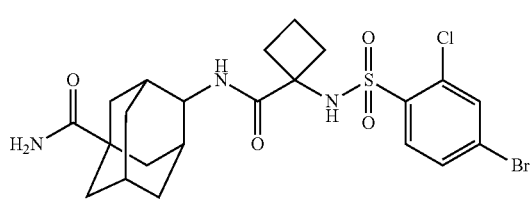
163 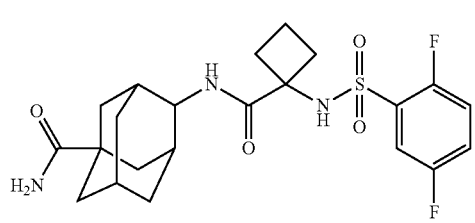
164 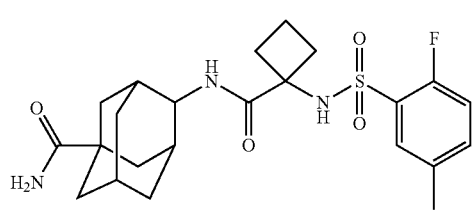
165 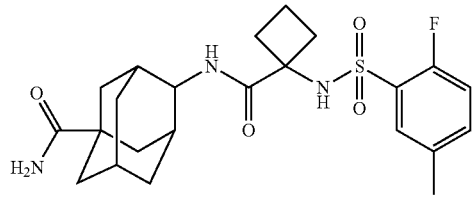
166 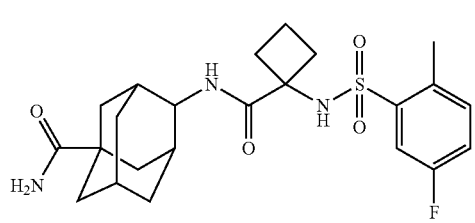
167 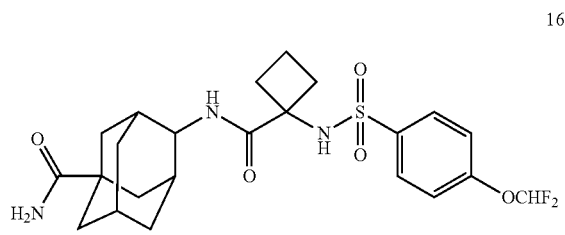
168 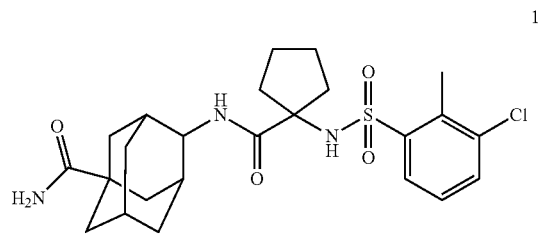
169 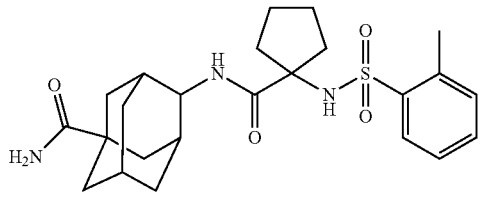
170 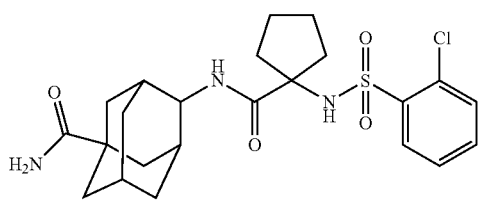
171 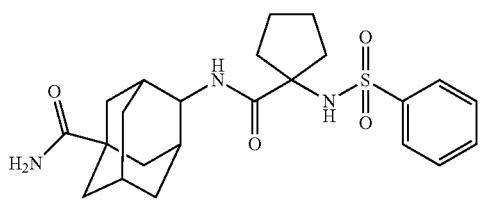
172 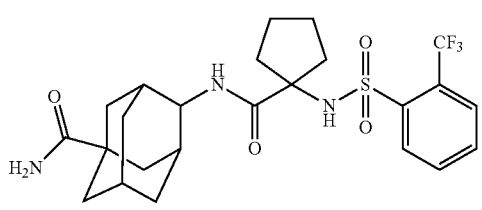
173 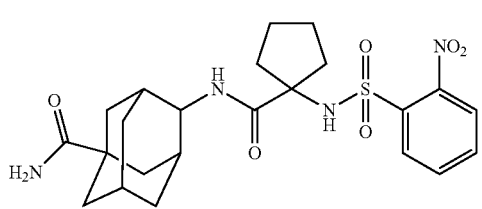
174 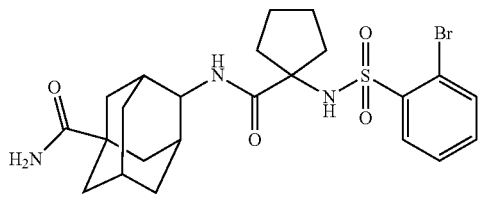
175 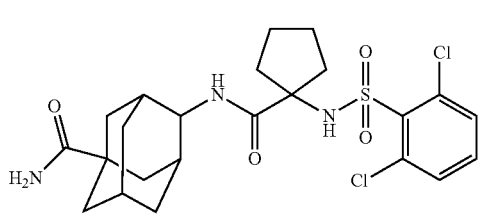

176
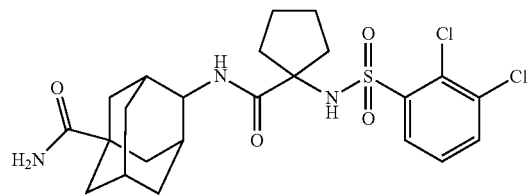
177
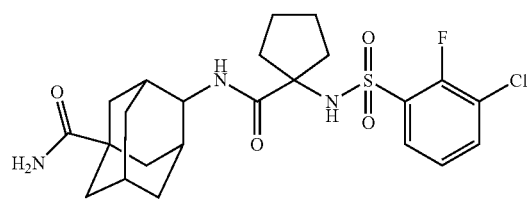
178
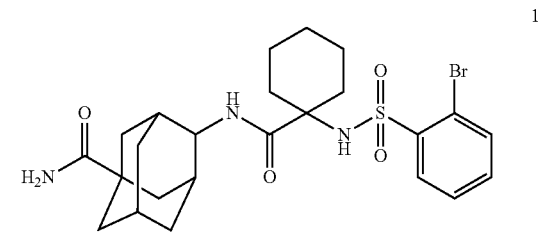
179
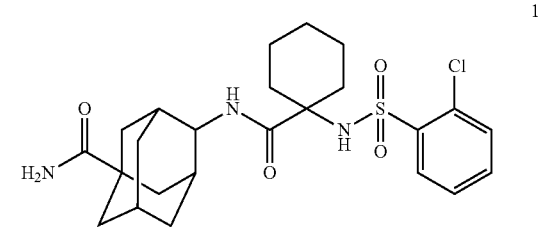
180
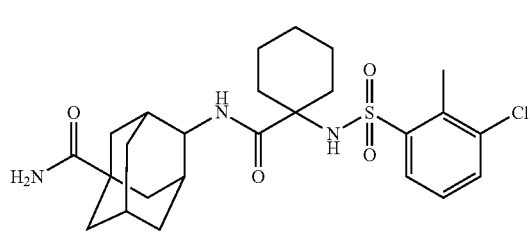
181
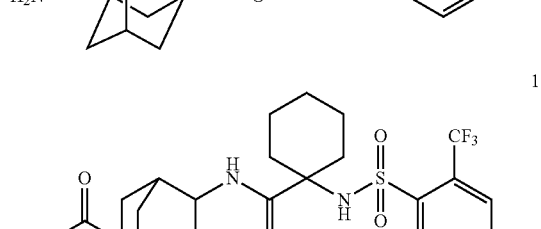
182
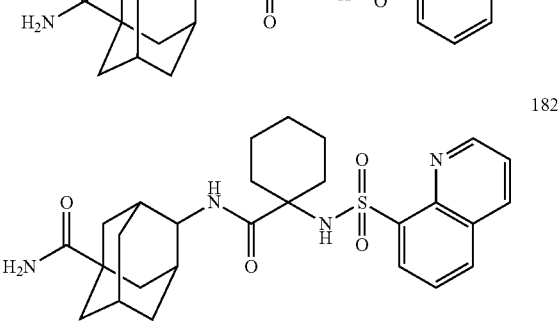
183
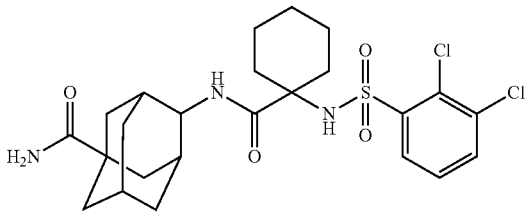
184
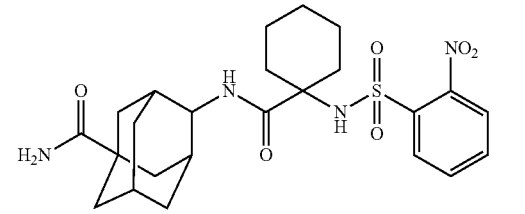
185
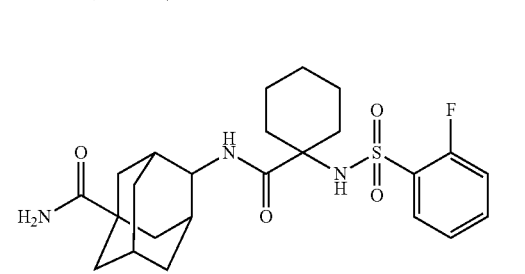
186
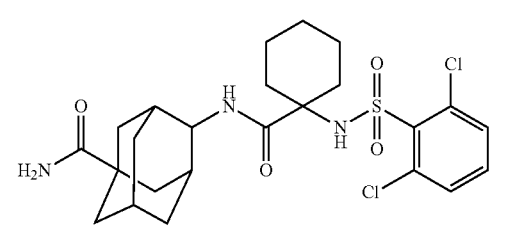
187
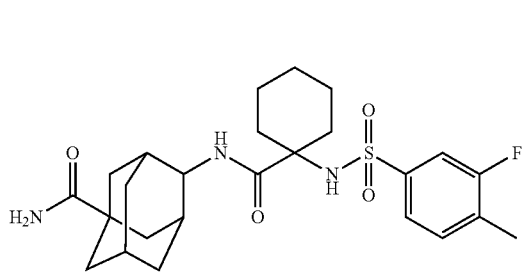
188
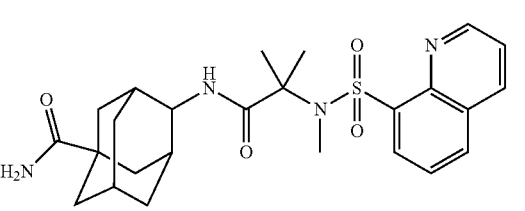
189
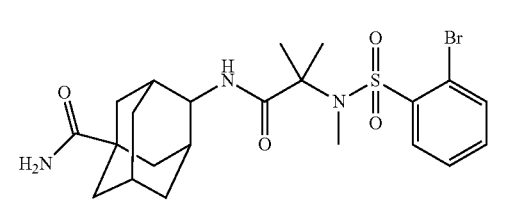

-continued
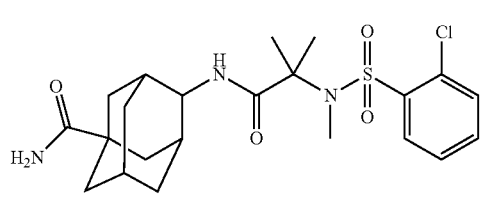
190
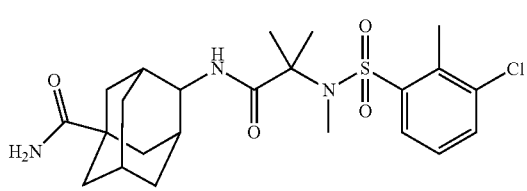
191
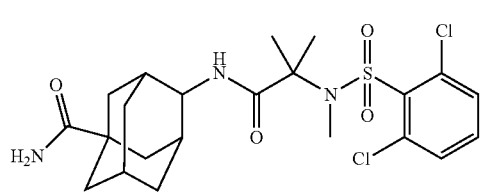
192
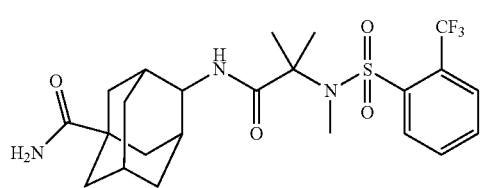
193
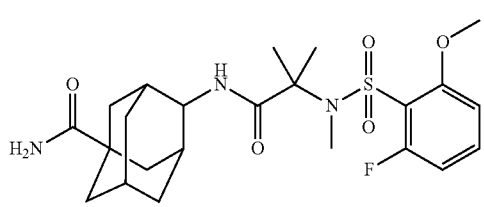
194
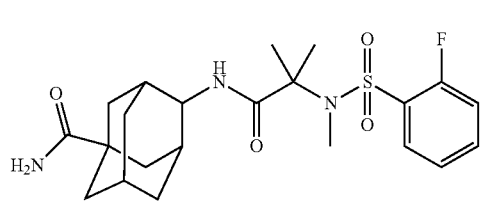
195
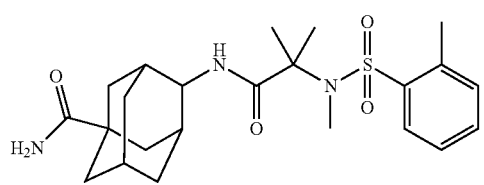
196
197
-continued
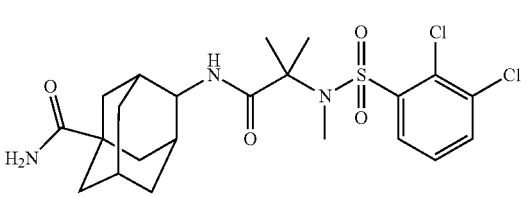
198
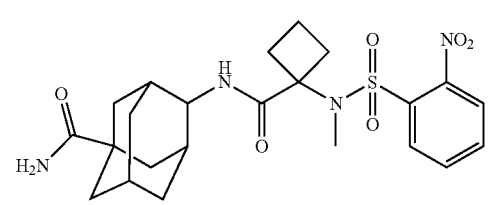
199
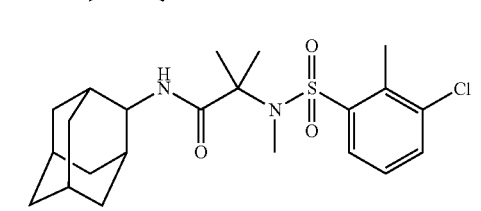
200
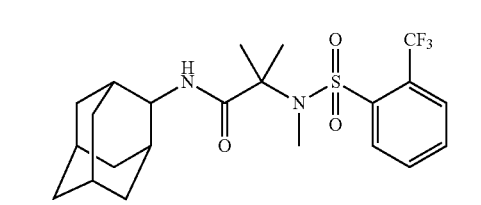
201
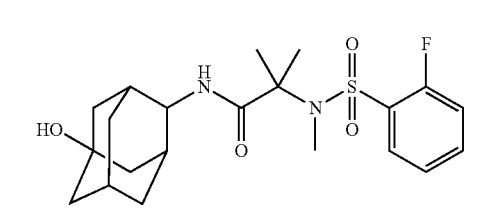
202
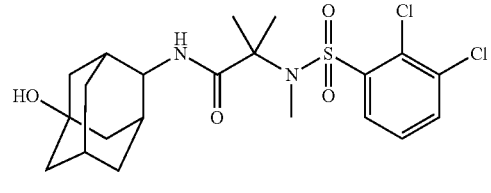
203
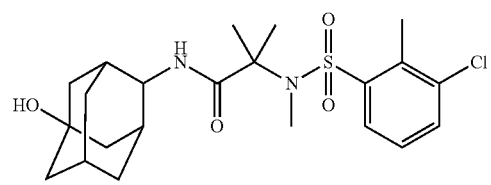
204
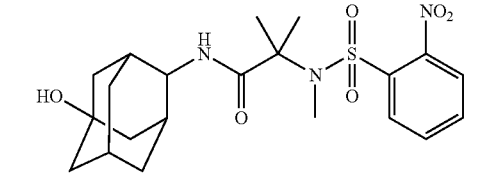
205

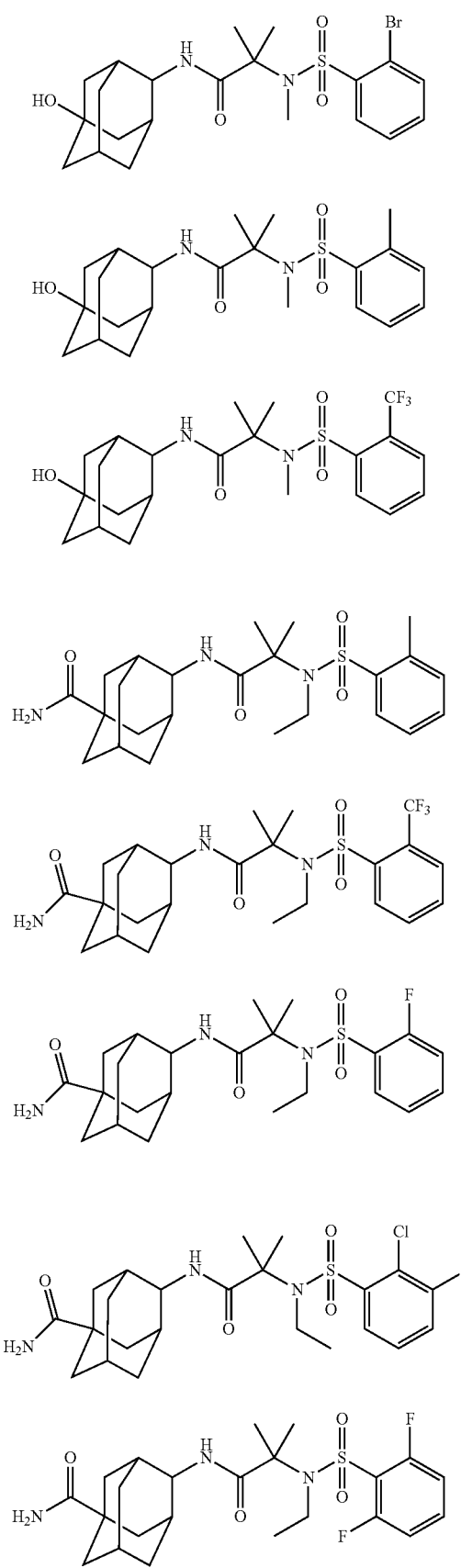
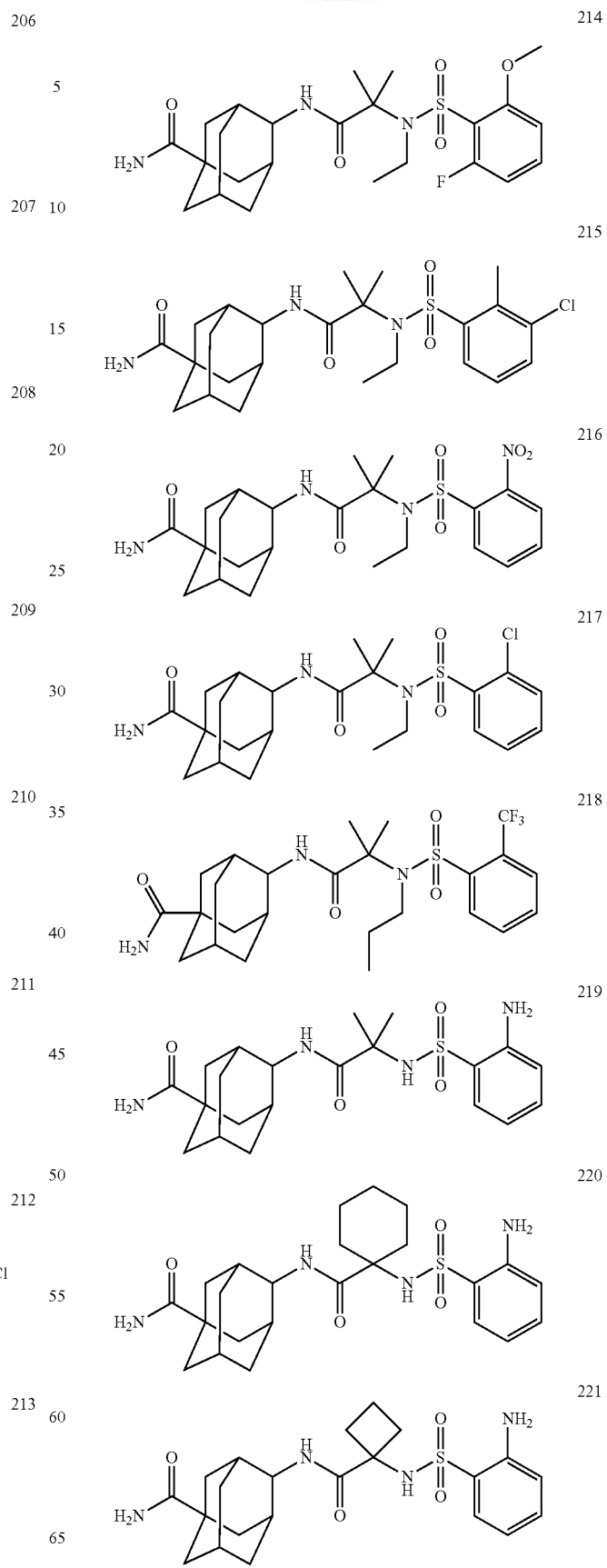

| 222 | 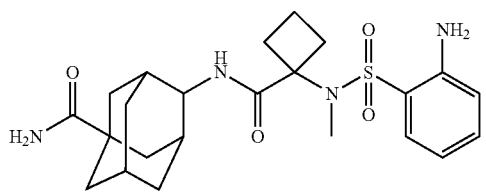 |
| 223 | 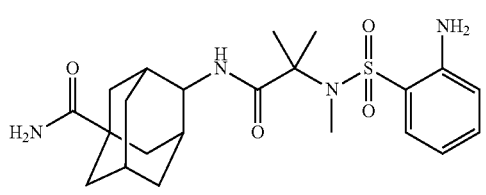 |
| 224 | 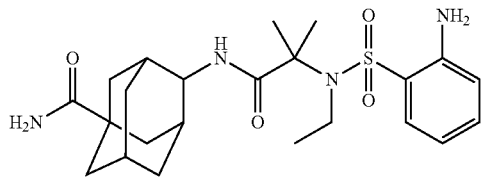 |
| 225 | 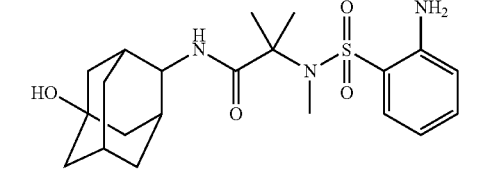 |
| 226 | 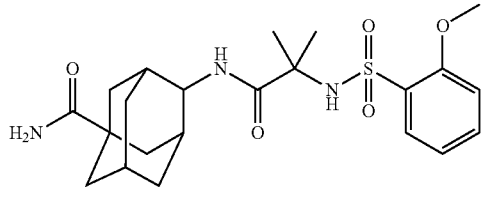 |
| 227 | 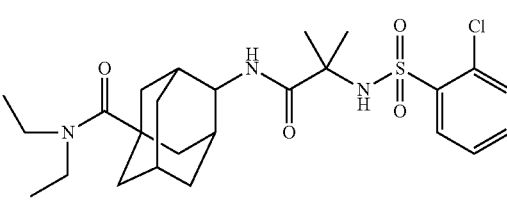 |
| 228 | 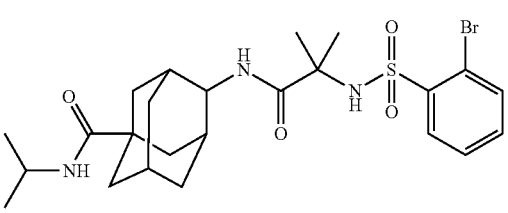 |
| 229 | 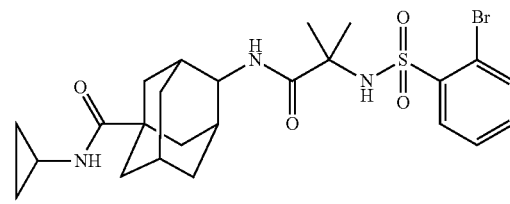 |
| 230 | 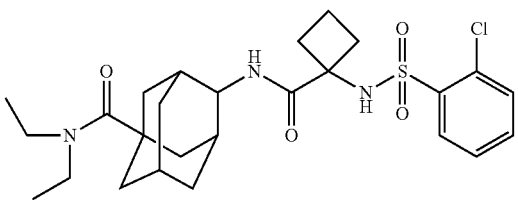 |
| 231 | 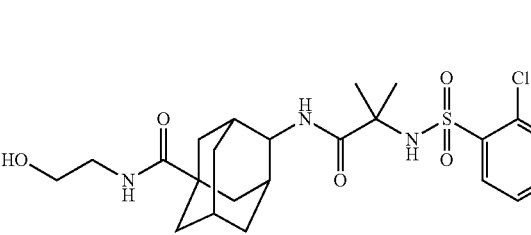 |
| 232 | 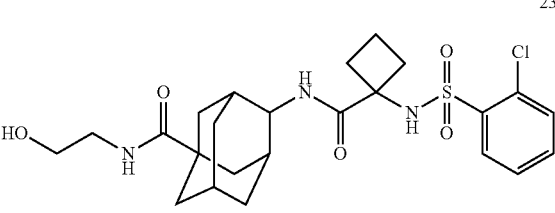 |
| 233 | 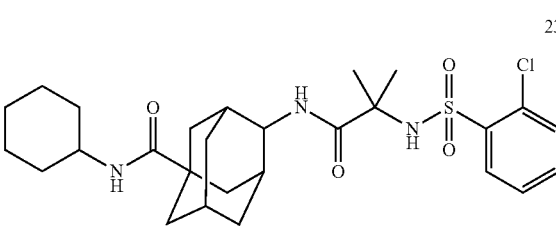 |
| 234 | 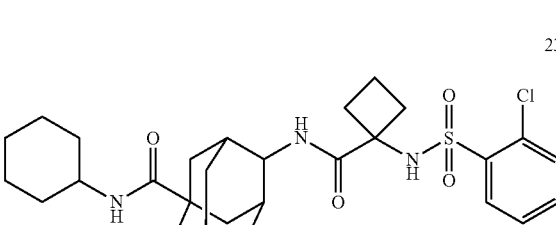 |
| 235 | 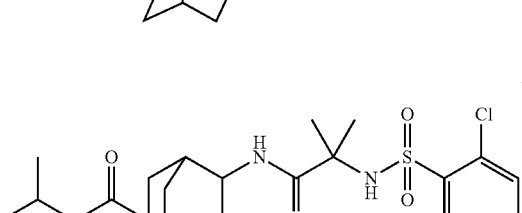 |
| 236 | 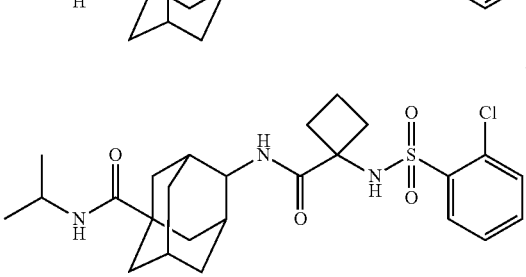 |

201
-continued

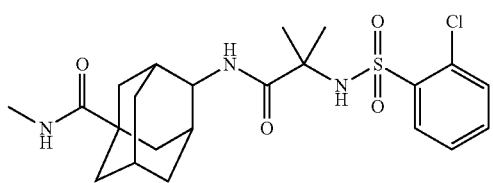
237

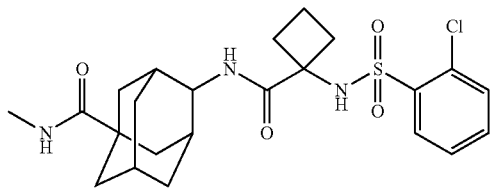
238

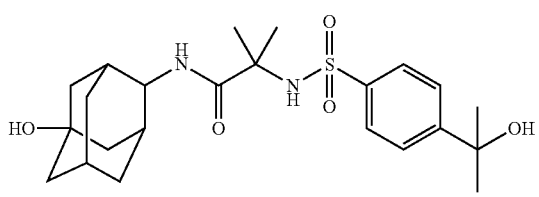
239

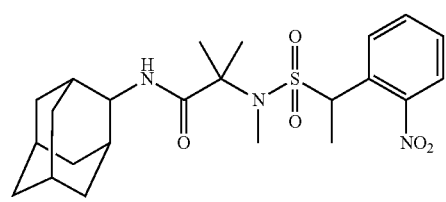
240

202
-continued

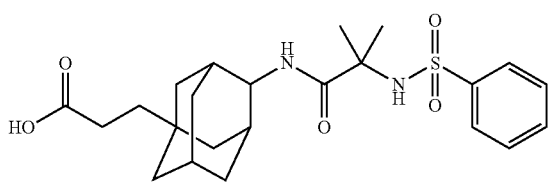
241

Example 18

Enzyme Activity Analysis on Human/Mouse 11β-HSD1

An enzyme activity on human 11β-HSD1 was measured using an analysis mixture in a final volume 10 μl, containing 20 mM tris, 5 mM EDTA buffer (pH 6.0), 200 uM NADPH, a test compound, 100 ug/ml human/mouse liver microsomes, and 160 nM cortisone (Sigma) as a substrate.

After culturing at 37° C. for 2 hours, 5 μl of cryptate-labeled anti-cortisol antibody and 5 μl of d2-labeled cortisol were added thereto. After further culturing at room temperature for 2 hours, a homogeneous time-resolved fluorescence (HTRF, Cisbio) signal was measured. From each analysis, based on a standard curve calculated using cortisols of several known concentrations, an amount of produced cortisol was tested.

While an amount of cortisol, produced without the compound, was used as a control, an inhibition percentage by the test compound, at each concentration, was calculated. By using an inhibition curve calculated by coordinates of inhibition percentage to test compound concentration, an IC50 value of the compound on 11β-HSD1 was obtained. The results are noted in table 1 below.

TABLE 1

| Patent Compound Structure Number | Structure | Cell-based Activity 11β-HSD1 Human (IC50 μM) 11β-HSD1 Mouse (IC50 μM) | Remark |
|---|---|---|---|
| 1 | 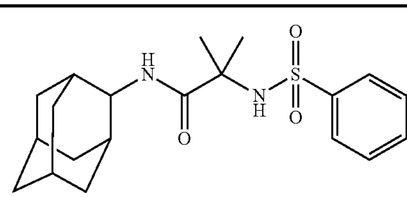 | Human 0.04<br>Mouse 0.19 | |
| 2 | 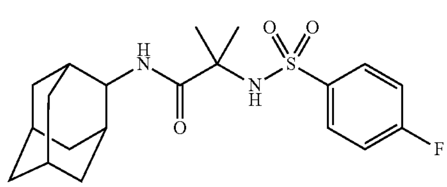 [SMILES: CC(C)(NS(=O)(=O)c1ccc(F)cc1)C(=O)NC1C2CC3CC(C2)CC1C3] | Human 0.1<br>Mouse 0.888 | |
| 3 | 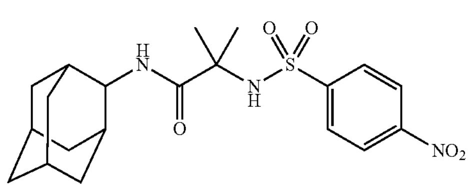 [SMILES: CC(C)(NS(=O)(=O)c1ccc([N+](=O)[O-])cc1)C(=O)NC1C2CC3CC(C2)CC1C3] | Human 1.33<br>Mouse 1.70 | |

TABLE 1-continued
| Patent Compound Structure Number | Structure | Cell-based Activity 11β-HSD1 Human (IC50 μM) | 11β-HSD1 Mouse (IC50 μM) | Remark |
|---|---|---|---|---|
| 4 | 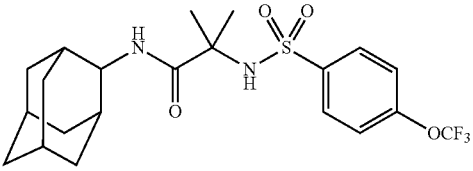 [SMILES: CC(C)(NS(=O)(=O)c1ccc(OC(F)(F)F)cc1)C(=O)NC1C2CC3CC(C2)CC1C3] | Human 1.32 | Mouse 1.68 | |
| 5 | 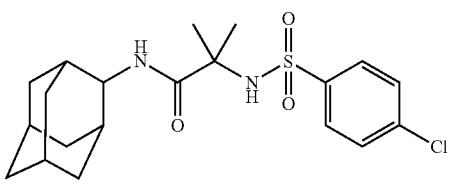 [SMILES: CC(C)(NS(=O)(=O)c1ccc(Cl)cc1)C(=O)NC1C2CC3CC(C2)CC1C3] | Human 0.43 | Mouse 1.05 | |
| 6 | 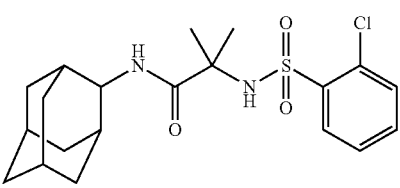 [SMILES: CC(C)(NS(=O)(=O)c1ccccc1Cl)C(=O)NC1C2CC3CC(C2)CC1C3] | Human 0.02 | Mouse 0.04 | |
| 7 | 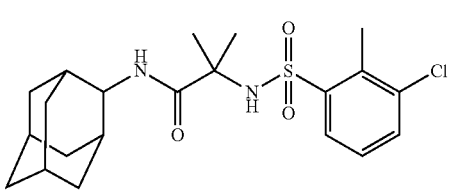 | Human 0.08 | Mouse 0.33 | |
| 8 | 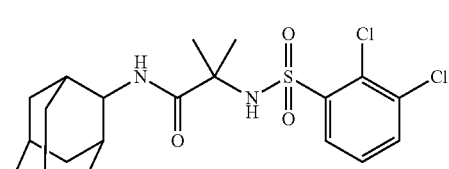 | Human 0.052 | Mouse 0.264 | |
| 9 | 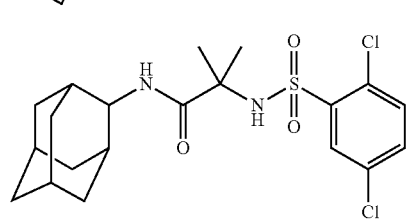 | Human 0.091 | Mouse >2.5 | |
| 10 | 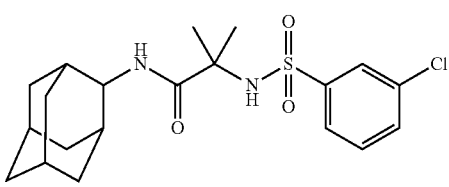 [SMILES: CC(C)(NS(=O)(=O)c1cccc(Cl)c1)C(=O)NC1C2CC3CC(C2)CC1C3] | Human 0.212 | Mouse 0.735 | |
| 11 | 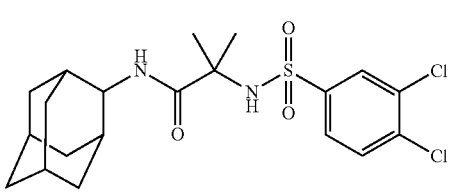 | Human 0.350 | Mouse | |

TABLE 1-continued

| Patent Compound Structure Number | Structure | Cell-based Activity 11β-HSD1 Human (IC50 μM) 11β-HSD1 Mouse (IC50 μM) | | Remark |
|---|---|---|---|---|
| 12 | 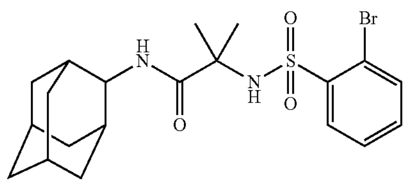 | Human<br>Mouse | 0.020<br>0.051 | |
| 13 | 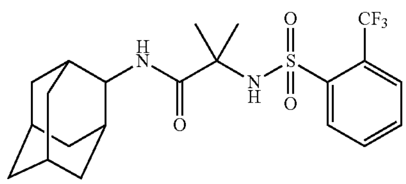 | Human<br>Mouse | 0.032<br>0.267 | |
| 14 | 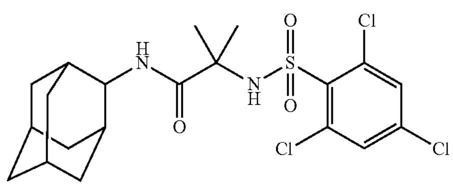 [SMILES: CC(C)(NS(=O)(=O)c1c(Cl)cc(Cl)cc1Cl)C(=O)NC1C2CC3CC(C2)CC1C3] | Human<br>Mouse | 0.170 | |
| 15 | 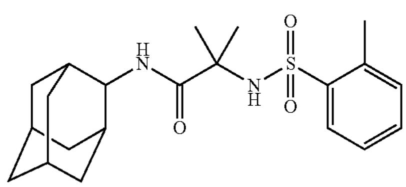 | Human<br>Mouse | 0.036<br>0.313 | |
| 16 | 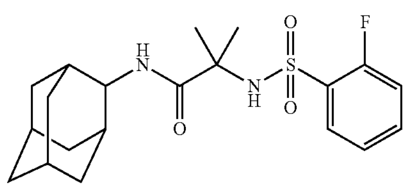 | Human<br>Mouse | 0.034<br>0.255 | |
| 17 | 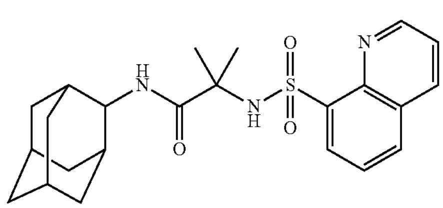 [SMILES: CC(C)(NS(=O)(=O)c1cccc2cccnc12)C(=O)NC1C2CC3CC(C2)CC1C3] | Human<br>Mouse | 0.008<br>0.008 | |
| 18 | 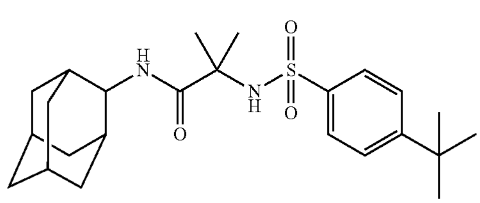 [SMILES: CC(C)(NS(=O)(=O)c1ccc(C(C)(C)C)cc1)C(=O)NC1C2CC3CC(C2)CC1C3] | Human<br>Mouse | 1.138 | |

TABLE 1-continued

| Patent Compound Structure Number | Structure | Cell-based Activity | | Remark |
|---|---|---|---|---|
| | | Human Mouse | 11β-HSD1 (IC50 μM) Human 11β-HSD1 (IC50 μM) Mouse | |
| 19 | 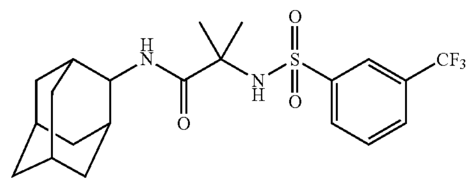 [SMILES: CC(C)(NS(=O)(=O)c1cccc(C(F)(F)F)c1)C(=O)NC1C2CC3CC(C2)CC1C3] | Human Mouse | 0.478 | |
| 20 | 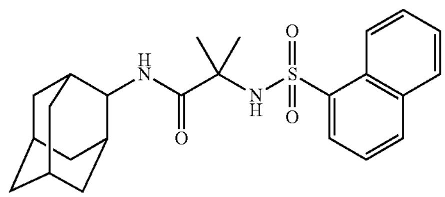 [SMILES: CC(C)(NS(=O)(=O)c1cccc2ccccc12)C(=O)NC1C2CC3CC(C2)CC1C3] | Human Mouse | 0.304 | |
| 21 | 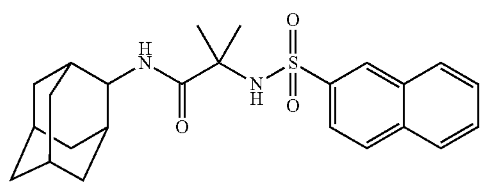 [SMILES: CC(C)(NS(=O)(=O)c1ccc2ccccc2c1)C(=O)NC1C2CC3CC(C2)CC1C3] | Human Mouse | 0.466 | |
| 22 | 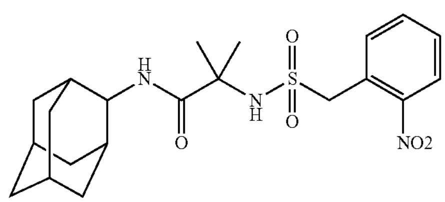 [SMILES: CC(C)(NS(=O)(=O)Cc1ccccc1[N+](=O)[O-])C(=O)NC1C2CC3CC(C2)CC1C3] | Human Mouse | 0.033 1.061 | |
| 23 | 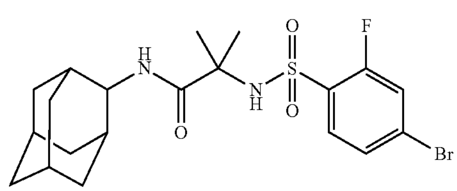 [SMILES: CC(C)(NS(=O)(=O)c1ccc(Br)cc1F)C(=O)NC1C2CC3CC(C2)CC1C3] | Human Mouse | 0.322 | |
| 24 | 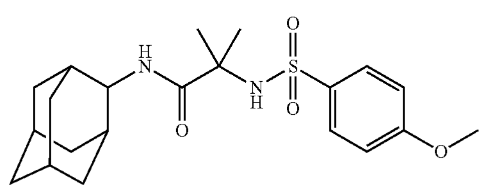 [SMILES: COc1ccc(S(=O)(=O)NC(C)(C)C(=O)NC2C3CC4CC(C3)CC2C4)cc1] | Human Mouse | 0.404 | |
| 25 | 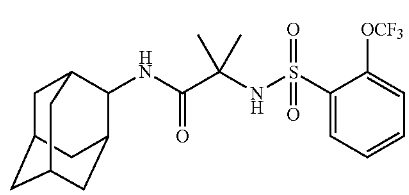 | Human Mouse | 0.045 0.420 | |

TABLE 1-continued

| Patent Compound Structure Number | Structure | Cell-based Activity 11β-HSD1 Human (IC50 μM) 11β-HSD1 Mouse (IC50 μM) | | Remark |
|---|---|---|---|---|
| 26 | 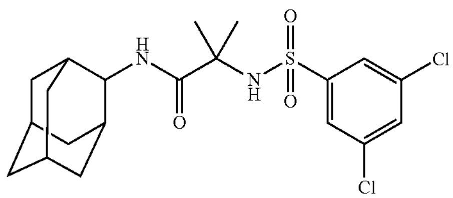 [SMILES: CC(C)(NS(=O)(=O)c1cc(Cl)cc(Cl)c1)C(=O)NC1C2CC3CC(C2)CC1C3] | Human<br>Mouse | 1.275<br>>2.5 | |
| 27 | 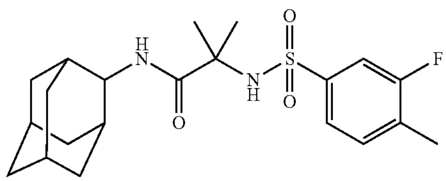 [SMILES: Cc1ccc(S(=O)(=O)NC(C)(C)C(=O)NC2C3CC4CC(C3)CC2C4)cc1F] | Human<br>Mouse | 0.555<br>1.116 | |
| 28 | 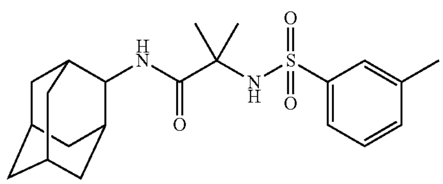 [SMILES: Cc1cccc(S(=O)(=O)NC(C)(C)C(=O)NC2C3CC4CC(C3)CC2C4)c1] | Human<br>Mouse | 0.133<br>0.437 | |
| 29 | 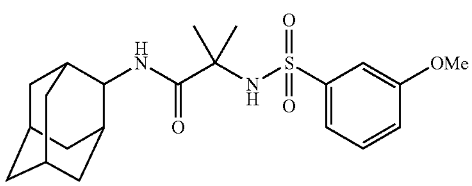 [SMILES: COc1cccc(S(=O)(=O)NC(C)(C)C(=O)NC2C3CC4CC(C3)CC2C4)c1] | Human<br>Mouse | 0.216<br>0.329 | |
| 30 | 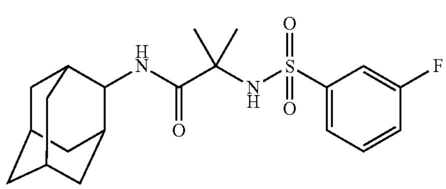 [SMILES: CC(C)(NS(=O)(=O)c1cccc(F)c1)C(=O)NC1C2CC3CC(C2)CC1C3] | Human<br>Mouse | 0.192<br>0.462 | |
| 31 | 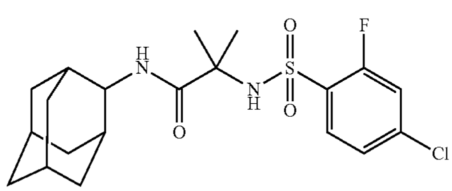 | Human<br>Mouse | 0.409<br>1.059 | |
| 32 | 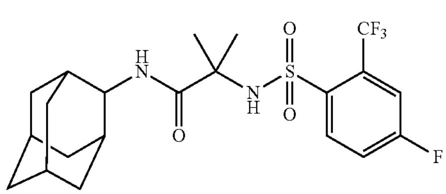 [SMILES: CC(C)(NS(=O)(=O)c1ccc(F)cc1C(F)(F)F)C(=O)NC1C2CC3CC(C2)CC1C3] | Human<br>Mouse | 0.051<br>0.583 | |

TABLE 1-continued

| Patent Compound Structure Number | Structure | Cell-based Activity Human Mouse | 11β-HSD1 (IC50 μM) 11β-HSD1 (IC50 μM) | Remark |
|---|---|---|---|---|
| 33 | 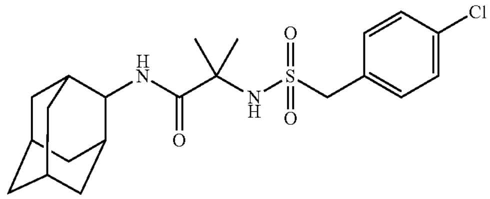 [SMILES: CC(C)(NS(=O)(=O)Cc1ccc(Cl)cc1)C(=O)NC1C2CC3CC(C2)CC1C3] | Human Mouse | 0.065 1.674 | |
| 34 | 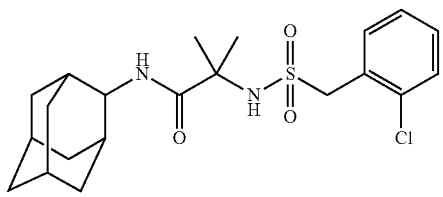 [SMILES: CC(C)(NS(=O)(=O)Cc1ccccc1Cl)C(=O)NC1C2CC3CC(C2)CC1C3] | Human Mouse | 0.048 0.700 | |
| 35 | 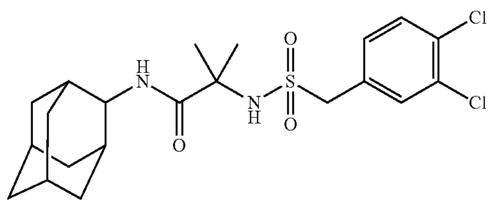 [SMILES: CC(C)(NS(=O)(=O)Cc1ccc(Cl)c(Cl)c1)C(=O)NC1C2CC3CC(C2)CC1C3] | Human Mouse | >2.5 >2.5 | |
| 36 | 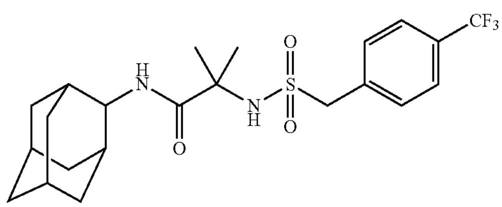 [SMILES: CC(C)(NS(=O)(=O)Cc1ccc(C(F)(F)F)cc1)C(=O)NC1C2CC3CC(C2)CC1C3] | Human Mouse | 0.040 >2.5 | |
| 37 | 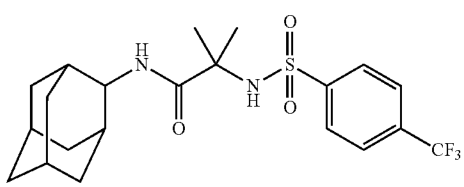 [SMILES: CC(C)(NS(=O)(=O)c1ccc(C(F)(F)F)cc1)C(=O)NC1C2CC3CC(C2)CC1C3] | Human Mouse | >2.5 >2.5 | |
| 38 | 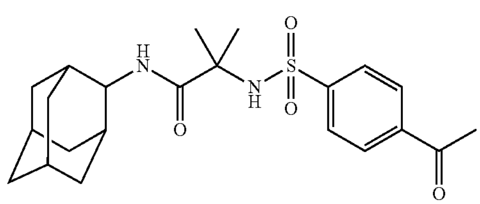 [SMILES: CC(=O)c1ccc(S(=O)(=O)NC(C)(C)C(=O)NC2C3CC4CC(C3)CC2C4)cc1] | Human Mouse | 0.829 0.847 | |
| 39 | 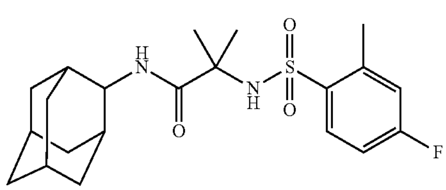 [SMILES: Cc1cc(F)ccc1S(=O)(=O)NC(C)(C)C(=O)NC1C2CC3CC(C2)CC1C3] | Human Mouse | 0.043 0.561 | |

TABLE 1-continued
| Patent Compound Structure Number | Structure | Cell-based Activity Human Mouse | 11β-HSD1 (IC50 μM) 11β-HSD1 (IC50 μM) | Remark |
|---|---|---|---|---|
| 40 | 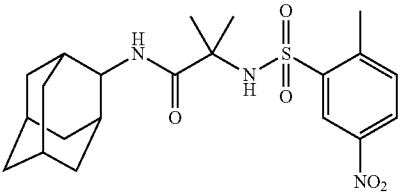 | Human Mouse | 0.098 1.854 | |
| 41 | 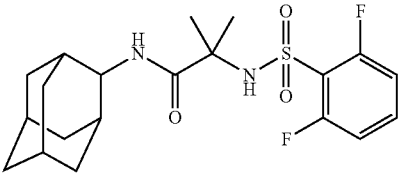 [SMILES: CC(C)(NS(=O)(=O)c1c(F)cccc1F)C(=O)NC1C2CC3CC(C2)CC1C3] | Human Mouse | 0.041 0.156 | |
| 42 | 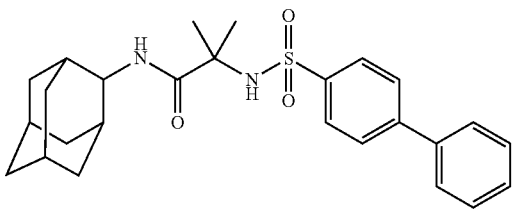 [SMILES: CC(C)(NS(=O)(=O)c1ccc(-c2ccccc2)cc1)C(=O)NC1C2CC3CC(C2)CC1C3] | Human Mouse | 1.804 1.701 | |
| 43 | 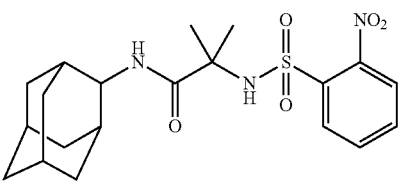 | Human Mouse | 0.016 0.085 | |
| 44 | 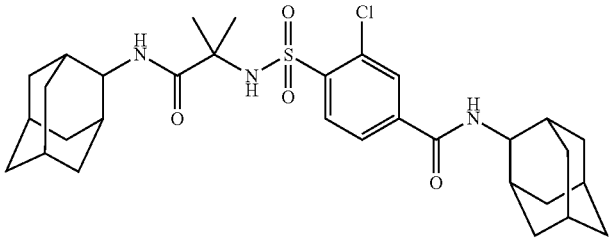 [SMILES: CC(C)(NS(=O)(=O)c1ccc(C(=O)NC2C3CC4CC(C3)CC2C4)cc1Cl)C(=O)NC1C2CC3CC(C2)CC1C3] | Human Mouse | 0.481 0.167 | |
| 45 | 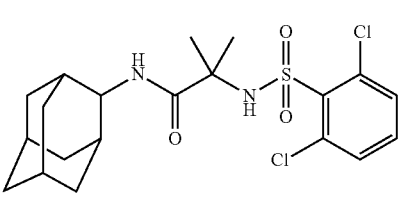 | Human Mouse | 0.009 0.020 | |
| 46 | 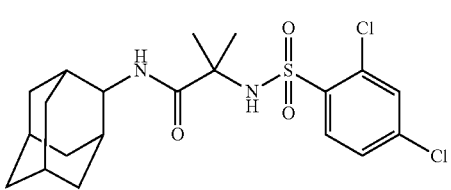 | Human Mouse | 0.105 0.621 | |

TABLE 1-continued

| Patent Compound Structure Number | Structure | Cell-based Activity | 11β-HSD1 (IC50 μM) 11β-HSD1 (IC50 μM) | Remark |
|---|---|---|---|---|
| 47 | 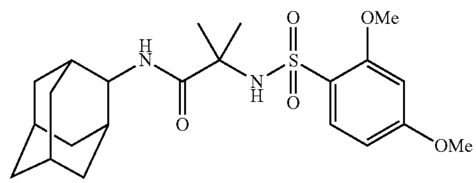 [SMILES: COc1ccc(S(=O)(=O)NC(C)(C)C(=O)NC2C3CC4CC(C3)CC2C4)c(OC)c1] | Human Mouse | 0.082 1.915 | |
| 48 | 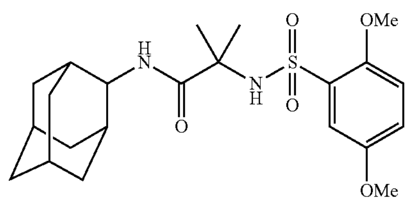 [SMILES: COc1ccc(OC)c(S(=O)(=O)NC(C)(C)C(=O)NC2C3CC4CC(C3)CC2C4)c1] | Human Mouse | 0.020 1.828 | |
| 49 | 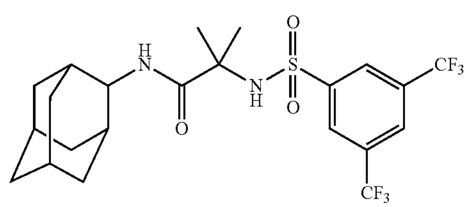 [SMILES: CC(C)(NS(=O)(=O)c1cc(C(F)(F)F)cc(C(F)(F)F)c1)C(=O)NC1C2CC3CC(C2)CC1C3] | Human Mouse | 1.351 >2.5 | |
| 50 | 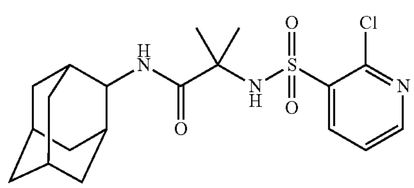 [SMILES: CC(C)(NS(=O)(=O)c1cccnc1Cl)C(=O)NC1C2CC3CC(C2)CC1C3] | Human Mouse | 0.105 0.292 | |
| 51 | 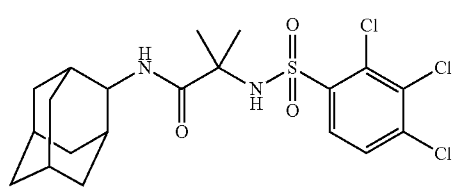 [SMILES: CC(C)(NS(=O)(=O)c1ccc(Cl)c(Cl)c1Cl)C(=O)NC1C2CC3CC(C2)CC1C3] | Human Mouse | 0.183 1.305 | |
| 52 | 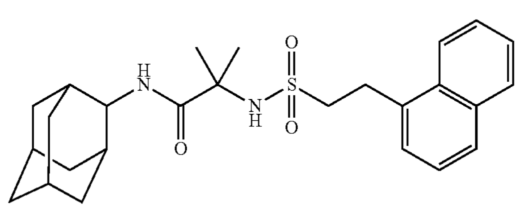 [SMILES: CC(C)(NS(=O)(=O)CCc1cccc2ccccc12)C(=O)NC1C2CC3CC(C2)CC1C3] | Human Mouse | 1.175 2.137 | |
| 53 | 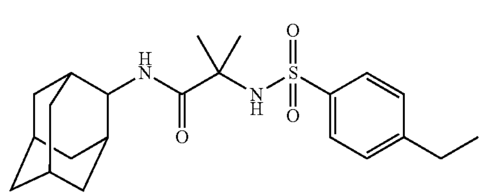 [SMILES: CCc1ccc(S(=O)(=O)NC(C)(C)C(=O)NC2C3CC4CC(C3)CC2C4)cc1] | Human Mouse | 0.210 0.673 | |

TABLE 1-continued

| Patent Compound Structure Number | Structure | Cell-based Activity | | Remark |
|---|---|---|---|---|
| | | | 11β-HSD1 Human (IC50 μM) 11β-HSD1 Mouse (IC50 μM) | |
| 54 | 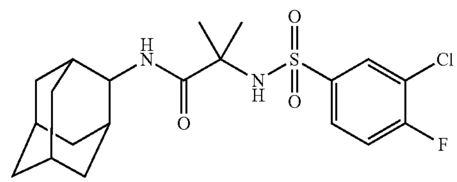 [SMILES: CC(C)(NS(=O)(=O)c1ccc(F)c(Cl)c1)C(=O)NC1C2CC3CC(C2)CC1C3] | Human Mouse | 0.223 0.904 | |
| 55 | 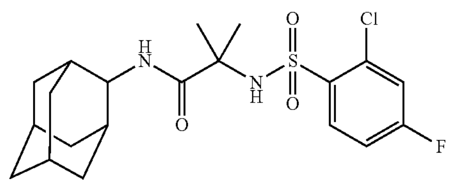 | Human Mouse | 0.039 0.186 | |
| 56 | 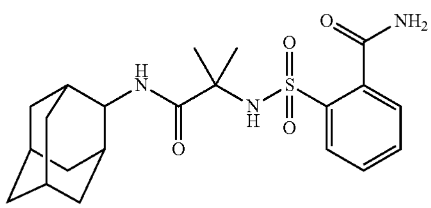 [SMILES: CC(C)(NS(=O)(=O)c1ccccc1C(N)=O)C(=O)NC1C2CC3CC(C2)CC1C3] | Human Mouse | 0.532 >2.5 | |
| 57 | 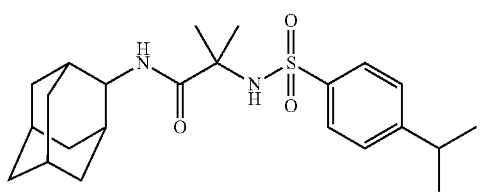 | Human Mouse | 1.043 1.316 | |
| 58 | 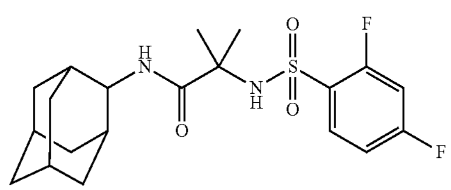 | Human Mouse | 0.199 0.621 | |
| 59 | 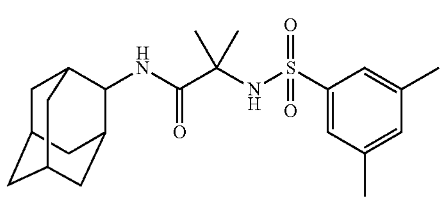 [SMILES: Cc1cc(C)cc(S(=O)(=O)NC(C)(C)C(=O)NC2C3CC4CC(C3)CC2C4)c1] | Human Mouse | 0.331 1.210 | |
| 60 | 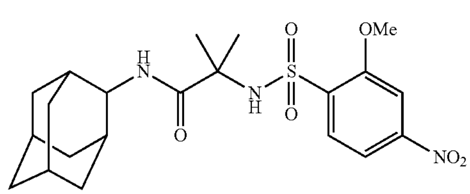 [SMILES: COc1cc([N+](=O)[O-])ccc1S(=O)(=O)NC(C)(C)C(=O)NC1C2CC3CC(C2)CC1C3] | Human Mouse | 0.135 0.644 | |

TABLE 1-continued

| Patent Compound Structure Number | Structure | Cell-based Activity 11β-HSD1 Human (IC50 μM) 11β-HSD1 Mouse (IC50 μM) | | Remark |
|---|---|---|---|---|
| 61 | 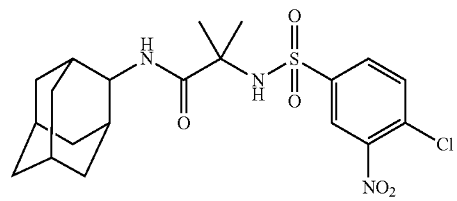 [SMILES: CC(C)(NS(=O)(=O)c1ccc(Cl)c([N+](=O)[O-])c1)C(=O)NC1C2CC3CC(C2)CC1C3] | Human<br>Mouse | >2.5<br>>2.5 | |
| 62 | 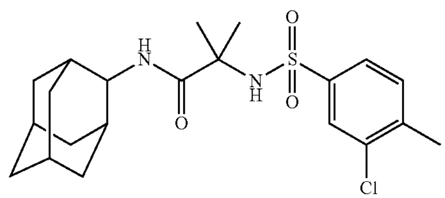 [SMILES: Cc1ccc(S(=O)(=O)NC(C)(C)C(=O)NC2C3CC4CC(C3)CC2C4)cc1Cl] | Human<br>Mouse | 0.215<br>0.686 | |
| 63 | 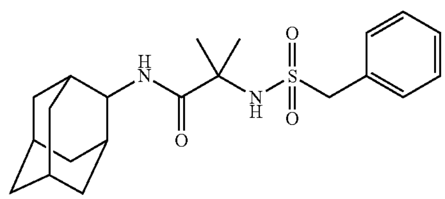 [SMILES: CC(C)(NS(=O)(=O)Cc1ccccc1)C(=O)NC1C2CC3CC(C2)CC1C3] | Human<br>Mouse | 0.039<br>0.283 | |
| 64 | 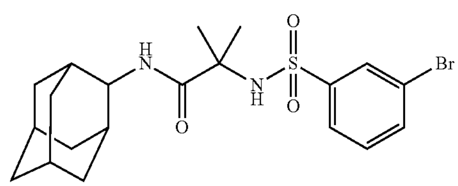 [SMILES: CC(C)(NS(=O)(=O)c1cccc(Br)c1)C(=O)NC1C2CC3CC(C2)CC1C3] | Human<br>Mouse | 0.433<br>1.023 | |
| 65 | 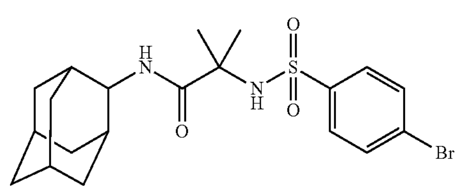 [SMILES: CC(C)(NS(=O)(=O)c1ccc(Br)cc1)C(=O)NC1C2CC3CC(C2)CC1C3] | Human<br>Mouse | 0.996<br>1.647 | |
| 66 | 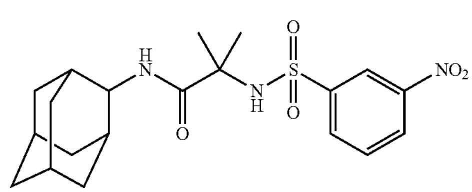 [SMILES: CC(C)(NS(=O)(=O)c1cccc([N+](=O)[O-])c1)C(=O)NC1C2CC3CC(C2)CC1C3] | Human<br>Mouse | 0.511<br>0.914 | |
| 67 | 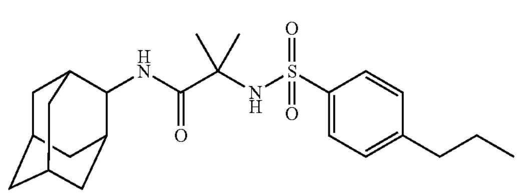 [SMILES: CCCc1ccc(S(=O)(=O)NC(C)(C)C(=O)NC2C3CC4CC(C3)CC2C4)cc1] | Human<br>Mouse | 1.287<br>1.263 | |

TABLE 1-continued

| Patent Compound Structure Number | Structure | Cell-based Activity 11β-HSD1 Human (IC50 μM) 11β-HSD1 Mouse (IC50 μM) | | Remark |
|---|---|---|---|---|
| 68 | 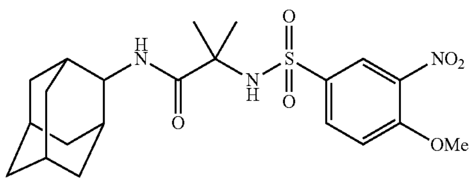 [SMILES: COc1ccc(S(=O)(=O)NC(C)(C)C(=O)NC2C3CC4CC(C3)CC2C4)cc1[N+](=O)[O-]] | Human Mouse | 1.202 1.118 | |
| 69 | 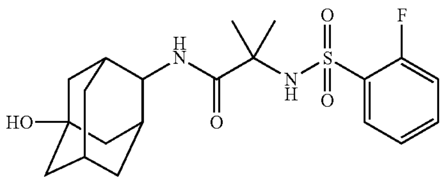 [SMILES: CC(C)(NS(=O)(=O)c1ccccc1F)C(=O)NC1C2CC3CC1CC(O)(C3)C2] | Human Mouse | 0.118 0.258 | |
| 70 | 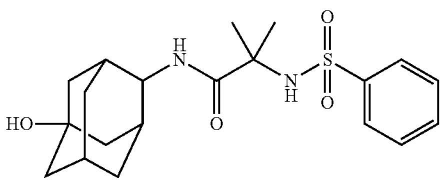 [SMILES: CC(C)(NS(=O)(=O)c1ccccc1)C(=O)NC1C2CC3CC1CC(O)(C3)C2] | Human Mouse | 0.093 0.378 | |
| 71 | 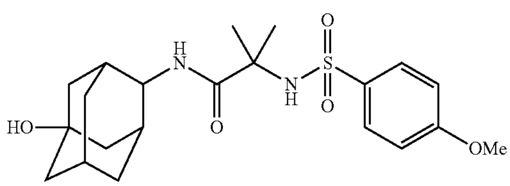 [SMILES: COc1ccc(S(=O)(=O)NC(C)(C)C(=O)NC2C3CC4CC2CC(O)(C4)C3)cc1] | Human Mouse | 0.196 0.631 | |
| 72 | 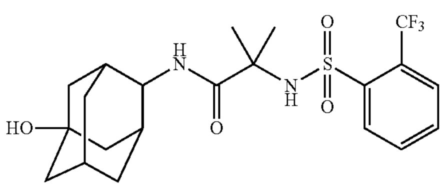 [SMILES: CC(C)(NS(=O)(=O)c1ccccc1C(F)(F)F)C(=O)NC1C2CC3CC1CC(O)(C3)C2] | Human Mouse | 0.111 0.138 | |
| 73 | 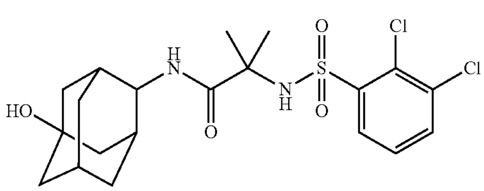 [SMILES: CC(C)(NS(=O)(=O)c1cccc(Cl)c1Cl)C(=O)NC1C2CC3CC1CC(O)(C3)C2] | Human Mouse | 0.017 0.042 | |
| 74 | 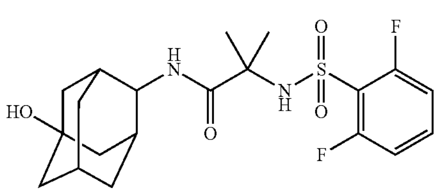 [SMILES: CC(C)(NS(=O)(=O)c1c(F)cccc1F)C(=O)NC1C2CC3CC1CC(O)(C3)C2] | Human Mouse | 0.079 0.305 | |

TABLE 1-continued

| Patent Compound Structure Number | Structure | Cell-based Activity 11β-HSD1 Human (IC50 μM) 11β-HSD1 Mouse (IC50 μM) | | Remark |
|---|---|---|---|---|
| 75 | 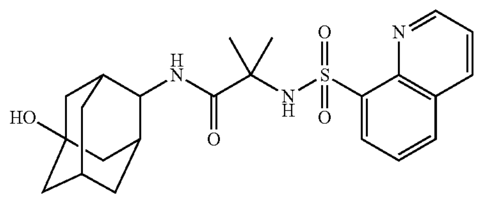 [SMILES: CC(C)(NS(=O)(=O)c1cccc2cccnc12)C(=O)NC1C2CC3CC1CC(O)(C3)C2] | Human Mouse | 0.006 0.005 | |
| 76 | 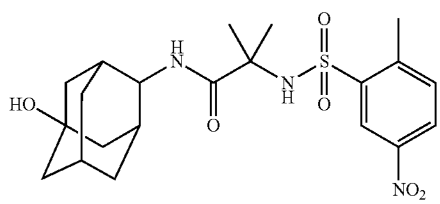 [SMILES: Cc1ccc([N+](=O)[O-])cc1S(=O)(=O)NC(C)(C)C(=O)NC1C2CC3CC1CC(O)(C3)C2] | Human Mouse | 0.146 2.085 | |
| 77 | 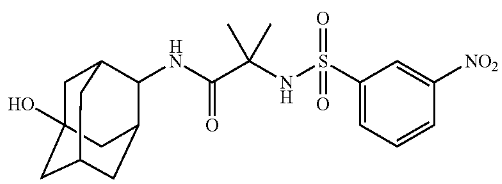 [SMILES: CC(C)(NS(=O)(=O)c1cccc([N+](=O)[O-])c1)C(=O)NC1C2CC3CC1CC(O)(C3)C2] | Human Mouse | 0.492 0.575 | |
| 78 | 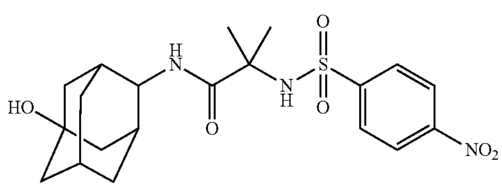 [SMILES: CC(C)(NS(=O)(=O)c1ccc([N+](=O)[O-])cc1)C(=O)NC1C2CC3CC1CC(O)(C3)C2] | Human Mouse | 0.692 1.21 | |
| 79 | 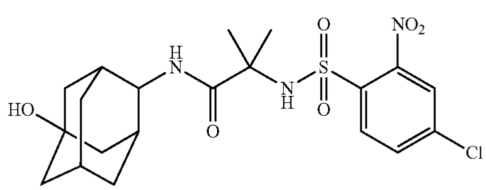 [SMILES: CC(C)(NS(=O)(=O)c1ccc(Cl)cc1[N+](=O)[O-])C(=O)NC1C2CC3CC1CC(O)(C3)C2] | Human Mouse | 0.083 0.797 | |
| 80 | 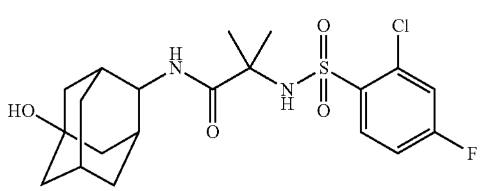 [SMILES: CC(C)(NS(=O)(=O)c1ccc(F)cc1Cl)C(=O)NC1C2CC3CC1CC(O)(C3)C2] | Human Mouse | 0.072 0.213 | |
| 81 | 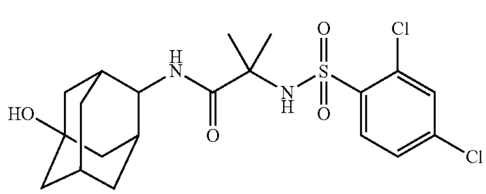 [SMILES: CC(C)(NS(=O)(=O)c1ccc(Cl)cc1Cl)C(=O)NC1C2CC3CC1CC(O)(C3)C2] | Human Mouse | 0.03 0.221 | |

TABLE 1-continued

| Patent Compound Structure Number | Structure | Cell-based Activity | | Remark |
|---|---|---|---|---|
| | | | 11β-HSD1 Human (IC50 μM) 11β-HSD1 Mouse (IC50 μM) | |
| 82 | 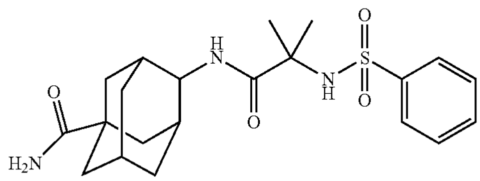 [SMILES: CC(C)(NS(=O)(=O)c1ccccc1)C(=O)NC1C2CC3CC1CC(C(N)=O)(C3)C2] | Human Mouse | >2.5 >2.5 | |
| 83 | 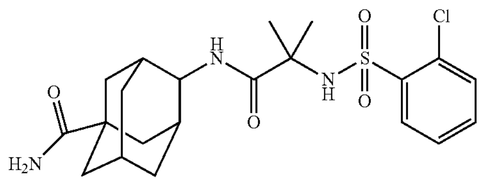 | Human Mouse | 0.009 0.018 | |
| 84 | 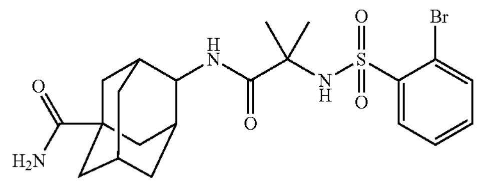 | Human Mouse | 0.011 0.008 | |
| 85 | 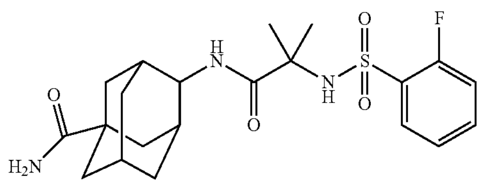 [SMILES: CC(C)(NS(=O)(=O)c1ccccc1F)C(=O)NC1C2CC3CC1CC(C(N)=O)(C3)C2] | Human Mouse | 0.039 0.113 | |
| 86 | 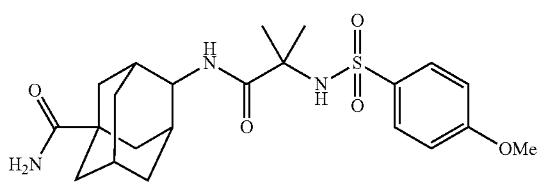 [SMILES: COc1ccc(S(=O)(=O)NC(C)(C)C(=O)NC2C3CC4CC2CC(C(N)=O)(C4)C3)cc1] | Human Mouse | >2.5 >2.5 | |
| 87 | 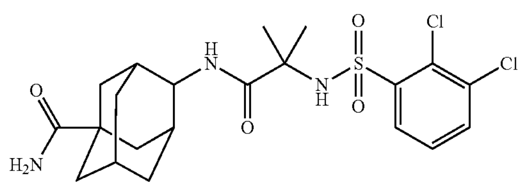 [SMILES: CC(C)(NS(=O)(=O)c1cccc(Cl)c1Cl)C(=O)NC1C2CC3CC1CC(C(N)=O)(C3)C2] | Human Mouse | 0.005 0.007 | |
| 88 | 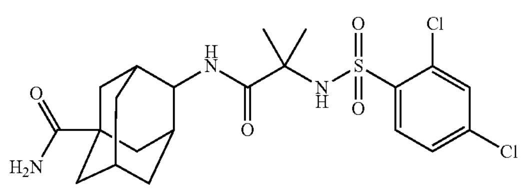 [SMILES: CC(C)(NS(=O)(=O)c1ccc(Cl)cc1Cl)C(=O)NC1C2CC3CC1CC(C(N)=O)(C3)C2] | Human Mouse | 0.014 0.056 | |
| 89 | 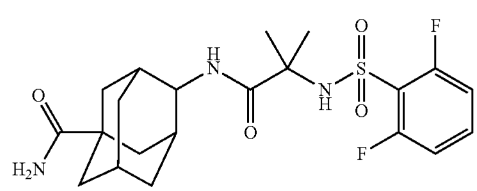 [SMILES: CC(C)(NS(=O)(=O)c1c(F)cccc1F)C(=O)NC1C2CC3CC1CC(C(N)=O)(C3)C2] | Human Mouse | 0.031 0.148 | |

TABLE 1-continued

| Patent Compound Structure Number | Structure | Cell-based Activity 11β-HSD1 Human (IC50 μM) 11β-HSD1 Mouse (IC50 μM) | | Remark |
|---|---|---|---|---|
| 90 | 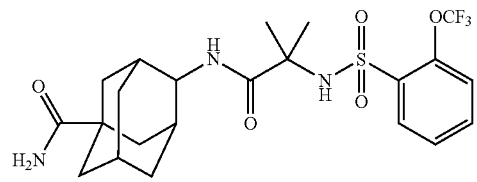 | Human | 0.017 | |
| | | Mouse | 0.030 | |
| 91 | 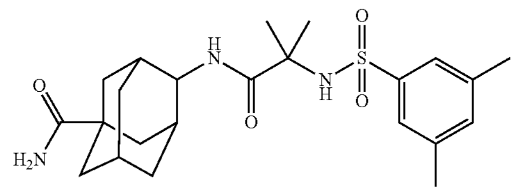 [SMILES: Cc1cc(C)cc(S(=O)(=O)NC(C)(C)C(=O)NC2C3CC4CC2CC(C(N)=O)(C4)C3)c1] | Human | 0.016 | |
| | | Mouse | 0.107 | |
| 92 | 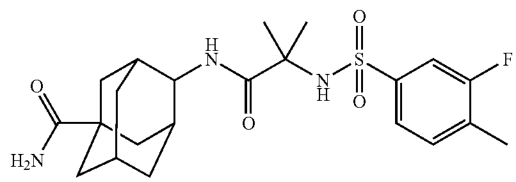 [SMILES: Cc1ccc(S(=O)(=O)NC(C)(C)C(=O)NC2C3CC4CC2CC(C(N)=O)(C4)C3)cc1F] | Human | 0.032 | |
| | | Mouse | 0.077 | |
| 93 | 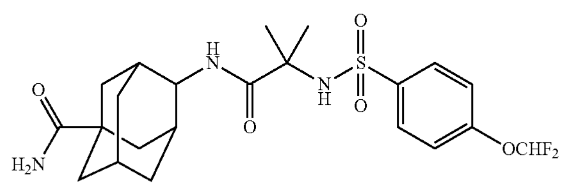 [SMILES: CC(C)(NS(=O)(=O)c1ccc(OC(F)F)cc1)C(=O)NC1C2CC3CC1CC(C(N)=O)(C3)C2] | Human | 0.153 | |
| | | Mouse | 0.571 | |
| 94 | 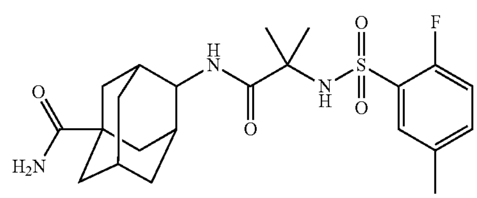 [SMILES: Cc1ccc(F)c(S(=O)(=O)NC(C)(C)C(=O)NC2C3CC4CC2CC(C(N)=O)(C4)C3)c1] | Human | 0.013 | |
| | | Mouse | 0.123 | |
| 95 | 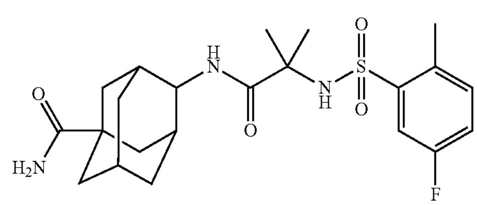 [SMILES: Cc1ccc(F)cc1S(=O)(=O)NC(C)(C)C(=O)NC1C2CC3CC1CC(C(N)=O)(C3)C2] | Human | 0.013 | |
| | | Mouse | 0.144 | |
| 96 | 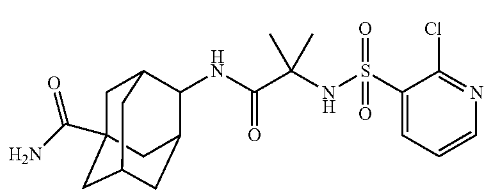 [SMILES: CC(C)(NS(=O)(=O)c1cccnc1Cl)C(=O)NC1C2CC3CC1CC(C(N)=O)(C3)C2] | Human | 0.223 | |
| | | Mouse | 0.289 | |

TABLE 1-continued

| Patent Compound Structure Number | Structure | Cell-based Activity 11β-HSD1 Human (IC50 μM) 11β-HSD1 Mouse (IC50 μM) | Remark |
|---|---|---|---|
| 97 | (adamantane-carboxamide)-NH-C(CH₃)₂-C(O)-NH-SO₂-(3-Cl,2-methylphenyl) | Human 0.005 Mouse 0.010 | |
| 98 | (adamantane-carboxamide)-NH-C(CH₃)₂-C(O)-NH-SO₂-CH₂-(2-Cl-phenyl) | Human >2.5 Mouse >2.5 | |
| 99 | (adamantane-carboxamide)-NH-C(CH₃)₂-C(O)-NH-SO₂-(4-propylphenyl) | Human 0.047 Mouse 0.124 | |
| 100 | (adamantane-carboxamide)-NH-C(CH₃)₂-C(O)-NH-SO₂-(2-OCF₃,4-Br-phenyl) | Human 0.018 Mouse 0.210 | |
| 101 | (adamantane-carboxamide)-NH-C(CH₃)₂-C(O)-NH-SO₂-(2-Br,4-F-phenyl) | Human 0.009 Mouse 0.014 | |
| 102 | (adamantane-carboxamide)-NH-C(CH₃)₂-C(O)-NH-SO₂-(2-F,3-Cl-phenyl) | Human 0.020 Mouse 0.037 | |
| 103 | (adamantane-carboxamide)-NH-C(CH₃)₂-C(O)-NH-SO₂-(3-Cl,4-methylphenyl) | Human 0.026 Mouse 0.037 | |

TABLE 1-continued

| Patent Compound Structure Number | Structure | Cell-based Activity | | Remark |
|---|---|---|---|---|
| | | Human | 11β-HSD1 (IC50 μM) | |
| | | Mouse | 11β-HSD1 (IC50 μM) | |
| 104 | 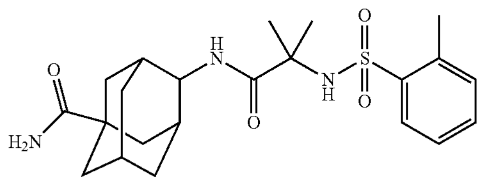 [SMILES: Cc1ccccc1S(=O)(=O)NC(C)(C)C(=O)NC1C2CC3CC1CC(C(N)=O)(C3)C2] | Human<br>Mouse | 0.014<br>0.046 | |
| 105 | 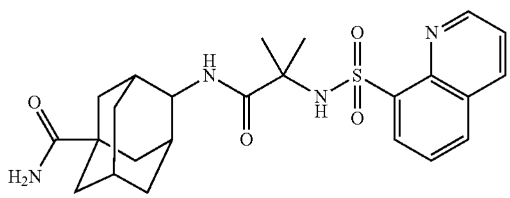 [SMILES: CC(C)(NS(=O)(=O)c1cccc2cccnc12)C(=O)NC1C2CC3CC1CC(C(N)=O)(C3)C2] | Human<br>Mouse | 0.023<br>0.006 | |
| 106 | 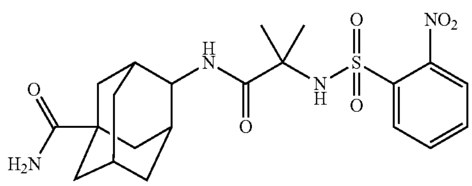 | Human<br>Mouse | 0.041<br>0.040 | |
| 107 | 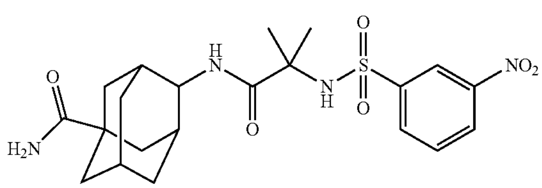 [SMILES: CC(C)(NS(=O)(=O)c1cccc([N+](=O)[O-])c1)C(=O)NC1C2CC3CC1CC(C(N)=O)(C3)C2] | Human<br>Mouse | 0.178<br>0.563 | |
| 108 | 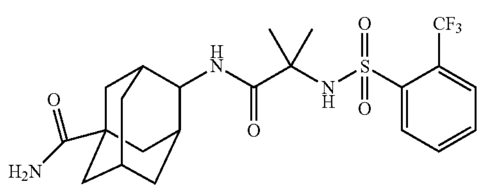 [SMILES: CC(C)(NS(=O)(=O)c1ccccc1C(F)(F)F)C(=O)NC1C2CC3CC1CC(C(N)=O)(C3)C2] | Human<br>Mouse | 0.011<br>0.029 | |
| 109 | 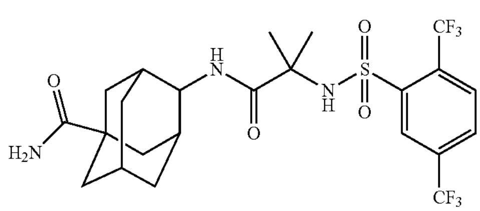 [SMILES: CC(C)(NS(=O)(=O)c1cc(C(F)(F)F)ccc1C(F)(F)F)C(=O)NC1C2CC3CC1CC(C(N)=O)(C3)C2] | Human<br>Mouse | 0.045<br>1.242 | |
| 110 | 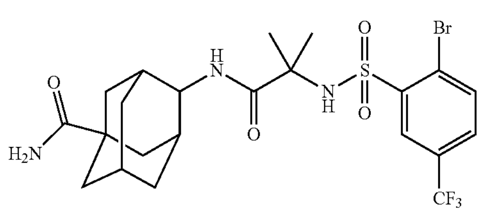 [SMILES: CC(C)(NS(=O)(=O)c1cc(C(F)(F)F)ccc1Br)C(=O)NC1C2CC3CC1CC(C(N)=O)(C3)C2] | Human<br>Mouse | 0.014<br>0.556 | |

TABLE 1-continued

| Patent Compound Structure Number | Structure | Cell-based Activity 11β-HSD1 Human (IC50 μM) 11β-HSD1 Mouse (IC50 μM) | | Remark |
|---|---|---|---|---|
| 111 | 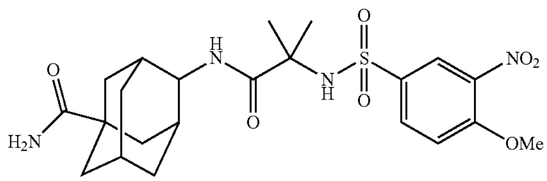 [SMILES: COc1ccc(S(=O)(=O)NC(C)(C)C(=O)NC2C3CC4CC2CC(C(N)=O)(C4)C3)cc1[N+](=O)[O-]] | Human<br>Mouse | 1.301<br>2.459 | |
| 112 | 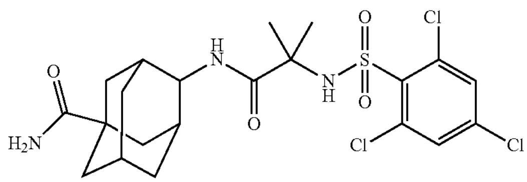 [SMILES: CC(C)(NS(=O)(=O)c1c(Cl)cc(Cl)cc1Cl)C(=O)NC1C2CC3CC1CC(C(N)=O)(C3)C2] | Human<br>Mouse | 0.024<br>0.011 | |
| 113 | 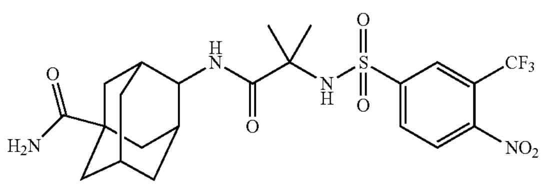 [SMILES: CC(C)(NS(=O)(=O)c1ccc([N+](=O)[O-])c(C(F)(F)F)c1)C(=O)NC1C2CC3CC1CC(C(N)=O)(C3)C2] | Human<br>Mouse | 0.208<br>0.215 | |
| 114 | 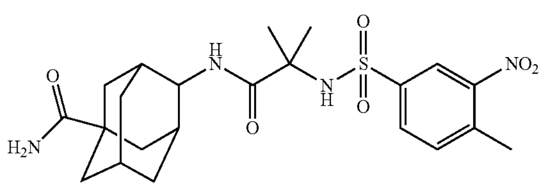 [SMILES: Cc1ccc(S(=O)(=O)NC(C)(C)C(=O)NC2C3CC4CC2CC(C(N)=O)(C4)C3)cc1[N+](=O)[O-]] | Human<br>Mouse | 0.093<br>0.207 | |
| 115 | 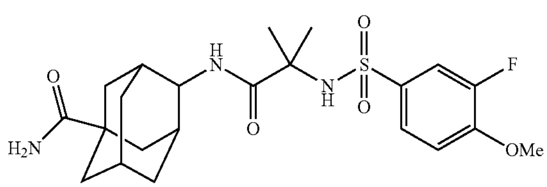 [SMILES: COc1ccc(S(=O)(=O)NC(C)(C)C(=O)NC2C3CC4CC2CC(C(N)=O)(C4)C3)cc1F] | Human<br>Mouse | 0.235<br>0.456 | |
| 116 | 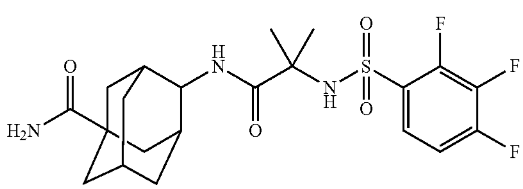 [SMILES: CC(C)(NS(=O)(=O)c1ccc(F)c(F)c1F)C(=O)NC1C2CC3CC1CC(C(N)=O)(C3)C2] | Human<br>Mouse | 0.035<br>0.122 | |
| 117 | 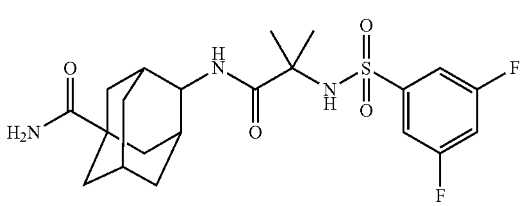 [SMILES: CC(C)(NS(=O)(=O)c1cc(F)cc(F)c1)C(=O)NC1C2CC3CC1CC(C(N)=O)(C3)C2] | Human<br>Mouse | 0.066<br>0.082 | |

TABLE 1-continued

| Patent Compound Structure Number | Structure | Cell-based Activity 11β-HSD1 Human (IC50 μM) 11β-HSD1 Mouse (IC50 μM) | | Remark |
|---|---|---|---|---|
| 118 | 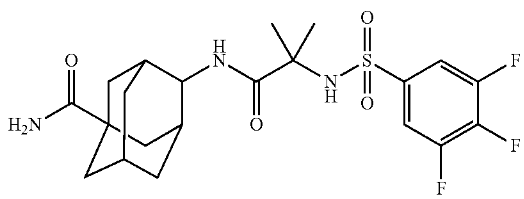 [SMILES: CC(C)(NS(=O)(=O)c1cc(F)c(F)c(F)c1)C(=O)NC1C2CC3CC1CC(C(N)=O)(C3)C2] | Human Mouse | 0.116 0.224 | |
| 119 | 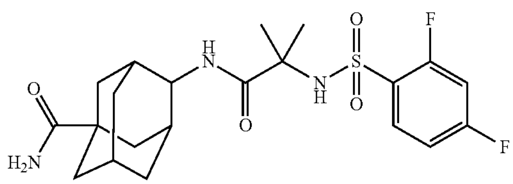 [SMILES: CC(C)(NS(=O)(=O)c1ccc(F)cc1F)C(=O)NC1C2CC3CC1CC(C(N)=O)(C3)C2] | Human Mouse | 0.042 0.096 | |
| 120 | 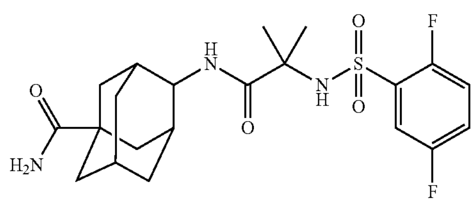 [SMILES: CC(C)(NS(=O)(=O)c1cc(F)ccc1F)C(=O)NC1C2CC3CC1CC(C(N)=O)(C3)C2] | Human Mouse | 0.051 0.453 | |
| 121 | 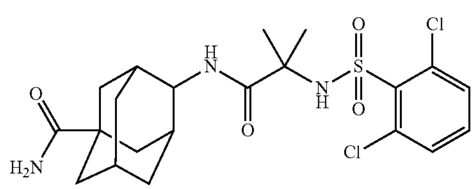 | Human Mouse | 0.009 0.004 | |
| 122 | 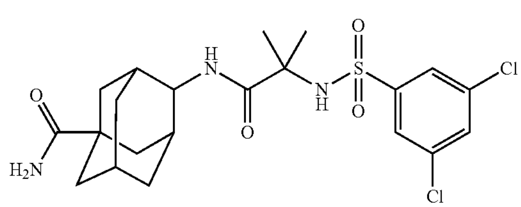 | Human Mouse | 0.108 0.290 | |
| 123 | 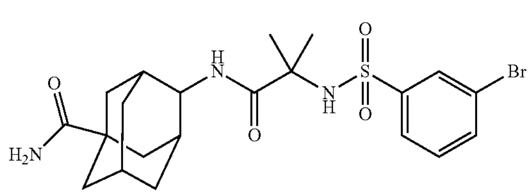 [SMILES: CC(C)(NS(=O)(=O)c1cccc(Br)c1)C(=O)NC1C2CC3CC1CC(C(N)=O)(C3)C2] | Human Mouse | 0.139 0.291 | |
| 124 | 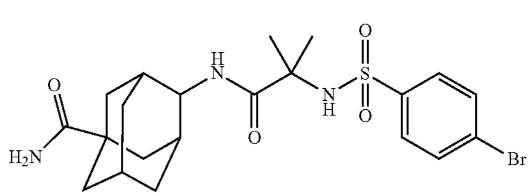 [SMILES: CC(C)(NS(=O)(=O)c1ccc(Br)cc1)C(=O)NC1C2CC3CC1CC(C(N)=O)(C3)C2] | Human Mouse | 0.024 0.220 | |

TABLE 1-continued

| Patent Compound Structure Number | Structure | Cell-based Activity 11β-HSD1 Human (IC50 μM) 11β-HSD1 Mouse (IC50 μM) | | Remark |
|---|---|---|---|---|
| 125 | 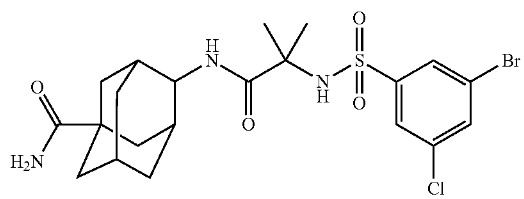 [SMILES: CC(C)(NS(=O)(=O)c1cc(Cl)cc(Br)c1)C(=O)NC1C2CC3CC1CC(C(N)=O)(C3)C2] | Human Mouse | 0.021 0.168 | |
| 126 | 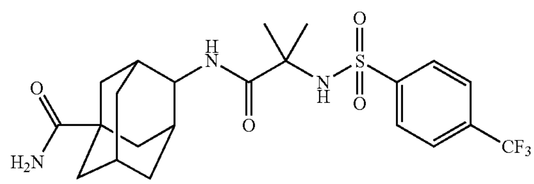 [SMILES: CC(C)(NS(=O)(=O)c1ccc(C(F)(F)F)cc1)C(=O)NC1C2CC3CC1CC(C(N)=O)(C3)C2] | Human Mouse | 0.182 0.455 | |
| 127 | 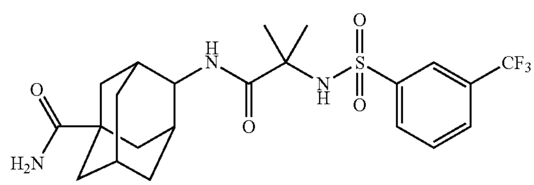 [SMILES: CC(C)(NS(=O)(=O)c1cccc(C(F)(F)F)c1)C(=O)NC1C2CC3CC1CC(C(N)=O)(C3)C2] | Human Mouse | 0.062 0.053 | |
| 128 | 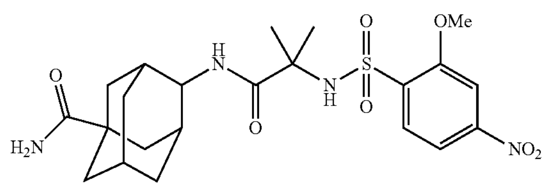 [SMILES: COc1cc([N+](=O)[O-])ccc1S(=O)(=O)NC(C)(C)C(=O)NC1C2CC3CC1CC(C(N)=O)(C3)C2] | Human Mouse | 0.076 0.22 | |
| 129 | 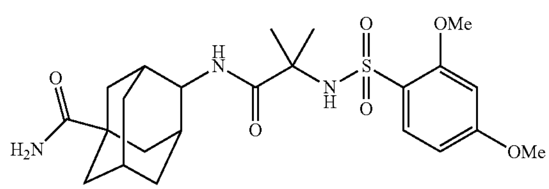 [SMILES: COc1ccc(S(=O)(=O)NC(C)(C)C(=O)NC2C3CC4CC2CC(C(N)=O)(C4)C3)c(OC)c1] | Human Mouse | 0.096 0.589 | |
| 130 | 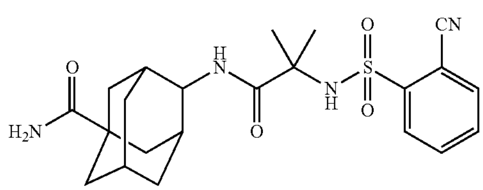 [SMILES: CC(C)(NS(=O)(=O)c1ccccc1C#N)C(=O)NC1C2CC3CC1CC(C(N)=O)(C3)C2] | Human Mouse | 0.078 0.405 | |
| 131 | 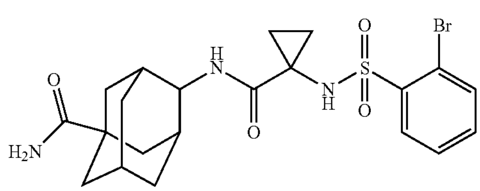 [SMILES: NC(=O)C12CC3CC(C1)C(NC(=O)C1(NS(=O)(=O)c4ccccc4Br)CC1)C(C3)C2] | Human Mouse | 0.008 0.048 | |

TABLE 1-continued

| Patent Compound Structure Number | Structure | Cell-based Activity 11β-HSD1 Human (IC50 μM) 11β-HSD1 Mouse (IC50 μM) | | Remark |
|---|---|---|---|---|
| 132 | 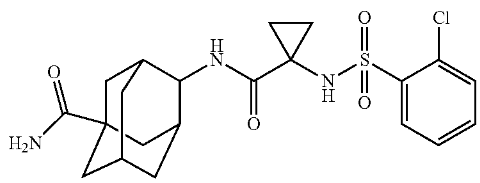 | Human Mouse | 0.037 0.148 | |
| 133 | 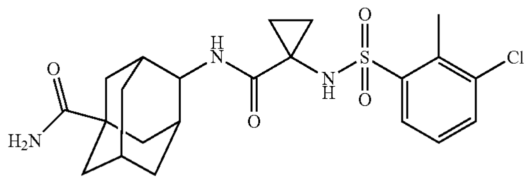 [SMILES: Cc1c(Cl)cccc1S(=O)(=O)NC1(C(=O)NC2C3CC4CC2CC(C(N)=O)(C4)C3)CC1] | Human Mouse | 0.015 0.074 | |
| 134 | 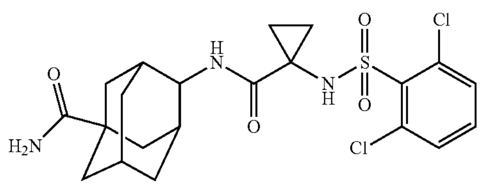 [SMILES: NC(=O)C12CC3CC(C1)C(NC(=O)C1(NS(=O)(=O)c4c(Cl)cccc4Cl)CC1)C(C3)C2] | Human Mouse | 0.021 0.021 | |
| 135 | 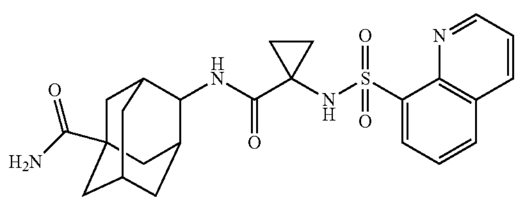 [SMILES: NC(=O)C12CC3CC(C1)C(NC(=O)C1(NS(=O)(=O)c4cccc5cccnc45)CC1)C(C3)C2] | Human Mouse | 0.042 0.02 | |
| 136 | 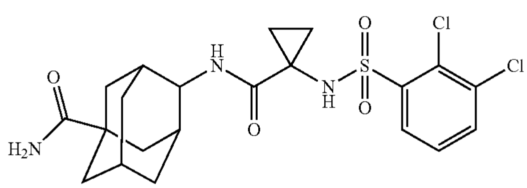 | Human Mouse | 0.009 0.028 | |
| 137 | 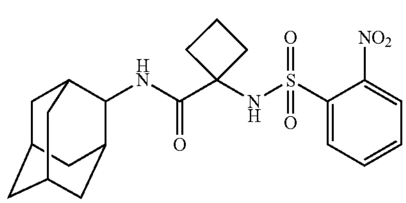 [SMILES: O=C(NC1C2CC3CC(C2)CC1C3)C1(NS(=O)(=O)c2ccccc2[N+](=O)[O-])CCC1] | Human Mouse | 0.255 1.100 | |
| 138 | 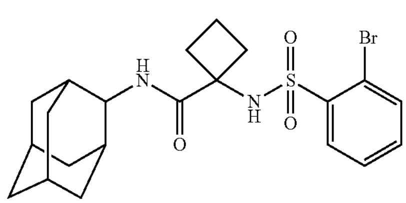 | Human Mouse | 0.113 0.806 | |

TABLE 1-continued

| Patent Compound Structure Number | Structure | Cell-based Activity | 11β-HSD1 (IC50 μM) | Remark |
|---|---|---|---|---|
| 139 | 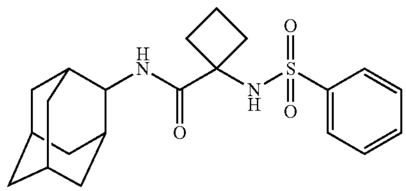 [SMILES: O=C(NC1C2CC3CC(C2)CC1C3)C1(NS(=O)(=O)c2ccccc2)CCC1] | Human<br>Mouse | 0.547<br>0.178 | |
| 140 | 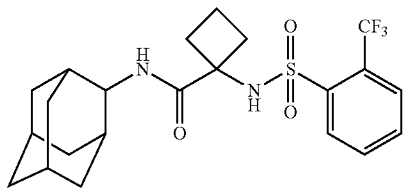 | Human<br>Mouse | 0.184<br>1.683 | |
| 141 | 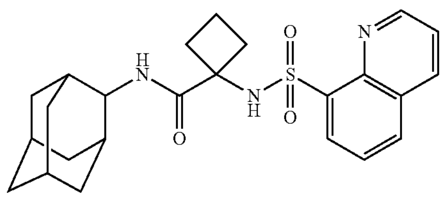 [SMILES: O=C(NC1C2CC3CC(C2)CC1C3)C1(NS(=O)(=O)c2cccc3cccnc23)CCC1] | Human<br>Mouse | 0.139<br>0.208 | |
| 142 | 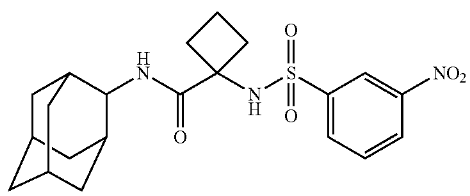 [SMILES: O=C(NC1C2CC3CC(C2)CC1C3)C1(NS(=O)(=O)c2cccc([N+](=O)[O-])c2)CCC1] | Human<br>Mouse | >2.5<br>1.442 | |
| 143 | 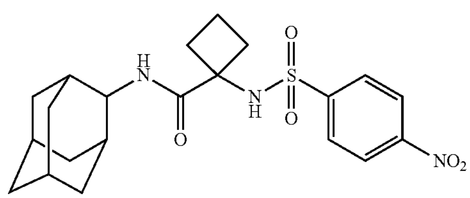 [SMILES: O=C(NC1C2CC3CC(C2)CC1C3)C1(NS(=O)(=O)c2ccc([N+](=O)[O-])cc2)CCC1] | Human<br>Mouse | >2.5<br>>2.5 | |
| 144 | 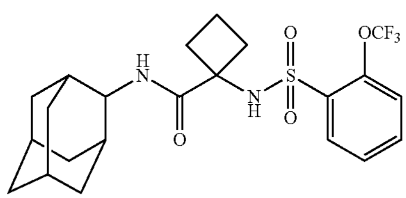 [SMILES: O=C(NC1C2CC3CC(C2)CC1C3)C1(NS(=O)(=O)c2ccccc2OC(F)(F)F)CCC1] | Human<br>Mouse | 0.265<br>1.824 | |
| 145 | 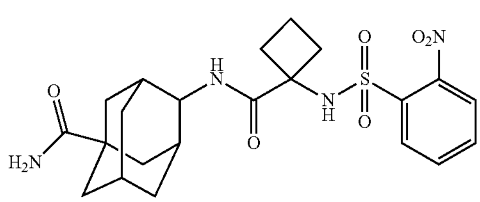 [SMILES: NC(=O)C12CC3CC(C1)C(NC(=O)C1(NS(=O)(=O)c4ccccc4[N+](=O)[O-])CCC1)C(C3)C2] | Human<br>Mouse | 0.080<br>0.509 | |

TABLE 1-continued
| Patent Compound Structure Number | Structure | Cell-based Activity Human Mouse | 11β-HSD1 Human (IC50 μM) 11β-HSD1 Mouse (IC50 μM) | Remark |
|---|---|---|---|---|
| 146 | 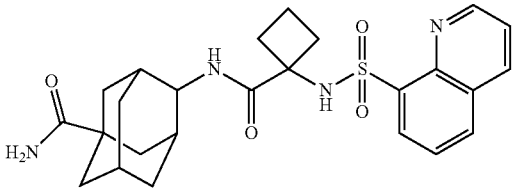 [SMILES: NC(=O)C12CC3CC(C1)C(NC(=O)C1(NS(=O)(=O)c4cccc5cccnc45)CCC1)C(C3)C2] | Human Mouse | 0.029 0.020 | |
| 147 | 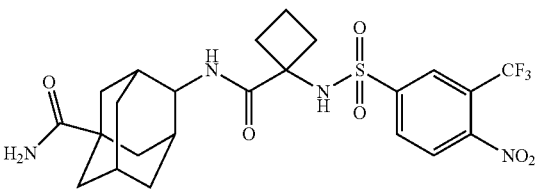 [SMILES: NC(=O)C12CC3CC(C1)C(NC(=O)C1(NS(=O)(=O)c4ccc([N+](=O)[O-])c(C(F)(F)F)c4)CCC1)C(C3)C2] | Human Mouse | 1.3 0.505 | |
| 148 | 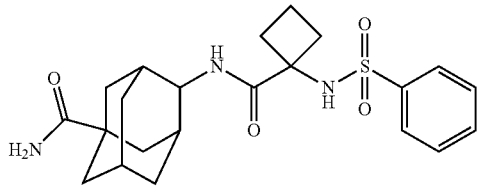 [SMILES: NC(=O)C12CC3CC(C1)C(NC(=O)C1(NS(=O)(=O)c4ccccc4)CCC1)C(C3)C2] | Human Mouse | 0.163 0.056 | |
| 149 | 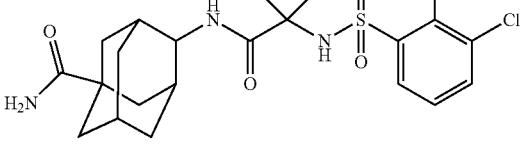 | Human Mouse | 0.015 0.040 | |
| 150 | 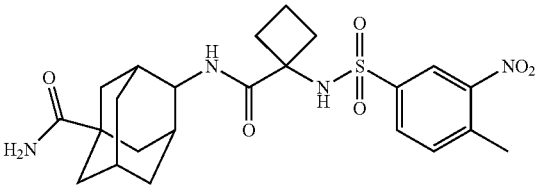 [SMILES: Cc1ccc(S(=O)(=O)NC2(C(=O)NC3C4CC5CC3CC(C(N)=O)(C5)C4)CCC2)cc1[N+](=O)[O-]] | Human Mouse | 0.639 0.187 | |
| 151 | 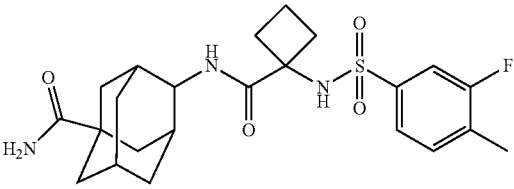 [SMILES: Cc1ccc(S(=O)(=O)NC2(C(=O)NC3C4CC5CC3CC(C(N)=O)(C5)C4)CCC2)cc1F] | Human Mouse | 0.182 0.062 | |
| 152 | 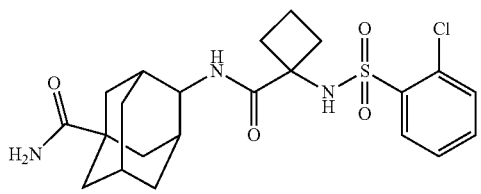 | Human Mouse | 0.021 0.099 | |

TABLE 1-continued

| Patent Compound Structure Number | Structure | Cell-based Activity | | Remark |
|---|---|---|---|---|
| | | | 11β-HSD1 Human (IC50 μM) 11β-HSD1 Mouse (IC50 μM) | |
| 153 | 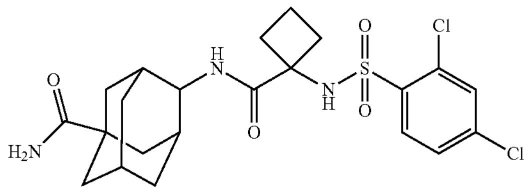 [SMILES: NC(=O)C12CC3CC(C1)C(NC(=O)C1(NS(=O)(=O)c4ccc(Cl)cc4Cl)CCC1)C(C3)C2] | Human Mouse | 0.058 0.459 | |
| 154 | 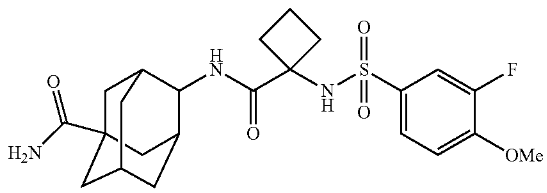 [SMILES: COc1ccc(S(=O)(=O)NC2(C(=O)NC3C4CC5CC3CC(C(N)=O)(C5)C4)CCC2)cc1F] | Human Mouse | 1.634 0.565 | |
| 155 | 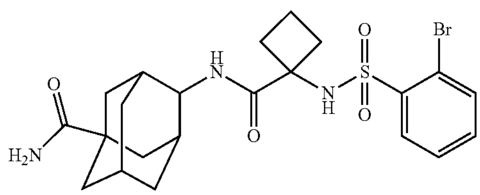 [SMILES: NC(=O)C12CC3CC(C1)C(NC(=O)C1(NS(=O)(=O)c4ccccc4Br)CCC1)C(C3)C2] | Human Mouse | 0.024 0.145 | |
| 156 | 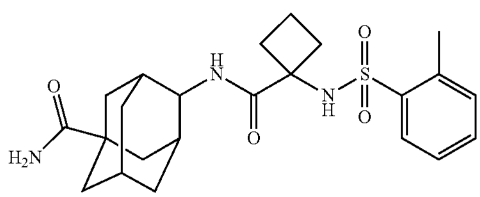 [SMILES: Cc1ccccc1S(=O)(=O)NC1(C(=O)NC2C3CC4CC2CC(C(N)=O)(C4)C3)CCC1] | Human Mouse | 0.046 0.138 | |
| 157 | 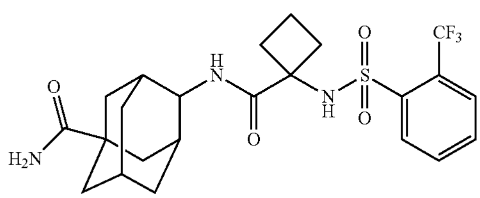 [SMILES: NC(=O)C12CC3CC(C1)C(NC(=O)C1(NS(=O)(=O)c4ccccc4C(F)(F)F)CCC1)C(C3)C2] | Human Mouse | 0.061 0.410 | |
| 158 | 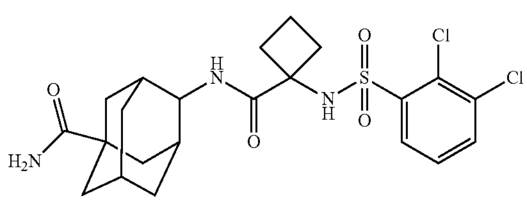 | Human Mouse | 0.018 0.058 | |
| 159 | 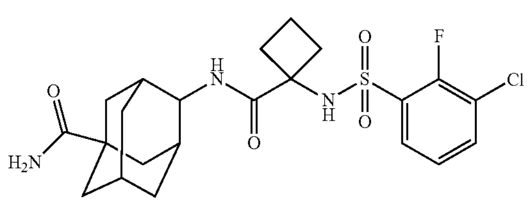 [SMILES: NC(=O)C12CC3CC(C1)C(NC(=O)C1(NS(=O)(=O)c4cccc(Cl)c4F)CCC1)C(C3)C2] | Human Mouse | 0.096 0.126 | |

TABLE 1-continued

| Patent Compound Structure Number | Structure | Cell-based Activity | | Remark |
|---|---|---|---|---|
| | | Human Mouse | 11β-HSD1 (IC50 μM) 11β-HSD1 (IC50 μM) | |
| 160 | 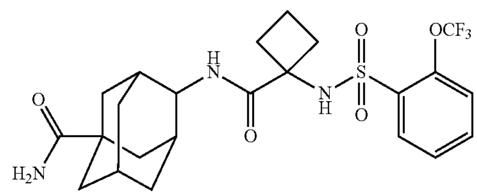 [SMILES: NC(=O)C12CC3CC(C1)C(NC(=O)C1(NS(=O)(=O)c4ccccc4OC(F)(F)F)CCC1)C(C3)C2] | Human Mouse | 0.018 0.113 | |
| 161 | 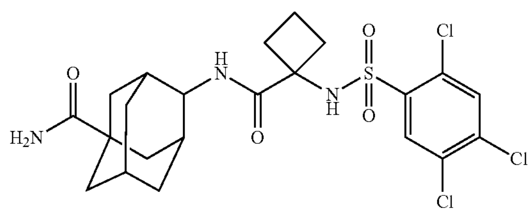 [SMILES: NC(=O)C12CC3CC(C1)C(NC(=O)C1(NS(=O)(=O)c4cc(Cl)c(Cl)cc4Cl)CCC1)C(C3)C2] | Human Mouse | 0.052 0.428 | |
| 162 | 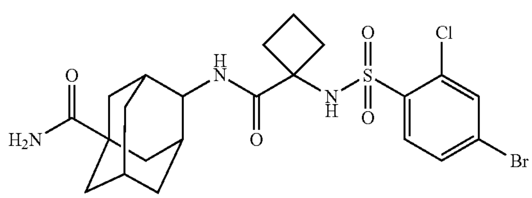 [SMILES: NC(=O)C12CC3CC(C1)C(NC(=O)C1(NS(=O)(=O)c4ccc(Br)cc4Cl)CCC1)C(C3)C2] | Human Mouse | 0.040 0.453 | |
| 163 | 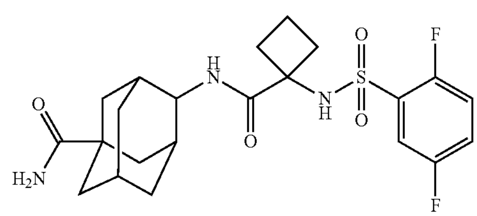 | Human Mouse | 0.373 0.443 | |
| 164 | 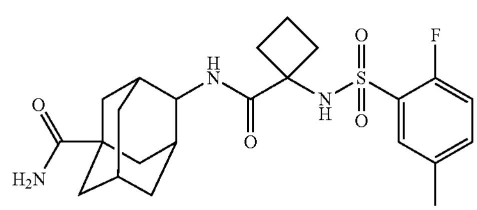 [SMILES: Cc1ccc(F)c(S(=O)(=O)NC2(C(=O)NC3C4CC5CC3CC(C(N)=O)(C5)C4)CCC2)c1] | Human Mouse | 0.058 0.298 | |
| 165 | 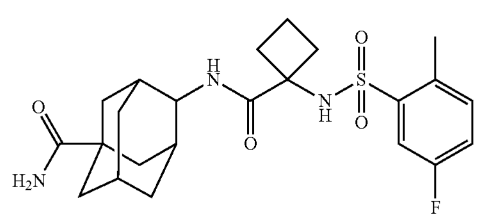 [SMILES: Cc1ccc(F)cc1S(=O)(=O)NC1(C(=O)NC2C3CC4CC2CC(C(N)=O)(C4)C3)CCC1] | Human Mouse | 0.101 0.290 | |
| 166 | 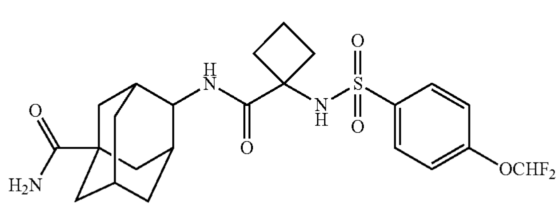 [SMILES: NC(=O)C12CC3CC(C1)C(NC(=O)C1(NS(=O)(=O)c4ccc(OC(F)F)cc4)CCC1)C(C3)C2] | Human Mouse | 0.724 0.559 | |

TABLE 1-continued

| Patent Compound Structure Number | Structure | Cell-based Activity | | Remark |
|---|---|---|---|---|
| | | Human Mouse | 11β-HSD1 (IC50 μM) 11β-HSD1 (IC50 μM) | |
| 167 | 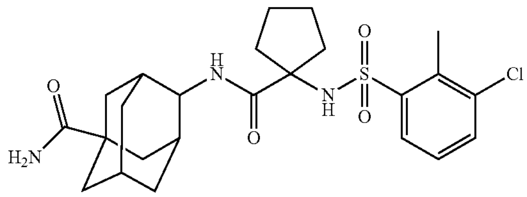 | Human Mouse | 0.008 0.016 | |
| 168 | 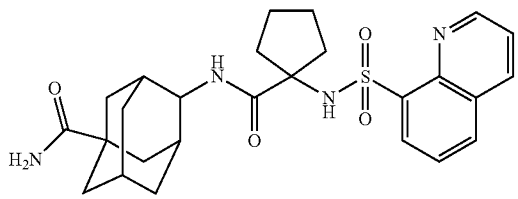 [SMILES: NC(=O)C12CC3CC(C1)C(NC(=O)C1(NS(=O)(=O)c4cccc5cccnc45)CCCC1)C(C3)C2] | Human Mouse | 0.022 0.007 | |
| 169 | 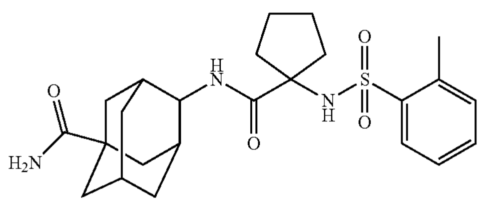 [SMILES: Cc1ccccc1S(=O)(=O)NC1(C(=O)NC2C3CC4CC2CC(C(N)=O)(C4)C3)CCCC1] | Human Mouse | 0.030 0.049 | |
| 170 | 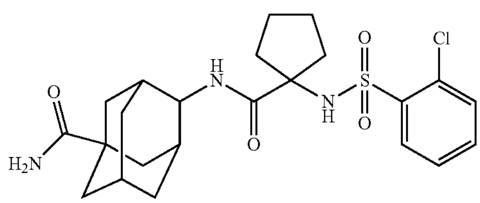 [SMILES: NC(=O)C12CC3CC(C1)C(NC(=O)C1(NS(=O)(=O)c4ccccc4Cl)CCCC1)C(C3)C2] | Human Mouse | 0.011 0.012 | |
| 171 | 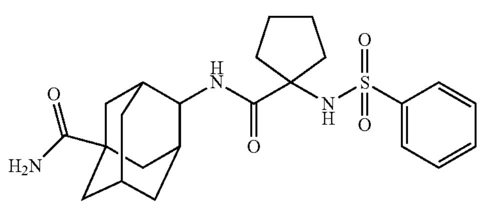 [SMILES: NC(=O)C12CC3CC(C1)C(NC(=O)C1(NS(=O)(=O)c4ccccc4)CCCC1)C(C3)C2] | Human Mouse | 0.038 0.12 | |
| 172 | 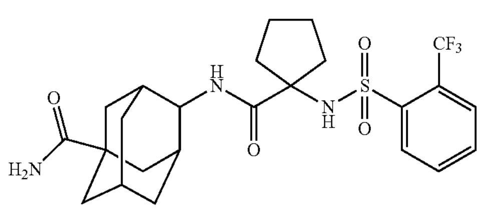 [SMILES: NC(=O)C12CC3CC(C1)C(NC(=O)C1(NS(=O)(=O)c4ccccc4C(F)(F)F)CCCC1)C(C3)C2] | Human Mouse | 0.016 0.053 | |
| 173 | 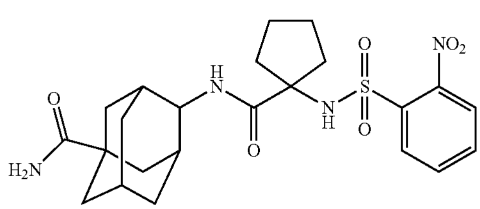 [SMILES: NC(=O)C12CC3CC(C1)C(NC(=O)C1(NS(=O)(=O)c4ccccc4[N+](=O)[O-])CCCC1)C(C3)C2] | Human Mouse | 0.014 0.038 | |

TABLE 1-continued

| Patent Compound Structure Number | Structure | Cell-based Activity 11β-HSD1 Human (IC50 μM) Mouse 11β-HSD1 (IC50 μM) | | Remark |
|---|---|---|---|---|
| 174 | 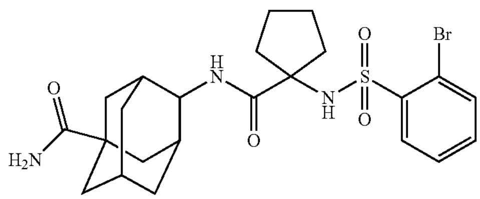 [SMILES: NC(=O)C12CC3CC(C1)C(NC(=O)C1(NS(=O)(=O)c4ccccc4Br)CCCC1)C(C3)C2] | Human Mouse | 0.017 0.015 | |
| 175 | 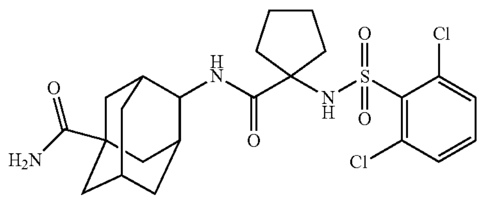 [SMILES: NC(=O)C12CC3CC(C1)C(NC(=O)C1(NS(=O)(=O)c4c(Cl)cccc4Cl)CCCC1)C(C3)C2] | Human Mouse | 0.006 0.003 | |
| 176 | 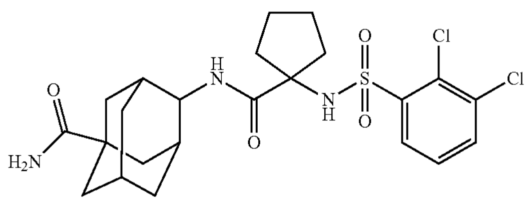 | Human Mouse | 0.009 0.007 | |
| 177 | 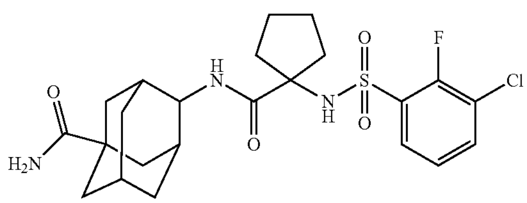 [SMILES: NC(=O)C12CC3CC(C1)C(NC(=O)C1(NS(=O)(=O)c4cccc(Cl)c4F)CCCC1)C(C3)C2] | Human Mouse | 0.009 0.006 | |
| 178 | 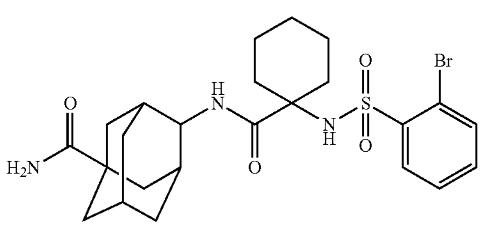 [SMILES: NC(=O)C12CC3CC(C1)C(NC(=O)C1(NS(=O)(=O)c4ccccc4Br)CCCCC1)C(C3)C2] | Human Mouse | 0.009 0.048 | |
| 179 | 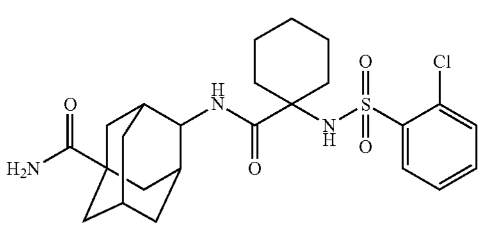 [SMILES: NC(=O)C12CC3CC(C1)C(NC(=O)C1(NS(=O)(=O)c4ccccc4Cl)CCCCC1)C(C3)C2] | Human Mouse | 0.008 0.037 | |
| 180 | 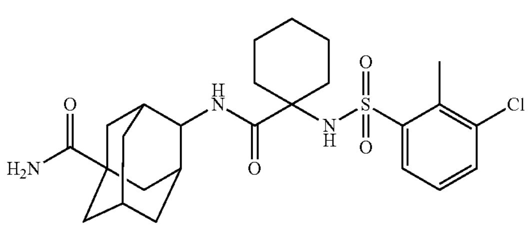 [SMILES: Cc1c(Cl)cccc1S(=O)(=O)NC1(C(=O)NC2C3CC4CC2CC(C(N)=O)(C4)C3)CCCCC1] | Human Mouse | 0.023 0.328 | |

TABLE 1-continued

| Patent Compound Structure Number | Structure | Cell-based Activity 11β-HSD1 Human (IC50 μM) 11β-HSD1 Mouse (IC50 μM) | | Remark |
|---|---|---|---|---|
| 181 | 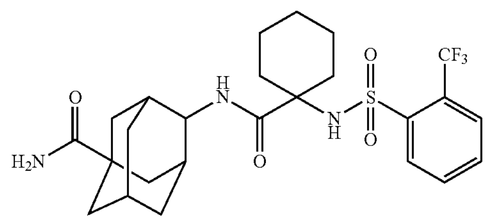 [SMILES: NC(=O)C12CC3CC(C1)C(NC(=O)C1(NS(=O)(=O)c4ccccc4C(F)(F)F)CCCCC1)C(C3)C2] | Human<br>Mouse | 0.019<br>0.132 | |
| 182 | 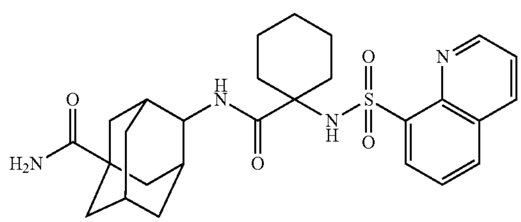 [SMILES: NC(=O)C12CC3CC(C1)C(NC(=O)C1(NS(=O)(=O)c4cccc5cccnc45)CCCCC1)C(C3)C2] | Human<br>Mouse | 0.018<br>0.006 | |
| 183 | 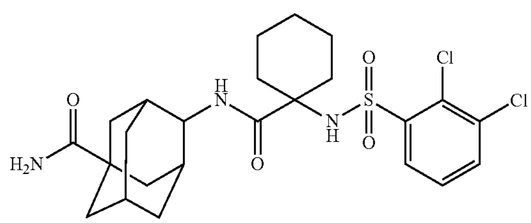 [SMILES: NC(=O)C12CC3CC(C1)C(NC(=O)C1(NS(=O)(=O)c4cccc(Cl)c4Cl)CCCCC1)C(C3)C2] | Human<br>Mouse | 0.017<br>0.044 | |
| 184 | 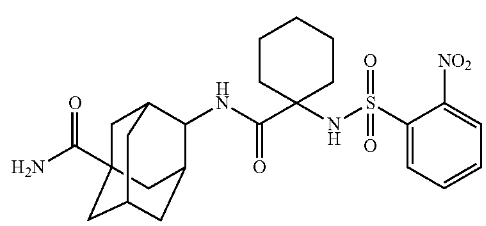 [SMILES: NC(=O)C12CC3CC(C1)C(NC(=O)C1(NS(=O)(=O)c4ccccc4[N+](=O)[O-])CCCCC1)C(C3)C2] | Human<br>Mouse | 0.005<br>0.104 | |
| 185 | 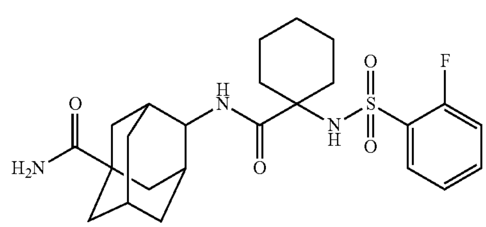 [SMILES: NC(=O)C12CC3CC(C1)C(NC(=O)C1(NS(=O)(=O)c4ccccc4F)CCCCC1)C(C3)C2] | Human<br>Mouse | 0.028<br>0.119 | |
| 186 | 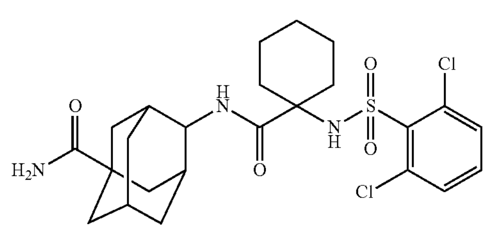 [SMILES: NC(=O)C12CC3CC(C1)C(NC(=O)C1(NS(=O)(=O)c4c(Cl)cccc4Cl)CCCCC1)C(C3)C2] | Human<br>Mouse | 0.012<br>0.005 | |

TABLE 1-continued

| Patent Compound Structure Number | Structure | Cell-based Activity 11β-HSD1 Human (IC50 μM) 11β-HSD1 Mouse (IC50 μM) | | Remark |
|---|---|---|---|---|
| 187 | 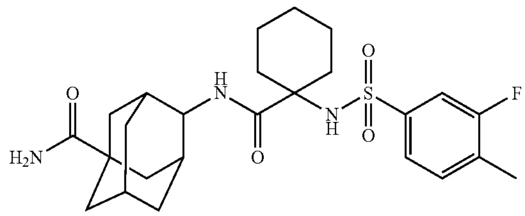 [SMILES: Cc1ccc(S(=O)(=O)NC2(C(=O)NC3C4CC5CC3CC(C(N)=O)(C5)C4)CCCCC2)cc1F] | Human | 0.076 | |
| | | Mouse | >2.5 | |
| 188 | 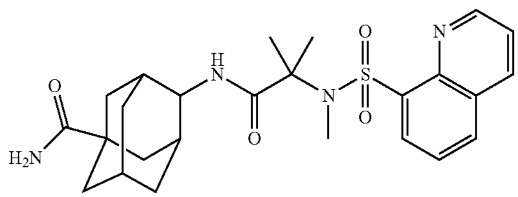 [SMILES: CN(C(C)(C)C(=O)NC1C2CC3CC1CC(C(N)=O)(C3)C2)S(=O)(=O)c1cccc2cccnc12] | Human | 0.013 | |
| | | Mouse | 0.007 | |
| 189 | 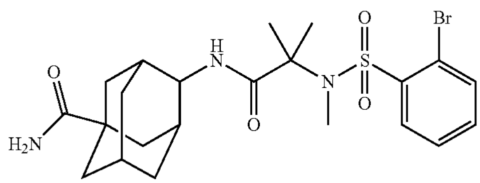 [SMILES: CN(C(C)(C)C(=O)NC1C2CC3CC1CC(C(N)=O)(C3)C2)S(=O)(=O)c1ccccc1Br] | Human | 0.018 | |
| | | Mouse | >2.5 | |
| 190 | 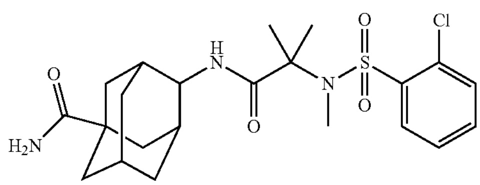 [SMILES: CN(C(C)(C)C(=O)NC1C2CC3CC1CC(C(N)=O)(C3)C2)S(=O)(=O)c1ccccc1Cl] | Human | 0.002 | |
| | | Mouse | 0.005 | |
| 191 | 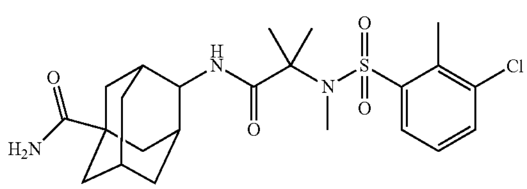 [SMILES: Cc1c(Cl)cccc1S(=O)(=O)N(C)C(C)(C)C(=O)NC1C2CC3CC1CC(C(N)=O)(C3)C2] | Human | 0.009 | |
| | | Mouse | 0.006 | |
| 192 | 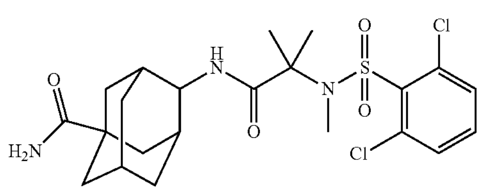 [SMILES: CN(C(C)(C)C(=O)NC1C2CC3CC1CC(C(N)=O)(C3)C2)S(=O)(=O)c1c(Cl)cccc1Cl] | Human | 0.008 | |
| | | Mouse | 0.002 | |
| 193 | 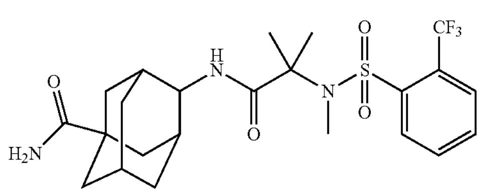 [SMILES: CN(C(C)(C)C(=O)NC1C2CC3CC1CC(C(N)=O)(C3)C2)S(=O)(=O)c1ccccc1C(F)(F)F] | Human | 0.007 | |
| | | Mouse | 0.012 | |

TABLE 1-continued

| Patent Compound Structure Number | Structure | Cell-based Activity 11β-HSD1 Human (IC50 μM) 11β-HSD1 Mouse (IC50 μM) | | Remark |
|---|---|---|---|---|
| 194 | 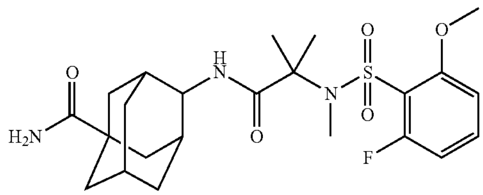 [SMILES: COc1cccc(F)c1S(=O)(=O)N(C)C(C)(C)C(=O)NC1C2CC3CC1CC(C(N)=O)(C3)C2] | Human | 0.012 | |
| | | Mouse | 0.006 | |
| 195 | 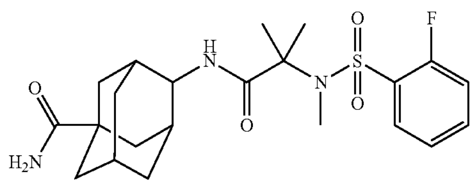 [SMILES: CN(C(C)(C)C(=O)NC1C2CC3CC1CC(C(N)=O)(C3)C2)S(=O)(=O)c1ccccc1F] | Human | 0.005 | |
| | | Mouse | 0.015 | |
| 196 | 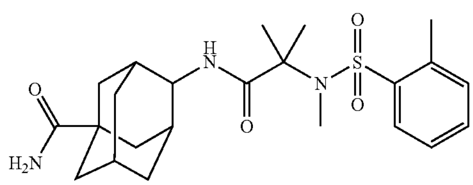 [SMILES: Cc1ccccc1S(=O)(=O)N(C)C(C)(C)C(=O)NC1C2CC3CC1CC(C(N)=O)(C3)C2] | Human | 0.003 | |
| | | Mouse | 0.005 | |
| 197 | 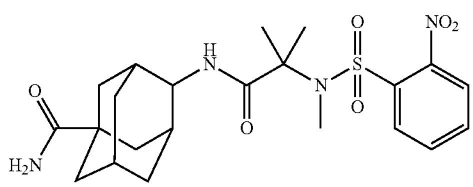 | Human | 0.004 | |
| | | Mouse | 0.008 | |
| 198 | 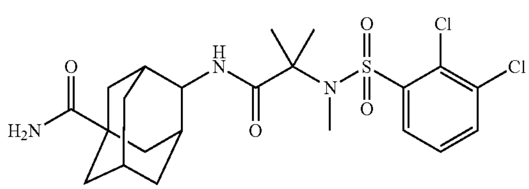 [SMILES: CN(C(C)(C)C(=O)NC1C2CC3CC1CC(C(N)=O)(C3)C2)S(=O)(=O)c1cccc(Cl)c1Cl] | Human | 0.008 | |
| | | Mouse | 0.003 | |
| 199 | 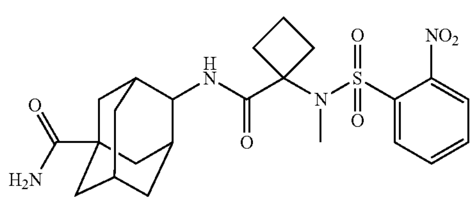 [SMILES: CN(C1(C(=O)NC2C3CC4CC2CC(C(N)=O)(C4)C3)CCC1)S(=O)(=O)c1ccccc1[N+](=O)[O-]] | Human | 0.004 | |
| | | Mouse | 0.016 | |
| 200 | 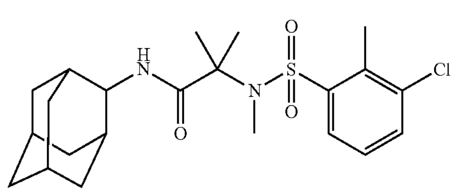 | Human | 0.023 | |
| | | Mouse | 0.143 | |

TABLE 1-continued
| Patent Compound Structure Number | Structure | Cell-based Activity | | Remark |
|---|---|---|---|---|
| | | Human Mouse | 11β-HSD1 Human (IC50 μM) 11β-HSD1 Mouse (IC50 μM) | |
| 201 | 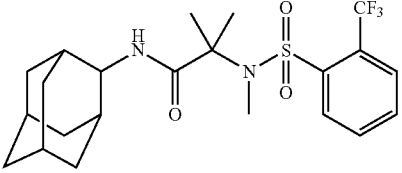 [SMILES: CN(C(C)(C)C(=O)NC1C2CC3CC(C2)CC1C3)S(=O)(=O)c1ccccc1C(F)(F)F] | Human Mouse | 0.012 0.088 | |
| 202 | 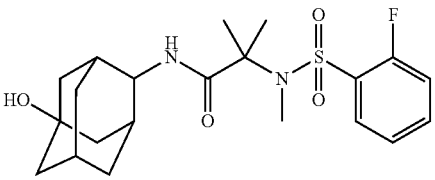 [SMILES: CN(C(C)(C)C(=O)NC1C2CC3CC1CC(O)(C3)C2)S(=O)(=O)c1ccccc1F] | Human Mouse | 0.011 0.208 | |
| 203 | 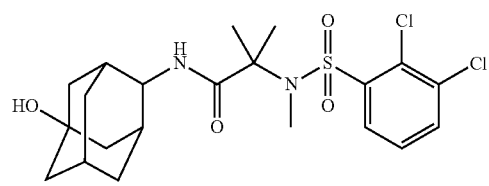 [SMILES: CN(C(C)(C)C(=O)NC1C2CC3CC1CC(O)(C3)C2)S(=O)(=O)c1cccc(Cl)c1Cl] | Human Mouse | 0.01 0.039 | |
| 204 | 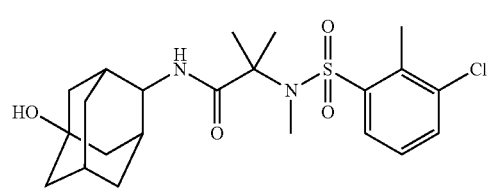 [SMILES: Cc1c(Cl)cccc1S(=O)(=O)N(C)C(C)(C)C(=O)NC1C2CC3CC1CC(O)(C3)C2] | Human Mouse | 0.004 0.042 | |
| 205 | 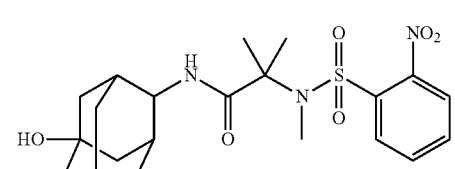 | Human Mouse | 0.005 0.068 | |
| 206 | 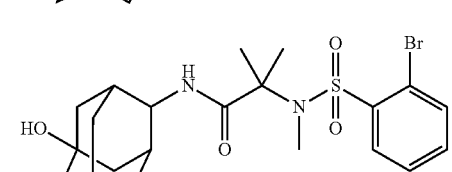 | Human Mouse | 0.005 0.041 | |
| 207 | 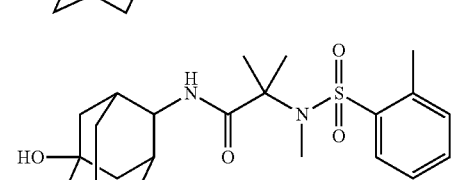 | Human Mouse | 0.006 0.107 | |
| 208 | 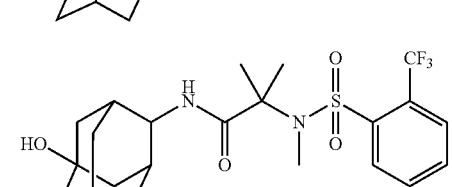 | Human Mouse | 0.006 0.092 | |

TABLE 1-continued

| Patent Compound Structure Number | Structure | Cell-based Activity 11β-HSD1 Human (IC50 μM) 11β-HSD1 Mouse (IC50 μM) | | Remark |
|---|---|---|---|---|
| 209 | 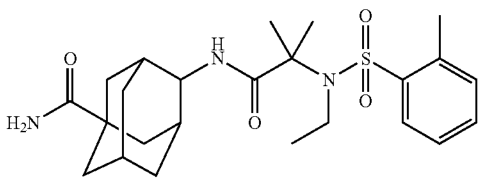 [SMILES: CCN(C(C)(C)C(=O)NC1C2CC3CC1CC(C(N)=O)(C3)C2)S(=O)(=O)c1ccccc1C] | Human<br>Mouse | 0.008<br>0.182 | |
| 210 | 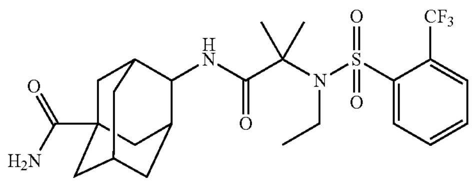 [SMILES: CCN(C(C)(C)C(=O)NC1C2CC3CC1CC(C(N)=O)(C3)C2)S(=O)(=O)c1ccccc1C(F)(F)F] | Human<br>Mouse | 0.006<br>1.438 | |
| 211 | 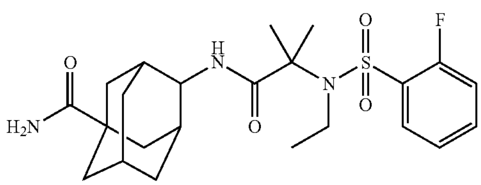 [SMILES: CCN(C(C)(C)C(=O)NC1C2CC3CC1CC(C(N)=O)(C3)C2)S(=O)(=O)c1ccccc1F] | Human<br>Mouse | 0.006<br>0.079 | |
| 212 | 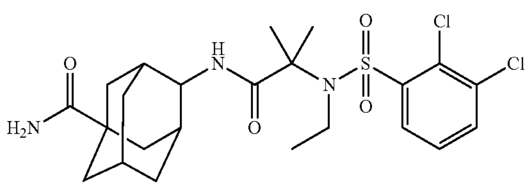 [SMILES: CCN(C(C)(C)C(=O)NC1C2CC3CC1CC(C(N)=O)(C3)C2)S(=O)(=O)c1cccc(Cl)c1Cl] | Human<br>Mouse | 0.024<br>0.191 | |
| 213 | 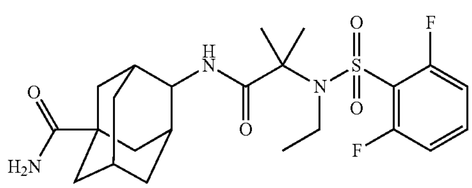 [SMILES: CCN(C(C)(C)C(=O)NC1C2CC3CC1CC(C(N)=O)(C3)C2)S(=O)(=O)c1c(F)cccc1F] | Human<br>Mouse | 0.005<br>0.235 | |
| 214 | 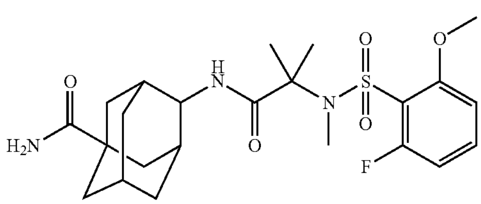 [SMILES: COc1cccc(F)c1S(=O)(=O)N(C)C(C)(C)C(=O)NC1C2CC3CC1CC(C(N)=O)(C3)C2] | Human<br>Mouse | 0.012<br>0.006 | |
| 215 | 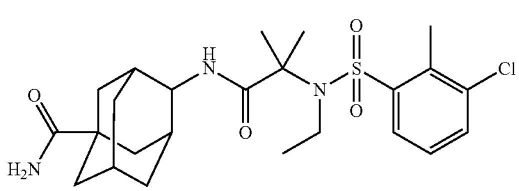 [SMILES: CCN(C(C)(C)C(=O)NC1C2CC3CC1CC(C(N)=O)(C3)C2)S(=O)(=O)c1cccc(Cl)c1C] | Human<br>Mouse | 0.004<br>0.284 | |

TABLE 1-continued

| Patent Compound Structure Number | Structure | Cell-based Activity 11β-HSD1 Human (IC50 μM) 11β-HSD1 Mouse (IC50 μM) | | Remark |
|---|---|---|---|---|
| 216 | 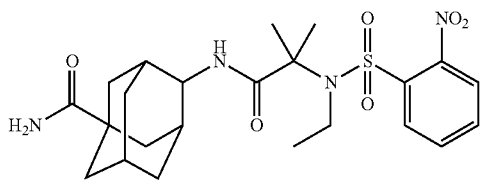 [SMILES: CCN(C(C)(C)C(=O)NC1C2CC3CC1CC(C(N)=O)(C3)C2)S(=O)(=O)c1ccccc1[N+](=O)[O-]] | Human Mouse | 0.009 0.974 | |
| 217 | 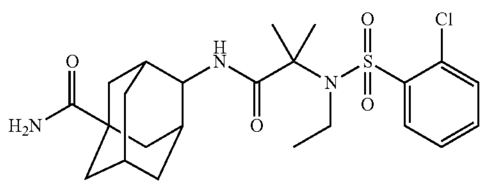 | Human Mouse | 0.004 0.098 | |
| 218 | 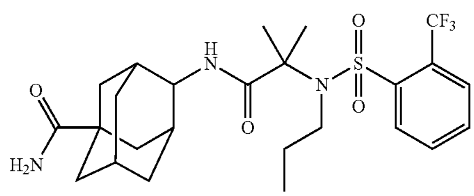 [SMILES: CCCN(C(C)(C)C(=O)NC1C2CC3CC1CC(C(N)=O)(C3)C2)S(=O)(=O)c1ccccc1C(F)(F)F] | Human Mouse | 0.053 0.462 | |
| 219 | 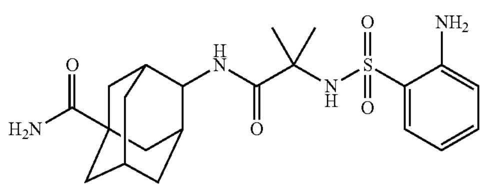 | Human Mouse | 0.085 0.117 | |
| 220 | 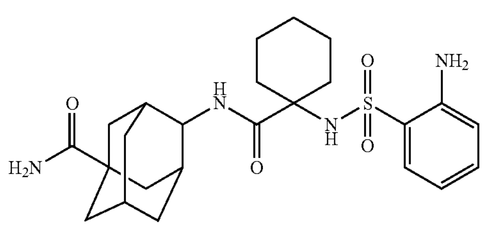 | Human Mouse | 0.032 0.266 | |
| 221 | 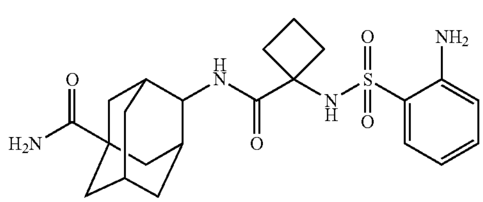 [SMILES: NC(=O)C12CC3CC(C1)C(NC(=O)C1(NS(=O)(=O)c4ccccc4N)CCC1)C(C3)C2] | Human Mouse | 0.079 0.151 | |
| 222 | 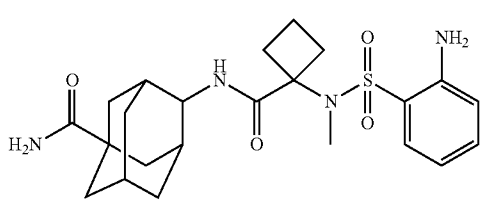 [SMILES: CN(C1(C(=O)NC2C3CC4CC2CC(C(N)=O)(C4)C3)CCC1)S(=O)(=O)c1ccccc1N] | Human Mouse | 0.005 0.004 | |

TABLE 1-continued
| Patent Compound Structure Number | Structure | Cell-based Activity 11β-HSD1 Human (IC50 μM) 11β-HSD1 Mouse (IC50 μM) | | Remark |
|---|---|---|---|---|
| 223 | 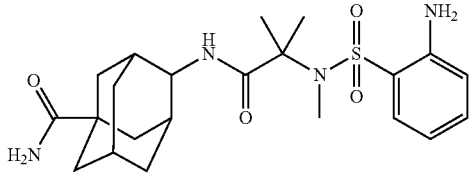 [SMILES: CN(C(C)(C)C(=O)NC1C2CC3CC1CC(C(N)=O)(C3)C2)S(=O)(=O)c1ccccc1N] | Human<br>Mouse | 0.011<br>0.023 | |
| 224 | 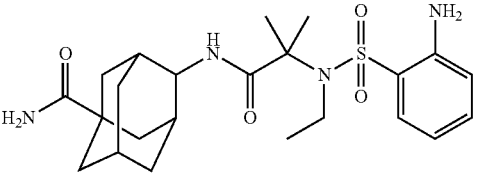 [SMILES: CCN(C(C)(C)C(=O)NC1C2CC3CC1CC(C(N)=O)(C3)C2)S(=O)(=O)c1ccccc1N] | Human<br>Mouse | 0.011<br>0.154 | |
| 225 | 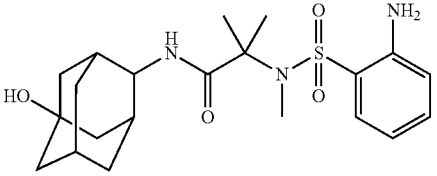 | Human<br>Mouse | 0.011<br>0.083 | |
| 226 | 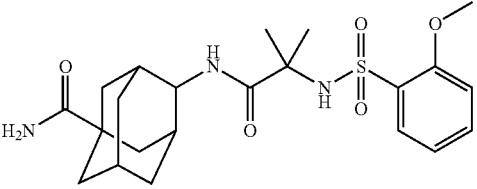 [SMILES: COc1ccccc1S(=O)(=O)NC(C)(C)C(=O)NC1C2CC3CC1CC(C(N)=O)(C3)C2] | Human<br>Mouse | 0.062<br>0.038 | |
| 227 | 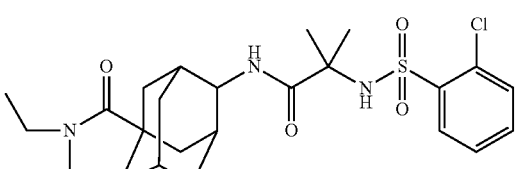 | Human<br>Mouse | >2.5<br>>2.5 | |
| 228 | 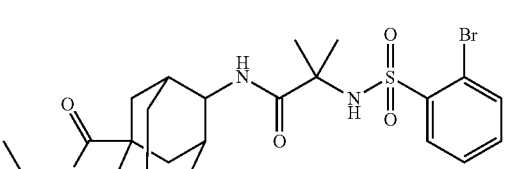 | Human<br>Mouse | >2.5<br>>2.5 | |
| 229 | 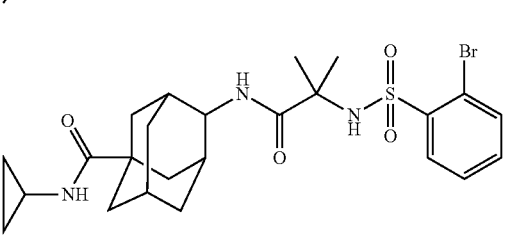 | Human<br>Mouse | >2.5<br>>2.5 | |

TABLE 1-continued

| Patent Compound Structure Number | Structure | Cell-based Activity 11β-HSD1 Human (IC50 μM) 11β-HSD1 Mouse (IC50 μM) | | Remark |
|---|---|---|---|---|
| 230 | 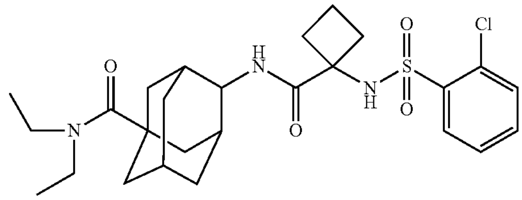 [SMILES: CCN(CC)C(=O)C12CC3CC(C1)C(NC(=O)C1(NS(=O)(=O)c4ccccc4Cl)CCC1)C(C3)C2] | Human Mouse | >2.5 >2.5 | |
| 231 | 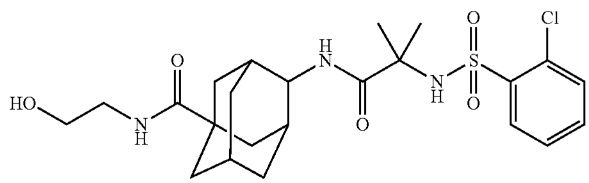 [SMILES: CC(C)(NS(=O)(=O)c1ccccc1Cl)C(=O)NC1C2CC3CC1CC(C(=O)NCCO)(C3)C2] | Human Mouse | >2.5 >2.5 | |
| 232 | 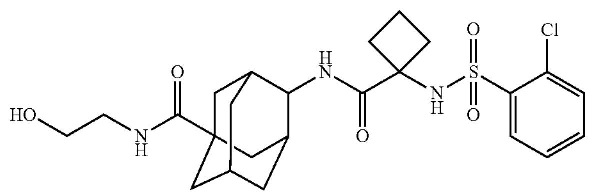 [SMILES: O=C(NCCO)C12CC3CC(C1)C(NC(=O)C1(NS(=O)(=O)c4ccccc4Cl)CCC1)C(C3)C2] | Human Mouse | >2.5 >2.5 | |
| 233 | 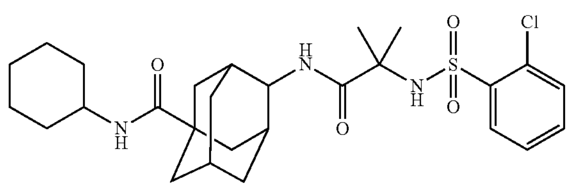 [SMILES: CC(C)(NS(=O)(=O)c1ccccc1Cl)C(=O)NC1C2CC3CC1CC(C(=O)NC1CCCCC1)(C3)C2] | Human Mouse | >2.5 >2.5 | |
| 234 | 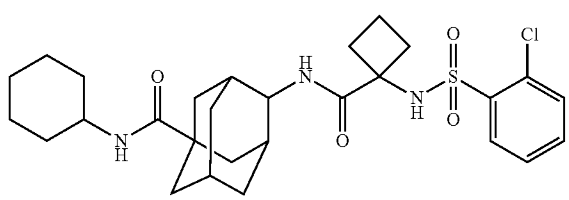 [SMILES: O=C(NC1CCCCC1)C12CC3CC(C1)C(NC(=O)C1(NS(=O)(=O)c4ccccc4Cl)CCC1)C(C3)C2] | Human Mouse | >2.5 >2.5 | |
| 235 | 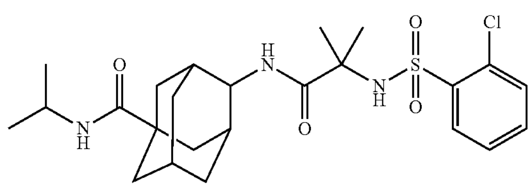 [SMILES: CC(C)NC(=O)C12CC3CC(C1)C(NC(=O)C(C)(C)NS(=O)(=O)c1ccccc1Cl)C(C3)C2] | Human Mouse | >2.5 >2.5 | |
| 236 | 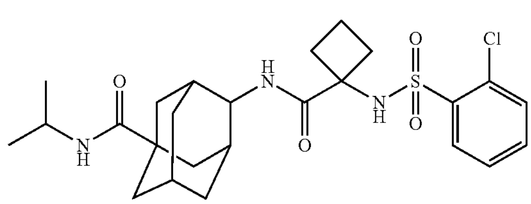 [SMILES: CC(C)NC(=O)C12CC3CC(C1)C(NC(=O)C1(NS(=O)(=O)c4ccccc4Cl)CCC1)C(C3)C2] | Human Mouse | >2.5 >2.5 | |

TABLE 1-continued

| Patent Compound Structure Number | Structure | Cell-based Activity 11β-HSD1 Human (IC50 µM) 11β-HSD1 Mouse (IC50 µM) | | Remark |
|---|---|---|---|---|
| 237 | 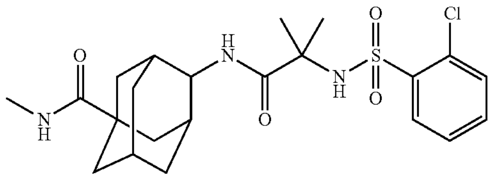 [SMILES: CNC(=O)C12CC3CC(C1)C(NC(=O)C(C)(C)NS(=O)(=O)c1ccccc1Cl)C(C3)C2] | Human<br>Mouse | 1.499<br>0.437 | |
| 238 | 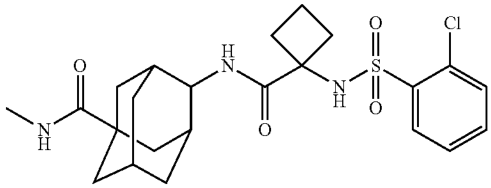 [SMILES: CNC(=O)C12CC3CC(C1)C(NC(=O)C1(NS(=O)(=O)c4ccccc4Cl)CCC1)C(C3)C2] | Human<br>Mouse | >2.5<br>>2.5 | |
| 239 | 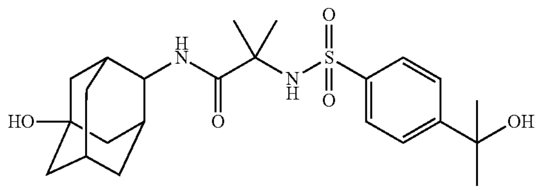 [SMILES: CC(C)(NS(=O)(=O)c1ccc(C(C)(C)O)cc1)C(=O)NC1C2CC3CC1CC(O)(C3)C2] | Human<br>Mouse | | |
| 240 | 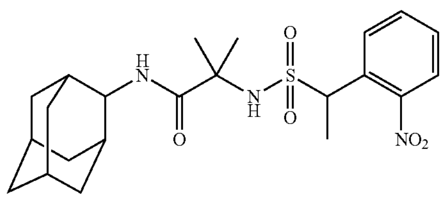 [SMILES: CC(c1ccccc1[N+](=O)[O-])S(=O)(=O)NC(C)(C)C(=O)NC1C2CC3CC(C2)CC1C3] | Human<br>Mouse | | |
| 241 | 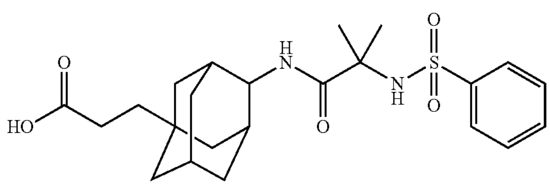 [SMILES: CC(C)(NS(=O)(=O)c1ccccc1)C(=O)NC1C2CC3CC1CC(CCC(=O)O)(C3)C2] | Human<br>Mouse | | |

Example 19

Cell-Based Enzyme Activity Analysis on Human/Mouse 11β-HSD1

CHO cells which had been stably transfected with human/mouse 11β-HSD1 cDNA were plated on a 96 well plate with RPMI medium (Wellgene, phenol red free) containing 100 µl of 10% FBS, 100 ug/ml of penicillin, 100 ug/ml of streptomycin and puromycin (12 ug/ml) (2×10$^4$ cells/well), and cultured at 37° C. overnight. 17 hours from the plating of the cells, 160 nM cortisone (Sigma) in the presence or absence of a diluted test compound at various concentrations was added thereto, followed by culturing at 37° C., for 3 hours. 10 µl of the resultant supernatant liquid was transferred to a 384 well plate, and each well was added with 5 µl of cryptate-labeled anti-cortisol antibody and 5 µl of d2-labeled cortisol. After further culturing at room temperature for 2 hours, a homogeneous time-resolved fluorescence (HTRF, Cisbio) signal was measured. From each analysis, based on a standard curve calculated using cortisol of several known concentrations, an amount of produced cortisol was tested.

Example 20

11b-HSD2 Inhibition Test

CHO cells were plated on a 96 well plate with RPMI (Wellgene) medium (phenol red free) containing 100 µl of 10% FBS, 100 ug/ml of penicillin and 100 ug/ml of streptomycin (2×10$^4$ cells/well). CHO cells were transfected with plasmid (Origene, SC122552) (pCMV6-XL5 vector) expressing human 11β-HSD2 by using FuGENE6 reagent (Promega, E2311). 24 hours after transfection, the transfected cells were added with 50 nM of cortisol (Sigma) in the presence or absence of the compound at various concentrations. On the following day (24 hours later), the supernatant liquid was obtained, and through HTRF (Cisbio, 62CO2PEB) analysis, a competitive amount of cortisol was measured.

Compound 92, compound 105, compound 106, compound 108, compound 119, compound 121, compound 146 showed an inhibitory effect of 40% or less at a concentration of 10 uM.

Example 21

Test Method on Competitive Binding of Glucocorticoid Receptor

In order to confirm the selective inhibitory ability of 11β-HSD1 inhibitor, competitive binding between 11β-HSD1 inhibitor and glucocorticoid ligand was tested by using LanthaScreen TR-FRET Glucocorticoid Receptor Competitive Binding Assay (Invitrogen, PV6040). The test material was dissolved in DMSO (Sigma, 276855) up to a 100× concentration of its final concentration (10 uM), and then Complete Nuclear Receptor Buffer F (1× stabilizing peptide, 5 mM DTT, Nuclear Receptor Buffer F) was used to dilute the test material up to a concentration of 2×, 4× Fluormone™ GS1 Green up to 20 nM, 4× GR-LBD up to 4 nM, and 4× Tb anti-GST Antibody up to 8 nM.

In order to obtain 60 μl of a final product through a reaction, on a 96-well plate, 2× test material 30 μl, 4× Fluormone™ GS1 Green 15 μl, and 4× GR-LBD/Tb anti-GST Antibody 15 μl were mixed, and reacted for 1 hour. In a positive control group, instead of the test material, Dexamethasone (Sigma, D1756), known as a ligand for glucocorticoid receptor, was used, and in a maximum active control group, DMSO was used, instead of the test material. In a negative control group, instead of the test material, DMSO was used, instead of Fluormone™ GS1 Green, Complete Nuclear Receptor Buffer F was used. On a 384-well white plate, 20 μl each was plated. By using Time-Resolved program in Flexstation3, a fluorescence value was read after excitation (332 nM), emission (515 nM/486 nM), Delay time (100 μs), and Integration time (1500 μs) were programmed. By using the obtained value, a value of 515 nM/486 nM was calculated, from which the value in the negative control group was subtracted. The degree of binding of the test material to glucocorticoid receptor of was calculated by the active value of the test material with respect to the active value (100%) in the maximum active control group.

As a result, compound 43, compound 83, compound 84, compound 85, compound 87, compound 89, compound 90, compound 92, compound 97, compound 104, compound 106, compound 108, and compound 119 did not bind to glucocorticoid receptor.

Example 22

Analysis on In Vitro Enzyme Activity on Mouse 11β-HSD1

12 hours before this test, feeding for C57BL/6N mice was stopped but they were allowed to freely drink only drinking water. After quarantine, acclimation and fasting, only healthy animals without abnormalities were intragastrically administered with the test compound by using mouse sonde. 2 hours after the administration of the test compound, they were subjected to cervical dislocation. By opening their abdominal cavity, left lobe of liver and subcutaneous fat opposite to inguinal region were extracted. The extracted organs were washed with saline water, and blood and hair were removed. The edge portion (10-30 mg) of the liver and the middle portion (50-100 mg) of the subcutaneous fat were sectioned using a blade, and then transferred to a 48 well plate 500 μl containing PBS (refrigerated). The tissues placed on the plate were transferred to a 48 well plate in which each well contained 500 μl of DMEM medium (Wellgene) (phenol red free) containing 1 uM cortisone and 100 nM NADPH, and reacted at 37° C. for 3 hours. Then, 300 μl of the resultant liquid within the plate was transferred to a 1.5 ml tube, and stored at −20° C.

Cortisol in the liquid was subjected to quantitative analysis using cortisol EIA (Assay Design, 900-071). A 96 well plate coated with primary antibody was added with 100 μl each of 1/20-diluted analysis sample and cortisol standard, and added 50 μl of each of cortisol conjugate and anti-cortisol EIA antibody, followed by a reaction in an orbital shaker at room temperature for 2 hours. Then, the wells were turned upside down and emptied, and washed with 400 μl of wash buffer three times. 200 μl of substrate solution (pNpp) was added to each well, and reacted at room temperature for 1 hour. Then, 50 μl of sodium triphosphate was added to each well to stop the reaction, and absorbency at a wavelength of 405 nM was measured. Through interpolation from a standard curve of cortisol standard, a quantitative value of cortisol of each analysis sample was calculated. An analysis sample of an animal not administered with the test compound was used as a control, and the inhibitory percentage was calculated.

As a result, through in vitro enzyme activity analysis of compound 26, compound 75, compound 83, compound 84, compound 85, compound 87, compound 89, compound 90, compound 92, compound 97, compound 101, compound 102, compound 104, compound 105, compound 106, compound 108, compound 112, compound 119, compound 121, compound 127, compound 146, compound 159, compound 188, compound 190, compound 219, compound 221, and compound 226, it was found that most compounds showed 11b-HSD1 enzyme inhibitory effect of 70% or more in liver and subcutaneous fat.

Although the present invention has been described with reference to exemplary embodiments, those skilled in the art will understand that various changes may be made without departing from the scope of the invention, and may be substituted with equivalents thereof. Further, many modifications may be implemented without departing from the essential scope of the invention, and then specific conditions and materials may be employed in the claimed features of the invention. Accordingly, it should be understood that the present invention is not limited to any specific embodiment disclosed as a best embodiment planned for implementation of the invention, but includes all embodiments within the scope of claims of the invention.

The invention claimed is:

1. A compound of Formula I, or an enantiomer, a diastereomer, a geometric isomer, a solvate or a pharmaceutically acceptable salt thereof:

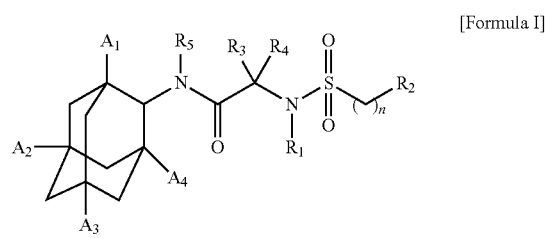

[Formula I]

wherein $A_{1-4}$ each is independently selected from the group consisting of H, —CHR'R", —OR', —COOR', and —CONR'R", wherein R' and R" each is independently H, a linear or branched optionally substituted $C_{1-5}$ alkyl group, or $C_{3-10}$ cycloalkyl group;

$R_1$ and $R_5$ each is independently H or a linear or branched optionally substituted $C_{1-5}$ alkyl group;

$R_2$ is selected from the group consisting of an optionally substituted $C_{5-10}$ aryl group, an optionally substituted $C_{5-10}$ heteroaryl group, an optionally substituted $C_{3-10}$ cycloalkyl group, an optionally substituted $C_{3-12}$ heterocycloalkyl group and a combination thereof;

$R_3$ and $R_4$ each is independently a linear or branched optionally substituted $C_{1-5}$ alkyl group, wherein $R_3$ and $R_4$ are capable of being linked to each other to form an optionally substituted $C_{3-10}$ cycloalkyl group; and n represents an integer of 0 to 2, wherein if n is 1 or 2, a constituent carbon is capable of being substituted with a linear or branched $C_{1-5}$ alkyl group, wherein, a $C_{5-10}$ heteroaryl group and a $C_{3-12}$ heterocycloalkyl group each represents a group in which a carbon constituting a ring is substituted with at least one atom selected from the group consisting of N, O and S;

a substituted $C_{1-5}$ alkyl, a substituted $C_{5-10}$ aryl group, a substituted $C_{5-10}$ heteroaryl group, a substituted $C_{3-10}$ cycloalkyl group and a substituted $C_{3-12}$ heterocycloalkyl group each independently represents a group substituted with at least one substituent selected from the group consisting of —OR', —SR', —NO$_2$, —CN, azide, halogen, $C_{1-5}$ alkyl, $C_{1-5}$ alkyl substituted with at least one —OH group or halogen atom, a $C_{3-10}$ cycloalkyl group, a $C_{5-10}$ aryl group, a $C_{5-10}$ heteroaryl group, —COR', —COOR', —CONR'R", and —NR'R", wherein R' and R" are the same as previously defined.

2. The compound, or the enantiomer, the diastereomer, the geometric isomer, the solvate or the pharmaceutically acceptable salt thereof, as claimed in claim 1, wherein $R_2$ is selected from the group consisting of an optionally substituted $C_{5-10}$ aryl group, an optionally substituted $C_{5-10}$ heteroaryl group and a combination thereof, wherein the substituted $C_{5-10}$ aryl group or the substituted $C_{5-10}$ heteroaryl group each independently represents a group substituted with at least one substituent selected from the group consisting of —OR', —SR', —NO$_2$, —CN, azide, halogen, $C_{1-5}$ alkyl, $C_{1-5}$ alkyl substituted with at least one —OH group or halogen atom, a $C_{3-10}$ cycloalkyl group, a $C_{5-10}$ aryl group, a $C_{5-10}$ heteroaryl group, —COR', —COOR', —CONR'R", and —NR'R".

3. The compound, or the enantiomer, the diastereomer, the geometric isomer, the solvate or the pharmaceutically acceptable salt thereof, as claimed in claim 1, wherein $A_2$ is selected from the group consisting of H, —OR', —COOR', and —CONR'R".

4. The compound, or the enantiomer, the diastereomer, the geometric isomer, the solvate or the pharmaceutically acceptable salt thereof, as claimed in claim 1, wherein the compound of Formula 1 is any one selected from the group consisting of the compounds below:

1
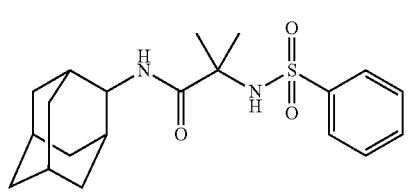

2
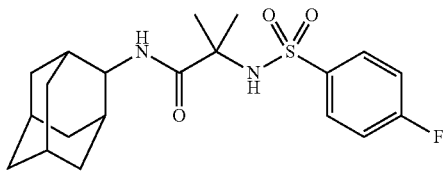

3
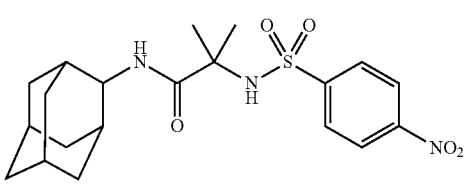

4
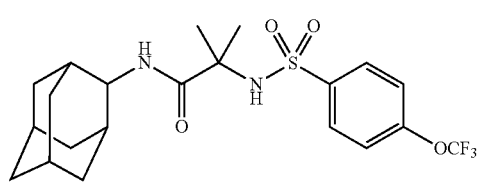

5
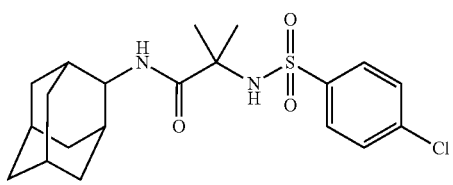

6
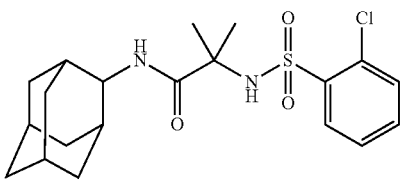

7
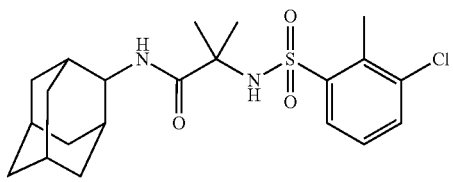

8
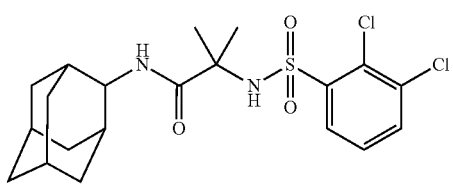

9
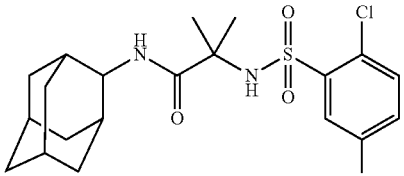

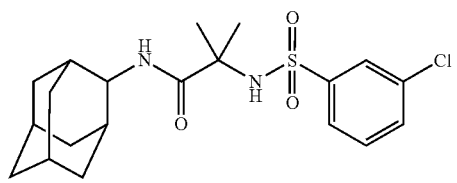
10
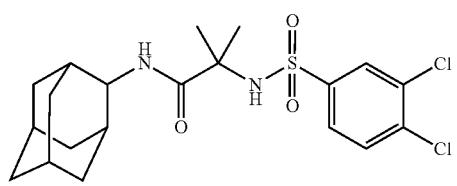
11
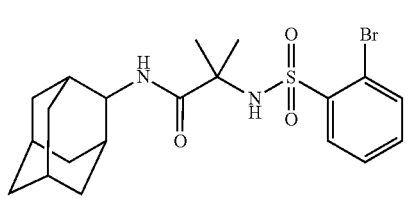
12
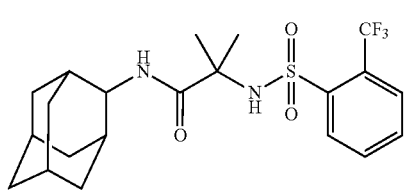
13
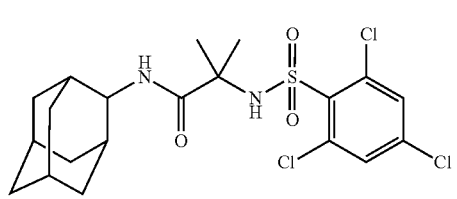
14
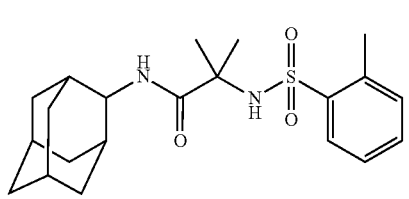
15
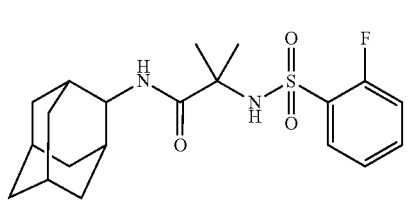
16
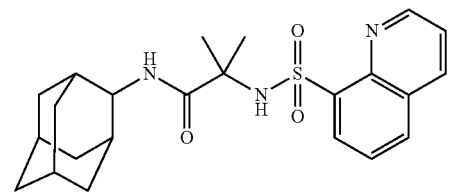
17
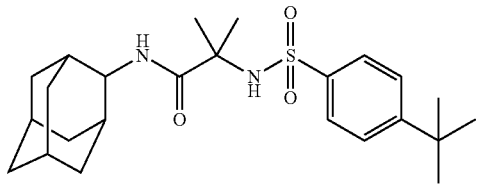
18
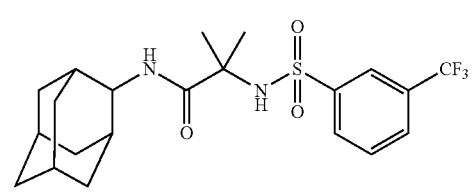
19
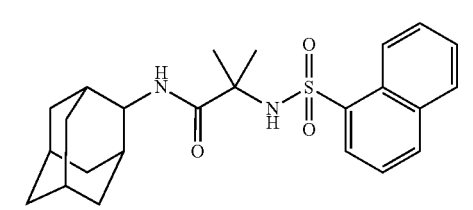
20
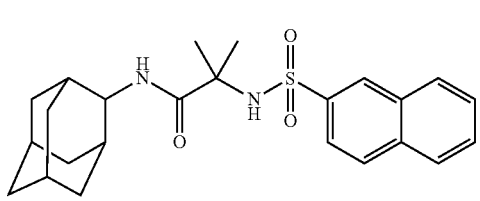
21
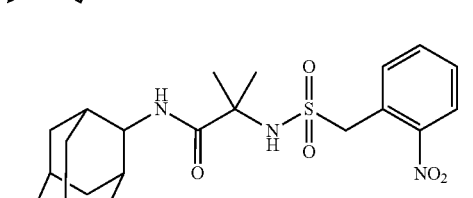
22
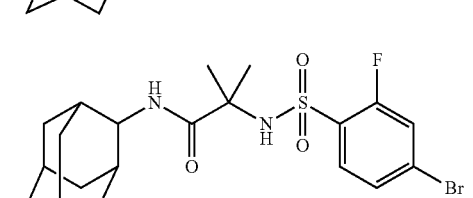
23
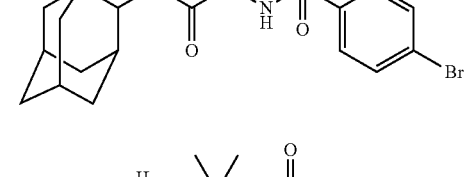
24
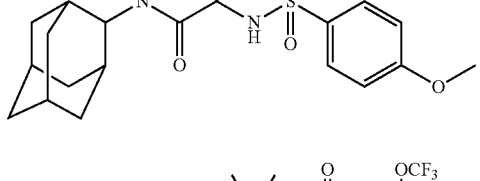
25
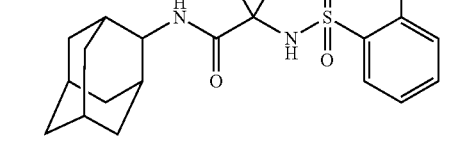

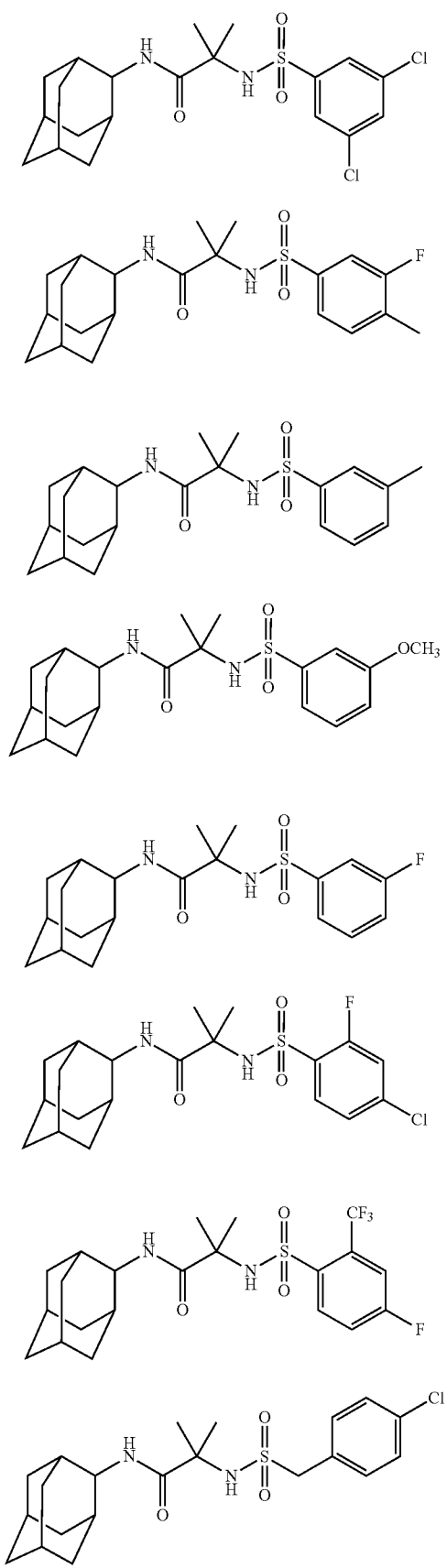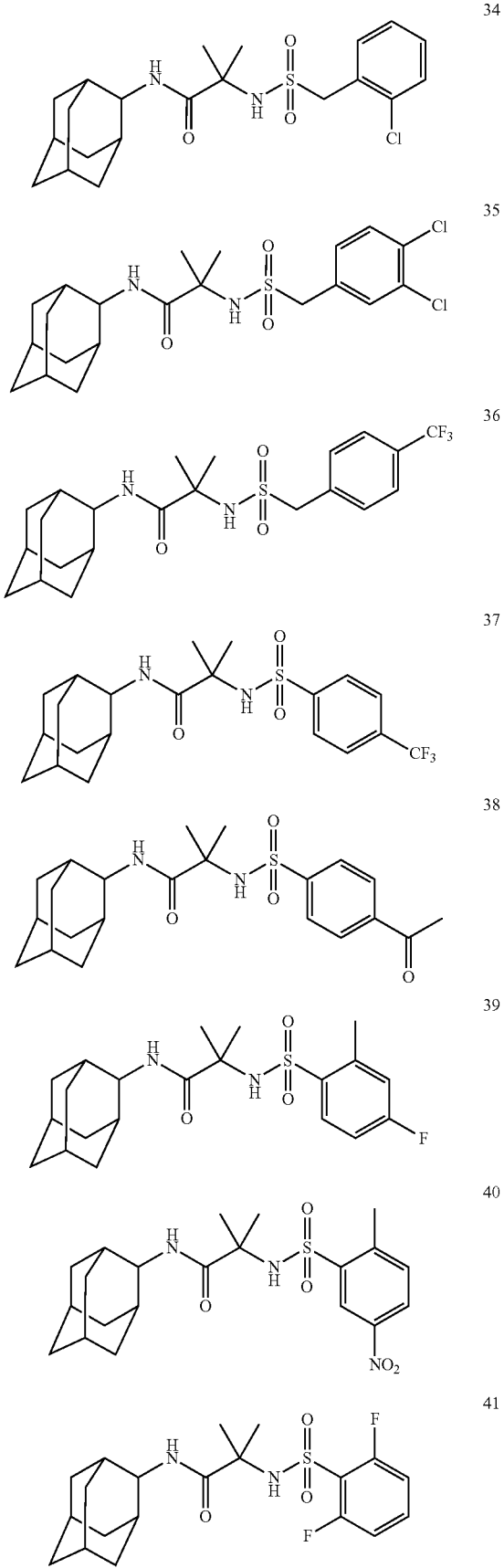

-continued
42 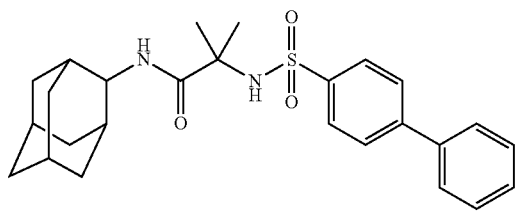
43 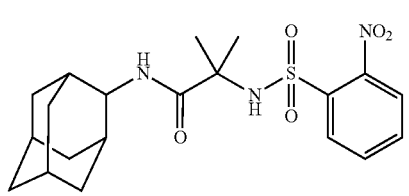
44 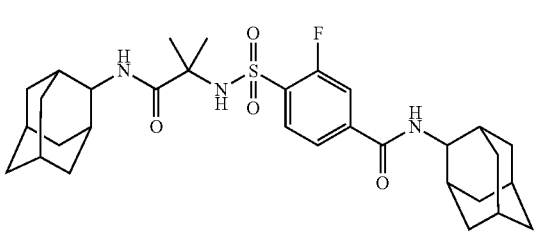
45 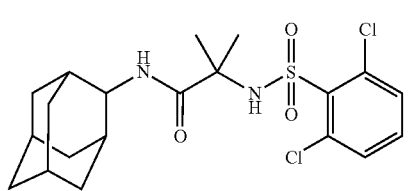
46 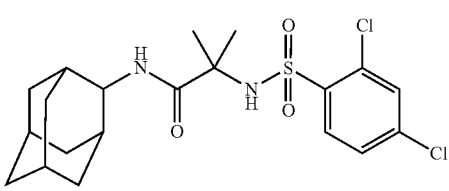
47 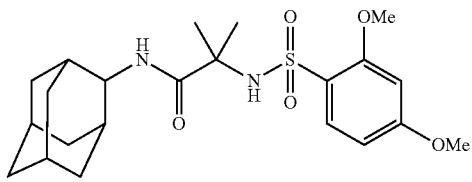
48 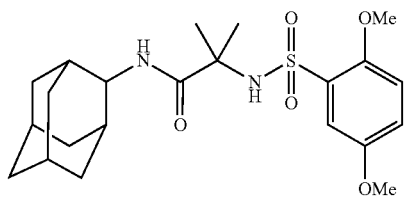
49 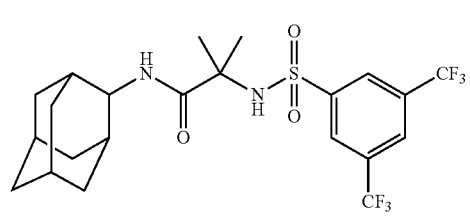
-continued
50 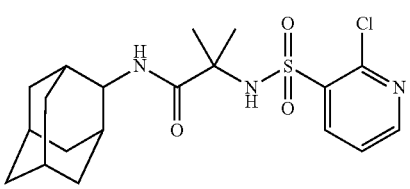
51 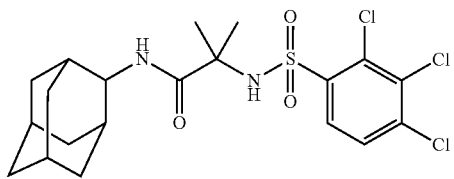
52 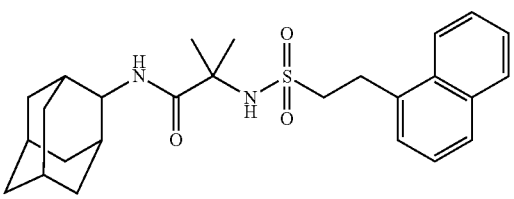
53 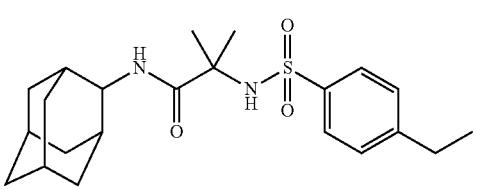
54 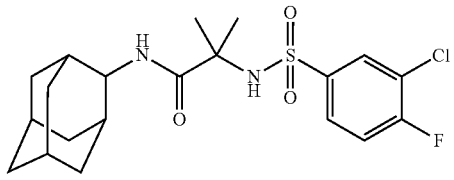
55 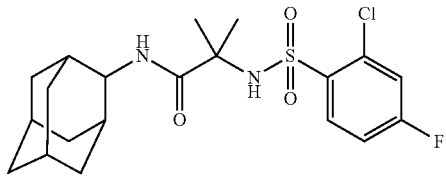
56 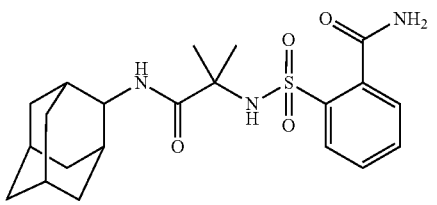
57 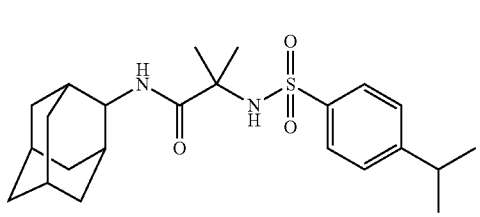

| | |
|---|---|
| 58 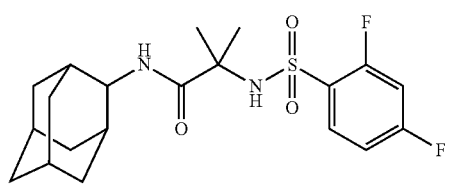 | 66 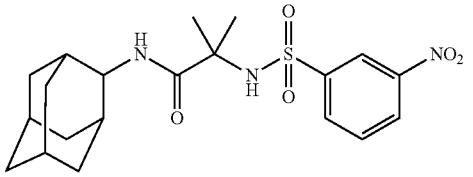 |
| 59 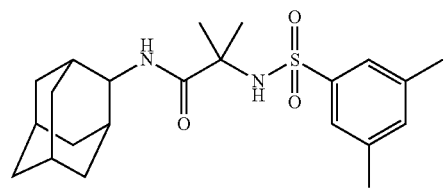 | 67 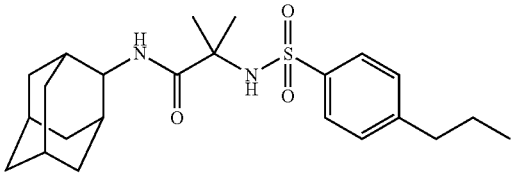 |
| 60 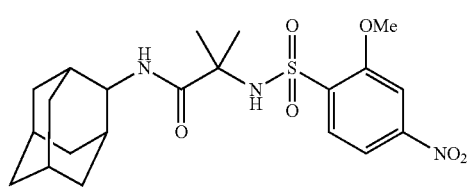 | 68 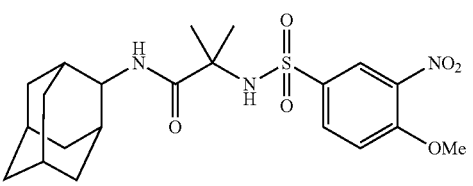 |
| 61 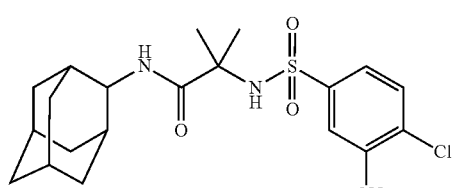 | 69 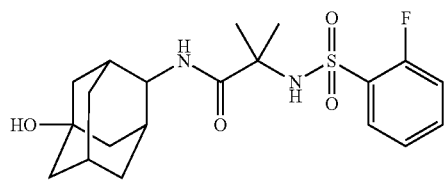 |
| 62 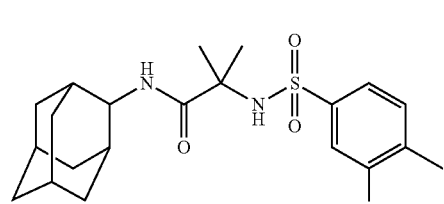 | 70 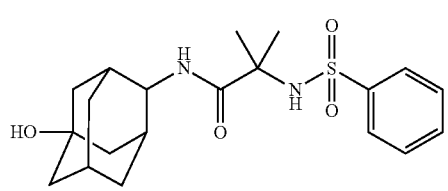 |
| 63 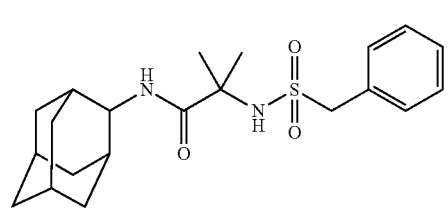 | 71 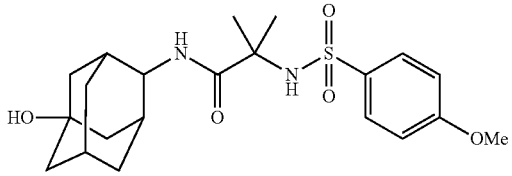 |
| 64 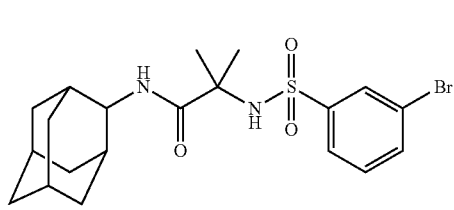 | 72 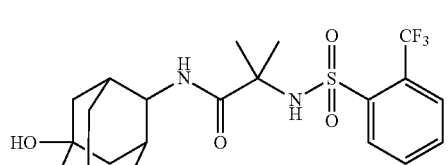 |
| 65 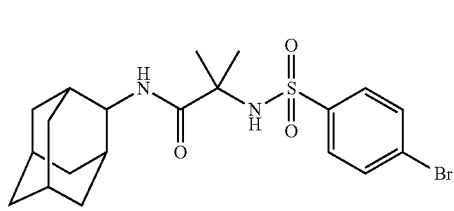 | 73 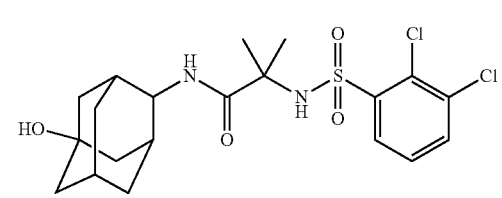 |

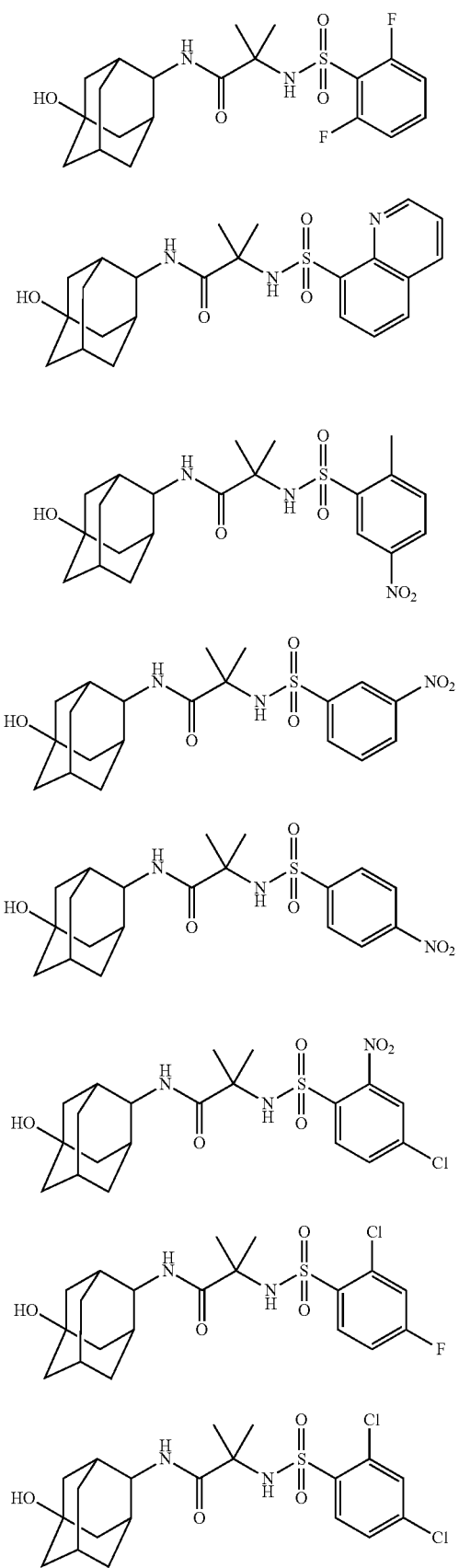
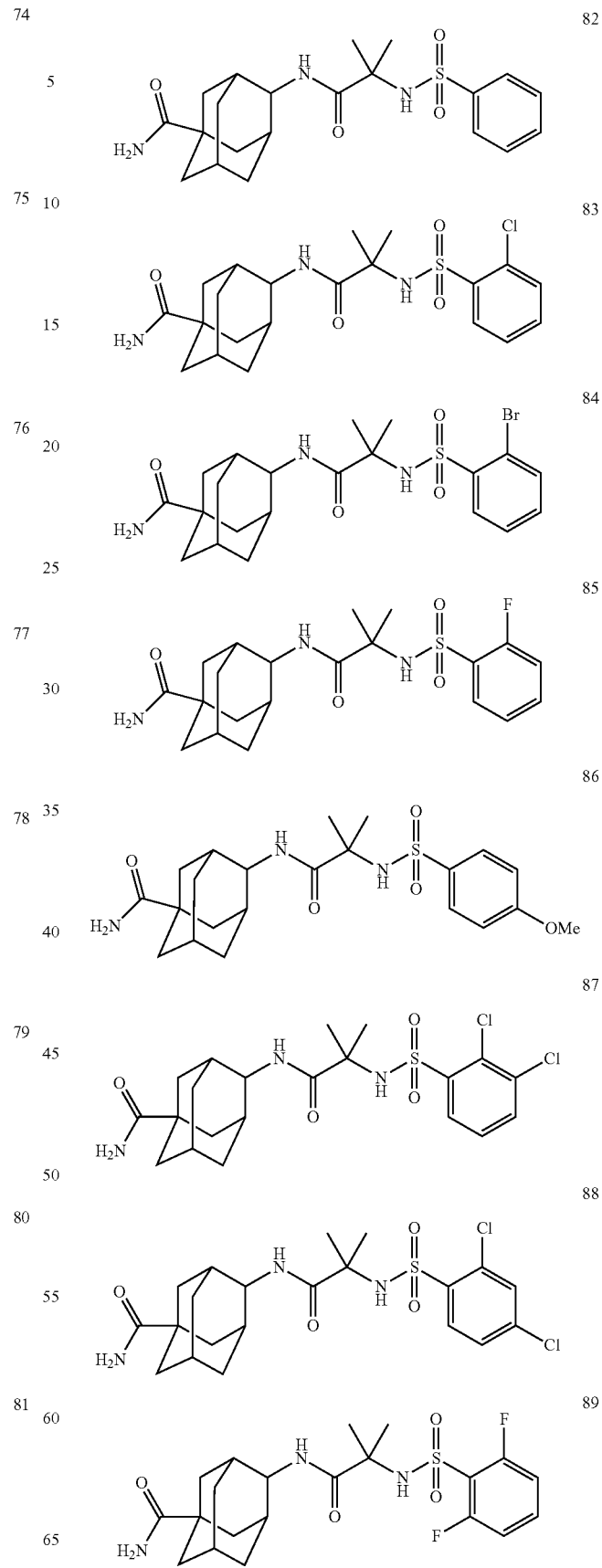

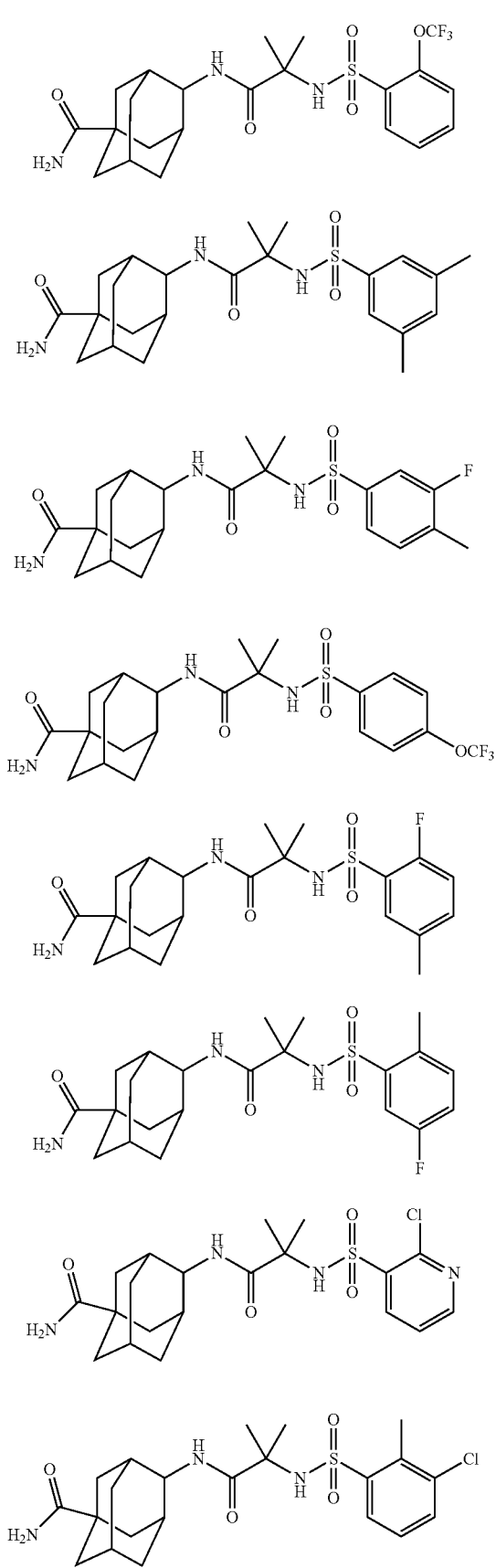
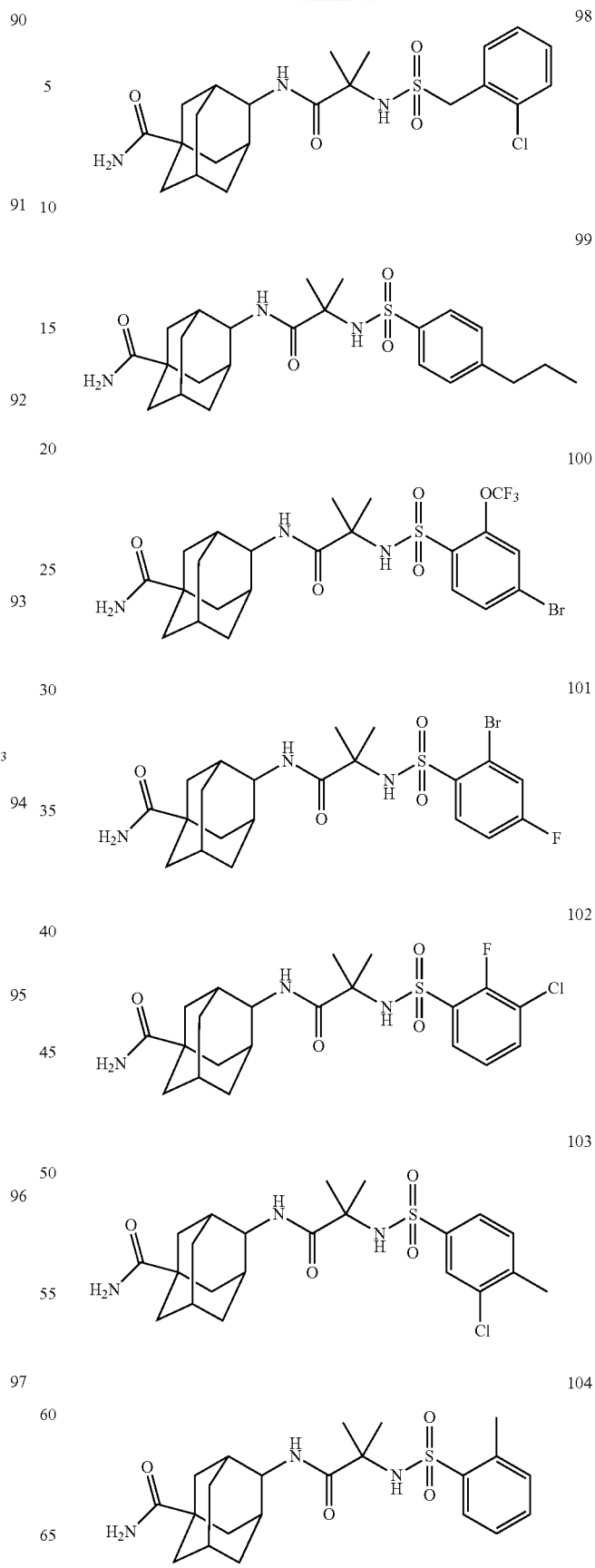

105 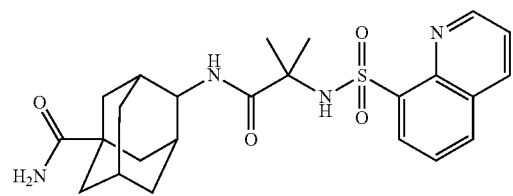
106 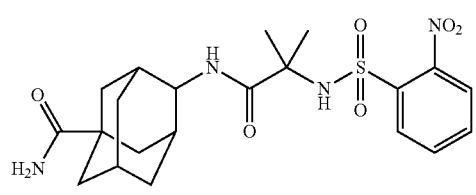
107 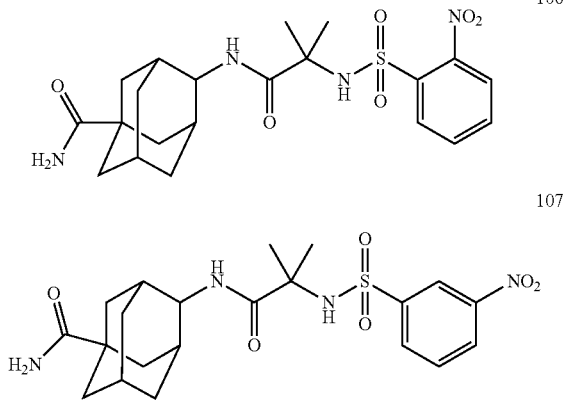
108 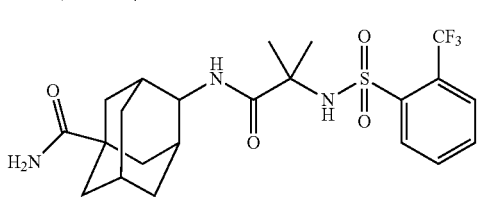
109 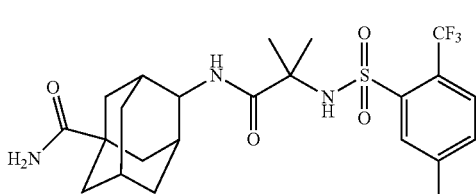
110 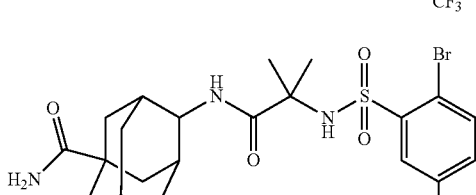
111 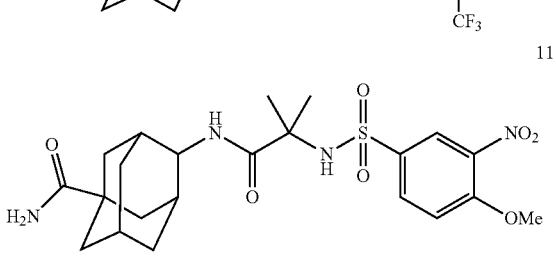
112 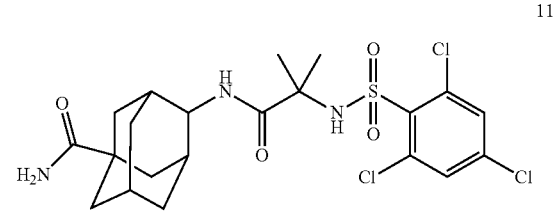
113 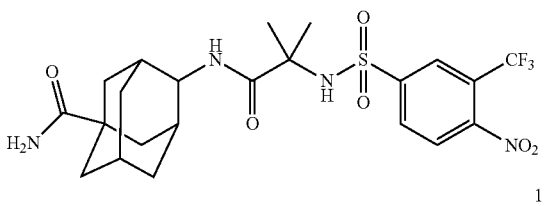
114 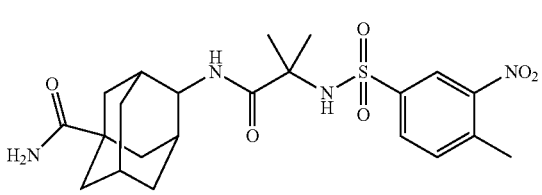
115 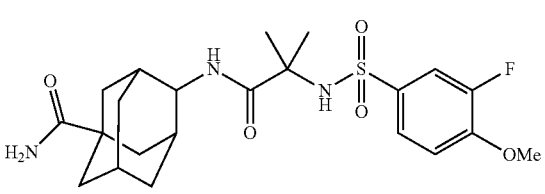
116 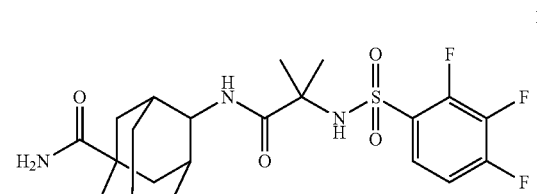
117 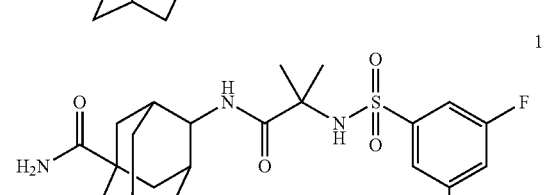
118 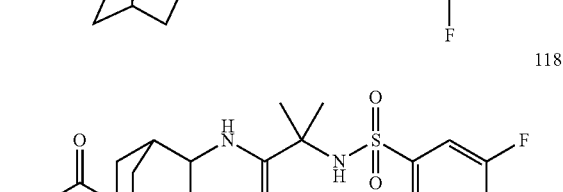
119 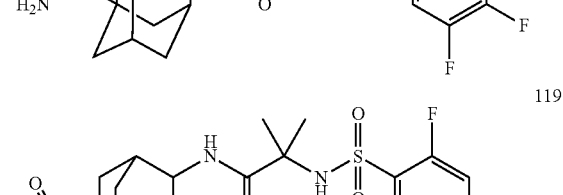
120 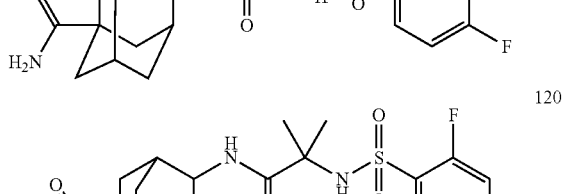

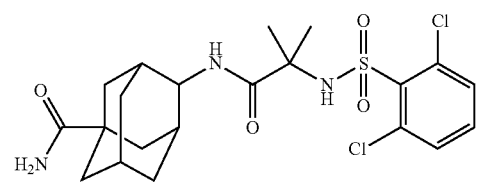
121
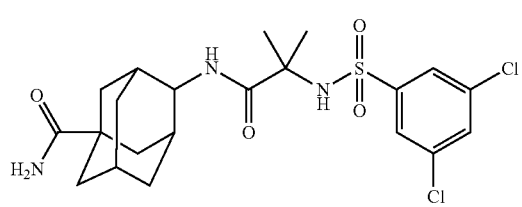
122
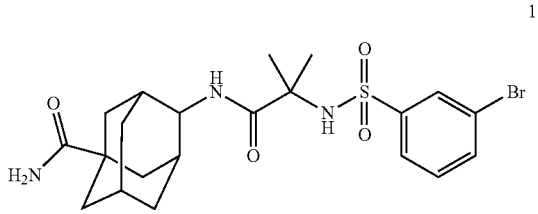
123
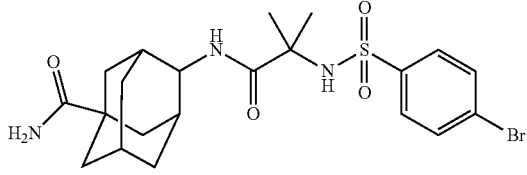
124
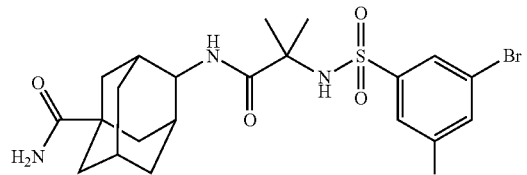
125
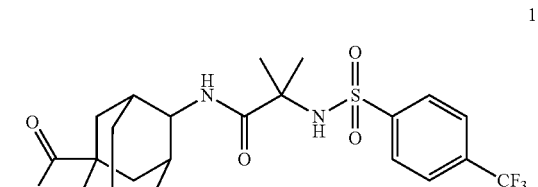
126
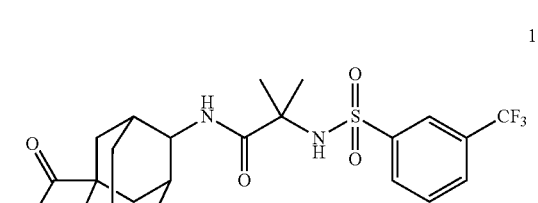
127
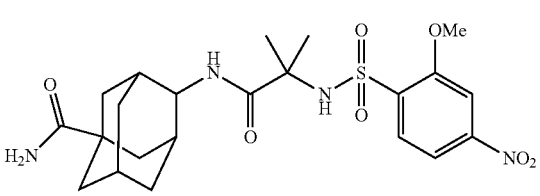
128
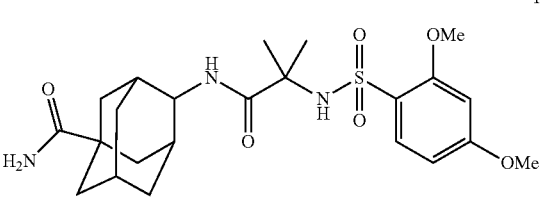
129
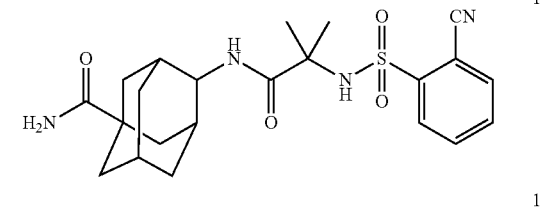
130
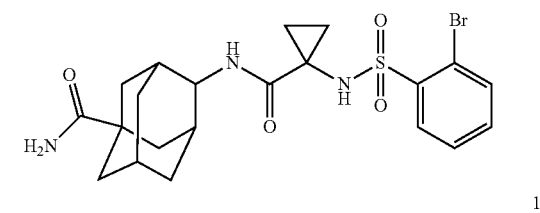
131
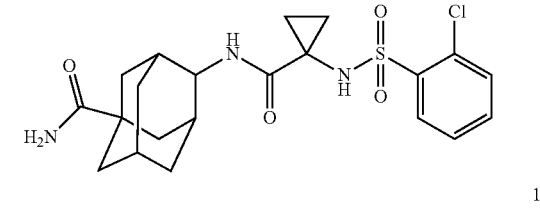
132
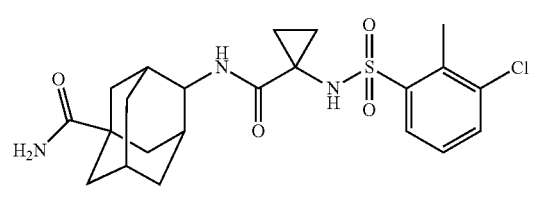
133
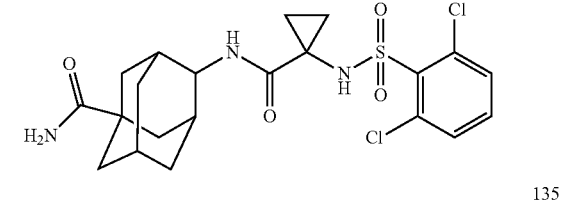
134
135

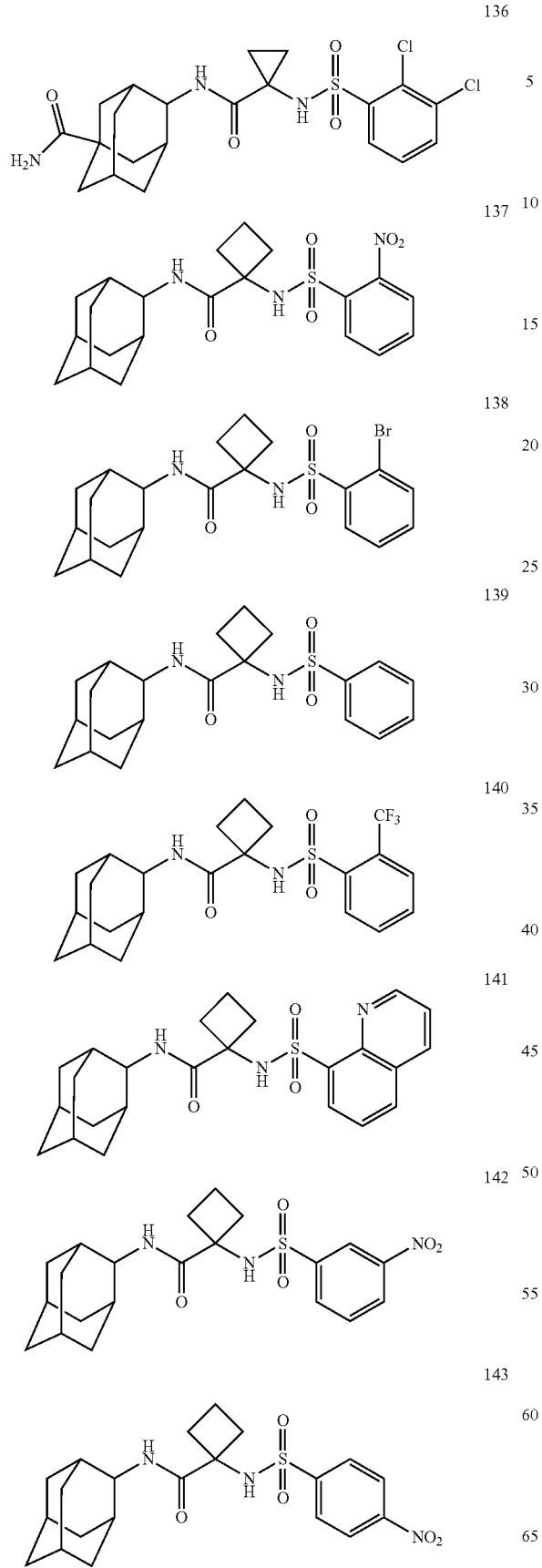
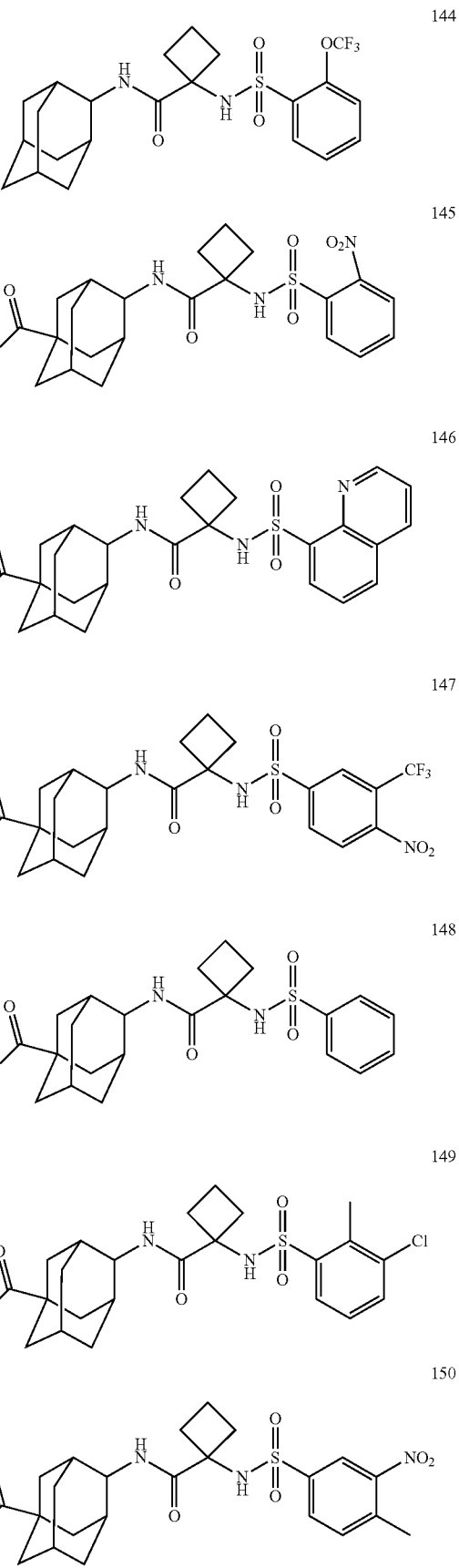

293
-continued
151
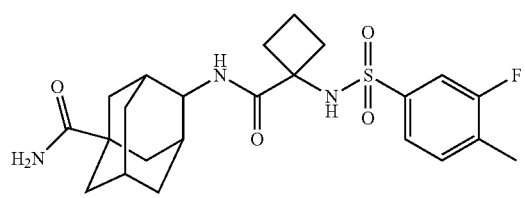
152
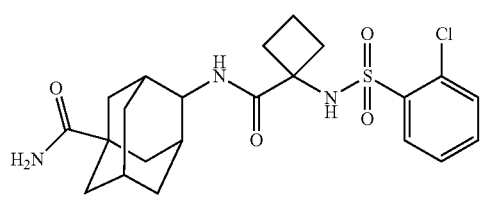
153
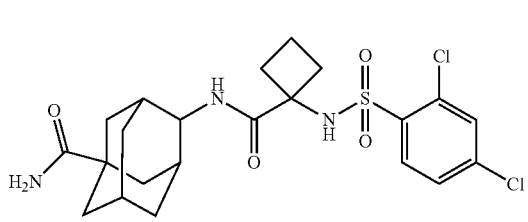
154
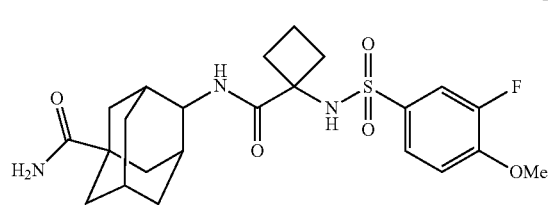
155
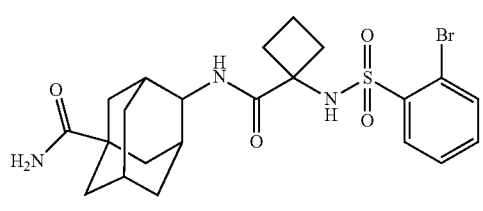
156
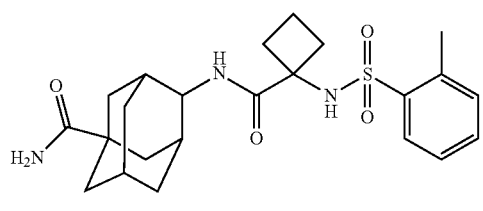
157
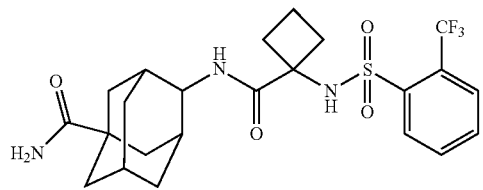
294
-continued
158
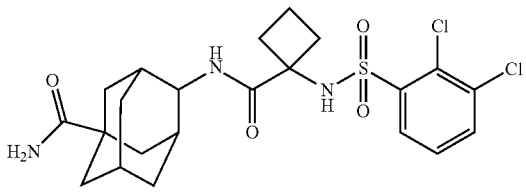
159
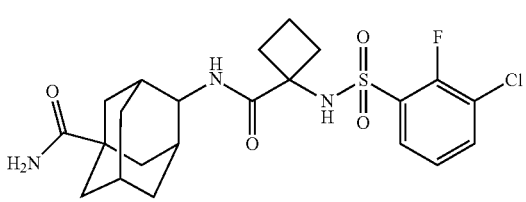
160
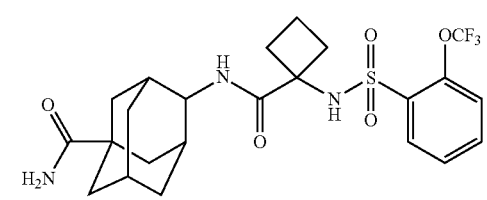
161
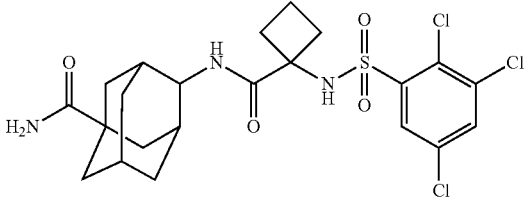
162
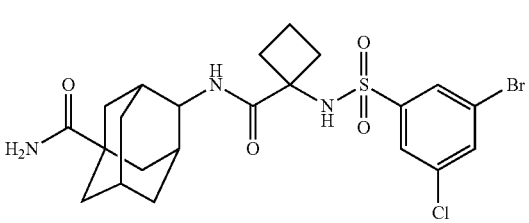
163
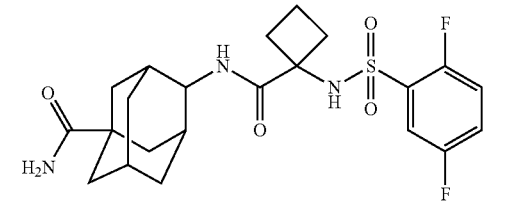
164
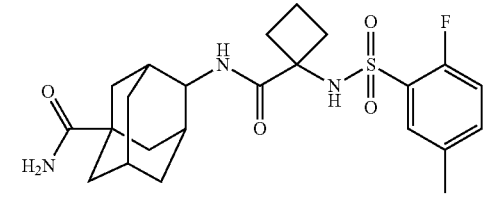

165
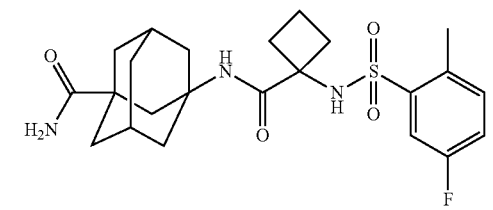
166
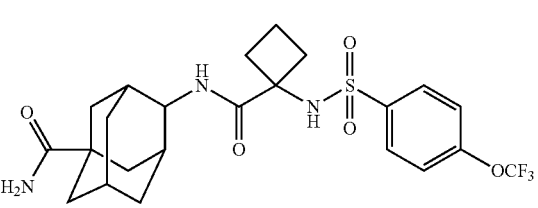
167
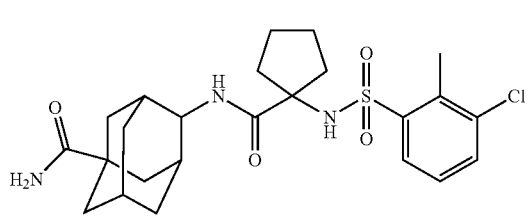
168
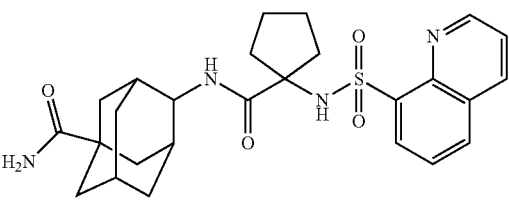
169
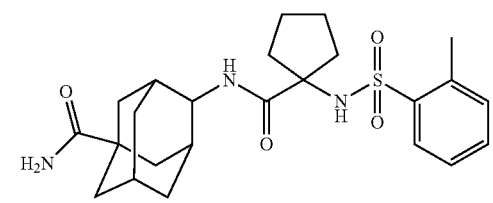
170
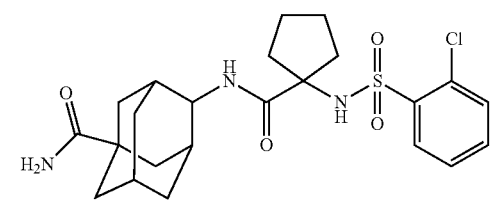
171
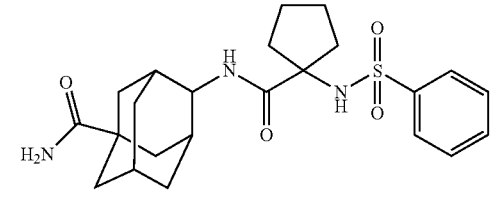
172
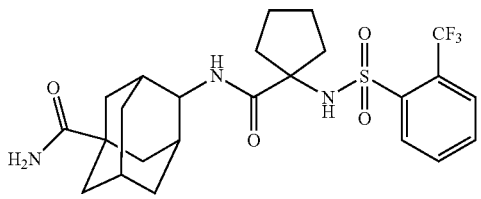
173
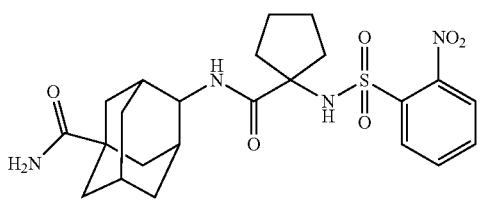
174
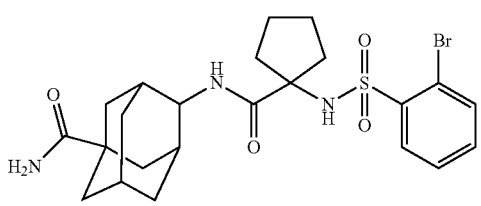
175
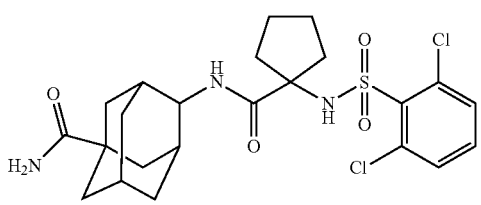
176
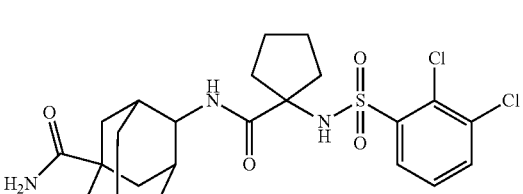
177
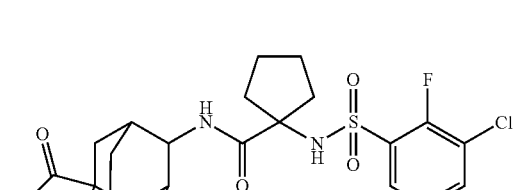
178
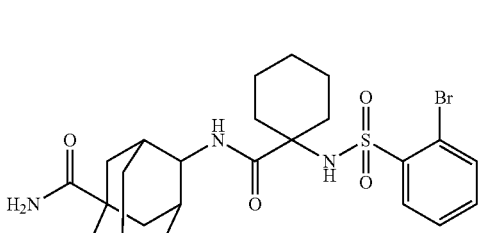

179
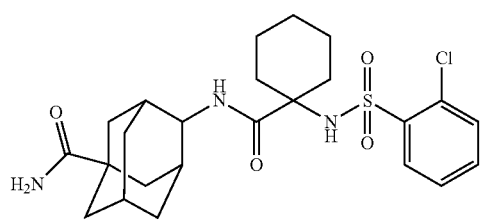
180
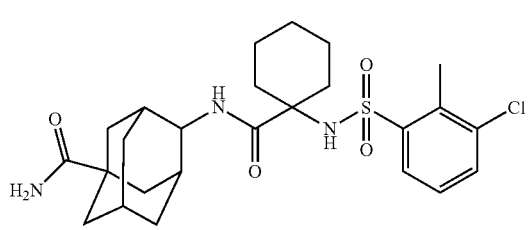
181
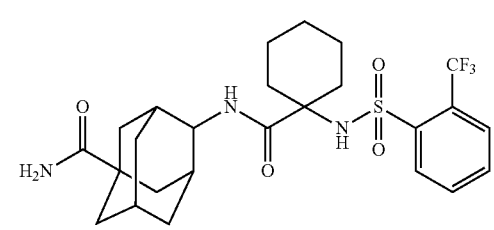
182
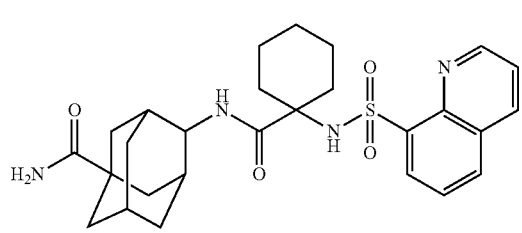
183
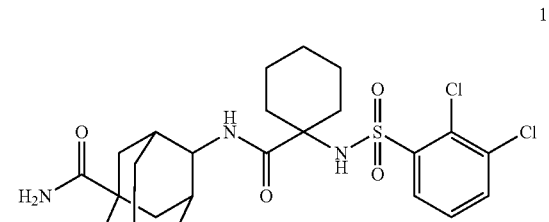
184
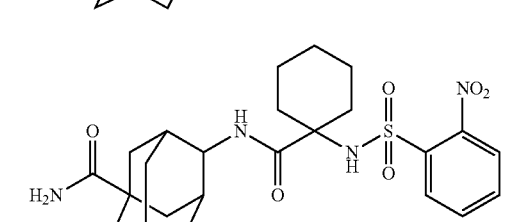
185
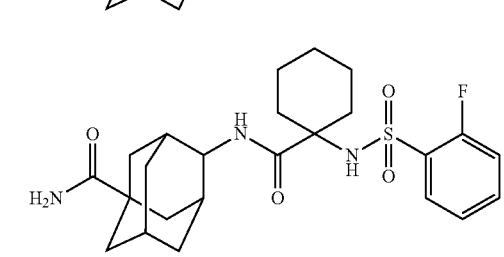
186
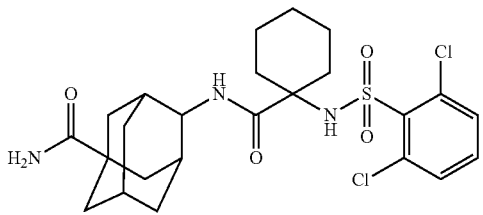
187
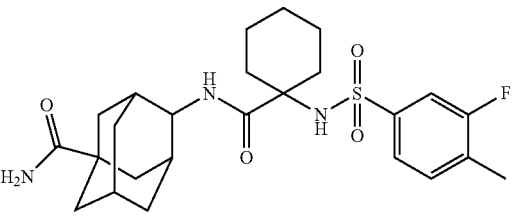
188
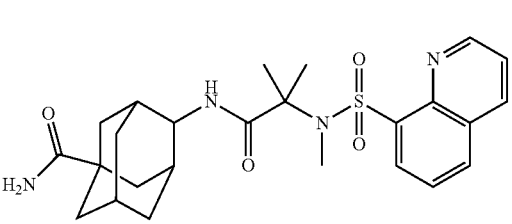
189
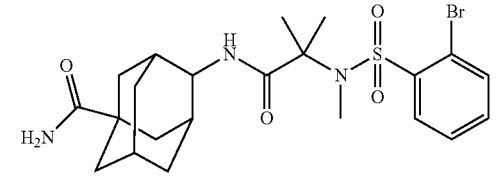
190
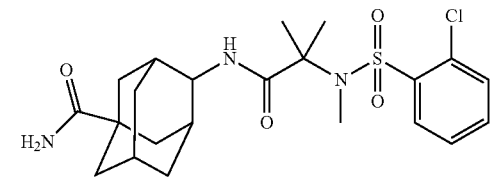
191
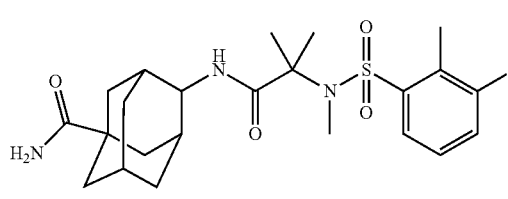
192
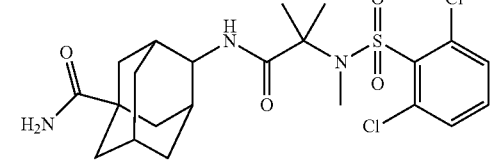
193
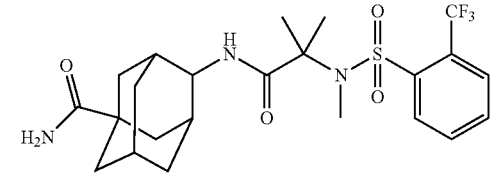

-continued
194 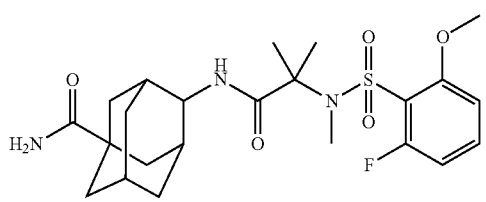
195 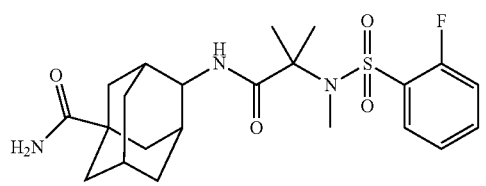
196 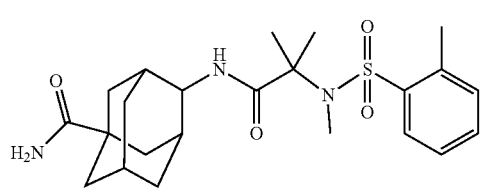
197 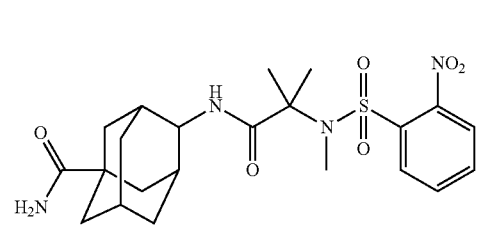
198 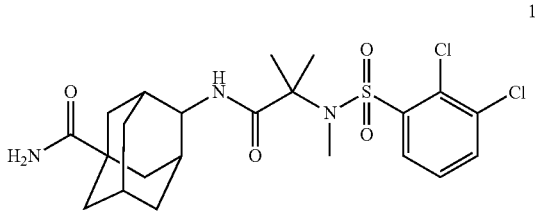
199 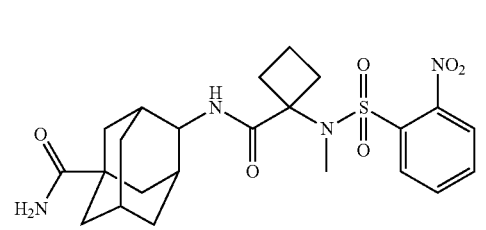
200 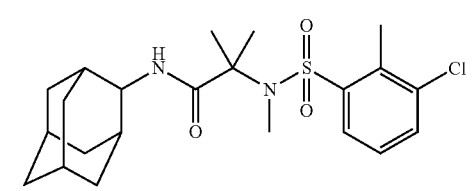
201 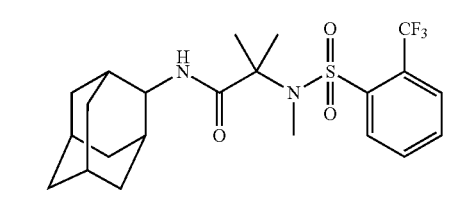
-continued
202 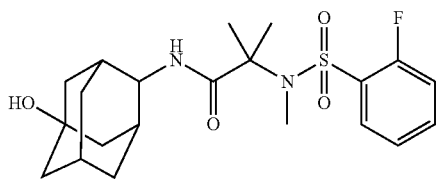
203 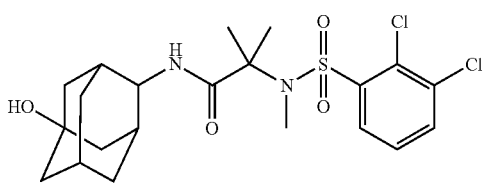
204 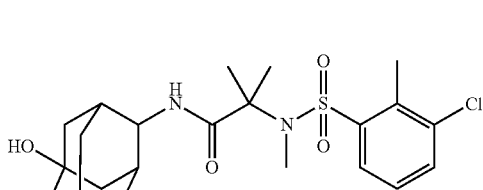
205 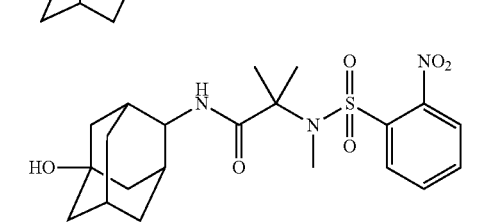
206 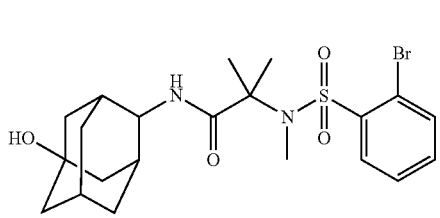
207 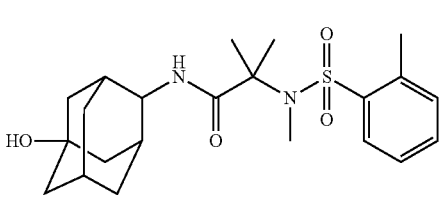
208 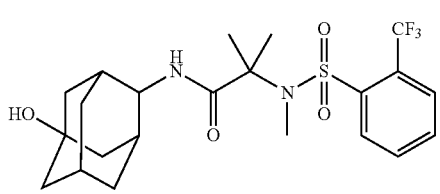
209 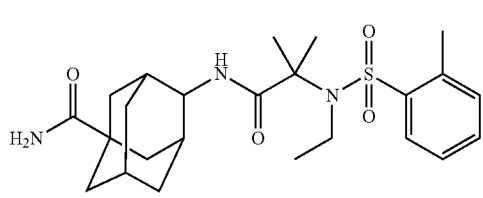

301
-continued
210
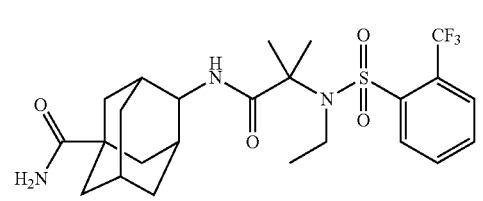
211
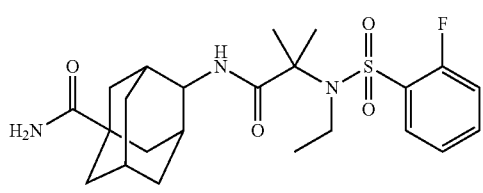
212
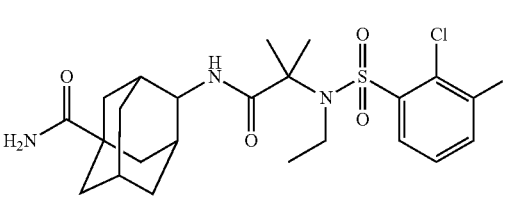
213
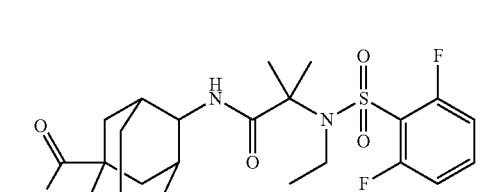
214
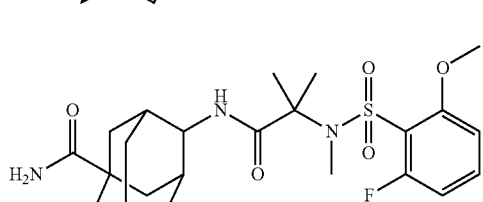
215
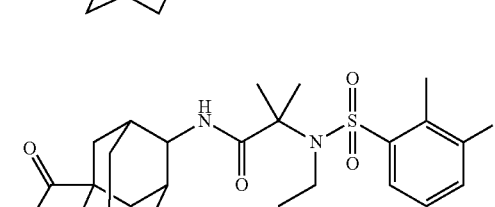
216
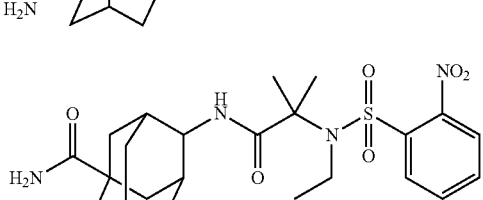
217
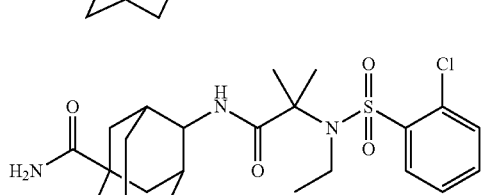
302
-continued
218
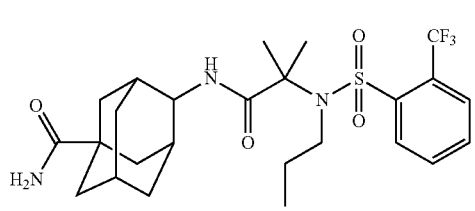
219
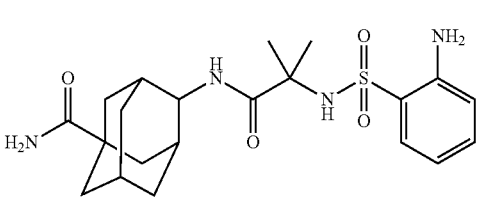
220
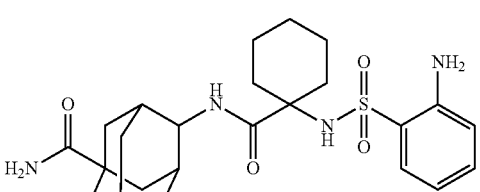
221
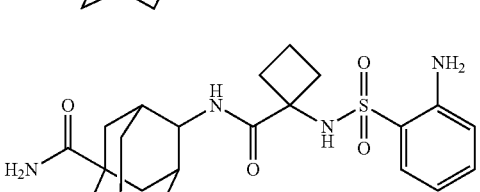
222
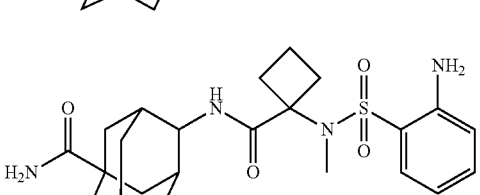
223
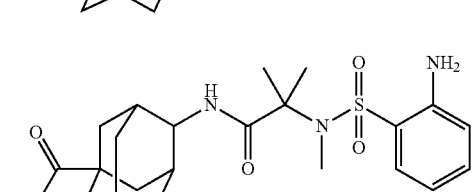
224
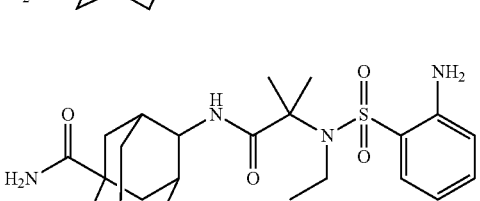
225
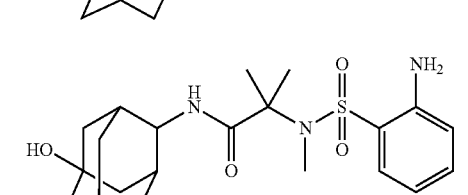

303
-continued
226
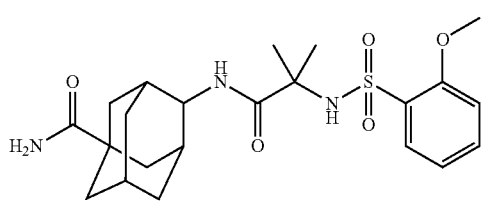
227
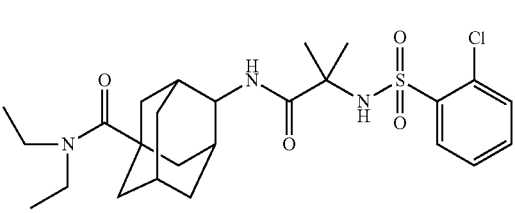
228
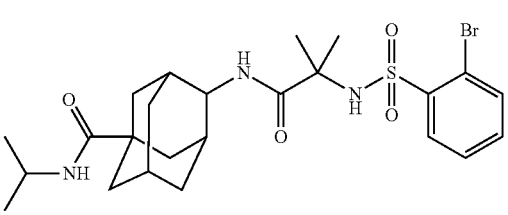
229
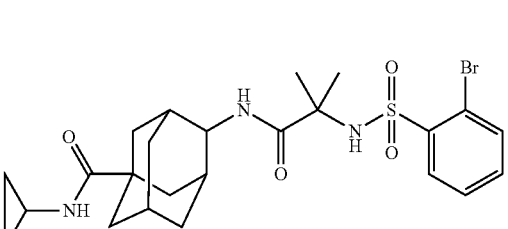
230
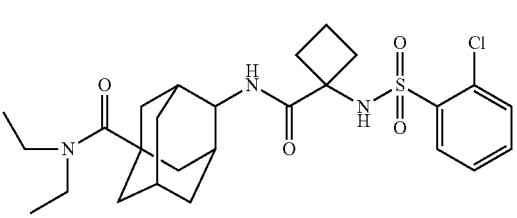
231
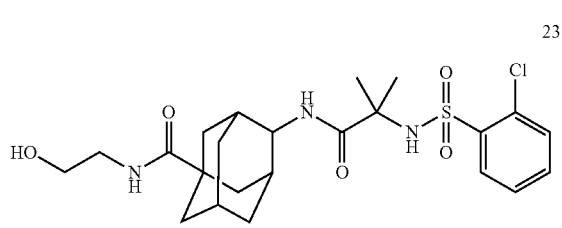
232
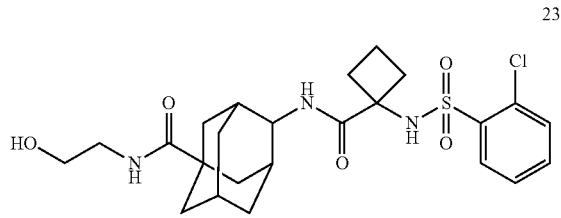
304
-continued
233
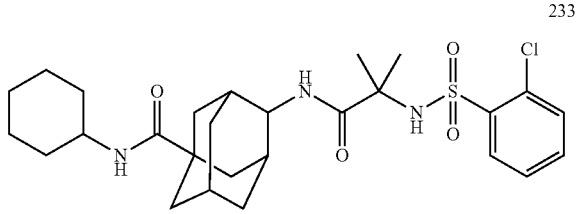
234
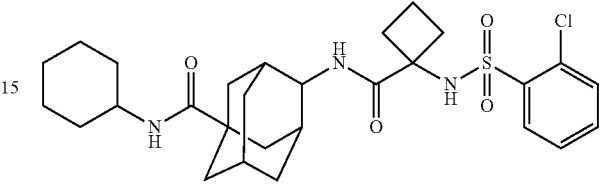
235
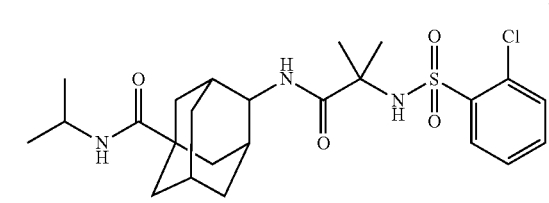
236
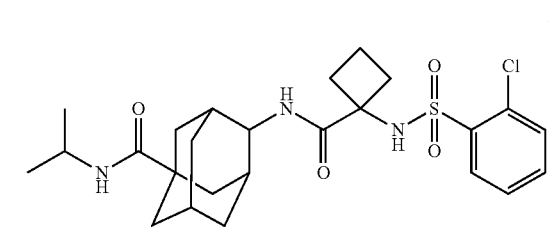
237
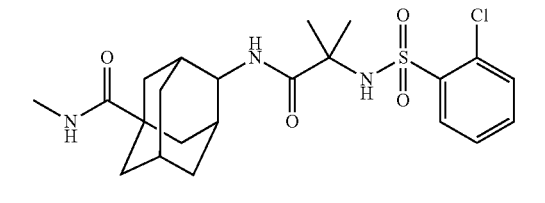
238
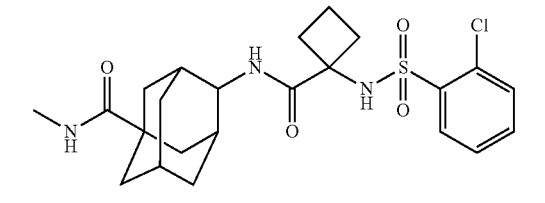
239
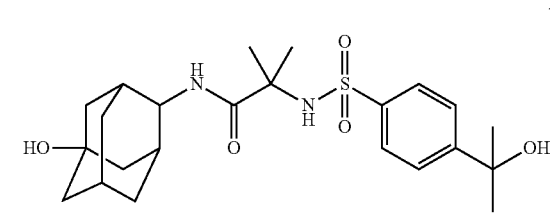

305
-continued
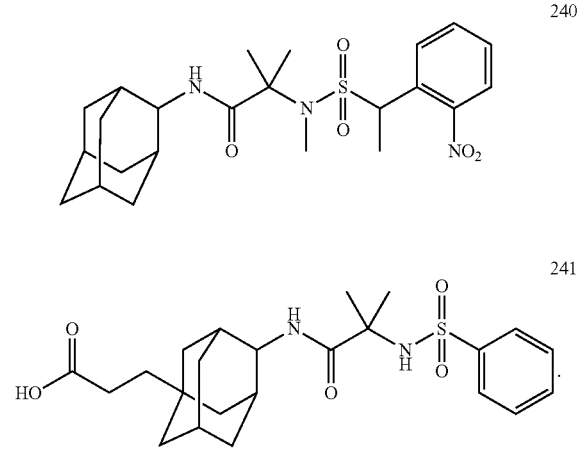
5. The compound, or the enantiomer, the diastereomer, the geometric isomer, the solvate or the pharmaceutically acceptable salt thereof, as claimed in claim 1, wherein the compound of Formula 1 is any one selected from the group consisting of compounds below:
306
-continued
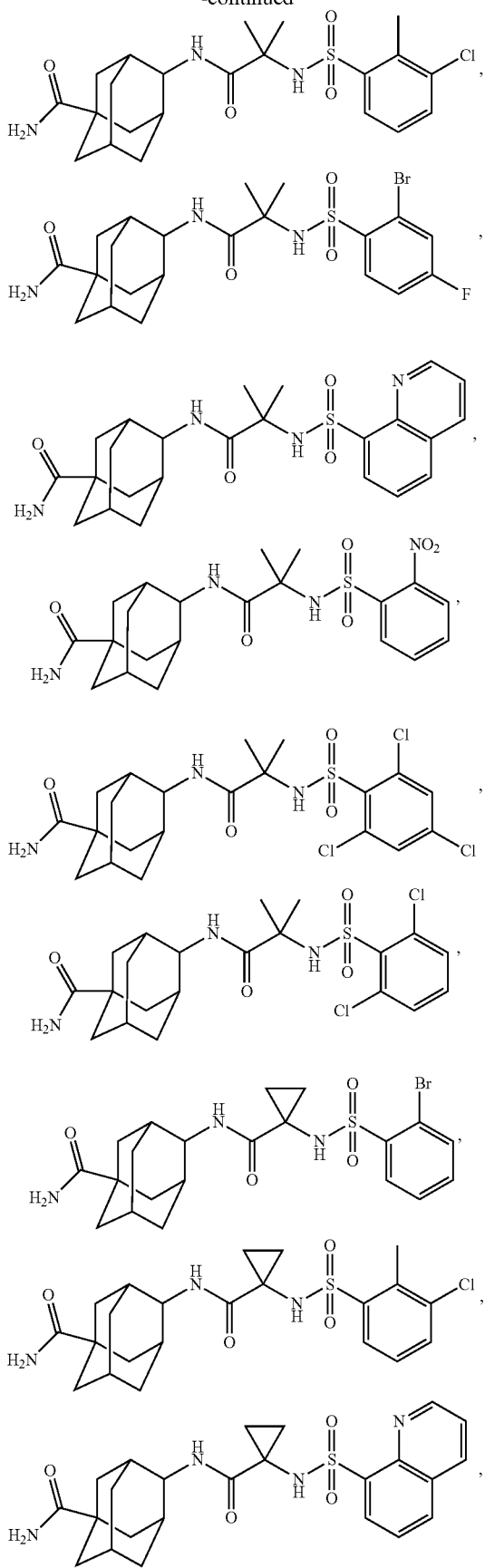

307
-continued
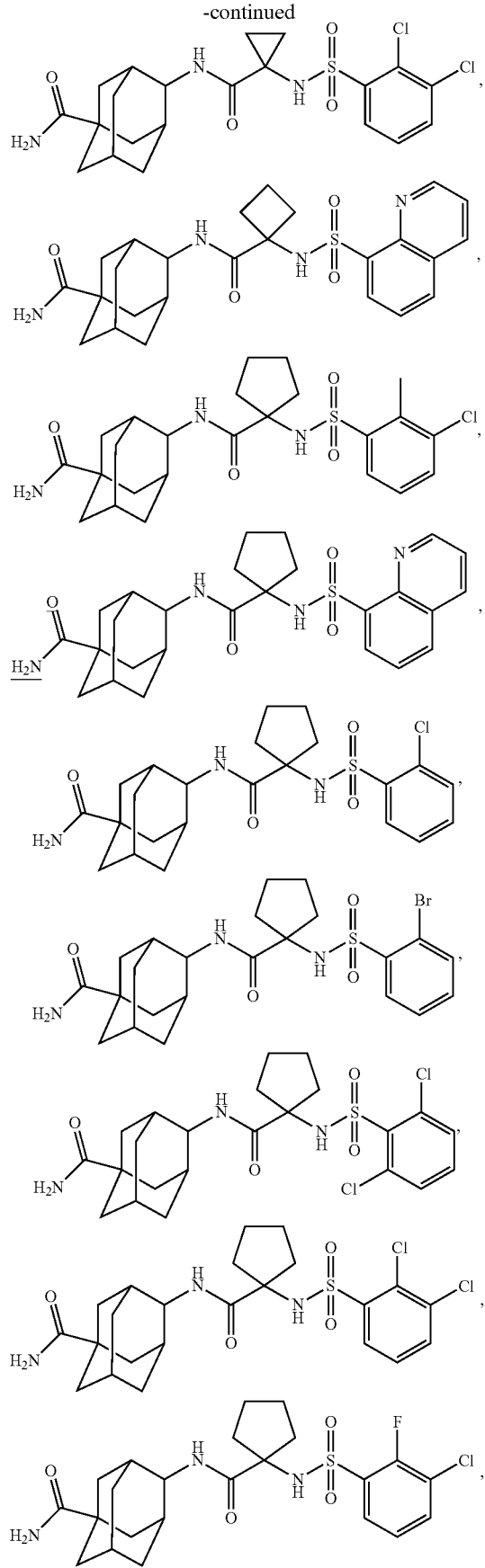
308
-continued
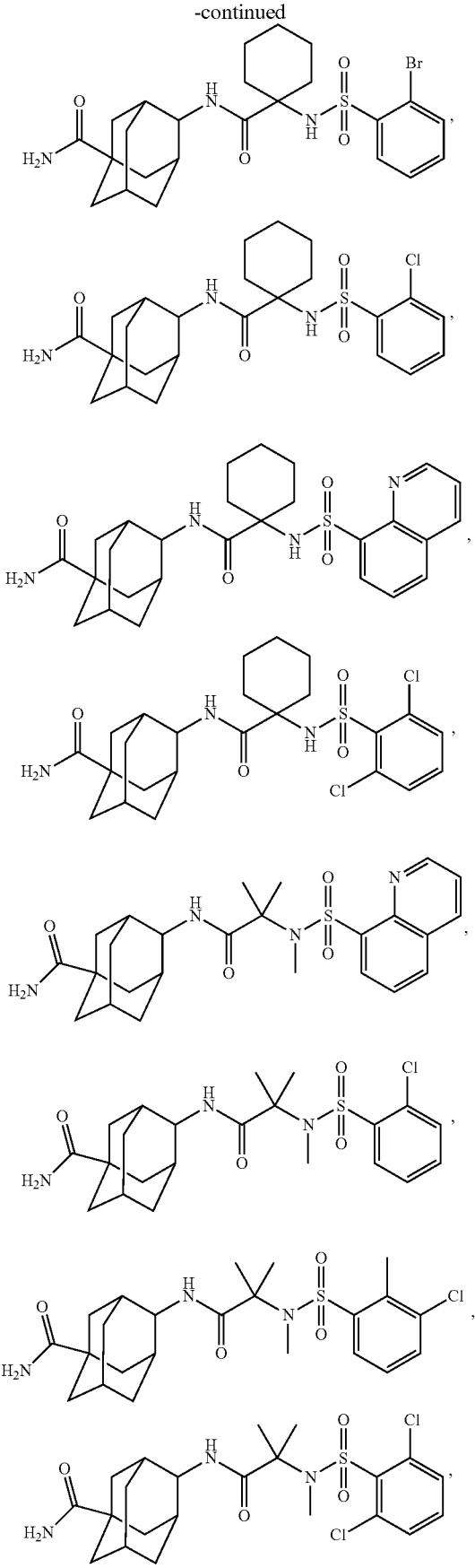

6. A pharmaceutical composition for inhibiting human 11-β-hydroxy steroid dehydrogenase type 1, comprising the compound or the pharmaceutically acceptable salt thereof, as claimed in claim 1, as an active ingredient.

7. A pharmaceutical composition for treating diabetes mellitus which comprises the compound or the pharmaceutically acceptable salt thereof, as claimed in claim 1, as an active ingredient.

* * * * *